US011091534B2

(12) United States Patent
Chhabra et al.

(10) Patent No.: US 11,091,534 B2
(45) Date of Patent: Aug. 17, 2021

(54) FACTOR VIII COMPLEX WITH XTEN AND VON WILLEBRAND FACTOR PROTEIN, AND USES THEREOF

(71) Applicant: Bioverativ Therapeutics Inc., Waltham, MA (US)

(72) Inventors: Ekta Seth Chhabra, Framingham, MA (US); Tongyao Liu, Lexington, MA (US); Pei-yun Chang, Menlo Park, CA (US); Robert T. Peters, Needham, MA (US); John Kulman, Belmont, MA (US); Haiyan Jiang, Belmont, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 11 days.

(21) Appl. No.: 16/154,310

(22) Filed: Oct. 8, 2018

(65) Prior Publication Data
US 2019/0169267 A1    Jun. 6, 2019

Related U.S. Application Data

(62) Division of application No. 14/413,765, filed as application No. PCT/US2013/049989 on Jul. 10, 2013, now Pat. No. 10,138,291.
(Continued)

(51) Int. Cl.
*C07K 14/755* (2006.01)
*A61K 47/55* (2017.01)
(Continued)

(52) U.S. Cl.
CPC ............ *C07K 14/755* (2013.01); *A61K 38/36* (2013.01); *A61K 38/37* (2013.01); *A61K 47/55* (2017.08);
(Continued)

(58) Field of Classification Search
CPC ........ A61K 38/00; A61K 38/36; A61K 38/37; A61K 47/55; C07K 14/755; C07K 16/00;
(Continued)

(56) References Cited

U.S. PATENT DOCUMENTS

| 4,179,337 A | 12/1979 | Davis et al. |
| 4,215,051 A | 7/1980 | Palmer et al. |

(Continued)

FOREIGN PATENT DOCUMENTS

| EP | 0295597 A2 | 12/1988 |
| EP | 1935430 A1 | 6/2008 |

(Continued)

OTHER PUBLICATIONS

Schellenberger et al., A recombinant polypeptide extends the in vivo half-life of peptides and proteins in a tunable manner, Nature Biotechnology, vol. 27(12): 1186-1190 and 20 pages of online supplemental material (Nov. 15, 2009) (Year: 2009).*
(Continued)

*Primary Examiner* — Randall L Beane
(74) *Attorney, Agent, or Firm* — Lathrop GPM LLP; James V. De Giulio, Esq.; James H. Velema, Esq.

(57) ABSTRACT

The present invention provides a chimeric protein comprising a VWF protein comprising the D' domain and D3 domain of VWF, one or more XTEN sequence, and a FVIII protein, wherein the VWF fragment, the XTEN sequence, or the FVIII protein are linked to or associated with each other. The chimeric protein can further comprise one or more Ig constant region or a portion thereof (e.g., an Fc region). A polypeptide chain comprising a VWF fragment of the invention binds to or is associated with a polypeptide chain comprising a FVIII protein linked to an XTEN sequence and the polypeptide chain comprising the VWF fragment can prevent or inhibit binding of endogenous VWF to the FVIII
(Continued)

FVIIIFC/VWF heterodimer Constructs (variable linker)

Figure 15:
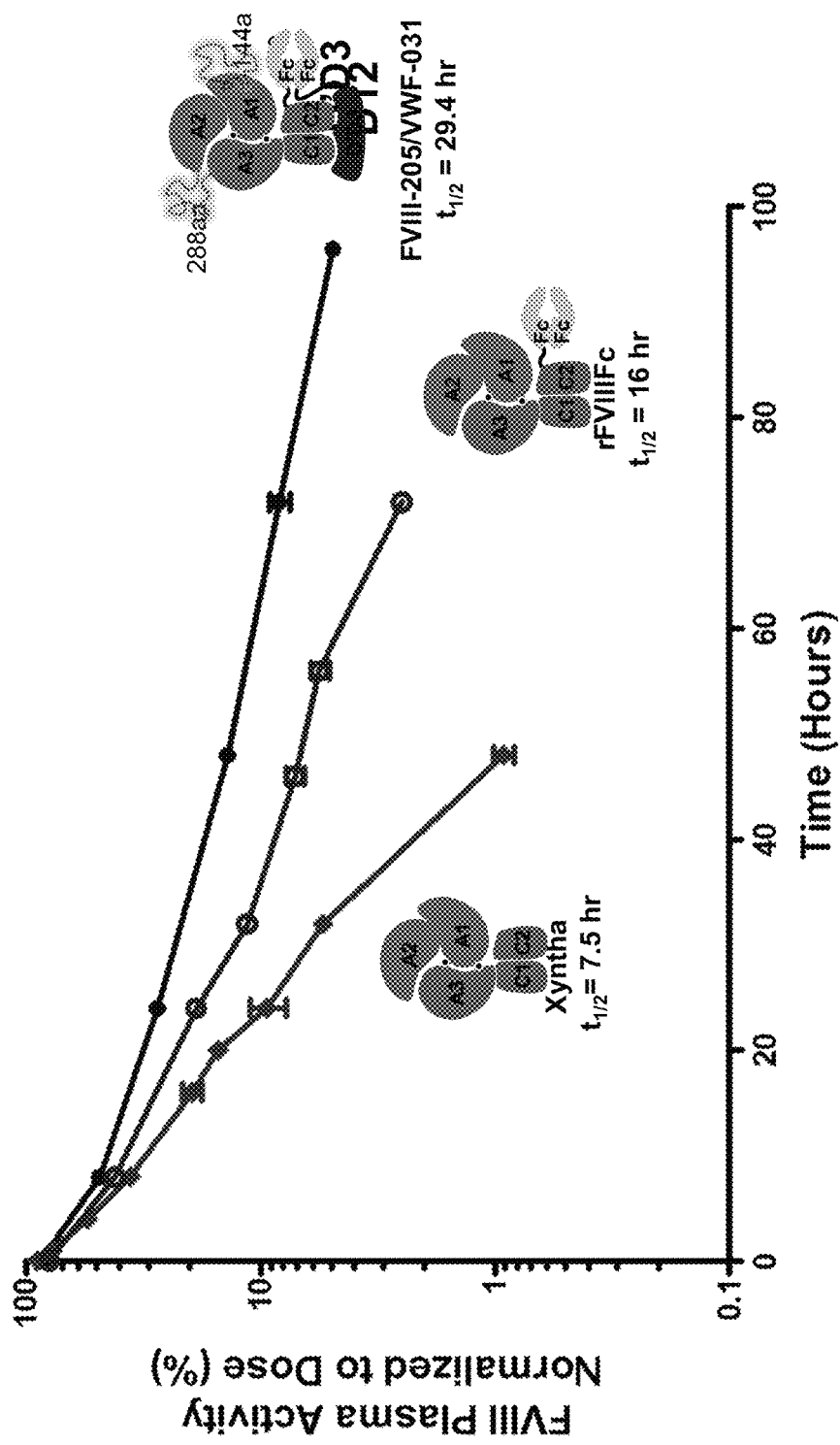

| DNA construct | Linker between VWF and Fc |
|---|---|
| FVIII-161 | 288AE XTEN + IS{5X(GGGGS)}LVPRGSGG (SEQ ID NO: 171) |
| D'D3= 1-477aa with C336A/C379A | | protein linked to the XTEN sequence. By preventing or inhibiting binding of endogenous VWF to the FVIII protein, which is a half-life limiting factor for FVIII, the VWF fragment can induce extension of half-life of the chimeric protein comprising a FVIII protein. The invention also includes nucleotides, vectors, host cells, methods of using the VWF fragment, or the chimeric proteins.

20 Claims, 21 Drawing Sheets

Specification includes a Sequence Listing.

Related U.S. Application Data

(60) Provisional application No. 61/670,401, filed on Jul. 11, 2012, provisional application No. 61/759,819, filed on Feb. 1, 2013, provisional application No. 61/801,504, filed on Mar. 15, 2013, provisional application No. 61/801,544, filed on Mar. 15, 2013, provisional application No. 61/827,158, filed on May 24, 2013, provisional application No. 61/840,811, filed on Jun. 28, 2013.

(51) Int. Cl.
*A61K 38/36* (2006.01)
*A61K 38/37* (2006.01)
*C07K 16/00* (2006.01)
*C12N 15/11* (2006.01)

(52) U.S. Cl.
CPC .............. *C07K 16/00* (2013.01); *C12N 15/11* (2013.01); *C07K 2319/00* (2013.01); *C07K 2319/30* (2013.01); *C07K 2319/31* (2013.01); *C07K 2319/35* (2013.01); *C07K 2319/50* (2013.01)

(58) Field of Classification Search
CPC ............ C07K 2319/00; C07K 2319/30; C07K 2319/31; C07K 2319/35; C07K 2319/50; A61P 43/00; A61P 7/04; C12N 15/11
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,713,339 A | 12/1987 | Levinson et al. |
| 4,757,006 A | 7/1988 | Toole et al. |
| 4,800,159 A | 1/1989 | Mullis et al. |
| 4,868,112 A | 9/1989 | Toole et al. |
| 4,965,188 A | 10/1990 | Mullis et al. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Ooyen et al. |
| 5,364,771 A | 11/1994 | Lollar et al. |
| 5,543,502 A | 8/1996 | Nordfang et al. |
| 5,595,886 A | 1/1997 | Chapman et al. |
| 5,610,278 A | 3/1997 | Nordfang et al. |
| 5,643,575 A | 7/1997 | Martinez et al. |
| 5,648,260 A | 7/1997 | Winter et al. |
| 5,658,570 A | 8/1997 | Newman et al. |
| 5,739,277 A | 4/1998 | Presta et al. |
| 5,789,203 A | 8/1998 | Chapman et al. |
| 5,834,250 A | 11/1998 | Wells et al. |
| 5,846,951 A | 12/1998 | Gregoriadis et al. |
| 5,859,204 A | 1/1999 | Lollar et al. |
| 5,869,046 A | 2/1999 | Presta et al. |
| 5,972,885 A | 10/1999 | Spira et al. |
| 5,981,216 A | 11/1999 | Kenten et al. |
| 6,030,613 A | 2/2000 | Blumberg et al. |
| 6,037,452 A | 3/2000 | Minamino et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward et al. |
| 6,316,226 B1 | 11/2001 | Van Ooyen et al. |
| 6,346,513 B1 | 2/2002 | Van Ooyen et al. |
| 6,376,463 B1 | 4/2002 | Lollar et al. |
| 6,458,563 B1 | 10/2002 | Lollar et al. |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta et al. |
| 6,818,439 B1 | 11/2004 | Jolly et al. |
| 6,821,505 B2 | 11/2004 | Ward et al. |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,199,223 B2 | 4/2007 | Bossard et al. |
| 7,211,559 B2 | 5/2007 | Saenko et al. |
| 7,317,091 B2 | 1/2008 | Lazar et al. |
| 7,348,004 B2 | 3/2008 | Peters et al. |
| 7,404,956 B2 | 7/2008 | Peters et al. |
| 7,566,701 B2 | 7/2009 | Diener et al. |
| 7,846,445 B2 | 12/2010 | Schellenberger et al. |
| 7,862,820 B2 | 1/2011 | Peters et al. |
| 10,138,291 B2 * | 11/2018 | Chhabra ................ A61K 38/37 |
| 2003/0069395 A1 | 4/2003 | Sato et al. |
| 2003/0235536 A1 | 12/2003 | Blumberg et al. |
| 2004/0101740 A1 | 5/2004 | Sanders et al. |
| 2005/0100990 A1 | 5/2005 | Saenko et al. |
| 2005/0147618 A1 | 7/2005 | Rivera et al. |
| 2006/0074199 A1 | 4/2006 | Hirata et al. |
| 2007/0191597 A1 | 8/2007 | Jain et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0146782 A1 | 6/2008 | Defrees et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0255040 A1 | 10/2008 | Defrees et al. |
| 2008/0261877 A1 | 10/2008 | Ballance et al. |
| 2009/0118185 A1 | 5/2009 | Fay et al. |
| 2009/0192076 A1 | 7/2009 | Matthiessen et al. |
| 2010/0120664 A1 | 5/2010 | Schulte et al. |
| 2010/0239554 A1 * | 9/2010 | Schellenberger ......... A61P 5/06 424/94.3 |
| 2010/0285021 A1 | 11/2010 | Jacquemin et al. |
| 2010/0292130 A1 | 11/2010 | Skerra et al. |
| 2010/0323956 A1 | 12/2010 | Schellenberger et al. |
| 2011/0046060 A1 * | 2/2011 | Schellenberger ......... A61P 7/02 514/13.7 |
| 2011/0046061 A1 * | 2/2011 | Schellenberger ......... A61P 7/04 514/13.7 |
| 2011/0077199 A1 | 3/2011 | Schellenberger et al. |
| 2011/0172146 A1 | 7/2011 | Schellenberger et al. |
| 2011/0183907 A1 * | 7/2011 | Weimer ................... A61P 7/04 514/14.1 |
| 2011/0287517 A1 | 11/2011 | Steward et al. |
| 2012/0121706 A1 | 5/2012 | Kuliopulos et al. |
| 2012/0178691 A1 | 7/2012 | Schellenberger et al. |
| 2012/0289468 A1 | 11/2012 | Barnett et al. |

(56) References Cited

U.S. PATENT DOCUMENTS

| | | |
|---|---|---|
| 2013/0017997 A1 | 1/2013 | Schellenberger et al. |
| 2013/0108629 A1 | 5/2013 | Dumont et al. |
| 2015/0023959 A1 | 1/2015 | Chhabra et al. |
| 2015/0266943 A1 | 9/2015 | Chhabra et al. |
| 2016/0229903 A1 | 8/2016 | Chhabra et al. |
| 2016/0251408 A1* | 9/2016 | Chhabra ............... A61P 19/00 514/14.1 |
| 2017/0073393 A1* | 3/2017 | Chhabra ............... A61P 19/00 |

FOREIGN PATENT DOCUMENTS

| | | | |
|---|---|---|---|
| WO | 8704187 A1 | 7/1987 | |
| WO | 8800831 A1 | 2/1988 | |
| WO | 8803558 A1 | 5/1988 | |
| WO | 8807089 A1 | 9/1988 | |
| WO | 8808035 A1 | 10/1988 | |
| WO | 9109122 A1 | 6/1991 | |
| WO | 9320093 A1 | 10/1993 | |
| WO | 9411503 A2 | 5/1994 | |
| WO | 9614339 A1 | 5/1996 | |
| WO | 9805787 A1 | 2/1998 | |
| WO | 9823289 A1 | 6/1998 | |
| WO | 9951642 A1 | 10/1999 | |
| WO | 9958572 A1 | 11/1999 | |
| WO | 0009560 A2 | 2/2000 | |
| WO | 0032767 A1 | 6/2000 | |
| WO | 0042072 A2 | 7/2000 | |
| WO | 0187922 A2 | 11/2001 | |
| WO | 0244215 A2 | 6/2002 | |
| WO | 02060919 A2 | 8/2002 | |
| WO | 03074569 A2 | 9/2003 | |
| WO | 03077834 A2 | 9/2003 | |
| WO | 2004016750 A2 | 2/2004 | |
| WO | 2004029207 A2 | 4/2004 | |
| WO | 2004035752 A2 | 4/2004 | |
| WO | 2004044859 A1 | 5/2004 | |
| WO | 2004063351 A2 | 7/2004 | |
| WO | 2004074455 A2 | 9/2004 | |
| WO | 2004099249 A2 | 11/2004 | |
| WO | 2005040217 A2 | 5/2005 | |
| WO | 2005047327 A2 | 5/2005 | |
| WO | 2005070963 A1 | 8/2005 | |
| WO | 2005077981 A2 | 8/2005 | |
| WO | 2005092925 A2 | 10/2005 | |
| WO | 2005123780 A2 | 12/2005 | |
| WO | 2006019447 A1 | 2/2006 | |
| WO | 2006047350 A2 | 5/2006 | |
| WO | 2006085967 A2 | 8/2006 | |
| WO | 2007021494 A2 | 2/2007 | |
| WO | 2007103515 A2 | 9/2007 | |
| WO | 2007144173 A1 | 12/2007 | |
| WO | 2008033413 A2 | 3/2008 | |
| WO | 2008057683 A2 | 5/2008 | |
| WO | 2008155134 A1 | 12/2008 | |
| WO | 2009023270 A3 | 2/2009 | |
| WO | 2009058322 A1 | 5/2009 | |
| WO | 2009062100 A1 | 5/2009 | |
| WO | 2009156137 A1 | 12/2009 | |
| WO | 2010060081 A1 | 5/2010 | |
| WO | 2010091122 A1 | 8/2010 | |
| WO | 2010144502 A2 | 12/2010 | |
| WO | 2010144508 A2 | 12/2010 | |
| WO | 2011020866 A2 | 2/2011 | |
| WO | 2011028228 A1 | 3/2011 | |
| WO | 2011028229 A1 | 3/2011 | |
| WO | 2011028344 A2 | 3/2011 | |
| WO | 2011060242 A2 | 5/2011 | |
| WO | WO-2011060242 A2 * | 5/2011 | ............... A61P 7/00 |
| WO | 2011069164 A2 | 6/2011 | |
| WO | WO-2011069164 A2 * | 6/2011 | ............ A61K 38/37 |
| WO | 2011101242 A2 | 8/2011 | |
| WO | 2011101284 A1 | 8/2011 | |
| WO | 2012006623 A1 | 1/2012 | |
| WO | 2012006633 A1 | 1/2012 | |
| WO | 2012006635 A1 | 1/2012 | |
| WO | 2013106787 A1 | 7/2013 | |
| WO | PCT/US2013/049989 | 7/2013 | |
| WO | 2013122617 A1 | 8/2013 | |
| WO | 2013123457 A1 | 8/2013 | |
| WO | 2014011819 A1 | 1/2014 | |
| WO | 2014210547 A1 | 12/2014 | |
| WO | 2014210558 A1 | 12/2014 | |
| WO | 2015106052 A1 | 7/2015 | |

OTHER PUBLICATIONS

Yoon et al., NF-kB and STAT3 cooperatively induce IL6 in starved cancer cells, Oncogene, vol. 31:3467-3481 (published online Nov. 21, 2011) (Year: 2011).*

Healey, J.F., et al., "The cDNA and Derived Amino Acid Sequence of Porcine Factor VIII," Blood 88(11):4209-4214, The American Society of Hematology, United States (1996).

Ho, S.N., et al., "Site-Directed Mutagenesis by Overlap Extension Using the Polymerase Chain Reaction," Gene 77 (1):51-59, Elsevier Science Publishers B.V., Netherlands (1989).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

Horton, R.M., et al., "Gene Splicing by Overlap Extension," Methods in Enzymology 217:270-279, Academic Press, United States (1993).

International Search Report and Written Opinion for International Application No. PCT/US2015/010738, ISA/US, Alexandria, Virginia, dated May 15, 2015, 4 pages.

International Search Report and Written Opinion for International Application No. PCT/US2013/021330, United States Patent Office, Alexandria, Virgina, dated Apr. 29, 2013, 4 pages.

International Search Report and Written Opinion for International Patent Application No. PCT/US2013/049989, United States Patent Office, Alexandria, Virgina, dated Dec. 16, 2013, 5 pages.

International Search Report and Written Opinion for International Patent Application No. PCT/US2014/044731, United States Patent Office, Alexandria, Virginia, dated Nov. 4, 2014, 4 pages.

International Search Report and Written Opinion for International Patent Application No. PCT/US2014/044718, United States Patent Office, Alexandria, Virginia, dated Nov. 4, 2014, 10 pages.

Srael, EJ., et al., "Expression of the neonatal Fc receptor, FcRn, on human intestinal epithelial cells," Immunology, 92(1):69-74, Blackwell Sciences, England (1997).

Kasuda, S. et al., "Establishment of Embryonic Stem Cells Secreting Human Factor VIII for Cell-Based Treatment of Hemophilia A," Journal of Thrombosis and Haemostasis 6(8):1352-1359, International Society on Thrombosis and Haemostasis, England (2008).

Kobayashi, N. et al., "FcRn-Mediated Transcytosis of Immunoglobulin G in Human Renal Proximal Tubular Epithelial Cells," American Journal of Physiology 282(2):F358-F365, American Physiological Society, United States (2002).

Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B. V., Netherlands (1998).

Langner, K-D., et al., "Synthesis of Biologically Active Deletion Mutants of Human Factor VIII:C," Behring Institute Mitteilungen 82:16-25, Behnngwerke AG, Germany (1988).

Larrick, J.W., et al., "Rapid Cloning Rearranged Immunoglobulin Genes form Human Hybridoma Cells using Mixed Primers and the Polymerase Chain Reaction," Biochemical and Biophysical Research Communications 160 (3):1250-1256, Academic Press, United States (1989).

Lee, M.T., "Ch. 12: Disorders of Coagulation" in Pediatric Hematology Secrets, Weiner M.A. and Cario, M.S. eds., pp. 47-52, Hanley & Belfus, United States (2001).

(56) References Cited

OTHER PUBLICATIONS

Lenting, P.J., et al., "Clearance Mechanisms of Von Willebrand Factor and Factor VIII," Journal of Thrombosis and Heamostasis 5(7):1353-1360, International Society on Thrombosis and Haemostasis, England (2007).
Lenting, P.J., et al., "The Life Cycle of Coagulation Factor VIII in View of its Structure and Function," Blood, 92 (11):3983-3996, American Society of Hematology, United States (1998).
Leyte, A. et al., "Sulfation of Tyr1680 of Human Blood Coagulation Factor VIII is Essential for the Interaction of Factor VIII with Von Willebrand factor," The Journal of Biological Chemistry 266(2):740-746, The American Society for Biochemistry and Molecular Biology, Inc., United States (1991).
Lillicrap, D., "Extending Half-life in Coagulation Factors; Where Do We Stand?," Thrombosis Research, 122 Suppl 4:S2-58, Pergamon Press, United States (2008).
Liu, T. et al., "Evaluation of Peg-FVIII Molecules with Prolonged Half-lives in a Murine FVIII-Dependent Bleeding Model," Journal of Thrombosis and Haemostasis 5(Suppl. 2): Abstract P-M-035, Abstracts form 2007 ISTH Congress, International Society on Thrombosis and Haemostasis, United States (2007).
Liu, T. et al., "Recombinant FVIII Fc Fusion Protein is Fully Active in Treating Acute Injury and Deomstrates Prolonged Prophylactic Efficacy in Hemophilia a Mice," Journal of Thrombosis and Heamostasis 9(Suppl. 2):561, Abstract P-WE-131, Abstracts from 2011 ISTH Congress, International Society on Thrombosis and Heamostasis, United States (Jul. 27, 2011).
Logan, J. et al., "Adenovirus Tripartite Leader Sequence Enhances Translation of mRNAs Late After Infection," Proceedings of the National Academy of Sciences USA 81(12):3655-3659, National Academy of Sciences, United States (1984).
Mackett, M. et al., "General Method for Production and Selection of Infectious Vaccinia Virus Recombinants Expressing Foreign Genes," Journal of Virology 49(3):857-864, American Society for Microbiology, United States (1984).
Mackett, M. et al., "Vaccinia Virus: A Selectable Eukaryotic Cloning and Expression Vector," Proceedings of the National Academy of Sciences USA 79(23):7415-7419, National Academy of Sciences, United States (1982).
McCue, J.T. et al., "Application of a Novel Affinity Adsorbent for the Capture and Purification of Recombinant Factor VIII Compounds," Journal of Chromatography A 1216(45):7824-7830, Elsevier, Netherlands (2009).
Mei, B. et al., "Expression of Human Coagulation Factor VIII in a Human Hybrid Cell Line, HKB11," Molecular Biotechnology 34(2):165-178, Humama Press Inc., United States (2006).
Meulien, P. et al., "A New Recombinant Procoagulant Protein Derived from the cDNA Encoding Human Factor VIII," Protein Engineering 2(4):301-306, IRL Press Ltd., England (1988).
Miao, H.Z., et al., :Bioengineering of Coagulation Factor VIII for Improved Secretion, Blood 103(9):3412-3419, The American Society of Hematology, United States (2004).
Morpurgo, M. et al., "Covalent Modification of Mushroom Tyrosinase with Different Amphiphic Polymers for Pharmaceutical and Biocatalysis Applications," Applied Biochemistry and Biotechnology 56(1):59-72, Humana Press, Inc., United States (1996).
Mount, J.D. et al., "Sustained Phenotypic Correction of Hemophilia B dogs with a Factor IX Null Mutation by Liver-Directed Gene Therapy," Blood 99(8)::2670-2676, The American Society of Hematology, United States (2002).
National Heart Lung and Blood Institute, The Diagnosis, Evaluation and Management of von Willebrand Disease Scientific Overview, accessed at http://nhlbi.nih.gov/guidelines/vwd/2scientificoverview.htm, accessed on Oct. 22, 2011.
Neumann, E., et al., "Gene Transfer into Mouse Lyoma Cells By Electroporation in High Electric Fields," The EMBO Journal 1(7):841-845, IRL Press Limited, England (1982).
Ngo, J.C. et al., "Crystal Structure of Human Factor VIII: implications for the Formation of the Factor IXa-factor VIIIa Complex," Structure 16(4):597-606, Elsevier Ltd., United States (2008).

Panicali, D., et al., "Construction of Poxviruses as Cloning Vectors: Insertion of the Thymidine Kinase Gene from Herpes Simplex Virus into the DNA of Infectious Vaccinia Virus," Proceedings of the National Academy of Sciences of the United States of America 79(16):4927-4931, The National Academy of Sciences of the United States (1982).
Peters, R.T., et al., "Biochemical and Functional Characterization of a Recombinant Monomeric Factor VIII-Fc Fusion Protein," Journal of Thrombosis and Haemostasis 11(1):132-141, Blackwell Pub, England (Jan. 2013).
Pipe, S.W., et al., "Functional Factor VIII made with Von Willebrand Factor at High Levels in Transgenic Milk," Journal of Thrombosis and Haemostasis 9(11):2235-2242, International Society on Thrombosis and Haemostasis, England (Nov. 2011).
Powell, J.S., et al., "Safety and Prolonged Activity of Recombinant Factor VIII Fc Fusion Protein in Hemophilia a Patients," Blood 119(13):3031-3037, The American Society of Hematology, United States (Mar. 29, 2012).
Roth, J. et al., "From Microbes to Man," in Polysialic Acid, Roth J. Rutishauser U., Troy F.A., eds., pp. 335-348, Birkhauser Verlag, Basel, Switzerland (1993).
Routledge, E.G., et al., "The Effect of Aglycosylation on the Immunogenicity of a Humanized Therapeutic CD3 Monoclonal Antibody," Transplantation 60(8):847-853, Williams & wilkins, United States (1995).
Ruberti, F. et al., "The Use of the RACE Method to Clone Hybridoma cDNA When V Region Primers Fail," Journal of Immunological Methods 173(1):33-39, Elsevier, United States (1994).
Ruther U. and Muller-Hill, B., "Easy Identification of cDNA Clones," The EMBO Journal 2(10):1791-1794, IRL Press Ltd, England (1983).
Saenko, E.L., et al., "A Role for the C2 Domain of Factor VIII in Binding to Von Willebrand Factor," Journal of Biological Chemistry 269(15):11601-11605, American Society for Biochemistry and Molecular Biology, United States (1994).
Sambrook, J., et al., "Molecular Cloning: A Laboratory Manual," Second Edition, Cold Spring Harbor Laboratory Press, United States (1989).
Sarver, N., et al., "Stable Expression of Recombinant Factor VIII Molecules Using a Bovine Papillomavirus Vector," DNA 6(6):553-564, Mary Ann Liebert, Inc., United States (1987).
Schellenberger, V., et al., "A Recombinant Polypeptide Extends the in Vivo Half-Life of Peptides and Proteins in a Tunable Manner," Nature Biotechnology 27(12):1186-1190, Nature America, Inc. United States (2009).
Schlapschy, M., et al., "Fusion of a Recombinant Antibody Fragment with a Homo-amino-acid Polymer: Effect on Biophysical Properties and Prolonged Plasma Half-Life," Protein Engineering Design and Selection 20(6):273-284, Oxford University Press, England (2007).
Shen, B.W., et al., "The Tertiary Structure and Domain Organization of Coagulation Factor VIII," Blood 111 (3):1240-1247, The American Society of Hematology, United States (2008).
Shields, R.L., et al., "High Resolution Mapping of the Binding Site on Human IgG1 for Fc gamma RI, Fc gamma RII, 7c gamma RIII, and FcRn and Design of IgG1 Variants with Improved Binding to the Fc gamma R," The Journal of Biological Chemistry 276(9):6591-6604, American Society for Biochemistry and Molecular Biology, United States (2001).
Simonsen, C.C., et al., "Isolation and Expression of an Altered Mouse Dihydrofolate Reductase cDNA," Proceedings of the National Academy of Sceinces 80(9):2495-2499, National Academy of Sciences, United States (1983).
Nieman, M.T., et al., "Interaction of thrombin with PAR1 and PAR4 at the thrombin cleavage site," Biochemsitry 46 (29):8603-8610, American Chemistry Society, United States (2007).
Office Action dated Dec. 15, 2017, in the U.S. Appl. No. 14/894,108, inventor Ekta Seth Chhabra, filed May 3, 2016.
Office Action dated Jan. 26, 2018, in U.S. Appl. No. 14/895,264 inventor Ekta Seth Chhabra, filed Dec. 2, 2015.
Office Action dated Apr. 30, 2018, in U.S. Appl. No. 14/379,196 inventor Ekta Seth Chhabra, filed Aug. 15, 2014.

(56) References Cited

OTHER PUBLICATIONS

Li, X. et al., "The physical exchange of factor VIII (FVIII) between von Willebrand factor and Activated Platelets and the Effect of the FVIII B-domain on Platelet Binding," Biochemistry 36:10760-10767, Portland Press, United States (1997).

Woof, J.M., et al, "Human antibody-FC receptor interactions illuminated by crystal structures," Nat. Rev. Immunology, 4(2):89-99, Nature Publishing Group, United States (2004).

Office Action dated Mar. 16, 2018, in U.S. Appl. No. 14/379,192 inventors Schellenberger et al., filed Feb. 20, 2015.

Office Action dated Jun. 25, 2018, in U.S. Appl. No. 14/371,948 inventor Ekta Seth Chhabra, filed Jul. 11, 2014.

Alvarez, P. et al., "Improving Protein Pharmacokinetics by genetics Fusion to Simple Amino Acid Sequences," The Journal of Biological Chemistry 279(5):3375-3381, American Society for Biochemistry and Molecular Biology, United States (2003).

Proft, T., "Sortase-mediated protein ligation: an emerginG biotechnology tool for protein modification and immobilization," Biotechnology Letters 32:1-10, Springer Science+Business Medica B.V., Netherlands (Sep. 2009).

Counts, R.B., et al., "Disulfide Bonds and the Quaternary Structure of Factor VIII/von Willebrand Factor," J. Clin. Invest. 62(3):702-709, The American Society for Clinical Investigation, Inc (1978).

Nogami, K. et al., "A novel mechanism of factor VIII protection by von Willebrand factor from activated protein C-Catalyzed inactivation," Blood 99(11):3993-98, American Society of Hematology (2002).

Nogami, K. et al., "Relationship between the binding sites for von Willebrand factor, phospholipid and human factor VIII C2 inhibitor alloantibodies within the factor VIII C2 domain," Int J. Hematol. 85(4):371-22 Springer (2007).

Office Action dated Sep. 25, 2017, in U.S. Appl. No. 14/379,196, Kulman, J. et al., filed Aug. 15, 2014, 14 pages.

Office Action dated May 23, 2017 in U.S. Appl. No. 14/894,108, inventor Ekta Seth Chhabra, filed May 3, 2016.

Office Action dated May 17, 2017 in U.S. Appl. No. 14/371,948, inventor Ekta Seth Chhabra, filed Jul. 11, 2014.

Engels et al., "Gene Synthesis," Angewandte Chemie International Edition 28(6):716-734, VCH Verlagsgesellschaft mbH, Germany (1989).

Pool, J.G. et al., "Ineffectiveness of intramuscularly injected Factor 8 concentrated in two hemophilic patients," The New England Journal of Medicine 275(10):547-548, Massachusetts Medical Society, United States (1996).

Office Action dated Sep. 27, 2017, in U.S. Appl. No. 14/379,192, inventor Ekta Seth Chhabra, filed Feb. 20, 2015.

Melou, B. et al., "Complete Amino Acid Sequence of Human Serum Albumin," FEBS LETTER 58(1):134-137, John Wiley & Sons, United States (1975).

Office Action dated May 30, 2017, in U.S. Appl. No. 14/379,192, inventor Ekta Seth Chhabra, filed Feb. 20, 2015.

Office Action dated Nov. 1, 2016, in U.S. Appl. No. 14/379,192, inventor Ekta Seth Chhabra, filed Feb. 20, 2015.

Heinz, S. et al., "Factor VIII-eGFP fusion proteins with preserved functional activity for the analysis of the early secretory pathway of factor VIII," Thromb. Heamost, 102:925-935, Wiley-Blackwell, United States (2009).

Armour, K.L., et al., Recombinant Human IgG Molecules Lacking Fc Gamma Receptor I Binding and Monocyte Triggering Activities, European Journal of Immunology 29(8):2613-2624, Wiley-VCH, Germany (1999).

Arnau, J., et al., "Current strategies for the Use of Affinity Tags and Tag Removal for the Purification of Recombinant Proteins," Protein Expression and Purification 48(1):1-13, Elsevier Inc., United States (2006).

Benhar, I. and Pastan, I., "Cloning Expression and Characterization of the Fv Fragments of the Anti-Carbohydrate mAbs B1 and B5 as Single-Chain Immunotoxins," Protein Engineering Design and Selection 7(11):1509-1515, Oxford University Press, England (1994).

Burmeister, W.P., et al., "Crystal Structure of the Complex of Rat Neonatal Fc Receptor with Fc," Nature 372 (6504):379-383, Nature Publishing Group, England (1994).

Caliceti, P., et al., "Biopharmaceutical Properties of Uricase Conjugated to Neutral and Amphiphilic Polymers," Bioconjugate Chemistry 10(4):638-646, American Chemical Society, United States (1999).

Cameron, C., et al., "The Canine Factor VIII cDNA and 5'Flanking Sequence," Thrombosis and Haemostasis 79 (2):317-322, Schattauer, Germany (1998).

Capon, D.J., et al., Designing CD4 Immunoadhesins for AIDS Therapy,: Nature 337(6207):525-531, Nature Publishing Group, England (1989).

Cho, J.W. and Troy, F.A., III "Polysialic Acid Engineering: Synthesis of Polysialylated Neoglycosphingolipids by Using the Polysialyltransferase from Neuroinvasive *Escherichia coli* K1," Proceedings of the National Academy of Sciences USA 91(24):11427-11431, National Academy of Sciences, United States (1994).

Delgado, C. et al., "The Uses and Properties of PEG-Linked Proteins," Critical Reviews in Therapeutic Drug Carrier Systems 9(3-4):249-304, CRC Press, Inc., United States (1992).

Dumont, J.A., et al., "Prolonged Activity of a Recombinant Factor VIII-Fc Fusion Protein in Hemophilia A Mice and Dogs," Blood 119(13):3024-3030, The American Society of Hematology, United States (Mar. 29, 2012).

Eaton, D.L., et al., "Construction and Characterization of an Active Factor VIII Variant Lacking the Central One-Third of the Molecule," Biochemistry 25(26):8343-8347, American Chemical Society, United States (1986).

Friend, P.J., et al., "Phase 1 Study of an Engineered Aglycosylated Humanized CD3 Antibody in Renal Transplant Rejection," Transplantation 68(11):1632-1637, Lippincott Williams & Wilkins, Inc., United States (1999).

GenBank, "*Homo sapiens* Transferrin (TF) mRNA," Accession No. NM001063.3 published on May 25, 2014, accessed at http://www.ncbi.nlm.nih.gov/nuccore/NM_001063, accessed on Sep. 24, 2014, 5 pages.

GenBank, "*Homo sapiens* Transferrin (TF) mRNA," Accession No. XM002793 published on May 13, 2002, accessed at http://www.ncbi.nlm.nih.gov/nuccore/XM_002793.7?report=genbank, accessed on Sep. 24, 2014, 2 pages.

GenBank, "*Homo sapiens* Transferrin (TF) mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.

GenBank, "*Homo sapiens* Transferrin (TF) mRNA," Accession No. XM039845 published on Jul. 16, 2001, accessed at http://www.ncbi.nlm.nih.gov/nuccore/XM_039845.1?report=genbank, accessed on Sep. 24, 2014, 2 pages.

GenBank, "*Homo sapiens* von Willbrand factor (VWF), mRNA," NCBI Reference No. NM_000552.3, accessed at http://www.ncbi.nlm.nih.gov/nuccore/NM_000552_3, accessed on Mar. 29, 2016, 10 pages.

GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.

GenBank, "Transferrin [human, liver, mRNA, 2347 nt" Accession No. S95936.1, published on May 7, 1993, accessed at http://www.ncbi.nlm.nih.gov/nuccore/S95936, accessed on Sep. 24, 2014, 2 pages.

Genbank, "transferrin precursor [*Homo sapiens*]" Accession No. AAA61140.1, accessed at http://www.ncbi.nlm.nih.gov/protein/AAA61140, accessed on Mar. 29, 2016, 3 pages.

Genbank, "Von Willebrand factor preprorotein [*Homo sapiens*]," NCBI Reference Sequence: NP_000543.2, accessed at http://ncbi.nlm.nih.gov/protein/NP_000543.2, accessed on Mar. 29, 2016, 6 pages.

Gitschier, J. et al., "Characterization of the Human Factor VIII Gene," Nature 312(5992):326-330, Nature Publishing Group, England (1984).

Goudemand, J. et al., "Pharmacokinetic Studies on Wilfactin, a Von Willebrand Factor Concentrate with a Low Factor VIII Content

(56) References Cited

OTHER PUBLICATIONS

Treated with Three Virus-inactivation/removal Methods," Journal of Thrombosis and Haemostasis 3 (10):2219-2227, Blackwell Publishers, England (2005).

Graw, J. et al., "Haemophilia A: From Mutation Analysis to New Therapies," Nature Reviews, Genetics 6(6):488-501, Nature Publishing Group, England (2005).

Smith, G.E., et al., "Molecular Engineering of the Autographa California Nuclear Polyhedrosis Virus Genome: Deletion Mutations Within the Polyhedrin Gene," Journal of Virology 46(2):584-593 American Society for Microbiology, United States (1983).

Smith, T.F. and Waterman, M.S, "Comparison of Biosequences," Advances in Applied Mathematics 2(4):482-489, Academic Press, Inc., United States (1981).

Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).

Story, C.M., et al., "A Major Histocompatibility Complex Class I-Like Fc Receptor Cloned from Human Placenta: Possible Role in Transfer of Immunoglobulin G from Mother to Fertus," The Journal of Experimental Medicine 180 (6):2377-2381, The Rockefeller University Press, United States (1994).

Toole, J.J., et al., "A Large Region (about 95 kDa) of Human Factor VIII is Dispensable for in vitro Procoagulant Activity," Proceedings of the National Academy of Sciences USA 83(16):5939-5942, National Academy of Sciences, United States (1986).

Toole, J.J., et al., "Molecular Cloning of a cDNA Encoding Human Antihaemophilic Factor," Nature 312 (5992):342-347, Nature Publishing Group, England (1984).

Vehar, G.A., et al., "Structure of Human Factor VIII," Nature 312(5992):337-342, Nature Publishing Group. England (1984).

Vorobjev, P.E., et al., "Oligonucleotide Conjugated to Linear and Branched High Molecular Weight Polyethylene Glycol as Substrates for RNase H.," Nucleosides & Nucleotides 18(11-12):2745-2750, Marcel Dekker, Inc., United States (1999).

Ward., E.S., and Ghetie, V., "The Effector Functions of Immunoglobulins: Implications for Therapy," Therapeutic Immunology 2(2):77-94, Blackwell Science Ltd., England (1995).

Weidler, B. et al., "Pharmakokinetische Merkmale als Kristerien fur den klinischen Einsatz von Hydroxyethylstarke," Arzneimittel-Forschung 41(5):494-498, Editio Cantor, Germany (1991).

Wigler, M., et al., "Biochemical Transfer of Single-Copy Eucaryotic Genes Using Total Cellular DNA as Donor," Cell 14(3):725-731, Cell Press, United States (1978).

Zhou, Y.F., et al., "Sequence and Structure Relationships within von Willebrand Factor," Blood 120(2):449-458, American Society of Hematology, United States (Jul. 12, 2012).

Co-pending U.S. Appl. No. 15/110,673, inventors Chhabra, E.S. et al., filed Jan. 9, 2015 (Publication US 2017-0073393 A1, Publication Date Mar. 16, 2017).

Dennis, M.S., et al. "Albumin Binding as a General Strategy for Improving the Pharmacokinetics of Proteins," The Journal of Biological Chemistry 277(38):35035-35043, American Society for Biochemistry and Molecular Biology, United States (2002).

U.S. Appl. No. 14/413,765 2015/0266943 U.S. Pat. No. 10,138,291, filed Jan. 9, 2015, Sep. 24, 2015, Nov. 27, 2018, Ekta Seth Chhabra.

U.S. Appl. No. 14/894,108 2016/0251408, filed May 3, 2016 Sep. 1, 2016, Ekta Seth Chhabra.

U.S. Appl. No. 14/371,947 2015/0023959, filed Jul. 11, 2014 Jan. 22, 2015, Ekta Seth Chhabra.

U.S. Appl. No. 16/357,189, filed Mar. 18, 2019, Ekta Seth Chhabra.

U.S. Appl. No. 14/895,264 2016/0229903, filed Dec. 2, 2015 Aug. 11, 2016, Ekta Seth Chhabra.

U.S. Appl. No. 15/110,673 2017/0073393, filed Jul. 8, 2016, Mar. 16, 2017, Ekta Seth Chhabra.

Agersoe et al., "Prolonged effect of N8-Gp in haemophilia A dogs supports less frequent dosing", Journal of Thrombosis and Haemostasis 9, Suppl. 2, Abstract P-MO-181, Abstracts from 2011 ISTH Congress, International Society on Thrombosis and Haemostasis, USA, Jul. 31, 2011.

Wood et al., "Expression of active human factor VIII from recombinant DNA clones", Nature, 1984, vol. 312, No. 22, pp. 330-337.

Thermo Scientific, "Instructions: Imidoester Crosslinkers: DMA, DMP, DMS, DTBP", obtained from url: https://tools.thermofisher.com/content/sfs/manuals/MAN0011314_ImidoesterCRsLnk_DMA_DMP_DMS_DTBP_UG.pdf, 2012, 2 pages.

* cited by examiner

FIG. 1A
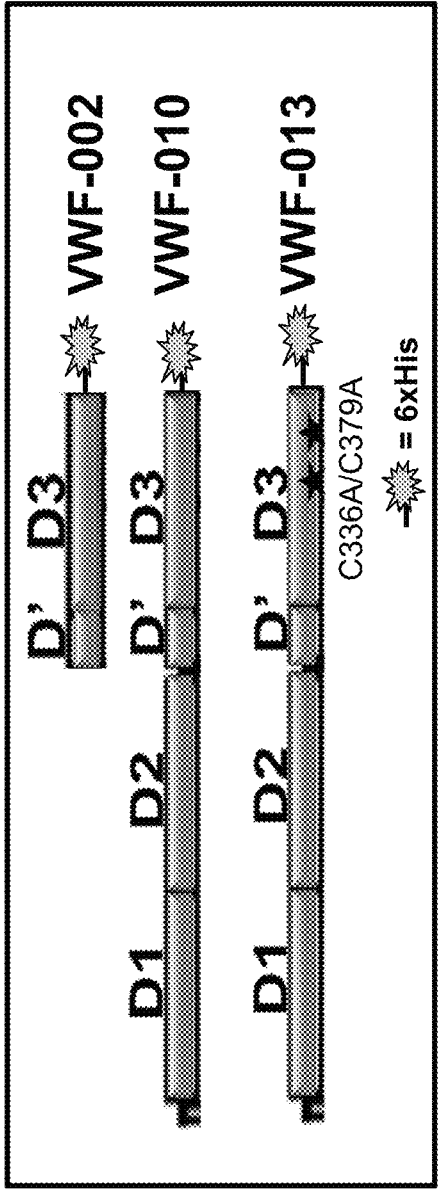
FIG. 1B
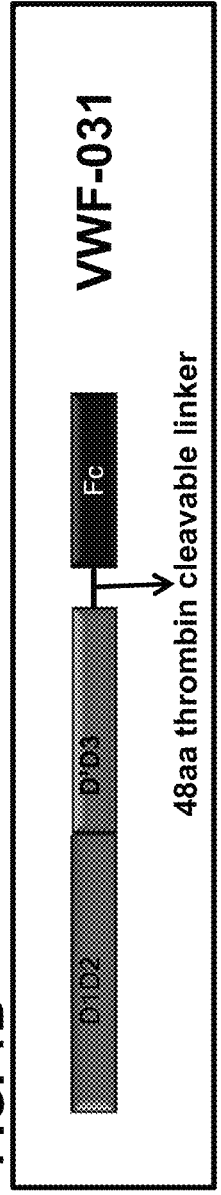
FIG. 1C
VWF-025: D1D2D'D3 codon sequence in pLIVE vector
VWF-029: D1D2D'D3C$_{336A/C379A}$ in pLIVE vector

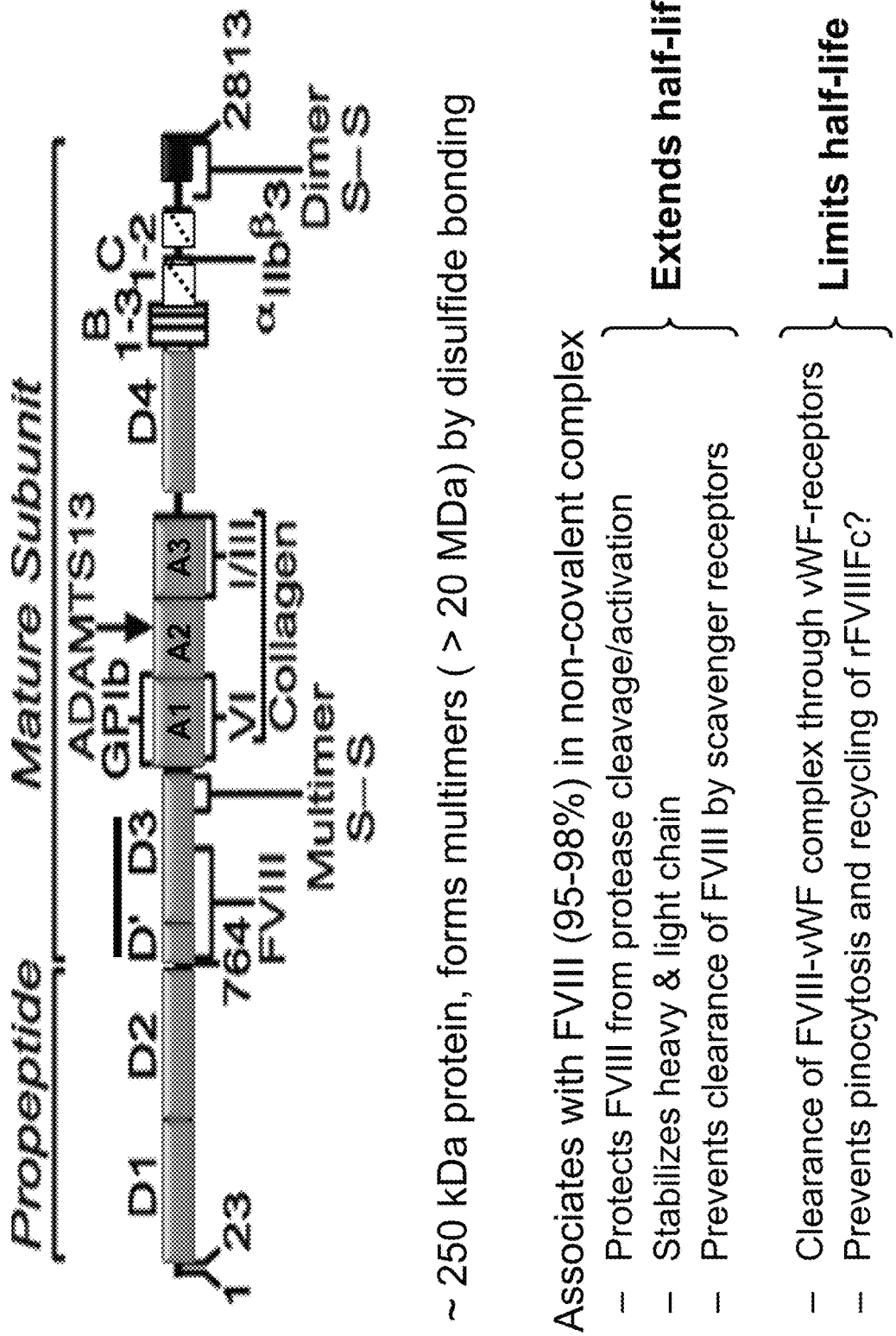
FIG. 1D. Von Willebrand Factor

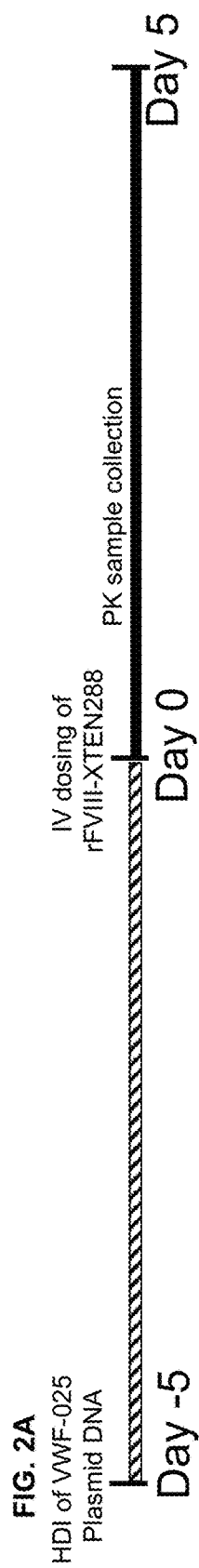
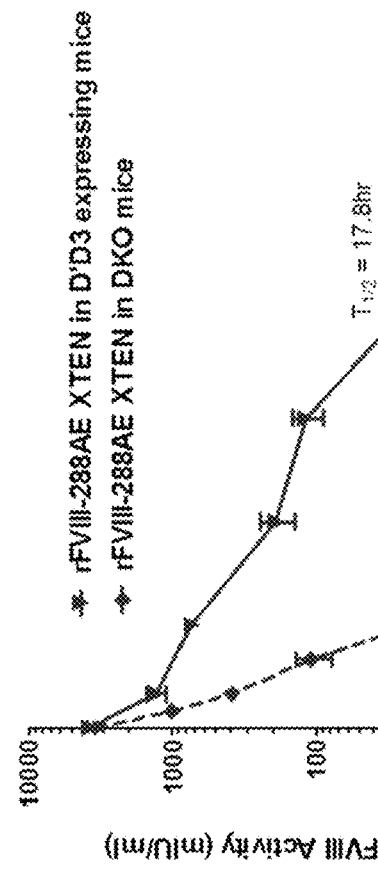
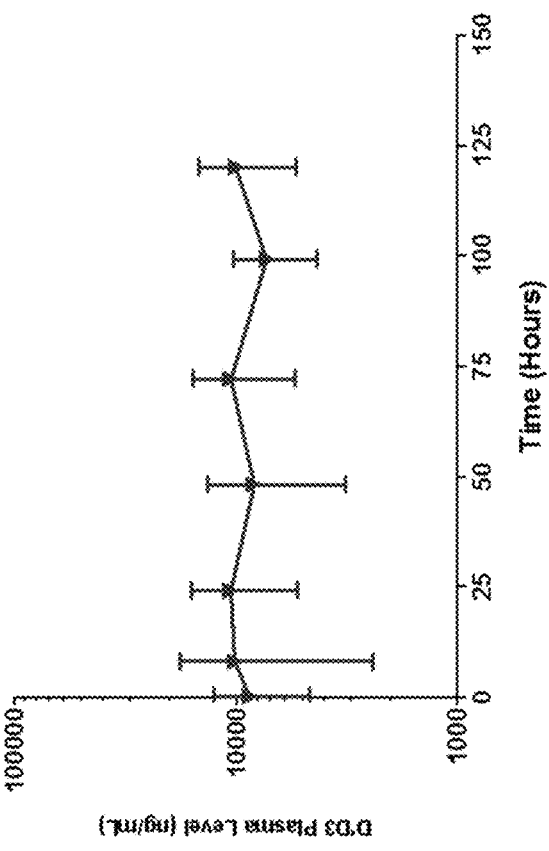
FIG. 2A
HDI of VWF-025 Plasmid DNA
IV dosing of rFVIII-XTEN288
PK sample collection
Day -5 | Day 0 | Day 5
FIG. 2B
FIG. 2C
5 fold additional half-life extension of FVIII-XTEN from VWF D'D3 fragment

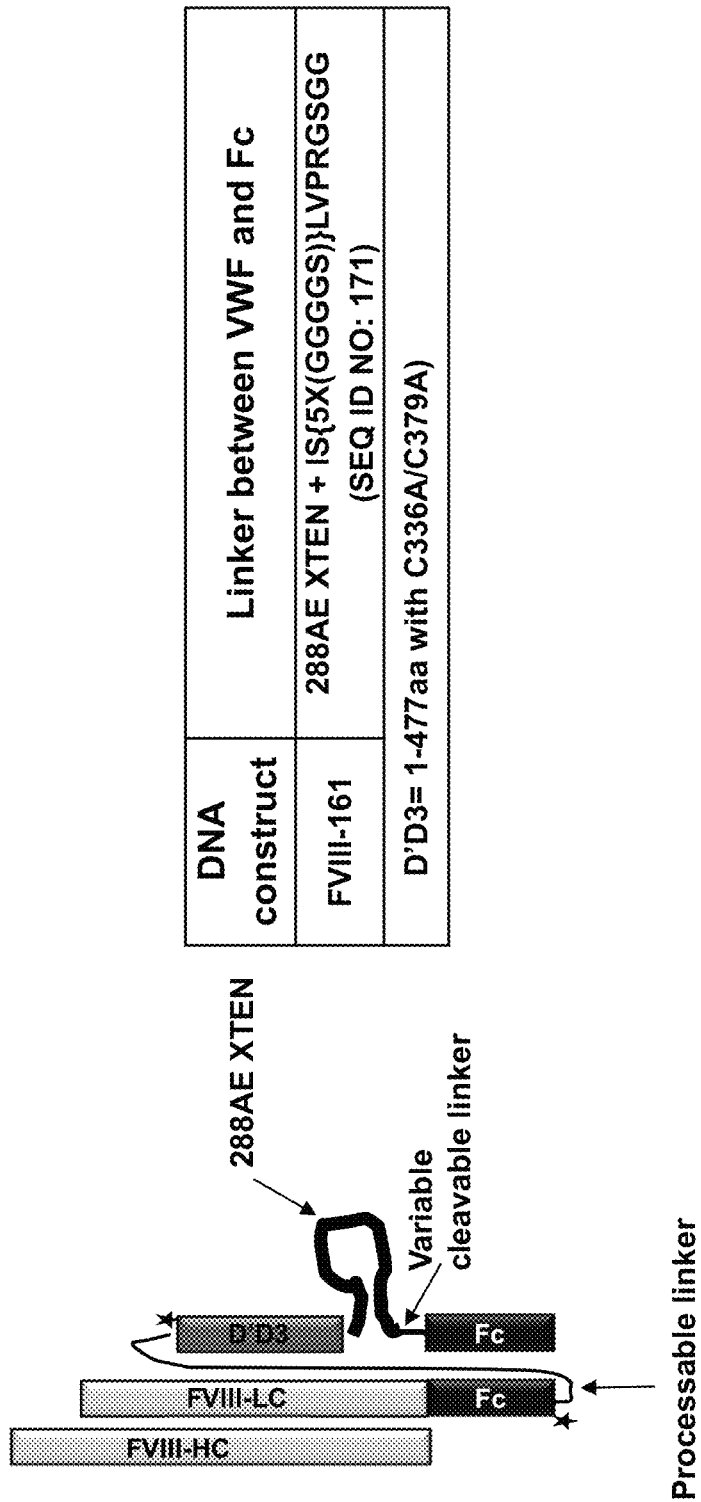
FIG. 3: FVIIIFC/VWF heterodimer Constructs (variable linker)

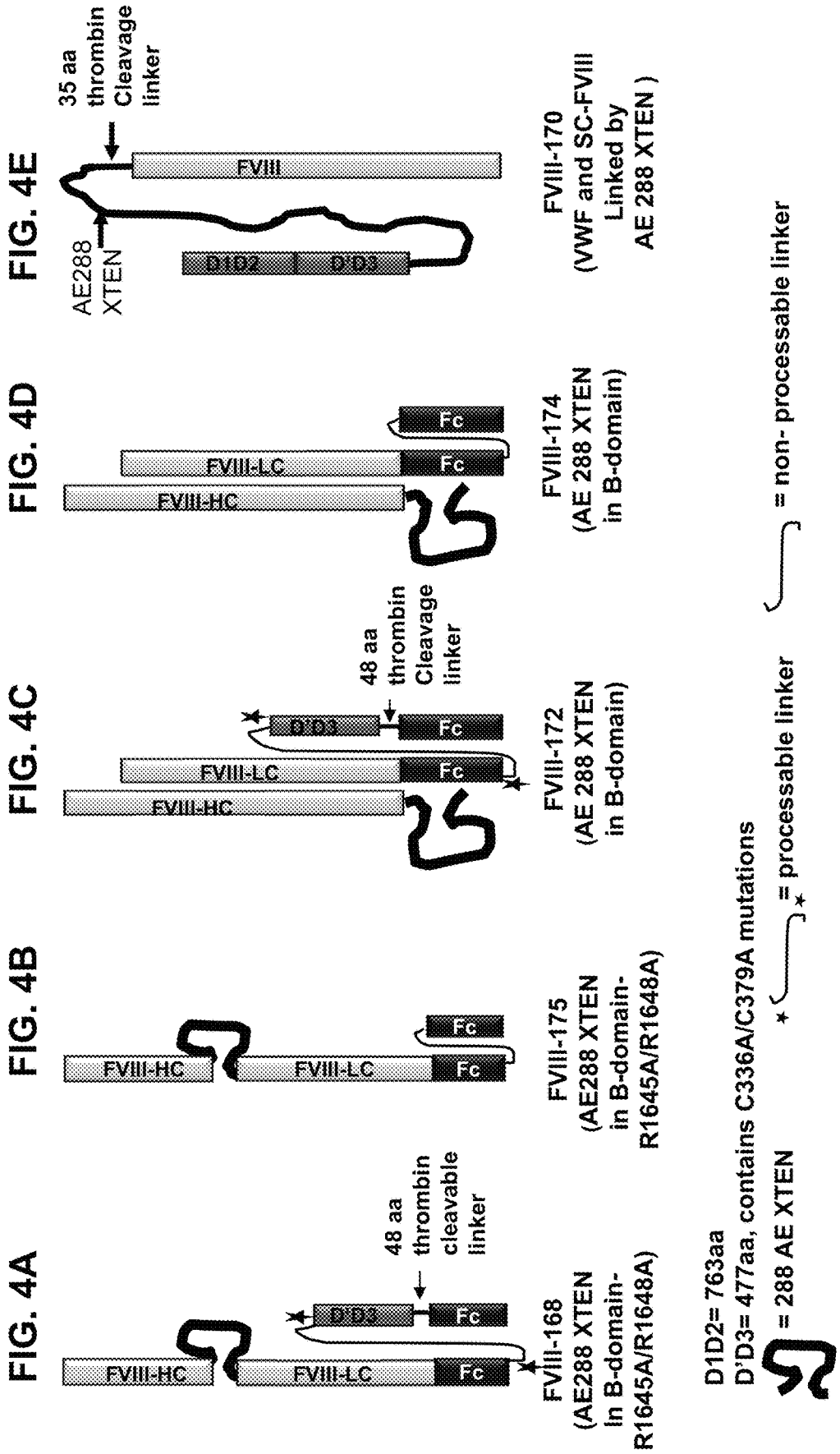

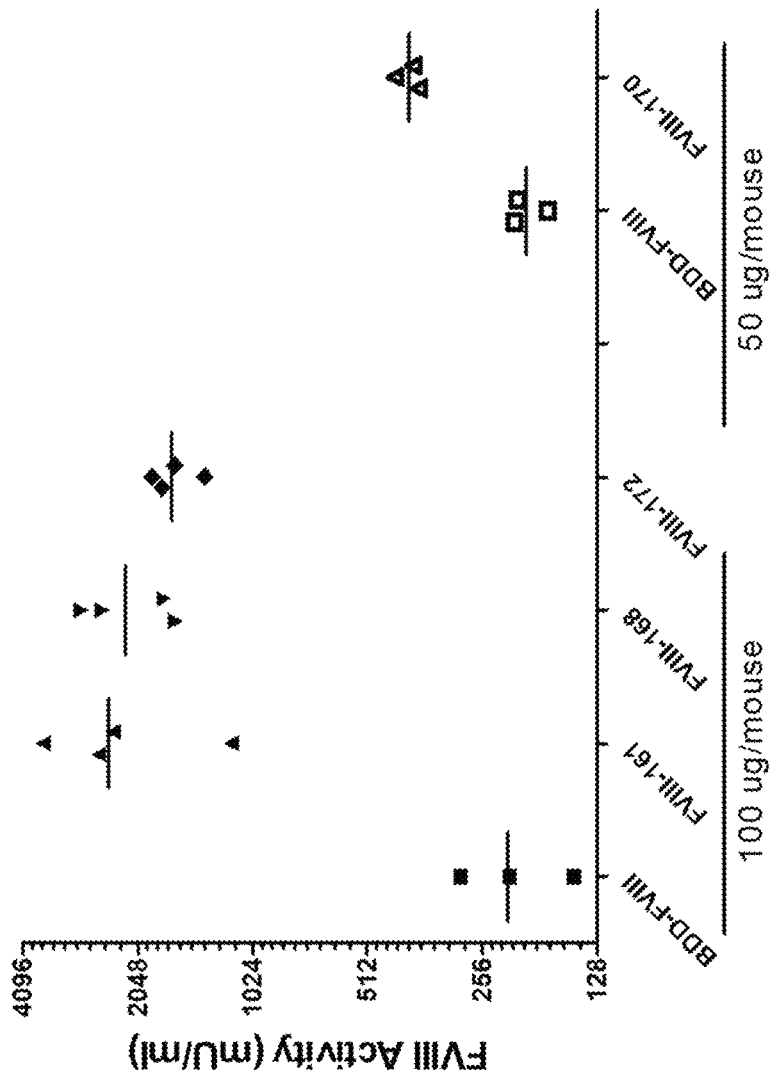
FIG. 5: XTEN insertion improves the PK of FVIII/VWF heterodimers

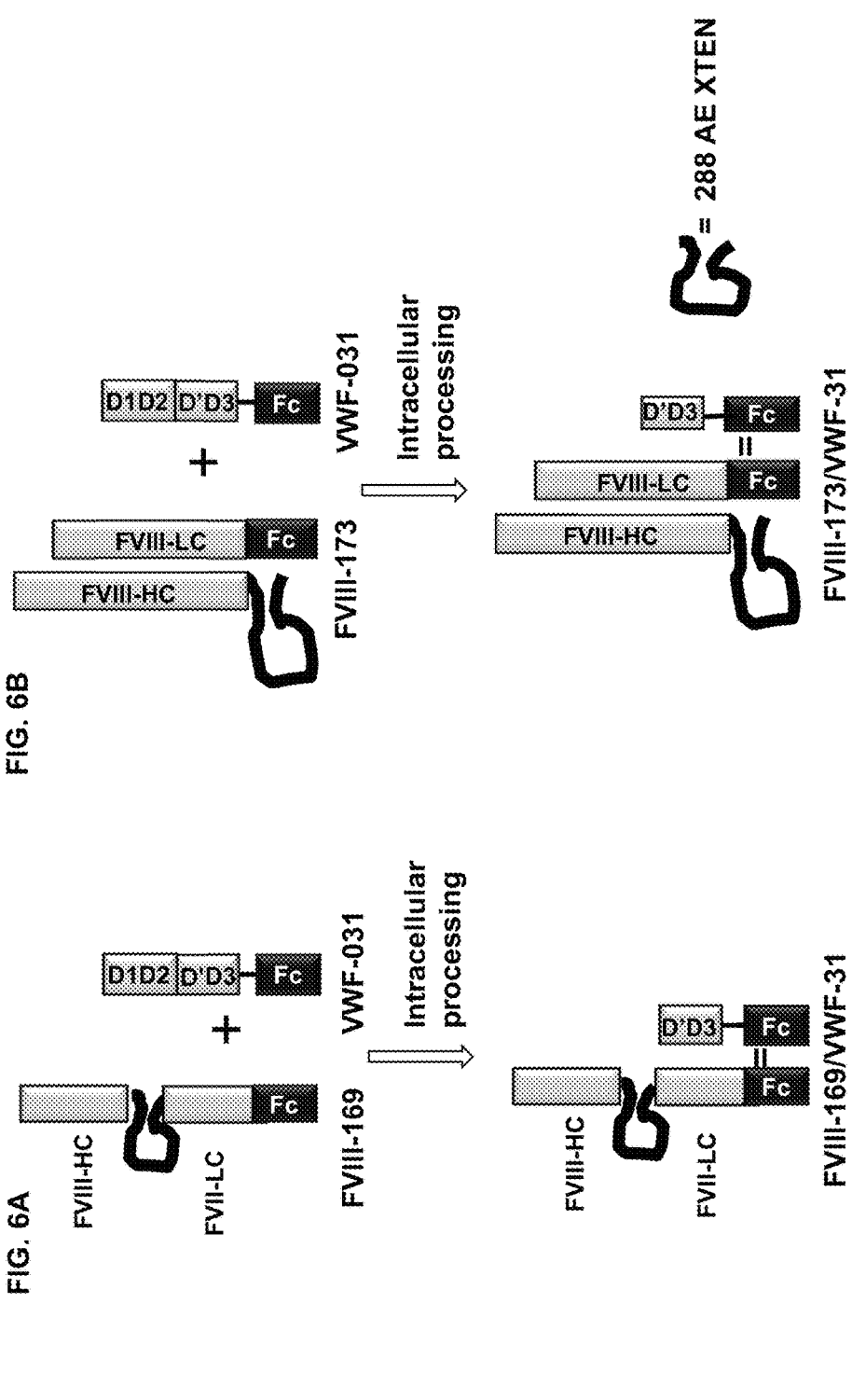

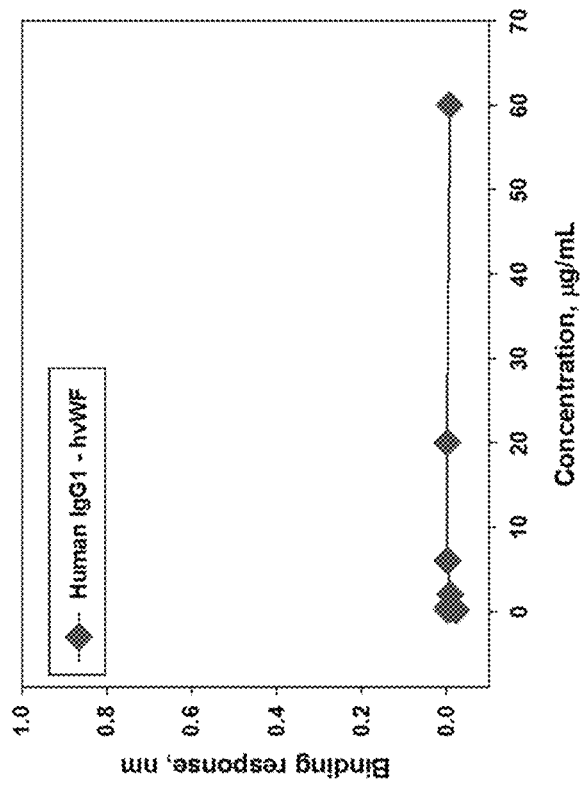
FIG. 7A  Octet Evaluation Subtracted Data
APS + hvWF, 20 µg/mL + BSA, 1.0%
FIG. 7B  Octet Evaluation Subtracted Data
APS + hvWF, 20 µg/mL + BSA, 1.0%
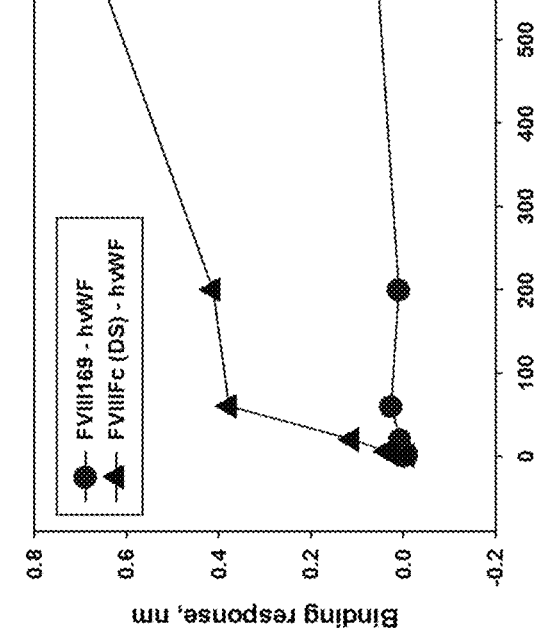
| Analyte | APS Probe + hvWF | Protein G Probe |
|---|---|---|
| FVIII-169/VWF-031 | − | + |
| rFVIIIFc | + | + |
| Human IgG1 | − | + |

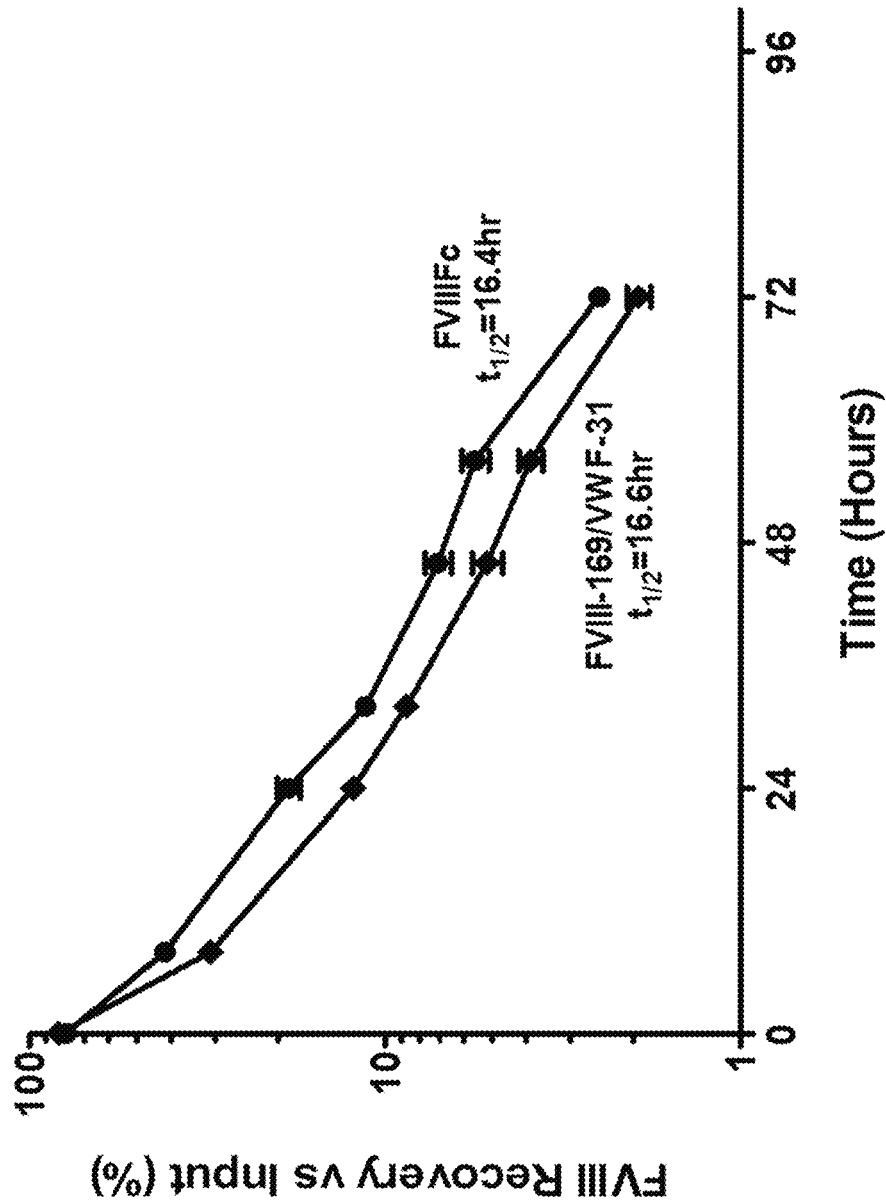
FIG. 8A: FVIII-169/VWF-031 PK in HemA

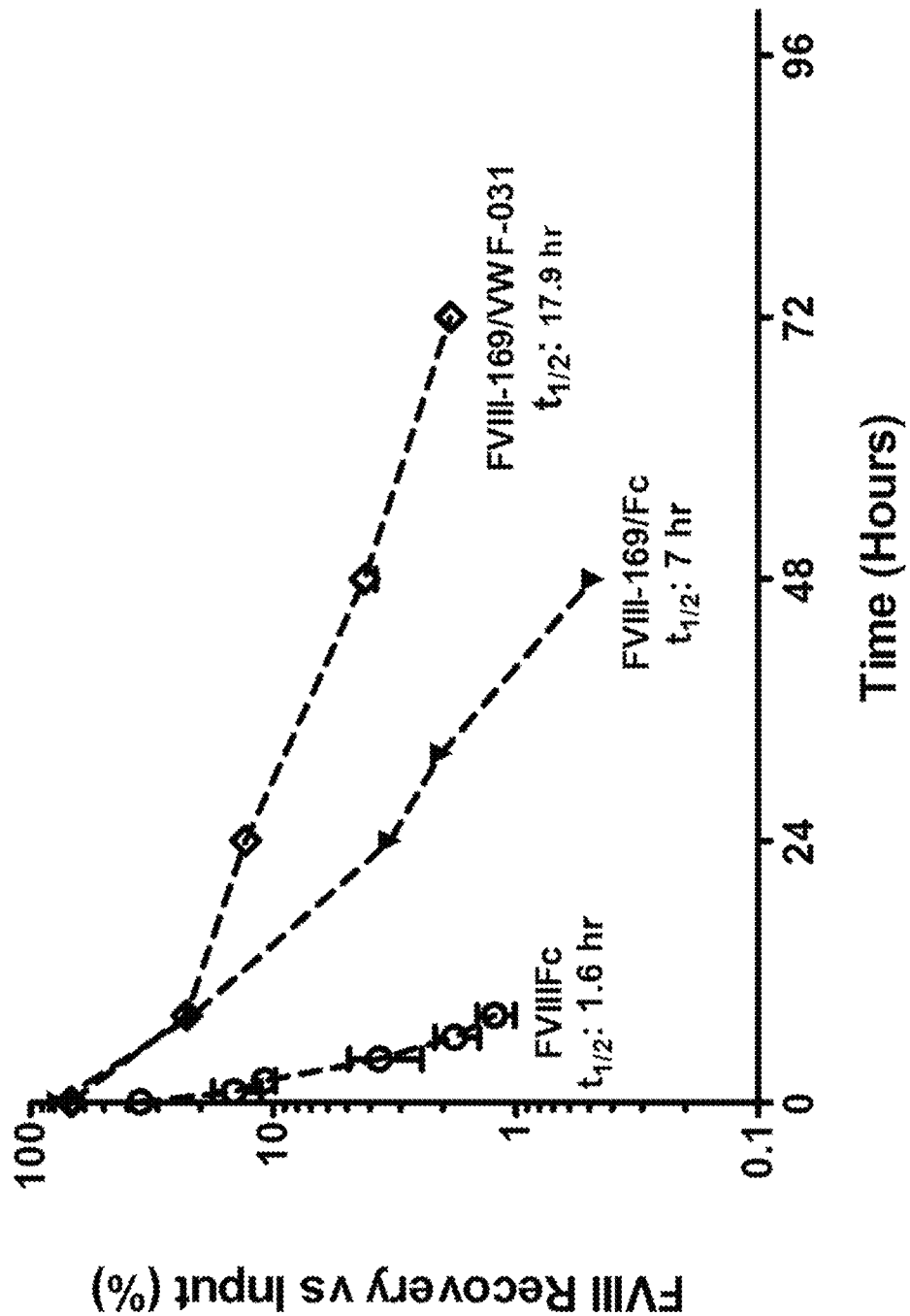
FIG. 8B: FVIII-169/VWF-031 PK in FVIII/VWF DKO Mice

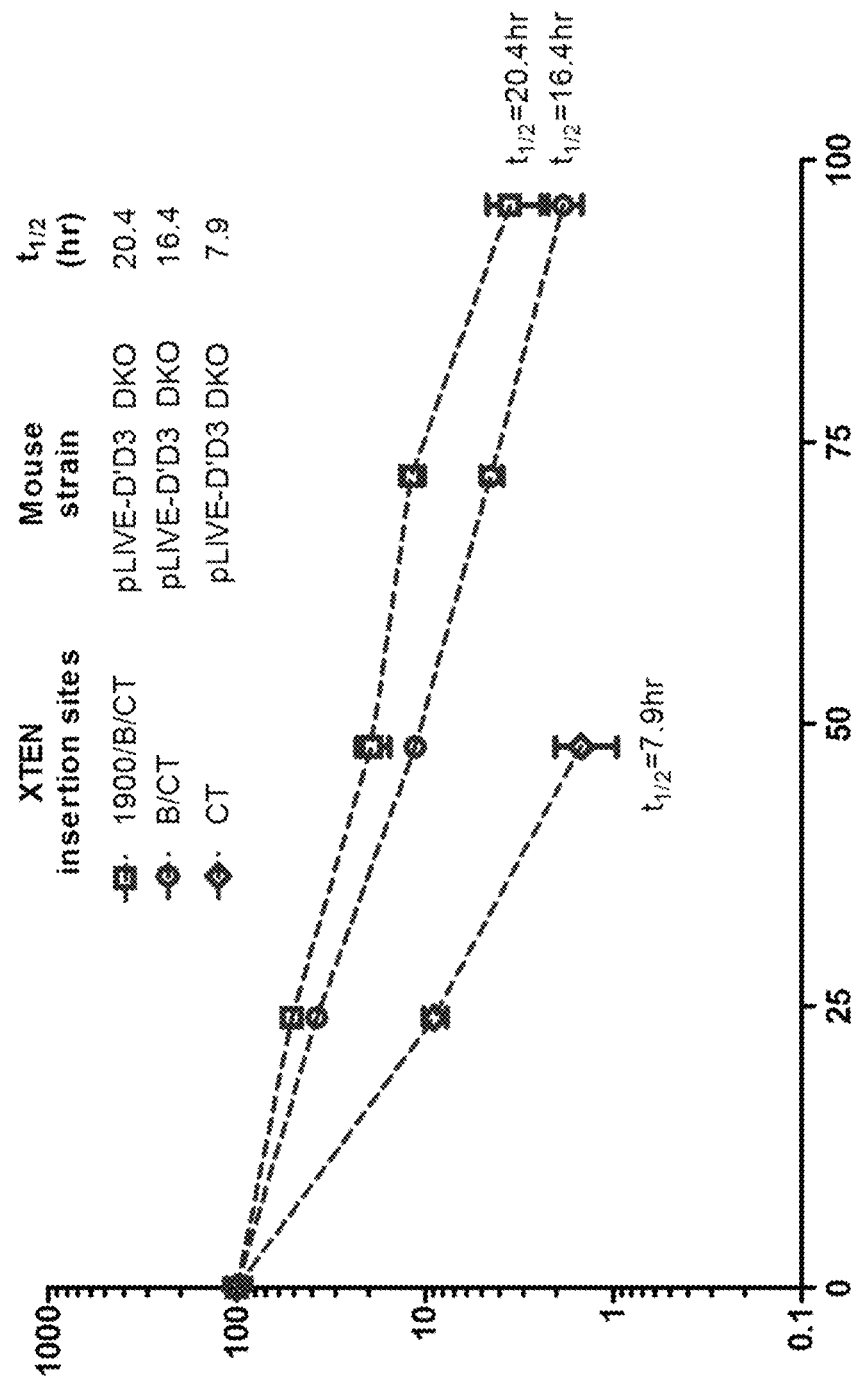
FIG. 9A: FVIII-XTEN variants half-life in D'D3 expressing FVIII/VWF DKO mice

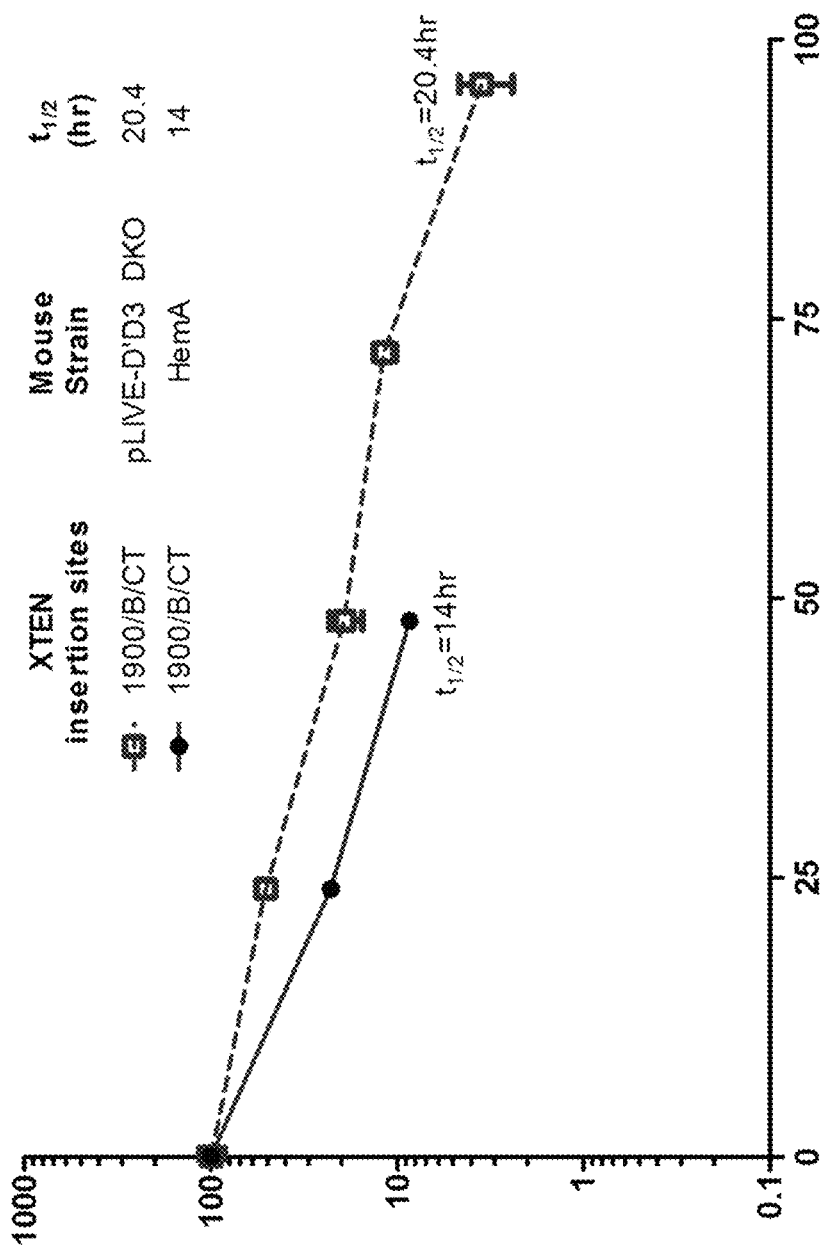
Figure 9B: PK of FVIII-XTEN with three XTEN insertions

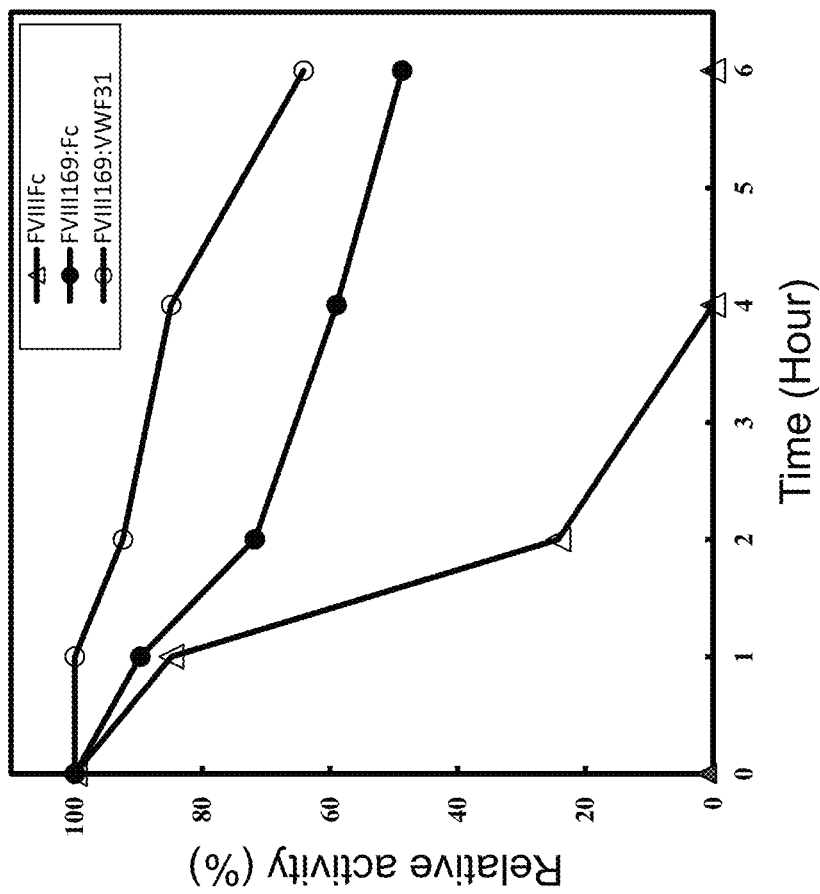
FIG. 10: FVIIIFc activity in mouse DKO plasma

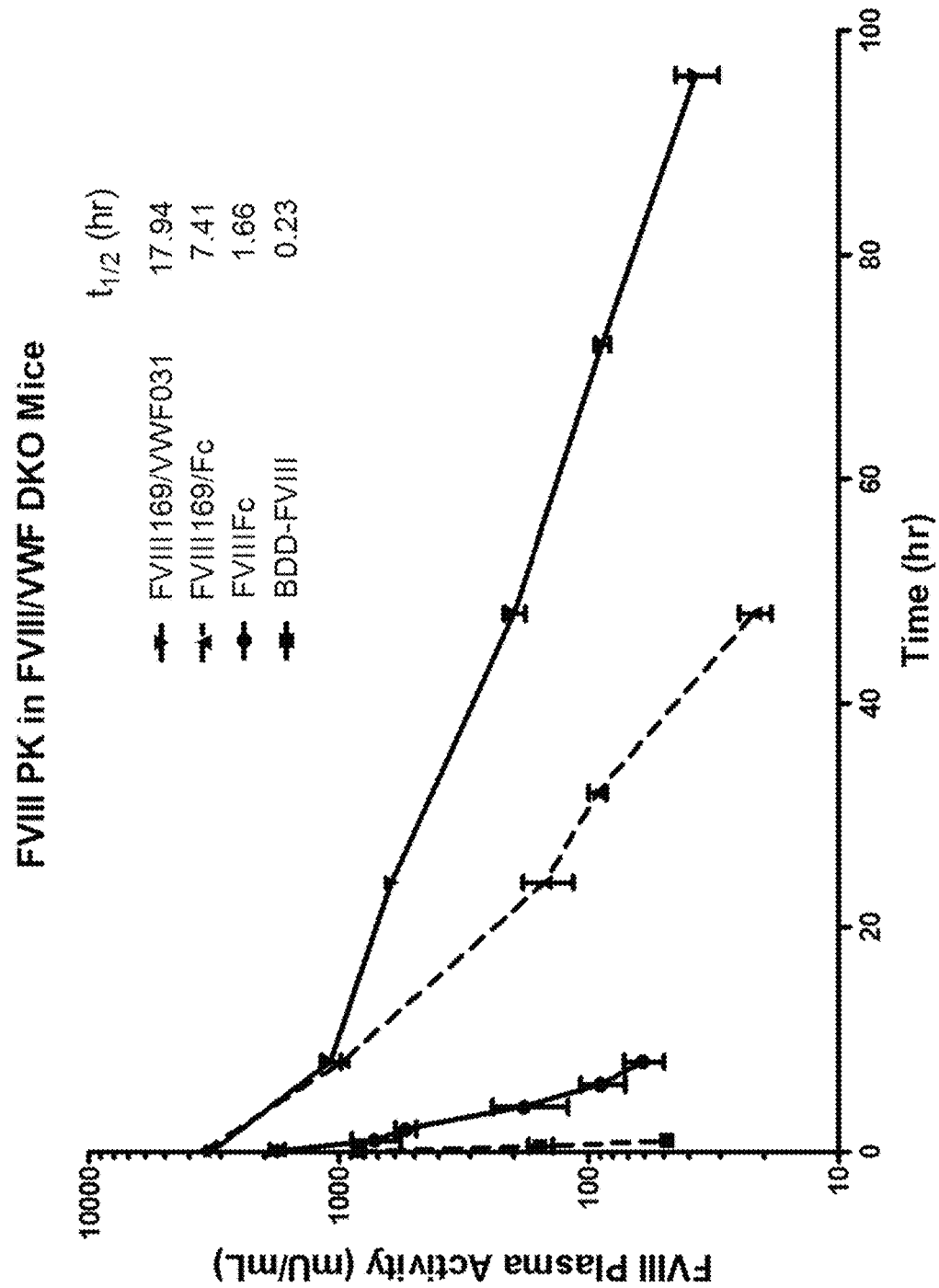
FIG. 11: Additive effect of Fc, XTEN and VWF-D'D3 fragment on FVIII half-life extension

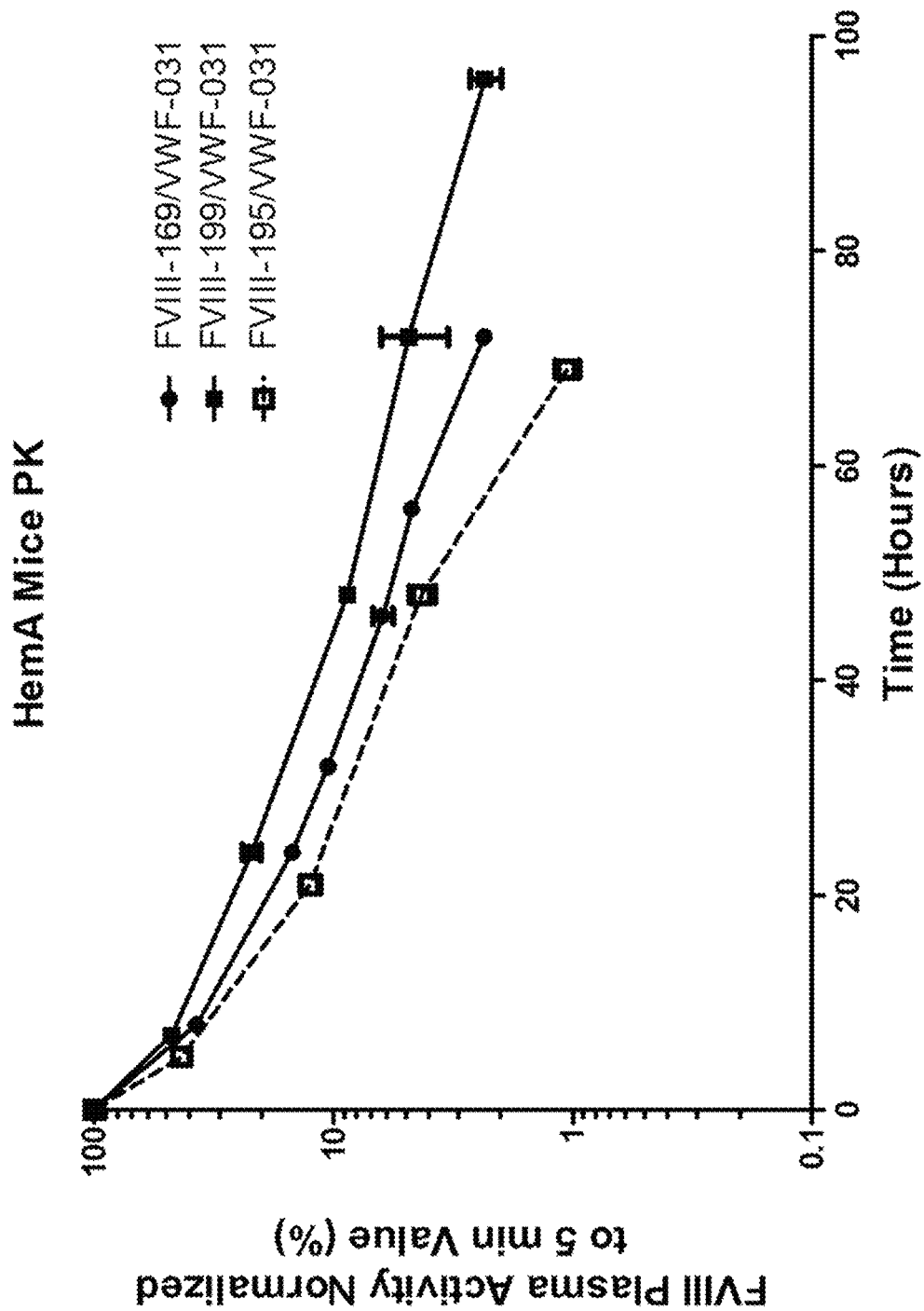
FIG. 12A: Effect of different XTEN on rFVIII-XTEN/VWF heterodimer PK in HemA mice

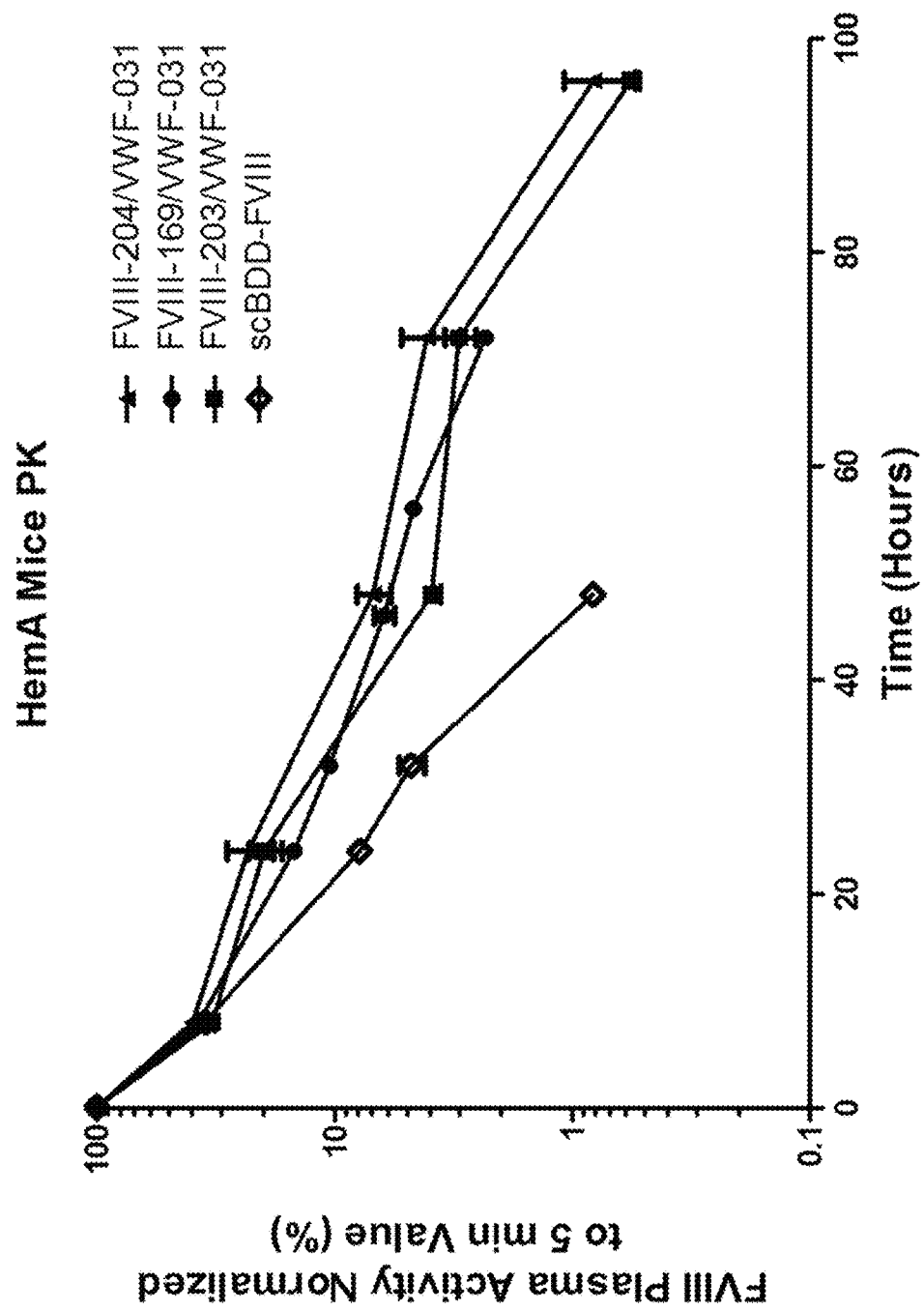
FIG. 12B: Effect of different XTEN on rFVIII-XTEN/VWF heterodimer PK in HemA mice

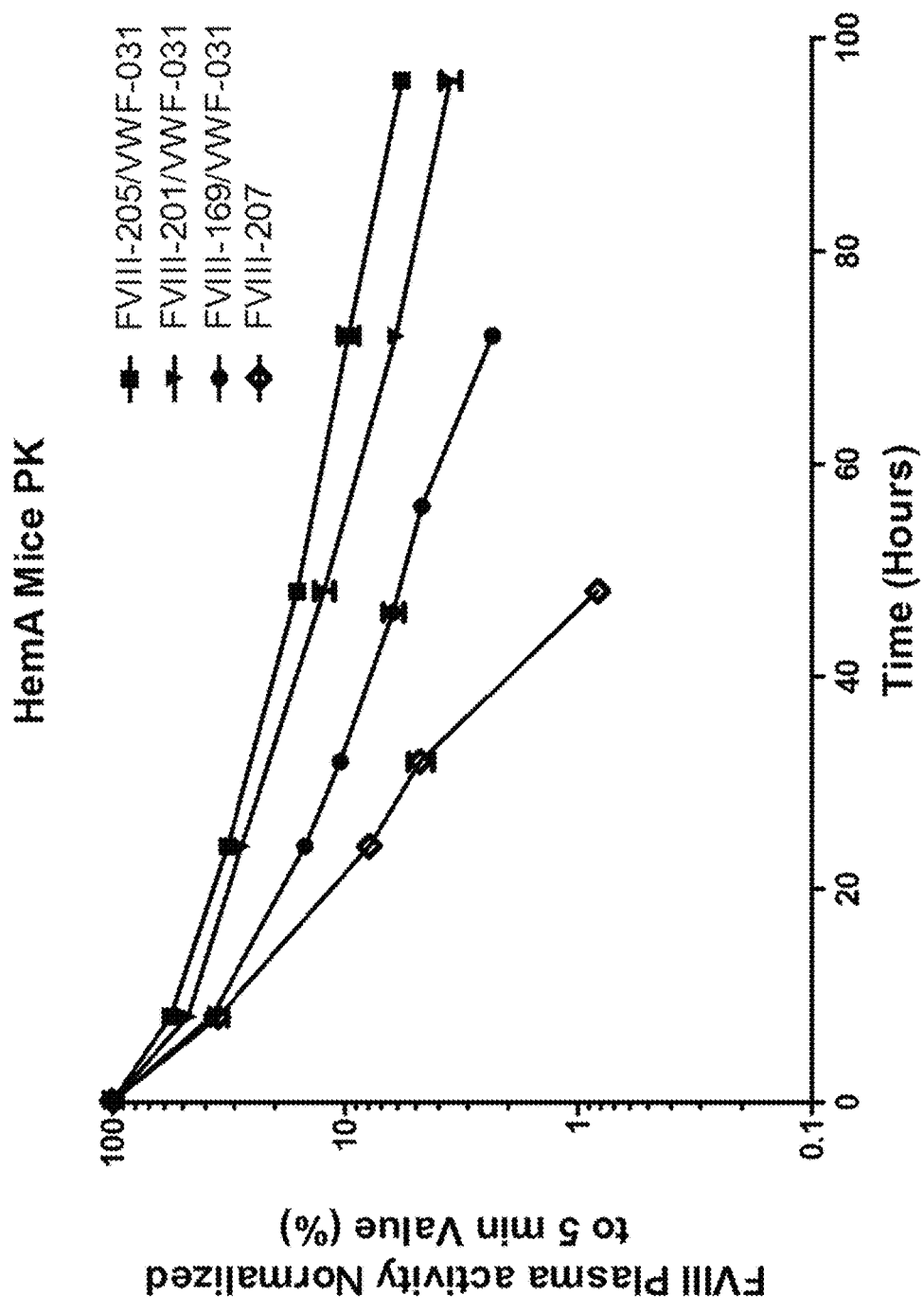
FIG. 12C: Effect of different XTEN on rFVIII-XTEN/VWF heterodimer PK in HemA mice

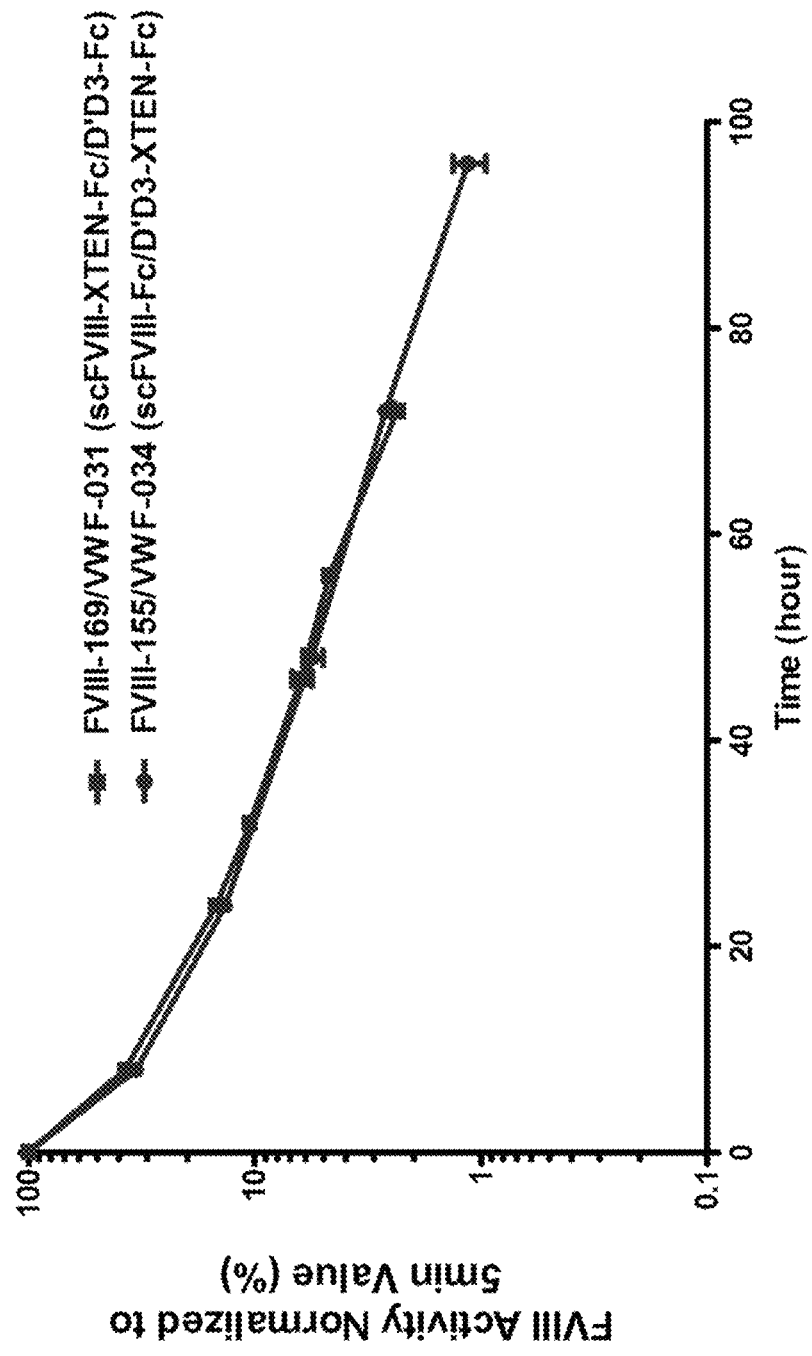
FIG. 13: rFVIII-XTEN/VWF-XTEN heterodimer PK in FVIII/VWF DKO mice

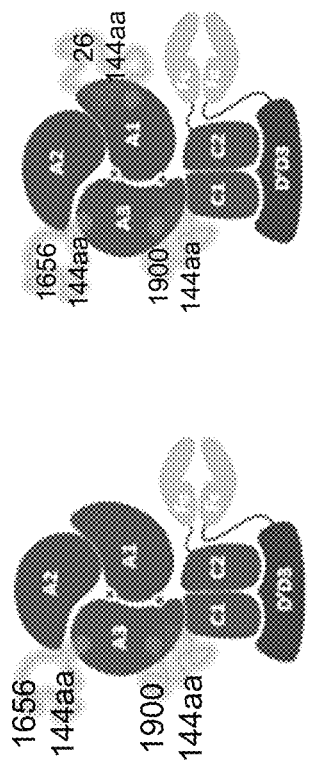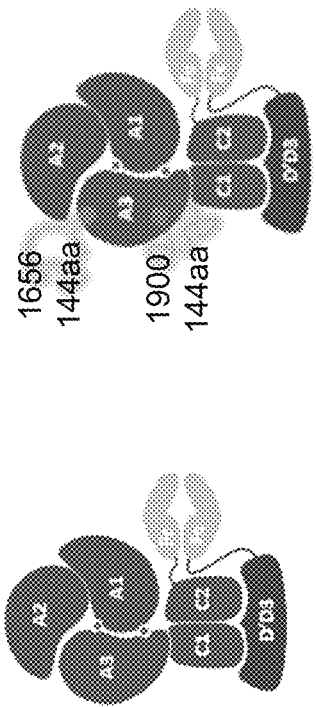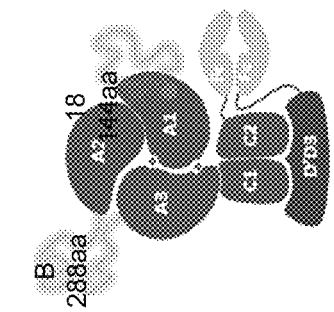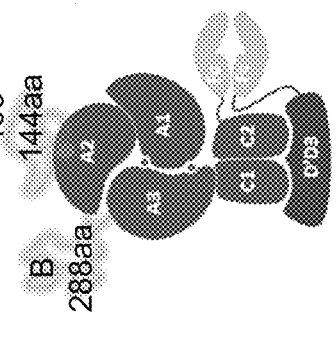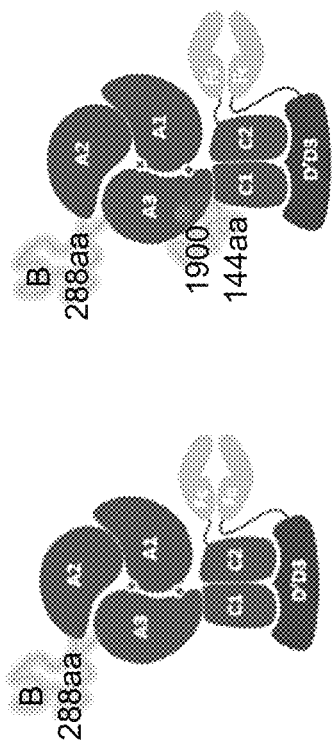

Half-life extension in HemA mice by rFVIII-XTEN/VWF

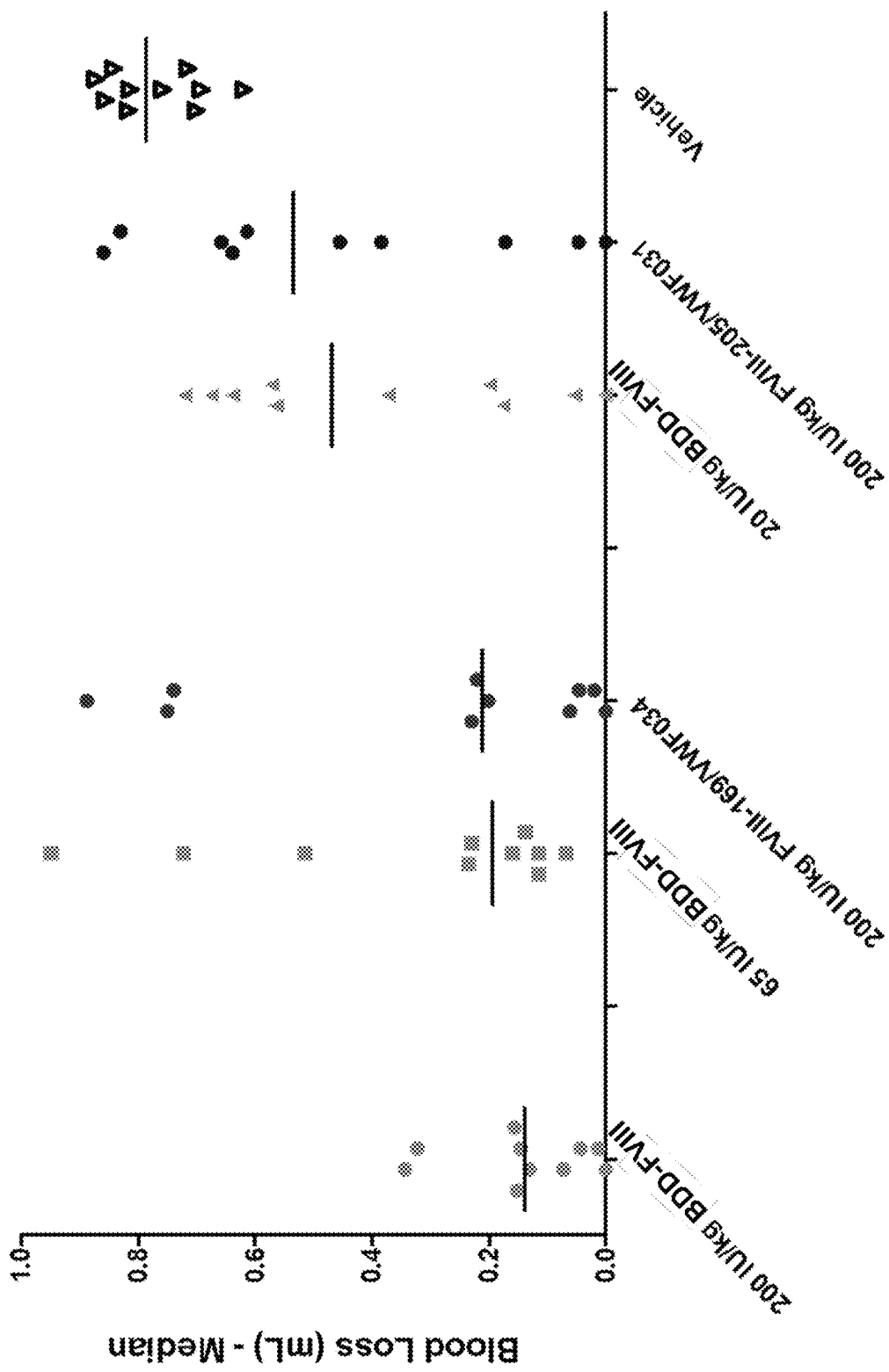
FIG. 16: Acute efficacy of FVIII-XTEN-Fc : VWF-Fc heterodimer in HemA mice Tail Clip bleeding model

SEQUENCE LISTING

<160> NUMBER OF SEQ ID NOS: 171

<210> SEQ ID NO 1
<211> LENGTH: 8442
<212> TYPE: DNA
<213> ORGANISM: Homo sapiens

<400> SEQUENCE: 1

| | | | | | | |
|---|---|---|---|---|---|---|
| atgattcctg | ccagatttgc | cggggtgctg | cttgctctgg | ccctcatttt | gccagggacc | 60 |
| ctttgtgcag | aaggaactcg | cggcaggtca | tccacggccc | gatgcagcct | tttcggaagt | 120 |
| gacttcgtca | acacctttga | tgggagcatg | tacagctttg | cgggatactg | cagttacctc | 180 |
| ctggcagggg | gctgccagaa | cgctccttc | tcgattattg | ggacttcca | gaatggcaag | 240 |
| agagtgagcc | tctccgtgta | tcttggggaa | ttttttgaca | tccatttgtt | tgtcaatggt | 300 |
| accgtgacac | aggggacca | aagagtctcc | atgccctatg | cctccaaagg | gctgtatcta | 360 |
| gaaactgagg | ctgggtacta | caagctgtcc | ggtgaggcct | atggctttgt | ggccaggatc | 420 |
| gatggcagcg | gcaactttca | agtcctgctg | tcagacagat | acttcaacaa | gacctgcggg | 480 |
| ctgtgtggca | actttaacat | ctttgctgaa | gatgacttta | tgacccaaga | agggaccttg | 540 |
| acctcggacc | cttatgactt | tgccaactca | tgggctctga | gcagtggaga | acagtggtgt | 600 |
| gaacgggcat | ctcctcccag | cagctcatgc | aacatctcct | ctgggaaat | gcagaagggc | 660 |
| ctgtgggagc | agtgccagct | tctgaagagc | acctcggtgt | tgcccgctg | ccaccctctg | 720 |
| gtggaccccg | agccttttgt | ggccctgtgt | gagaagactt | tgtgtgagtg | tgctgggggg | 780 |
| ctggagtgcg | cctgccctgc | cctcctggag | tacgcccgga | cctgtgccca | ggagggaatg | 840 |
| gtgctgtacg | gctggaccga | ccacagcgcg | tgcagcccag | tgccctgc | tggtatggag | 900 |
| tataggcagt | gtgtgtcccc | ttgcgccagg | acctgccaga | gcctgcacat | caatgaaatg | 960 |
| tgtcaggagc | gatgcgtgga | tggctgcagc | tgccctgagg | acagctcct | ggatgaaggc | 1020 |
| ctctgcgtgg | agagcaccga | gtgtccctgc | gtgcattccg | gaagcgcta | ccctcccggc | 1080 |
| acctccctct | ctcgagactg | caacacctgc | atttgccgaa | acagccagtg | gatctgcagc | 1140 |
| aatgaagaat | gtccagggga | gtgccttgtc | actggtcaat | cccacttcaa | gagctttgac | 1200 |
| aacagatact | tcaccttcag | tgggatctgc | cagtacctgc | tggcccggga | ttgccaggac | 1260 |
| cactccttct | ccattgtcat | tgagactgtc | cagtgtgctg | atgaccgcga | cgctgtgtgc | 1320 |
| acccgctccg | tcaccgtccg | gctgcctggc | ctgcacaaca | gccttgtgaa | actgaagcat | 1380 |
| ggggcaggag | ttgccatgga | tggccaggac | atccagctcc | ccctcctgaa | aggtgacctc | 1440 |
| cgcatccagc | atacagtgac | ggcctccgtg | cgcctcagct | acgggagga | cctgcagatg | 1500 |
| gactgggatg | gccgcgggag | gctgctggtg | aagctgtccc | ccgtctatgc | cgggaagacc | 1560 |
| tgcggcctgt | gtgggaatta | caatggcaac | cagggcgacg | acttccttac | ccctctgggg | 1620 |
| ctggcrgagc | cccgggtgga | ggacttcggg | aacgcctgga | agctgcacgg | ggactgccag | 1680 |
| gacctgcaga | agcagcacag | cgatccctgc | gccctcaacc | cgcgcatgac | caggttctcc | 1740 |
| gaggaggcgt | gcgcggtcct | gacgtccccc | acattcgagg | cctgccatcg | tgccgtcagc | 1800 |
| ccgctgccct | acctgcggaa | ctgccgctac | gacgtgtgct | cctgctcgga | cggccgcgag | 1860 |
| tgcctgtgcg | gcgccctggc | cagctatgcc | gcggcctgcg | cggggagagg | cgtgcgcgtc | 1920 |
| gcgtggcgcg | agccaggccg | ctgtgagctg | aactgcccga | aaggccaggt | gtacctgcag | 1980 |
| tgcgggaccc | cctgcaacct | gacctgccgc | tctctctctt | acccggatga | ggaatgcaat | 2040 |
| gaggcctgcc | tggagggctg | cttctgcccc | ccagggctct | acatggatga | agggggggac | 2100 |

```
tgcgtgccca aggcccagtg ccctgttac tatgacggtg agatcttcca gccagaagac    2160
atcttctcag accatcacac catgtgctac tgtgaggat gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc ccccgggga tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
ggcatccaga caatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatccag tgaccctgag    3660
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc caacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcc ttagctacct ctgtgacctt    4380
gcccctgaag cccctcctcc tactctgccc ccgacatgg cacaagtcac tgtgggcccg    4440
```

```
gggctcttgg gggtttcgac cctggggccc aagaggaact ccatggttct ggatgtggcg   4500
ttcgtcctgg aaggatcgga caaaattggt gaagccgact tcaacaggag caaggagttc   4560
atggaggagg tgattcagcg gatggatgtg ggccaggaca gcatccacgt cacggtgctg   4620
cagtactcct acatggtgac cgtggagtac cccttcagcg aggcacagtc caaaggggac   4680
atcctgcagc gggtgcgaga gatccgctac cagggcggca acaggaccaa cactgggctg   4740
gccctgcggt acctctctga ccacagcttc ttggtcagcc agggtgaccg ggagcaggcg   4800
cccaacctgg tctacatggt caccggaaat cctgcctctg atgagatcaa gaggctgcct   4860
ggagacatcc aggtggtgcc cattggagtg ggccctaatg ccaacgtgca ggagctggag   4920
aggattggct ggcccaatgc ccctatcctc atccaggact ttgagacgct ccccccgagag  4980
gctcctgacc tggtgctgca gaggtgctgc tccggagagg ggctgcagat ccccacccct   5040
tcccctgcac ctgactgcag ccagcccctg gacgtgatcc ttctcctgga tggctcctcc   5100
agtttcccag cttcttattt tgatgaaatg aagagtttcg ccaaggcttt catttcaaaa   5160
gccaatatag ggcctcgtct cactcaggtg tcagtgctgc agtatggaag catcaccacc   5220
attgacgtgc catggaacgt ggtcccggag aaagcccatt tgctgagcct tgtggacgtc   5280
atgcagcggg agggaggccc cagccaaatc ggggatgcct gggctttgc tgtgcgatac    5340
ttgacttcag aaatgcatgg tgccaggccg ggagcctcaa aggcggtggt catcctggtc   5400
acggacgtct ctgtggattc agtggatgca gcagctgatg ccgccaggtc caacagagtg   5460
acagtgttcc ctattggaat tggagatcgc tacgatgcag cccagctacg atcttggca    5520
ggcccagcag gcgactccaa cgtggtgaag ctccagcgaa tcgaagacct ccctaccatg   5580
gtcaccttgg gcaattcctt cctccacaaa ctgtgctctg gatttgttag gatttgcatg   5640
gatgaggatg ggaatgagaa gaggcccggg gacgtctgga ccttgccaga ccagtgccac   5700
accgtgactt gccagccaga tggccagacc ttgctgaaga gtcatcgggt caactgtgac   5760
cgggggctga ggccttcgtg ccctaacagc cagtcccctg ttaaagtgga agagacctgt   5820
ggctgccgct ggacctgccc ctgygtgtgc acaggcagct ccactcggca catcgtgacc   5880
tttgatgggc agaatttcaa gctgactggc agctgttctt atgtcctatt tcaaaacaag   5940
gagcaggacc tggaggtgat tctccataat ggtgcctgca gccctggagc aaggcagggc   6000
tgcatgaaat ccatcgaggt gaagcacagt gccctctccg tcgagstgca cagtgacatg   6060
gaggtgacgg tgaatgggag actggtctct gttccttacg tgggtgggaa catggaagtc   6120
aacgtttatg gtgccatcat gcatgaggtc agattcaatc accttggtca catcttcaca   6180
ttcactccac aaaacaatga gttccaactg cagctcagcc caagactttt tgcttcaaag   6240
acgtatggtc tgtgtgggat ctgtgatgag aacggagcca atgacttcat gctgagggat   6300
ggcacagtca ccacagactg aaaacacttt gttcaggaat ggactgtgca gcggccaggg   6360
cagacgtgcc agcccatcct ggaggagcag tgtcttgtcc ccgacagctc ccactgccag   6420
gtcctcctct taccactgtt tgctgaatgc acaaggtcc tggctccagc cacattctat    6480
gccatctgcc agcaggacag ttgccaccag gagcaagtgt gtgaggtgat cgcctcttat   6540
gcccacctct gtcggaccaa cggggtctgc gttgactgga ggacacctga tttctgtgct   6600
atgtcatgcc caccatctct ggtctacaac cactgtgagc atggctgtcc ccggcactgt   6660
gatggcaacg tgagcctctg tgggaccat ccctccgaag ctgtttctg ccctccagat     6720
aaagtcatgt tggaaggcag ctgtgtccct gaagaggcct gcactcagtg cattggtgag   6780
gatggagtcc agcaccagtt cctggaagcc tgggtcccgg accaccagcc ctgtcagatc   6840
```

-continued

```
tgcacatgcc tcagcgggcg aaggtcaac tgcacaacgc agccctgccc cacggccaaa      6900
gctcccacgt gtggcctgtg tgaagtagcc cgcctccgcc agaatgcaga ccagtgctgc      6960
cccgagtatg agtgtgtgtg tgacccagtg agctgtgacc tgcccccagt gcctcactgt      7020
gaacgtggcc tccagcccac actgaccaac cctggcgagt gcagacccaa cttcacctgc      7080
gcctgcagga aggaggagtg caaaagagtg tccccaccct cctgcccccc gcaccgtttg      7140
cccacccttc ggaagaccca gtgctgtgat gagtatgagt gtgcctgcaa ctgtgtcaac      7200
tccacagtga gctgtccct tgggtacttg gcctcaaccg ccaccaatga ctgtggctgt      7260
accacaacca cctgccttcc cgacaaggtg tgtgtccacc gaagcaccat ctaccctgtg      7320
ggccagttct gggaggaggg ctgcgatgtg tgcacctgca ccgacatgga ggatgccgtg      7380
atgggcctcc gcgtggccca gtgctcccag aagccctgtg aggacagctg tcggtcgggc      7440
ttcacttacg ttctgcatga aggcgagtgc tgtggaaggt gcctgccatc tgcctgtgag      7500
gtggtgactg gctcaccgcg gggggactcc cagtcttcct ggaagagtgt cggctcccag      7560
tgggcctccc cggagaaccc ctgcctcatc aatgagtgtg tccgagtgaa ggaggaggtc      7620
tttatacaac aaaggaacgt ctcctgcccc cagctggagg tccctgtctg ccccctcgggc    7680 tttcagctga gctgtaagac ctcagcgtgc tgcccaagct gtcgctgtga gcgcatggag      7740
gcctgcatgc tcaatggcac tgtcattggg cccgggaaga ctgtgatgat cgatgtgtgc      7800
acgacctgcc gctgcatggt gcaggtgggg gtcatctctg gattcaagct ggagtgcagg      7860
aagaccacct gcaaccctg ccccctgggt tacaaggaag aaaataacac aggtgaatgt      7920
tgtgggagat gtttgcctac ggcttgcacc attcagctaa gaggaggaca gatcatgaca      7980
ctgaagcgtg atgagacgct ccaggatggc tgtgatactc acttctgcaa ggtcaatgag      8040
agaggagagt acttctggga aagagggtc acaggctgcc cacccttttga tgaacacaag      8100 tgtcttgctg agggaggtaa aattatgaaa attccaggca cctgctgtga cacatgtgag      8160
gagcctgagt gcaacgacat cactgccagg ctgcagtatg tcaaggtggg aagctgtaag      8220
tctgaagtag aggtggatat ccactactgc caggcaaat gtgccagcaa agccatgtac      8280
tccattgaca tcaacgatgt gcaggaccag tgctcctgct gctctccgac acggacggag      8340
cccatgcagg tggccctgca ctgcaccaat ggctctgttg tgtaccatga ggttctcaat      8400
gccatggagt gcaaatgctc ccccaggaag tgcagcaagt ga                         8442
```

```
<210> SEQ ID NO 2
<211> LENGTH: 2813
<212> TYPE: PRT
<213> ORGANISM: Homo sapiens
<220> FEATURE:
<221> NAME/KEY: misc_feature
<222> LOCATION: (1)..(22)
<223> OTHER INFORMATION: VWF Signal Peptide
<220> FEATURE:
<221> NAME/KEY: misc_feature
<222> LOCATION: (23)..(763)
<223> OTHER INFORMATION: VWF D1D2 region
<220> FEATURE:
<221> NAME/KEY: misc_feature
<222> LOCATION: (764)..(866)
<223> OTHER INFORMATION: VWF D'Domain
<220> FEATURE:
<221> NAME/KEY: misc_feature
<222> LOCATION: (867)..(1240)
<223> OTHER INFORMATION: VWF D3 Domain
<220> FEATURE:
<221> NAME/KEY: misc_feature
<222> LOCATION: (1241)..(1479)
```

<223> OTHER INFORMATION: VWF A1 Domain
<220> FEATURE:
<221> NAME/KEY: misc_feature
<222> LOCATION: (2016)..(2016)
<223> OTHER INFORMATION: Xaa can be any naturally occurring amino acid

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Ser Thr Cys Pro Cys Val His
            340                 345                 350                   His

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380
```

```
Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
        420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
        450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
        610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800
```

```
Ser Met Gly Cys Val Ser Gly Cys Leu Cys Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
            995                1000                1005

Ser Ser Asn Leu Gln Val Glu Glu Asp Pro Val Asp Phe Gly Asn
            1010                1015                1020

Ser Trp Lys Val Ser Ser Gln Cys Ala Asp Thr Arg Lys Val Pro
            1025                1030                1035

Leu Asp Ser Ser Pro Ala Thr Cys His Asn Asn Ile Met Lys Gln
            1040                1045                1050

Thr Met Val Asp Ser Ser Cys Arg Ile Leu Thr Ser Asp Val Phe
            1055                1060                1065

Gln Asp Cys Asn Lys Leu Val Asp Pro Glu Pro Tyr Leu Asp Val
            1070                1075                1080

Cys Ile Tyr Asp Thr Cys Ser Cys Glu Ser Ile Gly Asp Cys Ala
            1085                1090                1095

Cys Phe Cys Asp Thr Ile Ala Ala Tyr Ala His Val Cys Ala Gln
            1100                1105                1110

His Gly Lys Val Val Thr Trp Arg Thr Ala Thr Leu Cys Pro Gln
            1115                1120                1125

Ser Cys Glu Glu Arg Asn Leu Arg Glu Asn Gly Tyr Glu Cys Glu
            1130                1135                1140

Trp Arg Tyr Asn Ser Cys Ala Pro Ala Cys Gln Val Thr Cys Gln
            1145                1150                1155

His Pro Glu Pro Leu Ala Cys Pro Val Gln Cys Val Glu Gly Cys
            1160                1165                1170

His Ala His Cys Pro Pro Gly Lys Ile Leu Asp Glu Leu Leu Gln
            1175                1180                1185

Thr Cys Val Asp Pro Glu Asp Cys Pro Val Cys Glu Val Ala Gly
            1190                1195                1200

Arg Arg Phe Ala Ser Gly Lys Lys Val Thr Leu Asn Pro Ser Asp
```

-continued

```
            1205               1210                1215

Pro Glu His Cys Gln Ile Cys His Cys Asp Val Val Asn Leu Thr
        1220                1225                1230

Cys Glu Ala Cys Gln Glu Pro Gly Gly Leu Val Val Pro Pro Thr
        1235                1240                1245

Asp Ala Pro Val Ser Pro Thr Thr Leu Tyr Val Glu Asp Ile Ser
        1250                1255                1260

Glu Pro Pro Leu His Asp Phe Tyr Cys Ser Arg Leu Leu Asp Leu
        1265                1270                1275

Val Phe Leu Leu Asp Gly Ser Ser Arg Leu Ser Glu Ala Glu Phe
        1280                1285                1290

Glu Val Leu Lys Ala Phe Val Val Asp Met Met Glu Arg Leu Arg
        1295                1300                1305

Ile Ser Gln Lys Trp Val Arg Val Ala Val Val Glu Tyr His Asp
        1310                1315                1320

Gly Ser His Ala Tyr Ile Gly Leu Lys Asp Arg Lys Arg Pro Ser
        1325                1330                1335

Glu Leu Arg Arg Ile Ala Ser Gln Val Lys Tyr Ala Gly Ser Gln
        1340                1345                1350

Val Ala Ser Thr Ser Glu Val Leu Lys Tyr Thr Leu Phe Gln Ile
        1355                1360                1365

Phe Ser Lys Ile Asp Arg Pro Glu Ala Ser Arg Ile Ala Leu Leu
        1370                1375                1380

Leu Met Ala Ser Gln Glu Pro Gln Arg Met Ser Arg Asn Phe Val
        1385                1390                1395

Arg Tyr Val Gln Gly Leu Lys Lys Lys Val Ile Val Ile Pro
        1400                1405                1410

Val Gly Ile Gly Pro His Ala Asn Leu Lys Gln Ile Arg Leu Ile
        1415                1420                1425

Glu Lys Gln Ala Pro Glu Asn Lys Ala Phe Val Leu Ser Ser Val
        1430                1435                1440

Asp Glu Leu Glu Gln Gln Arg Asp Glu Ile Val Ser Tyr Leu Cys
        1445                1450                1455

Asp Leu Ala Pro Glu Ala Pro Pro Thr Leu Pro Pro Asp Met
        1460                1465                1470

Ala Gln Val Thr Val Gly Pro Gly Leu Leu Gly Val Ser Thr Leu
        1475                1480                1485

Gly Pro Lys Arg Asn Ser Met Val Leu Asp Val Ala Phe Val Leu
        1490                1495                1500

Glu Gly Ser Asp Lys Ile Gly Glu Ala Asp Phe Asn Arg Ser Lys
        1505                1510                1515

Glu Phe Met Glu Glu Val Ile Gln Arg Met Asp Val Gly Gln Asp
        1520                1525                1530

Ser Ile His Val Thr Val Leu Gln Tyr Ser Tyr Met Val Thr Val
        1535                1540                1545

Glu Tyr Pro Phe Ser Glu Ala Gln Ser Lys Gly Asp Ile Leu Gln
        1550                1555                1560

Arg Val Arg Glu Ile Arg Tyr Gln Gly Gly Asn Arg Thr Asn Thr
        1565                1570                1575

Gly Leu Ala Leu Arg Tyr Leu Ser Asp His Ser Phe Leu Val Ser
        1580                1585                1590

Gln Gly Asp Arg Glu Gln Ala Pro Asn Leu Val Tyr Met Val Thr
        1595                1600                1605
```

Gly Asn Pro Ala Ser Asp Glu Ile Lys Arg Leu Pro Gly Asp Ile
    1610            1615            1620

Gln Val Val Pro Ile Gly Val Gly Pro Asn Ala Asn Val Gln Glu
    1625            1630            1635

Leu Glu Arg Ile Gly Trp Pro Asn Ala Pro Ile Leu Ile Gln Asp
    1640            1645            1650

Phe Glu Thr Leu Pro Arg Glu Ala Pro Asp Leu Val Leu Gln Arg
    1655            1660            1665

Cys Cys Ser Gly Glu Gly Leu Gln Ile Pro Thr Leu Ser Pro Ala
    1670            1675            1680

Pro Asp Cys Ser Gln Pro Leu Asp Val Ile Leu Leu Leu Asp Gly
    1685            1690            1695

Ser Ser Ser Phe Pro Ala Ser Tyr Phe Asp Glu Met Lys Ser Phe
    1700            1705            1710

Ala Lys Ala Phe Ile Ser Lys Ala Asn Ile Gly Pro Arg Leu Thr
    1715            1720            1725

Gln Val Ser Val Leu Gln Tyr Gly Ser Ile Thr Thr Ile Asp Val
    1730            1735            1740

Pro Trp Asn Val Val Pro Glu Lys Ala His Leu Leu Ser Leu Val
    1745            1750            1755

Asp Val Met Gln Arg Glu Gly Gly Pro Ser Gln Ile Gly Asp Ala
    1760            1765            1770

Leu Gly Phe Ala Val Arg Tyr Leu Thr Ser Glu Met His Gly Ala
    1775            1780            1785

Arg Pro Gly Ala Ser Lys Ala Val Val Ile Leu Val Thr Asp Val
    1790            1795            1800

Ser Val Asp Ser Val Asp Ala Ala Ala Asp Ala Ala Arg Ser Asn
    1805            1810            1815

Arg Val Thr Val Phe Pro Ile Gly Ile Gly Asp Arg Tyr Asp Ala
    1820            1825            1830

Ala Gln Leu Arg Ile Leu Ala Gly Pro Ala Gly Asp Ser Asn Val
    1835            1840            1845

Val Lys Leu Gln Arg Ile Glu Asp Leu Pro Thr Met Val Thr Leu
    1850            1855            1860

Gly Asn Ser Phe Leu His Lys Leu Cys Ser Gly Phe Val Arg Ile
    1865            1870            1875

Cys Met Asp Glu Asp Gly Asn Glu Lys Arg Pro Gly Asp Val Trp
    1880            1885            1890

Thr Leu Pro Asp Gln Cys His Thr Val Thr Cys Gln Pro Asp Gly
    1895            1900            1905

Gln Thr Leu Leu Lys Ser His Arg Val Asn Cys Asp Arg Gly Leu
    1910            1915            1920

Arg Pro Ser Cys Pro Asn Ser Gln Ser Pro Val Lys Val Glu Glu
    1925            1930            1935

Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

```
Gln Gly Cys Met Lys Ser Ile Glu Val Lys His Ser Ala Leu Ser
2000                 2005                2010

Val Glu Xaa His Ser Asp Met Glu Val Thr Val Asn Gly Arg Leu
2015                 2020                2025

Val Ser Val Pro Tyr Val Gly Gly Asn Met Glu Val Asn Val Tyr
2030                 2035                2040

Gly Ala Ile Met His Glu Val Arg Phe Asn His Leu Gly His Ile
2045                 2050                2055

Phe Thr Phe Thr Pro Gln Asn Asn Glu Phe Gln Leu Gln Leu Ser
2060                 2065                2070

Pro Lys Thr Phe Ala Ser Lys Thr Tyr Gly Leu Cys Gly Ile Cys
2075                 2080                2085

Asp Glu Asn Gly Ala Asn Asp Phe Met Leu Arg Asp Gly Thr Val
2090                 2095                2100

Thr Thr Asp Trp Lys Thr Leu Val Gln Glu Trp Thr Val Gln Arg
2105                 2110                2115

Pro Gly Gln Thr Cys Gln Pro Ile Leu Glu Glu Gln Cys Leu Val
2120                 2125                2130

Pro Asp Ser Ser His Cys Gln Val Leu Leu Leu Pro Leu Phe Ala
2135                 2140                2145

Glu Cys His Lys Val Leu Ala Pro Ala Thr Phe Tyr Ala Ile Cys
2150                 2155                2160

Gln Gln Asp Ser Cys His Gln Glu Gln Val Cys Glu Val Ile Ala
2165                 2170                2175

Ser Tyr Ala His Leu Cys Arg Thr Asn Gly Val Cys Val Asp Trp
2180                 2185                2190

Arg Thr Pro Asp Phe Cys Ala Met Ser Cys Pro Pro Ser Leu Val
2195                 2200                2205

Tyr Asn His Cys Glu His Gly Cys Pro Arg His Cys Asp Gly Asn
2210                 2215                2220

Val Ser Ser Cys Gly Asp His Pro Ser Glu Gly Cys Phe Cys Pro
2225                 2230                2235

Pro Asp Lys Val Met Leu Glu Gly Ser Cys Val Pro Glu Glu Ala
2240                 2245                2250

Cys Thr Gln Cys Ile Gly Glu Asp Gly Val Gln His Gln Phe Leu
2255                 2260                2265

Glu Ala Trp Val Pro Asp His Gln Pro Cys Gln Ile Cys Thr Cys
2270                 2275                2280

Leu Ser Gly Arg Lys Val Asn Cys Thr Thr Gln Pro Cys Pro Thr
2285                 2290                2295

Ala Lys Ala Pro Thr Cys Gly Leu Cys Glu Val Ala Arg Leu Arg
2300                 2305                2310

Gln Asn Ala Asp Gln Cys Cys Pro Glu Tyr Glu Cys Val Cys Asp
2315                 2320                2325

Pro Val Ser Cys Asp Leu Pro Pro Val Pro His Cys Glu Arg Gly
2330                 2335                2340

Leu Gln Pro Thr Leu Thr Asn Pro Gly Glu Cys Arg Pro Asn Phe
2345                 2350                2355

Thr Cys Ala Cys Arg Lys Glu Glu Cys Lys Arg Val Ser Pro Pro
2360                 2365                2370

Ser Cys Pro Pro His Arg Leu Pro Thr Leu Arg Lys Thr Gln Cys
2375                 2380                2385

Cys Asp Glu Tyr Glu Cys Ala Cys Asn Cys Val Asn Ser Thr Val
```

-continued

```
                2390                2395                2400
Ser Cys Pro Leu Gly Tyr Leu Ala Ser Thr Ala Thr Asn Asp Cys
    2405                2410                2415
Gly Cys Thr Thr Thr Thr Cys Leu Pro Asp Lys Val Cys Val His
    2420                2425                2430
Arg Ser Thr Ile Tyr Pro Val Gly Gln Phe Trp Glu Glu Gly Cys
    2435                2440                2445
Asp Val Cys Thr Cys Thr Asp Met Glu Asp Ala Val Met Gly Leu
    2450                2455                2460
Arg Val Ala Gln Cys Ser Gln Lys Pro Cys Glu Asp Ser Cys Arg
    2465                2470                2475
Ser Gly Phe Thr Tyr Val Leu His Glu Gly Glu Cys Cys Gly Arg
    2480                2485                2490
Cys Leu Pro Ser Ala Cys Glu Val Val Thr Gly Ser Pro Arg Gly
    2495                2500                2505
Asp Ser Gln Ser Ser Trp Lys Ser Val Gly Ser Gln Trp Ala Ser
    2510                2515                2520
Pro Glu Asn Pro Cys Leu Ile Asn Glu Cys Val Arg Val Lys Glu
    2525                2530                2535
Glu Val Phe Ile Gln Gln Arg Asn Val Ser Cys Pro Gln Leu Glu
    2540                2545                2550
Val Pro Val Cys Pro Ser Gly Phe Gln Leu Ser Cys Lys Thr Ser
    2555                2560                2565
Ala Cys Cys Pro Ser Cys Arg Cys Glu Arg Met Glu Ala Cys Met
    2570                2575                2580
Leu Asn Gly Thr Val Ile Gly Pro Gly Lys Thr Val Met Ile Asp
    2585                2590                2595
Val Cys Thr Thr Cys Arg Cys Met Val Gln Val Gly Val Ile Ser
    2600                2605                2610
Gly Phe Lys Leu Glu Cys Arg Lys Thr Thr Cys Asn Pro Cys Pro
    2615                2620                2625
Leu Gly Tyr Lys Glu Glu Asn Asn Thr Gly Glu Cys Cys Gly Arg
    2630                2635                2640
Cys Leu Pro Thr Ala Cys Thr Ile Gln Leu Arg Gly Gly Gln Ile
    2645                2650                2655
Met Thr Leu Lys Arg Asp Glu Thr Leu Gln Asp Gly Cys Asp Thr
    2660                2665                2670
His Phe Cys Lys Val Asn Glu Arg Gly Glu Tyr Phe Trp Glu Lys
    2675                2680                2685
Arg Val Thr Gly Cys Pro Pro Phe Asp Glu His Lys Cys Leu Ala
    2690                2695                2700
Glu Gly Gly Lys Ile Met Lys Ile Pro Gly Thr Cys Cys Asp Thr
    2705                2710                2715
Cys Glu Glu Pro Glu Cys Asn Asp Ile Thr Ala Arg Leu Gln Tyr
    2720                2725                2730
Val Lys Val Gly Ser Cys Lys Ser Glu Val Glu Val Asp Ile His
    2735                2740                2745
Tyr Cys Gln Gly Lys Cys Ala Ser Lys Ala Met Tyr Ser Ile Asp
    2750                2755                2760
Ile Asn Asp Val Gln Asp Gln Cys Ser Cys Cys Ser Pro Thr Arg
    2765                2770                2775
Thr Glu Pro Met Gln Val Ala Leu His Cys Thr Asn Gly Ser Val
    2780                2785                2790
```

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 19
<212> TYPE: PRT
<213> ORGANISM: Homo sapiens

<400> SEQUENCE: 3

Met Gln Ile Glu Leu Ser Thr Cys Phe Phe Leu Cys Leu Leu Arg Phe
1               5                   10                  15

Cys Phe Ser

<210> SEQ ID NO 4
<211> LENGTH: 2332
<212> TYPE: PRT
<213> ORGANISM: Homo sapiens

<400> SEQUENCE: 4

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

```
Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
    355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
```

```
            690             695             700
Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Ser Arg His Pro Ser Thr Arg
            740             745             750

Gln Lys Gln Phe Asn Ala Thr Thr Ile Pro Glu Asn Asp Ile Glu Lys
        755             760             765

Thr Asp Pro Trp Phe Ala His Arg Thr Pro Met Pro Lys Ile Gln Asn
        770             775             780

Val Ser Ser Ser Asp Leu Leu Met Leu Leu Arg Gln Ser Pro Thr Pro
785             790             795             800

His Gly Leu Ser Leu Ser Asp Leu Gln Glu Ala Lys Tyr Glu Thr Phe
            805             810             815

Ser Asp Asp Pro Ser Pro Gly Ala Ile Asp Ser Asn Asn Ser Leu Ser
            820             825             830

Glu Met Thr His Phe Arg Pro Gln Leu His His Ser Gly Asp Met Val
        835             840             845

Phe Thr Pro Glu Ser Gly Leu Gln Leu Arg Leu Asn Glu Lys Leu Gly
850             855             860

Thr Thr Ala Ala Thr Glu Leu Lys Lys Leu Asp Phe Lys Val Ser Ser
865             870             875             880

Thr Ser Asn Asn Leu Ile Ser Thr Ile Pro Ser Asp Asn Leu Ala Ala
            885             890             895

Gly Thr Asp Asn Thr Ser Ser Leu Gly Pro Pro Ser Met Pro Val His
        900             905             910

Tyr Asp Ser Gln Leu Asp Thr Thr Leu Phe Gly Lys Lys Ser Ser Pro
        915             920             925

Leu Thr Glu Ser Gly Gly Pro Leu Ser Leu Ser Glu Glu Asn Asn Asp
930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
            965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
        995             1000            1005

Thr Asn Arg Lys Thr His Ile Asp Gly Pro Ser Leu Leu Ile Glu
        1010            1015            1020

Asn Ser Pro Ser Val Trp Gln Asn Ile Leu Glu Ser Asp Thr Glu
        1025            1030            1035

Phe Lys Lys Val Thr Pro Leu Ile His Asp Arg Met Leu Met Asp
        1040            1045            1050

Lys Asn Ala Thr Ala Leu Arg Leu Asn His Met Ser Asn Lys Thr
        1055            1060            1065

Thr Ser Ser Lys Asn Met Glu Met Val Gln Gln Lys Lys Glu Gly
        1070            1075            1080

Pro Ile Pro Pro Asp Ala Gln Asn Pro Asp Met Ser Phe Phe Lys
        1085            1090            1095

Met Leu Phe Leu Pro Glu Ser Ala Arg Trp Ile Gln Arg Thr His
        1100            1105            1110
```

```
Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500
```

```
Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
```

```
                1895                1900                1905

Asp Pro Thr Phe Lys Glu Asn Tyr Arg Phe His Ala Ile Asn Gly
    1910            1915            1920

Tyr Ile Met Asp Thr Leu Pro Gly Leu Val Met Ala Gln Asp Gln
    1925            1930            1935

Arg Ile Arg Trp Tyr Leu Leu Ser Met Gly Ser Asn Glu Asn Ile
    1940            1945            1950

His Ser Ile His Phe Ser Gly His Val Phe Thr Val Arg Lys Lys
    1955            1960            1965

Glu Glu Tyr Lys Met Ala Leu Tyr Asn Leu Tyr Pro Gly Val Phe
    1970            1975            1980

Glu Thr Val Glu Met Leu Pro Ser Lys Ala Gly Ile Trp Arg Val
    1985            1990            1995

Glu Cys Leu Ile Gly Glu His Leu His Ala Gly Met Ser Thr Leu
    2000            2005            2010

Phe Leu Val Tyr Ser Asn Lys Cys Gln Thr Pro Leu Gly Met Ala
    2015            2020            2025

Ser Gly His Ile Arg Asp Phe Gln Ile Thr Ala Ser Gly Gln Tyr
    2030            2035            2040

Gly Gln Trp Ala Pro Lys Leu Ala Arg Leu His Tyr Ser Gly Ser
    2045            2050            2055

Ile Asn Ala Trp Ser Thr Lys Glu Pro Phe Ser Trp Ile Lys Val
    2060            2065            2070

Asp Leu Leu Ala Pro Met Ile Ile His Gly Ile Lys Thr Gln Gly
    2075            2080            2085

Ala Arg Gln Lys Phe Ser Ser Leu Tyr Ile Ser Gln Phe Ile Ile
    2090            2095            2100

Met Tyr Ser Leu Asp Gly Lys Lys Trp Gln Thr Tyr Arg Gly Asn
    2105            2110            2115

Ser Thr Gly Thr Leu Met Val Phe Phe Gly Asn Val Asp Ser Ser
    2120            2125            2130

Gly Ile Lys His Asn Ile Phe Asn Pro Pro Ile Ile Ala Arg Tyr
    2135            2140            2145

Ile Arg Leu His Pro Thr His Tyr Ser Ile Arg Ser Thr Leu Arg
    2150            2155            2160

Met Glu Leu Met Gly Cys Asp Leu Asn Ser Cys Ser Met Pro Leu
    2165            2170            2175

Gly Met Glu Ser Lys Ala Ile Ser Asp Ala Gln Ile Thr Ala Ser
    2180            2185            2190

Ser Tyr Phe Thr Asn Met Phe Ala Thr Trp Ser Pro Ser Lys Ala
    2195            2200            2205

Arg Leu His Leu Gln Gly Arg Ser Asn Ala Trp Arg Pro Gln Val
    2210            2215            2220

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295
```

```
Pro Pro Leu Leu Thr Arg Tyr Leu Arg Ile His Pro Gln Ser Trp
    2300            2305                2310
Val His Gln Ile Ala Leu Arg Met Glu Val Leu Gly Cys Glu Ala
    2315            2320                2325
Gln Asp Leu Tyr
    2330

<210> SEQ ID NO 5
<211> LENGTH: 7053
<212> TYPE: DNA
<213> ORGANISM: Homo sapiens

<400> SEQUENCE: 5
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaatctttt ccattcaac     180 acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaagacttt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agttctctac tgttttgtcat atctcttccc accaacatga tggcatggaa   1020
gcttatgtca aagtagacag ctgtccagag aaccccaac tacgaatgaa aaataatgaa     1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca aagttataaa agtcaatat ttgaacaatg ccctcagcg gattggtagg    1320 aagtacaaaa aagtccgatt tatggcatac acagatgaaa cctttaagac tcgtgaagct   1380
attcagcatg aatcaggaat cttgggacct tactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaacatttt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
```

```
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca tgccattga accaagaagc    2280 ttctcccaga attcaagaca ccctagcact aggcaaaagc aatttaatgc caccacaatt    2340
ccagaaaatg acatagagaa gactgacccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt attaccccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag gaccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga agactcaca ttgatggccc atcattatta    3120
attgagaata gtccatcagt ctggcaaaat atattagaaa gtgacactga gtttaaaaaa    3180 gtgacaccctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaattc aggaagaaat agaaagaag    3660 gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca aaggatatc tcctaataca    3960 agccagcaga attttgtcac gcaacgtagt aagagagctt tgaaacaatt cagactccca    4020
ctagaagaaa cagaacttga aaaaggata attgtggatg cacctcaac ccagtggtcc    4080 aaaaacatga acatttgac cccgagcacc ctcacacaga tagactacaa tgagaaggag    4140
aaaggggcca ttactcagtc tccccttatca gattgcctta cgaggagtca tagcatccct    4200
```

```
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc aaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac attgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa agatgtgca ctcaggcctg attggacccc ttctggtctg ccacactaac    5640
acactgaacc ctgctcatgg gagacaagtg acagtacagg aatttgctct gttttttcacc    5700
atctttgatg agaccaaaag ctggtacttc actgaaaata tggaaagaaa ctgcagggct    5760
ccctgcaata tccagatgga agatcccact ttttaaagaga attatcgctt ccatgcaatc    5820
aatggctaca taatggatac actacctggc ttagtaatgg ctcaggatca aaggattcga    5880
tggtatctgc tcagcatggg cagcaatgaa aacatccatt ctattcatt cagtggacat    5940
gtgttcactg tacgaaaaaa agaggagtat aaaatggcac tgtacaatct ctatccaggt    6000
gtttttgaga cagtggaaat gttaccatcc aaagctggaa tttggcgggt ggaatgcctt    6060
attggcgagc atctacatgc tgggatgagc acactttttc tggtgtacag caataagtgt    6120
cagactcccc tgggaatggc ttctggacac attagagatt ttcagattac agcttcagga    6180
caatatggac agtgggcccc aaagctggcc agacttcatt attccggatc aatcaatgcc    6240
tggagcacca aggagcccett ttcttggatc aaggtggatc tgttggcacc aatgattatt    6300
cacggcatca agaccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaaacacaa tatttttaac    6480
cctccaatta ttgctcgata catccgtttg cacccaactc attatagcat tcgcagcact    6540
cttcgcatgg agttgatggg ctgtgattta aatagttgca gcatgccatt gggaatggag    6600
```

```
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900 gttttttcagg gaaatcaaga ctccttcaca cctgtggtga actctctaga cccaccgtta    6960
ctgactcgct accttcgaat tcaccccccag agttgggtgc accagattgc cctgaggatg    7020
gaggttctgg gctgcgaggc acaggacctc tac                                  7053
```

<210> SEQ ID NO 6
<211> LENGTH: 1438
<212> TYPE: PRT
<213> ORGANISM: Artificial Sequence
<220> FEATURE:
<223> OTHER INFORMATION: BDDD FVIII

<400> SEQUENCE: 6

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
```

-continued

```
                275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
    690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
            725                 730                 735

Ile Glu Pro Arg Ser Phe Ser Gln Asn Pro Val Leu Lys Arg His
                740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
            770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
        850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110
```

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 7
<211> LENGTH: 4371
<212> TYPE: DNA
<213> ORGANISM: Artificial Sequence
<220> FEATURE:
<223> OTHER INFORMATION: BDDD FVIII

<400> SEQUENCE: 7
atgcaaatag agctctccac ctgcttcttt ctgtgccttt tgcgattctg ctttagtgcc      60
accagaagat actacctggg tgcagtggaa ctgtcatggg actatatgca aagtgatctc     120

```
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggataggggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt cctggaaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa     1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcctt agtcctcgcc    1260
cccgatgaca gaagttataa aagtcaatat ttgaacaatg ccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga ccaagaagc    2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
```

| | |
|---|---|
| cgacactatt ttattgctgc agtggagagg ctctgggatt atgggatgag tagctcccca | 2520 |
| catgttctaa gaaacagggc tcagagtggc agtgtccctc agttcaagaa agttgttttc | 2580 |
| caggaattta ctgatggctc ctttactcag cccttatacc gtggagaact aaatgaacat | 2640 |
| ttgggactcc tggggccata tataagagca gaagttgaag ataatatcat ggtaactttc | 2700 |
| agaaatcagg cctctcgtcc ctattccttc tattctagcc ttatttctta tgaggaagat | 2760 |
| cagaggcaag gagcagaacc tagaaaaaac tttgtcaagc ctaatgaaac caaaacttac | 2820 |
| ttttggaaag tgcaacatca tatggcaccc actaaagatg agtttgactg caaagcctgg | 2880 |
| gcttatttct ctgatgttga cctggaaaaa gatgtgcact caggcctgat ggacccctt | 2940 |
| ctggtctgcc acactaacac actgaaccct gctcatggga gacaagtgac agtacaggaa | 3000 |
| tttgctctgt ttttcaccat ctttgatgag accaaaagct ggtacttcac tgaaaatatg | 3060 |
| gaaagaaact gcagggctcc ctgcaatatc agatggaag atcccacttt taaagagaat | 3120 |
| tatcgcttcc atgcaatcaa tggctacata atggatacac tacctggctt agtaatggct | 3180 |
| caggatcaaa ggattcgatg gtatctgctc agcatgggca gcaatgaaaa catccattct | 3240 |
| attcatttca gtggacatgt gttcactgta cgaaaaaaag aggagtataa aatggcactg | 3300 |
| tacaatctct atccaggtgt ttttgagaca gtggaaatgt taccatccaa agctggaatt | 3360 |
| tggcgggtgg aatgccttat tggcgagcat ctacatgctg ggatgagcac acttttctg | 3420 |
| gtgtacagca ataagtgtca gactcccctg ggaatggctt ctggacacat tagagatttt | 3480 |
| cagattacag cttcaggaca atatggacag tgggccccaa agctggccag acttcattat | 3540 |
| tccggatcaa tcaatgcctg gagcaccaag gagcccttt cttggatcaa ggtggatctg | 3600 |
| ttggcaccaa tgattattca cggcatcaag acccagggtg cccgtcagaa gttctccagc | 3660 |
| ctctacatct ctcagtttat catcatgtat agtcttgatg ggaagaagtg gcagacttat | 3720 |
| cgaggaaatt ccactggaac cttaatggtc ttctttggca atgtggattc atctgggata | 3780 |
| aaacacaata ttttaaccc tccaattatt gctcgataca tccgtttgca cccaactcat | 3840 |
| tatagcattc gcagcactct tcgcatggag ttgatgggct gtgatttaaa tagttgcagc | 3900 |
| atgccattgg gaatggagag taaagcaata tcagatgcac agattactgc ttcatcctac | 3960 |
| tttaccaata tgtttgccac ctggtctcct tcaaaagctc gacttcacct ccaagggagg | 4020 |
| agtaatgcct ggagacctca ggtgaataat ccaaaagagt ggctgcaagt ggacttccag | 4080 |
| aagacaatga agtcacagg agtaactact cagggagtaa aatctctgct taccagcatg | 4140 |
| tatgtgaagg agttcctcat ctccagcagt caagatggcc atcagtggac tctctttttt | 4200 |
| cagaatggca agtaaaggt ttttcaggga aatcaagact ccttcacacc tgtggtgaac | 4260 |
| tctctagacc caccgttact gactcgctac cttcgaattc accccagag ttgggtgcac | 4320 |
| cagattgccc tgaggatgga ggttctgggc tgcgaggcac aggacctcta c | 4371 |

<210> SEQ ID NO 8
<211> LENGTH: 25
<212> TYPE: PRT
<213> ORGANISM: Artificial Sequence
<220> FEATURE:
<223> OTHER INFORMATION: cleavage site

<400> SEQUENCE: 8

Thr Leu Asp Pro Arg Ser Phe Leu Leu Arg Asn Pro Asn Asp Lys Tyr
1               5                   10                  15

Glu Pro Phe Trp Glu Asp Glu Glu Lys
            20                  25

<210> SEQ ID NO 9
<211> LENGTH: 4
<212> TYPE: PRT
<213> ORGANISM: Artificial Sequence
<220> FEATURE:
<223> OTHER INFORMATION: cleavage site

<400> SEQUENCE: 9

Arg Arg Arg Arg
1

<210> SEQ ID NO 10
<211> LENGTH: 6
<212> TYPE: PRT
<213> ORGANISM: Artificial Sequence
<220> FEATURE:
<223> OTHER INFORMATION: cleavage site

<400> SEQUENCE: 10

Arg Lys Arg Arg Lys Arg
1               5

<210> SEQ ID NO 11
<211> LENGTH: 5
<212> TYPE: PRT
<213> ORGANISM: Artificial Sequence
<220> FEATURE:
<223> OTHER INFORMATION: cleavage site

<400> SEQUENCE: 11

Arg Arg Arg Arg Ser
1               5

<210> SEQ ID NO 12
<211> LENGTH: 9
<212> TYPE: PRT
<213> ORGANISM: Artificial Sequence
<220> FEATURE:
<223> OTHER INFORMATION: cleavage site

<400> SEQUENCE: 12

Thr Gln Ser Phe Asn Asp Phe Thr Arg
1               5

<210> SEQ ID NO 13
<211> LENGTH: 10
<212> TYPE: PRT
<213> ORGANISM: Artificial Sequence
<220> FEATURE:
<223> OTHER INFORMATION: cleavage site

<400> SEQUENCE: 13

Ser Val Ser Gln Thr Ser Lys Leu Thr Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: cleavage site

<400> SEQUENCE: 14

Asp Phe Leu Ala Glu Gly Gly Gly Val Arg
1               5                   10

```
<210> SEQ ID NO 15
<211> LENGTH: 7
<212> TYPE: PRT
<213> ORGANISM: Artificial Sequence
<220> FEATURE:
<223> OTHER INFORMATION: cleavage site

<400> SEQUENCE: 15

Thr Thr Lys Ile Lys Pro Arg
1               5

<210> SEQ ID NO 16
<211> LENGTH: 5
<212> TYPE: PRT
<213> ORGANISM: Artificial Sequence
<220> FEATURE:
<223> OTHER INFORMATION: cleavage site

<400> SEQUENCE: 16

Leu Val Pro Arg Gly
1               5

<210> SEQ ID NO 17
<211> LENGTH: 5
<212> TYPE: PRT
<213> ORGANISM: Artificial Sequence
<220> FEATURE:
<223> OTHER INFORMATION: cleavage site

<400> SEQUENCE: 17

Ala Leu Arg Pro Arg
1               5

<210> SEQ ID NO 18
<211> LENGTH: 7
<212> TYPE: PRT
<213> ORGANISM: Artificial Sequence
<220> FEATURE:
<223> OTHER INFORMATION: cleavage site

<400> SEQUENCE: 18

Lys Leu Thr Arg Ala Glu Thr
1               5

<210> SEQ ID NO 19
<211> LENGTH: 7
<212> TYPE: PRT
<213> ORGANISM: Artificial Sequence
<220> FEATURE:
<223> OTHER INFORMATION: cleavage site

<400> SEQUENCE: 19

Asp Phe Thr Arg Val Val Gly
1               5

<210> SEQ ID NO 20
<211> LENGTH: 8
<212> TYPE: PRT
<213> ORGANISM: Artificial Sequence
<220> FEATURE:
<223> OTHER INFORMATION: cleavage site

<400> SEQUENCE: 20

Thr Met Thr Arg Ile Val Gly Gly
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: cleavage site

<400> SEQUENCE: 21

Ser Pro Phe Arg Ser Thr Gly Gly
1               5

<210> SEQ ID NO 22
<211> LENGTH: 8
<212> TYPE: PRT
<213> ORGANISM: Artificial Sequence
<220> FEATURE:
<223> OTHER INFORMATION: cleavage site

<400> SEQUENCE: 22

Leu Gln Val Arg Ile Val Gly Gly
1               5

<210> SEQ ID NO 23
<211> LENGTH: 8
<212> TYPE: PRT
<213> ORGANISM: Artificial Sequence
<220> FEATURE:
<223> OTHER INFORMATION: cleavage site

<400> SEQUENCE: 23

Pro Leu Gly Arg Ile Val Gly Gly
1               5

<210> SEQ ID NO 24
<211> LENGTH: 8
<212> TYPE: PRT
<213> ORGANISM: Artificial Sequence
<220> FEATURE:
<223> OTHER INFORMATION: cleavage site

<400> SEQUENCE: 24

Ile Glu Gly Arg Thr Val Gly Gly
1               5

<210> SEQ ID NO 25
<211> LENGTH: 8
<212> TYPE: PRT
<213> ORGANISM: Artificial Sequence
<220> FEATURE:
<223> OTHER INFORMATION: cleavage site

<400> SEQUENCE: 25

Leu Thr Pro Arg Ser Leu Leu Val
1               5

<210> SEQ ID NO 26
<211> LENGTH: 8
<212> TYPE: PRT
<213> ORGANISM: Artificial Sequence
<220> FEATURE:
<223> OTHER INFORMATION: cleavage site

<400> SEQUENCE: 26

Leu Gly Pro Val Ser Gly Val Pro
1               5

<210> SEQ ID NO 27
```

```
<211> LENGTH: 8
<212> TYPE: PRT
<213> ORGANISM: Artificial Sequence
<220> FEATURE:
<223> OTHER INFORMATION: cleavage site

<400> SEQUENCE: 27

Val Ala Gly Asp Ser Leu Glu Glu
1               5

<210> SEQ ID NO 28
<211> LENGTH: 8
<212> TYPE: PRT
<213> ORGANISM: Artificial Sequence
<220> FEATURE:
<223> OTHER INFORMATION: cleavage site

<400> SEQUENCE: 28

Gly Pro Ala Gly Leu Gly Gly Ala
1               5

<210> SEQ ID NO 29
<211> LENGTH: 8
<212> TYPE: PRT
<213> ORGANISM: Artificial Sequence
<220> FEATURE:
<223> OTHER INFORMATION: cleavage site

<400> SEQUENCE: 29

Gly Pro Ala Gly Leu Arg Gly Ala
1               5

<210> SEQ ID NO 30
<211> LENGTH: 8
<212> TYPE: PRT
<213> ORGANISM: Artificial Sequence
<220> FEATURE:
<223> OTHER INFORMATION: cleavage site

<400> SEQUENCE: 30

Ala Pro Leu Gly Leu Arg Leu Arg
1               5

<210> SEQ ID NO 31
<211> LENGTH: 8
<212> TYPE: PRT
<213> ORGANISM: Artificial Sequence
<220> FEATURE:
<223> OTHER INFORMATION: cleavage site

<400> SEQUENCE: 31

Pro Ala Leu Pro Leu Val Ala Gln
1               5

<210> SEQ ID NO 32
<211> LENGTH: 7
<212> TYPE: PRT
<213> ORGANISM: Artificial Sequence
<220> FEATURE:
<223> OTHER INFORMATION: cleavage site

<400> SEQUENCE: 32

Glu Asn Leu Tyr Phe Gln Gly
1               5

<210> SEQ ID NO 33
<211> LENGTH: 8
```

```
<212> TYPE: PRT
<213> ORGANISM: Artificial Sequence
<220> FEATURE:
<223> OTHER INFORMATION: cleavage site

<400> SEQUENCE: 33

Asp Asp Asp Lys Ile Val Gly Gly
1               5

<210> SEQ ID NO 34
<211> LENGTH: 8
<212> TYPE: PRT
<213> ORGANISM: Artificial Sequence
<220> FEATURE:
<223> OTHER INFORMATION: cleavage site

<400> SEQUENCE: 34

Leu Glu Val Leu Phe Gln Gly Pro
1               5

<210> SEQ ID NO 35
<211> LENGTH: 8
<212> TYPE: PRT
<213> ORGANISM: Artificial Sequence
<220> FEATURE:
<223> OTHER INFORMATION: cleavage site

<400> SEQUENCE: 35

Leu Pro Lys Thr Gly Ser Glu Ser
1               5

<210> SEQ ID NO 36
<211> LENGTH: 42
<212> TYPE: PRT
<213> ORGANISM: Artificial Sequence
<220> FEATURE:
<223> OTHER INFORMATION: AE42

<400> SEQUENCE: 36

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 37
<211> LENGTH: 143
<212> TYPE: PRT
<213> ORGANISM: Artificial Sequence
<220> FEATURE:
<223> OTHER INFORMATION: AE144

<400> SEQUENCE: 37

Gly Ser Glu Pro Ala Thr Ser Gly Ser Glu Thr Pro Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Ser Pro Ala Gly Ser Pro Thr Ser Thr Glu Glu
        35                  40                  45

Gly Thr Ser Thr Glu Pro Ser Glu Gly Ser Ala Pro Gly Ser Glu Pro
    50                  55                  60

Ala Thr Ser Gly Ser Glu Thr Pro Gly Ser Glu Pro Ala Thr Ser Gly
65                  70                  75                  80
```

-continued

Ser Glu Thr Pro Gly Ser Pro Ala Thr Gly Ser Glu Thr Pro
                85                  90                  95

Gly Thr Ser Thr Glu Pro Ser Glu Gly Ser Ala Pro Gly Thr Ser Glu
            100                 105                 110

Ser Ala Pro Glu Ser Gly Pro Gly Ser Glu Pro Ala Thr Ser Gly Ser
            115                 120                 125

Glu Thr Pro Gly Thr Ser Thr Glu Pro Ser Glu Gly Ser Ala Pro
            130                 135                 140

<210> SEQ ID NO 38
<211> LENGTH: 144
<212> TYPE: PRT
<213> ORGANISM: Artificial Sequence
<220> FEATURE:
<223> OTHER INFORMATION: AG144

<400> SEQUENCE: 38

Gly Thr Pro Gly Ser Gly Thr Ala Ser Ser Pro Gly Ser Ser Thr
1               5                   10                  15

Pro Ser Gly Ala Thr Gly Ser Pro Gly Ser Ser Pro Ser Ala Ser Thr
            20                  25                  30

Gly Thr Gly Pro Gly Ser Ser Pro Ser Ala Ser Thr Gly Thr Gly Pro
            35                  40                  45

Gly Ala Ser Pro Gly Thr Ser Ser Thr Gly Ser Pro Gly Ala Ser Pro
            50                  55                  60

Gly Thr Ser Ser Thr Gly Ser Pro Gly Ser Ser Thr Pro Ser Gly Ala
65                  70                  75                  80

Thr Gly Ser Pro Gly Ser Ser Pro Ser Ala Ser Thr Gly Thr Gly Pro
            85                  90                  95

Gly Ala Ser Pro Gly Thr Ser Ser Thr Gly Ser Pro Gly Ser Ser Pro
            100                 105                 110

Ser Ala Ser Thr Gly Thr Gly Pro Gly Thr Pro Gly Ser Gly Thr Ala
            115                 120                 125

Ser Ser Ser Pro Gly Ser Ser Thr Pro Ser Gly Ala Thr Gly Ser Pro
            130                 135                 140

<210> SEQ ID NO 39
<211> LENGTH: 288
<212> TYPE: PRT
<213> ORGANISM: Artificial Sequence
<220> FEATURE:
<223> OTHER INFORMATION: AE288

<400> SEQUENCE: 39

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
            20                  25                  30

Glu Ser Gly Pro Gly Ser Glu Pro Ala Thr Ser Gly Ser Glu Thr Pro
            35                  40                  45

Gly Thr Ser Glu Ser Ala Thr Pro Glu Ser Gly Pro Gly Thr Ser Thr
            50                  55                  60

Glu Pro Ser Glu Gly Ser Ala Pro Gly Ser Pro Ala Gly Ser Pro Thr
65                  70                  75                  80

Ser Thr Glu Glu Gly Thr Ser Glu Ser Ala Thr Pro Glu Ser Gly Pro
            85                  90                  95

Gly Ser Glu Pro Ala Thr Ser Gly Ser Glu Thr Pro Gly Thr Ser Glu

```
            100                 105                 110
Ser Ala Thr Pro Glu Ser Gly Pro Gly Ser Ala Gly Ser Pro Thr
            115                 120                 125

Ser Thr Glu Glu Gly Ser Pro Ala Gly Ser Pro Thr Ser Thr Glu
        130                 135                 140

Gly Thr Ser Thr Glu Pro Ser Glu Gly Ser Ala Pro Gly Thr Ser Glu
145                 150                 155                 160

Ser Ala Thr Pro Glu Ser Gly Pro Gly Thr Ser Glu Ser Ala Thr Pro
                165                 170                 175

Glu Ser Gly Pro Gly Thr Ser Glu Ser Ala Thr Pro Glu Ser Gly Pro
                180                 185                 190

Gly Ser Glu Pro Ala Thr Ser Gly Ser Glu Thr Pro Gly Ser Glu Pro
            195                 200                 205

Ala Thr Ser Gly Ser Glu Thr Pro Gly Ser Pro Ala Gly Ser Pro Thr
            210                 215                 220

Ser Thr Glu Glu Gly Thr Ser Thr Glu Pro Ser Glu Gly Ser Ala Pro
225                 230                 235                 240

Gly Thr Ser Thr Glu Pro Ser Glu Gly Ser Ala Pro Gly Ser Glu Pro
                245                 250                 255

Ala Thr Ser Gly Ser Glu Thr Pro Gly Thr Ser Glu Ser Ala Thr Pro
                260                 265                 270

Glu Ser Gly Pro Gly Thr Ser Thr Glu Pro Ser Glu Gly Ser Ala Pro
                275                 280                 285

<210> SEQ ID NO 40
<211> LENGTH: 288
<212> TYPE: PRT
<213> ORGANISM: Artificial Sequence
<220> FEATURE:
<223> OTHER INFORMATION: AG288

<400> SEQUENCE: 40

Pro Gly Ala Ser Pro Gly Thr Ser Ser Thr Gly Ser Pro Gly Ala Ser
1               5                   10                  15

Pro Gly Thr Ser Ser Thr Gly Ser Pro Gly Thr Pro Gly Ser Gly Thr
                20                  25                  30

Ala Ser Ser Ser Pro Gly Ser Ser Thr Pro Ser Gly Ala Thr Gly Ser
            35                  40                  45

Pro Gly Thr Pro Gly Ser Gly Thr Ala Ser Ser Ser Pro Gly Ser Ser
        50                  55                  60

Thr Pro Ser Gly Ala Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Ser Ser Thr Pro Ser Gly Ala Thr Gly Ser Pro Gly Ser Ser
                100                 105                 110

Pro Ser Ala Ser Thr Gly Thr Gly Pro Gly Ser Ser Pro Ser Ala Ser
            115                 120                 125

Thr Gly Thr Gly Pro Gly Ala Ser Pro Gly Thr Ser Ser Thr Gly Ser
        130                 135                 140

Pro Gly Thr Pro Gly Ser Gly Thr Ala Ser Ser Ser Pro Gly Ser Ser
145                 150                 155                 160

Thr Pro Ser Gly Ala Thr Gly Ser Pro Gly Ser Ser Pro Ser Ala Ser
                165                 170                 175

Thr Gly Thr Gly Pro Gly Ser Ser Pro Ser Ala Ser Thr Gly Thr Gly
```

```
                    180                 185                 190
Pro Gly Ala Ser Pro Gly Thr Ser Thr Gly Ser Pro Gly Ala Ser
                195                 200                 205

Pro Gly Thr Ser Ser Thr Gly Ser Pro Gly Ser Ser Thr Pro Ser Gly
210                 215                 220

Ala Thr Gly Ser Pro Gly Ser Ser Pro Ser Ala Ser Thr Gly Thr Gly
225                 230                 235                 240

Pro Gly Ala Ser Pro Gly Thr Ser Ser Thr Gly Ser Pro Gly Ser Ser
                245                 250                 255

Pro Ser Ala Ser Thr Gly Thr Gly Pro Gly Thr Pro Gly Ser Gly Thr
                260                 265                 270

Ala Ser Ser Ser Pro Gly Ser Ser Thr Pro Ser Gly Ala Thr Gly Ser
                275                 280                 285

<210> SEQ ID NO 41
<211> LENGTH: 576
<212> TYPE: PRT
<213> ORGANISM: Artificial Sequence
<220> FEATURE:
<223> OTHER INFORMATION: AE576

<400> SEQUENCE: 41

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
                20                  25                  30

Gly Ser Ala Pro Gly Ser Pro Ala Gly Ser Pro Thr Ser Thr Glu Glu
                35                  40                  45

Gly Thr Ser Thr Glu Pro Ser Glu Gly Ser Ala Pro Gly Thr Ser Thr
            50                  55                  60

Glu Pro Ser Glu Gly Ser Ala Pro Gly Thr Ser Glu Ser Ala Thr Pro
65              70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
                115                 120                 125

Glu Ser Gly Pro Gly Thr Ser Thr Glu Pro Ser Glu Gly Ser Ala Pro
                130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
                180                 185                 190

Gly Thr Ser Glu Ser Ala Thr Pro Glu Ser Gly Pro Gly Thr Ser Thr
                195                 200                 205

Glu Pro Ser Glu Gly Ser Ala Pro Gly Thr Ser Glu Ser Ala Thr Pro
                210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Ser Ala Thr Pro
```

260                 265                 270
Glu Ser Gly Pro Gly Thr Ser Glu Ser Ala Thr Pro Glu Ser Gly Pro
            275                 280                 285

Gly Ser Pro Ala Gly Ser Pro Thr Ser Thr Glu Glu Gly Thr Ser Glu
        290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
            340                 345                 350

Glu Pro Ser Glu Gly Ser Ala Pro Gly Thr Ser Thr Glu Pro Ser Glu
        355                 360                 365

Gly Ser Ala Pro Gly Thr Ser Thr Glu Pro Ser Glu Gly Ser Ala Pro
370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
            420                 425                 430

Gly Thr Ser Glu Ser Ala Thr Pro Glu Ser Gly Pro Gly Ser Glu Pro
        435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
        515                 520                 525

Gly Ser Pro Ala Gly Ser Pro Thr Ser Thr Glu Glu Gly Ser Pro Ala
    530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

<210> SEQ ID NO 42
<211> LENGTH: 576
<212> TYPE: PRT
<213> ORGANISM: Artificial Sequence
<220> FEATURE:
<223> OTHER INFORMATION: AG576

<400> SEQUENCE: 42

Pro Gly Thr Pro Gly Ser Gly Thr Ala Ser Ser Ser Pro Gly Ser Ser
1               5                   10                  15

Thr Pro Ser Gly Ala Thr Gly Ser Pro Gly Ser Ser Pro Ser Ala Ser
            20                  25                  30

Thr Gly Thr Gly Pro Gly Ser Ser Pro Ser Ala Ser Thr Gly Thr Gly
        35                  40                  45

Pro Gly Ser Ser Thr Pro Ser Gly Ala Thr Gly Ser Pro Gly Ser Ser

```
                50                  55                  60
Thr Pro Ser Gly Ala Thr Gly Ser Pro Gly Ala Ser Pro Gly Thr Ser
 65                  70                  75                  80

Ser Thr Gly Ser Pro Gly Ala Ser Pro Gly Thr Ser Ser Thr Gly Ser
                     85                  90                  95

Pro Gly Ala Ser Pro Gly Thr Ser Ser Thr Gly Ser Pro Gly Thr Pro
                100                 105                 110

Gly Ser Gly Thr Ala Ser Ser Ser Pro Gly Ala Ser Pro Gly Thr Ser
                115                 120                 125

Ser Thr Gly Ser Pro Gly Ala Ser Pro Gly Thr Ser Ser Thr Gly Ser
                130                 135                 140

Pro Gly Ala Ser Pro Gly Thr Ser Ser Thr Gly Ser Pro Gly Ser Ser
145                 150                 155                 160

Pro Ser Ala Ser Thr Gly Thr Gly Pro Gly Thr Pro Gly Ser Gly Thr
                165                 170                 175

Ala Ser Ser Ser Pro Gly Ala Ser Pro Gly Thr Ser Ser Thr Gly Ser
                180                 185                 190

Pro Gly Ala Ser Pro Gly Thr Ser Ser Thr Gly Ser Pro Gly Ala Ser
                195                 200                 205

Pro Gly Thr Ser Ser Thr Gly Ser Pro Gly Ser Ser Thr Pro Ser Gly
210                 215                 220

Ala Thr Gly Ser Pro Gly Ser Ser Thr Pro Ser Gly Ala Thr Gly Ser
225                 230                 235                 240

Pro Gly Ala Ser Pro Gly Thr Ser Ser Thr Gly Ser Pro Gly Thr Pro
                245                 250                 255

Gly Ser Gly Thr Ala Ser Ser Ser Pro Gly Ser Ser Thr Pro Ser Gly
                260                 265                 270

Ala Thr Gly Ser Pro Gly Ser Ser Thr Pro Ser Gly Ala Thr Gly Ser
                275                 280                 285

Pro Gly Ser Ser Thr Pro Ser Gly Ala Thr Gly Ser Pro Gly Ser Ser
                290                 295                 300

Pro Ser Ala Ser Thr Gly Thr Gly Pro Gly Ala Ser Pro Gly Thr Ser
305                 310                 315                 320

Ser Thr Gly Ser Pro Gly Ala Ser Pro Gly Thr Ser Ser Thr Gly Ser
                325                 330                 335

Pro Gly Thr Pro Gly Ser Gly Thr Ala Ser Ser Ser Pro Gly Ala Ser
                340                 345                 350

Pro Gly Thr Ser Ser Thr Gly Ser Pro Gly Ala Ser Pro Gly Thr Ser
                355                 360                 365

Ser Thr Gly Ser Pro Gly Ala Ser Pro Gly Thr Ser Ser Thr Gly Ser
                370                 375                 380

Pro Gly Ala Ser Pro Gly Thr Ser Ser Thr Gly Ser Pro Gly Thr Pro
385                 390                 395                 400

Gly Ser Gly Thr Ala Ser Ser Ser Pro Gly Ser Ser Thr Pro Ser Gly
                405                 410                 415

Ala Thr Gly Ser Pro Gly Thr Pro Gly Ser Gly Thr Ala Ser Ser Ser
                420                 425                 430

Pro Gly Ser Ser Thr Pro Ser Gly Ala Thr Gly Ser Pro Gly Thr Pro
                435                 440                 445

Gly Ser Gly Thr Ala Ser Ser Ser Pro Gly Ser Ser Thr Pro Ser Gly
                450                 455                 460

Ala Thr Gly Ser Pro Gly Ser Ser Thr Pro Ser Gly Ala Thr Gly Ser
465                 470                 475                 480
```

```
Pro Gly Ser Ser Pro Ser Ala Ser Thr Gly Thr Pro Gly Ser Ser
                485                 490                 495

Pro Ser Ala Ser Thr Gly Thr Gly Pro Gly Ala Ser Pro Gly Thr Ser
            500                 505                 510

Ser Thr Gly Ser Pro Gly Thr Pro Gly Ser Gly Thr Ala Ser Ser Ser
            515                 520                 525

Pro Gly Ser Ser Thr Pro Ser Gly Ala Thr Gly Ser Pro Gly Ser Ser
            530                 535                 540

Pro Ser Ala Ser Thr Gly Thr Gly Pro Gly Ser Ser Pro Ser Ala Ser
545                 550                 555                 560

Thr Gly Thr Gly Pro Gly Ala Ser Pro Gly Thr Ser Ser Thr Gly Ser
                565                 570                 575
```

<210> SEQ ID NO 43
<211> LENGTH: 864
<212> TYPE: PRT
<213> ORGANISM: Artificial Sequence
<220> FEATURE:
<223> OTHER INFORMATION: AE864

<400> SEQUENCE: 43

```
Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
                20                  25                  30

Gly Ser Ala Pro Gly Ser Pro Ala Gly Ser Pro Thr Ser Thr Glu Glu
            35                  40                  45

Gly Thr Ser Thr Glu Pro Ser Glu Gly Ser Ala Pro Gly Thr Ser Thr
        50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
            115                 120                 125

Glu Ser Gly Pro Gly Thr Ser Thr Glu Pro Ser Glu Gly Ser Ala Pro
        130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
                180                 185                 190

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Glu Ser Ala Thr Pro
        210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
                260                 265                 270
```

```
Glu Ser Gly Pro Gly Thr Ser Glu Ser Ala Thr Pro Glu Ser Gly Pro
            275                 280                 285

Gly Ser Pro Ala Gly Ser Pro Thr Ser Thr Glu Glu Gly Thr Ser Glu
            290                 295                 300

Ser Ala Thr Pro Glu Ser Gly Pro Gly Ser Glu Pro Ala Thr Ser Gly
305                     310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
                340                 345                 350

Glu Pro Ser Glu Gly Ser Ala Pro Gly Thr Ser Thr Glu Pro Ser Glu
            355                 360                 365

Gly Ser Ala Pro Gly Thr Ser Thr Glu Pro Ser Glu Gly Ser Ala Pro
            370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
                420                 425                 430

Gly Thr Ser Glu Ser Ala Thr Pro Glu Ser Gly Pro Gly Ser Glu Pro
            435                 440                 445

Ala Thr Ser Gly Ser Glu Thr Pro Gly Thr Ser Glu Ser Ala Thr Pro
            450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
            515                 520                 525

Gly Ser Pro Ala Gly Ser Pro Thr Ser Thr Glu Glu Gly Ser Pro Ala
            530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

Gly Thr Ser Glu Ser Ala Thr Pro Glu Ser Gly Pro Gly Ser Glu Pro
            580                 585                 590

Ala Thr Ser Gly Ser Glu Thr Pro Gly Thr Ser Glu Ser Ala Thr Pro
            595                 600                 605

Glu Ser Gly Pro Gly Ser Glu Pro Ala Thr Ser Gly Ser Glu Thr Pro
            610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
                645                 650                 655

Ser Thr Glu Glu Gly Thr Ser Glu Ser Ala Thr Pro Glu Ser Gly Pro
                660                 665                 670

Gly Ser Glu Pro Ala Thr Ser Gly Ser Glu Thr Pro Gly Thr Ser Glu
            675                 680                 685
```

```
Ser Ala Thr Pro Glu Ser Gly Pro Ser Pro Gly Ser Pro Thr
690                 695                 700
Ser Thr Glu Glu Gly Ser Pro Ala Gly Ser Pro Thr Ser Thr Glu Glu
705                 710                 715                 720
Gly Thr Ser Thr Glu Pro Ser Glu Gly Ser Ala Pro Gly Thr Ser Glu
                725                 730                 735
Ser Ala Thr Pro Glu Ser Gly Pro Gly Thr Ser Glu Ser Ala Thr Pro
                740                 745                 750
Glu Ser Gly Pro Gly Thr Ser Glu Ser Ala Thr Pro Glu Ser Gly Pro
                755                 760                 765
Gly Ser Glu Pro Ala Thr Ser Gly Ser Glu Thr Pro Gly Ser Glu Pro
770                 775                 780
Ala Thr Ser Gly Ser Glu Thr Pro Gly Ser Pro Ala Gly Ser Pro Thr
785                 790                 795                 800
Ser Thr Glu Glu Gly Thr Ser Thr Glu Pro Ser Glu Gly Ser Ala Pro
                805                 810                 815
Gly Thr Ser Thr Glu Pro Ser Glu Gly Ser Ala Pro Gly Ser Glu Pro
                820                 825                 830
Ala Thr Ser Gly Ser Glu Thr Pro Gly Thr Ser Glu Ser Ala Thr Pro
                835                 840                 845
Glu Ser Gly Pro Gly Thr Ser Thr Glu Pro Ser Glu Gly Ser Ala Pro
                850                 855                 860

<210> SEQ ID NO 44
<211> LENGTH: 864
<212> TYPE: PRT
<213> ORGANISM: Artificial Sequence
<220> FEATURE:
<223> OTHER INFORMATION: AG864

<400> SEQUENCE: 44

Gly Ala Ser Pro Gly Thr Ser Ser Thr Gly Ser Pro Gly Ser Ser Pro
1               5                   10                  15
Ser Ala Ser Thr Gly Thr Gly Pro Gly Ser Ser Pro Ser Ala Ser Thr
                20                  25                  30
Gly Thr Gly Pro Gly Thr Pro Gly Ser Gly Thr Ala Ser Ser Ser Pro
                35                  40                  45
Gly Ser Ser Thr Pro Ser Gly Ala Thr Gly Ser Pro Gly Ser Ser Pro
                50                  55                  60
Ser Ala Ser Thr Gly Thr Gly Pro Gly Ala Ser Pro Gly Thr Ser Ser
65                  70                  75                  80
Thr Gly Ser Pro Gly Thr Pro Gly Ser Gly Thr Ala Ser Ser Ser Pro
                85                  90                  95
Gly Ser Ser Thr Pro Ser Gly Ala Thr Gly Ser Pro Gly Thr Pro Gly
                100                 105                 110
Ser Gly Thr Ala Ser Ser Ser Pro Gly Ala Ser Pro Gly Thr Ser Ser
                115                 120                 125
Thr Gly Ser Pro Gly Ala Ser Pro Gly Thr Ser Ser Thr Gly Ser Pro
                130                 135                 140
Gly Thr Pro Gly Ser Gly Thr Ala Ser Ser Ser Pro Gly Ser Ser Thr
145                 150                 155                 160
Pro Ser Gly Ala Thr Gly Ser Pro Gly Ala Ser Pro Gly Thr Ser Ser
                165                 170                 175
Thr Gly Ser Pro Gly Thr Pro Gly Ser Gly Thr Ala Ser Ser Ser Pro
                180                 185                 190
```

```
Gly Ser Ser Thr Pro Ser Gly Ala Thr Gly Ser Ser Pro
            195                 200             205
Ser Ala Ser Thr Gly Thr Gly Pro Gly Ser Ser Pro Ser Ala Ser Thr
    210             215                 220
Gly Thr Gly Pro Gly Ser Ser Thr Pro Ser Gly Ala Thr Gly Ser Pro
225             230                 235                 240
Gly Ser Ser Thr Pro Ser Gly Ala Thr Gly Ser Pro Gly Ala Ser Pro
                245             250                 255
Gly Thr Ser Ser Thr Gly Ser Pro Gly Ala Ser Pro Gly Thr Ser Ser
            260                 265             270
Thr Gly Ser Pro Gly Ala Ser Pro Gly Thr Ser Thr Gly Ser Pro
        275                 280                 285
Gly Thr Pro Gly Ser Gly Thr Ala Ser Ser Pro Gly Ala Ser Pro
    290                 295                 300
Gly Thr Ser Ser Thr Gly Ser Pro Gly Ala Ser Pro Gly Thr Ser Ser
305             310                 315                 320
Thr Gly Ser Pro Gly Ala Ser Pro Gly Thr Ser Thr Gly Ser Pro
            325                 330                 335
Gly Ser Ser Pro Ser Ala Ser Thr Gly Thr Gly Pro Gly Thr Pro Gly
            340                 345                 350
Ser Gly Thr Ala Ser Ser Pro Gly Ala Ser Pro Gly Thr Ser Ser
            355                 360             365
Thr Gly Ser Pro Gly Ala Ser Pro Gly Thr Ser Ser Thr Gly Ser Pro
        370                 375                 380
Gly Ala Ser Pro Gly Thr Ser Thr Gly Ser Pro Gly Ser Ser Thr
385                 390                 395             400
Pro Ser Gly Ala Thr Gly Ser Pro Gly Ser Ser Thr Pro Ser Gly Ala
            405                 410                 415
Thr Gly Ser Pro Gly Ala Ser Pro Gly Thr Ser Ser Thr Gly Ser Pro
            420                 425                 430
Gly Thr Pro Gly Ser Gly Thr Ala Ser Ser Pro Gly Ser Ser Thr
        435                 440                 445
Pro Ser Gly Ala Thr Gly Ser Pro Gly Ser Ser Thr Pro Ser Gly Ala
    450                 455                 460
Thr Gly Ser Pro Gly Ser Ser Thr Pro Ser Gly Ala Thr Gly Ser Pro
465                 470                 475                 480
Gly Ser Ser Pro Ser Ala Ser Thr Gly Thr Gly Pro Gly Ala Ser Pro
            485                 490                 495
Gly Thr Ser Ser Thr Gly Ser Pro Gly Ala Ser Pro Gly Thr Ser Ser
            500                 505             510
Thr Gly Ser Pro Gly Thr Pro Gly Ser Gly Thr Ala Ser Ser Pro
        515                 520                 525
Gly Ala Ser Pro Gly Thr Ser Ser Thr Gly Ser Pro Gly Ala Ser Pro
    530                 535                 540
Gly Thr Ser Ser Thr Gly Ser Pro Gly Ala Ser Pro Gly Thr Ser Ser
545                 550                 555                 560
Thr Gly Ser Pro Gly Ala Ser Pro Gly Thr Ser Ser Thr Gly Ser Pro
                565                 570                 575
Gly Thr Pro Gly Ser Gly Thr Ala Ser Ser Pro Gly Ser Ser Thr
            580                 585             590
Pro Ser Gly Ala Thr Gly Ser Pro Gly Thr Pro Gly Ser Gly Thr Ala
            595                 600                 605
Ser Ser Ser Pro Gly Ser Ser Thr Pro Ser Gly Ala Thr Gly Ser Pro
```

```
            610                 615                 620
Gly Thr Pro Gly Ser Gly Thr Ala Ser Ser Pro Gly Ser Thr
625                 630                 635                 640

Pro Ser Gly Ala Thr Gly Ser Pro Gly Ser Ser Thr Pro Ser Gly Ala
                645                 650                 655

Thr Gly Ser Pro Gly Ser Ser Pro Ser Ala Ser Thr Gly Thr Gly Pro
                660                 665                 670

Gly Ser Ser Pro Ser Ala Ser Thr Gly Thr Gly Pro Gly Ala Ser Pro
                675                 680                 685

Gly Thr Ser Ser Thr Gly Ser Pro Gly Thr Pro Gly Ser Gly Thr Ala
        690                 695                 700

Ser Ser Pro Gly Ser Ser Thr Pro Ser Gly Ala Thr Gly Ser Pro
705                 710                 715                 720

Gly Ser Ser Pro Ser Ala Ser Thr Gly Thr Gly Pro Gly Ser Ser Pro
                725                 730                 735

Ser Ala Ser Thr Gly Thr Gly Pro Gly Ala Ser Pro Gly Thr Ser Ser
                740                 745                 750

Thr Gly Ser Pro Gly Ala Ser Pro Gly Thr Ser Ser Thr Gly Ser Pro
                755                 760                 765

Gly Ser Ser Thr Pro Ser Gly Ala Thr Gly Ser Pro Gly Ser Ser Pro
        770                 775                 780

Ser Ala Ser Thr Gly Thr Gly Pro Gly Ala Ser Pro Gly Thr Ser Ser
785                 790                 795                 800

Thr Gly Ser Pro Gly Ser Ser Pro Ser Ala Ser Thr Gly Thr Gly Pro
                805                 810                 815

Gly Thr Pro Gly Ser Gly Thr Ala Ser Ser Pro Gly Ser Ser Thr
                820                 825                 830

Pro Ser Gly Ala Thr Gly Ser Pro Gly Ser Ser Thr Pro Ser Gly Ala
        835                 840                 845

Thr Gly Ser Pro Gly Ala Ser Pro Gly Thr Ser Ser Thr Gly Ser Pro
        850                 855                 860

<210> SEQ ID NO 45
<211> LENGTH: 9
<212> TYPE: PRT
<213> ORGANISM: Artificial Sequence
<220> FEATURE:
<223> OTHER INFORMATION: cleavage site

<400> SEQUENCE: 45

Thr Gln Ser Phe Asn Asp Phe Thr Arg
1               5

<210> SEQ ID NO 46
<211> LENGTH: 10
<212> TYPE: PRT
<213> ORGANISM: Artificial Sequence
<220> FEATURE:
<223> OTHER INFORMATION: cleavage site

<400> SEQUENCE: 46

Ser Val Ser Gln Thr Ser Lys Leu Thr Arg
1               5                   10

<210> SEQ ID NO 47
<211> LENGTH: 10
<212> TYPE: PRT
<213> ORGANISM: Artificial Sequence
<220> FEATURE:
```

```
<223> OTHER INFORMATION: cleavage site

<400> SEQUENCE: 47

Asp Phe Leu Ala Glu Gly Gly Gly Val Arg
1               5                   10

<210> SEQ ID NO 48
<211> LENGTH: 7
<212> TYPE: PRT
<213> ORGANISM: Artificial Sequence
<220> FEATURE:
<223> OTHER INFORMATION: cleavage site

<400> SEQUENCE: 48

Thr Thr Lys Ile Lys Pro Arg
1               5

<210> SEQ ID NO 49
<211> LENGTH: 5
<212> TYPE: PRT
<213> ORGANISM: Artificial Sequence
<220> FEATURE:
<223> OTHER INFORMATION: cleavage site

<400> SEQUENCE: 49

Leu Val Pro Arg Gly
1               5

<210> SEQ ID NO 50
<211> LENGTH: 5
<212> TYPE: PRT
<213> ORGANISM: Artificial Sequence
<220> FEATURE:
<223> OTHER INFORMATION: cleavage site

<400> SEQUENCE: 50

Ala Leu Arg Pro Arg
1               5

<210> SEQ ID NO 51
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 51

Leu Pro Xaa Thr Gly
1               5

<210> SEQ ID NO 52
<211> LENGTH: 11
<212> TYPE: PRT
<213> ORGANISM: Artificial Sequence
<220> FEATURE:
<223> OTHER INFORMATION: polypeptide

<400> SEQUENCE: 52

Pro Lys Asn Ser Ser Met Ile Ser Asn Thr Pro
1               5                   10

<210> SEQ ID NO 53
<211> LENGTH: 7
```

```
<212> TYPE: PRT
<213> ORGANISM: Artificial Sequence
<220> FEATURE:
<223> OTHER INFORMATION: polypeptide

<400> SEQUENCE: 53

His Gln Ser Leu Gly Thr Gln
1               5

<210> SEQ ID NO 54
<211> LENGTH: 8
<212> TYPE: PRT
<213> ORGANISM: Artificial Sequence
<220> FEATURE:
<223> OTHER INFORMATION: polypeptide

<400> SEQUENCE: 54

His Gln Asn Leu Ser Asp Gly Lys
1               5

<210> SEQ ID NO 55
<211> LENGTH: 8
<212> TYPE: PRT
<213> ORGANISM: Artificial Sequence
<220> FEATURE:
<223> OTHER INFORMATION: polypeptide

<400> SEQUENCE: 55

His Gln Asn Ile Ser Asp Gly Lys
1               5

<210> SEQ ID NO 56
<211> LENGTH: 8
<212> TYPE: PRT
<213> ORGANISM: Artificial Sequence
<220> FEATURE:
<223> OTHER INFORMATION: polypeptide

<400> SEQUENCE: 56

Val Ile Ser Ser His Leu Gly Gln
1               5

<210> SEQ ID NO 57
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(4)
<223> OTHER INFORMATION: Repeat from 1 to 100 times

<400> SEQUENCE: 57

Gly Gly Gly Ser
1

<210> SEQ ID NO 58
<211> LENGTH: 8
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(3)
<223> OTHER INFORMATION: May be repeated 1 to 100 times
<220> FEATURE:
<221> NAME/KEY: REPEAT
```

```
<222> LOCATION: (4)..(8)
<223> OTHER INFORMATION: May be repeated 1 to 100 times

<400> SEQUENCE: 58

Gly Gly Ser Gly Gly Gly Gly Ser
1               5

<210> SEQ ID NO 59
<211> LENGTH: 7
<212> TYPE: PRT
<213> ORGANISM: Artificial Sequence
<220> FEATURE:
<223> OTHER INFORMATION: linker

<400> SEQUENCE: 59

Ser Gly Gly Ser Gly Gly Ser
1               5

<210> SEQ ID NO 60
<211> LENGTH: 15
<212> TYPE: PRT
<213> ORGANISM: Artificial Sequence
<220> FEATURE:
<223> OTHER INFORMATION: linker

<400> SEQUENCE: 60

Gly Gly Ser Gly Gly Ser Gly Gly Ser Gly Gly Ser Gly Gly Gly
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: linker

<400> SEQUENCE: 61

Gly Gly Ser Gly Gly Ser Gly Gly Gly Gly Ser Gly Gly Gly Gly Ser
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: linker

<400> SEQUENCE: 62

Gly Gly Ser Gly Gly Ser Gly Gly Ser Gly Gly Ser Gly Gly Ser Gly
1               5                   10                  15

Gly Ser

<210> SEQ ID NO 63
<211> LENGTH: 15
<212> TYPE: PRT
<213> ORGANISM: Artificial Sequence
<220> FEATURE:
<223> OTHER INFORMATION: linker

<400> SEQUENCE: 63

Gly Gly Gly Gly Ser Gly Gly Gly Gly Ser Gly Gly Gly Gly Ser
1               5                   10                  15

<210> SEQ ID NO 64
<211> LENGTH: 5
<212> TYPE: PRT
```

```
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: May be repeated 1-20 times

<400> SEQUENCE: 64

Gly Gly Gly Gly Ser
1               5

<210> SEQ ID NO 65
<211> LENGTH: 7
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 65

Lys Leu Thr Arg Ala Glu Thr
1               5

<210> SEQ ID NO 66
<211> LENGTH: 7
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 66

Asp Phe Thr Arg Val Val Gly
1               5

<210> SEQ ID NO 67
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage Site

<400> SEQUENCE: 67

Thr Met Thr Arg Ile Val Gly Gly
1               5

<210> SEQ ID NO 68
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 68

Ser Pro Phe Arg Ser Thr Gly Gly
```

```
<210> SEQ ID NO 69
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 69

Leu Gln Val Arg Ile Val Gly Gly
 1               5

<210> SEQ ID NO 70
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 70

Pro Leu Gly Arg Ile Val Gly Gly
 1               5

<210> SEQ ID NO 71
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 71

Ile Glu Gly Arg Thr Val Gly Gly
 1               5

<210> SEQ ID NO 72
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: cleavage site

<400> SEQUENCE: 72

Leu Thr Pro Arg Ser Leu Leu Val
 1               5

<210> SEQ ID NO 73
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
```

```
<222> LOCATION: (4)..(5)
<223> OTHER INFORMATION: cleavage site

<400> SEQUENCE: 73

Leu Gly Pro Val Ser Gly Val Pro
1               5

<210> SEQ ID NO 74
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 74

Val Ala Gly Asp Ser Leu Glu Glu
1               5

<210> SEQ ID NO 75
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 75

Gly Pro Ala Gly Leu Gly Gly Ala
1               5

<210> SEQ ID NO 76
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 76

Gly Pro Ala Gly Leu Arg Gly Ala
1               5

<210> SEQ ID NO 77
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 77

Ala Pro Leu Gly Leu Arg Leu Arg
1               5

<210> SEQ ID NO 78
<211> LENGTH: 8
```

```
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 78

Pro Ala Leu Pro Leu Val Ala Gln
1               5

<210> SEQ ID NO 79
<211> LENGTH: 7
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (6)..(7)
<223> OTHER INFORMATION: Cleavage site

<400> SEQUENCE: 79

Glu Asn Leu Tyr Phe Gln Gly
1               5

<210> SEQ ID NO 80
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 80

Asp Asp Asp Lys Ile Val Gly Gly
1               5

<210> SEQ ID NO 81
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (6)..(7)
<223> OTHER INFORMATION: Cleavage site

<400> SEQUENCE: 81

Leu Glu Val Leu Phe Gln Gly Pro
1               5

<210> SEQ ID NO 82
<211> LENGTH: 8
<212> TYPE: PRT
<213> ORGANISM: Artificial Sequence
<220> FEATURE:
<223> OTHER INFORMATION: cleavage site
<220> FEATURE:
<221> NAME/KEY: MISC_FEATURE
<222> LOCATION: (4)..(5)
<223> OTHER INFORMATION: Cleavage site

<400> SEQUENCE: 82
```

Leu Pro Lys Thr Gly Ser Glu Ser
1               5

<210> SEQ ID NO 83
<211> LENGTH: 9
<212> TYPE: PRT
<213> ORGANISM: Artificial Sequence
<220> FEATURE:
<223> OTHER INFORMATION: cleavage site

<400> SEQUENCE: 83

Thr Gln Ser Phe Asn Asp Phe Thr Arg
1               5

<210> SEQ ID NO 84
<211> LENGTH: 10
<212> TYPE: PRT
<213> ORGANISM: Artificial Sequence
<220> FEATURE:
<223> OTHER INFORMATION: cleavage site

<400> SEQUENCE: 84

Ser Val Ser Gln Thr Ser Lys Leu Thr Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: cleavage site

<400> SEQUENCE: 85

Asp Phe Leu Ala Glu Gly Gly Gly Val Arg
1               5                   10

<210> SEQ ID NO 86
<211> LENGTH: 7
<212> TYPE: PRT
<213> ORGANISM: Artificial Sequence
<220> FEATURE:
<223> OTHER INFORMATION: cleavage site

<400> SEQUENCE: 86

Thr Thr Lys Ile Lys Pro Arg
1               5

<210> SEQ ID NO 87
<211> LENGTH: 5
<212> TYPE: PRT
<213> ORGANISM: Artificial Sequence
<220> FEATURE:
<223> OTHER INFORMATION: cleavage site

<400> SEQUENCE: 87

Leu Val Pro Arg Gly
1               5

<210> SEQ ID NO 88
<211> LENGTH: 10
<212> TYPE: PRT
<213> ORGANISM: Artificial Sequence
<220> FEATURE:
<223> OTHER INFORMATION: cleavage site

<400> SEQUENCE: 88

Ala Leu Arg Pro Arg Val Val Gly Gly Ala

<210> SEQ ID NO 89
<211> LENGTH: 1896
<212> TYPE: PRT
<213> ORGANISM: Artificial Sequence
<220> FEATURE:
<223> OTHER INFORMATION: FVIII 198

<400> SEQUENCE: 89

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
```

-continued

```
                355                 360                 365
Leu Thr Asp Ser Glu Met Asp Val Val Arg Phe Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
            405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
        690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
```

-continued

```
Ile Glu Lys Thr Asp Pro Trp Phe Ala His Arg Thr Pro Met Pro Lys
785                 790                 795                 800

Ile Gln Asn Val Ser Ser Asp Leu Leu Met Leu Leu Arg Gln Ser
            805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Glu Ile Thr Arg Thr Thr Leu
            980                 985                 990

Gln Ser Asp Gln Glu Glu Ile Asp  Tyr Asp Asp Thr Ile Ser Val Glu
            995                 1000                1005

Met Lys Lys Glu Asp Phe Asp  Ile Tyr Asp Glu Asp  Glu Asn Gln
    1010                1015                1020

Ser Pro Arg Ser Phe Gln Lys  Lys Thr Arg His Tyr  Phe Ile Ala
    1025                1030                1035

Ala Val Glu Arg Leu Trp Asp  Tyr Gly Met Ser Ser  Ser Pro His
    1040                1045                1050

Val Leu Arg Asn Arg Ala Gln  Ser Gly Ser Val Pro  Gln Phe Lys
    1055                1060                1065

Lys Val Val Phe Gln Glu Phe  Thr Asp Gly Ser Phe  Thr Gln Pro
    1070                1075                1080

Leu Tyr Arg Gly Glu Leu Asn  Glu His Leu Gly Leu  Leu Gly Pro
    1085                1090                1095

Tyr Ile Arg Ala Glu Val Glu  Asp Asn Ile Met Val  Thr Phe Arg
    1100                1105                1110

Asn Gln Ala Ser Arg Pro Tyr  Ser Phe Tyr Ser Ser  Leu Ile Ser
    1115                1120                1125

Tyr Glu Glu Asp Gln Arg Gln  Gly Ala Glu Pro Arg  Lys Asn Phe
    1130                1135                1140

Val Lys Pro Asn Glu Thr Lys  Thr Tyr Phe Trp Lys  Val Gln His
    1145                1150                1155

His Met Ala Pro Thr Lys Asp  Glu Phe Asp Cys Lys  Ala Trp Ala
    1160                1165                1170

Tyr Phe Ser Asp Val Asp Leu  Glu Lys Asp Val His  Ser Gly Leu
    1175                1180                1185
```

```
Ile Gly Pro Leu Leu Val Cys His Thr Asn Thr Leu Asn Pro Ala
1190             1195                 1200

His Gly Arg Gln Val Thr Val Gln Glu Phe Ala Leu Phe Phe Thr
1205             1210                 1215

Ile Phe Asp Glu Thr Lys Ser Trp Tyr Phe Thr Glu Asn Met Glu
1220             1225                 1230

Arg Asn Cys Arg Ala Pro Cys Asn Ile Gln Met Glu Asp Pro Thr
1235             1240                 1245

Phe Lys Glu Asn Tyr Arg Phe His Ala Ile Asn Gly Tyr Ile Met
1250             1255                 1260

Asp Thr Leu Pro Gly Leu Val Met Ala Gln Asp Gln Arg Ile Arg
1265             1270                 1275

Trp Tyr Leu Leu Ser Met Gly Ser Asn Glu Asn Ile His Ser Ile
1280             1285                 1290

His Phe Ser Gly His Val Phe Thr Val Arg Lys Lys Glu Glu Tyr
1295             1300                 1305

Lys Met Ala Leu Tyr Asn Leu Tyr Pro Gly Val Phe Glu Thr Val
1310             1315                 1320

Glu Met Leu Pro Ser Lys Ala Gly Ile Trp Arg Val Glu Cys Leu
1325             1330                 1335

Ile Gly Glu His Leu His Ala Gly Met Ser Thr Leu Phe Leu Val
1340             1345                 1350

Tyr Ser Asn Lys Cys Gln Thr Pro Leu Gly Met Ala Ser Gly His
1355             1360                 1365

Ile Arg Asp Phe Gln Ile Thr Ala Ser Gly Gln Tyr Gly Gln Trp
1370             1375                 1380

Ala Pro Lys Leu Ala Arg Leu His Tyr Ser Gly Ser Ile Asn Ala
1385             1390                 1395

Trp Ser Thr Lys Glu Pro Phe Ser Trp Ile Lys Val Asp Leu Leu
1400             1405                 1410

Ala Pro Met Ile Ile His Gly Ile Lys Thr Gln Gly Ala Arg Gln
1415             1420                 1425

Lys Phe Ser Ser Leu Tyr Ile Ser Gln Phe Ile Ile Met Tyr Ser
1430             1435                 1440

Leu Asp Gly Lys Lys Trp Gln Thr Tyr Arg Gly Asn Ser Thr Gly
1445             1450                 1455

Thr Leu Met Val Phe Phe Gly Asn Val Asp Ser Ser Gly Ile Lys
1460             1465                 1470

His Asn Ile Phe Asn Pro Pro Ile Ile Ala Arg Tyr Ile Arg Leu
1475             1480                 1485

His Pro Thr His Tyr Ser Ile Arg Ser Thr Leu Arg Met Glu Leu
1490             1495                 1500

Met Gly Cys Asp Leu Asn Ser Cys Ser Met Pro Leu Gly Met Glu
1505             1510                 1515

Ser Lys Ala Ile Ser Asp Ala Gln Ile Thr Ala Ser Ser Tyr Phe
1520             1525                 1530

Thr Asn Met Phe Ala Thr Trp Ser Pro Ser Lys Ala Arg Leu His
1535             1540                 1545

Leu Gln Gly Arg Ser Asn Ala Trp Arg Pro Gln Val Asn Asn Pro
1550             1555                 1560

Lys Glu Trp Leu Gln Val Asp Phe Gln Lys Thr Met Lys Val Thr
1565             1570                 1575

Gly Val Thr Thr Gln Gly Val Lys Ser Leu Leu Thr Ser Met Tyr
```

```
                         1580                1585                1590
Val  Lys  Glu  Phe  Leu  Ile  Ser  Ser  Ser  Gln  Asp  Gly  His  Gln  Trp
          1595                1600                1605

Thr  Leu  Phe  Phe  Gln  Asn  Gly  Lys  Val  Lys  Val  Phe  Gln  Gly  Asn
1610                1615                     1620

Gln  Asp  Ser  Phe  Thr  Pro  Val  Val  Asn  Ser  Leu  Asp  Pro  Pro  Leu
     1625                1630                     1635

Leu  Thr  Arg  Tyr  Leu  Arg  Ile  His  Pro  Gln  Ser  Trp  Val  His  Gln
1640                1645                     1650

Ile  Ala  Leu  Arg  Met  Glu  Val  Leu  Gly  Cys  Glu  Ala  Gln  Asp  Leu
     1655                1660                     1665

Tyr  Asp  Lys  Thr  His  Thr  Cys  Pro  Pro  Cys  Pro  Ala  Pro  Glu  Leu
1670                1675                     1680

Leu  Gly  Gly  Pro  Ser  Val  Phe  Leu  Phe  Pro  Pro  Lys  Pro  Lys  Asp
     1685                1690                     1695

Thr  Leu  Met  Ile  Ser  Arg  Thr  Pro  Glu  Val  Thr  Cys  Val  Val  Val
1700                1705                     1710

Asp  Val  Ser  His  Glu  Asp  Pro  Glu  Val  Lys  Phe  Asn  Trp  Tyr  Val
     1715                1720                     1725

Asp  Gly  Val  Glu  Val  His  Asn  Ala  Lys  Thr  Lys  Pro  Arg  Glu  Glu
1730                1735                     1740

Gln  Tyr  Asn  Ser  Thr  Tyr  Arg  Val  Val  Ser  Val  Leu  Thr  Val  Leu
     1745                1750                     1755

His  Gln  Asp  Trp  Leu  Asn  Gly  Lys  Glu  Tyr  Lys  Cys  Lys  Val  Ser
1760                1765                     1770

Asn  Lys  Ala  Leu  Pro  Ala  Pro  Ile  Glu  Lys  Thr  Ile  Ser  Lys  Ala
     1775                1780                     1785

Lys  Gly  Gln  Pro  Arg  Glu  Pro  Gln  Val  Tyr  Thr  Leu  Pro  Pro  Ser
1790                1795                     1800

Arg  Asp  Glu  Leu  Thr  Lys  Asn  Gln  Val  Ser  Leu  Thr  Cys  Leu  Val
     1805                1810                     1815

Lys  Gly  Phe  Tyr  Pro  Ser  Asp  Ile  Ala  Val  Glu  Trp  Glu  Ser  Asn
1820                1825                     1830

Gly  Gln  Pro  Glu  Asn  Asn  Tyr  Lys  Thr  Thr  Pro  Pro  Val  Leu  Asp
     1835                1840                     1845

Ser  Asp  Gly  Ser  Phe  Phe  Leu  Tyr  Ser  Lys  Leu  Thr  Val  Asp  Lys
1850                1855                     1860

Ser  Arg  Trp  Gln  Gln  Gly  Asn  Val  Phe  Ser  Cys  Ser  Val  Met  His
     1865                1870                     1875

Glu  Ala  Leu  His  Asn  His  Tyr  Thr  Gln  Lys  Ser  Leu  Ser  Leu  Ser
1880                1885                     1890

Pro  Gly  Lys
     1895

<210> SEQ ID NO 90
<211> LENGTH: 99
<212> TYPE: DNA
<213> ORGANISM: Artificial Sequence
<220> FEATURE:
<223> OTHER INFORMATION: ESC48- Fwd - VWF-D'D3 with VIII signal and
      BsiW1 site

<400> SEQUENCE: 90
tcgcgacgta cggccgccac catgcaaata gagctctcca cctgcttctt tctgtgcctt    60
ttgcgattct gctttagcct atcctgtcgg ccccccatg                           99
```

<210> SEQ ID NO 91
<211> LENGTH: 74
<212> TYPE: DNA
<213> ORGANISM: Artificial Sequence
<220> FEATURE:
<223> OTHER INFORMATION: ESC51- Rev- VWF D'D3 (1-477 amino acid) with
      6His and Not 1 site

<400> SEQUENCE: 91
tgacctcgag cggccgctca gtggtgatgg tgatgatgcg ctcctggca ggcttcacag    60 gtgaggttga caac                                                    74

<210> SEQ ID NO 92
<211> LENGTH: 32
<212> TYPE: DNA
<213> ORGANISM: Artificial Sequence
<220> FEATURE:
<223> OTHER INFORMATION: ESC 89-fwd with Nhe1site

<400> SEQUENCE: 92
ctcactatag ggagacccaa gctggctagc cg                                32

<210> SEQ ID NO 93
<211> LENGTH: 43
<212> TYPE: DNA
<213> ORGANISM: Artificial Sequence
<220> FEATURE:
<223> OTHER INFORMATION: ESC 91-rev with Sal1

<400> SEQUENCE: 93
ctggatcccg ggagtcgact cgtcagtggt gatggtgatg atg                    43

<210> SEQ ID NO 94
<211> LENGTH: 40
<212> TYPE: PRT
<213> ORGANISM: Artificial Sequence
<220> FEATURE:
<223> OTHER INFORMATION: linker

<400> SEQUENCE: 94

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser Gly Gly Gly
            20                  25                  30

Gly Gly Ser Gly Gly Gly Gly Ser
        35                  40

<210> SEQ ID NO 95
<211> LENGTH: 92
<212> TYPE: DNA
<213> ORGANISM: Artificial Sequence
<220> FEATURE:
<223> OTHER INFORMATION: LW 22-FWD-VWF-D'D3 with FVIII signal sequence
      and BsiW1 site

<400> SEQUENCE: 95
gcgccggccg tacgatgcaa atagagctct ccacctgctt ctttctgtgc cttttgcgat    60
tctgctttag cctatcctgt cggccccca tg                                  92

<210> SEQ ID NO 96
<211> LENGTH: 47
<212> TYPE: DNA
<213> ORGANISM: Artificial Sequence

```
<220> FEATURE:
<223> OTHER INFORMATION: LW 23-Rev- Fc with stop codon and Not1 site

<400> SEQUENCE: 96
tcatcaatgt atcttatcat gtctgaattc gcggccgctc atttacc                    47

<210> SEQ ID NO 97
<211> LENGTH: 41
<212> TYPE: DNA
<213> ORGANISM: Artificial Sequence
<220> FEATURE:
<223> OTHER INFORMATION: LW24- Fwd- VWF D1D2D'D3 cloning oligo with
      BsiW1 site

<400> SEQUENCE: 97
gcgccggccg tacgatgatt cctgccagat ttgccggggt g                          41

<210> SEQ ID NO 98
<211> LENGTH: 41
<212> TYPE: DNA
<213> ORGANISM: Artificial Sequence
<220> FEATURE:
<223> OTHER INFORMATION: LW27-Rev-VWF  D'D3 oligo with EcoRV

<400> SEQUENCE: 98
ccaccgccag atatcggctc ctggcaggct tcacaggtga g                          41

<210> SEQ ID NO 99
<211> LENGTH: 1240
<212> TYPE: PRT
<213> ORGANISM: Artificial Sequence
<220> FEATURE:
<223> OTHER INFORMATION: VWF-D1D2D'D3 protein sequence 1

<400> SEQUENCE: 99
```

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser

```
            195                 200                 205
Ser Cys Asn Ile Ser Ser Gly Glu Met Gln Lys Gly Leu Trp Glu Gln
        210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
        450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
        530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
        610                 615                 620
```

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

```
Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro
    1235            1240

<210> SEQ ID NO 100
<211> LENGTH: 477
<212> TYPE: PRT
<213> ORGANISM: Artificial Sequence
<220> FEATURE:
<223> OTHER INFORMATION: VWF-D'D3 protein sequence 2

<400> SEQUENCE: 100

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140
```

```
Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro
465                 470                 475

<210> SEQ ID NO 101
<211> LENGTH: 2754
<212> TYPE: PRT
<213> ORGANISM: Artificial Sequence
<220> FEATURE:
<223> OTHER INFORMATION: pSYN-FVIII-161

<400> SEQUENCE: 101

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30
```

Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu

```
              450              455              460
Ser Gly Ile Leu Gly Pro Leu Leu Tyr Gly Glu Val Gly Asp Thr Leu
465                  470                  475                  480

Leu Ile Ile Phe Lys Asn Gln Ala Ser Arg Pro Tyr Asn Ile Tyr Pro
                485                  490                  495

His Gly Ile Thr Asp Val Arg Pro Leu Tyr Ser Arg Arg Leu Pro Lys
            500                  505                  510

Gly Val Lys His Leu Lys Asp Phe Pro Ile Leu Pro Gly Glu Ile Phe
        515                  520                  525

Lys Tyr Lys Trp Thr Val Thr Val Glu Asp Gly Pro Thr Lys Ser Asp
    530                  535                  540

Pro Arg Cys Leu Thr Arg Tyr Tyr Ser Ser Phe Val Asn Met Glu Arg
545                  550                  555                  560

Asp Leu Ala Ser Gly Leu Ile Gly Pro Leu Leu Ile Cys Tyr Lys Glu
                565                  570                  575

Ser Val Asp Gln Arg Gly Asn Gln Ile Met Ser Asp Lys Arg Asn Val
            580                  585                  590

Ile Leu Phe Ser Val Phe Asp Glu Asn Arg Ser Trp Tyr Leu Thr Glu
        595                  600                  605

Asn Ile Gln Arg Phe Leu Pro Asn Pro Ala Gly Val Gln Leu Glu Asp
    610                  615                  620

Pro Glu Phe Gln Ala Ser Asn Ile Met His Ser Ile Asn Gly Tyr Val
625                  630                  635                  640

Phe Asp Ser Leu Gln Leu Ser Val Cys Leu His Glu Val Ala Tyr Trp
                645                  650                  655

Tyr Ile Leu Ser Ile Gly Ala Gln Thr Asp Phe Leu Ser Val Phe Phe
            660                  665                  670

Ser Gly Tyr Thr Phe Lys His Lys Met Val Tyr Glu Asp Thr Leu Thr
        675                  680                  685

Leu Phe Pro Phe Ser Gly Glu Thr Val Phe Met Ser Met Glu Asn Pro
    690                  695                  700

Gly Leu Trp Ile Leu Gly Cys His Asn Ser Asp Phe Arg Asn Arg Gly
705                  710                  715                  720

Met Thr Ala Leu Leu Lys Val Ser Ser Cys Asp Lys Asn Thr Gly Asp
                725                  730                  735

Tyr Tyr Glu Asp Ser Tyr Glu Asp Ile Ser Ala Tyr Leu Leu Ser Lys
            740                  745                  750

Asn Asn Ala Ile Glu Pro Arg Ser Phe Ser Gln Asn Pro Pro Val Leu
        755                  760                  765

Lys Arg His Gln Arg Glu Ile Thr Arg Thr Thr Leu Gln Ser Asp Gln
    770                  775                  780

Glu Glu Ile Asp Tyr Asp Asp Thr Ile Ser Val Glu Met Lys Lys Glu
785                  790                  795                  800

Asp Phe Asp Ile Tyr Asp Glu Asp Glu Asn Gln Ser Pro Arg Ser Phe
                805                  810                  815

Gln Lys Lys Thr Arg His Tyr Phe Ile Ala Ala Val Glu Arg Leu Trp
            820                  825                  830

Asp Tyr Gly Met Ser Ser Ser Pro His Val Leu Arg Asn Arg Ala Gln
        835                  840                  845

Ser Gly Ser Val Pro Gln Phe Lys Lys Val Val Phe Gln Glu Phe Thr
    850                  855                  860

Asp Gly Ser Phe Thr Gln Pro Leu Tyr Arg Gly Glu Leu Asn Glu His
865                  870                  875                  880
```

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
                995                 1000                1005

Asp Glu Thr Lys Ser Trp Tyr Phe Thr Glu Asn Met Glu Arg Asn
            1010                1015                1020

Cys Arg Ala Pro Cys Asn Ile Gln Met Glu Asp Pro Thr Phe Lys
            1025                1030                1035

Glu Asn Tyr Arg Phe His Ala Ile Asn Gly Tyr Ile Met Asp Thr
            1040                1045                1050

Leu Pro Gly Leu Val Met Ala Gln Asp Gln Arg Ile Arg Trp Tyr
            1055                1060                1065

Leu Leu Ser Met Gly Ser Asn Glu Asn Ile His Ser Ile His Phe
            1070                1075                1080

Ser Gly His Val Phe Thr Val Arg Lys Lys Glu Glu Tyr Lys Met
            1085                1090                1095

Ala Leu Tyr Asn Leu Tyr Pro Gly Val Phe Glu Thr Val Glu Met
            1100                1105                1110

Leu Pro Ser Lys Ala Gly Ile Trp Arg Val Glu Cys Leu Ile Gly
            1115                1120                1125

Glu His Leu His Ala Gly Met Ser Thr Leu Phe Leu Val Tyr Ser
            1130                1135                1140

Asn Lys Cys Gln Thr Pro Leu Gly Met Ala Ser Gly His Ile Arg
            1145                1150                1155

Asp Phe Gln Ile Thr Ala Ser Gly Gln Tyr Gly Gln Trp Ala Pro
            1160                1165                1170

Lys Leu Ala Arg Leu His Tyr Ser Gly Ser Ile Asn Ala Trp Ser
            1175                1180                1185

Thr Lys Glu Pro Phe Ser Trp Ile Lys Val Asp Leu Leu Ala Pro
            1190                1195                1200

Met Ile Ile His Gly Ile Lys Thr Gln Gly Ala Arg Gln Lys Phe
            1205                1210                1215

Ser Ser Leu Tyr Ile Ser Gln Phe Ile Ile Met Tyr Ser Leu Asp
            1220                1225                1230

Gly Lys Lys Trp Gln Thr Tyr Arg Gly Asn Ser Thr Gly Thr Leu
            1235                1240                1245

Met Val Phe Phe Gly Asn Val Asp Ser Ser Gly Ile Lys His Asn
            1250                1255                1260

Ile Phe Asn Pro Pro Ile Ile Ala Arg Tyr Ile Arg Leu His Pro
            1265                1270                1275

```
Thr His Tyr Ser Ile Arg Ser Thr Leu Arg Met Glu Leu Met Gly
    1280            1285            1290

Cys Asp Leu Asn Ser Cys Ser Met Pro Leu Gly Met Glu Ser Lys
    1295            1300            1305

Ala Ile Ser Asp Ala Gln Ile Thr Ala Ser Ser Tyr Phe Thr Asn
    1310            1315            1320

Met Phe Ala Thr Trp Ser Pro Ser Lys Ala Arg Leu His Leu Gln
    1325            1330            1335

Gly Arg Ser Asn Ala Trp Arg Pro Gln Val Asn Asn Pro Lys Glu
    1340            1345            1350

Trp Leu Gln Val Asp Phe Gln Lys Thr Met Lys Val Thr Gly Val
    1355            1360            1365

Thr Thr Gln Gly Val Lys Ser Leu Leu Thr Ser Met Tyr Val Lys
    1370            1375            1380

Glu Phe Leu Ile Ser Ser Ser Gln Asp Gly His Gln Trp Thr Leu
    1385            1390            1395

Phe Phe Gln Asn Gly Lys Val Lys Val Phe Gln Gly Asn Gln Asp
    1400            1405            1410

Ser Phe Thr Pro Val Val Asn Ser Leu Asp Pro Pro Leu Leu Thr
    1415            1420            1425

Arg Tyr Leu Arg Ile His Pro Gln Ser Trp Val His Gln Ile Ala
    1430            1435            1440

Leu Arg Met Glu Val Leu Gly Cys Glu Ala Gln Asp Leu Tyr Asp
    1445            1450            1455

Lys Thr His Thr Cys Pro Pro Cys Pro Ala Pro Glu Leu Leu Gly
    1460            1465            1470

Gly Pro Ser Val Phe Leu Phe Pro Pro Lys Pro Lys Asp Thr Leu
    1475            1480            1485

Met Ile Ser Arg Thr Pro Glu Val Thr Cys Val Val Val Asp Val
    1490            1495            1500

Ser His Glu Asp Pro Glu Val Lys Phe Asn Trp Tyr Val Asp Gly
    1505            1510            1515

Val Glu Val His Asn Ala Lys Thr Lys Pro Arg Glu Glu Gln Tyr
    1520            1525            1530

Asn Ser Thr Tyr Arg Val Val Ser Val Leu Thr Val Leu His Gln
    1535            1540            1545

Asp Trp Leu Asn Gly Lys Glu Tyr Lys Cys Lys Val Ser Asn Lys
    1550            1555            1560

Ala Leu Pro Ala Pro Ile Glu Lys Thr Ile Ser Lys Ala Lys Gly
    1565            1570            1575

Gln Pro Arg Glu Pro Gln Val Tyr Thr Leu Pro Pro Ser Arg Asp
    1580            1585            1590

Glu Leu Thr Lys Asn Gln Val Ser Leu Thr Cys Leu Val Lys Gly
    1595            1600            1605

Phe Tyr Pro Ser Asp Ile Ala Val Glu Trp Glu Ser Asn Gly Gln
    1610            1615            1620

Pro Glu Asn Asn Tyr Lys Thr Thr Pro Pro Val Leu Asp Ser Asp
    1625            1630            1635

Gly Ser Phe Phe Leu Tyr Ser Lys Leu Thr Val Asp Lys Ser Arg
    1640            1645            1650

Trp Gln Gln Gly Asn Val Phe Ser Cys Ser Val Met His Glu Ala
    1655            1660            1665

Leu His Asn His Tyr Thr Gln Lys Ser Leu Ser Leu Ser Pro Gly
```

```
                1670                1675                1680
Lys Arg Arg Arg Arg Ser Gly Gly Gly Ser Gly Gly Gly
        1685                1690                1695
Ser Gly Gly Gly Gly Ser Gly Gly Gly Ser Gly Gly Gly
        1700                1705                1710
Ser Gly Gly Gly Ser Arg Lys Arg Lys Arg Ser Leu Ser
        1715                1720                1725
Cys Arg Pro Pro Met Val Lys Leu Val Cys Pro Ala Asp Asn Leu
        1730                1735                1740
Arg Ala Glu Gly Leu Glu Cys Thr Lys Thr Cys Gln Asn Tyr Asp
        1745                1750                1755
Leu Glu Cys Met Ser Met Gly Cys Val Ser Gly Cys Leu Cys Pro
        1760                1765                1770
Pro Gly Met Val Arg His Glu Asn Arg Cys Val Ala Leu Glu Arg
        1775                1780                1785
Cys Pro Cys Phe His Gln Gly Lys Glu Tyr Ala Pro Gly Glu Thr
        1790                1795                1800
Val Lys Ile Gly Cys Asn Thr Cys Val Cys Arg Asp Arg Lys Trp
        1805                1810                1815
Asn Cys Thr Asp His Val Cys Asp Ala Thr Cys Ser Thr Ile Gly
        1820                1825                1830
Met Ala His Tyr Leu Thr Phe Asp Gly Leu Lys Tyr Leu Phe Pro
        1835                1840                1845
Gly Glu Cys Gln Tyr Val Leu Val Gln Asp Tyr Cys Gly Ser Asn
        1850                1855                1860
Pro Gly Thr Phe Arg Ile Leu Val Gly Asn Lys Gly Cys Ser His
        1865                1870                1875
Pro Ser Val Lys Cys Lys Lys Arg Val Thr Ile Leu Val Glu Gly
        1880                1885                1890
Gly Glu Ile Glu Leu Phe Asp Gly Glu Val Asn Val Lys Arg Pro
        1895                1900                1905
Met Lys Asp Glu Thr His Phe Glu Val Val Glu Ser Gly Arg Tyr
        1910                1915                1920
Ile Ile Leu Leu Leu Gly Lys Ala Leu Ser Val Val Trp Asp Arg
        1925                1930                1935
His Leu Ser Ile Ser Val Val Leu Lys Gln Thr Tyr Gln Glu Lys
        1940                1945                1950
Val Cys Gly Leu Cys Gly Asn Phe Asp Gly Ile Gln Asn Asn Asp
        1955                1960                1965
Leu Thr Ser Ser Asn Leu Gln Val Glu Glu Asp Pro Val Asp Phe
        1970                1975                1980
Gly Asn Ser Trp Lys Val Ser Ser Gln Cys Ala Asp Thr Arg Lys
        1985                1990                1995
Val Pro Leu Asp Ser Ser Pro Ala Thr Cys His Asn Asn Ile Met
        2000                2005                2010
Lys Gln Thr Met Val Asp Ser Ser Cys Arg Ile Leu Thr Ser Asp
        2015                2020                2025
Val Phe Gln Asp Cys Asn Lys Leu Val Asp Pro Glu Pro Tyr Leu
        2030                2035                2040
Asp Val Cys Ile Tyr Asp Thr Cys Ser Cys Glu Ser Ile Gly Asp
        2045                2050                2055
Cys Ala Ala Phe Cys Asp Thr Ile Ala Ala Tyr Ala His Val Cys
        2060                2065                2070
```

```
Ala Gln His Gly Lys Val Val Thr Trp Arg Thr Ala Thr Leu Cys
2075                2080                2085

Pro Gln Ser Cys Glu Glu Arg Asn Leu Arg Glu Asn Gly Tyr Glu
2090                2095                2100

Ala Glu Trp Arg Tyr Asn Ser Cys Ala Pro Ala Cys Gln Val Thr
2105                2110                2115

Cys Gln His Pro Glu Pro Leu Ala Cys Pro Val Gln Cys Val Glu
2120                2125                2130

Gly Cys His Ala His Cys Pro Pro Gly Lys Ile Leu Asp Glu Leu
2135                2140                2145

Leu Gln Thr Cys Val Asp Pro Glu Asp Cys Pro Val Cys Glu Val
2150                2155                2160

Ala Gly Arg Arg Phe Ala Ser Gly Lys Lys Val Thr Leu Asn Pro
2165                2170                2175

Ser Asp Pro Glu His Cys Gln Ile Cys His Cys Asp Val Val Asn
2180                2185                2190

Leu Thr Cys Glu Ala Cys Gln Glu Pro Ile Ser Gly Thr Ser Glu
2195                2200                2205

Ser Ala Thr Pro Glu Ser Gly Pro Gly Ser Glu Pro Ala Thr Ser
2210                2215                2220

Gly Ser Glu Thr Pro Gly Thr Ser Glu Ser Ala Thr Pro Glu Ser
2225                2230                2235

Gly Pro Gly Ser Glu Pro Ala Thr Ser Gly Ser Glu Thr Pro Gly
2240                2245                2250

Thr Ser Glu Ser Ala Thr Pro Glu Ser Gly Pro Gly Thr Ser Thr
2255                2260                2265

Glu Pro Ser Glu Gly Ser Ala Pro Gly Ser Pro Ala Gly Ser Pro
2270                2275                2280

Thr Ser Thr Glu Glu Gly Thr Ser Glu Ser Ala Thr Pro Glu Ser
2285                2290                2295

Gly Pro Gly Ser Glu Pro Ala Thr Ser Gly Ser Glu Thr Pro Gly
2300                2305                2310

Thr Ser Glu Ser Ala Thr Pro Glu Ser Gly Pro Gly Ser Pro Ala
2315                2320                2325

Gly Ser Pro Thr Ser Thr Glu Glu Gly Ser Pro Ala Gly Ser Pro
2330                2335                2340

Thr Ser Thr Glu Glu Gly Thr Ser Thr Glu Pro Ser Glu Gly Ser
2345                2350                2355

Ala Pro Gly Thr Ser Glu Ser Ala Thr Pro Glu Ser Gly Pro Gly
2360                2365                2370

Thr Ser Glu Ser Ala Thr Pro Glu Ser Gly Pro Gly Thr Ser Glu
2375                2380                2385

Ser Ala Thr Pro Glu Ser Gly Pro Gly Ser Glu Pro Ala Thr Ser
2390                2395                2400

Gly Ser Glu Thr Pro Gly Ser Glu Pro Ala Thr Ser Gly Ser Glu
2405                2410                2415

Thr Pro Gly Ser Pro Ala Gly Ser Pro Thr Ser Thr Glu Glu Gly
2420                2425                2430

Thr Ser Thr Glu Pro Ser Glu Gly Ser Ala Pro Gly Thr Ser Thr
2435                2440                2445

Glu Pro Ser Glu Gly Ser Ala Pro Gly Ser Glu Pro Ala Thr Ser
2450                2455                2460
```

| Gly | Ser | Glu | Thr | Pro | Gly | Thr | Ser | Glu | Ser | Ala | Thr | Pro | Glu | Ser |
|-----|-----|-----|-----|-----|-----|-----|-----|-----|-----|-----|-----|-----|-----|-----|
| | 2465 | | | | 2470 | | | | 2475 | | | | | |
| Gly | Pro | Gly | Thr | Ser | Thr | Glu | Pro | Ser | Glu | Gly | Ser | Ala | Pro | Asp |
| 2480 | | | | | 2485 | | | | | 2490 | | | | |
| Ser | Gly | Gly | Gly | Gly | Ser | Gly | Gly | Gly | Ser | Gly | Gly | Gly | | |
| | 2495 | | | | 2500 | | | | 2505 | | | | | |
| Ser | Gly | Gly | Gly | Gly | Ser | Gly | Gly | Gly | Ser | Leu | Val | Pro | Arg | |
| 2510 | | | | | 2515 | | | | | 2520 | | | | |
| Gly | Ser | Gly | Gly | Asp | Lys | Thr | His | Thr | Cys | Pro | Pro | Cys | Pro | Ala |
| | 2525 | | | | 2530 | | | | | 2535 | | | | |
| Pro | Glu | Leu | Leu | Gly | Gly | Pro | Ser | Val | Phe | Leu | Phe | Pro | Pro | Lys |
| 2540 | | | | | 2545 | | | | | 2550 | | | | |
| Pro | Lys | Asp | Thr | Leu | Met | Ile | Ser | Arg | Thr | Pro | Glu | Val | Thr | Cys |
| | 2555 | | | | 2560 | | | | | 2565 | | | | |
| Val | Val | Val | Asp | Val | Ser | His | Glu | Asp | Pro | Glu | Val | Lys | Phe | Asn |
| 2570 | | | | | 2575 | | | | | 2580 | | | | |
| Trp | Tyr | Val | Asp | Gly | Val | Glu | Val | His | Asn | Ala | Lys | Thr | Lys | Pro |
| | 2585 | | | | 2590 | | | | | 2595 | | | | |
| Arg | Glu | Glu | Gln | Tyr | Asn | Ser | Thr | Tyr | Arg | Val | Val | Ser | Val | Leu |
| 2600 | | | | | 2605 | | | | | 2610 | | | | |
| Thr | Val | Leu | His | Gln | Asp | Trp | Leu | Asn | Gly | Lys | Glu | Tyr | Lys | Cys |
| | 2615 | | | | 2620 | | | | | 2625 | | | | |
| Lys | Val | Ser | Asn | Lys | Ala | Leu | Pro | Ala | Pro | Ile | Glu | Lys | Thr | Ile |
| 2630 | | | | | 2635 | | | | | 2640 | | | | |
| Ser | Lys | Ala | Lys | Gly | Gln | Pro | Arg | Glu | Pro | Gln | Val | Tyr | Thr | Leu |
| | 2645 | | | | 2650 | | | | | 2655 | | | | |
| Pro | Pro | Ser | Arg | Asp | Glu | Leu | Thr | Lys | Asn | Gln | Val | Ser | Leu | Thr |
| 2660 | | | | | 2665 | | | | | 2670 | | | | |
| Cys | Leu | Val | Lys | Gly | Phe | Tyr | Pro | Ser | Asp | Ile | Ala | Val | Glu | Trp |
| | 2675 | | | | 2680 | | | | | 2685 | | | | |
| Glu | Ser | Asn | Gly | Gln | Pro | Glu | Asn | Asn | Tyr | Lys | Thr | Thr | Pro | Pro |
| | 2690 | | | | 2695 | | | | | 2700 | | | | |
| Val | Leu | Asp | Ser | Asp | Gly | Ser | Phe | Phe | Leu | Tyr | Ser | Lys | Leu | Thr |
| | 2705 | | | | 2710 | | | | | 2715 | | | | |
| Val | Asp | Lys | Ser | Arg | Trp | Gln | Gln | Gly | Asn | Val | Phe | Ser | Cys | Ser |
| | 2720 | | | | 2725 | | | | | 2730 | | | | |
| Val | Met | His | Glu | Ala | Leu | His | Asn | His | Tyr | Thr | Gln | Lys | Ser | Leu |
| | 2735 | | | | 2740 | | | | | 2745 | | | | |
| Ser | Leu | Ser | Pro | Gly | Lys | | | | | | | | | |
| | 2750 | | | | | | | | | | | | | |

<210> SEQ ID NO 102
<211> LENGTH: 2242
<212> TYPE: PRT
<213> ORGANISM: Artificial Sequence
<220> FEATURE:
<223> OTHER INFORMATION: pSYN-FVIII-170 protein sequence

<400> SEQUENCE: 102

| Ser | Leu | Ser | Cys | Arg | Pro | Pro | Met | Val | Lys | Leu | Val | Cys | Pro | Ala | Asp |
|-----|-----|-----|-----|-----|-----|-----|-----|-----|-----|-----|-----|-----|-----|-----|-----|
| 1 | | | | 5 | | | | | 10 | | | | | 15 | |
| Asn | Leu | Arg | Ala | Glu | Gly | Leu | Glu | Cys | Thr | Lys | Thr | Cys | Gln | Asn | Tyr |
| | | | 20 | | | | | 25 | | | | | 30 | | |
| Asp | Leu | Glu | Cys | Met | Ser | Met | Gly | Cys | Val | Ser | Gly | Cys | Leu | Cys | Pro |
| | 35 | | | | | 40 | | | | | 45 | | | | |

-continued

```
Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Ala
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
355                 360                 365

Glu Arg Asn Leu Arg Glu Asn Gly Tyr Glu Ala Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Ile Ser Gly
```

-continued

```
            465                 470                 475                 480
        Thr Ser Glu Ser Ala Thr Pro Glu Ser Gly Pro Gly Ser Pro Ala
                        485                 490                 495
        Thr Ser Gly Ser Glu Thr Pro Gly Thr Ser Glu Ser Ala Thr Pro Glu
                    500                 505                 510
        Ser Gly Pro Gly Ser Glu Pro Ala Thr Ser Gly Ser Glu Thr Pro Gly
                    515                 520                 525
        Thr Ser Glu Ser Ala Thr Pro Glu Ser Gly Pro Gly Thr Ser Thr Glu
                    530                 535                 540
        Pro Ser Glu Gly Ser Ala Pro Gly Ser Pro Ala Gly Ser Pro Thr Ser
        545                 550                 555                 560
        Thr Glu Glu Gly Thr Ser Glu Ser Ala Thr Pro Glu Ser Gly Pro Gly
                        565                 570                 575
        Ser Glu Pro Ala Thr Ser Gly Ser Glu Thr Pro Gly Thr Ser Glu Ser
                    580                 585                 590
        Ala Thr Pro Glu Ser Gly Pro Gly Ser Pro Ala Gly Ser Pro Thr Ser
                    595                 600                 605
        Thr Glu Glu Gly Ser Pro Ala Gly Ser Pro Thr Ser Thr Glu Glu Gly
            610                 615                 620
        Thr Ser Thr Glu Pro Ser Glu Gly Ser Ala Pro Gly Thr Ser Glu Ser
        625                 630                 635                 640
        Ala Thr Pro Glu Ser Gly Pro Gly Thr Ser Glu Ser Ala Thr Pro Glu
                        645                 650                 655
        Ser Gly Pro Gly Thr Ser Glu Ser Ala Thr Pro Glu Ser Gly Pro Gly
                    660                 665                 670
        Ser Glu Pro Ala Thr Ser Gly Ser Glu Thr Pro Gly Ser Glu Pro Ala
                    675                 680                 685
        Thr Ser Gly Ser Glu Thr Pro Gly Ser Pro Ala Gly Ser Pro Thr Ser
                    690                 695                 700
        Thr Glu Glu Gly Thr Ser Thr Glu Pro Ser Glu Gly Ser Ala Pro Gly
        705                 710                 715                 720
        Thr Ser Thr Glu Pro Ser Glu Gly Ser Ala Pro Gly Ser Glu Pro Ala
                        725                 730                 735
        Thr Ser Gly Ser Glu Thr Pro Gly Thr Ser Glu Ser Ala Thr Pro Glu
                    740                 745                 750
        Ser Gly Pro Gly Thr Ser Thr Glu Pro Ser Glu Gly Ser Ala Pro Asp
                    755                 760                 765
        Ser Gly Gly Gly Ser Gly Gly Gly Ser Gly Gly Gly Ser
                    770                 775                 780
        Gly Gly Gly Gly Ser Gly Gly Gly Ser Leu Val Pro Arg Gly Ser
        785                 790                 795                 800
        Gly Gly Ala Ser Ala Thr Arg Arg Tyr Tyr Leu Gly Ala Val Glu Leu
                        805                 810                 815
        Ser Trp Asp Tyr Met Gln Ser Asp Leu Gly Glu Leu Pro Val Asp Ala
                    820                 825                 830
        Arg Phe Pro Pro Arg Val Pro Lys Ser Phe Pro Phe Asn Thr Ser Val
                    835                 840                 845
        Val Tyr Lys Lys Thr Leu Phe Val Glu Phe Thr Asp His Leu Phe Asn
            850                 855                 860
        Ile Ala Lys Pro Arg Pro Pro Trp Met Gly Leu Leu Gly Pro Thr Ile
        865                 870                 875                 880
        Gln Ala Glu Val Tyr Asp Thr Val Val Ile Thr Leu Lys Asn Met Ala
                        885                 890                 895
```

-continued

```
Ser His Pro Val Ser Leu His Ala Val Gly Val Ser Tyr Trp Lys Ala
            900                 905                 910

Ser Glu Gly Ala Glu Tyr Asp Asp Gln Thr Ser Gln Arg Glu Lys Glu
            915                 920                 925

Asp Asp Lys Val Phe Pro Gly Gly Ser His Thr Tyr Val Trp Gln Val
            930                 935                 940

Leu Lys Glu Asn Gly Pro Met Ala Ser Asp Pro Leu Cys Leu Thr Tyr
945                 950                 955                 960

Ser Tyr Leu Ser His Val Asp Leu Val Lys Asp Leu Asn Ser Gly Leu
                965                 970                 975

Ile Gly Ala Leu Leu Val Cys Arg Glu Gly Ser Leu Ala Lys Glu Lys
            980                 985                 990

Thr Gln Thr Leu His Lys Phe Ile Leu Leu Phe Ala Val Phe Asp Glu
            995                 1000                1005

Gly Lys Ser Trp His Ser Glu Thr Lys Asn Ser Leu Met Gln Asp
        1010                1015                1020

Arg Asp Ala Ala Ser Ala Arg Ala Trp Pro Lys Met His Thr Val
        1025                1030                1035

Asn Gly Tyr Val Asn Arg Ser Leu Pro Gly Leu Ile Gly Cys His
        1040                1045                1050

Arg Lys Ser Val Tyr Trp His Val Ile Gly Met Gly Thr Thr Pro
        1055                1060                1065

Glu Val His Ser Ile Phe Leu Glu Gly His Thr Phe Leu Val Arg
        1070                1075                1080

Asn His Arg Gln Ala Ser Leu Glu Ile Ser Pro Ile Thr Phe Leu
        1085                1090                1095

Thr Ala Gln Thr Leu Leu Met Asp Leu Gly Gln Phe Leu Leu Phe
        1100                1105                1110

Cys His Ile Ser Ser His Gln His Asp Gly Met Glu Ala Tyr Val
        1115                1120                1125

Lys Val Asp Ser Cys Pro Glu Glu Pro Gln Leu Arg Met Lys Asn
        1130                1135                1140

Asn Glu Glu Ala Glu Asp Tyr Asp Asp Asp Leu Thr Asp Ser Glu
        1145                1150                1155

Met Asp Val Val Arg Phe Asp Asp Asp Asn Ser Pro Ser Phe Ile
        1160                1165                1170

Gln Ile Arg Ser Val Ala Lys Lys His Pro Lys Thr Trp Val His
        1175                1180                1185

Tyr Ile Ala Ala Glu Glu Glu Asp Trp Asp Tyr Ala Pro Leu Val
        1190                1195                1200

Leu Ala Pro Asp Asp Arg Ser Tyr Lys Ser Gln Tyr Leu Asn Asn
        1205                1210                1215

Gly Pro Gln Arg Ile Gly Arg Lys Tyr Lys Lys Val Arg Phe Met
        1220                1225                1230

Ala Tyr Thr Asp Glu Thr Phe Lys Thr Arg Glu Ala Ile Gln His
        1235                1240                1245

Glu Ser Gly Ile Leu Gly Pro Leu Leu Tyr Gly Glu Val Gly Asp
        1250                1255                1260

Thr Leu Leu Ile Ile Phe Lys Asn Gln Ala Ser Arg Pro Tyr Asn
        1265                1270                1275

Ile Tyr Pro His Gly Ile Thr Asp Val Arg Pro Leu Tyr Ser Arg
        1280                1285                1290
```

Arg Leu Pro Lys Gly Val Lys His Leu Lys Asp Phe Pro Ile Leu
    1295                1300                1305

Pro Gly Glu Ile Phe Lys Tyr Lys Trp Thr Val Thr Val Glu Asp
    1310                1315                1320

Gly Pro Thr Lys Ser Asp Pro Arg Cys Leu Thr Arg Tyr Tyr Ser
    1325                1330                1335

Ser Phe Val Asn Met Glu Arg Asp Leu Ala Ser Gly Leu Ile Gly
    1340                1345                1350

Pro Leu Leu Ile Cys Tyr Lys Glu Ser Val Asp Gln Arg Gly Asn
    1355                1360                1365

Gln Ile Met Ser Asp Lys Arg Asn Val Ile Leu Phe Ser Val Phe
    1370                1375                1380

Asp Glu Asn Arg Ser Trp Tyr Leu Thr Glu Asn Ile Gln Arg Phe
    1385                1390                1395

Leu Pro Asn Pro Ala Gly Val Gln Leu Glu Asp Pro Glu Phe Gln
    1400                1405                1410

Ala Ser Asn Ile Met His Ser Ile Asn Gly Tyr Val Phe Asp Ser
    1415                1420                1425

Leu Gln Leu Ser Val Cys Leu His Glu Val Ala Tyr Trp Tyr Ile
    1430                1435                1440

Leu Ser Ile Gly Ala Gln Thr Asp Phe Leu Ser Val Phe Phe Ser
    1445                1450                1455

Gly Tyr Thr Phe Lys His Lys Met Val Tyr Glu Asp Thr Leu Thr
    1460                1465                1470

Leu Phe Pro Phe Ser Gly Glu Thr Val Phe Met Ser Met Glu Asn
    1475                1480                1485

Pro Gly Leu Trp Ile Leu Gly Cys His Asn Ser Asp Phe Arg Asn
    1490                1495                1500

Arg Gly Met Thr Ala Leu Leu Lys Val Ser Ser Cys Asp Lys Asn
    1505                1510                1515

Thr Gly Asp Tyr Tyr Glu Asp Ser Tyr Glu Asp Ile Ser Ala Tyr
    1520                1525                1530

Leu Leu Ser Lys Asn Asn Ala Ile Glu Pro Arg Ser Phe Ser Gln
    1535                1540                1545

Asn Pro Pro Val Leu Lys Arg His Gln Arg Glu Ile Thr Arg Thr
    1550                1555                1560

Thr Leu Gln Ser Asp Gln Glu Glu Ile Asp Tyr Asp Asp Thr Ile
    1565                1570                1575

Ser Val Glu Met Lys Lys Glu Asp Phe Asp Ile Tyr Asp Glu Asp
    1580                1585                1590

Glu Asn Gln Ser Pro Arg Ser Phe Gln Lys Lys Thr Arg His Tyr
    1595                1600                1605

Phe Ile Ala Ala Val Glu Arg Leu Trp Asp Tyr Gly Met Ser Ser
    1610                1615                1620

Ser Pro His Val Leu Arg Asn Arg Ala Gln Ser Gly Ser Val Pro
    1625                1630                1635

Gln Phe Lys Lys Val Val Phe Gln Glu Phe Thr Asp Gly Ser Phe
    1640                1645                1650

Thr Gln Pro Leu Tyr Arg Gly Glu Leu Asn Glu His Leu Gly Leu
    1655                1660                1665

Leu Gly Pro Tyr Ile Arg Ala Glu Val Glu Asp Asn Ile Met Val
    1670                1675                1680

Thr Phe Arg Asn Gln Ala Ser Arg Pro Tyr Ser Phe Tyr Ser Ser

```
                1685                1690                1695

Leu Ile Ser Tyr Glu Glu Asp Gln Arg Gln Gly Ala Glu Pro Arg
    1700                1705                1710

Lys Asn Phe Val Lys Pro Asn Glu Thr Lys Thr Tyr Phe Trp Lys
    1715                1720                1725

Val Gln His His Met Ala Pro Thr Lys Asp Glu Phe Asp Cys Lys
    1730                1735                1740

Ala Trp Ala Tyr Phe Ser Asp Val Asp Leu Glu Lys Asp Val His
    1745                1750                1755

Ser Gly Leu Ile Gly Pro Leu Leu Val Cys His Thr Asn Thr Leu
    1760                1765                1770

Asn Pro Ala His Gly Arg Gln Val Thr Val Gln Glu Phe Ala Leu
    1775                1780                1785

Phe Phe Thr Ile Phe Asp Glu Thr Lys Ser Trp Tyr Phe Thr Glu
    1790                1795                1800

Asn Met Glu Arg Asn Cys Arg Ala Pro Cys Asn Ile Gln Met Glu
    1805                1810                1815

Asp Pro Thr Phe Lys Glu Asn Tyr Arg Phe His Ala Ile Asn Gly
    1820                1825                1830

Tyr Ile Met Asp Thr Leu Pro Gly Leu Val Met Ala Gln Asp Gln
    1835                1840                1845

Arg Ile Arg Trp Tyr Leu Leu Ser Met Gly Ser Asn Glu Asn Ile
    1850                1855                1860

His Ser Ile His Phe Ser Gly His Val Phe Thr Val Arg Lys Lys
    1865                1870                1875

Glu Glu Tyr Lys Met Ala Leu Tyr Asn Leu Tyr Pro Gly Val Phe
    1880                1885                1890

Glu Thr Val Glu Met Leu Pro Ser Lys Ala Gly Ile Trp Arg Val
    1895                1900                1905

Glu Cys Leu Ile Gly Glu His Leu His Ala Gly Met Ser Thr Leu
    1910                1915                1920

Phe Leu Val Tyr Ser Asn Lys Cys Gln Thr Pro Leu Gly Met Ala
    1925                1930                1935

Ser Gly His Ile Arg Asp Phe Gln Ile Thr Ala Ser Gly Gln Tyr
    1940                1945                1950

Gly Gln Trp Ala Pro Lys Leu Ala Arg Leu His Tyr Ser Gly Ser
    1955                1960                1965

Ile Asn Ala Trp Ser Thr Lys Glu Pro Phe Ser Trp Ile Lys Val
    1970                1975                1980

Asp Leu Leu Ala Pro Met Ile Ile His Gly Ile Lys Thr Gln Gly
    1985                1990                1995

Ala Arg Gln Lys Phe Ser Ser Leu Tyr Ile Ser Gln Phe Ile Ile
    2000                2005                2010

Met Tyr Ser Leu Asp Gly Lys Lys Trp Gln Thr Tyr Arg Gly Asn
    2015                2020                2025

Ser Thr Gly Thr Leu Met Val Phe Phe Gly Asn Val Asp Ser Ser
    2030                2035                2040

Gly Ile Lys His Asn Ile Phe Asn Pro Pro Ile Ile Ala Arg Tyr
    2045                2050                2055

Ile Arg Leu His Pro Thr His Tyr Ser Ile Arg Ser Thr Leu Arg
    2060                2065                2070

Met Glu Leu Met Gly Cys Asp Leu Asn Ser Cys Ser Met Pro Leu
    2075                2080                2085
```

```
Gly Met Glu Ser Lys Ala Ile Ser Asp Ala Gln Ile Thr Ala Ser
    2090                2095                2100

Ser Tyr Phe Thr Asn Met Phe Ala Thr Trp Ser Pro Ser Lys Ala
    2105                2110                2115

Arg Leu His Leu Gln Gly Arg Ser Asn Ala Trp Arg Pro Gln Val
    2120                2125                2130

Asn Asn Pro Lys Glu Trp Leu Gln Val Asp Phe Gln Lys Thr Met
    2135                2140                2145

Lys Val Thr Gly Val Thr Thr Gln Gly Val Lys Ser Leu Leu Thr
    2150                2155                2160

Ser Met Tyr Val Lys Glu Phe Leu Ile Ser Ser Ser Gln Asp Gly
    2165                2170                2175

His Gln Trp Thr Leu Phe Phe Gln Asn Gly Lys Val Lys Val Phe
    2180                2185                2190

Gln Gly Asn Gln Asp Ser Phe Thr Pro Val Val Asn Ser Leu Asp
    2195                2200                2205

Pro Pro Leu Leu Thr Arg Tyr Leu Arg Ile His Pro Gln Ser Trp
    2210                2215                2220

Val His Gln Ile Ala Leu Arg Met Glu Val Leu Gly Cys Glu Ala
    2225                2230                2235

Gln Asp Leu Tyr
    2240

<210> SEQ ID NO 103
<211> LENGTH: 1959
<212> TYPE: PRT
<213> ORGANISM: Artificial Sequence
<220> FEATURE:
<223> OTHER INFORMATION: pSYN-FVIII-169 mature Protein sequence

<400> SEQUENCE: 103

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190
```

```
His Lys Phe Ile Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
    595                 600                 605
```

-continued

Gln Ala Ser Asn Ile Met His Ser Ile Asn Gly Tyr Val Phe Asp Ser
610                615                620

Leu Gln Leu Ser Val Cys Leu His Glu Val Ala Tyr Trp Tyr Ile Leu
625                630                635                640

Ser Ile Gly Ala Gln Thr Asp Phe Leu Ser Val Phe Phe Ser Gly Tyr
                645                650                655

Thr Phe Lys His Lys Met Val Tyr Glu Asp Thr Leu Thr Leu Phe Pro
                660                665                670

Phe Ser Gly Glu Thr Val Phe Met Ser Met Glu Asn Pro Gly Leu Trp
            675                680                685

Ile Leu Gly Cys His Asn Ser Asp Phe Arg Asn Arg Gly Met Thr Ala
690                695                700

Leu Leu Lys Val Ser Ser Cys Asp Lys Asn Thr Gly Asp Tyr Tyr Glu
705                710                715                720

Asp Ser Tyr Glu Asp Ile Ser Ala Tyr Leu Leu Ser Lys Asn Asn Ala
                725                730                735

Ile Glu Pro Arg Ser Phe Ser Gln Asn Gly Ala Pro Gly Thr Ser Glu
            740                745                750

Ser Ala Thr Pro Glu Ser Gly Pro Gly Ser Glu Pro Ala Thr Ser Gly
            755                760                765

Ser Glu Thr Pro Gly Thr Ser Glu Ser Ala Thr Pro Glu Ser Gly Pro
770                775                780

Gly Ser Glu Pro Ala Thr Ser Gly Ser Glu Thr Pro Gly Thr Ser Glu
785                790                795                800

Ser Ala Thr Pro Glu Ser Gly Pro Gly Thr Thr Glu Pro Ser Glu
            805                810                815

Gly Ser Ala Pro Gly Ser Pro Ala Gly Ser Pro Thr Ser Thr Glu Glu
            820                825                830

Gly Thr Ser Glu Ser Ala Thr Pro Glu Ser Gly Pro Gly Ser Glu Pro
            835                840                845

Ala Thr Ser Gly Ser Glu Thr Pro Gly Thr Ser Glu Ser Ala Thr Pro
850                855                860

Glu Ser Gly Pro Gly Ser Pro Ala Gly Ser Pro Thr Ser Thr Glu Glu
865                870                875                880

Gly Ser Pro Ala Gly Ser Pro Thr Ser Thr Glu Glu Gly Thr Ser Thr
            885                890                895

Glu Pro Ser Glu Gly Ser Ala Pro Gly Thr Ser Glu Ser Ala Thr Pro
            900                905                910

Glu Ser Gly Pro Gly Thr Ser Glu Ser Ala Thr Pro Glu Ser Gly Pro
            915                920                925

Gly Thr Ser Glu Ser Ala Thr Pro Glu Ser Gly Pro Gly Ser Glu Pro
930                935                940

Ala Thr Ser Gly Ser Glu Thr Pro Gly Ser Glu Pro Ala Thr Ser Gly
945                950                955                960

Ser Glu Thr Pro Gly Ser Pro Ala Gly Ser Pro Thr Ser Thr Glu Glu
            965                970                975

Gly Thr Ser Thr Glu Pro Ser Glu Gly Ser Ala Pro Gly Thr Ser Thr
            980                985                990

Glu Pro Ser Glu Gly Ser Ala Pro Gly Ser Glu Pro Ala Thr Ser Gly
            995                1000                1005

Ser Glu Thr Pro Gly Thr Ser Glu Ser Ala Thr Pro Glu Ser Gly
            1010                1015                1020

Pro Gly Thr Ser Thr Glu Pro Ser Glu Gly Ser Ala Pro Ala Ser

-continued

```
           1025                1030                1035
Ser Pro Pro Val Leu Lys Arg His Gln Ala Glu Ile Thr Arg Thr
           1040                1045                1050
Thr Leu Gln Ser Asp Gln Glu Glu Ile Asp Tyr Asp Asp Thr Ile
           1055                1060                1065
Ser Val Glu Met Lys Lys Glu Asp Phe Asp Ile Tyr Asp Glu Asp
           1070                1075                1080
Glu Asn Gln Ser Pro Arg Ser Phe Gln Lys Lys Thr Arg His Tyr
           1085                1090                1095
Phe Ile Ala Ala Val Glu Arg Leu Trp Asp Tyr Gly Met Ser Ser
           1100                1105                1110
Ser Pro His Val Leu Arg Asn Arg Ala Gln Ser Gly Ser Val Pro
           1115                1120                1125
Gln Phe Lys Lys Val Val Phe Gln Glu Phe Thr Asp Gly Ser Phe
           1130                1135                1140
Thr Gln Pro Leu Tyr Arg Gly Glu Leu Asn Glu His Leu Gly Leu
           1145                1150                1155
Leu Gly Pro Tyr Ile Arg Ala Glu Val Glu Asp Asn Ile Met Val
           1160                1165                1170
Thr Phe Arg Asn Gln Ala Ser Arg Pro Tyr Ser Phe Tyr Ser Ser
           1175                1180                1185
Leu Ile Ser Tyr Glu Glu Asp Gln Arg Gln Gly Ala Glu Pro Arg
           1190                1195                1200
Lys Asn Phe Val Lys Pro Asn Glu Thr Lys Thr Tyr Phe Trp Lys
           1205                1210                1215
Val Gln His His Met Ala Pro Thr Lys Asp Glu Phe Asp Cys Lys
           1220                1225                1230
Ala Trp Ala Tyr Phe Ser Asp Val Asp Leu Glu Lys Asp Val His
           1235                1240                1245
Ser Gly Leu Ile Gly Pro Leu Leu Val Cys His Thr Asn Thr Leu
           1250                1255                1260
Asn Pro Ala His Gly Arg Gln Val Thr Val Gln Glu Phe Ala Leu
           1265                1270                1275
Phe Phe Thr Ile Phe Asp Glu Thr Lys Ser Trp Tyr Phe Thr Glu
           1280                1285                1290
Asn Met Glu Arg Asn Cys Arg Ala Pro Cys Asn Ile Gln Met Glu
           1295                1300                1305
Asp Pro Thr Phe Lys Glu Asn Tyr Arg Phe His Ala Ile Asn Gly
           1310                1315                1320
Tyr Ile Met Asp Thr Leu Pro Gly Leu Val Met Ala Gln Asp Gln
           1325                1330                1335
Arg Ile Arg Trp Tyr Leu Leu Ser Met Gly Ser Asn Glu Asn Ile
           1340                1345                1350
His Ser Ile His Phe Ser Gly His Val Phe Thr Val Arg Lys Lys
           1355                1360                1365
Glu Glu Tyr Lys Met Ala Leu Tyr Asn Leu Tyr Pro Gly Val Phe
           1370                1375                1380
Glu Thr Val Glu Met Leu Pro Ser Lys Ala Gly Ile Trp Arg Val
           1385                1390                1395
Glu Cys Leu Ile Gly Glu His Leu His Ala Gly Met Ser Thr Leu
           1400                1405                1410
Phe Leu Val Tyr Ser Asn Lys Cys Gln Thr Pro Leu Gly Met Ala
           1415                1420                1425
```

-continued

```
Ser Gly His Ile Arg Asp Phe Gln Ile Thr Ala Ser Gly Gln Tyr
    1430                1435                1440

Gly Gln Trp Ala Pro Lys Leu Ala Arg Leu His Tyr Ser Gly Ser
    1445                1450                1455

Ile Asn Ala Trp Ser Thr Lys Glu Pro Phe Ser Trp Ile Lys Val
    1460                1465                1470

Asp Leu Leu Ala Pro Met Ile Ile His Gly Ile Lys Thr Gln Gly
    1475                1480                1485

Ala Arg Gln Lys Phe Ser Ser Leu Tyr Ile Ser Gln Phe Ile Ile
    1490                1495                1500

Met Tyr Ser Leu Asp Gly Lys Lys Trp Gln Thr Tyr Arg Gly Asn
    1505                1510                1515

Ser Thr Gly Thr Leu Met Val Phe Phe Gly Asn Val Asp Ser Ser
    1520                1525                1530

Gly Ile Lys His Asn Ile Phe Asn Pro Pro Ile Ile Ala Arg Tyr
    1535                1540                1545

Ile Arg Leu His Pro Thr His Tyr Ser Ile Arg Ser Thr Leu Arg
    1550                1555                1560

Met Glu Leu Met Gly Cys Asp Leu Asn Ser Cys Ser Met Pro Leu
    1565                1570                1575

Gly Met Glu Ser Lys Ala Ile Ser Asp Ala Gln Ile Thr Ala Ser
    1580                1585                1590

Ser Tyr Phe Thr Asn Met Phe Ala Thr Trp Ser Pro Ser Lys Ala
    1595                1600                1605

Arg Leu His Leu Gln Gly Arg Ser Asn Ala Trp Arg Pro Gln Val
    1610                1615                1620

Asn Asn Pro Lys Glu Trp Leu Gln Val Asp Phe Gln Lys Thr Met
    1625                1630                1635

Lys Val Thr Gly Val Thr Thr Gln Gly Val Lys Ser Leu Leu Thr
    1640                1645                1650

Ser Met Tyr Val Lys Glu Phe Leu Ile Ser Ser Ser Gln Asp Gly
    1655                1660                1665

His Gln Trp Thr Leu Phe Phe Gln Asn Gly Lys Val Lys Val Phe
    1670                1675                1680

Gln Gly Asn Gln Asp Ser Phe Thr Pro Val Val Asn Ser Leu Asp
    1685                1690                1695

Pro Pro Leu Leu Thr Arg Tyr Leu Arg Ile His Pro Gln Ser Trp
    1700                1705                1710

Val His Gln Ile Ala Leu Arg Met Glu Val Leu Gly Cys Glu Ala
    1715                1720                1725

Gln Asp Leu Tyr Asp Lys Thr His Thr Cys Pro Pro Cys Pro Ala
    1730                1735                1740

Pro Glu Leu Leu Gly Gly Pro Ser Val Phe Leu Phe Pro Pro Lys
    1745                1750                1755

Pro Lys Asp Thr Leu Met Ile Ser Arg Thr Pro Glu Val Thr Cys
    1760                1765                1770

Val Val Val Asp Val Ser His Glu Asp Pro Glu Val Lys Phe Asn
    1775                1780                1785

Trp Tyr Val Asp Gly Val Glu Val His Asn Ala Lys Thr Lys Pro
    1790                1795                1800

Arg Glu Glu Gln Tyr Asn Ser Thr Tyr Arg Val Val Ser Val Leu
    1805                1810                1815
```

```
Thr Val Leu His Gln Asp Trp Leu Asn Gly Lys Glu Tyr Lys Cys
    1820                1825                1830

Lys Val Ser Asn Lys Ala Leu Pro Ala Pro Ile Glu Lys Thr Ile
    1835                1840                1845

Ser Lys Ala Lys Gly Gln Pro Arg Glu Pro Gln Val Tyr Thr Leu
    1850                1855                1860

Pro Pro Ser Arg Asp Glu Leu Thr Lys Asn Gln Val Ser Leu Thr
    1865                1870                1875

Cys Leu Val Lys Gly Phe Tyr Pro Ser Asp Ile Ala Val Glu Trp
    1880                1885                1890

Glu Ser Asn Gly Gln Pro Glu Asn Asn Tyr Lys Thr Thr Pro Pro
    1895                1900                1905

Val Leu Asp Ser Asp Gly Ser Phe Phe Leu Tyr Ser Lys Leu Thr
    1910                1915                1920

Val Asp Lys Ser Arg Trp Gln Gln Gly Asn Val Phe Ser Cys Ser
    1925                1930                1935

Val Met His Glu Ala Leu His Asn His Tyr Thr Gln Lys Ser Leu
    1940                1945                1950

Ser Leu Ser Pro Gly Lys
    1955

<210> SEQ ID NO 104
<211> LENGTH: 1959
<212> TYPE: PRT
<213> ORGANISM: Artificial Sequence
<220> FEATURE:
<223> OTHER INFORMATION: pSYN-FVIII-173 mature Protein

<400> SEQUENCE: 104

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205
```

-continued

```
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asn Ser Pro Ser Phe
    355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
    435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
    515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
    595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
```

-continued

```
            625                 630                 635                 640
Ser Ile Gly Ala Gln Thr Asp Phe Leu Ser Val Phe Ser Gly Tyr
                    645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                    725                 730                 735

Ile Glu Pro Arg Ser Phe Ser Gln Asn Gly Ala Pro Gly Thr Ser Glu
                740                 745                 750

Ser Ala Thr Pro Glu Ser Gly Pro Gly Ser Glu Pro Ala Thr Ser Gly
            755                 760                 765

Ser Glu Thr Pro Gly Thr Ser Glu Ser Ala Thr Pro Glu Ser Gly Pro
        770                 775                 780

Gly Ser Glu Pro Ala Thr Ser Gly Ser Glu Thr Pro Gly Thr Ser Glu
785                 790                 795                 800

Ser Ala Thr Pro Glu Ser Gly Pro Gly Thr Ser Thr Glu Pro Ser Glu
                    805                 810                 815

Gly Ser Ala Pro Gly Ser Pro Ala Gly Ser Pro Thr Ser Thr Glu Glu
                820                 825                 830

Gly Thr Ser Glu Ser Ala Thr Pro Glu Ser Gly Pro Gly Ser Glu Pro
            835                 840                 845

Ala Thr Ser Gly Ser Glu Thr Pro Gly Thr Ser Glu Ser Ala Thr Pro
        850                 855                 860

Glu Ser Gly Pro Gly Ser Pro Ala Gly Ser Pro Thr Ser Thr Glu Glu
865                 870                 875                 880

Gly Ser Pro Ala Gly Ser Pro Thr Ser Thr Glu Glu Gly Thr Ser Thr
                    885                 890                 895

Glu Pro Ser Glu Gly Ser Ala Pro Gly Thr Ser Glu Ser Ala Thr Pro
                900                 905                 910

Glu Ser Gly Pro Gly Thr Ser Glu Ser Ala Thr Pro Glu Ser Gly Pro
            915                 920                 925

Gly Thr Ser Glu Ser Ala Thr Pro Glu Ser Gly Pro Gly Ser Glu Pro
        930                 935                 940

Ala Thr Ser Gly Ser Glu Thr Pro Gly Ser Glu Pro Ala Thr Ser Gly
945                 950                 955                 960

Ser Glu Thr Pro Gly Ser Pro Ala Gly Ser Pro Thr Ser Thr Glu Glu
                    965                 970                 975

Gly Thr Ser Thr Glu Pro Ser Glu Gly Ser Ala Pro Gly Thr Ser Thr
                980                 985                 990

Glu Pro Ser Glu Gly Ser Ala Pro  Gly Ser Glu Pro Ala  Thr Ser Gly
            995                 1000                1005

Ser Glu  Thr Pro Gly Thr Ser  Glu Ser Ala Thr  Pro Glu Ser Gly
       1010                 1015                1020

Pro Gly  Thr Ser Thr Glu Pro  Ser Glu Gly Ser Ala  Pro Ala Ser
       1025                 1030                1035

Ser Pro  Pro Val Leu Lys Arg  His Gln Arg Glu Ile  Thr Arg Thr
       1040                 1045                1050
```

```
Thr Leu Gln Ser Asp Gln Glu Ile Asp Tyr Asp Asp Thr Ile
    1055            1060            1065

Ser Val Glu Met Lys Lys Glu Asp Phe Asp Ile Tyr Asp Glu Asp
    1070            1075            1080

Glu Asn Gln Ser Pro Arg Ser Phe Gln Lys Lys Thr Arg His Tyr
    1085            1090            1095

Phe Ile Ala Ala Val Glu Arg Leu Trp Asp Tyr Gly Met Ser Ser
    1100            1105            1110

Ser Pro His Val Leu Arg Asn Arg Ala Gln Ser Gly Ser Val Pro
    1115            1120            1125

Gln Phe Lys Lys Val Val Phe Gln Glu Phe Thr Asp Gly Ser Phe
    1130            1135            1140

Thr Gln Pro Leu Tyr Arg Gly Glu Leu Asn Glu His Leu Gly Leu
    1145            1150            1155

Leu Gly Pro Tyr Ile Arg Ala Glu Val Glu Asp Asn Ile Met Val
    1160            1165            1170

Thr Phe Arg Asn Gln Ala Ser Arg Pro Tyr Ser Phe Tyr Ser Ser
    1175            1180            1185

Leu Ile Ser Tyr Glu Glu Asp Gln Arg Gln Gly Ala Glu Pro Arg
    1190            1195            1200

Lys Asn Phe Val Lys Pro Asn Glu Thr Lys Thr Tyr Phe Trp Lys
    1205            1210            1215

Val Gln His His Met Ala Pro Thr Lys Asp Glu Phe Asp Cys Lys
    1220            1225            1230

Ala Trp Ala Tyr Phe Ser Asp Val Asp Leu Glu Lys Asp Val His
    1235            1240            1245

Ser Gly Leu Ile Gly Pro Leu Leu Val Cys His Thr Asn Thr Leu
    1250            1255            1260

Asn Pro Ala His Gly Arg Gln Val Thr Val Gln Glu Phe Ala Leu
    1265            1270            1275

Phe Phe Thr Ile Phe Asp Glu Thr Lys Ser Trp Tyr Phe Thr Glu
    1280            1285            1290

Asn Met Glu Arg Asn Cys Arg Ala Pro Cys Asn Ile Gln Met Glu
    1295            1300            1305

Asp Pro Thr Phe Lys Glu Asn Tyr Arg Phe His Ala Ile Asn Gly
    1310            1315            1320

Tyr Ile Met Asp Thr Leu Pro Gly Leu Val Met Ala Gln Asp Gln
    1325            1330            1335

Arg Ile Arg Trp Tyr Leu Leu Ser Met Gly Ser Asn Glu Asn Ile
    1340            1345            1350

His Ser Ile His Phe Ser Gly His Val Phe Thr Val Arg Lys Lys
    1355            1360            1365

Glu Glu Tyr Lys Met Ala Leu Tyr Asn Leu Tyr Pro Gly Val Phe
    1370            1375            1380

Glu Thr Val Glu Met Leu Pro Ser Lys Ala Gly Ile Trp Arg Val
    1385            1390            1395

Glu Cys Leu Ile Gly Glu His Leu His Ala Gly Met Ser Thr Leu
    1400            1405            1410

Phe Leu Val Tyr Ser Asn Lys Cys Gln Thr Pro Leu Gly Met Ala
    1415            1420            1425

Ser Gly His Ile Arg Asp Phe Gln Ile Thr Ala Ser Gly Gln Tyr
    1430            1435            1440
```

```
Gly Gln Trp Ala Pro Lys Leu Ala Arg Leu His Tyr Ser Gly Ser
    1445                1450                1455

Ile Asn Ala Trp Ser Thr Lys Glu Pro Phe Ser Trp Ile Lys Val
    1460                1465                1470

Asp Leu Leu Ala Pro Met Ile Ile His Gly Ile Lys Thr Gln Gly
    1475                1480                1485

Ala Arg Gln Lys Phe Ser Ser Leu Tyr Ile Ser Gln Phe Ile Ile
    1490                1495                1500

Met Tyr Ser Leu Asp Gly Lys Lys Trp Gln Thr Tyr Arg Gly Asn
    1505                1510                1515

Ser Thr Gly Thr Leu Met Val Phe Phe Gly Asn Val Asp Ser Ser
    1520                1525                1530

Gly Ile Lys His Asn Ile Phe Asn Pro Pro Ile Ile Ala Arg Tyr
    1535                1540                1545

Ile Arg Leu His Pro Thr His Tyr Ser Ile Arg Ser Thr Leu Arg
    1550                1555                1560

Met Glu Leu Met Gly Cys Asp Leu Asn Ser Cys Ser Met Pro Leu
    1565                1570                1575

Gly Met Glu Ser Lys Ala Ile Ser Asp Ala Gln Ile Thr Ala Ser
    1580                1585                1590

Ser Tyr Phe Thr Asn Met Phe Ala Thr Trp Ser Pro Ser Lys Ala
    1595                1600                1605

Arg Leu His Leu Gln Gly Arg Ser Asn Ala Trp Arg Pro Gln Val
    1610                1615                1620

Asn Asn Pro Lys Glu Trp Leu Gln Val Asp Phe Gln Lys Thr Met
    1625                1630                1635

Lys Val Thr Gly Val Thr Thr Gln Gly Val Lys Ser Leu Leu Thr
    1640                1645                1650

Ser Met Tyr Val Lys Glu Phe Leu Ile Ser Ser Ser Gln Asp Gly
    1655                1660                1665

His Gln Trp Thr Leu Phe Phe Gln Asn Gly Lys Val Lys Val Phe
    1670                1675                1680

Gln Gly Asn Gln Asp Ser Phe Thr Pro Val Val Asn Ser Leu Asp
    1685                1690                1695

Pro Pro Leu Leu Thr Arg Tyr Leu Arg Ile His Pro Gln Ser Trp
    1700                1705                1710

Val His Gln Ile Ala Leu Arg Met Glu Val Leu Gly Cys Glu Ala
    1715                1720                1725

Gln Asp Leu Tyr Asp Lys Thr His Thr Cys Pro Pro Cys Pro Ala
    1730                1735                1740

Pro Glu Leu Leu Gly Gly Pro Ser Val Phe Leu Phe Pro Pro Lys
    1745                1750                1755

Pro Lys Asp Thr Leu Met Ile Ser Arg Thr Pro Glu Val Thr Cys
    1760                1765                1770

Val Val Val Asp Val Ser His Glu Asp Pro Glu Val Lys Phe Asn
    1775                1780                1785

Trp Tyr Val Asp Gly Val Glu Val His Asn Ala Lys Thr Lys Pro
    1790                1795                1800

Arg Glu Glu Gln Tyr Asn Ser Thr Tyr Arg Val Val Ser Val Leu
    1805                1810                1815

Thr Val Leu His Gln Asp Trp Leu Asn Gly Lys Glu Tyr Lys Cys
    1820                1825                1830

Lys Val Ser Asn Lys Ala Leu Pro Ala Pro Ile Glu Lys Thr Ile
```

```
                  1835                1840                1845

Ser Lys Ala Lys Gly Gln Pro Arg Glu Pro Gln Val Tyr Thr Leu
        1850                1855                1860

Pro Pro Ser Arg Asp Glu Leu Thr Lys Asn Gln Val Ser Leu Thr
    1865                1870                1875

Cys Leu Val Lys Gly Phe Tyr Pro Ser Asp Ile Ala Val Glu Trp
    1880                1885                1890

Glu Ser Asn Gly Gln Pro Glu Asn Asn Tyr Lys Thr Thr Pro Pro
    1895                1900                1905

Val Leu Asp Ser Asp Gly Ser Phe Phe Leu Tyr Ser Lys Leu Thr
    1910                1915                1920

Val Asp Lys Ser Arg Trp Gln Gln Gly Asn Val Phe Ser Cys Ser
    1925                1930                1935

Val Met His Glu Ala Leu His Asn His Tyr Thr Gln Lys Ser Leu
    1940                1945                1950

Ser Leu Ser Pro Gly Lys
    1955

<210> SEQ ID NO 105
<211> LENGTH: 1984
<212> TYPE: PRT
<213> ORGANISM: Artificial Sequence
<220> FEATURE:
<223> OTHER INFORMATION: FVIII 195 protein sequence

<400> SEQUENCE: 105

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
```

```
            225                 230                 235                 240
        Ala Ala Ser Ala Arg Ala Trp Pro Lys Met His Thr Val Asn Gly Tyr
                        245                 250                 255

Val Asn Arg Ser Leu Pro Gly Leu Ile Gly Cys His Arg Lys Ser Val
                        260                 265                 270

Tyr Trp His Val Ile Gly Met Gly Thr Thr Pro Glu Val His Ser Ile
                        275                 280                 285

Phe Leu Glu Gly His Thr Phe Leu Val Arg Asn His Arg Gln Ala Ser
                290                 295                 300

Leu Glu Ile Ser Pro Ile Thr Phe Leu Thr Ala Gln Thr Leu Leu Met
        305                 310                 315                 320

Asp Leu Gly Gln Phe Leu Leu Phe Cys His Ile Ser Ser His Gln His
                        325                 330                 335

Asp Gly Met Glu Ala Tyr Val Lys Val Asp Ser Cys Pro Glu Glu Pro
                        340                 345                 350

Gln Leu Arg Met Lys Asn Asn Glu Glu Ala Glu Asp Tyr Asp Asp Asp
                        355                 360                 365

Leu Thr Asp Ser Glu Met Asp Val Val Arg Phe Asp Asp Asn Ser
                370                 375                 380

Pro Ser Phe Ile Gln Ile Arg Ser Val Ala Lys Lys His Pro Lys Thr
        385                 390                 395                 400

Trp Val His Tyr Ile Ala Ala Glu Glu Asp Trp Asp Tyr Ala Pro
                        405                 410                 415

Leu Val Leu Ala Pro Asp Asp Arg Ser Tyr Lys Ser Gln Tyr Leu Asn
                        420                 425                 430

Asn Gly Pro Gln Arg Ile Gly Arg Lys Tyr Lys Lys Val Arg Phe Met
                        435                 440                 445

Ala Tyr Thr Asp Glu Thr Phe Lys Thr Arg Glu Ala Ile Gln His Glu
                        450                 455                 460

Ser Gly Ile Leu Gly Pro Leu Leu Tyr Gly Glu Val Gly Asp Thr Leu
        465                 470                 475                 480

Leu Ile Ile Phe Lys Asn Gln Ala Ser Arg Pro Tyr Asn Ile Tyr Pro
                        485                 490                 495

His Gly Ile Thr Asp Val Arg Pro Leu Tyr Ser Arg Arg Leu Pro Lys
                        500                 505                 510

Gly Val Lys His Leu Lys Asp Phe Pro Ile Leu Pro Gly Glu Ile Phe
                        515                 520                 525

Lys Tyr Lys Trp Thr Val Thr Val Glu Asp Gly Pro Thr Lys Ser Asp
                        530                 535                 540

Pro Arg Cys Leu Thr Arg Tyr Tyr Ser Ser Phe Val Asn Met Glu Arg
        545                 550                 555                 560

Asp Leu Ala Ser Gly Leu Ile Gly Pro Leu Leu Ile Cys Tyr Lys Glu
                        565                 570                 575

Ser Val Asp Gln Arg Gly Asn Gln Ile Met Ser Asp Lys Arg Asn Val
                        580                 585                 590

Ile Leu Phe Ser Val Phe Asp Glu Asn Arg Ser Trp Tyr Leu Thr Glu
                        595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
        625                 630                 635                 640

Phe Asp Ser Leu Gln Leu Ser Val Cys Leu His Glu Val Ala Tyr Trp
                        645                 650                 655
```

```
Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Gly Ala Pro
770                 775                 780

Gly Thr Pro Gly Ser Gly Thr Ala Ser Ser Ser Pro Gly Ala Ser Pro
785                 790                 795                 800

Gly Thr Ser Ser Thr Gly Ser Pro Gly Ala Ser Pro Gly Thr Ser Ser
                805                 810                 815

Thr Gly Ser Pro Gly Ala Ser Pro Gly Thr Ser Ser Thr Gly Ser Pro
            820                 825                 830

Gly Ser Ser Pro Ser Ala Ser Thr Gly Thr Gly Pro Gly Thr Pro Gly
            835                 840                 845

Ser Gly Thr Ala Ser Ser Ser Pro Gly Ala Ser Pro Gly Thr Ser Ser
850                 855                 860

Thr Gly Ser Pro Gly Ala Ser Pro Gly Thr Ser Ser Thr Gly Ser Pro
865                 870                 875                 880

Gly Ala Ser Pro Gly Thr Ser Ser Thr Gly Ser Pro Gly Ser Ser Thr
                885                 890                 895

Pro Ser Gly Ala Thr Gly Ser Pro Gly Ser Ser Thr Pro Ser Gly Ala
            900                 905                 910

Thr Gly Ser Pro Gly Ala Ser Pro Gly Thr Ser Ser Thr Gly Ser Pro
            915                 920                 925

Ala Ser Ser Ser Asp Gln Glu Glu Ile Asp Tyr Asp Asp Thr Ile Ser
930                 935                 940

Val Glu Met Lys Lys Glu Asp Phe Asp Ile Tyr Asp Glu Asp Glu Asn
945                 950                 955                 960

Gln Ser Pro Arg Ser Phe Gln Lys Lys Thr Arg His Tyr Phe Ile Ala
                965                 970                 975

Ala Val Glu Arg Leu Trp Asp Tyr Gly Met Ser Ser Ser Pro His Val
            980                 985                 990

Leu Arg Asn Arg Ala Gln Ser Gly Ser Val Pro Gln Phe Lys Lys Val
            995                 1000                1005

Val Phe Gln Glu Phe Thr Asp Gly Ser Phe Thr Gln Pro Leu Tyr
    1010                1015                1020

Arg Gly Glu Leu Asn Glu His Leu Gly Leu Leu Gly Pro Tyr Ile
    1025                1030                1035

Arg Ala Glu Val Glu Asp Asn Ile Met Val Thr Phe Arg Asn Gln
    1040                1045                1050

Ala Ser Arg Pro Tyr Ser Phe Tyr Ser Ser Leu Ile Ser Tyr Glu
    1055                1060                1065
```

```
Glu Asp Gln Arg Gln Gly Ala Glu Pro Arg Lys Asn Phe Val Lys
1070                1075                1080

Pro Asn Glu Thr Lys Thr Tyr Phe Trp Lys Val Gln His His Met
    1085                1090                1095

Ala Pro Thr Lys Asp Glu Phe Asp Cys Lys Ala Trp Ala Tyr Phe
1100                1105                1110

Ser Asp Val Asp Leu Glu Lys Asp Val His Ser Gly Leu Ile Gly
    1115                1120                1125

Pro Leu Leu Val Cys His Thr Asn Thr Leu Asn Pro Ala His Gly
1130                1135                1140

Arg Gln Val Thr Val Gln Glu Phe Ala Leu Phe Phe Thr Ile Phe
    1145                1150                1155

Asp Glu Thr Lys Ser Trp Tyr Phe Thr Glu Asn Met Glu Arg Asn
1160                1165                1170

Cys Arg Gly Ala Pro Thr Ser Glu Ser Ala Thr Pro Glu Ser Gly
    1175                1180                1185

Pro Gly Ser Glu Pro Ala Thr Ser Gly Ser Glu Thr Pro Gly Thr
1190                1195                1200

Ser Glu Ser Ala Thr Pro Glu Ser Gly Pro Gly Ser Glu Pro Ala
    1205                1210                1215

Thr Ser Gly Ser Glu Thr Pro Gly Thr Ser Glu Ser Ala Thr Pro
1220                1225                1230

Glu Ser Gly Pro Gly Thr Ser Thr Glu Pro Ser Glu Gly Ser Ala
    1235                1240                1245

Pro Gly Thr Ser Glu Ser Ala Thr Pro Glu Ser Gly Pro Gly Ser
1250                1255                1260

Pro Ala Gly Ser Pro Thr Ser Thr Glu Glu Gly Ser Pro Ala Gly
    1265                1270                1275

Ser Pro Thr Ser Thr Glu Glu Gly Ser Pro Ala Gly Ser Pro Thr
1280                1285                1290

Ser Thr Glu Glu Gly Thr Ser Glu Ser Ala Thr Pro Glu Ser Gly
    1295                1300                1305

Pro Gly Thr Ser Thr Glu Pro Ser Glu Gly Ser Ala Pro Gly Ala
1310                1315                1320

Ser Ser Ala Pro Cys Asn Ile Gln Met Glu Asp Pro Thr Phe Lys
    1325                1330                1335

Glu Asn Tyr Arg Phe His Ala Ile Asn Gly Tyr Ile Met Asp Thr
1340                1345                1350

Leu Pro Gly Leu Val Met Ala Gln Asp Gln Arg Ile Arg Trp Tyr
    1355                1360                1365

Leu Leu Ser Met Gly Ser Asn Glu Asn Ile His Ser Ile His Phe
1370                1375                1380

Ser Gly His Val Phe Thr Val Arg Lys Lys Glu Glu Tyr Lys Met
    1385                1390                1395

Ala Leu Tyr Asn Leu Tyr Pro Gly Val Phe Glu Thr Val Glu Met
1400                1405                1410

Leu Pro Ser Lys Ala Gly Ile Trp Arg Val Glu Cys Leu Ile Gly
    1415                1420                1425

Glu His Leu His Ala Gly Met Ser Thr Leu Phe Leu Val Tyr Ser
1430                1435                1440

Asn Lys Cys Gln Thr Pro Leu Gly Met Ala Ser Gly His Ile Arg
    1445                1450                1455

Asp Phe Gln Ile Thr Ala Ser Gly Gln Tyr Gly Gln Trp Ala Pro
```

```
                    1460                1465                1470

Lys Leu Ala Arg Leu His Tyr Ser Gly Ser Ile Asn Ala Trp Ser
                1475                1480                1485

Thr Lys Glu Pro Phe Ser Trp Ile Lys Val Asp Leu Leu Ala Pro
            1490                1495                1500

Met Ile Ile His Gly Ile Lys Thr Gln Gly Ala Arg Gln Lys Phe
        1505                1510                1515

Ser Ser Leu Tyr Ile Ser Gln Phe Ile Ile Met Tyr Ser Leu Asp
        1520                1525                1530

Gly Lys Lys Trp Gln Thr Tyr Arg Gly Asn Ser Thr Gly Thr Leu
        1535                1540                1545

Met Val Phe Phe Gly Asn Val Asp Ser Ser Gly Ile Lys His Asn
        1550                1555                1560

Ile Phe Asn Pro Pro Ile Ile Ala Arg Tyr Ile Arg Leu His Pro
        1565                1570                1575

Thr His Tyr Ser Ile Arg Ser Thr Leu Arg Met Glu Leu Met Gly
        1580                1585                1590

Cys Asp Leu Asn Ser Cys Ser Met Pro Leu Gly Met Glu Ser Lys
        1595                1600                1605

Ala Ile Ser Asp Ala Gln Ile Thr Ala Ser Ser Tyr Phe Thr Asn
        1610                1615                1620

Met Phe Ala Thr Trp Ser Pro Ser Lys Ala Arg Leu His Leu Gln
        1625                1630                1635

Gly Arg Ser Asn Ala Trp Arg Pro Gln Val Asn Asn Pro Lys Glu
        1640                1645                1650

Trp Leu Gln Val Asp Phe Gln Lys Thr Met Lys Val Thr Gly Val
        1655                1660                1665

Thr Thr Gln Gly Val Lys Ser Leu Leu Thr Ser Met Tyr Val Lys
        1670                1675                1680

Glu Phe Leu Ile Ser Ser Ser Gln Asp Gly His Gln Trp Thr Leu
        1685                1690                1695

Phe Phe Gln Asn Gly Lys Val Lys Val Phe Gln Gly Asn Gln Asp
        1700                1705                1710

Ser Phe Thr Pro Val Val Asn Ser Leu Asp Pro Pro Leu Leu Thr
        1715                1720                1725

Arg Tyr Leu Arg Ile His Pro Gln Ser Trp Val His Gln Ile Ala
        1730                1735                1740

Leu Arg Met Glu Val Leu Gly Cys Glu Ala Gln Asp Leu Tyr Asp
        1745                1750                1755

Lys Thr His Thr Cys Pro Pro Cys Pro Ala Pro Glu Leu Leu Gly
        1760                1765                1770

Gly Pro Ser Val Phe Leu Phe Pro Pro Lys Pro Lys Asp Thr Leu
        1775                1780                1785

Met Ile Ser Arg Thr Pro Glu Val Thr Cys Val Val Val Asp Val
        1790                1795                1800

Ser His Glu Asp Pro Glu Val Lys Phe Asn Trp Tyr Val Asp Gly
        1805                1810                1815

Val Glu Val His Asn Ala Lys Thr Lys Pro Arg Glu Glu Gln Tyr
        1820                1825                1830

Asn Ser Thr Tyr Arg Val Val Ser Val Leu Thr Val Leu His Gln
        1835                1840                1845

Asp Trp Leu Asn Gly Lys Glu Tyr Lys Cys Lys Val Ser Asn Lys
        1850                1855                1860
```

Ala Leu Pro Ala Pro Ile Glu Lys Thr Ile Ser Lys Ala Lys Gly
    1865                1870                1875

Gln Pro Arg Glu Pro Gln Val Tyr Thr Leu Pro Pro Ser Arg Asp
    1880                1885                1890

Glu Leu Thr Lys Asn Gln Val Ser Leu Thr Cys Leu Val Lys Gly
    1895                1900                1905

Phe Tyr Pro Ser Asp Ile Ala Val Glu Trp Glu Ser Asn Gly Gln
    1910                1915                1920

Pro Glu Asn Asn Tyr Lys Thr Thr Pro Pro Val Leu Asp Ser Asp
    1925                1930                1935

Gly Ser Phe Phe Leu Tyr Ser Lys Leu Thr Val Asp Lys Ser Arg
    1940                1945                1950

Trp Gln Gln Gly Asn Val Phe Ser Cys Ser Val Met His Glu Ala
    1955                1960                1965

Leu His Asn His Tyr Thr Gln Lys Ser Leu Ser Leu Ser Pro Gly
    1970                1975                1980

Lys

<210> SEQ ID NO 106
<211> LENGTH: 2134
<212> TYPE: PRT
<213> ORGANISM: Artificial Sequence
<220> FEATURE:
<223> OTHER INFORMATION: FVIII 196 protein sequence

<400> SEQUENCE: 106

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Gly Ala Pro
        35                  40                  45

Gly Ser Ser Pro Ser Ala Ser Thr Gly Thr Gly Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Ala Ser Pro Gly Thr Ser Ser Thr Gly Ser Pro
                85                  90                  95

Gly Ser Ser Thr Pro Ser Gly Ala Thr Gly Ser Pro Gly Ser Ser Pro
            100                 105                 110

Ser Ala Ser Thr Gly Thr Gly Pro Gly Ala Ser Pro Gly Thr Ser Ser
        115                 120                 125

Thr Gly Ser Pro Gly Ser Ser Pro Ser Ala Ser Thr Gly Thr Gly Pro
    130                 135                 140

Gly Thr Pro Gly Ser Gly Thr Ala Ser Ser Ser Pro Gly Ser Ser Thr
145                 150                 155                 160

Pro Ser Gly Ala Thr Gly Ser Pro Gly Ser Ser Thr Pro Ser Gly Ala
                165                 170                 175

Thr Gly Ser Pro Gly Ala Ser Pro Gly Thr Ser Ser Thr Gly Ser Pro
            180                 185                 190

Ala Ser Ser Asp Ala Arg Phe Pro Pro Arg Val Pro Lys Ser Phe Pro
        195                 200                 205

Phe Asn Thr Ser Val Val Tyr Lys Lys Thr Leu Phe Val Glu Phe Thr
    210                 215                 220

-continued

```
Asp His Leu Phe Asn Ile Ala Lys Pro Arg Pro Pro Trp Met Gly Leu
225                 230                 235                 240

Leu Gly Pro Thr Ile Gln Ala Glu Val Tyr Asp Thr Val Val Ile Thr
            245                 250                 255

Leu Lys Asn Met Ala Ser His Pro Val Ser Leu His Ala Val Gly Val
        260                 265                 270

Ser Tyr Trp Lys Ala Ser Glu Gly Ala Glu Tyr Asp Asp Gln Thr Ser
    275                 280                 285

Gln Arg Glu Lys Glu Asp Asp Lys Val Phe Pro Gly Gly Ser His Thr
290                 295                 300

Tyr Val Trp Gln Val Leu Lys Glu Asn Gly Pro Met Ala Ser Asp Pro
305                 310                 315                 320

Leu Cys Leu Thr Tyr Ser Tyr Leu Ser His Val Asp Leu Val Lys Asp
                325                 330                 335

Leu Asn Ser Gly Leu Ile Gly Ala Leu Leu Val Cys Arg Glu Gly Ser
            340                 345                 350

Leu Ala Lys Glu Lys Thr Gln Thr Leu His Lys Phe Ile Leu Leu Phe
        355                 360                 365

Ala Val Phe Asp Glu Gly Lys Ser Trp His Ser Glu Thr Lys Asn Ser
370                 375                 380

Leu Met Gln Asp Arg Asp Ala Ala Ser Ala Arg Ala Trp Pro Lys Met
385                 390                 395                 400

His Thr Val Asn Gly Tyr Val Asn Arg Ser Leu Pro Gly Leu Ile Gly
                405                 410                 415

Cys His Arg Lys Ser Val Tyr Trp His Val Ile Gly Met Gly Thr Thr
            420                 425                 430

Pro Glu Val His Ser Ile Phe Leu Glu Gly His Thr Phe Leu Val Arg
        435                 440                 445

Asn His Arg Gln Ala Ser Leu Glu Ile Ser Pro Ile Thr Phe Leu Thr
450                 455                 460

Ala Gln Thr Leu Leu Met Asp Leu Gly Gln Phe Leu Leu Phe Cys His
465                 470                 475                 480

Ile Ser Ser His Gln His Asp Gly Met Glu Ala Tyr Val Lys Val Asp
                485                 490                 495

Ser Cys Pro Glu Glu Pro Gln Leu Arg Met Lys Asn Asn Glu Glu Ala
            500                 505                 510

Glu Asp Tyr Asp Asp Asp Leu Thr Asp Ser Glu Met Asp Val Val Arg
        515                 520                 525

Phe Asp Asp Asp Asn Ser Pro Ser Phe Ile Gln Ile Arg Ser Val Ala
530                 535                 540

Lys Lys His Pro Lys Thr Trp Val His Tyr Ile Ala Ala Glu Glu Glu
545                 550                 555                 560

Asp Trp Asp Tyr Ala Pro Leu Val Leu Ala Pro Asp Asp Arg Ser Tyr
                565                 570                 575

Lys Ser Gln Tyr Leu Asn Asn Gly Pro Gln Arg Ile Gly Arg Lys Tyr
            580                 585                 590

Lys Lys Val Arg Phe Met Ala Tyr Thr Asp Glu Thr Phe Lys Thr Arg
        595                 600                 605

Glu Ala Ile Gln His Glu Ser Gly Ile Leu Gly Pro Leu Leu Tyr Gly
610                 615                 620

Glu Val Gly Asp Thr Leu Leu Ile Ile Phe Lys Asn Gln Ala Ser Arg
625                 630                 635                 640

Pro Tyr Asn Ile Tyr Pro His Gly Ile Thr Asp Val Arg Pro Leu Tyr
```

-continued

```
                645                 650                 655
Ser Arg Arg Leu Pro Lys Gly Val Lys His Leu Lys Asp Phe Pro Ile
            660                 665                 670

Leu Pro Gly Glu Ile Phe Lys Tyr Lys Trp Thr Val Thr Val Glu Asp
            675                 680                 685

Gly Pro Thr Lys Ser Asp Pro Arg Cys Leu Thr Arg Tyr Tyr Ser Ser
            690                 695                 700

Phe Val Asn Met Glu Arg Asp Leu Ala Ser Gly Leu Ile Gly Pro Leu
705                 710                 715                 720

Leu Ile Cys Tyr Lys Glu Ser Val Asp Gln Arg Gly Asn Gln Ile Met
                725                 730                 735

Ser Asp Lys Arg Asn Val Ile Leu Phe Ser Val Phe Asp Glu Asn Arg
                740                 745                 750

Ser Trp Tyr Leu Thr Glu Asn Ile Gln Arg Phe Leu Pro Asn Pro Ala
                755                 760                 765

Gly Val Gln Leu Glu Asp Pro Glu Phe Gln Ala Ser Asn Ile Met His
            770                 775                 780

Ser Ile Asn Gly Tyr Val Phe Asp Ser Leu Gln Leu Ser Val Cys Leu
785                 790                 795                 800

His Glu Val Ala Tyr Trp Tyr Ile Leu Ser Ile Gly Ala Gln Thr Asp
                805                 810                 815

Phe Leu Ser Val Phe Phe Ser Gly Tyr Thr Phe Lys His Lys Met Val
                820                 825                 830

Tyr Glu Asp Thr Leu Thr Leu Phe Pro Phe Ser Gly Glu Thr Val Phe
            835                 840                 845

Met Ser Met Glu Asn Pro Gly Leu Trp Ile Leu Gly Cys His Asn Ser
850                 855                 860

Asp Phe Arg Asn Arg Gly Met Thr Ala Leu Leu Lys Val Ser Ser Cys
865                 870                 875                 880

Asp Lys Asn Thr Gly Asp Tyr Tyr Glu Asp Ser Tyr Glu Asp Ile Ser
                885                 890                 895

Ala Tyr Leu Leu Ser Lys Asn Asn Ala Ile Glu Pro Arg Ser Phe Ser
            900                 905                 910

Gln Asn Pro Pro Val Leu Lys Arg His Gln Arg Glu Ile Thr Arg Thr
            915                 920                 925

Thr Leu Gln Gly Ala Pro Gly Thr Pro Gly Ser Gly Thr Ala Ser Ser
            930                 935                 940

Ser Pro Gly Ala Ser Pro Gly Thr Ser Ser Thr Gly Ser Pro Gly Ala
945                 950                 955                 960

Ser Pro Gly Thr Ser Ser Thr Gly Ser Pro Gly Ala Ser Pro Gly Thr
                965                 970                 975

Ser Ser Thr Gly Ser Pro Gly Ser Ser Pro Ser Ala Ser Thr Gly Thr
            980                 985                 990

Gly Pro Gly Thr Pro Gly Ser Gly Thr Ala Ser Ser Ser Pro Gly Ala
            995                 1000                1005

Ser Pro Gly Thr Ser Ser Thr Gly Ser Pro Gly Ala Ser Pro Gly
        1010                1015                1020

Thr Ser Ser Thr Gly Ser Pro Gly Ala Ser Pro Gly Thr Ser Ser
        1025                1030                1035

Thr Gly Ser Pro Gly Ser Ser Thr Pro Ser Gly Ala Thr Gly Ser
        1040                1045                1050

Pro Gly Ser Ser Thr Pro Ser Gly Ala Thr Gly Ser Pro Gly Ala
        1055                1060                1065
```

-continued

```
Ser Pro Gly Thr Ser Ser Thr Gly Ser Pro Ala Ser     Ser Ser Asp
    1070                1075                1080

Gln Glu Glu Ile Asp Tyr Asp Thr Ile Ser Val     Glu Met Lys
    1085                1090                1095

Lys Glu Asp Phe Asp Ile Tyr Asp Glu Asp Glu Asn     Gln Ser Pro
    1100                1105                1110

Arg Ser Phe Gln Lys Lys Thr Arg His Tyr Phe Ile     Ala Ala Val
    1115                1120                1125

Glu Arg Leu Trp Asp Tyr Gly Met Ser Ser Pro     His Val Leu
    1130                1135                1140

Arg Asn Arg Ala Gln Ser Gly Ser Val Pro Gln Phe     Lys Lys Val
    1145                1150                1155

Val Phe Gln Glu Phe Thr Asp Gly Ser Phe Thr Gln     Pro Leu Tyr
    1160                1165                1170

Arg Gly Glu Leu Asn Glu His Leu Gly Leu Leu Gly     Pro Tyr Ile
    1175                1180                1185

Arg Ala Glu Val Glu Asp Asn Ile Met Val Thr Phe     Arg Asn Gln
    1190                1195                1200

Ala Ser Arg Pro Tyr Ser Phe Tyr Ser Ser Leu Ile     Ser Tyr Glu
    1205                1210                1215

Glu Asp Gln Arg Gln Gly Ala Glu Pro Arg Lys Asn     Phe Val Lys
    1220                1225                1230

Pro Asn Glu Thr Lys Thr Tyr Phe Trp Lys Val Gln     His His Met
    1235                1240                1245

Ala Pro Thr Lys Asp Glu Phe Asp Cys Lys Ala Trp     Ala Tyr Phe
    1250                1255                1260

Ser Asp Val Asp Leu Glu Lys Asp Val His Ser Gly     Leu Ile Gly
    1265                1270                1275

Pro Leu Leu Val Cys His Thr Asn Thr Leu Asn Pro     Ala His Gly
    1280                1285                1290

Arg Gln Val Thr Val Gln Glu Phe Ala Leu Phe Phe     Thr Ile Phe
    1295                1300                1305

Asp Glu Thr Lys Ser Trp Tyr Phe Thr Glu Asn Met     Glu Arg Asn
    1310                1315                1320

Cys Arg Gly Ala Pro Thr Ser Glu Ser Ala Thr Pro     Glu Ser Gly
    1325                1330                1335

Pro Gly Ser Glu Pro Ala Thr Ser Gly Ser Glu Thr     Pro Gly Thr
    1340                1345                1350

Ser Glu Ser Ala Thr Pro Glu Ser Gly Pro Gly Ser     Glu Pro Ala
    1355                1360                1365

Thr Ser Gly Ser Glu Thr Pro Gly Thr Ser Glu Ser     Ala Thr Pro
    1370                1375                1380

Glu Ser Gly Pro Gly Thr Ser Thr Glu Pro Ser Glu     Gly Ser Ala
    1385                1390                1395

Pro Gly Thr Ser Glu Ser Ala Thr Pro Glu Ser Gly     Pro Gly Ser
    1400                1405                1410

Pro Ala Gly Ser Pro Thr Ser Thr Glu Glu Gly Ser     Pro Ala Gly
    1415                1420                1425

Ser Pro Thr Ser Thr Glu Glu Gly Ser Pro Ala Gly     Ser Pro Thr
    1430                1435                1440

Ser Thr Glu Glu Gly Thr Ser Glu Ser Ala Thr Pro     Glu Ser Gly
    1445                1450                1455
```

```
Pro Gly Thr Ser Thr Glu Pro Ser Glu Gly Ser Ala Pro Gly Ala
    1460            1465            1470

Ser Ser Ala Pro Cys Asn Ile Gln Met Glu Asp Pro Thr Phe Lys
    1475            1480            1485

Glu Asn Tyr Arg Phe His Ala Ile Asn Gly Tyr Ile Met Asp Thr
    1490            1495            1500

Leu Pro Gly Leu Val Met Ala Gln Asp Gln Arg Ile Arg Trp Tyr
    1505            1510            1515

Leu Leu Ser Met Gly Ser Asn Glu Asn Ile His Ser Ile His Phe
    1520            1525            1530

Ser Gly His Val Phe Thr Val Arg Lys Lys Glu Glu Tyr Lys Met
    1535            1540            1545

Ala Leu Tyr Asn Leu Tyr Pro Gly Val Phe Glu Thr Val Glu Met
    1550            1555            1560

Leu Pro Ser Lys Ala Gly Ile Trp Arg Val Glu Cys Leu Ile Gly
    1565            1570            1575

Glu His Leu His Ala Gly Met Ser Thr Leu Phe Leu Val Tyr Ser
    1580            1585            1590

Asn Lys Cys Gln Thr Pro Leu Gly Met Ala Ser Gly His Ile Arg
    1595            1600            1605

Asp Phe Gln Ile Thr Ala Ser Gly Gln Tyr Gly Gln Trp Ala Pro
    1610            1615            1620

Lys Leu Ala Arg Leu His Tyr Ser Gly Ser Ile Asn Ala Trp Ser
    1625            1630            1635

Thr Lys Glu Pro Phe Ser Trp Ile Lys Val Asp Leu Leu Ala Pro
    1640            1645            1650

Met Ile Ile His Gly Ile Lys Thr Gln Gly Ala Arg Gln Lys Phe
    1655            1660            1665

Ser Ser Leu Tyr Ile Ser Gln Phe Ile Ile Met Tyr Ser Leu Asp
    1670            1675            1680

Gly Lys Lys Trp Gln Thr Tyr Arg Gly Asn Ser Thr Gly Thr Leu
    1685            1690            1695

Met Val Phe Phe Gly Asn Val Asp Ser Ser Gly Ile Lys His Asn
    1700            1705            1710

Ile Phe Asn Pro Pro Ile Ile Ala Arg Tyr Ile Arg Leu His Pro
    1715            1720            1725

Thr His Tyr Ser Ile Arg Ser Thr Leu Arg Met Glu Leu Met Gly
    1730            1735            1740

Cys Asp Leu Asn Ser Cys Ser Met Pro Leu Gly Met Glu Ser Lys
    1745            1750            1755

Ala Ile Ser Asp Ala Gln Ile Thr Ala Ser Ser Tyr Phe Thr Asn
    1760            1765            1770

Met Phe Ala Thr Trp Ser Pro Ser Lys Ala Arg Leu His Leu Gln
    1775            1780            1785

Gly Arg Ser Asn Ala Trp Arg Pro Gln Val Asn Asn Pro Lys Glu
    1790            1795            1800

Trp Leu Gln Val Asp Phe Gln Lys Thr Met Lys Val Thr Gly Val
    1805            1810            1815

Thr Thr Gln Gly Val Lys Ser Leu Leu Thr Ser Met Tyr Val Lys
    1820            1825            1830

Glu Phe Leu Ile Ser Ser Ser Gln Asp Gly His Gln Trp Thr Leu
    1835            1840            1845

Phe Phe Gln Asn Gly Lys Val Lys Val Phe Gln Gly Asn Gln Asp
```

Ser Phe Thr Pro Val Val Asn Ser Leu Asp Pro Pro Leu Leu Thr
1865                1870                1875

Arg Tyr Leu Arg Ile His Pro Gln Ser Trp Val His Gln Ile Ala
1880                1885                1890

Leu Arg Met Glu Val Leu Gly Cys Glu Ala Gln Asp Leu Tyr Asp
1895                1900                1905

Lys Thr His Thr Cys Pro Cys Pro Ala Pro Glu Leu Leu Gly
1910                1915                1920

Gly Pro Ser Val Phe Leu Phe Pro Pro Lys Pro Lys Asp Thr Leu
1925                1930                1935

Met Ile Ser Arg Thr Pro Glu Val Thr Cys Val Val Val Asp Val
1940                1945                1950

Ser His Glu Asp Pro Glu Val Lys Phe Asn Trp Tyr Val Asp Gly
1955                1960                1965

Val Glu Val His Asn Ala Lys Thr Lys Pro Arg Glu Glu Gln Tyr
1970                1975                1980

Asn Ser Thr Tyr Arg Val Val Ser Val Leu Thr Val Leu His Gln
1985                1990                1995

Asp Trp Leu Asn Gly Lys Glu Tyr Lys Cys Lys Val Ser Asn Lys
2000                2005                2010

Ala Leu Pro Ala Pro Ile Glu Lys Thr Ile Ser Lys Ala Lys Gly
2015                2020                2025

Gln Pro Arg Glu Pro Gln Val Tyr Thr Leu Pro Pro Ser Arg Asp
2030                2035                2040

Glu Leu Thr Lys Asn Gln Val Ser Leu Thr Cys Leu Val Lys Gly
2045                2050                2055

Phe Tyr Pro Ser Asp Ile Ala Val Glu Trp Glu Ser Asn Gly Gln
2060                2065                2070

Pro Glu Asn Asn Tyr Lys Thr Thr Pro Pro Val Leu Asp Ser Asp
2075                2080                2085

Gly Ser Phe Phe Leu Tyr Ser Lys Leu Thr Val Asp Lys Ser Arg
2090                2095                2100

Trp Gln Gln Gly Asn Val Phe Ser Cys Ser Val Met His Glu Ala
2105                2110                2115

Leu His Asn His Tyr Thr Gln Lys Ser Leu Ser Leu Ser Pro Gly
2120                2125                2130

Lys

<210> SEQ ID NO 107
<211> LENGTH: 1984
<212> TYPE: PRT
<213> ORGANISM: Artificial Sequence
<220> FEATURE:
<223> OTHER INFORMATION: FVIII 199 protein sequence

<400> SEQUENCE: 107

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
             85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Ala Glu Ile Thr Arg Thr Thr Leu Gln Gly Ala Pro
    770                 775                 780

Gly Thr Pro Gly Ser Gly Thr Ala Ser Ser Pro Gly Ala Ser Pro
785                 790                 795                 800

Gly Thr Ser Ser Thr Gly Ser Pro Gly Ala Ser Pro Gly Thr Ser Ser
                805                 810                 815

Thr Gly Ser Pro Gly Ala Ser Pro Gly Thr Ser Ser Thr Gly Ser Pro
            820                 825                 830

Gly Ser Ser Pro Ser Ala Ser Thr Gly Thr Gly Pro Gly Thr Pro Gly
        835                 840                 845

Ser Gly Thr Ala Ser Ser Ser Pro Gly Ala Ser Pro Gly Thr Ser Ser
    850                 855                 860

Thr Gly Ser Pro Gly Ala Ser Pro Gly Thr Ser Ser Thr Gly Ser Pro
865                 870                 875                 880

Gly Ala Ser Pro Gly Thr Ser Ser Thr Gly Ser Pro Gly Ser Ser Thr
                885                 890                 895

Pro Ser Gly Ala Thr Gly Ser Pro Gly Ser Ser Thr Pro Ser Gly Ala
```

```
              900             905              910
Thr Gly Ser Pro Gly Ala Ser Pro Gly Thr Ser Ser Thr Gly Ser Pro
            915             920              925

Ala Ser Ser Ser Asp Gln Glu Glu Ile Asp Tyr Asp Asp Thr Ile Ser
            930             935              940

Val Glu Met Lys Lys Glu Asp Phe Asp Ile Tyr Asp Glu Asp Glu Asn
945             950              955              960

Gln Ser Pro Arg Ser Phe Gln Lys Lys Thr Arg His Tyr Phe Ile Ala
            965             970              975

Ala Val Glu Arg Leu Trp Asp Tyr Gly Met Ser Ser Ser Pro His Val
            980             985              990

Leu Arg Asn Arg Ala Gln Ser Gly Ser Val Pro Gln Phe Lys Lys Val
            995            1000             1005

Val Phe Gln Glu Phe Thr Asp Gly Ser Phe Thr Gln Pro Leu Tyr
    1010            1015             1020

Arg Gly Glu Leu Asn Glu His Leu Gly Leu Leu Gly Pro Tyr Ile
    1025            1030             1035

Arg Ala Glu Val Glu Asp Asn Ile Met Val Thr Phe Arg Asn Gln
    1040            1045             1050

Ala Ser Arg Pro Tyr Ser Phe Tyr Ser Ser Leu Ile Ser Tyr Glu
    1055            1060             1065

Glu Asp Gln Arg Gln Gly Ala Glu Pro Arg Lys Asn Phe Val Lys
    1070            1075             1080

Pro Asn Glu Thr Lys Thr Tyr Phe Trp Lys Val Gln His His Met
    1085            1090             1095

Ala Pro Thr Lys Asp Glu Phe Asp Cys Lys Ala Trp Ala Tyr Phe
    1100            1105             1110

Ser Asp Val Asp Leu Glu Lys Asp Val His Ser Gly Leu Ile Gly
    1115            1120             1125

Pro Leu Leu Val Cys His Thr Asn Thr Leu Asn Pro Ala His Gly
    1130            1135             1140

Arg Gln Val Thr Val Gln Glu Phe Ala Leu Phe Phe Thr Ile Phe
    1145            1150             1155

Asp Glu Thr Lys Ser Trp Tyr Phe Thr Glu Asn Met Glu Arg Asn
    1160            1165             1170

Cys Arg Gly Ala Pro Thr Ser Glu Ser Ala Thr Pro Glu Ser Gly
    1175            1180             1185

Pro Gly Ser Glu Pro Ala Ser Gly Ser Glu Thr Pro Gly Thr
    1190            1195             1200

Ser Glu Ser Ala Thr Pro Glu Ser Gly Pro Gly Ser Glu Pro Ala
    1205            1210             1215

Thr Ser Gly Ser Glu Thr Pro Gly Thr Ser Glu Ser Ala Thr Pro
    1220            1225             1230

Glu Ser Gly Pro Gly Thr Ser Thr Glu Pro Ser Glu Gly Ser Ala
    1235            1240             1245

Pro Gly Thr Ser Glu Ser Ala Thr Pro Glu Ser Gly Pro Gly Ser
    1250            1255             1260

Pro Ala Gly Ser Pro Thr Ser Thr Glu Glu Gly Ser Pro Ala Gly
    1265            1270             1275

Ser Pro Thr Ser Thr Glu Glu Gly Ser Pro Ala Gly Ser Pro Thr
    1280            1285             1290

Ser Thr Glu Glu Gly Thr Ser Glu Ser Ala Thr Pro Glu Ser Gly
    1295            1300             1305
```

```
Pro Gly Thr Ser Thr Glu Pro Ser Glu Gly Ser Ala Pro Gly Ala
    1310            1315            1320

Ser Ser Ala Pro Cys Asn Ile Gln Met Glu Asp Pro Thr Phe Lys
    1325            1330            1335

Glu Asn Tyr Arg Phe His Ala Ile Asn Gly Tyr Ile Met Asp Thr
    1340            1345            1350

Leu Pro Gly Leu Val Met Ala Gln Asp Gln Arg Ile Arg Trp Tyr
    1355            1360            1365

Leu Leu Ser Met Gly Ser Asn Glu Asn Ile His Ser Ile His Phe
    1370            1375            1380

Ser Gly His Val Phe Thr Val Arg Lys Lys Glu Glu Tyr Lys Met
    1385            1390            1395

Ala Leu Tyr Asn Leu Tyr Pro Gly Val Phe Glu Thr Val Glu Met
    1400            1405            1410

Leu Pro Ser Lys Ala Gly Ile Trp Arg Val Glu Cys Leu Ile Gly
    1415            1420            1425

Glu His Leu His Ala Gly Met Ser Thr Leu Phe Leu Val Tyr Ser
    1430            1435            1440

Asn Lys Cys Gln Thr Pro Leu Gly Met Ala Ser Gly His Ile Arg
    1445            1450            1455

Asp Phe Gln Ile Thr Ala Ser Gly Gln Tyr Gly Gln Trp Ala Pro
    1460            1465            1470

Lys Leu Ala Arg Leu His Tyr Ser Gly Ser Ile Asn Ala Trp Ser
    1475            1480            1485

Thr Lys Glu Pro Phe Ser Trp Ile Lys Val Asp Leu Leu Ala Pro
    1490            1495            1500

Met Ile Ile His Gly Ile Lys Thr Gln Gly Ala Arg Gln Lys Phe
    1505            1510            1515

Ser Ser Leu Tyr Ile Ser Gln Phe Ile Ile Met Tyr Ser Leu Asp
    1520            1525            1530

Gly Lys Lys Trp Gln Thr Tyr Arg Gly Asn Ser Thr Gly Thr Leu
    1535            1540            1545

Met Val Phe Phe Gly Asn Val Asp Ser Ser Gly Ile Lys His Asn
    1550            1555            1560

Ile Phe Asn Pro Pro Ile Ile Ala Arg Tyr Ile Arg Leu His Pro
    1565            1570            1575

Thr His Tyr Ser Ile Arg Ser Thr Leu Arg Met Glu Leu Met Gly
    1580            1585            1590

Cys Asp Leu Asn Ser Cys Ser Met Pro Leu Gly Met Glu Ser Lys
    1595            1600            1605

Ala Ile Ser Asp Ala Gln Ile Thr Ala Ser Ser Tyr Phe Thr Asn
    1610            1615            1620

Met Phe Ala Thr Trp Ser Pro Ser Lys Ala Arg Leu His Leu Gln
    1625            1630            1635

Gly Arg Ser Asn Ala Trp Arg Pro Gln Val Asn Asn Pro Lys Glu
    1640            1645            1650

Trp Leu Gln Val Asp Phe Gln Lys Thr Met Lys Val Thr Gly Val
    1655            1660            1665

Thr Thr Gln Gly Val Lys Ser Leu Leu Thr Ser Met Tyr Val Lys
    1670            1675            1680

Glu Phe Leu Ile Ser Ser Ser Gln Asp Gly His Gln Trp Thr Leu
    1685            1690            1695
```

-continued

```
Phe Phe Gln Asn Gly Lys Val Lys Val Phe Gln Gly Asn Gln Asp
    1700                1705                1710

Ser Phe Thr Pro Val Val Asn Ser Leu Asp Pro Pro Leu Leu Thr
    1715                1720                1725

Arg Tyr Leu Arg Ile His Pro Gln Ser Trp Val His Gln Ile Ala
    1730                1735                1740

Leu Arg Met Glu Val Leu Gly Cys Glu Ala Gln Asp Leu Tyr Asp
    1745                1750                1755

Lys Thr His Thr Cys Pro Pro Cys Pro Ala Pro Glu Leu Leu Gly
    1760                1765                1770

Gly Pro Ser Val Phe Leu Phe Pro Pro Lys Pro Lys Asp Thr Leu
    1775                1780                1785

Met Ile Ser Arg Thr Pro Glu Val Thr Cys Val Val Val Asp Val
    1790                1795                1800

Ser His Glu Asp Pro Glu Val Lys Phe Asn Trp Tyr Val Asp Gly
    1805                1810                1815

Val Glu Val His Asn Ala Lys Thr Lys Pro Arg Glu Glu Gln Tyr
    1820                1825                1830

Asn Ser Thr Tyr Arg Val Val Ser Val Leu Thr Val Leu His Gln
    1835                1840                1845

Asp Trp Leu Asn Gly Lys Glu Tyr Lys Cys Lys Val Ser Asn Lys
    1850                1855                1860

Ala Leu Pro Ala Pro Ile Glu Lys Thr Ile Ser Lys Ala Lys Gly
    1865                1870                1875

Gln Pro Arg Glu Pro Gln Val Tyr Thr Leu Pro Pro Ser Arg Asp
    1880                1885                1890

Glu Leu Thr Lys Asn Gln Val Ser Leu Thr Cys Leu Val Lys Gly
    1895                1900                1905

Phe Tyr Pro Ser Asp Ile Ala Val Glu Trp Glu Ser Asn Gly Gln
    1910                1915                1920

Pro Glu Asn Asn Tyr Lys Thr Thr Pro Pro Val Leu Asp Ser Asp
    1925                1930                1935

Gly Ser Phe Phe Leu Tyr Ser Lys Leu Thr Val Asp Lys Ser Arg
    1940                1945                1950

Trp Gln Gln Gly Asn Val Phe Ser Cys Ser Val Met His Glu Ala
    1955                1960                1965

Leu His Asn His Tyr Thr Gln Lys Ser Leu Ser Leu Ser Pro Gly
    1970                1975                1980

Lys
```

<210> SEQ ID NO 108
<211> LENGTH: 2134
<212> TYPE: PRT
<213> ORGANISM: Artificial Sequence
<220> FEATURE:
<223> OTHER INFORMATION: FVIII 201 protein sequence

<400> SEQUENCE: 108

```
Met Gln Ile Glu Leu Ser Thr Cys Phe Phe Leu Cys Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Gly Ala Pro
        35                  40                  45

Gly Ser Ser Pro Ser Ala Ser Thr Gly Thr Gly Pro Gly Ser Ser Pro
```

-continued

```
                50                  55                  60
Ser Ala Ser Thr Gly Thr Gly Pro Gly Ala Ser Pro Gly Thr Ser Ser
 65                  70                  75                  80
Thr Gly Ser Pro Gly Ala Ser Pro Gly Thr Ser Ser Thr Gly Ser Pro
                     85                  90                  95
Gly Ser Ser Thr Pro Ser Gly Ala Thr Gly Ser Pro Gly Ser Ser Pro
                    100                 105                 110
Ser Ala Ser Thr Gly Thr Gly Pro Gly Ala Ser Pro Gly Thr Ser Ser
                    115                 120                 125
Thr Gly Ser Pro Gly Ser Ser Pro Ser Ala Ser Thr Gly Thr Gly Pro
                    130                 135                 140
Gly Thr Pro Gly Ser Gly Thr Ala Ser Ser Pro Gly Ser Ser Thr
145                 150                 155                 160
Pro Ser Gly Ala Thr Gly Ser Pro Gly Ser Ser Thr Pro Ser Gly Ala
                    165                 170                 175
Thr Gly Ser Pro Gly Ala Ser Pro Gly Thr Ser Ser Thr Gly Ser Pro
                    180                 185                 190
Ala Ser Ser Asp Ala Arg Phe Pro Pro Arg Val Pro Lys Ser Phe Pro
                    195                 200                 205
Phe Asn Thr Ser Val Val Tyr Lys Lys Thr Leu Phe Val Glu Phe Thr
                    210                 215                 220
Asp His Leu Phe Asn Ile Ala Lys Pro Arg Pro Pro Trp Met Gly Leu
225                 230                 235                 240
Leu Gly Pro Thr Ile Gln Ala Glu Val Tyr Asp Thr Val Val Ile Thr
                    245                 250                 255
Leu Lys Asn Met Ala Ser His Pro Val Ser Leu His Ala Val Gly Val
                    260                 265                 270
Ser Tyr Trp Lys Ala Ser Glu Gly Ala Glu Tyr Asp Asp Gln Thr Ser
                    275                 280                 285
Gln Arg Glu Lys Glu Asp Asp Lys Val Phe Pro Gly Gly Ser His Thr
                    290                 295                 300
Tyr Val Trp Gln Val Leu Lys Glu Asn Gly Pro Met Ala Ser Asp Pro
305                 310                 315                 320
Leu Cys Leu Thr Tyr Ser Tyr Leu Ser His Val Asp Leu Val Lys Asp
                    325                 330                 335
Leu Asn Ser Gly Leu Ile Gly Ala Leu Leu Val Cys Arg Glu Gly Ser
                    340                 345                 350
Leu Ala Lys Glu Lys Thr Gln Thr Leu His Lys Phe Ile Leu Leu Phe
                    355                 360                 365
Ala Val Phe Asp Glu Gly Lys Ser Trp His Ser Glu Thr Lys Asn Ser
                    370                 375                 380
Leu Met Gln Asp Arg Asp Ala Ala Ser Ala Arg Ala Trp Pro Lys Met
385                 390                 395                 400
His Thr Val Asn Gly Tyr Val Asn Arg Ser Leu Pro Gly Leu Ile Gly
                    405                 410                 415
Cys His Arg Lys Ser Val Tyr Trp His Val Ile Gly Met Gly Thr Thr
                    420                 425                 430
Pro Glu Val His Ser Ile Phe Leu Glu Gly His Thr Phe Leu Val Arg
                    435                 440                 445
Asn His Arg Gln Ala Ser Leu Glu Ile Ser Pro Ile Thr Phe Leu Thr
                    450                 455                 460
Ala Gln Thr Leu Leu Met Asp Leu Gly Gln Phe Leu Leu Phe Cys His
465                 470                 475                 480
```

```
Ile Ser Ser His Gln His Asp Gly Met Glu Ala Tyr Val Lys Val Asp
            485                 490                 495
Ser Cys Pro Glu Pro Gln Leu Arg Met Lys Asn Asn Glu Glu Ala
            500                 505                 510
Glu Asp Tyr Asp Asp Leu Thr Asp Ser Glu Met Asp Val Val Arg
            515                 520                 525
Phe Asp Asp Asn Ser Pro Ser Phe Ile Gln Ile Arg Ser Val Ala
            530                 535                 540
Lys Lys His Pro Lys Thr Trp Val His Tyr Ile Ala Ala Glu Glu Glu
545                 550                 555                 560
Asp Trp Asp Tyr Ala Pro Leu Val Leu Ala Pro Asp Asp Arg Ser Tyr
                565                 570                 575
Lys Ser Gln Tyr Leu Asn Asn Gly Pro Gln Arg Ile Gly Arg Lys Tyr
                580                 585                 590
Lys Lys Val Arg Phe Met Ala Tyr Thr Asp Glu Thr Phe Lys Thr Arg
        595                 600                 605
Glu Ala Ile Gln His Glu Ser Gly Ile Leu Gly Pro Leu Leu Tyr Gly
        610                 615                 620
Glu Val Gly Asp Thr Leu Leu Ile Ile Phe Lys Asn Gln Ala Ser Arg
625                 630                 635                 640
Pro Tyr Asn Ile Tyr Pro His Gly Ile Thr Asp Val Arg Pro Leu Tyr
                645                 650                 655
Ser Arg Arg Leu Pro Lys Gly Val Lys His Leu Lys Asp Phe Pro Ile
                660                 665                 670
Leu Pro Gly Glu Ile Phe Lys Tyr Lys Trp Thr Val Thr Val Glu Asp
        675                 680                 685
Gly Pro Thr Lys Ser Asp Pro Arg Cys Leu Thr Arg Tyr Tyr Ser Ser
        690                 695                 700
Phe Val Asn Met Glu Arg Asp Leu Ala Ser Gly Leu Ile Gly Pro Leu
705                 710                 715                 720
Leu Ile Cys Tyr Lys Glu Ser Val Asp Gln Arg Gly Asn Gln Ile Met
                725                 730                 735
Ser Asp Lys Arg Asn Val Ile Leu Phe Ser Val Phe Asp Glu Asn Arg
            740                 745                 750
Ser Trp Tyr Leu Thr Glu Asn Ile Gln Arg Phe Leu Pro Asn Pro Ala
            755                 760                 765
Gly Val Gln Leu Glu Asp Pro Glu Phe Gln Ala Ser Asn Ile Met His
        770                 775                 780
Ser Ile Asn Gly Tyr Val Phe Asp Ser Leu Gln Leu Ser Val Cys Leu
785                 790                 795                 800
His Glu Val Ala Tyr Trp Tyr Ile Leu Ser Ile Gly Ala Gln Thr Asp
                805                 810                 815
Phe Leu Ser Val Phe Phe Ser Gly Tyr Thr Phe Lys His Lys Met Val
            820                 825                 830
Tyr Glu Asp Thr Leu Thr Leu Phe Pro Phe Ser Gly Glu Thr Val Phe
        835                 840                 845
Met Ser Met Glu Asn Pro Gly Leu Trp Ile Leu Gly Cys His Asn Ser
850                 855                 860
Asp Phe Arg Asn Arg Gly Met Thr Ala Leu Leu Lys Val Ser Ser Cys
865                 870                 875                 880
Asp Lys Asn Thr Gly Asp Tyr Tyr Glu Asp Ser Tyr Glu Asp Ile Ser
                885                 890                 895
```

```
Ala Tyr Leu Leu Ser Lys Asn Asn Ala Ile Glu Pro Arg Ser Phe Ser
                900                 905                 910

Gln Asn Pro Pro Val Leu Lys Arg His Gln Ala Glu Ile Thr Arg Thr
            915                 920                 925

Thr Leu Gln Gly Ala Pro Gly Thr Pro Gly Ser Gly Thr Ala Ser Ser
        930                 935                 940

Ser Pro Gly Ala Ser Pro Gly Thr Ser Ser Thr Gly Ser Pro Gly Ala
945                 950                 955                 960

Ser Pro Gly Thr Ser Ser Thr Gly Ser Pro Gly Ala Ser Pro Gly Thr
                965                 970                 975

Ser Ser Thr Gly Ser Pro Gly Ser Ser Pro Ser Ala Ser Thr Gly Thr
            980                 985                 990

Gly Pro Gly Thr Pro Gly Ser Gly Thr Ala Ser Ser Ser Pro Gly Ala
        995                 1000                1005

Ser Pro Gly Thr Ser Ser Thr Gly Ser Pro Gly Ala Ser Pro Gly
    1010                1015                1020

Thr Ser Ser Thr Gly Ser Pro Gly Ala Ser Pro Gly Thr Ser Ser
    1025                1030                1035

Thr Gly Ser Pro Gly Ser Ser Thr Pro Ser Gly Ala Thr Gly Ser
    1040                1045                1050

Pro Gly Ser Ser Thr Pro Ser Gly Ala Thr Gly Ser Pro Gly Ala
    1055                1060                1065

Ser Pro Gly Thr Ser Ser Thr Gly Ser Pro Ala Ser Ser Ser Asp
    1070                1075                1080

Gln Glu Glu Ile Asp Tyr Asp Asp Thr Ile Ser Val Glu Met Lys
    1085                1090                1095

Lys Glu Asp Phe Asp Ile Tyr Asp Glu Asp Glu Asn Gln Ser Pro
    1100                1105                1110

Arg Ser Phe Gln Lys Lys Thr Arg His Tyr Phe Ile Ala Ala Val
    1115                1120                1125

Glu Arg Leu Trp Asp Tyr Gly Met Ser Ser Ser Pro His Val Leu
    1130                1135                1140

Arg Asn Arg Ala Gln Ser Gly Ser Val Pro Gln Phe Lys Lys Val
    1145                1150                1155

Val Phe Gln Glu Phe Thr Asp Gly Ser Phe Thr Gln Pro Leu Tyr
    1160                1165                1170

Arg Gly Glu Leu Asn Glu His Leu Gly Leu Leu Gly Pro Tyr Ile
    1175                1180                1185

Arg Ala Glu Val Glu Asp Asn Ile Met Val Thr Phe Arg Asn Gln
    1190                1195                1200

Ala Ser Arg Pro Tyr Ser Phe Tyr Ser Ser Leu Ile Ser Tyr Glu
    1205                1210                1215

Glu Asp Gln Arg Gln Gly Ala Glu Pro Arg Lys Asn Phe Val Lys
    1220                1225                1230

Pro Asn Glu Thr Lys Thr Tyr Phe Trp Lys Val Gln His His Met
    1235                1240                1245

Ala Pro Thr Lys Asp Glu Phe Asp Cys Lys Ala Trp Ala Tyr Phe
    1250                1255                1260

Ser Asp Val Asp Leu Glu Lys Asp Val His Ser Gly Leu Ile Gly
    1265                1270                1275

Pro Leu Leu Val Cys His Thr Asn Thr Leu Asn Pro Ala His Gly
    1280                1285                1290

Arg Gln Val Thr Val Gln Glu Phe Ala Leu Phe Phe Thr Ile Phe
```

```
            1295                1300                1305

Asp Glu Thr Lys Ser Trp Tyr Phe Thr Glu Asn Met Glu Arg Asn
    1310                1315                1320

Cys Arg Gly Ala Pro Thr Ser Glu Ser Ala Thr Pro Glu Ser Gly
    1325                1330                1335

Pro Gly Ser Glu Pro Ala Thr Ser Gly Ser Glu Thr Pro Gly Thr
    1340                1345                1350

Ser Glu Ser Ala Thr Pro Glu Ser Gly Pro Gly Ser Glu Pro Ala
    1355                1360                1365

Thr Ser Gly Ser Glu Thr Pro Gly Thr Ser Glu Ser Ala Thr Pro
    1370                1375                1380

Glu Ser Gly Pro Gly Thr Ser Thr Glu Pro Ser Glu Gly Ser Ala
    1385                1390                1395

Pro Gly Thr Ser Glu Ser Ala Thr Pro Glu Ser Gly Pro Gly Ser
    1400                1405                1410

Pro Ala Gly Ser Pro Thr Ser Thr Glu Glu Gly Ser Pro Ala Gly
    1415                1420                1425

Ser Pro Thr Ser Thr Glu Glu Gly Ser Pro Ala Gly Ser Pro Thr
    1430                1435                1440

Ser Thr Glu Glu Gly Thr Ser Glu Ser Ala Thr Pro Glu Ser Gly
    1445                1450                1455

Pro Gly Thr Ser Thr Glu Pro Ser Glu Gly Ser Ala Pro Gly Ala
    1460                1465                1470

Ser Ser Ala Pro Cys Asn Ile Gln Met Glu Asp Pro Thr Phe Lys
    1475                1480                1485

Glu Asn Tyr Arg Phe His Ala Ile Asn Gly Tyr Ile Met Asp Thr
    1490                1495                1500

Leu Pro Gly Leu Val Met Ala Gln Asp Gln Arg Ile Arg Trp Tyr
    1505                1510                1515

Leu Leu Ser Met Gly Ser Asn Glu Asn Ile His Ser Ile His Phe
    1520                1525                1530

Ser Gly His Val Phe Thr Val Arg Lys Lys Glu Glu Tyr Lys Met
    1535                1540                1545

Ala Leu Tyr Asn Leu Tyr Pro Gly Val Phe Glu Thr Val Glu Met
    1550                1555                1560

Leu Pro Ser Lys Ala Gly Ile Trp Arg Val Glu Cys Leu Ile Gly
    1565                1570                1575

Glu His Leu His Ala Gly Met Ser Thr Leu Phe Leu Val Tyr Ser
    1580                1585                1590

Asn Lys Cys Gln Thr Pro Leu Gly Met Ala Ser Gly His Ile Arg
    1595                1600                1605

Asp Phe Gln Ile Thr Ala Ser Gly Gln Tyr Gly Gln Trp Ala Pro
    1610                1615                1620

Lys Leu Ala Arg Leu His Tyr Ser Gly Ser Ile Asn Ala Trp Ser
    1625                1630                1635

Thr Lys Glu Pro Phe Ser Trp Ile Lys Val Asp Leu Leu Ala Pro
    1640                1645                1650

Met Ile Ile His Gly Ile Lys Thr Gln Gly Ala Arg Gln Lys Phe
    1655                1660                1665

Ser Ser Leu Tyr Ile Ser Gln Phe Ile Ile Met Tyr Ser Leu Asp
    1670                1675                1680

Gly Lys Lys Trp Gln Thr Tyr Arg Gly Asn Ser Thr Gly Thr Leu
    1685                1690                1695
```

```
Met Val Phe Phe Gly Asn Val Asp Ser Ser Gly Ile Lys His Asn
1700                1705                1710

Ile Phe Asn Pro Pro Ile Ile Ala Arg Tyr Ile Arg Leu His Pro
1715                1720                1725

Thr His Tyr Ser Ile Arg Ser Thr Leu Arg Met Glu Leu Met Gly
1730                1735                1740

Cys Asp Leu Asn Ser Cys Ser Met Pro Leu Gly Met Glu Ser Lys
1745                1750                1755

Ala Ile Ser Asp Ala Gln Ile Thr Ala Ser Ser Tyr Phe Thr Asn
1760                1765                1770

Met Phe Ala Thr Trp Ser Pro Ser Lys Ala Arg Leu His Leu Gln
1775                1780                1785

Gly Arg Ser Asn Ala Trp Arg Pro Gln Val Asn Asn Pro Lys Glu
1790                1795                1800

Trp Leu Gln Val Asp Phe Gln Lys Thr Met Lys Val Thr Gly Val
1805                1810                1815

Thr Thr Gln Gly Val Lys Ser Leu Leu Thr Ser Met Tyr Val Lys
1820                1825                1830

Glu Phe Leu Ile Ser Ser Ser Gln Asp Gly His Gln Trp Thr Leu
1835                1840                1845

Phe Phe Gln Asn Gly Lys Val Lys Val Phe Gln Gly Asn Gln Asp
1850                1855                1860

Ser Phe Thr Pro Val Val Asn Ser Leu Asp Pro Pro Leu Leu Thr
1865                1870                1875

Arg Tyr Leu Arg Ile His Pro Gln Ser Trp Val His Gln Ile Ala
1880                1885                1890

Leu Arg Met Glu Val Leu Gly Cys Glu Ala Gln Asp Leu Tyr Asp
1895                1900                1905

Lys Thr His Thr Cys Pro Pro Cys Pro Ala Pro Glu Leu Leu Gly
1910                1915                1920

Gly Pro Ser Val Phe Leu Phe Pro Pro Lys Pro Lys Asp Thr Leu
1925                1930                1935

Met Ile Ser Arg Thr Pro Glu Val Thr Cys Val Val Val Asp Val
1940                1945                1950

Ser His Glu Asp Pro Glu Val Lys Phe Asn Trp Tyr Val Asp Gly
1955                1960                1965

Val Glu Val His Asn Ala Lys Thr Lys Pro Arg Glu Glu Gln Tyr
1970                1975                1980

Asn Ser Thr Tyr Arg Val Val Ser Val Leu Thr Val Leu His Gln
1985                1990                1995

Asp Trp Leu Asn Gly Lys Glu Tyr Lys Cys Lys Val Ser Asn Lys
2000                2005                2010

Ala Leu Pro Ala Pro Ile Glu Lys Thr Ile Ser Lys Ala Lys Gly
2015                2020                2025

Gln Pro Arg Glu Pro Gln Val Tyr Thr Leu Pro Pro Ser Arg Asp
2030                2035                2040

Glu Leu Thr Lys Asn Gln Val Ser Leu Thr Cys Leu Val Lys Gly
2045                2050                2055

Phe Tyr Pro Ser Asp Ile Ala Val Glu Trp Glu Ser Asn Gly Gln
2060                2065                2070

Pro Glu Asn Asn Tyr Lys Thr Thr Pro Pro Val Leu Asp Ser Asp
2075                2080                2085
```

```
Gly Ser Phe Phe Leu Tyr Ser Lys Leu Thr Val Asp Lys Ser Arg
    2090            2095            2100

Trp Gln Gln Gly Asn Val Phe Ser Cys Ser Val Met His Glu Ala
    2105            2110            2115

Leu His Asn His Tyr Thr Gln Lys Ser Leu Ser Leu Ser Pro Gly
    2120            2125            2130

Lys

<210> SEQ ID NO 109
<211> LENGTH: 2128
<212> TYPE: PRT
<213> ORGANISM: Artificial Sequence
<220> FEATURE:
<223> OTHER INFORMATION: FVIII 203 protein sequence

<400> SEQUENCE: 109

Met Gln Ile Glu Leu Ser Thr Cys Phe Phe Leu Cys Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

```
            305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Ala Glu Asp Tyr Asp Asp Asp
                355                 360                 365
Leu Thr Asp Ser Glu Met Asp Val Val Arg Phe Asp Asp Asn Ser
                370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
                530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
                690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Gly Ala Pro Gly
            755                 760                 765

Thr Ser Glu Ser Ala Thr Pro Glu Ser Gly Pro Gly Ser Glu Pro Ala
            770                 775                 780

Thr Ser Gly Ser Glu Thr Pro Gly Thr Ser Glu Ser Ala Thr Pro Glu
785                 790                 795                 800

Ser Gly Pro Gly Ser Glu Pro Ala Thr Ser Gly Ser Glu Thr Pro Gly
                805                 810                 815

Thr Ser Glu Ser Ala Thr Pro Glu Ser Gly Pro Gly Ser Thr Ser Glu
            820                 825                 830

Pro Ser Glu Gly Ser Ala Pro Gly Ser Pro Ala Gly Ser Pro Thr Ser
            835                 840                 845

Thr Glu Glu Gly Thr Ser Glu Ser Ala Thr Pro Glu Ser Gly Pro Gly
            850                 855                 860

Ser Glu Pro Ala Thr Ser Gly Ser Glu Thr Pro Gly Thr Ser Glu Ser
865                 870                 875                 880

Ala Thr Pro Glu Ser Gly Pro Gly Ser Pro Ala Gly Ser Pro Thr Ser
                885                 890                 895

Thr Glu Glu Gly Ser Pro Ala Gly Ser Pro Thr Ser Thr Glu Glu Gly
            900                 905                 910

Thr Ser Thr Glu Pro Ser Glu Gly Ser Ala Pro Gly Thr Ser Glu Ser
            915                 920                 925

Ala Thr Pro Glu Ser Gly Pro Gly Thr Ser Glu Ser Ala Thr Pro Glu
            930                 935                 940

Ser Gly Pro Gly Thr Ser Glu Ser Ala Thr Pro Glu Ser Gly Pro Gly
945                 950                 955                 960

Ser Glu Pro Ala Thr Ser Gly Ser Glu Thr Pro Gly Ser Glu Pro Ala
                965                 970                 975

Thr Ser Gly Ser Glu Thr Pro Gly Ser Pro Ala Gly Ser Pro Thr Ser
            980                 985                 990

Thr Glu Glu Gly Thr Ser Thr Glu Pro Ser Glu Gly Ser Ala Pro Gly
            995                 1000                1005

Thr Ser Thr Glu Pro Ser Glu Gly Ser Ala Pro Gly Ser Glu Pro
     1010                1015                1020

Ala Thr Ser Gly Ser Glu Thr Pro Gly Thr Ser Glu Ser Ala Thr
     1025                1030                1035

Pro Glu Ser Gly Pro Gly Thr Ser Thr Glu Pro Ser Glu Gly Ser
     1040                1045                1050

Ala Pro Ala Ser Ser Pro Pro Val Leu Lys Arg His Gln Ala Glu
     1055                1060                1065

Ile Thr Arg Thr Thr Leu Gln Ser Asp Gln Glu Glu Ile Asp Tyr
     1070                1075                1080

Asp Asp Thr Ile Ser Val Glu Met Lys Lys Glu Asp Phe Asp Ile
     1085                1090                1095

Tyr Asp Glu Asp Glu Asn Gln Ser Pro Arg Ser Phe Gln Lys Lys
     1100                1105                1110

Thr Arg His Tyr Phe Ile Ala Ala Val Glu Arg Leu Trp Asp Tyr
     1115                1120                1125

Gly Met Ser Ser Ser Pro His Val Leu Arg Asn Arg Ala Gln Ser
     1130                1135                1140
```

```
Gly Ser Val Pro Gln Phe Lys Lys Val Val Phe Gln Glu Phe Thr
1145                1150                1155

Asp Gly Ser Phe Thr Gln Pro Leu Tyr Arg Gly Glu Leu Asn Glu
1160                1165                1170

His Leu Gly Leu Leu Gly Pro Tyr Ile Arg Ala Glu Val Glu Asp
1175                1180                1185

Asn Ile Met Val Thr Phe Arg Asn Gln Ala Ser Arg Pro Tyr Ser
1190                1195                1200

Phe Tyr Ser Ser Leu Ile Ser Tyr Glu Glu Asp Gln Arg Gln Gly
1205                1210                1215

Ala Glu Pro Arg Lys Asn Phe Val Lys Pro Asn Glu Thr Lys Thr
1220                1225                1230

Tyr Phe Trp Lys Val Gln His His Met Ala Pro Thr Lys Asp Glu
1235                1240                1245

Phe Asp Cys Lys Ala Trp Ala Tyr Phe Ser Asp Val Asp Leu Glu
1250                1255                1260

Lys Asp Val His Ser Gly Leu Ile Gly Pro Leu Leu Val Cys His
1265                1270                1275

Thr Asn Thr Leu Asn Pro Ala His Gly Arg Gln Val Thr Val Gln
1280                1285                1290

Glu Phe Ala Leu Phe Phe Thr Ile Phe Asp Glu Thr Lys Ser Trp
1295                1300                1305

Tyr Phe Thr Glu Asn Met Glu Arg Asn Cys Arg Gly Ala Pro Thr
1310                1315                1320

Ser Glu Ser Ala Thr Pro Glu Ser Gly Pro Gly Ser Glu Pro Ala
1325                1330                1335

Thr Ser Gly Ser Glu Thr Pro Gly Thr Ser Glu Ser Ala Thr Pro
1340                1345                1350

Glu Ser Gly Pro Gly Ser Glu Pro Ala Thr Ser Gly Ser Glu Thr
1355                1360                1365

Pro Gly Thr Ser Glu Ser Ala Thr Pro Glu Ser Gly Pro Gly Thr
1370                1375                1380

Ser Thr Glu Pro Ser Glu Gly Ser Ala Pro Gly Thr Ser Glu Ser
1385                1390                1395

Ala Thr Pro Glu Ser Gly Pro Gly Ser Pro Ala Gly Ser Pro Thr
1400                1405                1410

Ser Thr Glu Glu Gly Ser Pro Ala Gly Ser Pro Thr Ser Thr Glu
1415                1420                1425

Glu Gly Ser Pro Ala Gly Ser Pro Thr Ser Thr Glu Glu Gly Thr
1430                1435                1440

Ser Glu Ser Ala Thr Pro Glu Ser Gly Pro Gly Thr Ser Thr Glu
1445                1450                1455

Pro Ser Glu Gly Ser Ala Pro Gly Ala Ser Ser Ala Pro Cys Asn
1460                1465                1470

Ile Gln Met Glu Asp Pro Thr Phe Lys Glu Asn Tyr Arg Phe His
1475                1480                1485

Ala Ile Asn Gly Tyr Ile Met Asp Thr Leu Pro Gly Leu Val Met
1490                1495                1500

Ala Gln Asp Gln Arg Ile Arg Trp Tyr Leu Leu Ser Met Gly Ser
1505                1510                1515

Asn Glu Asn Ile His Ser Ile His Phe Ser Gly His Val Phe Thr
1520                1525                1530

Val Arg Lys Lys Glu Glu Tyr Lys Met Ala Leu Tyr Asn Leu Tyr
```

-continued

```
              1535                1540                1545
Pro  Gly  Val  Phe  Glu  Thr  Val  Glu  Met  Leu  Pro  Ser  Lys  Ala  Gly
              1550                1555                1560
Ile  Trp  Arg  Val  Glu  Cys  Leu  Ile  Gly  Glu  His  Leu  His  Ala  Gly
              1565                1570                1575
Met  Ser  Thr  Leu  Phe  Leu  Val  Tyr  Ser  Asn  Lys  Cys  Gln  Thr  Pro
              1580                1585                1590
Leu  Gly  Met  Ala  Ser  Gly  His  Ile  Arg  Asp  Phe  Gln  Ile  Thr  Ala
              1595                1600                1605
Ser  Gly  Gln  Tyr  Gly  Gln  Trp  Ala  Pro  Lys  Leu  Ala  Arg  Leu  His
              1610                1615                1620
Tyr  Ser  Gly  Ser  Ile  Asn  Ala  Trp  Ser  Thr  Lys  Glu  Pro  Phe  Ser
              1625                1630                1635
Trp  Ile  Lys  Val  Asp  Leu  Leu  Ala  Pro  Met  Ile  Ile  His  Gly  Ile
              1640                1645                1650
Lys  Thr  Gln  Gly  Ala  Arg  Gln  Lys  Phe  Ser  Ser  Leu  Tyr  Ile  Ser
              1655                1660                1665
Gln  Phe  Ile  Ile  Met  Tyr  Ser  Leu  Asp  Gly  Lys  Lys  Trp  Gln  Thr
              1670                1675                1680
Tyr  Arg  Gly  Asn  Ser  Thr  Gly  Thr  Leu  Met  Val  Phe  Phe  Gly  Asn
              1685                1690                1695
Val  Asp  Ser  Ser  Gly  Ile  Lys  His  Asn  Ile  Phe  Asn  Pro  Pro  Ile
              1700                1705                1710
Ile  Ala  Arg  Tyr  Ile  Arg  Leu  His  Pro  Thr  His  Tyr  Ser  Ile  Arg
              1715                1720                1725
Ser  Thr  Leu  Arg  Met  Glu  Leu  Met  Gly  Cys  Asp  Leu  Asn  Ser  Cys
              1730                1735                1740
Ser  Met  Pro  Leu  Gly  Met  Glu  Ser  Lys  Ala  Ile  Ser  Asp  Ala  Gln
              1745                1750                1755
Ile  Thr  Ala  Ser  Ser  Tyr  Phe  Thr  Asn  Met  Phe  Ala  Thr  Trp  Ser
              1760                1765                1770
Pro  Ser  Lys  Ala  Arg  Leu  His  Leu  Gln  Gly  Arg  Ser  Asn  Ala  Trp
              1775                1780                1785
Arg  Pro  Gln  Val  Asn  Asn  Pro  Lys  Glu  Trp  Leu  Gln  Val  Asp  Phe
              1790                1795                1800
Gln  Lys  Thr  Met  Lys  Val  Thr  Gly  Val  Thr  Thr  Gln  Gly  Val  Lys
              1805                1810                1815
Ser  Leu  Leu  Thr  Ser  Met  Tyr  Val  Lys  Glu  Phe  Leu  Ile  Ser  Ser
              1820                1825                1830
Ser  Gln  Asp  Gly  His  Gln  Trp  Thr  Leu  Phe  Phe  Gln  Asn  Gly  Lys
              1835                1840                1845
Val  Lys  Val  Phe  Gln  Gly  Asn  Gln  Asp  Ser  Phe  Thr  Pro  Val  Val
              1850                1855                1860
Asn  Ser  Leu  Asp  Pro  Pro  Leu  Leu  Thr  Arg  Tyr  Leu  Arg  Ile  His
              1865                1870                1875
Pro  Gln  Ser  Trp  Val  His  Gln  Ile  Ala  Leu  Arg  Met  Glu  Val  Leu
              1880                1885                1890
Gly  Cys  Glu  Ala  Gln  Asp  Leu  Tyr  Asp  Lys  Thr  His  Thr  Cys  Pro
              1895                1900                1905
Pro  Cys  Pro  Ala  Pro  Glu  Leu  Leu  Gly  Gly  Pro  Ser  Val  Phe  Leu
              1910                1915                1920
Phe  Pro  Pro  Lys  Pro  Lys  Asp  Thr  Leu  Met  Ile  Ser  Arg  Thr  Pro
              1925                1930                1935
```

```
Glu Val Thr Cys Val Val Asp Val Ser His Glu Asp Pro Glu
    1940            1945                1950

Val Lys Phe Asn Trp Tyr Val Asp Gly Val Glu Val His Asn Ala
    1955            1960                1965

Lys Thr Lys Pro Arg Glu Glu Gln Tyr Asn Ser Thr Tyr Arg Val
    1970            1975                1980

Val Ser Val Leu Thr Val Leu His Gln Asp Trp Leu Asn Gly Lys
    1985            1990                1995

Glu Tyr Lys Cys Lys Val Ser Asn Lys Ala Leu Pro Ala Pro Ile
    2000            2005                2010

Glu Lys Thr Ile Ser Lys Ala Lys Gly Gln Pro Arg Glu Pro Gln
    2015            2020                2025

Val Tyr Thr Leu Pro Pro Ser Arg Asp Glu Leu Thr Lys Asn Gln
    2030            2035                2040

Val Ser Leu Thr Cys Leu Val Lys Gly Phe Tyr Pro Ser Asp Ile
    2045            2050                2055

Ala Val Glu Trp Glu Ser Asn Gly Gln Pro Glu Asn Asn Tyr Lys
    2060            2065                2070

Thr Thr Pro Pro Val Leu Asp Ser Asp Gly Ser Phe Phe Leu Tyr
    2075            2080                2085

Ser Lys Leu Thr Val Asp Lys Ser Arg Trp Gln Gln Gly Asn Val
    2090            2095                2100

Phe Ser Cys Ser Val Met His Glu Ala Leu His Asn His Tyr Thr
    2105            2110                2115

Gln Lys Ser Leu Ser Leu Ser Pro Gly Lys
    2120            2125

<210> SEQ ID NO 110
<211> LENGTH: 2128
<212> TYPE: PRT
<213> ORGANISM: Artificial Sequence
<220> FEATURE:
<223> OTHER INFORMATION: FVIII 204 protein sequence

<400> SEQUENCE: 110

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160
```

```
Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Gly Ala Pro Thr Ser Thr Glu Pro Ser Glu
            420                 425                 430

Gly Ser Ala Pro Gly Ser Pro Ala Gly Ser Pro Thr Ser Thr Glu Glu
        435                 440                 445

Gly Thr Ser Thr Glu Pro Ser Glu Gly Ser Ala Pro Gly Thr Ser Thr
    450                 455                 460

Glu Pro Ser Glu Gly Ser Ala Pro Gly Thr Ser Glu Ser Ala Thr Pro
465                 470                 475                 480

Glu Ser Gly Pro Gly Thr Ser Thr Glu Pro Ser Glu Gly Ser Ala Pro
                485                 490                 495

Gly Thr Ser Glu Ser Ala Thr Pro Glu Ser Gly Pro Gly Ser Glu Pro
            500                 505                 510

Ala Thr Ser Gly Ser Glu Thr Pro Gly Thr Ser Thr Glu Pro Ser Glu
        515                 520                 525

Gly Ser Ala Pro Gly Thr Ser Thr Glu Pro Ser Glu Gly Ser Ala Pro
    530                 535                 540

Gly Thr Ser Glu Ser Ala Thr Pro Glu Ser Gly Pro Gly Thr Ser Glu
545                 550                 555                 560

Ser Ala Thr Pro Glu Ser Gly Pro Gly Ala Ser Ser Asp Arg Ser Tyr
                565                 570                 575
```

```
Lys Ser Gln Tyr Leu Asn Asn Gly Pro Gln Arg Ile Gly Arg Lys Tyr
            580                 585                 590

Lys Lys Val Arg Phe Met Ala Tyr Thr Asp Glu Thr Phe Lys Thr Arg
        595                 600                 605

Glu Ala Ile Gln His Glu Ser Gly Ile Leu Gly Pro Leu Leu Tyr Gly
    610                 615                 620

Glu Val Gly Asp Thr Leu Leu Ile Ile Phe Lys Asn Gln Ala Ser Arg
625                 630                 635                 640

Pro Tyr Asn Ile Tyr Pro His Gly Ile Thr Asp Val Arg Pro Leu Tyr
                645                 650                 655

Ser Arg Arg Leu Pro Lys Gly Val Lys His Leu Lys Asp Phe Pro Ile
            660                 665                 670

Leu Pro Gly Glu Ile Phe Lys Tyr Lys Trp Thr Val Thr Val Glu Asp
        675                 680                 685

Gly Pro Thr Lys Ser Asp Pro Arg Cys Leu Thr Arg Tyr Tyr Ser Ser
    690                 695                 700

Phe Val Asn Met Glu Arg Asp Leu Ala Ser Gly Leu Ile Gly Pro Leu
705                 710                 715                 720

Leu Ile Cys Tyr Lys Glu Ser Val Asp Gln Arg Gly Asn Gln Ile Met
                725                 730                 735

Ser Asp Lys Arg Asn Val Ile Leu Phe Ser Val Phe Asp Glu Asn Arg
            740                 745                 750

Ser Trp Tyr Leu Thr Glu Asn Ile Gln Arg Phe Leu Pro Asn Pro Ala
        755                 760                 765

Gly Val Gln Leu Glu Asp Pro Glu Phe Gln Ala Ser Asn Ile Met His
    770                 775                 780

Ser Ile Asn Gly Tyr Val Phe Asp Ser Leu Gln Leu Ser Val Cys Leu
785                 790                 795                 800

His Glu Val Ala Tyr Trp Tyr Ile Leu Ser Ile Gly Ala Gln Thr Asp
                805                 810                 815

Phe Leu Ser Val Phe Phe Ser Gly Tyr Thr Phe Lys His Lys Met Val
            820                 825                 830

Tyr Glu Asp Thr Leu Thr Leu Phe Pro Phe Ser Gly Glu Thr Val Phe
        835                 840                 845

Met Ser Met Glu Asn Pro Gly Leu Trp Ile Leu Gly Cys His Asn Ser
    850                 855                 860

Asp Phe Arg Asn Arg Gly Met Thr Ala Leu Leu Lys Val Ser Ser Cys
865                 870                 875                 880

Asp Lys Asn Thr Gly Asp Tyr Tyr Glu Asp Ser Tyr Glu Asp Ile Ser
                885                 890                 895

Ala Tyr Leu Leu Ser Lys Asn Asn Ala Ile Glu Pro Arg Ser Phe Ser
            900                 905                 910

Gln Asn Gly Ala Pro Gly Thr Ser Glu Ser Ala Thr Pro Glu Ser Gly
        915                 920                 925

Pro Gly Ser Glu Pro Ala Thr Ser Gly Ser Glu Thr Pro Gly Thr Ser
930                 935                 940

Glu Ser Ala Thr Pro Glu Ser Gly Pro Gly Ser Glu Pro Ala Thr Ser
945                 950                 955                 960

Gly Ser Glu Thr Pro Gly Thr Ser Glu Ser Ala Thr Pro Glu Ser Gly
                965                 970                 975

Pro Gly Thr Ser Thr Glu Pro Ser Glu Gly Ser Ala Pro Gly Ser Pro
            980                 985                 990

Ala Gly Ser Pro Thr Ser Thr Glu  Glu Gly Thr Ser Glu  Ser Ala Thr
```

-continued

```
                995                 1000                1005
    Pro Glu Ser Gly Pro Gly Ser Glu Pro Ala Thr Ser Gly Ser Glu
        1010                1015                1020

Thr Pro Gly Thr Ser Glu Ser Ala Thr Pro Glu Ser Gly Pro Gly
        1025                1030                1035

Ser Pro Ala Gly Ser Pro Thr Ser Thr Glu Glu Gly Ser Pro Ala
        1040                1045                1050

Gly Ser Pro Thr Ser Thr Glu Glu Gly Thr Ser Thr Glu Pro Ser
        1055                1060                1065

Glu Gly Ser Ala Pro Gly Thr Ser Glu Ser Ala Thr Pro Glu Ser
        1070                1075                1080

Gly Pro Gly Thr Ser Glu Ser Ala Thr Pro Glu Ser Gly Pro Gly
        1085                1090                1095

Thr Ser Glu Ser Ala Thr Pro Glu Ser Gly Pro Gly Ser Glu Pro
        1100                1105                1110

Ala Thr Ser Gly Ser Glu Thr Pro Gly Ser Glu Pro Ala Thr Ser
        1115                1120                1125

Gly Ser Glu Thr Pro Gly Ser Pro Ala Gly Ser Pro Thr Ser Thr
        1130                1135                1140

Glu Glu Gly Thr Ser Thr Glu Pro Ser Glu Gly Ser Ala Pro Gly
        1145                1150                1155

Thr Ser Thr Glu Pro Ser Glu Gly Ser Ala Pro Gly Ser Glu Pro
        1160                1165                1170

Ala Thr Ser Gly Ser Glu Thr Pro Gly Thr Ser Glu Ser Ala Thr
        1175                1180                1185

Pro Glu Ser Gly Pro Gly Thr Ser Thr Glu Pro Ser Glu Gly Ser
        1190                1195                1200

Ala Pro Ala Ser Ser Pro Pro Val Leu Lys Arg His Gln Ala Glu
        1205                1210                1215

Ile Thr Arg Thr Thr Leu Gln Ser Asp Gln Glu Glu Ile Asp Tyr
        1220                1225                1230

Asp Asp Thr Ile Ser Val Glu Met Lys Lys Glu Asp Phe Asp Ile
        1235                1240                1245

Tyr Asp Glu Asp Glu Asn Gln Ser Pro Arg Ser Phe Gln Lys Lys
        1250                1255                1260

Thr Arg His Tyr Phe Ile Ala Ala Val Glu Arg Leu Trp Asp Tyr
        1265                1270                1275

Gly Met Ser Ser Ser Pro His Val Leu Arg Asn Arg Ala Gln Ser
        1280                1285                1290

Gly Ser Val Pro Gln Phe Lys Lys Val Val Phe Gln Glu Phe Thr
        1295                1300                1305

Asp Gly Ser Phe Thr Gln Pro Leu Tyr Arg Gly Glu Leu Asn Glu
        1310                1315                1320

His Leu Gly Leu Leu Gly Pro Tyr Ile Arg Ala Glu Val Glu Asp
        1325                1330                1335

Asn Ile Met Val Thr Phe Arg Asn Gln Ala Ser Arg Pro Tyr Ser
        1340                1345                1350

Phe Tyr Ser Ser Leu Ile Ser Tyr Glu Glu Asp Gln Arg Gln Gly
        1355                1360                1365

Ala Glu Pro Arg Lys Asn Phe Val Lys Pro Asn Glu Thr Lys Thr
        1370                1375                1380

Tyr Phe Trp Lys Val Gln His His Met Ala Pro Thr Lys Asp Glu
        1385                1390                1395
```

-continued

```
Phe Asp Cys Lys Ala Trp Ala Tyr Phe Ser Asp Val Asp Leu Glu
    1400            1405            1410

Lys Asp Val His Ser Gly Leu Ile Gly Pro Leu Leu Val Cys His
    1415            1420            1425

Thr Asn Thr Leu Asn Pro Ala His Gly Arg Gln Val Thr Val Gln
    1430            1435            1440

Glu Phe Ala Leu Phe Phe Thr Ile Phe Asp Glu Thr Lys Ser Trp
    1445            1450            1455

Tyr Phe Thr Glu Asn Met Glu Arg Asn Cys Arg Ala Pro Cys Asn
    1460            1465            1470

Ile Gln Met Glu Asp Pro Thr Phe Lys Glu Asn Tyr Arg Phe His
    1475            1480            1485

Ala Ile Asn Gly Tyr Ile Met Asp Thr Leu Pro Gly Leu Val Met
    1490            1495            1500

Ala Gln Asp Gln Arg Ile Arg Trp Tyr Leu Leu Ser Met Gly Ser
    1505            1510            1515

Asn Glu Asn Ile His Ser Ile His Phe Ser Gly His Val Phe Thr
    1520            1525            1530

Val Arg Lys Lys Glu Glu Tyr Lys Met Ala Leu Tyr Asn Leu Tyr
    1535            1540            1545

Pro Gly Val Phe Glu Thr Val Glu Met Leu Pro Ser Lys Ala Gly
    1550            1555            1560

Ile Trp Arg Val Glu Cys Leu Ile Gly Glu His Leu His Ala Gly
    1565            1570            1575

Met Ser Thr Leu Phe Leu Val Tyr Ser Asn Lys Cys Gln Thr Pro
    1580            1585            1590

Leu Gly Met Ala Ser Gly His Ile Arg Asp Phe Gln Ile Thr Ala
    1595            1600            1605

Ser Gly Gln Tyr Gly Gln Trp Ala Pro Lys Leu Ala Arg Leu His
    1610            1615            1620

Tyr Ser Gly Ser Ile Asn Ala Trp Ser Thr Lys Glu Pro Phe Ser
    1625            1630            1635

Trp Ile Lys Val Asp Leu Leu Ala Pro Met Ile Ile His Gly Ile
    1640            1645            1650

Lys Thr Gln Gly Ala Arg Gln Lys Phe Ser Ser Leu Tyr Ile Ser
    1655            1660            1665

Gln Phe Ile Ile Met Tyr Ser Leu Asp Gly Lys Lys Trp Gln Thr
    1670            1675            1680

Tyr Arg Gly Asn Ser Thr Gly Thr Leu Met Val Phe Phe Gly Asn
    1685            1690            1695

Val Asp Ser Ser Gly Ile Lys His Asn Ile Phe Asn Pro Pro Ile
    1700            1705            1710

Ile Ala Arg Tyr Ile Arg Leu His Pro Thr His Tyr Ser Ile Arg
    1715            1720            1725

Ser Thr Leu Arg Met Glu Leu Met Gly Cys Asp Leu Asn Ser Cys
    1730            1735            1740

Ser Met Pro Leu Gly Met Glu Ser Lys Ala Ile Ser Asp Ala Gln
    1745            1750            1755

Ile Thr Ala Ser Ser Tyr Phe Thr Asn Met Phe Ala Thr Trp Ser
    1760            1765            1770

Pro Ser Lys Ala Arg Leu His Leu Gln Gly Arg Ser Asn Ala Trp
    1775            1780            1785
```

Arg Pro Gln Val Asn Asn Pro Lys Glu Trp Leu Gln Val Asp Phe
1790                1795                1800

Gln Lys Thr Met Lys Val Thr Gly Val Thr Thr Gln Gly Val Lys
1805                1810                1815

Ser Leu Leu Thr Ser Met Tyr Val Lys Glu Phe Leu Ile Ser Ser
1820                1825                1830

Ser Gln Asp Gly His Gln Trp Thr Leu Phe Phe Gln Asn Gly Lys
1835                1840                1845

Val Lys Val Phe Gln Gly Asn Gln Asp Ser Phe Thr Pro Val Val
1850                1855                1860

Asn Ser Leu Asp Pro Pro Leu Leu Thr Arg Tyr Leu Arg Ile His
1865                1870                1875

Pro Gln Ser Trp Val His Gln Ile Ala Leu Arg Met Glu Val Leu
1880                1885                1890

Gly Cys Glu Ala Gln Asp Leu Tyr Asp Lys Thr His Thr Cys Pro
1895                1900                1905

Pro Cys Pro Ala Pro Glu Leu Leu Gly Gly Pro Ser Val Phe Leu
1910                1915                1920

Phe Pro Pro Lys Pro Lys Asp Thr Leu Met Ile Ser Arg Thr Pro
1925                1930                1935

Glu Val Thr Cys Val Val Val Asp Val Ser His Glu Asp Pro Glu
1940                1945                1950

Val Lys Phe Asn Trp Tyr Val Asp Gly Val Glu Val His Asn Ala
1955                1960                1965

Lys Thr Lys Pro Arg Glu Glu Gln Tyr Asn Ser Thr Tyr Arg Val
1970                1975                1980

Val Ser Val Leu Thr Val Leu His Gln Asp Trp Leu Asn Gly Lys
1985                1990                1995

Glu Tyr Lys Cys Lys Val Ser Asn Lys Ala Leu Pro Ala Pro Ile
2000                2005                2010

Glu Lys Thr Ile Ser Lys Ala Lys Gly Gln Pro Arg Glu Pro Gln
2015                2020                2025

Val Tyr Thr Leu Pro Pro Ser Arg Asp Glu Leu Thr Lys Asn Gln
2030                2035                2040

Val Ser Leu Thr Cys Leu Val Lys Gly Phe Tyr Pro Ser Asp Ile
2045                2050                2055

Ala Val Glu Trp Glu Ser Asn Gly Gln Pro Glu Asn Asn Tyr Lys
2060                2065                2070

Thr Thr Pro Pro Val Leu Asp Ser Asp Gly Ser Phe Phe Leu Tyr
2075                2080                2085

Ser Lys Leu Thr Val Asp Lys Ser Arg Trp Gln Gln Gly Asn Val
2090                2095                2100

Phe Ser Cys Ser Val Met His Glu Ala Leu His Asn His Tyr Thr
2105                2110                2115

Gln Lys Ser Leu Ser Leu Ser Pro Gly Lys
2120                2125

<210> SEQ ID NO 111
<211> LENGTH: 2128
<212> TYPE: PRT
<213> ORGANISM: Artificial Sequence
<220> FEATURE:
<223> OTHER INFORMATION: FVIII 205 protein sequence

<400> SEQUENCE: 111

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Gly Ala Pro Thr Ser Glu Ser Ala Thr Pro Glu
                35                  40                  45

Ser Gly Pro Gly Ser Glu Pro Ala Thr Ser Gly Ser Glu Thr Pro Gly
    50                  55                  60

Thr Ser Glu Ser Ala Thr Pro Glu Ser Gly Pro Gly Ser Glu Pro Ala
65                  70                  75                  80

Thr Ser Gly Ser Glu Thr Pro Gly Thr Ser Glu Ser Ala Thr Pro Glu
                85                  90                  95

Ser Gly Pro Gly Thr Ser Thr Glu Pro Ser Glu Gly Ser Ala Pro Gly
                100                 105                 110

Ser Pro Ala Gly Ser Pro Thr Ser Thr Glu Glu Gly Thr Ser Glu Ser
            115                 120                 125

Ala Thr Pro Glu Ser Gly Pro Gly Ser Glu Pro Ala Thr Ser Gly Ser
            130                 135                 140

Glu Thr Pro Gly Thr Ser Glu Ser Ala Thr Pro Glu Ser Gly Pro Gly
145                 150                 155                 160

Ser Pro Ala Gly Ser Pro Thr Ser Thr Glu Glu Gly Ser Pro Ala Gly
                165                 170                 175

Ser Pro Thr Ser Thr Glu Glu Gly Ala Ser Ser Asp Leu Gly Glu
                180                 185                 190

Leu Pro Val Asp Ala Arg Phe Pro Pro Arg Val Pro Lys Ser Phe Pro
    195                 200                 205

Phe Asn Thr Ser Val Val Tyr Lys Lys Thr Leu Phe Val Glu Phe Thr
    210                 215                 220

Asp His Leu Phe Asn Ile Ala Lys Pro Arg Pro Pro Trp Met Gly Leu
225                 230                 235                 240

Leu Gly Pro Thr Ile Gln Ala Glu Val Tyr Asp Thr Val Val Ile Thr
                245                 250                 255

Leu Lys Asn Met Ala Ser His Pro Val Ser Leu His Ala Val Gly Val
                260                 265                 270

Ser Tyr Trp Lys Ala Ser Glu Gly Ala Glu Tyr Asp Asp Gln Thr Ser
    275                 280                 285

Gln Arg Glu Lys Glu Asp Asp Lys Val Phe Pro Gly Gly Ser His Thr
    290                 295                 300

Tyr Val Trp Gln Val Leu Lys Glu Asn Gly Pro Met Ala Ser Asp Pro
305                 310                 315                 320

Leu Cys Leu Thr Tyr Ser Tyr Leu Ser His Val Asp Leu Val Lys Asp
                325                 330                 335

Leu Asn Ser Gly Leu Ile Gly Ala Leu Leu Val Cys Arg Glu Gly Ser
                340                 345                 350

Leu Ala Lys Glu Lys Thr Gln Thr Leu His Lys Phe Ile Leu Leu Phe
            355                 360                 365

Ala Val Phe Asp Glu Gly Lys Ser Trp His Ser Glu Thr Lys Asn Ser
    370                 375                 380

Leu Met Gln Asp Arg Asp Ala Ala Ser Ala Arg Ala Trp Pro Lys Met
385                 390                 395                 400

His Thr Val Asn Gly Tyr Val Asn Arg Ser Leu Pro Gly Leu Ile Gly
                405                 410                 415

Cys His Arg Lys Ser Val Tyr Trp His Val Ile Gly Met Gly Thr Thr
```

```
            420                 425                 430
Pro Glu Val His Ser Ile Phe Leu Glu Gly His Thr Phe Leu Val Arg
        435                 440                 445

Asn His Arg Gln Ala Ser Leu Glu Ile Ser Pro Ile Thr Phe Leu Thr
    450                 455                 460

Ala Gln Thr Leu Leu Met Asp Leu Gly Gln Phe Leu Leu Phe Cys His
465                 470                 475                 480

Ile Ser Ser His Gln His Asp Gly Met Glu Ala Tyr Val Lys Val Asp
                485                 490                 495

Ser Cys Pro Glu Glu Pro Gln Leu Arg Met Lys Asn Asn Glu Glu Ala
            500                 505                 510

Glu Asp Tyr Asp Asp Leu Thr Asp Ser Glu Met Asp Val Val Arg
        515                 520                 525

Phe Asp Asp Asp Asn Ser Pro Ser Phe Ile Gln Ile Arg Ser Val Ala
        530                 535                 540

Lys Lys His Pro Lys Thr Trp Val His Tyr Ile Ala Ala Glu Glu Glu
545                 550                 555                 560

Asp Trp Asp Tyr Ala Pro Leu Val Leu Ala Pro Asp Asp Arg Ser Tyr
                565                 570                 575

Lys Ser Gln Tyr Leu Asn Asn Gly Pro Gln Arg Ile Gly Arg Lys Tyr
            580                 585                 590

Lys Lys Val Arg Phe Met Ala Tyr Thr Asp Glu Thr Phe Lys Thr Arg
        595                 600                 605

Glu Ala Ile Gln His Glu Ser Gly Ile Leu Gly Pro Leu Leu Tyr Gly
        610                 615                 620

Glu Val Gly Asp Thr Leu Leu Ile Ile Phe Lys Asn Gln Ala Ser Arg
625                 630                 635                 640

Pro Tyr Asn Ile Tyr Pro His Gly Ile Thr Asp Val Arg Pro Leu Tyr
                645                 650                 655

Ser Arg Arg Leu Pro Lys Gly Val Lys His Leu Lys Asp Phe Pro Ile
            660                 665                 670

Leu Pro Gly Glu Ile Phe Lys Tyr Lys Trp Thr Val Thr Val Glu Asp
        675                 680                 685

Gly Pro Thr Lys Ser Asp Pro Arg Cys Leu Thr Arg Tyr Tyr Ser Ser
        690                 695                 700

Phe Val Asn Met Glu Arg Asp Leu Ala Ser Gly Leu Ile Gly Pro Leu
705                 710                 715                 720

Leu Ile Cys Tyr Lys Glu Ser Val Asp Gln Arg Gly Asn Gln Ile Met
                725                 730                 735

Ser Asp Lys Arg Asn Val Ile Leu Phe Ser Val Phe Asp Glu Asn Arg
            740                 745                 750

Ser Trp Tyr Leu Thr Glu Asn Ile Gln Arg Phe Leu Pro Asn Pro Ala
        755                 760                 765

Gly Val Gln Leu Glu Asp Pro Glu Phe Gln Ala Ser Asn Ile Met His
        770                 775                 780

Ser Ile Asn Gly Tyr Val Phe Asp Ser Leu Gln Leu Ser Val Cys Leu
785                 790                 795                 800

His Glu Val Ala Tyr Trp Tyr Ile Leu Ser Ile Gly Ala Gln Thr Asp
                805                 810                 815

Phe Leu Ser Val Phe Phe Ser Gly Tyr Thr Phe Lys His Lys Met Val
            820                 825                 830

Tyr Glu Asp Thr Leu Thr Leu Phe Pro Phe Ser Gly Glu Thr Val Phe
        835                 840                 845
```

```
Met Ser Met Glu Asn Pro Gly Leu Trp Ile Leu Gly Cys His Asn Ser
    850                 855                 860
Asp Phe Arg Asn Arg Gly Met Thr Ala Leu Leu Lys Val Ser Ser Cys
865                 870                 875                 880
Asp Lys Asn Thr Gly Asp Tyr Tyr Glu Asp Ser Tyr Glu Asp Ile Ser
            885                 890                 895
Ala Tyr Leu Leu Ser Lys Asn Asn Ala Ile Glu Pro Arg Ser Phe Ser
                900                 905                 910
Gln Asn Gly Ala Pro Gly Thr Ser Glu Ser Ala Thr Pro Glu Ser Gly
            915                 920                 925
Pro Gly Ser Glu Pro Ala Thr Ser Gly Ser Glu Thr Pro Gly Thr Ser
    930                 935                 940
Glu Ser Ala Thr Pro Glu Ser Gly Pro Gly Ser Glu Pro Ala Thr Ser
945                 950                 955                 960
Gly Ser Glu Thr Pro Gly Thr Ser Glu Ser Ala Thr Pro Glu Ser Gly
                965                 970                 975
Pro Gly Thr Ser Thr Glu Pro Ser Glu Gly Ser Ala Pro Gly Ser Pro
            980                 985                 990
Ala Gly Ser Pro Thr Ser Thr Glu Glu Gly Thr Ser Glu Ser Ala Thr
        995                 1000                1005
Pro Glu Ser Gly Pro Gly Ser Glu Pro Ala Thr Ser Gly Ser Glu
    1010                1015                1020
Thr Pro Gly Thr Ser Glu Ser Ala Thr Pro Glu Ser Gly Pro Gly
    1025                1030                1035
Ser Pro Ala Gly Ser Pro Thr Ser Thr Glu Glu Gly Ser Pro Ala
    1040                1045                1050
Gly Ser Pro Thr Ser Thr Glu Glu Gly Thr Ser Thr Glu Pro Ser
    1055                1060                1065
Glu Gly Ser Ala Pro Gly Ser Glu Ser Ala Thr Pro Glu Ser
    1070                1075                1080
Gly Pro Gly Thr Ser Glu Ser Ala Thr Pro Glu Ser Gly Pro Gly
    1085                1090                1095
Thr Ser Glu Ser Ala Thr Pro Glu Ser Gly Pro Gly Ser Glu Pro
    1100                1105                1110
Ala Thr Ser Gly Ser Glu Thr Pro Gly Ser Glu Pro Ala Thr Ser
    1115                1120                1125
Gly Ser Glu Thr Pro Gly Ser Pro Ala Gly Ser Pro Thr Ser Thr
    1130                1135                1140
Glu Glu Gly Thr Ser Thr Glu Pro Ser Glu Gly Ser Ala Pro Gly
    1145                1150                1155
Thr Ser Thr Glu Pro Ser Glu Gly Ser Ala Pro Gly Ser Glu Pro
    1160                1165                1170
Ala Thr Ser Gly Ser Glu Thr Pro Gly Thr Ser Glu Ser Ala Thr
    1175                1180                1185
Pro Glu Ser Gly Pro Gly Thr Ser Thr Glu Pro Ser Glu Gly Ser
    1190                1195                1200
Ala Pro Ala Ser Ser Pro Pro Val Leu Lys Arg His Gln Ala Glu
    1205                1210                1215
Ile Thr Arg Thr Thr Leu Gln Ser Asp Gln Glu Glu Ile Asp Tyr
    1220                1225                1230
Asp Asp Thr Ile Ser Val Glu Met Lys Lys Glu Asp Phe Asp Ile
    1235                1240                1245
```

```
Tyr Asp Glu Asp Glu Asn Gln Ser Pro Arg Ser Phe Gln Lys Lys
1250                1255                1260

Thr Arg His Tyr Phe Ile Ala Ala Val Glu Arg Leu Trp Asp Tyr
1265                1270                1275

Gly Met Ser Ser Ser Pro His Val Leu Arg Asn Arg Ala Gln Ser
1280                1285                1290

Gly Ser Val Pro Gln Phe Lys Lys Val Val Phe Gln Glu Phe Thr
1295                1300                1305

Asp Gly Ser Phe Thr Gln Pro Leu Tyr Arg Gly Glu Leu Asn Glu
1310                1315                1320

His Leu Gly Leu Leu Gly Pro Tyr Ile Arg Ala Glu Val Glu Asp
1325                1330                1335

Asn Ile Met Val Thr Phe Arg Asn Gln Ala Ser Arg Pro Tyr Ser
1340                1345                1350

Phe Tyr Ser Ser Leu Ile Ser Tyr Glu Glu Asp Gln Arg Gln Gly
1355                1360                1365

Ala Glu Pro Arg Lys Asn Phe Val Lys Pro Asn Glu Thr Lys Thr
1370                1375                1380

Tyr Phe Trp Lys Val Gln His His Met Ala Pro Thr Lys Asp Glu
1385                1390                1395

Phe Asp Cys Lys Ala Trp Ala Tyr Phe Ser Asp Val Asp Leu Glu
1400                1405                1410

Lys Asp Val His Ser Gly Leu Ile Gly Pro Leu Leu Val Cys His
1415                1420                1425

Thr Asn Thr Leu Asn Pro Ala His Gly Arg Gln Val Thr Val Gln
1430                1435                1440

Glu Phe Ala Leu Phe Phe Thr Ile Phe Asp Glu Thr Lys Ser Trp
1445                1450                1455

Tyr Phe Thr Glu Asn Met Glu Arg Asn Cys Arg Ala Pro Cys Asn
1460                1465                1470

Ile Gln Met Glu Asp Pro Thr Phe Lys Glu Asn Tyr Arg Phe His
1475                1480                1485

Ala Ile Asn Gly Tyr Ile Met Asp Thr Leu Pro Gly Leu Val Met
1490                1495                1500

Ala Gln Asp Gln Arg Ile Arg Trp Tyr Leu Leu Ser Met Gly Ser
1505                1510                1515

Asn Glu Asn Ile His Ser Ile His Phe Ser Gly His Val Phe Thr
1520                1525                1530

Val Arg Lys Lys Glu Glu Tyr Lys Met Ala Leu Tyr Asn Leu Tyr
1535                1540                1545

Pro Gly Val Phe Glu Thr Val Glu Met Leu Pro Ser Lys Ala Gly
1550                1555                1560

Ile Trp Arg Val Glu Cys Leu Ile Gly Glu His Leu His Ala Gly
1565                1570                1575

Met Ser Thr Leu Phe Leu Val Tyr Ser Asn Lys Cys Gln Thr Pro
1580                1585                1590

Leu Gly Met Ala Ser Gly His Ile Arg Asp Phe Gln Ile Thr Ala
1595                1600                1605

Ser Gly Gln Tyr Gly Gln Trp Ala Pro Lys Leu Ala Arg Leu His
1610                1615                1620

Tyr Ser Gly Ser Ile Asn Ala Trp Ser Thr Lys Glu Pro Phe Ser
1625                1630                1635

Trp Ile Lys Val Asp Leu Leu Ala Pro Met Ile Ile His Gly Ile
```

```
            1640                1645                1650

Lys Thr Gln Gly Ala Arg Gln Lys Phe Ser Ser Leu Tyr Ile Ser
            1655                1660                1665

Gln Phe Ile Ile Met Tyr Ser Leu Asp Gly Lys Lys Trp Gln Thr
            1670                1675                1680

Tyr Arg Gly Asn Ser Thr Gly Thr Leu Met Val Phe Phe Gly Asn
            1685                1690                1695

Val Asp Ser Ser Gly Ile Lys His Asn Ile Phe Asn Pro Pro Ile
            1700                1705                1710

Ile Ala Arg Tyr Ile Arg Leu His Pro Thr His Tyr Ser Ile Arg
            1715                1720                1725

Ser Thr Leu Arg Met Glu Leu Met Gly Cys Asp Leu Asn Ser Cys
            1730                1735                1740

Ser Met Pro Leu Gly Met Glu Ser Lys Ala Ile Ser Asp Ala Gln
            1745                1750                1755

Ile Thr Ala Ser Ser Tyr Phe Thr Asn Met Phe Ala Thr Trp Ser
            1760                1765                1770

Pro Ser Lys Ala Arg Leu His Leu Gln Gly Arg Ser Asn Ala Trp
            1775                1780                1785

Arg Pro Gln Val Asn Asn Pro Lys Glu Trp Leu Gln Val Asp Phe
            1790                1795                1800

Gln Lys Thr Met Lys Val Thr Gly Val Thr Thr Gln Gly Val Lys
            1805                1810                1815

Ser Leu Leu Thr Ser Met Tyr Val Lys Glu Phe Leu Ile Ser Ser
            1820                1825                1830

Ser Gln Asp Gly His Gln Trp Thr Leu Phe Phe Gln Asn Gly Lys
            1835                1840                1845

Val Lys Val Phe Gln Gly Asn Gln Asp Ser Phe Thr Pro Val Val
            1850                1855                1860

Asn Ser Leu Asp Pro Pro Leu Leu Thr Arg Tyr Leu Arg Ile His
            1865                1870                1875

Pro Gln Ser Trp Val His Gln Ile Ala Leu Arg Met Glu Val Leu
            1880                1885                1890

Gly Cys Glu Ala Gln Asp Leu Tyr Asp Lys Thr His Thr Cys Pro
            1895                1900                1905

Pro Cys Pro Ala Pro Glu Leu Leu Gly Gly Pro Ser Val Phe Leu
            1910                1915                1920

Phe Pro Pro Lys Pro Lys Asp Thr Leu Met Ile Ser Arg Thr Pro
            1925                1930                1935

Glu Val Thr Cys Val Val Val Asp Val Ser His Glu Asp Pro Glu
            1940                1945                1950

Val Lys Phe Asn Trp Tyr Val Asp Gly Val Glu Val His Asn Ala
            1955                1960                1965

Lys Thr Lys Pro Arg Glu Glu Gln Tyr Asn Ser Thr Tyr Arg Val
            1970                1975                1980

Val Ser Val Leu Thr Val Leu His Gln Asp Trp Leu Asn Gly Lys
            1985                1990                1995

Glu Tyr Lys Cys Lys Val Ser Asn Lys Ala Leu Pro Ala Pro Ile
            2000                2005                2010

Glu Lys Thr Ile Ser Lys Ala Lys Gly Gln Pro Arg Glu Pro Gln
            2015                2020                2025

Val Tyr Thr Leu Pro Pro Ser Arg Asp Glu Leu Thr Lys Asn Gln
            2030                2035                2040
```

Val Ser Leu Thr Cys Leu Val Lys Gly Phe Tyr Pro Ser Asp Ile
    2045                2050                2055

Ala Val Glu Trp Glu Ser Asn Gly Gln Pro Glu Asn Asn Tyr Lys
    2060                2065                2070

Thr Thr Pro Pro Val Leu Asp Ser Asp Gly Ser Phe Phe Leu Tyr
    2075                2080                2085

Ser Lys Leu Thr Val Asp Lys Ser Arg Trp Gln Gln Gly Asn Val
    2090                2095                2100

Phe Ser Cys Ser Val Met His Glu Ala Leu His Asn His Tyr Thr
    2105                2110                2115

Gln Lys Ser Leu Ser Leu Ser Pro Gly Lys
    2120                2125

<210> SEQ ID NO 112
<211> LENGTH: 2020
<212> TYPE: PRT
<213> ORGANISM: Artificial Sequence
<220> FEATURE:
<223> OTHER INFORMATION: pSYN FVIII 266 protein sequence

<400> SEQUENCE: 112

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Gly Ala Pro Gly Ser Pro Ala Gly Ser Pro Thr
        35                  40                  45

Ser Thr Glu Glu Gly Thr Ser Glu Ser Ala Thr Pro Glu Ser Gly Pro
    50                  55                  60

Gly Ser Glu Pro Ala Thr Ser Gly Ser Glu Thr Pro Ala Ser Ser Ser
65                  70                  75                  80

Asp Leu Gly Glu Leu Pro Val Asp Ala Arg Phe Pro Pro Arg Val Pro
                85                  90                  95

Lys Ser Phe Pro Phe Asn Thr Ser Val Val Tyr Lys Lys Thr Leu Phe
            100                 105                 110

Val Glu Phe Thr Asp His Leu Phe Asn Ile Ala Lys Pro Arg Pro Pro
        115                 120                 125

Trp Met Gly Leu Leu Gly Pro Thr Ile Gln Ala Glu Val Tyr Asp Thr
    130                 135                 140

Val Val Ile Thr Leu Lys Asn Met Ala Ser His Pro Val Ser Leu His
145                 150                 155                 160

Ala Val Gly Val Ser Tyr Trp Lys Ala Ser Glu Gly Ala Glu Tyr Asp
                165                 170                 175

Asp Gln Thr Ser Gln Arg Glu Lys Glu Asp Asp Lys Val Phe Pro Gly
            180                 185                 190

Gly Ser His Thr Tyr Val Trp Gln Val Leu Lys Glu Asn Gly Pro Met
        195                 200                 205

Ala Ser Asp Pro Leu Cys Leu Thr Tyr Ser Tyr Leu Ser His Val Asp
    210                 215                 220

Leu Val Lys Asp Leu Asn Ser Gly Leu Ile Gly Ala Leu Leu Val Cys
225                 230                 235                 240

Arg Glu Gly Ser Leu Ala Lys Glu Lys Thr Gln Thr Leu His Lys Phe
                245                 250                 255

Ile Leu Leu Phe Ala Val Phe Asp Glu Gly Lys Ser Trp His Ser Glu
            260                 265                 270

```
Thr Lys Asn Ser Leu Met Gln Asp Arg Asp Ala Ala Ser Ala Arg Ala
            275                 280                 285

Trp Pro Lys Met His Thr Val Asn Gly Tyr Val Asn Arg Ser Leu Pro
        290                 295                 300

Gly Leu Ile Gly Cys His Arg Lys Ser Val Tyr Trp His Val Ile Gly
305                 310                 315                 320

Met Gly Thr Thr Pro Glu Val His Ser Ile Phe Leu Glu Gly His Thr
                325                 330                 335

Phe Leu Val Arg Asn His Arg Gln Ala Ser Leu Glu Ile Ser Pro Ile
                340                 345                 350

Thr Phe Leu Thr Ala Gln Thr Leu Leu Met Asp Leu Gly Gln Phe Leu
            355                 360                 365

Leu Phe Cys His Ile Ser Ser His Gln His Asp Gly Met Glu Ala Tyr
        370                 375                 380

Val Lys Val Asp Ser Cys Pro Glu Gly Pro Gln Leu Arg Met Lys Asn
385                 390                 395                 400

Asn Glu Glu Ala Glu Asp Tyr Asp Asp Asp Leu Thr Asp Ser Glu Met
                405                 410                 415

Asp Val Val Arg Phe Asp Asp Asn Ser Pro Ser Phe Ile Gln Ile
                420                 425                 430

Arg Ser Val Ala Lys Lys His Pro Lys Thr Trp Val His Tyr Ile Ala
            435                 440                 445

Ala Glu Glu Glu Asp Trp Asp Tyr Ala Pro Leu Val Leu Ala Pro Asp
        450                 455                 460

Asp Arg Ser Tyr Lys Ser Gln Tyr Leu Asn Asn Gly Pro Gln Arg Ile
465                 470                 475                 480

Gly Arg Lys Tyr Lys Lys Val Arg Phe Met Ala Tyr Thr Asp Glu Thr
                485                 490                 495

Phe Lys Thr Arg Glu Ala Ile Gln His Glu Ser Gly Ile Leu Gly Pro
                500                 505                 510

Leu Leu Tyr Gly Glu Val Gly Asp Thr Leu Leu Ile Ile Phe Lys Asn
            515                 520                 525

Gln Ala Ser Arg Pro Tyr Asn Ile Tyr Pro His Gly Ile Thr Asp Val
        530                 535                 540

Arg Pro Leu Tyr Ser Arg Arg Leu Pro Lys Gly Val Lys His Leu Lys
545                 550                 555                 560

Asp Phe Pro Ile Leu Pro Gly Glu Ile Phe Lys Tyr Lys Trp Thr Val
                565                 570                 575

Thr Val Glu Asp Gly Pro Thr Lys Ser Asp Pro Arg Cys Leu Thr Arg
                580                 585                 590

Tyr Tyr Ser Ser Phe Val Asn Met Glu Arg Asp Leu Ala Ser Gly Leu
            595                 600                 605

Ile Gly Pro Leu Leu Ile Cys Tyr Lys Glu Ser Val Asp Gln Arg Gly
        610                 615                 620

Asn Gln Ile Met Ser Asp Lys Arg Asn Val Ile Leu Phe Ser Val Phe
625                 630                 635                 640

Asp Glu Asn Arg Ser Trp Tyr Leu Thr Glu Asn Ile Gln Arg Phe Leu
                645                 650                 655

Pro Asn Pro Ala Gly Val Gln Leu Glu Asp Pro Glu Phe Gln Ala Ser
                660                 665                 670

Asn Ile Met His Ser Ile Asn Gly Tyr Val Phe Asp Ser Leu Gln Leu
            675                 680                 685
```

```
Ser Val Cys Leu His Glu Val Ala Tyr Trp Tyr Ile Leu Ser Ile Gly
690                 695                 700

Ala Gln Thr Asp Phe Leu Ser Val Phe Phe Ser Gly Tyr Thr Phe Lys
705                 710                 715                 720

His Lys Met Val Tyr Glu Asp Thr Leu Thr Leu Phe Pro Phe Ser Gly
                725                 730                 735

Glu Thr Val Phe Met Ser Met Glu Asn Pro Gly Leu Trp Ile Leu Gly
                740                 745                 750

Cys His Asn Ser Asp Phe Arg Asn Arg Gly Met Thr Ala Leu Leu Lys
                755                 760                 765

Val Ser Ser Cys Asp Lys Asn Thr Gly Asp Tyr Tyr Glu Asp Ser Tyr
770                 775                 780

Glu Asp Ile Ser Ala Tyr Leu Leu Ser Lys Asn Asn Ala Ile Glu Pro
785                 790                 795                 800

Arg Ser Phe Ser Gln Asn Gly Ala Pro Gly Thr Ser Glu Ser Ala Thr
                805                 810                 815

Pro Glu Ser Gly Pro Gly Ser Glu Pro Ala Thr Ser Gly Ser Glu Thr
                820                 825                 830

Pro Gly Thr Ser Glu Ser Ala Thr Pro Glu Ser Gly Pro Gly Ser Glu
                835                 840                 845

Pro Ala Thr Ser Gly Ser Glu Thr Pro Gly Thr Ser Glu Ser Ala Thr
850                 855                 860

Pro Glu Ser Gly Pro Gly Thr Ser Thr Glu Pro Ser Glu Gly Ser Ala
865                 870                 875                 880

Pro Gly Ser Pro Ala Gly Ser Pro Thr Ser Thr Glu Glu Gly Thr Ser
                885                 890                 895

Glu Ser Ala Thr Pro Glu Ser Gly Pro Gly Ser Glu Pro Ala Thr Ser
                900                 905                 910

Gly Ser Glu Thr Pro Gly Thr Ser Glu Ser Ala Thr Pro Glu Ser Gly
                915                 920                 925

Pro Gly Ser Pro Ala Gly Ser Pro Thr Ser Thr Glu Glu Gly Ser Pro
930                 935                 940

Ala Gly Ser Pro Thr Ser Thr Glu Glu Gly Thr Ser Thr Glu Pro Ser
945                 950                 955                 960

Glu Gly Ser Ala Pro Gly Thr Ser Glu Ser Ala Thr Pro Glu Ser Gly
                965                 970                 975

Pro Gly Thr Ser Glu Ser Ala Thr Pro Glu Ser Gly Pro Gly Thr Ser
                980                 985                 990

Glu Ser Ala Thr Pro Glu Ser Gly Pro Gly Ser Glu Pro Ala Thr Ser
                995                 1000                1005

Gly Ser Glu Thr Pro Gly Ser Glu Pro Ala Thr Ser Gly Ser Glu
                1010                1015                1020

Thr Pro Gly Ser Pro Ala Gly Ser Pro Thr Ser Thr Glu Glu Gly
                1025                1030                1035

Thr Ser Thr Glu Pro Ser Glu Gly Ser Ala Pro Gly Thr Ser Thr
                1040                1045                1050

Glu Pro Ser Glu Gly Ser Ala Pro Gly Ser Pro Ala Gly Ser Pro
                1055                1060                1065

Thr Ser Thr Glu Glu Gly Thr Ser Thr Glu Pro Ser Glu Gly Ser
                1070                1075                1080

Ala Pro Gly Thr Ser Thr Glu Pro Ser Glu Gly Ser Ala Pro Gly
                1085                1090                1095

Ser Ser Pro Pro Val Leu Lys Arg His Gln Ala Glu Ile Thr Arg
```

```
              1100               1105               1110
Thr Thr Leu Gln Ser Asp Gln Glu Ile Asp Tyr Asp Asp Thr
    1115                1120                1125
Ile Ser Val Glu Met Lys Lys Glu Asp Phe Asp Ile Tyr Asp Glu
    1130                1135                1140
Asp Glu Asn Gln Ser Pro Arg Ser Phe Gln Lys Lys Thr Arg His
    1145                1150                1155
Tyr Phe Ile Ala Ala Val Glu Arg Leu Trp Asp Tyr Gly Met Ser
    1160                1165                1170
Ser Ser Pro His Val Leu Arg Asn Arg Ala Gln Ser Gly Ser Val
    1175                1180                1185
Pro Gln Phe Lys Lys Val Val Phe Gln Glu Phe Thr Asp Gly Ser
    1190                1195                1200
Phe Thr Gln Pro Leu Tyr Arg Gly Glu Leu Asn Glu His Leu Gly
    1205                1210                1215
Leu Leu Gly Pro Tyr Ile Arg Ala Glu Val Glu Asp Asn Ile Met
    1220                1225                1230
Val Thr Phe Arg Asn Gln Ala Ser Arg Pro Tyr Ser Phe Tyr Ser
    1235                1240                1245
Ser Leu Ile Ser Tyr Glu Glu Asp Gln Arg Gln Gly Ala Glu Pro
    1250                1255                1260
Arg Lys Asn Phe Val Lys Pro Asn Glu Thr Lys Thr Tyr Phe Trp
    1265                1270                1275
Lys Val Gln His His Met Ala Pro Thr Lys Asp Glu Phe Asp Cys
    1280                1285                1290
Lys Ala Trp Ala Tyr Phe Ser Asp Val Asp Leu Glu Lys Asp Val
    1295                1300                1305
His Ser Gly Leu Ile Gly Pro Leu Leu Val Cys His Thr Asn Thr
    1310                1315                1320
Leu Asn Pro Ala His Gly Arg Gln Val Thr Val Gln Glu Phe Ala
    1325                1330                1335
Leu Phe Phe Thr Ile Phe Asp Glu Thr Lys Ser Trp Tyr Phe Thr
    1340                1345                1350
Glu Asn Met Glu Arg Asn Cys Arg Ala Pro Cys Asn Ile Gln Met
    1355                1360                1365
Glu Asp Pro Thr Phe Lys Glu Asn Tyr Arg Phe His Ala Ile Asn
    1370                1375                1380
Gly Tyr Ile Met Asp Thr Leu Pro Gly Leu Val Met Ala Gln Asp
    1385                1390                1395
Gln Arg Ile Arg Trp Tyr Leu Leu Ser Met Gly Ser Asn Glu Asn
    1400                1405                1410
Ile His Ser Ile His Phe Ser Gly His Val Phe Thr Val Arg Lys
    1415                1420                1425
Lys Glu Glu Tyr Lys Met Ala Leu Tyr Asn Leu Tyr Pro Gly Val
    1430                1435                1440
Phe Glu Thr Val Glu Met Leu Pro Ser Lys Ala Gly Ile Trp Arg
    1445                1450                1455
Val Glu Cys Leu Ile Gly Glu His Leu His Ala Gly Met Ser Thr
    1460                1465                1470
Leu Phe Leu Val Tyr Ser Asn Lys Cys Gln Thr Pro Leu Gly Met
    1475                1480                1485
Ala Ser Gly His Ile Arg Asp Phe Gln Ile Thr Ala Ser Gly Gln
    1490                1495                1500
```

```
Tyr Gly Gln Trp Ala Pro Lys Leu Ala Arg Leu His Tyr Ser Gly
1505                1510                1515

Ser Ile Asn Ala Trp Ser Thr Lys Glu Pro Phe Ser Trp Ile Lys
1520                1525                1530

Val Asp Leu Leu Ala Pro Met Ile Ile His Gly Ile Lys Thr Gln
1535                1540                1545

Gly Ala Arg Gln Lys Phe Ser Ser Leu Tyr Ile Ser Gln Phe Ile
1550                1555                1560

Ile Met Tyr Ser Leu Asp Gly Lys Lys Trp Gln Thr Tyr Arg Gly
1565                1570                1575

Asn Ser Thr Gly Thr Leu Met Val Phe Phe Gly Asn Val Asp Ser
1580                1585                1590

Ser Gly Ile Lys His Asn Ile Phe Asn Pro Pro Ile Ile Ala Arg
1595                1600                1605

Tyr Ile Arg Leu His Pro Thr His Tyr Ser Ile Arg Ser Thr Leu
1610                1615                1620

Arg Met Glu Leu Met Gly Cys Asp Leu Asn Ser Cys Ser Met Pro
1625                1630                1635

Leu Gly Met Glu Ser Lys Ala Ile Ser Asp Ala Gln Ile Thr Ala
1640                1645                1650

Ser Ser Tyr Phe Thr Asn Met Phe Ala Thr Trp Ser Pro Ser Lys
1655                1660                1665

Ala Arg Leu His Leu Gln Gly Arg Ser Asn Ala Trp Arg Pro Gln
1670                1675                1680

Val Asn Asn Pro Lys Glu Trp Leu Gln Val Asp Phe Gln Lys Thr
1685                1690                1695

Met Lys Val Thr Gly Val Thr Thr Gln Gly Val Lys Ser Leu Leu
1700                1705                1710

Thr Ser Met Tyr Val Lys Glu Phe Leu Ile Ser Ser Ser Gln Asp
1715                1720                1725

Gly His Gln Trp Thr Leu Phe Phe Gln Asn Gly Lys Val Lys Val
1730                1735                1740

Phe Gln Gly Asn Gln Asp Ser Phe Thr Pro Val Val Asn Ser Leu
1745                1750                1755

Asp Pro Pro Leu Leu Thr Arg Tyr Leu Arg Ile His Pro Gln Ser
1760                1765                1770

Trp Val His Gln Ile Ala Leu Arg Met Glu Val Leu Gly Cys Glu
1775                1780                1785

Ala Gln Asp Leu Tyr Asp Lys Thr His Thr Cys Pro Pro Cys Pro
1790                1795                1800

Ala Pro Glu Leu Leu Gly Gly Pro Ser Val Phe Leu Phe Pro Pro
1805                1810                1815

Lys Pro Lys Asp Thr Leu Met Ile Ser Arg Thr Pro Glu Val Thr
1820                1825                1830

Cys Val Val Val Asp Val Ser His Glu Asp Pro Glu Val Lys Phe
1835                1840                1845

Asn Trp Tyr Val Asp Gly Val Glu Val His Asn Ala Lys Thr Lys
1850                1855                1860

Pro Arg Glu Glu Gln Tyr Asn Ser Thr Tyr Arg Val Val Ser Val
1865                1870                1875

Leu Thr Val Leu His Gln Asp Trp Leu Asn Gly Lys Glu Tyr Lys
1880                1885                1890
```

```
Cys Lys Val Ser Asn Lys Ala Leu Pro Ala Pro Ile Glu Lys Thr
    1895                1900                1905

Ile Ser Lys Ala Lys Gly Gln Pro Arg Glu Pro Gln Val Tyr Thr
    1910                1915                1920

Leu Pro Pro Ser Arg Asp Glu Leu Thr Lys Asn Gln Val Ser Leu
    1925                1930                1935

Thr Cys Leu Val Lys Gly Phe Tyr Pro Ser Asp Ile Ala Val Glu
    1940                1945                1950

Trp Glu Ser Asn Gly Gln Pro Glu Asn Asn Tyr Lys Thr Thr Pro
    1955                1960                1965

Pro Val Leu Asp Ser Asp Gly Ser Phe Phe Leu Tyr Ser Lys Leu
    1970                1975                1980

Thr Val Asp Lys Ser Arg Trp Gln Gln Gly Asn Val Phe Ser Cys
    1985                1990                1995

Ser Val Met His Glu Ala Leu His Asn His Tyr Thr Gln Lys Ser
    2000                2005                2010

Leu Ser Leu Ser Pro Gly Lys
    2015                2020

<210> SEQ ID NO 113
<211> LENGTH: 2056
<212> TYPE: PRT
<213> ORGANISM: Artificial Sequence
<220> FEATURE:
<223> OTHER INFORMATION: pSYN FVIII 267 protein sequence

<400> SEQUENCE: 113

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Gly Ala Pro Thr Ser Glu Ser Ala Thr Pro Glu
        35                  40                  45

Ser Gly Pro Gly Ser Glu Pro Ala Thr Ser Gly Ser Glu Thr Pro Gly
    50                  55                  60

Thr Ser Glu Ser Ala Thr Pro Glu Ser Gly Pro Gly Ser Glu Pro Ala
65                  70                  75                  80

Thr Ser Gly Ser Glu Thr Pro Gly Thr Ser Glu Ser Ala Thr Pro Glu
                85                  90                  95

Ser Gly Pro Gly Thr Ser Thr Glu Pro Ser Glu Gly Ser Ala Pro Gly
            100                 105                 110

Ala Ser Ser Ser Asp Leu Gly Glu Leu Pro Val Asp Ala Arg Phe Pro
        115                 120                 125

Pro Arg Val Pro Lys Ser Phe Pro Phe Asn Thr Ser Val Val Tyr Lys
    130                 135                 140

Lys Thr Leu Phe Val Glu Phe Thr Asp His Leu Phe Asn Ile Ala Lys
145                 150                 155                 160

Pro Arg Pro Pro Trp Met Gly Leu Leu Gly Pro Thr Ile Gln Ala Glu
                165                 170                 175

Val Tyr Asp Thr Val Val Ile Thr Leu Lys Asn Met Ala Ser His Pro
            180                 185                 190

Val Ser Leu His Ala Val Gly Val Ser Tyr Trp Lys Ala Ser Glu Gly
        195                 200                 205

Ala Glu Tyr Asp Asp Gln Thr Ser Gln Arg Glu Lys Glu Asp Asp Lys
    210                 215                 220
```

Val Phe Pro Gly Gly Ser His Thr Tyr Val Trp Gln Val Leu Lys Glu
225                 230                 235                 240

Asn Gly Pro Met Ala Ser Asp Pro Leu Cys Leu Thr Tyr Ser Tyr Leu
                245                 250                 255

Ser His Val Asp Leu Val Lys Asp Leu Asn Ser Gly Leu Ile Gly Ala
            260                 265                 270

Leu Leu Val Cys Arg Glu Gly Ser Leu Ala Lys Glu Lys Thr Gln Thr
            275                 280                 285

Leu His Lys Phe Ile Leu Leu Phe Ala Val Phe Asp Glu Gly Lys Ser
    290                 295                 300

Trp His Ser Glu Thr Lys Asn Ser Leu Met Gln Asp Arg Asp Ala Ala
305                 310                 315                 320

Ser Ala Arg Ala Trp Pro Lys Met His Thr Val Asn Gly Tyr Val Asn
                325                 330                 335

Arg Ser Leu Pro Gly Leu Ile Gly Cys His Arg Lys Ser Val Tyr Trp
            340                 345                 350

His Val Ile Gly Met Gly Thr Thr Pro Glu Val His Ser Ile Phe Leu
        355                 360                 365

Glu Gly His Thr Phe Leu Val Arg Asn His Arg Gln Ala Ser Leu Glu
    370                 375                 380

Ile Ser Pro Ile Thr Phe Leu Thr Ala Gln Thr Leu Leu Met Asp Leu
385                 390                 395                 400

Gly Gln Phe Leu Leu Phe Cys His Ile Ser Ser His Gln His Asp Gly
                405                 410                 415

Met Glu Ala Tyr Val Lys Val Asp Ser Cys Pro Glu Glu Pro Gln Leu
            420                 425                 430

Arg Met Lys Asn Asn Glu Glu Ala Glu Asp Tyr Asp Asp Asp Leu Thr
        435                 440                 445

Asp Ser Glu Met Asp Val Val Arg Phe Asp Asp Asp Asn Ser Pro Ser
    450                 455                 460

Phe Ile Gln Ile Arg Ser Val Ala Lys Lys His Pro Lys Thr Trp Val
465                 470                 475                 480

His Tyr Ile Ala Ala Glu Glu Glu Asp Trp Asp Tyr Ala Pro Leu Val
                485                 490                 495

Leu Ala Pro Asp Asp Arg Ser Tyr Lys Ser Gln Tyr Leu Asn Asn Gly
            500                 505                 510

Pro Gln Arg Ile Gly Arg Lys Tyr Lys Lys Val Arg Phe Met Ala Tyr
        515                 520                 525

Thr Asp Glu Thr Phe Lys Thr Arg Glu Ala Ile Gln His Glu Ser Gly
    530                 535                 540

Ile Leu Gly Pro Leu Leu Tyr Gly Glu Val Gly Asp Thr Leu Leu Ile
545                 550                 555                 560

Ile Phe Lys Asn Gln Ala Ser Arg Pro Tyr Asn Ile Tyr Pro His Gly
                565                 570                 575

Ile Thr Asp Val Arg Pro Leu Tyr Ser Arg Arg Leu Pro Lys Gly Val
            580                 585                 590

Lys His Leu Lys Asp Phe Pro Ile Leu Pro Gly Glu Ile Phe Lys Tyr
        595                 600                 605

Lys Trp Thr Val Thr Val Glu Asp Gly Pro Thr Lys Ser Asp Pro Arg
    610                 615                 620

Cys Leu Thr Arg Tyr Tyr Ser Ser Phe Val Asn Met Glu Arg Asp Leu
625                 630                 635                 640

Ala Ser Gly Leu Ile Gly Pro Leu Leu Ile Cys Tyr Lys Glu Ser Val

```
                        645                 650                 655

Asp Gln Arg Gly Asn Gln Ile Met Ser Asp Lys Arg Asn Val Ile Leu
                    660                 665                 670

Phe Ser Val Phe Asp Glu Asn Arg Ser Trp Tyr Leu Thr Glu Asn Ile
            675                 680                 685

Gln Arg Phe Leu Pro Asn Pro Ala Gly Val Gln Leu Glu Asp Pro Glu
        690                 695                 700

Phe Gln Ala Ser Asn Ile Met His Ser Ile Asn Gly Tyr Val Phe Asp
705                 710                 715                 720

Ser Leu Gln Leu Ser Val Cys Leu His Glu Val Ala Tyr Trp Tyr Ile
                725                 730                 735

Leu Ser Ile Gly Ala Gln Thr Asp Phe Leu Ser Val Phe Phe Ser Gly
            740                 745                 750

Tyr Thr Phe Lys His Lys Met Val Tyr Glu Asp Thr Leu Thr Leu Phe
        755                 760                 765

Pro Phe Ser Gly Glu Thr Val Phe Met Ser Met Glu Asn Pro Gly Leu
    770                 775                 780

Trp Ile Leu Gly Cys His Asn Ser Asp Phe Arg Asn Arg Gly Met Thr
785                 790                 795                 800

Ala Leu Leu Lys Val Ser Ser Cys Asp Lys Asn Thr Gly Asp Tyr Tyr
                805                 810                 815

Glu Asp Ser Tyr Glu Asp Ile Ser Ala Tyr Leu Leu Ser Lys Asn Asn
            820                 825                 830

Ala Ile Glu Pro Arg Ser Phe Ser Gln Asn Gly Ala Pro Gly Thr Ser
        835                 840                 845

Glu Ser Ala Thr Pro Glu Ser Gly Pro Gly Ser Glu Pro Ala Thr Ser
    850                 855                 860

Gly Ser Glu Thr Pro Gly Thr Ser Glu Ser Ala Thr Pro Glu Ser Gly
865                 870                 875                 880

Pro Gly Ser Glu Pro Ala Thr Ser Gly Ser Glu Thr Pro Gly Thr Ser
                885                 890                 895

Glu Ser Ala Thr Pro Glu Ser Gly Pro Gly Thr Ser Thr Glu Pro Ser
            900                 905                 910

Glu Gly Ser Ala Pro Gly Ser Pro Ala Gly Ser Pro Thr Ser Thr Glu
        915                 920                 925

Glu Gly Thr Ser Glu Ser Ala Thr Pro Glu Ser Gly Pro Gly Ser Glu
    930                 935                 940

Pro Ala Thr Ser Gly Ser Glu Thr Pro Gly Thr Ser Glu Ser Ala Thr
945                 950                 955                 960

Pro Glu Ser Gly Pro Gly Ser Pro Ala Gly Ser Pro Thr Ser Thr Glu
                965                 970                 975

Glu Gly Ser Pro Ala Gly Ser Pro Thr Ser Thr Glu Glu Gly Thr Ser
            980                 985                 990

Thr Glu Pro Ser Glu Gly Ser Ala Pro Gly Thr Ser Glu Ser Ala Thr
        995                 1000                1005

Pro Glu Ser Gly Pro Gly Thr Ser Glu Ser Ala Thr Pro Glu Ser
    1010                1015                1020

Gly Pro Gly Thr Ser Glu Ser Ala Thr Pro Glu Ser Gly Pro Gly
    1025                1030                1035

Ser Glu Pro Ala Thr Ser Gly Ser Glu Thr Pro Gly Ser Glu Pro
    1040                1045                1050

Ala Thr Ser Gly Ser Glu Thr Pro Gly Ser Pro Ala Gly Ser Pro
    1055                1060                1065
```

-continued

```
Thr Ser Thr Glu Glu Gly Thr Ser Thr Glu Pro Ser Glu Gly Ser
    1070                1075                1080

Ala Pro Gly Thr Ser Thr Glu Pro Ser Glu Gly Ser Ala Pro Gly
    1085                1090                1095

Ser Glu Pro Ala Thr Ser Gly Ser Glu Thr Pro Gly Thr Ser Glu
    1100                1105                1110

Ser Ala Thr Pro Glu Ser Gly Pro Gly Thr Ser Thr Glu Pro Ser
    1115                1120                1125

Glu Gly Ser Ala Pro Ala Ser Ser Pro Pro Val Leu Lys Arg His
    1130                1135                1140

Gln Ala Glu Ile Thr Arg Thr Thr Leu Gln Ser Asp Gln Glu Glu
    1145                1150                1155

Ile Asp Tyr Asp Asp Thr Ile Ser Val Glu Met Lys Lys Glu Asp
    1160                1165                1170

Phe Asp Ile Tyr Asp Glu Asp Glu Asn Gln Ser Pro Arg Ser Phe
    1175                1180                1185

Gln Lys Lys Thr Arg His Tyr Phe Ile Ala Ala Val Glu Arg Leu
    1190                1195                1200

Trp Asp Tyr Gly Met Ser Ser Ser Pro His Val Leu Arg Asn Arg
    1205                1210                1215

Ala Gln Ser Gly Ser Val Pro Gln Phe Lys Lys Val Val Phe Gln
    1220                1225                1230

Glu Phe Thr Asp Gly Ser Phe Thr Gln Pro Leu Tyr Arg Gly Glu
    1235                1240                1245

Leu Asn Glu His Leu Gly Leu Leu Gly Pro Tyr Ile Arg Ala Glu
    1250                1255                1260

Val Glu Asp Asn Ile Met Val Thr Phe Arg Asn Gln Ala Ser Arg
    1265                1270                1275

Pro Tyr Ser Phe Tyr Ser Ser Leu Ile Ser Tyr Glu Glu Asp Gln
    1280                1285                1290

Arg Gln Gly Ala Glu Pro Arg Lys Asn Phe Val Lys Pro Asn Glu
    1295                1300                1305

Thr Lys Thr Tyr Phe Trp Lys Val Gln His His Met Ala Pro Thr
    1310                1315                1320

Lys Asp Glu Phe Asp Cys Lys Ala Trp Ala Tyr Phe Ser Asp Val
    1325                1330                1335

Asp Leu Glu Lys Asp Val His Ser Gly Leu Ile Gly Pro Leu Leu
    1340                1345                1350

Val Cys His Thr Asn Thr Leu Asn Pro Ala His Gly Arg Gln Val
    1355                1360                1365

Thr Val Gln Glu Phe Ala Leu Phe Phe Thr Ile Phe Asp Glu Thr
    1370                1375                1380

Lys Ser Trp Tyr Phe Thr Glu Asn Met Glu Arg Asn Cys Arg Ala
    1385                1390                1395

Pro Cys Asn Ile Gln Met Glu Asp Pro Thr Phe Lys Glu Asn Tyr
    1400                1405                1410

Arg Phe His Ala Ile Asn Gly Tyr Ile Met Asp Thr Leu Pro Gly
    1415                1420                1425

Leu Val Met Ala Gln Asp Gln Arg Ile Arg Trp Tyr Leu Leu Ser
    1430                1435                1440

Met Gly Ser Asn Glu Asn Ile His Ser Ile His Phe Ser Gly His
    1445                1450                1455
```

```
Val Phe Thr Val Arg Lys Lys Glu Glu Tyr Lys Met Ala Leu Tyr
1460                1465                1470

Asn Leu Tyr Pro Gly Val Phe Glu Thr Val Glu Met Leu Pro Ser
1475                1480                1485

Lys Ala Gly Ile Trp Arg Val Glu Cys Leu Ile Gly Glu His Leu
1490                1495                1500

His Ala Gly Met Ser Thr Leu Phe Leu Val Tyr Ser Asn Lys Cys
1505                1510                1515

Gln Thr Pro Leu Gly Met Ala Ser Gly His Ile Arg Asp Phe Gln
1520                1525                1530

Ile Thr Ala Ser Gly Gln Tyr Gly Gln Trp Ala Pro Lys Leu Ala
1535                1540                1545

Arg Leu His Tyr Ser Gly Ser Ile Asn Ala Trp Ser Thr Lys Glu
1550                1555                1560

Pro Phe Ser Trp Ile Lys Val Asp Leu Leu Ala Pro Met Ile Ile
1565                1570                1575

His Gly Ile Lys Thr Gln Gly Ala Arg Gln Lys Phe Ser Ser Leu
1580                1585                1590

Tyr Ile Ser Gln Phe Ile Ile Met Tyr Ser Leu Asp Gly Lys Lys
1595                1600                1605

Trp Gln Thr Tyr Arg Gly Asn Ser Thr Gly Thr Leu Met Val Phe
1610                1615                1620

Phe Gly Asn Val Asp Ser Ser Gly Ile Lys His Asn Ile Phe Asn
1625                1630                1635

Pro Pro Ile Ile Ala Arg Tyr Ile Arg Leu His Pro Thr His Tyr
1640                1645                1650

Ser Ile Arg Ser Thr Leu Arg Met Glu Leu Met Gly Cys Asp Leu
1655                1660                1665

Asn Ser Cys Ser Met Pro Leu Gly Met Glu Ser Lys Ala Ile Ser
1670                1675                1680

Asp Ala Gln Ile Thr Ala Ser Ser Tyr Phe Thr Asn Met Phe Ala
1685                1690                1695

Thr Trp Ser Pro Ser Lys Ala Arg Leu His Leu Gln Gly Arg Ser
1700                1705                1710

Asn Ala Trp Arg Pro Gln Val Asn Asn Pro Lys Glu Trp Leu Gln
1715                1720                1725

Val Asp Phe Gln Lys Thr Met Lys Val Thr Gly Val Thr Thr Gln
1730                1735                1740

Gly Val Lys Ser Leu Leu Thr Ser Met Tyr Val Lys Glu Phe Leu
1745                1750                1755

Ile Ser Ser Ser Gln Asp Gly His Gln Trp Thr Leu Phe Phe Gln
1760                1765                1770

Asn Gly Lys Val Lys Val Phe Gln Gly Asn Gln Asp Ser Phe Thr
1775                1780                1785

Pro Val Val Asn Ser Leu Asp Pro Pro Leu Leu Thr Arg Tyr Leu
1790                1795                1800

Arg Ile His Pro Gln Ser Trp Val His Gln Ile Ala Leu Arg Met
1805                1810                1815

Glu Val Leu Gly Cys Glu Ala Gln Asp Leu Tyr Asp Lys Thr His
1820                1825                1830

Thr Cys Pro Pro Cys Pro Ala Pro Glu Leu Leu Gly Gly Pro Ser
1835                1840                1845

Val Phe Leu Phe Pro Pro Lys Pro Lys Asp Thr Leu Met Ile Ser
```

```
                    1850                1855                1860

Arg  Thr  Pro  Glu  Val  Thr  Cys  Val  Val  Val  Asp  Val  Ser  His  Glu
          1865                1870                1875

Asp  Pro  Glu  Val  Lys  Phe  Asn  Trp  Tyr  Val  Asp  Gly  Val  Glu  Val
1880                1885                1890

His  Asn  Ala  Lys  Thr  Lys  Pro  Arg  Glu  Glu  Gln  Tyr  Asn  Ser  Thr
     1895                1900                1905

Tyr  Arg  Val  Val  Ser  Val  Leu  Thr  Val  Leu  His  Gln  Asp  Trp  Leu
1910                1915                1920

Asn  Gly  Lys  Glu  Tyr  Lys  Cys  Lys  Val  Ser  Asn  Lys  Ala  Leu  Pro
     1925                1930                1935

Ala  Pro  Ile  Glu  Lys  Thr  Ile  Ser  Lys  Ala  Lys  Gly  Gln  Pro  Arg
1940                1945                1950

Glu  Pro  Gln  Val  Tyr  Thr  Leu  Pro  Pro  Ser  Arg  Asp  Glu  Leu  Thr
     1955                1960                1965

Lys  Asn  Gln  Val  Ser  Leu  Thr  Cys  Leu  Val  Lys  Gly  Phe  Tyr  Pro
1970                1975                1980

Ser  Asp  Ile  Ala  Val  Glu  Trp  Glu  Ser  Asn  Gly  Gln  Pro  Glu  Asn
     1985                1990                1995

Asn  Tyr  Lys  Thr  Thr  Pro  Pro  Val  Leu  Asp  Ser  Asp  Gly  Ser  Phe
2000                2005                2010

Phe  Leu  Tyr  Ser  Lys  Leu  Thr  Val  Asp  Lys  Ser  Arg  Trp  Gln  Gln
     2015                2020                2025

Gly  Asn  Val  Phe  Ser  Cys  Ser  Val  Met  His  Glu  Ala  Leu  His  Asn
2030                2035                2040

His  Tyr  Thr  Gln  Lys  Ser  Leu  Ser  Leu  Ser  Pro  Gly  Lys
     2045                2050                2055

<210> SEQ ID NO 114
<211> LENGTH: 1834
<212> TYPE: PRT
<213> ORGANISM: Artificial Sequence
<220> FEATURE:
<223> OTHER INFORMATION: pSYN FVIII 268 protein sequence

<400> SEQUENCE: 114

Met  Gln  Ile  Glu  Leu  Ser  Thr  Cys  Phe  Phe  Leu  Cys  Leu  Leu  Arg  Phe
1                   5                   10                  15

Cys  Phe  Ser  Ala  Thr  Arg  Arg  Tyr  Tyr  Leu  Gly  Ala  Val  Glu  Leu  Ser
                20                  25                  30

Trp  Asp  Tyr  Met  Gln  Gly  Ala  Pro  Thr  Ser  Glu  Ser  Ala  Thr  Pro  Glu
            35                  40                  45

Ser  Gly  Pro  Gly  Ser  Glu  Pro  Ala  Thr  Ser  Gly  Ser  Glu  Thr  Pro  Gly
        50                  55                  60

Thr  Ser  Glu  Ser  Ala  Thr  Pro  Glu  Ser  Gly  Pro  Gly  Ser  Glu  Pro  Ala
65                  70                  75                  80

Thr  Ser  Gly  Ser  Glu  Thr  Pro  Gly  Thr  Ser  Glu  Ser  Ala  Thr  Pro  Glu
                85                  90                  95

Ser  Gly  Pro  Gly  Thr  Ser  Thr  Glu  Pro  Ser  Glu  Gly  Ser  Ala  Pro  Gly
            100                 105                 110

Ser  Pro  Ala  Gly  Ser  Pro  Thr  Ser  Thr  Glu  Glu  Gly  Ser  Glu  Ser
        115                 120                 125

Ala  Thr  Pro  Glu  Ser  Gly  Pro  Gly  Ser  Glu  Pro  Ala  Thr  Ser  Gly  Ser
        130                 135                 140

Glu  Thr  Pro  Gly  Thr  Ser  Glu  Ser  Ala  Thr  Pro  Glu  Ser  Gly  Pro  Gly
```

-continued

```
            145                 150                 155                 160
Ser Pro Ala Gly Ser Pro Thr Ser Thr Glu Glu Gly Ser Pro Ala Gly
                165                 170                 175
Ser Pro Thr Ser Thr Glu Glu Gly Ala Ser Ser Asp Leu Gly Glu
                180                 185                 190
Leu Pro Val Asp Ala Arg Phe Pro Arg Val Pro Lys Ser Phe Pro
                195                 200                 205
Phe Asn Thr Ser Val Val Tyr Lys Lys Thr Leu Phe Val Glu Phe Thr
210                 215                 220
Asp His Leu Phe Asn Ile Ala Lys Pro Arg Pro Pro Trp Met Gly Leu
225                 230                 235                 240
Leu Gly Pro Thr Ile Gln Ala Glu Val Tyr Asp Thr Val Val Ile Thr
                245                 250                 255
Leu Lys Asn Met Ala Ser His Pro Val Ser Leu His Ala Val Gly Val
                260                 265                 270
Ser Tyr Trp Lys Ala Ser Glu Gly Ala Glu Tyr Asp Asp Gln Thr Ser
                275                 280                 285
Gln Arg Glu Lys Glu Asp Asp Lys Val Phe Pro Gly Gly Ser His Thr
                290                 295                 300
Tyr Val Trp Gln Val Leu Lys Glu Asn Gly Pro Met Ala Ser Asp Pro
305                 310                 315                 320
Leu Cys Leu Thr Tyr Ser Tyr Leu Ser His Val Asp Leu Val Lys Asp
                325                 330                 335
Leu Asn Ser Gly Leu Ile Gly Ala Leu Leu Val Cys Arg Glu Gly Ser
                340                 345                 350
Leu Ala Lys Glu Lys Thr Gln Thr Leu His Lys Phe Ile Leu Leu Phe
                355                 360                 365
Ala Val Phe Asp Glu Gly Lys Ser Trp His Ser Glu Thr Lys Asn Ser
                370                 375                 380
Leu Met Gln Asp Arg Asp Ala Ala Ser Ala Arg Ala Trp Pro Lys Met
385                 390                 395                 400
His Thr Val Asn Gly Tyr Val Asn Arg Ser Leu Pro Gly Leu Ile Gly
                405                 410                 415
Cys His Arg Lys Ser Val Tyr Trp His Val Ile Gly Met Gly Thr Thr
                420                 425                 430
Pro Glu Val His Ser Ile Phe Leu Glu Gly His Thr Phe Leu Val Arg
                435                 440                 445
Asn His Arg Gln Ala Ser Leu Glu Ile Ser Pro Ile Thr Phe Leu Thr
                450                 455                 460
Ala Gln Thr Leu Leu Met Asp Leu Gly Gln Phe Leu Leu Phe Cys His
465                 470                 475                 480
Ile Ser Ser His Gln His Asp Gly Met Glu Ala Tyr Val Lys Val Asp
                485                 490                 495
Ser Cys Pro Glu Glu Pro Gln Leu Arg Met Lys Asn Asn Glu Glu Ala
                500                 505                 510
Glu Asp Tyr Asp Asp Asp Leu Thr Asp Ser Glu Met Asp Val Val Arg
                515                 520                 525
Phe Asp Asp Asp Asn Ser Pro Ser Phe Ile Gln Ile Arg Ser Val Ala
                530                 535                 540
Lys Lys His Pro Lys Thr Trp Val His Tyr Ile Ala Ala Glu Glu Glu
545                 550                 555                 560
Asp Trp Asp Tyr Ala Pro Leu Val Leu Ala Pro Asp Asp Arg Ser Tyr
                565                 570                 575
```

```
Lys Ser Gln Tyr Leu Asn Asn Gly Pro Gln Arg Ile Gly Arg Lys Tyr
            580                 585                 590

Lys Lys Val Arg Phe Met Ala Tyr Thr Asp Glu Thr Phe Lys Thr Arg
            595                 600                 605

Glu Ala Ile Gln His Glu Ser Gly Ile Leu Gly Pro Leu Leu Tyr Gly
    610                 615                 620

Glu Val Gly Asp Thr Leu Leu Ile Ile Phe Lys Asn Gln Ala Ser Arg
625                 630                 635                 640

Pro Tyr Asn Ile Tyr Pro His Gly Ile Thr Asp Val Arg Pro Leu Tyr
                645                 650                 655

Ser Arg Arg Leu Pro Lys Gly Val Lys His Leu Lys Asp Phe Pro Ile
            660                 665                 670

Leu Pro Gly Glu Ile Phe Lys Tyr Lys Trp Thr Val Thr Val Glu Asp
            675                 680                 685

Gly Pro Thr Lys Ser Asp Pro Arg Cys Leu Thr Arg Tyr Tyr Ser Ser
    690                 695                 700

Phe Val Asn Met Glu Arg Asp Leu Ala Ser Gly Leu Ile Gly Pro Leu
705                 710                 715                 720

Leu Ile Cys Tyr Lys Glu Ser Val Asp Gln Arg Gly Asn Gln Ile Met
                725                 730                 735

Ser Asp Lys Arg Asn Val Ile Leu Phe Ser Val Phe Asp Glu Asn Arg
            740                 745                 750

Ser Trp Tyr Leu Thr Glu Asn Ile Gln Arg Phe Leu Pro Asn Pro Ala
            755                 760                 765

Gly Val Gln Leu Glu Asp Pro Glu Phe Gln Ala Ser Asn Ile Met His
    770                 775                 780

Ser Ile Asn Gly Tyr Val Phe Asp Ser Leu Gln Leu Ser Val Cys Leu
785                 790                 795                 800

His Glu Val Ala Tyr Trp Tyr Ile Leu Ser Ile Gly Ala Gln Thr Asp
                805                 810                 815

Phe Leu Ser Val Phe Phe Ser Gly Tyr Thr Phe Lys His Lys Met Val
            820                 825                 830

Tyr Glu Asp Thr Leu Thr Leu Phe Pro Phe Ser Gly Glu Thr Val Phe
            835                 840                 845

Met Ser Met Glu Asn Pro Gly Leu Trp Ile Leu Gly Cys His Asn Ser
    850                 855                 860

Asp Phe Arg Asn Arg Gly Met Thr Ala Leu Leu Lys Val Ser Ser Cys
865                 870                 875                 880

Asp Lys Asn Thr Gly Asp Tyr Tyr Glu Asp Ser Tyr Glu Asp Ile Ser
                885                 890                 895

Ala Tyr Leu Leu Ser Lys Asn Asn Ala Ile Glu Pro Arg Ser Phe Ser
            900                 905                 910

Gln Asn Pro Pro Val Leu Lys Arg His Gln Ala Glu Ile Thr Arg Thr
            915                 920                 925

Thr Leu Gln Ser Asp Gln Glu Glu Ile Asp Tyr Asp Asp Thr Ile Ser
    930                 935                 940

Val Glu Met Lys Lys Glu Asp Phe Asp Ile Tyr Asp Glu Asp Glu Asn
945                 950                 955                 960

Gln Ser Pro Arg Ser Phe Gln Lys Lys Thr Arg His Tyr Phe Ile Ala
                965                 970                 975

Ala Val Glu Arg Leu Trp Asp Tyr Gly Met Ser Ser Ser Pro His Val
            980                 985                 990
```

-continued

Leu Arg Asn Arg Ala Gln Ser Gly Ser Val Pro Gln Phe Lys Lys Val
                995                 1000                1005

Val Phe Gln Glu Phe Thr Asp Gly Ser Phe Thr Gln Pro Leu Tyr
    1010                1015                1020

Arg Gly Glu Leu Asn Glu His Leu Gly Leu Leu Gly Pro Tyr Ile
    1025                1030                1035

Arg Ala Glu Val Glu Asp Asn Ile Met Val Thr Phe Arg Asn Gln
    1040                1045                1050

Ala Ser Arg Pro Tyr Ser Phe Tyr Ser Ser Leu Ile Ser Tyr Glu
    1055                1060                1065

Glu Asp Gln Arg Gln Gly Ala Glu Pro Arg Lys Asn Phe Val Lys
    1070                1075                1080

Pro Asn Glu Thr Lys Thr Tyr Phe Trp Lys Val Gln His His Met
    1085                1090                1095

Ala Pro Thr Lys Asp Glu Phe Asp Cys Lys Ala Trp Ala Tyr Phe
    1100                1105                1110

Ser Asp Val Asp Leu Glu Lys Asp Val His Ser Gly Leu Ile Gly
    1115                1120                1125

Pro Leu Leu Val Cys His Thr Asn Thr Leu Asn Pro Ala His Gly
    1130                1135                1140

Arg Gln Val Thr Val Gln Glu Phe Ala Leu Phe Phe Thr Ile Phe
    1145                1150                1155

Asp Glu Thr Lys Ser Trp Tyr Phe Thr Glu Asn Met Glu Arg Asn
    1160                1165                1170

Cys Arg Ala Pro Cys Asn Ile Gln Met Glu Asp Pro Thr Phe Lys
    1175                1180                1185

Glu Asn Tyr Arg Phe His Ala Ile Asn Gly Tyr Ile Met Asp Thr
    1190                1195                1200

Leu Pro Gly Leu Val Met Ala Gln Asp Gln Arg Ile Arg Trp Tyr
    1205                1210                1215

Leu Leu Ser Met Gly Ser Asn Glu Asn Ile His Ser Ile His Phe
    1220                1225                1230

Ser Gly His Val Phe Thr Val Arg Lys Lys Glu Glu Tyr Lys Met
    1235                1240                1245

Ala Leu Tyr Asn Leu Tyr Pro Gly Val Phe Glu Thr Val Glu Met
    1250                1255                1260

Leu Pro Ser Lys Ala Gly Ile Trp Arg Val Glu Cys Leu Ile Gly
    1265                1270                1275

Glu His Leu His Ala Gly Met Ser Thr Leu Phe Leu Val Tyr Ser
    1280                1285                1290

Asn Lys Cys Gln Thr Pro Leu Gly Met Ala Ser Gly His Ile Arg
    1295                1300                1305

Asp Phe Gln Ile Thr Ala Ser Gly Gln Tyr Gly Gln Trp Ala Pro
    1310                1315                1320

Lys Leu Ala Arg Leu His Tyr Ser Gly Ser Ile Asn Ala Trp Ser
    1325                1330                1335

Thr Lys Glu Pro Phe Ser Trp Ile Lys Val Asp Leu Leu Ala Pro
    1340                1345                1350

Met Ile Ile His Gly Ile Lys Thr Gln Gly Ala Arg Gln Lys Phe
    1355                1360                1365

Ser Ser Leu Tyr Ile Ser Gln Phe Ile Ile Met Tyr Ser Leu Asp
    1370                1375                1380

Gly Lys Lys Trp Gln Thr Tyr Arg Gly Asn Ser Thr Gly Thr Leu

```
                1385                1390                1395
Met Val Phe Phe Gly Asn Val Asp Ser Ser Gly Ile Lys His Asn
    1400                1405                1410

Ile Phe Asn Pro Pro Ile Ile Ala Arg Tyr Ile Arg Leu His Pro
    1415                1420                1425

Thr His Tyr Ser Ile Arg Ser Thr Leu Arg Met Glu Leu Met Gly
    1430                1435                1440

Cys Asp Leu Asn Ser Cys Ser Met Pro Leu Gly Met Glu Ser Lys
    1445                1450                1455

Ala Ile Ser Asp Ala Gln Ile Thr Ala Ser Ser Tyr Phe Thr Asn
    1460                1465                1470

Met Phe Ala Thr Trp Ser Pro Ser Lys Ala Arg Leu His Leu Gln
    1475                1480                1485

Gly Arg Ser Asn Ala Trp Arg Pro Gln Val Asn Asn Pro Lys Glu
    1490                1495                1500

Trp Leu Gln Val Asp Phe Gln Lys Thr Met Lys Val Thr Gly Val
    1505                1510                1515

Thr Thr Gln Gly Val Lys Ser Leu Leu Thr Ser Met Tyr Val Lys
    1520                1525                1530

Glu Phe Leu Ile Ser Ser Ser Gln Asp Gly His Gln Trp Thr Leu
    1535                1540                1545

Phe Phe Gln Asn Gly Lys Val Lys Val Phe Gln Gly Asn Gln Asp
    1550                1555                1560

Ser Phe Thr Pro Val Val Asn Ser Leu Asp Pro Pro Leu Leu Thr
    1565                1570                1575

Arg Tyr Leu Arg Ile His Pro Gln Ser Trp Val His Gln Ile Ala
    1580                1585                1590

Leu Arg Met Glu Val Leu Gly Cys Glu Ala Gln Asp Leu Tyr Asp
    1595                1600                1605

Lys Thr His Thr Cys Pro Pro Cys Pro Ala Pro Glu Leu Leu Gly
    1610                1615                1620

Gly Pro Ser Val Phe Leu Phe Pro Pro Lys Pro Lys Asp Thr Leu
    1625                1630                1635

Met Ile Ser Arg Thr Pro Glu Val Thr Cys Val Val Val Asp Val
    1640                1645                1650

Ser His Glu Asp Pro Glu Val Lys Phe Asn Trp Tyr Val Asp Gly
    1655                1660                1665

Val Glu Val His Asn Ala Lys Thr Lys Pro Arg Glu Glu Gln Tyr
    1670                1675                1680

Asn Ser Thr Tyr Arg Val Val Ser Val Leu Thr Val Leu His Gln
    1685                1690                1695

Asp Trp Leu Asn Gly Lys Glu Tyr Lys Cys Lys Val Ser Asn Lys
    1700                1705                1710

Ala Leu Pro Ala Pro Ile Glu Lys Thr Ile Ser Lys Ala Lys Gly
    1715                1720                1725

Gln Pro Arg Glu Pro Gln Val Tyr Thr Leu Pro Pro Ser Arg Asp
    1730                1735                1740

Glu Leu Thr Lys Asn Gln Val Ser Leu Thr Cys Leu Val Lys Gly
    1745                1750                1755

Phe Tyr Pro Ser Asp Ile Ala Val Glu Trp Glu Ser Asn Gly Gln
    1760                1765                1770

Pro Glu Asn Asn Tyr Lys Thr Thr Pro Pro Val Leu Asp Ser Asp
    1775                1780                1785
```

```
Gly Ser Phe Phe Leu Tyr Ser Lys Leu Thr Val Asp Lys Ser Arg
        1790                1795                1800

Trp Gln Gln Gly Asn Val Phe Ser Cys Ser Val Met His Glu Ala
        1805                1810                1815

Leu His Asn His Tyr Thr Gln Lys Ser Leu Ser Leu Ser Pro Gly
        1820                1825                1830

Lys

<210> SEQ ID NO 115
<211> LENGTH: 1762
<212> TYPE: PRT
<213> ORGANISM: Artificial Sequence
<220> FEATURE:
<223> OTHER INFORMATION: pSYN FVIII 269 protein sequence

<400> SEQUENCE: 115

Met Gln Ile Glu Leu Ser Thr Cys Phe Phe Leu Cys Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Gly Ala Pro Thr Ser Glu Ser Ala Thr Pro Glu
            35                  40                  45

Ser Gly Pro Gly Ser Glu Pro Ala Thr Ser Gly Ser Glu Thr Pro Gly
        50                  55                  60

Thr Ser Glu Ser Ala Thr Pro Glu Ser Gly Pro Gly Ser Glu Pro Ala
65                  70                  75                  80

Thr Ser Gly Ser Glu Thr Pro Gly Thr Ser Glu Ser Ala Thr Pro Glu
                85                  90                  95

Ser Gly Pro Gly Thr Ser Thr Glu Pro Ser Glu Gly Ser Ala Pro Gly
            100                 105                 110

Ala Ser Ser Ser Asp Leu Gly Glu Leu Pro Val Asp Ala Arg Phe Pro
        115                 120                 125

Pro Arg Val Pro Lys Ser Phe Pro Phe Asn Thr Ser Val Val Tyr Lys
        130                 135                 140

Lys Thr Leu Phe Val Glu Phe Thr Asp His Leu Phe Asn Ile Ala Lys
145                 150                 155                 160

Pro Arg Pro Pro Trp Met Gly Leu Leu Gly Pro Thr Ile Gln Ala Glu
                165                 170                 175

Val Tyr Asp Thr Val Val Ile Thr Leu Lys Asn Met Ala Ser His Pro
            180                 185                 190

Val Ser Leu His Ala Val Gly Val Ser Tyr Trp Lys Ala Ser Glu Gly
        195                 200                 205

Ala Glu Tyr Asp Asp Gln Thr Ser Gln Arg Glu Lys Glu Asp Asp Lys
    210                 215                 220

Val Phe Pro Gly Gly Ser His Thr Tyr Val Trp Gln Val Leu Lys Glu
225                 230                 235                 240

Asn Gly Pro Met Ala Ser Asp Pro Leu Cys Leu Thr Tyr Ser Tyr Leu
                245                 250                 255

Ser His Val Asp Leu Val Lys Asp Leu Asn Ser Gly Leu Ile Gly Ala
            260                 265                 270

Leu Leu Val Cys Arg Glu Gly Ser Leu Ala Lys Glu Lys Thr Gln Thr
        275                 280                 285

Leu His Lys Phe Ile Leu Leu Phe Ala Val Phe Asp Glu Gly Lys Ser
        290                 295                 300
```

-continued

```
Trp His Ser Glu Thr Lys Asn Ser Leu Met Gln Asp Arg Asp Ala Ala
305                 310                 315                 320

Ser Ala Arg Ala Trp Pro Lys Met His Thr Val Asn Gly Tyr Val Asn
            325                 330                 335

Arg Ser Leu Pro Gly Leu Ile Gly Cys His Arg Lys Ser Val Tyr Trp
            340                 345                 350

His Val Ile Gly Met Gly Thr Thr Pro Glu Val His Ser Ile Phe Leu
            355                 360                 365

Glu Gly His Thr Phe Leu Val Arg Asn His Arg Gln Ala Ser Leu Glu
        370                 375                 380

Ile Ser Pro Ile Thr Phe Leu Thr Ala Gln Thr Leu Leu Met Asp Leu
385                 390                 395                 400

Gly Gln Phe Leu Leu Phe Cys His Ile Ser Ser His Gln His Asp Gly
                405                 410                 415

Met Glu Ala Tyr Val Lys Val Asp Ser Cys Pro Glu Pro Gln Leu
            420                 425                 430

Arg Met Lys Asn Asn Glu Glu Ala Glu Asp Tyr Asp Asp Leu Thr
        435                 440                 445

Asp Ser Glu Met Asp Val Val Arg Phe Asp Asp Asn Ser Pro Ser
450                 455                 460

Phe Ile Gln Ile Arg Ser Val Ala Lys Lys His Pro Lys Thr Trp Val
465                 470                 475                 480

His Tyr Ile Ala Ala Glu Glu Asp Trp Asp Tyr Ala Pro Leu Val
            485                 490                 495

Leu Ala Pro Asp Asp Arg Ser Tyr Lys Ser Gln Tyr Leu Asn Asn Gly
            500                 505                 510

Pro Gln Arg Ile Gly Arg Lys Tyr Lys Val Arg Phe Met Ala Tyr
        515                 520                 525

Thr Asp Glu Thr Phe Lys Thr Arg Glu Ala Ile Gln His Glu Ser Gly
        530                 535                 540

Ile Leu Gly Pro Leu Leu Tyr Gly Glu Val Gly Asp Thr Leu Leu Ile
545                 550                 555                 560

Ile Phe Lys Asn Gln Ala Ser Arg Pro Tyr Asn Ile Tyr Pro His Gly
                565                 570                 575

Ile Thr Asp Val Arg Pro Leu Tyr Ser Arg Arg Leu Pro Lys Gly Val
            580                 585                 590

Lys His Leu Lys Asp Phe Pro Ile Leu Pro Gly Glu Ile Phe Lys Tyr
        595                 600                 605

Lys Trp Thr Val Thr Val Glu Asp Gly Pro Thr Lys Ser Asp Pro Arg
610                 615                 620

Cys Leu Thr Arg Tyr Tyr Ser Ser Phe Val Asn Met Glu Arg Asp Leu
625                 630                 635                 640

Ala Ser Gly Leu Ile Gly Pro Leu Leu Ile Cys Tyr Lys Glu Ser Val
                645                 650                 655

Asp Gln Arg Gly Asn Gln Ile Met Ser Asp Lys Arg Asn Val Ile Leu
            660                 665                 670

Phe Ser Val Phe Asp Glu Asn Arg Ser Trp Tyr Leu Thr Glu Asn Ile
            675                 680                 685

Gln Arg Phe Leu Pro Asn Pro Ala Gly Val Gln Leu Glu Asp Pro Glu
        690                 695                 700

Phe Gln Ala Ser Asn Ile Met His Ser Ile Asn Gly Tyr Val Phe Asp
705                 710                 715                 720

Ser Leu Gln Leu Ser Val Cys Leu His Glu Val Ala Tyr Trp Tyr Ile
```

-continued

```
                725                 730                 735
Leu Ser Ile Gly Ala Gln Thr Asp Phe Leu Ser Val Phe Phe Ser Gly
                740                 745                 750

Tyr Thr Phe Lys His Lys Met Val Tyr Glu Asp Thr Leu Thr Leu Phe
                755                 760                 765

Pro Phe Ser Gly Glu Thr Val Phe Met Ser Met Glu Asn Pro Gly Leu
770                 775                 780

Trp Ile Leu Gly Cys His Asn Ser Asp Phe Arg Asn Arg Gly Met Thr
785                 790                 795                 800

Ala Leu Leu Lys Val Ser Ser Cys Asp Lys Asn Thr Gly Asp Tyr Tyr
                805                 810                 815

Glu Asp Ser Tyr Glu Asp Ile Ser Ala Tyr Leu Leu Ser Lys Asn Asn
                820                 825                 830

Ala Ile Glu Pro Arg Ser Phe Ser Gln Asn Pro Pro Val Leu Lys Arg
                835                 840                 845

His Gln Ala Glu Ile Thr Arg Thr Thr Leu Gln Ser Asp Gln Glu Glu
                850                 855                 860

Ile Asp Tyr Asp Asp Thr Ile Ser Val Glu Met Lys Lys Glu Asp Phe
865                 870                 875                 880

Asp Ile Tyr Asp Glu Asp Glu Asn Gln Ser Pro Arg Ser Phe Gln Lys
                885                 890                 895

Lys Thr Arg His Tyr Phe Ile Ala Ala Val Glu Arg Leu Trp Asp Tyr
                900                 905                 910

Gly Met Ser Ser Ser Pro His Val Leu Arg Asn Arg Ala Gln Ser Gly
                915                 920                 925

Ser Val Pro Gln Phe Lys Lys Val Val Phe Gln Glu Phe Thr Asp Gly
930                 935                 940

Ser Phe Thr Gln Pro Leu Tyr Arg Gly Glu Leu Asn Glu His Leu Gly
945                 950                 955                 960

Leu Leu Gly Pro Tyr Ile Arg Ala Glu Val Glu Asp Asn Ile Met Val
                965                 970                 975

Thr Phe Arg Asn Gln Ala Ser Arg Pro Tyr Ser Phe Tyr Ser Ser Leu
                980                 985                 990

Ile Ser Tyr Glu Glu Asp Gln Arg Gln Gly Ala Glu Pro Arg Lys Asn
                995                 1000                1005

Phe Val Lys Pro Asn Glu Thr Lys Thr Tyr Phe Trp Lys Val Gln
                1010                1015                1020

His His Met Ala Pro Thr Lys Asp Glu Phe Asp Cys Lys Ala Trp
                1025                1030                1035

Ala Tyr Phe Ser Asp Val Asp Leu Glu Lys Asp Val His Ser Gly
                1040                1045                1050

Leu Ile Gly Pro Leu Leu Val Cys His Thr Asn Thr Leu Asn Pro
                1055                1060                1065

Ala His Gly Arg Gln Val Thr Val Gln Glu Phe Ala Leu Phe Phe
                1070                1075                1080

Thr Ile Phe Asp Glu Thr Lys Ser Trp Tyr Phe Thr Glu Asn Met
                1085                1090                1095

Glu Arg Asn Cys Arg Ala Pro Cys Asn Ile Gln Met Glu Asp Pro
                1100                1105                1110

Thr Phe Lys Glu Asn Tyr Arg Phe His Ala Ile Asn Gly Tyr Ile
                1115                1120                1125

Met Asp Thr Leu Pro Gly Leu Val Met Ala Gln Asp Gln Arg Ile
                1130                1135                1140
```

```
Arg Trp Tyr Leu Leu Ser Met Gly Ser Asn Glu Asn Ile His Ser
1145                1150                1155

Ile His Phe Ser Gly His Val Phe Thr Val Arg Lys Lys Glu Glu
    1160            1165                1170

Tyr Lys Met Ala Leu Tyr Asn Leu Tyr Pro Gly Val Phe Glu Thr
    1175            1180                1185

Val Glu Met Leu Pro Ser Lys Ala Gly Ile Trp Arg Val Glu Cys
    1190            1195                1200

Leu Ile Gly Glu His Leu His Ala Gly Met Ser Thr Leu Phe Leu
    1205            1210                1215

Val Tyr Ser Asn Lys Cys Gln Thr Pro Leu Gly Met Ala Ser Gly
    1220            1225                1230

His Ile Arg Asp Phe Gln Ile Thr Ala Ser Gly Gln Tyr Gly Gln
    1235            1240                1245

Trp Ala Pro Lys Leu Ala Arg Leu His Tyr Ser Gly Ser Ile Asn
    1250            1255                1260

Ala Trp Ser Thr Lys Glu Pro Phe Ser Trp Ile Lys Val Asp Leu
    1265            1270                1275

Leu Ala Pro Met Ile Ile His Gly Ile Lys Thr Gln Gly Ala Arg
    1280            1285                1290

Gln Lys Phe Ser Ser Leu Tyr Ile Ser Gln Phe Ile Ile Met Tyr
    1295            1300                1305

Ser Leu Asp Gly Lys Lys Trp Gln Thr Tyr Arg Gly Asn Ser Thr
    1310            1315                1320

Gly Thr Leu Met Val Phe Phe Gly Asn Val Asp Ser Ser Gly Ile
    1325            1330                1335

Lys His Asn Ile Phe Asn Pro Pro Ile Ile Ala Arg Tyr Ile Arg
    1340            1345                1350

Leu His Pro Thr His Tyr Ser Ile Arg Ser Thr Leu Arg Met Glu
    1355            1360                1365

Leu Met Gly Cys Asp Leu Asn Ser Cys Ser Met Pro Leu Gly Met
    1370            1375                1380

Glu Ser Lys Ala Ile Ser Asp Ala Gln Ile Thr Ala Ser Ser Tyr
    1385            1390                1395

Phe Thr Asn Met Phe Ala Thr Trp Ser Pro Ser Lys Ala Arg Leu
    1400            1405                1410

His Leu Gln Gly Arg Ser Asn Ala Trp Arg Pro Gln Val Asn Asn
    1415            1420                1425

Pro Lys Glu Trp Leu Gln Val Asp Phe Gln Lys Thr Met Lys Val
    1430            1435                1440

Thr Gly Val Thr Thr Gln Gly Val Lys Ser Leu Leu Thr Ser Met
    1445            1450                1455

Tyr Val Lys Glu Phe Leu Ile Ser Ser Ser Gln Asp Gly His Gln
    1460            1465                1470

Trp Thr Leu Phe Phe Gln Asn Gly Lys Val Lys Val Phe Gln Gly
    1475            1480                1485

Asn Gln Asp Ser Phe Thr Pro Val Val Asn Ser Leu Asp Pro Pro
    1490            1495                1500

Leu Leu Thr Arg Tyr Leu Arg Ile His Pro Gln Ser Trp Val His
    1505            1510                1515

Gln Ile Ala Leu Arg Met Glu Val Leu Gly Cys Glu Ala Gln Asp
    1520            1525                1530
```

-continued

```
Leu Tyr Asp Lys Thr His Thr Cys Pro Pro Cys Pro Ala Pro Glu
1535                1540                1545

Leu Leu Gly Gly Pro Ser Val Phe Leu Phe Pro Pro Lys Pro Lys
    1550                1555                1560

Asp Thr Leu Met Ile Ser Arg Thr Pro Glu Val Thr Cys Val Val
1565                1570                1575

Val Asp Val Ser His Glu Asp Pro Glu Val Lys Phe Asn Trp Tyr
    1580                1585                1590

Val Asp Gly Val Glu Val His Asn Ala Lys Thr Lys Pro Arg Glu
1595                1600                1605

Glu Gln Tyr Asn Ser Thr Tyr Arg Val Val Ser Val Leu Thr Val
    1610                1615                1620

Leu His Gln Asp Trp Leu Asn Gly Lys Glu Tyr Lys Cys Lys Val
1625                1630                1635

Ser Asn Lys Ala Leu Pro Ala Pro Ile Glu Lys Thr Ile Ser Lys
    1640                1645                1650

Ala Lys Gly Gln Pro Arg Glu Pro Gln Val Tyr Thr Leu Pro Pro
1655                1660                1665

Ser Arg Asp Glu Leu Thr Lys Asn Gln Val Ser Leu Thr Cys Leu
    1670                1675                1680

Val Lys Gly Phe Tyr Pro Ser Asp Ile Ala Val Glu Trp Glu Ser
1685                1690                1695

Asn Gly Gln Pro Glu Asn Asn Tyr Lys Thr Thr Pro Pro Val Leu
    1700                1705                1710

Asp Ser Asp Gly Ser Phe Phe Leu Tyr Ser Lys Leu Thr Val Asp
1715                1720                1725

Lys Ser Arg Trp Gln Gln Gly Asn Val Phe Ser Cys Ser Val Met
    1730                1735                1740

His Glu Ala Leu His Asn His Tyr Thr Gln Lys Ser Leu Ser Leu
1745                1750                1755

Ser Pro Gly Lys
    1760

<210> SEQ ID NO 116
<211> LENGTH: 1726
<212> TYPE: PRT
<213> ORGANISM: Artificial Sequence
<220> FEATURE:
<223> OTHER INFORMATION: pSYNFVIII 271 protein sequence

<400> SEQUENCE: 116

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Gly Ala Pro Gly Ser Pro Ala Gly Ser Pro Thr
        35                  40                  45

Ser Thr Glu Glu Gly Thr Ser Glu Ser Ala Thr Pro Glu Ser Gly Pro
    50                  55                  60

Gly Ser Glu Pro Ala Thr Ser Gly Ser Glu Thr Pro Ala Ser Ser Ser
65                  70                  75                  80

Asp Leu Gly Glu Leu Pro Val Asp Ala Arg Phe Pro Pro Arg Val Pro
                85                  90                  95

Lys Ser Phe Pro Phe Asn Thr Ser Val Val Tyr Lys Lys Thr Leu Phe
            100                 105                 110
```

```
Val Glu Phe Thr Asp His Leu Phe Asn Ile Ala Lys Pro Arg Pro Pro
            115                 120                 125

Trp Met Gly Leu Leu Gly Pro Thr Ile Gln Ala Glu Val Tyr Asp Thr
130                 135                 140

Val Val Ile Thr Leu Lys Asn Met Ala Ser His Pro Val Ser Leu His
145                 150                 155                 160

Ala Val Gly Val Ser Tyr Trp Lys Ala Ser Glu Gly Ala Glu Tyr Asp
                165                 170                 175

Asp Gln Thr Ser Gln Arg Glu Lys Glu Asp Asp Lys Val Phe Pro Gly
            180                 185                 190

Gly Ser His Thr Tyr Val Trp Gln Val Leu Lys Glu Asn Gly Pro Met
        195                 200                 205

Ala Ser Asp Pro Leu Cys Leu Thr Tyr Ser Tyr Leu Ser His Val Asp
210                 215                 220

Leu Val Lys Asp Leu Asn Ser Gly Leu Ile Gly Ala Leu Leu Val Cys
225                 230                 235                 240

Arg Glu Gly Ser Leu Ala Lys Glu Lys Thr Gln Thr Leu His Lys Phe
                245                 250                 255

Ile Leu Leu Phe Ala Val Phe Asp Glu Gly Lys Ser Trp His Ser Glu
            260                 265                 270

Thr Lys Asn Ser Leu Met Gln Asp Arg Asp Ala Ala Ser Ala Arg Ala
        275                 280                 285

Trp Pro Lys Met His Thr Val Asn Gly Tyr Val Asn Arg Ser Leu Pro
    290                 295                 300

Gly Leu Ile Gly Cys His Arg Lys Ser Val Tyr Trp His Val Ile Gly
305                 310                 315                 320

Met Gly Thr Thr Pro Glu Val His Ser Ile Phe Leu Glu Gly His Thr
                325                 330                 335

Phe Leu Val Arg Asn His Arg Gln Ala Ser Leu Glu Ile Ser Pro Ile
            340                 345                 350

Thr Phe Leu Thr Ala Gln Thr Leu Leu Met Asp Leu Gly Gln Phe Leu
        355                 360                 365

Leu Phe Cys His Ile Ser Ser His Gln His Asp Gly Met Glu Ala Tyr
    370                 375                 380

Val Lys Val Asp Ser Cys Pro Glu Glu Pro Gln Leu Arg Met Lys Asn
385                 390                 395                 400

Asn Glu Glu Ala Glu Asp Tyr Asp Asp Asp Leu Thr Asp Ser Glu Met
                405                 410                 415

Asp Val Val Arg Phe Asp Asp Asn Ser Pro Ser Phe Ile Gln Ile
            420                 425                 430

Arg Ser Val Ala Lys Lys His Pro Lys Thr Trp Val His Tyr Ile Ala
        435                 440                 445

Ala Glu Glu Glu Asp Trp Asp Tyr Ala Pro Leu Val Leu Ala Pro Asp
    450                 455                 460

Asp Arg Ser Tyr Lys Ser Gln Tyr Leu Asn Asn Gly Pro Gln Arg Ile
465                 470                 475                 480

Gly Arg Lys Tyr Lys Lys Val Arg Phe Met Ala Tyr Thr Asp Glu Thr
                485                 490                 495

Phe Lys Thr Arg Glu Ala Ile Gln His Glu Ser Gly Ile Leu Gly Pro
            500                 505                 510

Leu Leu Tyr Gly Glu Val Gly Asp Thr Leu Leu Ile Ile Phe Lys Asn
        515                 520                 525

Gln Ala Ser Arg Pro Tyr Asn Ile Tyr Pro His Gly Ile Thr Asp Val
```

```
            530                 535                 540
Arg Pro Leu Tyr Ser Arg Arg Leu Pro Lys Gly Val Lys His Leu Lys
545                 550                 555                 560

Asp Phe Pro Ile Leu Pro Gly Glu Ile Phe Lys Tyr Lys Trp Thr Val
                565                 570                 575

Thr Val Glu Asp Gly Pro Thr Lys Ser Asp Pro Arg Cys Leu Thr Arg
            580                 585                 590

Tyr Tyr Ser Ser Phe Val Asn Met Glu Arg Asp Leu Ala Ser Gly Leu
            595                 600                 605

Ile Gly Pro Leu Leu Ile Cys Tyr Lys Glu Ser Val Asp Gln Arg Gly
        610                 615                 620

Asn Gln Ile Met Ser Asp Lys Arg Asn Val Ile Leu Phe Ser Val Phe
625                 630                 635                 640

Asp Glu Asn Arg Ser Trp Tyr Leu Thr Glu Asn Ile Gln Arg Phe Leu
                645                 650                 655

Pro Asn Pro Ala Gly Val Gln Leu Glu Asp Pro Glu Phe Gln Ala Ser
            660                 665                 670

Asn Ile Met His Ser Ile Asn Gly Tyr Val Phe Asp Ser Leu Gln Leu
            675                 680                 685

Ser Val Cys Leu His Glu Val Ala Tyr Trp Tyr Ile Leu Ser Ile Gly
        690                 695                 700

Ala Gln Thr Asp Phe Leu Ser Val Phe Phe Ser Gly Tyr Thr Phe Lys
705                 710                 715                 720

His Lys Met Val Tyr Glu Asp Thr Leu Thr Leu Phe Pro Phe Ser Gly
                725                 730                 735

Glu Thr Val Phe Met Ser Met Glu Asn Pro Gly Leu Trp Ile Leu Gly
            740                 745                 750

Cys His Asn Ser Asp Phe Arg Asn Arg Gly Met Thr Ala Leu Leu Lys
            755                 760                 765

Val Ser Ser Cys Asp Lys Asn Thr Gly Asp Tyr Tyr Glu Asp Ser Tyr
        770                 775                 780

Glu Asp Ile Ser Ala Tyr Leu Leu Ser Lys Asn Asn Ala Ile Glu Pro
785                 790                 795                 800

Arg Ser Phe Ser Gln Asn Pro Pro Val Leu Lys Arg His Gln Ala Glu
                805                 810                 815

Ile Thr Arg Thr Thr Leu Gln Ser Asp Gln Glu Glu Ile Asp Tyr Asp
            820                 825                 830

Asp Thr Ile Ser Val Glu Met Lys Lys Glu Asp Phe Asp Ile Tyr Asp
            835                 840                 845

Glu Asp Glu Asn Gln Ser Pro Arg Ser Phe Gln Lys Lys Thr Arg His
        850                 855                 860

Tyr Phe Ile Ala Ala Val Glu Arg Leu Trp Asp Tyr Gly Met Ser Ser
865                 870                 875                 880

Ser Pro His Val Leu Arg Asn Arg Ala Gln Ser Gly Ser Val Pro Gln
                885                 890                 895

Phe Lys Lys Val Val Phe Gln Glu Phe Thr Asp Gly Ser Phe Thr Gln
            900                 905                 910

Pro Leu Tyr Arg Gly Glu Leu Asn Glu His Leu Gly Leu Leu Gly Pro
            915                 920                 925

Tyr Ile Arg Ala Glu Val Glu Asp Asn Ile Met Val Thr Phe Arg Asn
        930                 935                 940

Gln Ala Ser Arg Pro Tyr Ser Phe Tyr Ser Ser Leu Ile Ser Tyr Glu
945                 950                 955                 960
```

-continued

```
Glu Asp Gln Arg Gln Gly Ala Glu Pro Arg Lys Asn Phe Val Lys Pro
                965                 970                 975
Asn Glu Thr Lys Thr Tyr Phe Trp Lys Val Gln His His Met Ala Pro
            980                 985                 990
Thr Lys Asp Glu Phe Asp Cys Lys Ala Trp Ala Tyr Phe Ser Asp Val
        995                 1000                1005
Asp Leu Glu Lys Asp Val His Ser Gly Leu Ile Gly Pro Leu Leu
    1010                1015                1020
Val Cys His Thr Asn Thr Leu Asn Pro Ala His Gly Arg Gln Val
    1025                1030                1035
Thr Val Gln Glu Phe Ala Leu Phe Phe Thr Ile Phe Asp Glu Thr
    1040                1045                1050
Lys Ser Trp Tyr Phe Thr Glu Asn Met Glu Arg Asn Cys Arg Ala
    1055                1060                1065
Pro Cys Asn Ile Gln Met Glu Asp Pro Thr Phe Lys Glu Asn Tyr
    1070                1075                1080
Arg Phe His Ala Ile Asn Gly Tyr Ile Met Asp Thr Leu Pro Gly
    1085                1090                1095
Leu Val Met Ala Gln Asp Gln Arg Ile Arg Trp Tyr Leu Leu Ser
    1100                1105                1110
Met Gly Ser Asn Glu Asn Ile His Ser Ile His Phe Ser Gly His
    1115                1120                1125
Val Phe Thr Val Arg Lys Lys Glu Glu Tyr Lys Met Ala Leu Tyr
    1130                1135                1140
Asn Leu Tyr Pro Gly Val Phe Glu Thr Val Glu Met Leu Pro Ser
    1145                1150                1155
Lys Ala Gly Ile Trp Arg Val Glu Cys Leu Ile Gly Glu His Leu
    1160                1165                1170
His Ala Gly Met Ser Thr Leu Phe Leu Val Tyr Ser Asn Lys Cys
    1175                1180                1185
Gln Thr Pro Leu Gly Met Ala Ser Gly His Ile Arg Asp Phe Gln
    1190                1195                1200
Ile Thr Ala Ser Gly Gln Tyr Gly Gln Trp Ala Pro Lys Leu Ala
    1205                1210                1215
Arg Leu His Tyr Ser Gly Ser Ile Asn Ala Trp Ser Thr Lys Glu
    1220                1225                1230
Pro Phe Ser Trp Ile Lys Val Asp Leu Leu Ala Pro Met Ile Ile
    1235                1240                1245
His Gly Ile Lys Thr Gln Gly Ala Arg Gln Lys Phe Ser Ser Leu
    1250                1255                1260
Tyr Ile Ser Gln Phe Ile Ile Met Tyr Ser Leu Asp Gly Lys Lys
    1265                1270                1275
Trp Gln Thr Tyr Arg Gly Asn Ser Thr Gly Thr Leu Met Val Phe
    1280                1285                1290
Phe Gly Asn Val Asp Ser Ser Gly Ile Lys His Asn Ile Phe Asn
    1295                1300                1305
Pro Pro Ile Ile Ala Arg Tyr Ile Arg Leu His Pro Thr His Tyr
    1310                1315                1320
Ser Ile Arg Ser Thr Leu Arg Met Glu Leu Met Gly Cys Asp Leu
    1325                1330                1335
Asn Ser Cys Ser Met Pro Leu Gly Met Glu Ser Lys Ala Ile Ser
    1340                1345                1350
```

-continued

Asp Ala Gln Ile Thr Ala Ser Ser Tyr Phe Thr Asn Met Phe Ala
1355                1360                1365

Thr Trp Ser Pro Ser Lys Ala Arg Leu His Leu Gln Gly Arg Ser
1370                1375                1380

Asn Ala Trp Arg Pro Gln Val Asn Asn Pro Lys Glu Trp Leu Gln
1385                1390                1395

Val Asp Phe Gln Lys Thr Met Lys Val Thr Gly Val Thr Thr Gln
1400                1405                1410

Gly Val Lys Ser Leu Leu Thr Ser Met Tyr Val Lys Glu Phe Leu
1415                1420                1425

Ile Ser Ser Ser Gln Asp Gly His Gln Trp Thr Leu Phe Phe Gln
1430                1435                1440

Asn Gly Lys Val Lys Val Phe Gln Gly Asn Gln Asp Ser Phe Thr
1445                1450                1455

Pro Val Val Asn Ser Leu Asp Pro Pro Leu Leu Thr Arg Tyr Leu
1460                1465                1470

Arg Ile His Pro Gln Ser Trp Val His Gln Ile Ala Leu Arg Met
1475                1480                1485

Glu Val Leu Gly Cys Glu Ala Gln Asp Leu Tyr Asp Lys Thr His
1490                1495                1500

Thr Cys Pro Pro Cys Pro Ala Pro Glu Leu Leu Gly Gly Pro Ser
1505                1510                1515

Val Phe Leu Phe Pro Pro Lys Pro Lys Asp Thr Leu Met Ile Ser
1520                1525                1530

Arg Thr Pro Glu Val Thr Cys Val Val Val Asp Val Ser His Glu
1535                1540                1545

Asp Pro Glu Val Lys Phe Asn Trp Tyr Val Asp Gly Val Glu Val
1550                1555                1560

His Asn Ala Lys Thr Lys Pro Arg Glu Glu Gln Tyr Asn Ser Thr
1565                1570                1575

Tyr Arg Val Val Ser Val Leu Thr Val Leu His Gln Asp Trp Leu
1580                1585                1590

Asn Gly Lys Glu Tyr Lys Cys Lys Val Ser Asn Lys Ala Leu Pro
1595                1600                1605

Ala Pro Ile Glu Lys Thr Ile Ser Lys Ala Lys Gly Gln Pro Arg
1610                1615                1620

Glu Pro Gln Val Tyr Thr Leu Pro Pro Ser Arg Asp Glu Leu Thr
1625                1630                1635

Lys Asn Gln Val Ser Leu Thr Cys Leu Val Lys Gly Phe Tyr Pro
1640                1645                1650

Ser Asp Ile Ala Val Glu Trp Glu Ser Asn Gly Gln Pro Glu Asn
1655                1660                1665

Asn Tyr Lys Thr Thr Pro Pro Val Leu Asp Ser Asp Gly Ser Phe
1670                1675                1680

Phe Leu Tyr Ser Lys Leu Thr Val Asp Lys Ser Arg Trp Gln Gln
1685                1690                1695

Gly Asn Val Phe Ser Cys Ser Val Met His Glu Ala Leu His Asn
1700                1705                1710

His Tyr Thr Gln Lys Ser Leu Ser Leu Ser Pro Gly Lys
1715                1720                1725

<210> SEQ ID NO 117
<211> LENGTH: 1901
<212> TYPE: PRT

<213> ORGANISM: Artificial Sequence
<220> FEATURE:
<223> OTHER INFORMATION: pSYN FVIII protein sequence 272

<400> SEQUENCE: 117

| | | | | | | | | | | | | | | |
|---|---|---|---|---|---|---|---|---|---|---|---|---|---|---|
| Met | Gln | Ile | Glu | Leu | Ser | Thr | Cys | Phe | Phe | Leu | Cys | Leu | Leu | Arg | Phe |
| 1 | | | | 5 | | | | | 10 | | | | | 15 | |
| Cys | Phe | Ser | Ala | Thr | Arg | Arg | Tyr | Tyr | Leu | Gly | Ala | Val | Glu | Leu | Ser |
| | | | 20 | | | | | 25 | | | | | 30 | | |
| Trp | Asp | Tyr | Met | Gln | Gly | Ala | Pro | Thr | Ser | Glu | Ser | Ala | Thr | Pro | Glu |
| | | | 35 | | | | | 40 | | | | | 45 | | |
| Ser | Gly | Pro | Gly | Ser | Glu | Pro | Ala | Thr | Ser | Gly | Ser | Glu | Thr | Pro | Gly |
| | 50 | | | | | 55 | | | | | 60 | | | | |
| Thr | Ser | Glu | Ser | Ala | Thr | Pro | Glu | Ser | Gly | Pro | Gly | Ser | Glu | Pro | Ala |
| 65 | | | | | 70 | | | | | 75 | | | | | 80 |
| Thr | Ser | Gly | Ser | Glu | Thr | Pro | Gly | Thr | Ser | Glu | Ser | Ala | Thr | Pro | Glu |
| | | | | 85 | | | | | 90 | | | | | 95 | |
| Ser | Gly | Pro | Gly | Thr | Ser | Thr | Glu | Pro | Ser | Glu | Gly | Ser | Ala | Pro | Gly |
| | | | 100 | | | | | 105 | | | | | 110 | | |
| Ser | Pro | Ala | Gly | Ser | Pro | Thr | Ser | Thr | Glu | Glu | Gly | Thr | Ser | Glu | Ser |
| | | 115 | | | | | 120 | | | | | 125 | | | |
| Ala | Thr | Pro | Glu | Ser | Gly | Pro | Gly | Ser | Glu | Pro | Ala | Thr | Ser | Gly | Ser |
| | 130 | | | | | 135 | | | | | 140 | | | | |
| Glu | Thr | Pro | Gly | Thr | Ser | Glu | Ser | Ala | Thr | Pro | Glu | Ser | Gly | Pro | Gly |
| 145 | | | | | 150 | | | | | 155 | | | | | 160 |
| Ser | Pro | Ala | Gly | Ser | Pro | Thr | Ser | Thr | Glu | Glu | Gly | Ser | Pro | Ala | Gly |
| | | | | 165 | | | | | 170 | | | | | 175 | |
| Ser | Pro | Thr | Ser | Thr | Glu | Glu | Gly | Ala | Ser | Ser | Ser | Asp | Leu | Gly | Glu |
| | | | 180 | | | | | 185 | | | | | 190 | | |
| Leu | Pro | Val | Asp | Ala | Arg | Phe | Pro | Pro | Arg | Val | Pro | Lys | Ser | Phe | Pro |
| | | 195 | | | | | 200 | | | | | 205 | | | |
| Phe | Asn | Thr | Ser | Val | Val | Tyr | Lys | Lys | Thr | Leu | Phe | Val | Glu | Phe | Thr |
| | 210 | | | | | 215 | | | | | 220 | | | | |
| Asp | His | Leu | Phe | Asn | Ile | Ala | Lys | Pro | Arg | Pro | Pro | Trp | Met | Gly | Leu |
| 225 | | | | | 230 | | | | | 235 | | | | | 240 |
| Leu | Gly | Pro | Thr | Ile | Gln | Ala | Glu | Val | Tyr | Asp | Thr | Val | Val | Ile | Thr |
| | | | | 245 | | | | | 250 | | | | | 255 | |
| Leu | Lys | Asn | Met | Ala | Ser | His | Pro | Val | Ser | Leu | His | Ala | Val | Gly | Val |
| | | | 260 | | | | | 265 | | | | | 270 | | |
| Ser | Tyr | Trp | Lys | Ala | Ser | Glu | Gly | Ala | Glu | Tyr | Asp | Asp | Gln | Thr | Ser |
| | | 275 | | | | | 280 | | | | | 285 | | | |
| Gln | Arg | Glu | Lys | Glu | Asp | Asp | Lys | Val | Phe | Pro | Gly | Gly | Ser | His | Thr |
| | 290 | | | | | 295 | | | | | 300 | | | | |
| Tyr | Val | Trp | Gln | Val | Leu | Lys | Glu | Asn | Gly | Pro | Met | Ala | Ser | Asp | Pro |
| 305 | | | | | 310 | | | | | 315 | | | | | 320 |
| Leu | Cys | Leu | Thr | Tyr | Ser | Tyr | Leu | Ser | His | Val | Asp | Leu | Val | Lys | Asp |
| | | | | 325 | | | | | 330 | | | | | 335 | |
| Leu | Asn | Ser | Gly | Leu | Ile | Gly | Ala | Leu | Leu | Val | Cys | Arg | Glu | Gly | Ser |
| | | | 340 | | | | | 345 | | | | | 350 | | |
| Leu | Ala | Lys | Glu | Lys | Thr | Gln | Thr | Leu | His | Lys | Phe | Ile | Leu | Leu | Phe |
| | | 355 | | | | | 360 | | | | | 365 | | | |
| Ala | Val | Phe | Asp | Glu | Gly | Lys | Ser | Trp | His | Ser | Glu | Thr | Lys | Asn | Ser |
| | 370 | | | | | 375 | | | | | 380 | | | | |
| Leu | Met | Gln | Asp | Arg | Asp | Ala | Ala | Ser | Ala | Arg | Ala | Trp | Pro | Lys | Met |

```
385                 390                 395                 400
His Thr Val Asn Gly Tyr Val Asn Arg Ser Leu Pro Gly Leu Ile Gly
                405                 410                 415
Cys His Arg Lys Ser Val Tyr Trp His Val Ile Gly Met Gly Thr Thr
                420                 425                 430
Pro Glu Val His Ser Ile Phe Leu Glu Gly His Thr Phe Leu Val Arg
                435                 440                 445
Asn His Arg Gln Ala Ser Leu Glu Ile Ser Pro Ile Thr Phe Leu Thr
                450                 455                 460
Ala Gln Thr Leu Leu Met Asp Leu Gly Gln Phe Leu Leu Phe Cys His
465                 470                 475                 480
Ile Ser Ser His Gln His Asp Gly Met Glu Ala Tyr Val Lys Val Asp
                485                 490                 495
Ser Cys Pro Glu Glu Pro Gln Leu Arg Met Lys Asn Asn Glu Glu Ala
                500                 505                 510
Glu Asp Tyr Asp Asp Asp Leu Thr Asp Ser Glu Met Asp Val Val Arg
                515                 520                 525
Phe Asp Asp Asp Asn Ser Pro Ser Phe Ile Gln Ile Arg Ser Val Ala
530                 535                 540
Lys Lys His Pro Lys Thr Trp Val His Tyr Ile Ala Ala Glu Glu Glu
545                 550                 555                 560
Asp Trp Asp Tyr Ala Pro Leu Val Leu Ala Pro Asp Asp Arg Ser Tyr
                565                 570                 575
Lys Ser Gln Tyr Leu Asn Asn Gly Pro Gln Arg Ile Gly Arg Lys Tyr
                580                 585                 590
Lys Lys Val Arg Phe Met Ala Tyr Thr Asp Glu Thr Phe Lys Thr Arg
                595                 600                 605
Glu Ala Ile Gln His Glu Ser Gly Ile Leu Gly Pro Leu Leu Tyr Gly
                610                 615                 620
Glu Val Gly Asp Thr Leu Leu Ile Ile Phe Lys Asn Gln Ala Ser Arg
625                 630                 635                 640
Pro Tyr Asn Ile Tyr Pro His Gly Ile Thr Asp Val Arg Pro Leu Tyr
                645                 650                 655
Ser Arg Arg Leu Pro Lys Gly Val Lys His Leu Lys Asp Phe Pro Ile
                660                 665                 670
Leu Pro Gly Glu Ile Phe Lys Tyr Lys Trp Thr Val Thr Val Glu Asp
                675                 680                 685
Gly Pro Thr Lys Ser Asp Pro Arg Cys Leu Thr Arg Tyr Tyr Ser Ser
                690                 695                 700
Phe Val Asn Met Glu Arg Asp Leu Ala Ser Gly Leu Ile Gly Pro Leu
705                 710                 715                 720
Leu Ile Cys Tyr Lys Glu Ser Val Asp Gln Arg Gly Asn Gln Ile Met
                725                 730                 735
Ser Asp Lys Arg Asn Val Ile Leu Phe Ser Val Phe Asp Glu Asn Arg
                740                 745                 750
Ser Trp Tyr Leu Thr Glu Asn Ile Gln Arg Phe Leu Pro Asn Pro Ala
                755                 760                 765
Gly Val Gln Leu Glu Asp Pro Glu Phe Gln Ala Ser Asn Ile Met His
                770                 775                 780
Ser Ile Asn Gly Tyr Val Phe Asp Ser Leu Gln Leu Ser Val Cys Leu
785                 790                 795                 800
His Glu Val Ala Tyr Trp Tyr Ile Leu Ser Ile Gly Ala Gln Thr Asp
                805                 810                 815
```

```
Phe Leu Ser Val Phe Ser Gly Tyr Thr Phe Lys His Lys Met Val
            820                 825                 830

Tyr Glu Asp Thr Leu Thr Leu Phe Pro Phe Ser Gly Glu Thr Val Phe
        835                 840                 845

Met Ser Met Glu Asn Pro Gly Leu Trp Ile Leu Gly Cys His Asn Ser
    850                 855                 860

Asp Phe Arg Asn Arg Gly Met Thr Ala Leu Leu Lys Val Ser Ser Cys
865                 870                 875                 880

Asp Lys Asn Thr Gly Asp Tyr Tyr Glu Asp Ser Tyr Glu Asp Ile Ser
            885                 890                 895

Ala Tyr Leu Leu Ser Lys Asn Asn Ala Ile Glu Pro Arg Ser Phe Ser
            900                 905                 910

Gln Asn Gly Ala Pro Gly Thr Ser Glu Ser Ala Thr Pro Glu Ser Gly
            915                 920                 925

Pro Gly Ser Glu Pro Ala Thr Ser Gly Ser Glu Thr Pro Gly Thr Ser
        930                 935                 940

Glu Ser Ala Thr Pro Glu Ser Gly Pro Gly Ser Glu Pro Ala Thr Ser
945                 950                 955                 960

Gly Ser Glu Thr Pro Gly Thr Ser Glu Ser Ala Thr Pro Glu Ser Gly
            965                 970                 975

Pro Gly Thr Ser Thr Glu Pro Ser Glu Gly Ser Ala Pro Gly Ser Pro
            980                 985                 990

Ala Gly Ser Pro Thr Ser Thr Glu Glu Gly Thr Ser Glu Ser Ala Thr
            995                 1000                1005

Pro Glu Ser Gly Pro Gly Ser Glu Pro Ala Thr Ser Gly Ser Glu
    1010                1015                1020

Thr Pro Gly Thr Ser Glu Ser Ala Thr Pro Glu Ser Gly Pro Gly
    1025                1030                1035

Ser Pro Ala Gly Ser Pro Thr Ser Thr Glu Glu Gly Ser Pro Ala
    1040                1045                1050

Gly Ser Pro Thr Ser Thr Glu Glu Gly Thr Ser Thr Glu Pro Ser
    1055                1060                1065

Glu Gly Ser Ala Pro Gly Thr Ser Glu Ser Ala Thr Pro Glu Ser
    1070                1075                1080

Gly Pro Gly Thr Ser Glu Ser Ala Thr Pro Glu Ser Gly Pro Gly
    1085                1090                1095

Thr Ser Glu Ser Ala Thr Pro Glu Ser Gly Pro Gly Ser Glu Pro
    1100                1105                1110

Ala Thr Ser Gly Ser Glu Thr Pro Gly Ser Glu Pro Ala Thr Ser
    1115                1120                1125

Gly Ser Glu Thr Pro Gly Ser Pro Ala Gly Ser Pro Thr Ser Thr
    1130                1135                1140

Glu Glu Gly Thr Ser Thr Glu Pro Ser Glu Gly Ser Ala Pro Gly
    1145                1150                1155

Thr Ser Thr Glu Pro Ser Glu Gly Ser Ala Pro Gly Ser Glu Pro
    1160                1165                1170

Ala Thr Ser Gly Ser Glu Thr Pro Gly Thr Ser Glu Ser Ala Thr
    1175                1180                1185

Pro Glu Ser Gly Pro Gly Thr Ser Thr Glu Pro Ser Glu Gly Ser
    1190                1195                1200

Ala Pro Ala Ser Ser Pro Pro Val Leu Lys Arg His Gln Ala Glu
    1205                1210                1215
```

```
Ile Thr Arg Thr Thr Leu Gln Ser Asp Gln Glu Glu Ile Asp Tyr
1220                1225                1230

Asp Asp Thr Ile Ser Val Glu Met Lys Lys Glu Asp Phe Asp Ile
1235                1240                1245

Tyr Asp Glu Asp Glu Asn Gln Ser Pro Arg Ser Phe Gln Lys Lys
1250                1255                1260

Thr Arg His Tyr Phe Ile Ala Ala Val Glu Arg Leu Trp Asp Tyr
1265                1270                1275

Gly Met Ser Ser Ser Pro His Val Leu Arg Asn Arg Ala Gln Ser
1280                1285                1290

Gly Ser Val Pro Gln Phe Lys Lys Val Val Phe Gln Glu Phe Thr
1295                1300                1305

Asp Gly Ser Phe Thr Gln Pro Leu Tyr Arg Gly Glu Leu Asn Glu
1310                1315                1320

His Leu Gly Leu Leu Gly Pro Tyr Ile Arg Ala Glu Val Glu Asp
1325                1330                1335

Asn Ile Met Val Thr Phe Arg Asn Gln Ala Ser Arg Pro Tyr Ser
1340                1345                1350

Phe Tyr Ser Ser Leu Ile Ser Tyr Glu Glu Asp Gln Arg Gln Gly
1355                1360                1365

Ala Glu Pro Arg Lys Asn Phe Val Lys Pro Asn Glu Thr Lys Thr
1370                1375                1380

Tyr Phe Trp Lys Val Gln His His Met Ala Pro Thr Lys Asp Glu
1385                1390                1395

Phe Asp Cys Lys Ala Trp Ala Tyr Phe Ser Asp Val Asp Leu Glu
1400                1405                1410

Lys Asp Val His Ser Gly Leu Ile Gly Pro Leu Leu Val Cys His
1415                1420                1425

Thr Asn Thr Leu Asn Pro Ala His Gly Arg Gln Val Thr Val Gln
1430                1435                1440

Glu Phe Ala Leu Phe Phe Thr Ile Phe Asp Glu Thr Lys Ser Trp
1445                1450                1455

Tyr Phe Thr Glu Asn Met Glu Arg Asn Cys Arg Ala Pro Cys Asn
1460                1465                1470

Ile Gln Met Glu Asp Pro Thr Phe Lys Glu Asn Tyr Arg Phe His
1475                1480                1485

Ala Ile Asn Gly Tyr Ile Met Asp Thr Leu Pro Gly Leu Val Met
1490                1495                1500

Ala Gln Asp Gln Arg Ile Arg Trp Tyr Leu Leu Ser Met Gly Ser
1505                1510                1515

Asn Glu Asn Ile His Ser Ile His Phe Ser Gly His Val Phe Thr
1520                1525                1530

Val Arg Lys Lys Glu Glu Tyr Lys Met Ala Leu Tyr Asn Leu Tyr
1535                1540                1545

Pro Gly Val Phe Glu Thr Val Glu Met Leu Pro Ser Lys Ala Gly
1550                1555                1560

Ile Trp Arg Val Glu Cys Leu Ile Gly Glu His Leu His Ala Gly
1565                1570                1575

Met Ser Thr Leu Phe Leu Val Tyr Ser Asn Lys Cys Gln Thr Pro
1580                1585                1590

Leu Gly Met Ala Ser Gly His Ile Arg Asp Phe Gln Ile Thr Ala
1595                1600                1605

Ser Gly Gln Tyr Gly Gln Trp Ala Pro Lys Leu Ala Arg Leu His
```

```
            1610                1615                1620

Tyr Ser Gly Ser Ile Asn Ala Trp Ser Thr Lys Glu Pro Phe Ser
        1625                1630                1635

Trp Ile Lys Val Asp Leu Leu Ala Pro Met Ile Ile His Gly Ile
    1640                1645                1650

Lys Thr Gln Gly Ala Arg Gln Lys Phe Ser Ser Leu Tyr Ile Ser
    1655                1660                1665

Gln Phe Ile Ile Met Tyr Ser Leu Asp Gly Lys Lys Trp Gln Thr
    1670                1675                1680

Tyr Arg Gly Asn Ser Thr Gly Thr Leu Met Val Phe Phe Gly Asn
    1685                1690                1695

Val Asp Ser Ser Gly Ile Lys His Asn Ile Phe Asn Pro Pro Ile
    1700                1705                1710

Ile Ala Arg Tyr Ile Arg Leu His Pro Thr His Tyr Ser Ile Arg
    1715                1720                1725

Ser Thr Leu Arg Met Glu Leu Met Gly Cys Asp Leu Asn Ser Cys
    1730                1735                1740

Ser Met Pro Leu Gly Met Glu Ser Lys Ala Ile Ser Asp Ala Gln
    1745                1750                1755

Ile Thr Ala Ser Ser Tyr Phe Thr Asn Met Phe Ala Thr Trp Ser
    1760                1765                1770

Pro Ser Lys Ala Arg Leu His Leu Gln Gly Arg Ser Asn Ala Trp
    1775                1780                1785

Arg Pro Gln Val Asn Asn Pro Lys Glu Trp Leu Gln Val Asp Phe
    1790                1795                1800

Gln Lys Thr Met Lys Val Thr Gly Val Thr Thr Gln Gly Val Lys
    1805                1810                1815

Ser Leu Leu Thr Ser Met Tyr Val Lys Glu Phe Leu Ile Ser Ser
    1820                1825                1830

Ser Gln Asp Gly His Gln Trp Thr Leu Phe Phe Gln Asn Gly Lys
    1835                1840                1845

Val Lys Val Phe Gln Gly Asn Gln Asp Ser Phe Thr Pro Val Val
    1850                1855                1860

Asn Ser Leu Asp Pro Pro Leu Leu Thr Arg Tyr Leu Arg Ile His
    1865                1870                1875

Pro Gln Ser Trp Val His Gln Ile Ala Leu Arg Met Glu Val Leu
    1880                1885                1890

Gly Cys Glu Ala Gln Asp Leu Tyr
    1895                1900

<210> SEQ ID NO 118
<211> LENGTH: 1515
<212> TYPE: PRT
<213> ORGANISM: Artificial Sequence
<220> FEATURE:
<223> OTHER INFORMATION: pSYN VWF 031 protein sequence

<400> SEQUENCE: 118

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
```

```
            50                  55                  60
Cys Gln Lys Arg Ser Phe Ser Ile Ile Gly Asp Phe Gln Asn Gly Lys
 65                  70                  75                  80

Arg Val Ser Leu Ser Val Tyr Leu Gly Glu Phe Asp Ile His Leu
                     85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
                115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
                195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
                275                 280                 285

Ser Ala Cys Ser Pro Val Cys Pro Ala Gly Met Glu Tyr Arg Gln Cys
                290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
                355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
                450                 455                 460

Ala Met Asp Gly Gln Asp Ile Gln Leu Pro Leu Leu Lys Gly Asp Leu
465                 470                 475                 480
```

```
Arg Ile Gln His Thr Val Thr Ala Ser Val Arg Leu Ser Tyr Gly Glu
            485                 490                 495
Asp Leu Gln Met Asp Trp Asp Gly Arg Gly Arg Leu Leu Val Lys Leu
            500                 505                 510
Ser Pro Val Tyr Ala Gly Lys Thr Cys Gly Leu Cys Gly Asn Tyr Asn
            515                 520                 525
Gly Asn Gln Gly Asp Asp Phe Leu Thr Pro Ser Gly Leu Ala Glu Pro
        530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
            565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
            595                 600                 605
Arg Tyr Asp Val Cys Ser Cys Ser Asp Gly Arg Glu Cys Leu Cys Gly
        610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
            645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
            675                 680                 685
Cys Pro Pro Gly Leu Tyr Met Asp Glu Arg Gly Asp Cys Val Pro Lys
            690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
            725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg Ser Leu Ser Cys Arg
            755                 760                 765
Pro Pro Met Val Lys Leu Val Cys Pro Ala Asp Asn Leu Arg Ala Glu
            770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
            805                 810                 815
His Glu Asn Arg Cys Val Ala Leu Glu Arg Cys Pro Cys Phe His Gln
            820                 825                 830
Gly Lys Glu Tyr Ala Pro Gly Glu Thr Val Lys Ile Gly Cys Asn Thr
            835                 840                 845
Cys Val Cys Arg Asp Arg Lys Trp Asn Cys Thr Asp His Val Cys Asp
            850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
            885                 890                 895
```

```
Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
        980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Ala Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Ala Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Ile Ser Gly Gly Gly Gly Ser Gly
    1235                1240                1245

Gly Gly Gly Ser Gly Gly Gly Gly Ser Gly Gly Gly Gly Ser Gly
    1250                1255                1260

Gly Gly Gly Ser Gly Gly Gly Gly Ser Leu Val Pro Arg Gly Ser
    1265                1270                1275

Gly Gly Gly Gly Ser Gly Gly Gly Gly Ser Asp Lys Thr His Thr
    1280                1285                1290

Cys Pro Pro Cys Pro Ala Pro Glu Leu Leu Gly Gly Pro Ser Val
```

```
                1295                1300                1305

Phe Leu Phe Pro Pro Lys Pro Lys Asp Thr Leu Met Ile Ser Arg
        1310                1315                1320

Thr Pro Glu Val Thr Cys Val Val Asp Val Ser His Glu Asp
    1325                1330                1335

Pro Glu Val Lys Phe Asn Trp Tyr Val Asp Gly Val Glu Val His
        1340                1345                1350

Asn Ala Lys Thr Lys Pro Arg Glu Glu Gln Tyr Asn Ser Thr Tyr
        1355                1360                1365

Arg Val Val Ser Val Leu Thr Val Leu His Gln Asp Trp Leu Asn
        1370                1375                1380

Gly Lys Glu Tyr Lys Cys Lys Val Ser Asn Lys Ala Leu Pro Ala
        1385                1390                1395

Pro Ile Glu Lys Thr Ile Ser Lys Ala Lys Gly Gln Pro Arg Glu
        1400                1405                1410

Pro Gln Val Tyr Thr Leu Pro Pro Ser Arg Asp Glu Leu Thr Lys
        1415                1420                1425

Asn Gln Val Ser Leu Thr Cys Leu Val Lys Gly Phe Tyr Pro Ser
        1430                1435                1440

Asp Ile Ala Val Glu Trp Glu Ser Asn Gly Gln Pro Glu Asn Asn
        1445                1450                1455

Tyr Lys Thr Thr Pro Pro Val Leu Asp Ser Asp Gly Ser Phe Phe
        1460                1465                1470

Leu Tyr Ser Lys Leu Thr Val Asp Lys Ser Arg Trp Gln Gln Gly
        1475                1480                1485

Asn Val Phe Ser Cys Ser Val Met His Glu Ala Leu His Asn His
        1490                1495                1500

Tyr Thr Gln Lys Ser Leu Ser Leu Ser Pro Gly Lys
        1505                1510                1515

<210> SEQ ID NO 119
<211> LENGTH: 1778
<212> TYPE: PRT
<213> ORGANISM: Artificial Sequence
<220> FEATURE:
<223> OTHER INFORMATION: pSYN VWF 034 protein sequence

<400> SEQUENCE: 119

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
```

```
            130                 135                 140
Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Ser Ser
                195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
            370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
                515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560
```

-continued

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
        610                 615                 620

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
        900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

```
His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Ala Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Ala Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Ile Ser Gly Thr Ser Glu Ser Ala
    1235                1240                1245

Thr Pro Glu Ser Gly Pro Gly Ser Glu Pro Ala Thr Ser Gly Ser
    1250                1255                1260

Glu Thr Pro Gly Thr Ser Glu Ser Ala Thr Pro Glu Ser Gly Pro
    1265                1270                1275

Gly Ser Glu Pro Ala Thr Ser Gly Ser Glu Thr Pro Gly Thr Ser
    1280                1285                1290

Glu Ser Ala Thr Pro Glu Ser Gly Pro Gly Thr Ser Thr Glu Pro
    1295                1300                1305

Ser Glu Gly Ser Ala Pro Gly Ser Pro Ala Gly Ser Pro Thr Ser
    1310                1315                1320

Thr Glu Glu Gly Thr Ser Glu Ser Ala Thr Pro Glu Ser Gly Pro
    1325                1330                1335

Gly Ser Glu Pro Ala Thr Ser Gly Ser Glu Thr Pro Gly Thr Ser
    1340                1345                1350

Glu Ser Ala Thr Pro Glu Ser Gly Pro Gly Ser Pro Ala Gly Ser
    1355                1360                1365

Pro Thr Ser Thr Glu Glu Gly Ser Pro Ala Gly Ser Pro Thr Ser
```

|   |   |   | 1370 |   |   |   |   | 1375 |   |   |   |   | 1380 |   |   |
|---|---|---|------|---|---|---|---|------|---|---|---|---|------|---|---|

Thr Glu Glu Gly Thr Ser Thr Glu Pro Ser Gly Ser Ala Pro
1385                     1390                1395

Gly Thr Ser Glu Ser Ala Thr Pro Glu Ser Gly Pro Gly Thr Ser
1400                    1405                1410

Glu Ser Ala Thr Pro Glu Ser Gly Pro Gly Thr Ser Glu Ser Ala
1415                    1420                1425

Thr Pro Glu Ser Gly Pro Gly Ser Glu Pro Ala Thr Ser Gly Ser
1430                    1435                1440

Glu Thr Pro Gly Ser Glu Pro Ala Thr Ser Gly Ser Glu Thr Pro
1445                    1450                1455

Gly Ser Pro Ala Gly Ser Pro Thr Ser Thr Glu Glu Gly Thr Ser
1460                    1465                1470

Thr Glu Pro Ser Glu Gly Ser Ala Pro Gly Thr Ser Thr Glu Pro
1475                    1480                1485

Ser Glu Gly Ser Ala Pro Gly Ser Glu Pro Ala Thr Ser Gly Ser
1490                    1495                1500

Glu Thr Pro Gly Thr Ser Glu Ser Ala Thr Pro Glu Ser Gly Pro
1505                    1510                1515

Gly Thr Ser Thr Glu Pro Ser Glu Gly Ser Ala Pro Asp Ile Gly
1520                    1525                1530

Gly Gly Gly Gly Ser Gly Gly Gly Ser Leu Val Pro Arg Gly
1535                    1540                1545

Ser Gly Gly Asp Lys Thr His Thr Cys Pro Pro Cys Pro Ala Pro
1550                    1555                1560

Glu Leu Leu Gly Gly Pro Ser Val Phe Leu Phe Pro Pro Lys Pro
1565                    1570                1575

Lys Asp Thr Leu Met Ile Ser Arg Thr Pro Glu Val Thr Cys Val
1580                    1585                1590

Val Val Asp Val Ser His Glu Asp Pro Glu Val Lys Phe Asn Trp
1595                    1600                1605

Tyr Val Asp Gly Val Glu Val His Asn Ala Lys Thr Lys Pro Arg
1610                    1615                1620

Glu Glu Gln Tyr Asn Ser Thr Tyr Arg Val Val Ser Val Leu Thr
1625                    1630                1635

Val Leu His Gln Asp Trp Leu Asn Gly Lys Glu Tyr Lys Cys Lys
1640                    1645                1650

Val Ser Asn Lys Ala Leu Pro Ala Pro Ile Glu Lys Thr Ile Ser
1655                    1660                1665

Lys Ala Lys Gly Gln Pro Arg Glu Pro Gln Val Tyr Thr Leu Pro
1670                    1675                1680

Pro Ser Arg Asp Glu Leu Thr Lys Asn Gln Val Ser Leu Thr Cys
1685                    1690                1695

Leu Val Lys Gly Phe Tyr Pro Ser Asp Ile Ala Val Glu Trp Glu
1700                    1705                1710

Ser Asn Gly Gln Pro Glu Asn Asn Tyr Lys Thr Thr Pro Pro Val
1715                    1720                1725

Leu Asp Ser Asp Gly Ser Phe Phe Leu Tyr Ser Lys Leu Thr Val
1730                    1735                1740

Asp Lys Ser Arg Trp Gln Gln Gly Asn Val Phe Ser Cys Ser Val
1745                    1750                1755

Met His Glu Ala Leu His Asn His Tyr Thr Gln Lys Ser Leu Ser
1760                    1765                1770

```
Leu Ser  Pro Gly Lys
    1775

<210> SEQ ID NO 120
<211> LENGTH: 1565
<212> TYPE: PRT
<213> ORGANISM: Artificial Sequence
<220> FEATURE:
<223> OTHER INFORMATION: pSYN VWF 036   protein sequence

<400> SEQUENCE: 120

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350
```

```
Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
                450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
                515                 520                 525

Gly Asn Gln Gly Asp Asp Phe Leu Thr Pro Ser Gly Leu Ala Glu Pro
                530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
                610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
                675                 680                 685

Cys Pro Pro Gly Leu Tyr Met Asp Glu Arg Gly Asp Cys Val Pro Lys
                690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765
```

```
Pro Pro Met Val Lys Leu Val Cys Pro Ala Asp Asn Leu Arg Ala Glu
770             775                 780

Gly Leu Glu Cys Thr Lys Thr Cys Gln Asn Tyr Asp Leu Glu Cys Met
785             790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
                915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
                995                 1000                1005

Ser Ser  Asn Leu Gln Val  Glu Asp Pro Val Asp  Phe Gly Asn
1010                1015                1020

Ser Trp  Lys Val Ser Ser  Gln Cys Ala Asp Thr Arg  Lys Val Pro
1025                1030                1035

Leu Asp  Ser Ser Pro Ala Thr  Cys His Asn Asn Ile  Met Lys Gln
1040                1045                1050

Thr Met  Val Asp Ser Ser Cys  Arg Ile Leu Thr Ser  Asp Val Phe
1055                1060                1065

Gln Asp  Cys Asn Lys Leu Val  Asp Pro Glu Pro Tyr  Leu Asp Val
1070                1075                1080

Cys Ile  Tyr Asp Thr Cys Ser  Cys Glu Ser Ile Gly  Asp Cys Ala
1085                1090                1095

Ala Phe  Cys Asp Thr Ile Ala  Ala Tyr Ala His Val  Cys Ala Gln
1100                1105                1110

His Gly  Lys Val Val Thr Trp  Arg Thr Ala Thr Leu  Cys Pro Gln
1115                1120                1125

Ser Cys  Glu Glu Arg Asn Leu  Arg Glu Asn Gly Tyr  Glu Ala Glu
1130                1135                1140

Trp Arg  Tyr Asn Ser Cys Ala  Pro Ala Cys Gln Val  Thr Cys Gln
1145                1150                1155

His Pro  Glu Pro Leu Ala Cys  Pro Val Gln Cys Val  Glu Gly Cys
1160                1165                1170

His Ala  His Cys Pro Pro Gly  Lys Ile Leu Asp Glu  Leu Leu Gln
```

```
              1175                1180                1185
Thr Cys Val Asp Pro Glu Asp Cys Pro Val Cys Glu Val Ala Gly
              1190                1195                1200

Arg Arg Phe Ala Ser Gly Lys Lys Val Thr Leu Asn Pro Ser Asp
              1205                1210                1215

Pro Glu His Cys Gln Ile Cys His Cys Asp Val Val Asn Leu Thr
              1220                1225                1230

Cys Glu Ala Cys Gln Glu Pro Ile Ser Gly Gly Gly Ser Gly
              1235                1240                1245

Gly Gly Gly Ser Gly Gly Gly Ser Gly Gly Gly Ser Gly
              1250                1255                1260

Gly Gly Gly Ser Gly Gly Gly Ser Gly Gly Gly Ser Gly
              1265                1270                1275

Gly Gly Gly Ser Gly Gly Gly Ser Gly Gly Gly Ser Gly
              1280                1285                1290

Gly Gly Gly Ser Gly Gly Gly Ser Gly Gly Gly Ser Gly
              1295                1300                1305

Gly Gly Gly Ser Gly Gly Gly Ser Gly Gly Gly Ser Leu
              1310                1315                1320

Val Pro Arg Gly Ser Gly Gly Gly Ser Gly Gly Gly Ser
              1325                1330                1335

Asp Lys Thr His Thr Cys Pro Pro Cys Pro Ala Pro Glu Leu Leu
              1340                1345                1350

Gly Gly Pro Ser Val Phe Leu Phe Pro Pro Lys Pro Lys Asp Thr
              1355                1360                1365

Leu Met Ile Ser Arg Thr Pro Glu Val Thr Cys Val Val Val Asp
              1370                1375                1380

Val Ser His Glu Asp Pro Glu Val Lys Phe Asn Trp Tyr Val Asp
              1385                1390                1395

Gly Val Glu Val His Asn Ala Lys Thr Lys Pro Arg Glu Glu Gln
              1400                1405                1410

Tyr Asn Ser Thr Tyr Arg Val Val Ser Val Leu Thr Val Leu His
              1415                1420                1425

Gln Asp Trp Leu Asn Gly Lys Glu Tyr Lys Cys Lys Val Ser Asn
              1430                1435                1440

Lys Ala Leu Pro Ala Pro Ile Glu Lys Thr Ile Ser Lys Ala Lys
              1445                1450                1455

Gly Gln Pro Arg Glu Pro Gln Val Tyr Thr Leu Pro Pro Ser Arg
              1460                1465                1470

Asp Glu Leu Thr Lys Asn Gln Val Ser Leu Thr Cys Leu Val Lys
              1475                1480                1485

Gly Phe Tyr Pro Ser Asp Ile Ala Val Glu Trp Glu Ser Asn Gly
              1490                1495                1500

Gln Pro Glu Asn Asn Tyr Lys Thr Thr Pro Pro Val Leu Asp Ser
              1505                1510                1515

Asp Gly Ser Phe Phe Leu Tyr Ser Lys Leu Thr Val Asp Lys Ser
              1520                1525                1530

Arg Trp Gln Gln Gly Asn Val Phe Ser Cys Ser Val Met His Glu
              1535                1540                1545

Ala Leu His Asn His Tyr Thr Gln Lys Ser Leu Ser Leu Ser Pro
              1550                1555                1560

Gly Lys
     1565
```

<210> SEQ ID NO 121
<211> LENGTH: 247
<212> TYPE: PRT
<213> ORGANISM: Artificial Sequence
<220> FEATURE:
<223> OTHER INFORMATION: pSYN Fc-015  protein sequence

<400> SEQUENCE: 121

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 122
<211> LENGTH: 33
<212> TYPE: PRT
<213> ORGANISM: Artificial Sequence
<220> FEATURE:
<223> OTHER INFORMATION: polypeptide

<400> SEQUENCE: 122

```
Gly Gly Gly Gly Ser Gly Gly Gly Ser Gly Gly Gly Ser Gly
1               5                   10                  15

Gly Gly Gly Ser Gly Gly Gly Gly Ser Leu Val Pro Arg Gly Ser Gly
            20                  25                  30

Gly
```

<210> SEQ ID NO 123

```
<211> LENGTH: 1240
<212> TYPE: PRT
<213> ORGANISM: Artificial Sequence
<220> FEATURE:
<223> OTHER INFORMATION: VWF-D1D2D'D3

<400> SEQUENCE: 123
```

| | | | | | | | | | | | | | | | |
|---|---|---|---|---|---|---|---|---|---|---|---|---|---|---|---|
| Met | Ile | Pro | Ala | Arg | Phe | Ala | Gly | Val | Leu | Ala | Leu | Ala | Leu | Ile |
| 1 | | | | 5 | | | | | 10 | | | | | 15 |
| Leu | Pro | Gly | Thr | Leu | Cys | Ala | Glu | Gly | Thr | Arg | Gly | Arg | Ser | Ser | Thr |
| | | | 20 | | | | | 25 | | | | | 30 | | |
| Ala | Arg | Cys | Ser | Leu | Phe | Gly | Ser | Asp | Phe | Val | Asn | Thr | Phe | Asp | Gly |
| | | 35 | | | | | 40 | | | | | 45 | | | |
| Ser | Met | Tyr | Ser | Phe | Ala | Gly | Tyr | Cys | Ser | Tyr | Leu | Leu | Ala | Gly | Gly |
| | 50 | | | | | 55 | | | | | 60 | | | | |
| Cys | Gln | Lys | Arg | Ser | Phe | Ser | Ile | Ile | Gly | Asp | Phe | Gln | Asn | Gly | Lys |
| 65 | | | | | 70 | | | | | 75 | | | | | 80 |
| Arg | Val | Ser | Leu | Ser | Val | Tyr | Leu | Gly | Glu | Phe | Phe | Asp | Ile | His | Leu |
| | | | | 85 | | | | | 90 | | | | | 95 | |
| Phe | Val | Asn | Gly | Thr | Val | Thr | Gln | Gly | Asp | Gln | Arg | Val | Ser | Met | Pro |
| | | | 100 | | | | | 105 | | | | | 110 | | |
| Tyr | Ala | Ser | Lys | Gly | Leu | Tyr | Leu | Glu | Thr | Glu | Ala | Gly | Tyr | Tyr | Lys |
| | | 115 | | | | | 120 | | | | | 125 | | | |
| Leu | Ser | Gly | Glu | Ala | Tyr | Gly | Phe | Val | Ala | Arg | Ile | Asp | Gly | Ser | Gly |
| | 130 | | | | | 135 | | | | | 140 | | | | |
| Asn | Phe | Gln | Val | Leu | Leu | Ser | Asp | Arg | Tyr | Phe | Asn | Lys | Thr | Cys | Gly |
| 145 | | | | | 150 | | | | | 155 | | | | | 160 |
| Leu | Cys | Gly | Asn | Phe | Asn | Ile | Phe | Ala | Glu | Asp | Asp | Phe | Met | Thr | Gln |
| | | | | 165 | | | | | 170 | | | | | 175 | |
| Glu | Gly | Thr | Leu | Thr | Ser | Asp | Pro | Tyr | Asp | Phe | Ala | Asn | Ser | Trp | Ala |
| | | | 180 | | | | | 185 | | | | | 190 | | |
| Leu | Ser | Ser | Gly | Glu | Gln | Trp | Cys | Glu | Arg | Ala | Ser | Pro | Pro | Ser | Ser |
| | | 195 | | | | | 200 | | | | | 205 | | | |
| Ser | Cys | Asn | Ile | Ser | Ser | Gly | Glu | Met | Gln | Lys | Gly | Leu | Trp | Glu | Gln |
| | 210 | | | | | 215 | | | | | 220 | | | | |
| Cys | Gln | Leu | Leu | Lys | Ser | Thr | Ser | Val | Phe | Ala | Arg | Cys | His | Pro | Leu |
| 225 | | | | | 230 | | | | | 235 | | | | | 240 |
| Val | Asp | Pro | Glu | Pro | Phe | Val | Ala | Leu | Cys | Glu | Lys | Thr | Leu | Cys | Glu |
| | | | | 245 | | | | | 250 | | | | | 255 | |
| Cys | Ala | Gly | Gly | Leu | Glu | Cys | Ala | Cys | Pro | Ala | Leu | Leu | Glu | Tyr | Ala |
| | | | 260 | | | | | 265 | | | | | 270 | | |
| Arg | Thr | Cys | Ala | Gln | Glu | Gly | Met | Val | Leu | Tyr | Gly | Trp | Thr | Asp | His |
| | | 275 | | | | | 280 | | | | | 285 | | | |
| Ser | Ala | Cys | Ser | Pro | Val | Cys | Pro | Ala | Gly | Met | Glu | Tyr | Arg | Gln | Cys |
| | 290 | | | | | 295 | | | | | 300 | | | | |
| Val | Ser | Pro | Cys | Ala | Arg | Thr | Cys | Gln | Ser | Leu | His | Ile | Asn | Glu | Met |
| 305 | | | | | 310 | | | | | 315 | | | | | 320 |
| Cys | Gln | Glu | Arg | Cys | Val | Asp | Gly | Cys | Ser | Cys | Pro | Glu | Gly | Gln | Leu |
| | | | | 325 | | | | | 330 | | | | | 335 | |
| Leu | Asp | Glu | Gly | Leu | Cys | Val | Glu | Ser | Thr | Glu | Cys | Pro | Cys | Val | His |
| | | | 340 | | | | | 345 | | | | | 350 | | |
| Ser | Gly | Lys | Arg | Tyr | Pro | Pro | Gly | Thr | Ser | Leu | Ser | Arg | Asp | Cys | Asn |
| | | 355 | | | | | 360 | | | | | 365 | | | |
| Thr | Cys | Ile | Cys | Arg | Asn | Ser | Gln | Trp | Ile | Cys | Ser | Asn | Glu | Glu | Cys |
| | 370 | | | | | 375 | | | | | 380 | | | | |

```
Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
        420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
        450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
    675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800
```

```
Ser Met Gly Cys Val Ser Gly Cys Leu Cys Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
      1010                1015                1020

Ser Trp  Lys Val Ser Ser Gln  Cys Ala Asp Thr Arg  Lys Val Pro
      1025                1030                1035

Leu Asp  Ser Ser Pro Ala Thr  Cys His Asn Asn Ile  Met Lys Gln
      1040                1045                1050

Thr Met  Val Asp Ser Ser Cys  Arg Ile Leu Thr Ser  Asp Val Phe
      1055                1060                1065

Gln Asp  Cys Asn Lys Leu Val  Asp Pro Glu Pro Tyr  Leu Asp Val
      1070                1075                1080

Cys Ile  Tyr Asp Thr Cys Ser  Cys Glu Ser Ile Gly  Asp Cys Ala
      1085                1090                1095

Cys Phe  Cys Asp Thr Ile Ala  Ala Tyr Ala His Val  Cys Ala Gln
      1100                1105                1110

His Gly  Lys Val Val Thr Trp  Arg Thr Ala Thr Leu  Cys Pro Gln
      1115                1120                1125

Ser Cys  Glu Glu Arg Asn Leu  Arg Glu Asn Gly Tyr  Glu Cys Glu
      1130                1135                1140

Trp Arg  Tyr Asn Ser Cys Ala  Pro Ala Cys Gln Val  Thr Cys Gln
      1145                1150                1155

His Pro  Glu Pro Leu Ala Cys  Pro Val Gln Cys Val  Glu Gly Cys
      1160                1165                1170

His Ala  His Cys Pro Pro Gly  Lys Ile Leu Asp Glu  Leu Leu Gln
      1175                1180                1185

Thr Cys  Val Asp Pro Glu Asp  Cys Pro Val Cys Glu  Val Ala Gly
      1190                1195                1200

Arg Arg  Phe Ala Ser Gly Lys  Lys Val Thr Leu Asn  Pro Ser Asp
```

-continued

```
               1205                1210                1215

Pro Glu His Cys Gln Ile Cys His Cys Asp Val Val Asn Leu Thr
        1220                1225                1230

Cys Glu Ala Cys Gln Glu Pro
        1235                1240

<210> SEQ ID NO 124
<211> LENGTH: 477
<212> TYPE: PRT
<213> ORGANISM: Artificial Sequence
<220> FEATURE:
<223> OTHER INFORMATION: VWF-D'D3

<400> SEQUENCE: 124

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
```

```
                325                 330                 335
Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
        370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
                450                 455                 460

Asp Val Val Asn Leu Thr Cys Glu Ala Cys Gln Glu Pro
465                 470                 475

<210> SEQ ID NO 125
<211> LENGTH: 5055
<212> TYPE: DNA
<213> ORGANISM: Artificial Sequence
<220> FEATURE:
<223> OTHER INFORMATION: pSYNFVIII 010

<400> SEQUENCE: 125
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
```

```
tgggtacatt acattgctgc tgaagaggag gactgggact atgctcccct agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct actgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc atcaacggg aaataactcg tactactctt    2340
cagtcagatc aagaggaaat tgactatgat gataccatat cagttgaaat gaagaaggaa    2400 gatttttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
```

```
ttggcaccaa tgattattca cggcatcaag acccagggtg cccgtcagaa gttctccagc      3660
ctctacatct ctcagtttat catcatgtat agtcttgatg ggaagaagtg gcagacttat      3720
cgaggaaatt ccactggaac cttaatggtc ttctttggca atgtggattc atctgggata      3780
aaacacaata ttttttaaccc tccaattatt gctcgataca tccgtttgca cccaactcat    3840
tatagcattc gcagcactct tcgcatggag ttgatgggct gtgatttaaa tagttgcagc      3900
atgccattgg gaatggagag taaagcaata tcagatgcac agattactgc ttcatcctac      3960
tttaccaata tgtttgccac ctggtctcct tcaaaagctc gacttcacct ccaagggagg      4020
agtaatgcct ggagacctca ggtgaataat ccaaaagagt ggctgcaagt ggacttccag      4080
aagacaatga agtcacagg agtaactact cagggagtaa atctctgct taccagcatg        4140 tatgtgaagg agttcctcat ctccagcagt caagatggcc atcagtggac tctcttttt      4200 cagaatggca agtaaaggt ttttcaggga aatcaagact ccttcacacc tgtggtgaac        4260
tctctagacc caccgttact gactcgctac cttcgaattc accccagag ttgggtgcac        4320 cagattgccc tgaggatgga ggttctgggc tgcgaggcac aggacctcta cgacaaaact      4380
cacacatgcc caccgtgccc agctccagaa ctcctgggcg gaccgtcagt cttcctcttc      4440
cccccaaaac ccaaggacac cctcatgatc tcccggaccc ctgaggtcac atgcgtggtg      4500
gtggacgtga gccacgaaga ccctgaggtc aagttcaact ggtacgtgga cggcgtggag      4560
gtgcataatg ccaagacaaa gccgcgggag gagcagtaca acagcacgta ccgtgtggtc      4620
agcgtcctca ccgtcctgca ccaggactgg ctgaatggca aggagtacaa gtgcaaggtc      4680
tccaacaaag ccctcccagc ccccatcgag aaaaccatct ccaaagccaa agggcagccc      4740
cgagaaccac aggtgtacac cctgccccca tcccgggatg agctgaccaa gaaccaggtc      4800
agcctgacct gcctggtcaa aggcttctat cccagcgaca tcgccgtgga gtgggagagc      4860
aatgggcagc cggagaacaa ctacaagacc acgcctcccg tgttggactc cgacggctcc      4920
ttcttcctct acagcaagct caccgtggac aagagcaggt ggcagcaggg gaacgtcttc      4980
tcatgctccg tgatgcatga ggctctgcac aaccactaca cgcagaagag cctctccctg      5040
tctccgggta aatga                                                      5055
```

<210> SEQ ID NO 126
<211> LENGTH: 1684
<212> TYPE: PRT
<213> ORGANISM: Artificial Sequence
<220> FEATURE:
<223> OTHER INFORMATION: pSYNFVIII 010

<400> SEQUENCE: 126

Met Gln Ile Glu Leu Ser Thr Cys Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe

```
            515                 520                 525
Lys Tyr Lys Trp Thr Val Thr Val Glu Asp Gly Pro Thr Lys Ser Asp
    530                 535                 540

Pro Arg Cys Leu Thr Arg Tyr Ser Ser Phe Val Asn Met Glu Arg
545                 550                 555                 560

Asp Leu Ala Ser Gly Leu Ile Gly Pro Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
        850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
        930                 935                 940
```

-continued

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

```
Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr Asp
    1445                1450                1455

Lys Thr His Thr Cys Pro Pro Cys Pro Ala Pro Glu Leu Leu Gly
    1460                1465                1470

Gly Pro Ser Val Phe Leu Phe Pro Pro Lys Pro Lys Asp Thr Leu
    1475                1480                1485

Met Ile Ser Arg Thr Pro Glu Val Thr Cys Val Val Val Asp Val
    1490                1495                1500

Ser His Glu Asp Pro Glu Val Lys Phe Asn Trp Tyr Val Asp Gly
    1505                1510                1515

Val Glu Val His Asn Ala Lys Thr Lys Pro Arg Glu Glu Gln Tyr
    1520                1525                1530

Asn Ser Thr Tyr Arg Val Val Ser Val Leu Thr Val Leu His Gln
    1535                1540                1545

Asp Trp Leu Asn Gly Lys Glu Tyr Lys Cys Lys Val Ser Asn Lys
    1550                1555                1560

Ala Leu Pro Ala Pro Ile Glu Lys Thr Ile Ser Lys Ala Lys Gly
    1565                1570                1575

Gln Pro Arg Glu Pro Gln Val Tyr Thr Leu Pro Pro Ser Arg Asp
    1580                1585                1590

Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys

<210> SEQ ID NO 127
<211> LENGTH: 78
<212> TYPE: PRT
<213> ORGANISM: Artificial Sequence
<220> FEATURE:
<223> OTHER INFORMATION: AE72 XTEN
```

<400> SEQUENCE: 127

Gly Ala Pro Thr Ser Glu Ser Ala Pro Glu Ser Gly Pro Gly Ser
1               5                   10                  15

Glu Pro Ala Thr Ser Gly Ser Glu Thr Pro Gly Thr Ser Glu Ser Ala
            20                  25                  30

Thr Pro Glu Ser Gly Pro Gly Ser Glu Pro Ala Thr Ser Gly Ser Glu
        35                  40                  45

Thr Pro Gly Thr Ser Glu Ser Ala Thr Pro Glu Ser Gly Pro Gly Thr
    50                  55                  60

Ser Thr Glu Pro Ser Glu Gly Ser Ala Pro Gly Ala Ser Ser
65                  70                  75

<210> SEQ ID NO 128
<211> LENGTH: 144
<212> TYPE: PRT
<213> ORGANISM: Artificial Sequence
<220> FEATURE:
<223> OTHER INFORMATION: AE144_2A

<400> SEQUENCE: 128

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Thr Ser Glu Ser Ala Thr Pro Glu
        115                 120                 125

Ser Gly Pro Gly Thr Ser Glu Ser Ala Thr Pro Glu Ser Gly Pro Gly
    130                 135                 140

<210> SEQ ID NO 129
<211> LENGTH: 144
<212> TYPE: PRT
<213> ORGANISM: Artificial Sequence
<220> FEATURE:
<223> OTHER INFORMATION: AE144_3B

<400> SEQUENCE: 129

Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly Thr Ser Thr Glu Pro Ser Glu Gly
65                  70                  75                  80

```
Ser Ala Pro Gly Thr Ser Glu Pro Ser Gly Ser Ala Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

<210> SEQ ID NO 130
<211> LENGTH: 144
<212> TYPE: PRT
<213> ORGANISM: Artificial Sequence
<220> FEATURE:
<223> OTHER INFORMATION: AE144_4A

<400> SEQUENCE: 130

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Pro Ala Gly Ser Pro Thr Ser Thr Glu Glu Gly
                85                  90                  95

Ser Pro Ala Gly Ser Pro Thr Ser Thr Glu Glu Gly Ser Pro Ala Gly
            100                 105                 110

Ser Pro Thr Ser Thr Glu Glu Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140

<210> SEQ ID NO 131
<211> LENGTH: 144
<212> TYPE: PRT
<213> ORGANISM: Artificial Sequence
<220> FEATURE:
<223> OTHER INFORMATION: AE144_5A

<400> SEQUENCE: 131

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Ser Pro Ala Gly Ser Pro Thr Ser
65                  70                  75                  80

Thr Glu Glu Gly Thr Ser Glu Ser Ala Thr Pro Glu Ser Gly Pro Gly
                85                  90                  95

Ser Glu Pro Ala Thr Ser Gly Ser Glu Thr Pro Gly Thr Ser Glu Ser
            100                 105                 110
```

```
Ala Thr Pro Glu Ser Gly Pro Gly Ser Pro Ala Gly Ser Pro Thr Ser
        115                 120                 125

Thr Glu Glu Gly Ser Pro Ala Gly Ser Pro Thr Thr Glu Glu Gly
        130                 135                 140

<210> SEQ ID NO 132
<211> LENGTH: 144
<212> TYPE: PRT
<213> ORGANISM: Artificial Sequence
<220> FEATURE:
<223> OTHER INFORMATION: AE144_6B

<400> SEQUENCE: 132

Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140

<210> SEQ ID NO 133
<211> LENGTH: 144
<212> TYPE: PRT
<213> ORGANISM: Artificial Sequence
<220> FEATURE:
<223> OTHER INFORMATION: AG144_A

<400> SEQUENCE: 133

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
```

```
                130                 135                 140

<210> SEQ ID NO 134
<211> LENGTH: 144
<212> TYPE: PRT
<213> ORGANISM: Artificial Sequence
<220> FEATURE:
<223> OTHER INFORMATION: AG144_B

<400> SEQUENCE: 134

Gly Thr Pro Gly Ser Gly Thr Ala Ser Ser Pro Gly Ser Ser Thr
  1               5                  10                  15

Pro Ser Gly Ala Thr Gly Ser Pro Gly Ala Ser Pro Gly Thr Ser Ser
                 20                  25                  30

Thr Gly Ser Pro Gly Thr Pro Gly Ser Gly Thr Ala Ser Ser Pro
         35                  40                  45

Gly Ser Ser Thr Pro Ser Gly Ala Thr Gly Ser Pro Gly Ser Ser Pro
     50                  55                  60

Ser Ala Ser Thr Gly Thr Gly Pro Gly Ser Ser Pro Ser Ala Ser Thr
 65                  70                  75                  80

Gly Thr Gly Pro Gly Ser Ser Thr Pro Ser Gly Ala Thr Gly Ser Pro
                 85                  90                  95

Gly Ser Ser Thr Pro Ser Gly Ala Thr Gly Ser Pro Gly Ala Ser Pro
                100                 105                 110

Gly Thr Ser Ser Thr Gly Ser Pro Gly Ala Ser Pro Gly Thr Ser Ser
                115                 120                 125

Thr Gly Ser Pro Gly Ala Ser Pro Gly Thr Ser Ser Thr Gly Ser Pro
                130                 135                 140

<210> SEQ ID NO 135
<211> LENGTH: 144
<212> TYPE: PRT
<213> ORGANISM: Artificial Sequence
<220> FEATURE:
<223> OTHER INFORMATION: AG144_C

<400> SEQUENCE: 135

Gly Thr Pro Gly Ser Gly Thr Ala Ser Ser Pro Gly Ala Ser Pro
  1               5                  10                  15

Gly Thr Ser Ser Thr Gly Ser Pro Gly Ala Ser Pro Gly Thr Ser Ser
                 20                  25                  30

Thr Gly Ser Pro Gly Ala Ser Pro Gly Thr Ser Ser Thr Gly Ser Pro
         35                  40                  45

Gly Ser Ser Pro Ser Ala Ser Thr Gly Thr Gly Pro Gly Thr Pro Gly
     50                  55                  60

Ser Gly Thr Ala Ser Ser Pro Gly Ala Ser Pro Gly Thr Ser Ser
 65                  70                  75                  80

Thr Gly Ser Pro Gly Ala Ser Pro Gly Thr Ser Ser Thr Gly Ser Pro
                 85                  90                  95

Gly Ala Ser Pro Gly Thr Ser Ser Thr Gly Ser Pro Gly Ser Ser Thr
                100                 105                 110

Pro Ser Gly Ala Thr Gly Ser Pro Gly Ser Ser Thr Pro Ser Gly Ala
                115                 120                 125

Thr Gly Ser Pro Gly Ala Ser Pro Gly Thr Ser Ser Thr Gly Ser Pro
                130                 135                 140

<210> SEQ ID NO 136
<211> LENGTH: 144
```

```
<212> TYPE: PRT
<213> ORGANISM: Artificial Sequence
<220> FEATURE:
<223> OTHER INFORMATION: AG144_F

<400> SEQUENCE: 136
```

| Gly | Ser | Ser | Pro | Ser | Ala | Ser | Thr | Gly | Thr | Gly | Pro | Gly | Ser | Ser | Pro |
|---|---|---|---|---|---|---|---|---|---|---|---|---|---|---|---|
| 1 | | | | 5 | | | | | 10 | | | | | 15 | |

| Ser | Ala | Ser | Thr | Gly | Thr | Gly | Pro | Gly | Ala | Ser | Pro | Gly | Thr | Ser | Ser |
|---|---|---|---|---|---|---|---|---|---|---|---|---|---|---|---|
| | | | 20 | | | | | 25 | | | | | 30 | | |

| Thr | Gly | Ser | Pro | Gly | Ala | Ser | Pro | Gly | Thr | Ser | Ser | Thr | Gly | Ser | Pro |
|---|---|---|---|---|---|---|---|---|---|---|---|---|---|---|---|
| | | 35 | | | | | 40 | | | | | 45 | | | |

| Gly | Ser | Ser | Thr | Pro | Ser | Ala | Thr | Gly | Ser | Pro | Gly | Ser | Ser | Pro |
|---|---|---|---|---|---|---|---|---|---|---|---|---|---|---|
| | 50 | | | | | 55 | | | | | 60 | | | |

| Ser | Ala | Ser | Thr | Gly | Thr | Gly | Pro | Gly | Ala | Ser | Pro | Gly | Thr | Ser | Ser |
|---|---|---|---|---|---|---|---|---|---|---|---|---|---|---|---|
| 65 | | | | | 70 | | | | | 75 | | | | | 80 |

| Thr | Gly | Ser | Pro | Gly | Ser | Ser | Pro | Ser | Ala | Ser | Thr | Gly | Thr | Gly | Pro |
|---|---|---|---|---|---|---|---|---|---|---|---|---|---|---|---|
| | | | | 85 | | | | | 90 | | | | | 95 | |

| Gly | Thr | Pro | Gly | Ser | Gly | Thr | Ala | Ser | Ser | Pro | Gly | Ser | Ser | Thr |
|---|---|---|---|---|---|---|---|---|---|---|---|---|---|---|
| | | | 100 | | | | | 105 | | | | | 110 | |

| Pro | Ser | Gly | Ala | Thr | Gly | Ser | Pro | Gly | Ser | Ser | Thr | Pro | Ser | Gly | Ala |
|---|---|---|---|---|---|---|---|---|---|---|---|---|---|---|---|
| | | | | 115 | | | | | 120 | | | | | 125 | |

| Thr | Gly | Ser | Pro | Gly | Ala | Ser | Pro | Gly | Thr | Ser | Ser | Thr | Gly | Ser | Pro |
|---|---|---|---|---|---|---|---|---|---|---|---|---|---|---|---|
| | | | 130 | | | | | 135 | | | | | 140 | | |

```
<210> SEQ ID NO 137
<211> LENGTH: 288
<212> TYPE: PRT
<213> ORGANISM: Artificial Sequence
<220> FEATURE:
<223> OTHER INFORMATION: AE288_2

<400> SEQUENCE: 137
```

| Gly | Ser | Pro | Ala | Gly | Ser | Pro | Thr | Ser | Thr | Glu | Glu | Gly | Thr | Ser | Glu |
|---|---|---|---|---|---|---|---|---|---|---|---|---|---|---|---|
| 1 | | | | 5 | | | | | 10 | | | | | 15 | |

| Ser | Ala | Thr | Pro | Glu | Ser | Gly | Pro | Gly | Ser | Glu | Pro | Ala | Thr | Ser | Gly |
|---|---|---|---|---|---|---|---|---|---|---|---|---|---|---|---|
| | | | 20 | | | | | 25 | | | | | 30 | | |

| Ser | Glu | Thr | Pro | Gly | Thr | Ser | Glu | Ser | Ala | Thr | Pro | Glu | Ser | Gly | Pro |
|---|---|---|---|---|---|---|---|---|---|---|---|---|---|---|---|
| | | 35 | | | | | 40 | | | | | 45 | | | |

| Gly | Thr | Ser | Thr | Glu | Pro | Ser | Glu | Gly | Ser | Ala | Pro | Gly | Thr | Ser | Thr |
|---|---|---|---|---|---|---|---|---|---|---|---|---|---|---|---|
| | 50 | | | | | 55 | | | | | 60 | | | | |

| Glu | Pro | Ser | Glu | Gly | Ser | Ala | Pro | Gly | Thr | Ser | Thr | Glu | Pro | Ser | Glu |
|---|---|---|---|---|---|---|---|---|---|---|---|---|---|---|---|
| 65 | | | | | 70 | | | | | 75 | | | | | 80 |

| Gly | Ser | Ala | Pro | Gly | Thr | Ser | Thr | Glu | Pro | Ser | Glu | Gly | Ser | Ala | Pro |
|---|---|---|---|---|---|---|---|---|---|---|---|---|---|---|---|
| | | | | 85 | | | | | 90 | | | | | 95 | |

| Gly | Thr | Ser | Thr | Glu | Pro | Ser | Glu | Gly | Ser | Ala | Pro | Gly | Thr | Ser | Thr |
|---|---|---|---|---|---|---|---|---|---|---|---|---|---|---|---|
| | | | 100 | | | | | 105 | | | | | 110 | | |

| Glu | Pro | Ser | Glu | Gly | Ser | Ala | Pro | Gly | Ser | Pro | Ala | Gly | Ser | Pro | Thr |
|---|---|---|---|---|---|---|---|---|---|---|---|---|---|---|---|
| | | | 115 | | | | | 120 | | | | | 125 | | |

| Ser | Thr | Glu | Glu | Gly | Thr | Ser | Thr | Glu | Pro | Ser | Glu | Gly | Ser | Ala | Pro |
|---|---|---|---|---|---|---|---|---|---|---|---|---|---|---|---|
| | 130 | | | | | 135 | | | | | 140 | | | | |

| Gly | Thr | Ser | Glu | Ser | Ala | Thr | Pro | Glu | Ser | Gly | Pro | Gly | Ser | Glu | Pro |
|---|---|---|---|---|---|---|---|---|---|---|---|---|---|---|---|
| 145 | | | | | 150 | | | | | 155 | | | | | 160 |

| Ala | Thr | Ser | Gly | Ser | Glu | Thr | Pro | Gly | Thr | Ser | Glu | Ser | Ala | Thr | Pro |
|---|---|---|---|---|---|---|---|---|---|---|---|---|---|---|---|
| | | | | 165 | | | | | 170 | | | | | 175 | |

| Glu | Ser | Gly | Pro | Gly | Ser | Glu | Pro | Ala | Thr | Ser | Gly | Ser | Glu | Thr | Pro |
|---|---|---|---|---|---|---|---|---|---|---|---|---|---|---|---|
| | | | | 180 | | | | | 185 | | | | | 190 | |

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Ser Glu Ser Ala Thr Pro
        210                 215                 220

Glu Ser Gly Pro Gly Ser Pro Ala Gly Ser Pro Thr Ser Thr Glu Glu
225                 230                 235                 240

Gly Ser Pro Ala Gly Ser Pro Thr Ser Thr Glu Glu Gly Ser Pro Ala
            245                 250                 255

Gly Ser Pro Thr Ser Thr Glu Glu Thr Ser Glu Ser Ala Thr Pro
            260                 265                 270

Glu Ser Gly Pro Gly Thr Ser Thr Glu Pro Ser Glu Gly Ser Ala Pro
            275                 280                 285

<210> SEQ ID NO 138
<211> LENGTH: 20
<212> TYPE: PRT
<213> ORGANISM: Artificial Sequence
<220> FEATURE:
<223> OTHER INFORMATION: linker

<400> SEQUENCE: 138

Gly Gly Gly Gly Ser Gly Gly Gly Ser Gly Gly Gly Ser Gly
1               5                   10                  15

Gly Gly Gly Ser
            20

<210> SEQ ID NO 139
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat 1 to 10 times

<400> SEQUENCE: 139

Gly Gly Gly Gly Ser
1               5

<210> SEQ ID NO 140
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (2)..(6)
<223> OTHER INFORMATION: Repeat 1 to 10 times

<400> SEQUENCE: 140

Ser Gly Gly Gly Gly Ser
1               5

<210> SEQ ID NO 141
<211> LENGTH: 12
<212> TYPE: PRT
<213> ORGANISM: Artificial Sequence
<220> FEATURE:
<223> OTHER INFORMATION: AD

<400> SEQUENCE: 141

```
Gly Glu Ser Pro Gly Gly Ser Ser Gly Ser Glu Ser
1               5                   10
```

<210> SEQ ID NO 142
<211> LENGTH: 12
<212> TYPE: PRT
<213> ORGANISM: Artificial Sequence
<220> FEATURE:
<223> OTHER INFORMATION: AD

<400> SEQUENCE: 142

```
Gly Ser Glu Gly Ser Ser Gly Pro Gly Glu Ser Ser
1               5                   10
```

<210> SEQ ID NO 143
<211> LENGTH: 12
<212> TYPE: PRT
<213> ORGANISM: Artificial Sequence
<220> FEATURE:
<223> OTHER INFORMATION: AD

<400> SEQUENCE: 143

```
Gly Ser Ser Glu Ser Gly Ser Ser Glu Gly Gly Pro
1               5                   10
```

<210> SEQ ID NO 144
<211> LENGTH: 12
<212> TYPE: PRT
<213> ORGANISM: Artificial Sequence
<220> FEATURE:
<223> OTHER INFORMATION: AD

<400> SEQUENCE: 144

```
Gly Ser Gly Gly Glu Pro Ser Glu Ser Gly Ser Ser
1               5                   10
```

<210> SEQ ID NO 145
<211> LENGTH: 12
<212> TYPE: PRT
<213> ORGANISM: Artificial Sequence
<220> FEATURE:
<223> OTHER INFORMATION: AE, AM

<400> SEQUENCE: 145

```
Gly Ser Pro Ala Gly Ser Pro Thr Ser Thr Glu Glu
1               5                   10
```

<210> SEQ ID NO 146
<211> LENGTH: 12
<212> TYPE: PRT
<213> ORGANISM: Artificial Sequence
<220> FEATURE:
<223> OTHER INFORMATION: AE, AM, AQ

<400> SEQUENCE: 146

```
Gly Ser Glu Pro Ala Thr Ser Gly Ser Glu Thr Pro
1               5                   10
```

<210> SEQ ID NO 147
<211> LENGTH: 12
<212> TYPE: PRT
<213> ORGANISM: Artificial Sequence
<220> FEATURE:
<223> OTHER INFORMATION: AE, AM, AQ

<400> SEQUENCE: 147

Gly Thr Ser Glu Ser Ala Thr Pro Glu Ser Gly Pro

```
1               5                   10
```

<210> SEQ ID NO 148
<211> LENGTH: 12
<212> TYPE: PRT
<213> ORGANISM: Artificial Sequence
<220> FEATURE:
<223> OTHER INFORMATION: AE, AM, AQ

<400> SEQUENCE: 148

```
Gly Thr Ser Thr Glu Pro Ser Glu Gly Ser Ala Pro
1               5                   10
```

<210> SEQ ID NO 149
<211> LENGTH: 12
<212> TYPE: PRT
<213> ORGANISM: Artificial Sequence
<220> FEATURE:
<223> OTHER INFORMATION: AF, AM

<400> SEQUENCE: 149

```
Gly Ser Thr Ser Glu Ser Pro Ser Gly Thr Ala Pro
1               5                   10
```

<210> SEQ ID NO 150
<211> LENGTH: 12
<212> TYPE: PRT
<213> ORGANISM: Artificial Sequence
<220> FEATURE:
<223> OTHER INFORMATION: AF, AM

<400> SEQUENCE: 150

```
Gly Thr Ser Thr Pro Glu Ser Gly Ser Ala Ser Pro
1               5                   10
```

<210> SEQ ID NO 151
<211> LENGTH: 12
<212> TYPE: PRT
<213> ORGANISM: Artificial Sequence
<220> FEATURE:
<223> OTHER INFORMATION: AF, AM

<400> SEQUENCE: 151

```
Gly Thr Ser Pro Ser Gly Glu Ser Ser Thr Ala Pro
1               5                   10
```

<210> SEQ ID NO 152
<211> LENGTH: 12
<212> TYPE: PRT
<213> ORGANISM: Artificial Sequence
<220> FEATURE:
<223> OTHER INFORMATION: AF, AM

<400> SEQUENCE: 152

```
Gly Ser Thr Ser Ser Thr Ala Glu Ser Pro Gly Pro
1               5                   10
```

<210> SEQ ID NO 153
<211> LENGTH: 12
<212> TYPE: PRT
<213> ORGANISM: Artificial Sequence
<220> FEATURE:
<223> OTHER INFORMATION: AG, AM

<400> SEQUENCE: 153

```
Gly Thr Pro Gly Ser Gly Thr Ala Ser Ser Ser Pro
1               5                   10
```

<210> SEQ ID NO 154
<211> LENGTH: 12
<212> TYPE: PRT
<213> ORGANISM: Artificial Sequence
<220> FEATURE:
<223> OTHER INFORMATION: AG, AM

<400> SEQUENCE: 154

Gly Ser Ser Thr Pro Ser Gly Ala Thr Gly Ser Pro
1               5                   10

<210> SEQ ID NO 155
<211> LENGTH: 12
<212> TYPE: PRT
<213> ORGANISM: Artificial Sequence
<220> FEATURE:
<223> OTHER INFORMATION: AG, AM

<400> SEQUENCE: 155

Gly Ser Ser Pro Ser Ala Ser Thr Gly Thr Gly Pro
1               5                   10

<210> SEQ ID NO 156
<211> LENGTH: 12
<212> TYPE: PRT
<213> ORGANISM: Artificial Sequence
<220> FEATURE:
<223> OTHER INFORMATION: AG, AM

<400> SEQUENCE: 156

Gly Ala Ser Pro Gly Thr Ser Ser Thr Gly Ser Pro
1               5                   10

<210> SEQ ID NO 157
<211> LENGTH: 12
<212> TYPE: PRT
<213> ORGANISM: Artificial Sequence
<220> FEATURE:
<223> OTHER INFORMATION: AQ

<400> SEQUENCE: 157

Gly Glu Pro Ala Gly Ser Pro Thr Ser Thr Ser Glu
1               5                   10

<210> SEQ ID NO 158
<211> LENGTH: 12
<212> TYPE: PRT
<213> ORGANISM: Artificial Sequence
<220> FEATURE:
<223> OTHER INFORMATION: AQ

<400> SEQUENCE: 158

Gly Thr Gly Glu Pro Ser Ser Thr Pro Ala Ser Glu
1               5                   10

<210> SEQ ID NO 159
<211> LENGTH: 12
<212> TYPE: PRT
<213> ORGANISM: Artificial Sequence
<220> FEATURE:
<223> OTHER INFORMATION: AQ

<400> SEQUENCE: 159

Gly Ser Gly Pro Ser Thr Glu Ser Ala Pro Thr Glu
1               5                   10

<210> SEQ ID NO 160
<211> LENGTH: 12
<212> TYPE: PRT
<213> ORGANISM: Artificial Sequence
<220> FEATURE:
<223> OTHER INFORMATION: AQ

<400> SEQUENCE: 160

Gly Ser Glu Thr Pro Ser Gly Pro Ser Glu Thr Ala
1               5                   10

<210> SEQ ID NO 161
<211> LENGTH: 12
<212> TYPE: PRT
<213> ORGANISM: Artificial Sequence
<220> FEATURE:
<223> OTHER INFORMATION: AQ

<400> SEQUENCE: 161

Gly Pro Ser Glu Thr Ser Thr Ser Glu Pro Gly Ala
1               5                   10

<210> SEQ ID NO 162
<211> LENGTH: 12
<212> TYPE: PRT
<213> ORGANISM: Artificial Sequence
<220> FEATURE:
<223> OTHER INFORMATION: AQ

<400> SEQUENCE: 162

Gly Ser Pro Ser Glu Pro Thr Glu Gly Thr Ser Ala
1               5                   10

<210> SEQ ID NO 163
<211> LENGTH: 12
<212> TYPE: PRT
<213> ORGANISM: Artificial Sequence
<220> FEATURE:
<223> OTHER INFORMATION: BC

<400> SEQUENCE: 163

Gly Ser Gly Ala Ser Glu Pro Thr Ser Thr Glu Pro
1               5                   10

<210> SEQ ID NO 164
<211> LENGTH: 12
<212> TYPE: PRT
<213> ORGANISM: Artificial Sequence
<220> FEATURE:
<223> OTHER INFORMATION: BC

<400> SEQUENCE: 164

Gly Ser Glu Pro Ala Thr Ser Gly Thr Glu Pro Ser
1               5                   10

<210> SEQ ID NO 165
<211> LENGTH: 12
<212> TYPE: PRT
<213> ORGANISM: Artificial Sequence
<220> FEATURE:
<223> OTHER INFORMATION: BC

<400> SEQUENCE: 165

Gly Thr Ser Glu Pro Ser Thr Ser Glu Pro Gly Ala
1               5                   10

```
<210> SEQ ID NO 166
<211> LENGTH: 12
<212> TYPE: PRT
<213> ORGANISM: Artificial Sequence
<220> FEATURE:
<223> OTHER INFORMATION: BC

<400> SEQUENCE: 166

Gly Thr Ser Thr Glu Pro Ser Glu Pro Gly Ser Ala
1               5                   10

<210> SEQ ID NO 167
<211> LENGTH: 12
<212> TYPE: PRT
<213> ORGANISM: Artificial Sequence
<220> FEATURE:
<223> OTHER INFORMATION: BD

<400> SEQUENCE: 167

Gly Ser Thr Ala Gly Ser Glu Thr Ser Thr Glu Ala
1               5                   10

<210> SEQ ID NO 168
<211> LENGTH: 12
<212> TYPE: PRT
<213> ORGANISM: Artificial Sequence
<220> FEATURE:
<223> OTHER INFORMATION: BD

<400> SEQUENCE: 168

Gly Ser Glu Thr Ala Thr Ser Gly Ser Glu Thr Ala
1               5                   10

<210> SEQ ID NO 169
<211> LENGTH: 12
<212> TYPE: PRT
<213> ORGANISM: Artificial Sequence
<220> FEATURE:
<223> OTHER INFORMATION: BD

<400> SEQUENCE: 169

Gly Thr Ser Glu Ser Ala Thr Ser Glu Ser Gly Ala
1               5                   10

<210> SEQ ID NO 170
<211> LENGTH: 12
<212> TYPE: PRT
<213> ORGANISM: Artificial Sequence
<220> FEATURE:
<223> OTHER INFORMATION: BD

<400> SEQUENCE: 170

Gly Thr Ser Thr Glu Ala Ser Glu Gly Ser Ala Ser
1               5                   10

<210> SEQ ID NO 171
<211> LENGTH: 35
<212> TYPE: PRT
<213> ORGANISM: Artificial Sequence
<220> FEATURE:
<223> OTHER INFORMATION: linker
```

```
<400> SEQUENCE: 171

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Leu Val Pro Arg Gly
                20                  25                  30

Ser Gly Gly
        35
```

FACTOR VIII COMPLEX WITH XTEN AND VON WILLEBRAND FACTOR PROTEIN, AND USES THEREOF

RELATED APPLICATIONS

This application is a divisional of U.S. application Ser. No. 14/413,765, which is the U.S. National Phase entry of International Application No. PCT/US2013/049989, filed on Jul. 10, 2013; which claims the benefit of U.S. Provisional Application Nos. 61/840,811, filed on Jun. 28, 2013; 61/827,158, filed on May 24, 2013; 61/801,544, filed on Mar. 15, 2013; 61/801,504, filed on Mar. 15, 2013; 61/759,819, filed on Feb. 1, 2013; and 61/670,401, filed on Jul. 11, 2012, each of which is incorporated by reference herein in its entirety.

REFERENCE TO A SEQUENCE LISTING SUBMITTED ELECTRONICALLY VIA EFS-WEB

The instant application contains a Sequence Listing, which has been submitted in ASCII format via EFS-Web, and is hereby incorporated by reference in its entirety. Said ASCII copy, created on Oct. 3, 2018, is named 41593650007_SeqListing.txt and is 577,335 Bytes in size.

BACKGROUND OF THE INVENTION

Haemophilia A is a bleeding disorder caused by defects in the gene encoding coagulation factor VIII (FVIII) and affects 1-2 in 10,000 male births. Graw et al., *Nat. Rev. Genet.* 6(6): 488-501 (2005). Patients affected with hemophilia A can be treated with infusion of purified or recombinantly produced FVIII. All commercially available FVIII products, however, are known to have a half-life of about 8-12 hours, requiring frequent intravenous administration to the patients. See Weiner M. A. and Cairo, M. S., Pediatric Hematology Secrets, Lee, M. T., 12. Disorders of Coagulation, Elsevier Health Sciences, 2001; Lillicrap, D. Thromb. Res. 122 Suppl 4:S2-8 (2008). In addition, a number of approaches have been tried in order to extend the FVIII half-life. For example, the approaches in development to extend the half-life of clotting factors include pegylation, glycopegylation, and conjugation with albumin. See Dumont et al., *Blood.* 119(13): 3024-3030 (Published online Jan. 13, 2012). Regardless of the protein engineering used, however, the long acting FVIII products currently under development are reported to have limited half-lives—only to about 1.5 to 2 hours in preclinical animal models. See id. Consistent results have been demonstrated in humans, for example, rFVIIIFc was reported to improve half-life up to ~1.7 fold compared with ADVATE® in hemophilia A patients. See Id. Therefore, the half-life increases, despite minor improvements, may indicate the presence of other T1/2 limiting factors. See Liu, T. et al., 2007 ISTH meeting, abstract #P-M-035; Henrik, A. et al., 2011 ISTH meeting, abstract #P=MO-181; Liu, T. et al., 2011 ISTH meeting abstract #P-WE-131.

Plasma von Willebrand Factor (VWF) has a half-life of approximately 12 hours (ranging from 9 to 15 hours). http://www.nhlbi.nih.gov/guidelines/vwd/2_scientificoverview.htm (last visited Oct. 22, 2011). The VWF half-life may be affected by a number of factors: glycosylation pattern, ADAMTS-13 (a disintegrin and metalloprotease with thrombospondin motif-13), and various mutations in VWF.

In plasma, 95-98% of FVIII circulates in a tight non-covalent complex with full-length VWF. The formation of this complex is important for the maintenance of appropriate plasma levels of FVIII in vivo. Lenting et al., *Blood.* 92(11): 3983-96 (1998); Lenting et al., *J. Thromb. Haemost.* 5(7): 1353-60 (2007). The full-length wild-type FVIII is mostly present as a heterodimer having a heavy chain (MW 200 kD) and a light chain (MW 73 kD). When FVIII is activated due to proteolysis at positions 372 and 740 in the heavy chain and at position 1689 in the light chain, the VWF bound to FVIII is removed from the activated FVIII. The activated FVIII, together with activated factor IX, calcium, and phospholipid ("tenase complex"), induces the activation of factor X, generating large amounts of thrombin. Thrombin, in turn, then cleaves fibrinogen to form soluble fibrin monomers, which then spontaneously polymerize to form the soluble fibrin polymer. Thrombin also activates factor XIII, which, together with calcium, serves to crosslink and stabilize the soluble fibrin polymer, forming crosslinked (insoluble) fibrin. The activated FVIII is cleared fast from the circulation by proteolysis.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

BRIEF SUMMARY OF THE INVENTION

The present invention is directed to a chimeric protein comprising (i) a von Willebrand Factor (VWF) fragment comprising the D' domain and the D3 domain of VWF, (ii) an XTEN sequence, and (iii) a FVIII protein, wherein the VWF fragment and the XTEN sequence are linked by an optional linker and wherein the VWF fragment or the XTEN sequence is linked to or associated with the FVIII protein. The chimeric protein can comprise a single polypeptide chain comprising the VWF fragment, the XTEN sequence, and the FVIII protein, or two polypeptide chains, a first chain comprising the VWF fragment and the second chain comprising the FVIII protein, wherein the XTEN polypeptide is linked either to the VWF fragment or the FVIII protein.

In one embodiment, the chimeric protein of the invention comprises a formula comprising:
  (a) V-X-FVIII,
  (b) FVIII-X-V,
  (c) V-X:FVIII,
  (d) X-V:FVIII,
  (e) FVIII:V-X, or
  (f) FVIII:X-V,
wherein V comprises a VWF fragment,
X comprises one or more XTEN sequences, and
FVIII comprises a FVIII protein. The hyphen (-) can be a
  peptide bond or a linker, e.g., a cleavable linker, while the
  colon (:) represents a chemical association or a physical
  association between the polypeptides, for example a covalent or non-covalent bond.

In another embodiment, the chimeric protein further comprises (iv) an immunoglobulin (Ig) constant region or a portion thereof (also indicated as F1 or a first Ig constant region or a portion thereof) linked to the VWF fragment, the XTEN sequence, the FVIII protein, or any combinations thereof. In other embodiments, the chimeric protein further comprises an additional Ig constant region or a portion thereof (also indicated as F2 or a second Ig constant region or a portion thereof). The first Ig constant region or a portion thereof can be linked to the VWF fragment or the XTEN sequence, and the second Ig constant region can be linked to the FVIII protein. The first Ig constant region, the second Ig constant region or a portion thereof, or both can extend the half-life of the FVIII protein.

In some embodiments, the second Ig constant region or a portion thereof (F2) is linked to the VWF fragment by a linker, e.g., a processable linker. In other embodiments, the second Ig constant region or a portion thereof (F2) is associated with the (first) Ig constant region or a portion thereof (F1). The second Ig constant region or a portion thereof (F2) and the first Ig constant region or a portion thereof (F1) can be identical or different. The second Ig constant region or a portion thereof can be associated with the Ig constant region or a portion thereof by a covalent bond, e.g., a disulfide bond. The VWF fragment linked to the first Ig constant region or a portion thereof may also be associated with the FVIII protein linked to the second Fc region by a non-covalent bond. In certain embodiments, the FVIII protein can further comprise one or more additional XTEN sequences which are linked to the C-terminus or N-terminus of the FVIII protein or inserted immediately downstream of one or more amino acids in the FVIII protein (e.g., one or more XTEN insertion sites). In some embodiments, the half-life of the FVIII protein is extended, compared to wild type FVIII or a FVIII protein without the VWF fragment.

In some embodiments, the chimeric protein comprises a formula comprising:
 (g) V-L2-X-L1-F1:FVIII-L3-F2;
 (h) V-L2-X-L1-F1:F2-L3-FVIII;
 (i) F1-L1-X-L2-V:FVIII-L3-F2;
 (j) F1-L1-X-L2-V:F2-L3-FVIII;
 (k) V-L2-X-L1-F1-L4-FVIII-L3-F2;
 (l) F2-L3-FVIII-L4-F1-L1-X-L2-V;
 (m) FVIII-L3-F2-L4-V-L2-X-L1-F1; or
 (n) F1-L1-X-L2-V-L4-F2-L3-FVIII,
wherein V comprises a VWF fragment,
each of L1, L2, and L3 comprises an optional linker, e.g., a cleavable linker,
L4 is an optional linker, e.g., a processable linker,
FVIII comprises a FVIII protein,
X comprises one or more XTEN sequences,
F1 comprises an optional first Ig constant region or a portion thereof,
F2 comprises an optional second Ig constant region or a portion thereof, and
(:) is a covalent bond or non-covalent bond.

The present invention is also directed to a chimeric protein comprising (i) a FVIII protein, (ii) an XTEN sequence, and (iii) an Ig constant region or a portion thereof, wherein the XTEN sequence is linked to the FVIII protein by an optional linker at the N-terminus or C terminus of the FVIII protein or inserted immediately downstream of one or more amino acids in the FVIII protein (e.g., one or more insertion sites) and wherein the Ig constant region or a portion thereof is linked to or associated with the FVIII protein or the XTEN sequence. In one embodiment, the Ig constant region or a portion thereof useful for the chimeric protein comprises a first Fc region. In another embodiment, the chimeric protein further comprises an additional Ig constant region or a portion thereof. The additional Ig constant region or a portion thereof useful for the invention can comprise a second Fc region, which is linked to or associated with the first Fc region, e.g., by a covalent bond. In other embodiments, the first Fc region is linked to the second Fc region by a linker, e.g., a processable linker.

In other aspects, a chimeric protein comprises (i) a FVIII protein, (ii) an XTEN sequence, (iii) a VWF fragment, and (iv) an Ig constant region or a portion thereof, which comprises the D' domain and the D3 domain of VWF, wherein the XTEN sequence is linked to the FVIII protein by an optional linker at the N-terminus or C terminus of the FVIII protein or inserted immediately downstream of one or more amino acids in the FVIII protein (e.g., one or more insertion sites), the VWF fragment is linked to or associated with the FVIII protein or the XTEN sequence, and the Ig constant region or a portion thereof is linked to the FVIII protein, the XTEN sequence, the VWF fragment, or any combinations thereof. Non-limiting examples of the chimeric proteins may comprise a formula, which comprises:
 (1) FVIII(X1)-L1-F1:V-L2-X2-L3-F2;
 (2) FVIII(X1)-L1-F1:F2-L3-X2-L2-V;
 (3) F1-L1-FVIII(X1):V-L2-X2-L3-F2;
 (4) F1-L1-FVIII(X1):F2-L3-X2-L2-V;
 (5) FVIII(X1)-L1-F1-L4-V-L2-X2-L3-F2;
 (6) FVIII(X1)-L1-F1-L4-F2-L3-X2-L2-V;
 (7) F1-L1-FVIII(X1)-L4-V-L2-X2-L3-F2, or
 (8) F1-L1-FVIII(X1)-L4-F2-L3-X2-L2-V,
wherein FVIII(X1) comprises a FVIII protein and one or more XTEN sequences, wherein one or more of the XTEN sequences are linked to the N-terminus or C-terminus of the FVIII protein or inserted immediately downstream of one or more amino acids in the FVIII protein (e.g., one or more XTEN insertion sites);
each of L1, L2, or L3 comprises an optional linker, e.g., a cleavable linker;
L4 is a linker, a processable linker;
X2 comprises one or more XTEN sequences;
F1 comprises an Ig constant region or a portion thereof;
F2 comprises an optional additional Ig constant region or a portion thereof, and
V comprises a VWF fragment;
(-) is a peptide bond or one or more amino acids; and
(:) comprises a covalent bond or a non-covalent bond.

One aspect of the invention is that the VWF fragment useful for the chimeric protein does not bind to a VWF clearance receptor, which prevents or inhibits interaction of the FVIII protein with endogenous VWF. The chimeric protein comprising the VWF fragment thus has reduced clearance or is not cleared through a VWF clearance pathway. Another aspect of the invention is that the VWF fragment is capable of protecting the FVIII protein from one or more protease cleavages, protecting the FVIII protein from activation, stabilizing the heavy chain and/or the light chain of the FVIII protein, or preventing clearance of the FVIII protein by one or more scavenger receptors.

Because of the VWF fragment's ability to prevent or inhibit interaction between the FVIII protein and endogenous VWF, the half-life of the FVIII protein, is extended compared to a FVIII protein without the VWF fragment. In one embodiment, the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of the FVIII protein is at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, or at least about 108 hours.

The Ig constant region or a portion thereof useful for the chimeric protein comprises a first Fc region, which is linked to the VWF fragment by an optional linker, e.g., a cleavable linker. The chimeric protein can further comprise an additional Ig constant region or a portion thereof, which is linked to the FVIII protein or the XTEN sequence, the Ig constant region or a portion thereof, the VWF fragment, or any combinations thereof by an optional linker. In one embodiment, the additional Ig constant region or a portion thereof is linked to the FVIII protein by an optional linker. The additional Ig constant region or a portion thereof can comprise a second Fc region.

The Ig constant region or a portion thereof useful in the present invention and the additional Ig constant region or a portion thereof useful in the present invention are identical or different.

In some aspects, the FVIII protein is linked to an XTEN sequence at the C-terminus or the N-terminus of the FVIII protein or inserted immediately downstream of one or more amino acids in mature native human FVIII (e.g., one or more [mature FVIII sequence-full length]) selected from the group consisting of the amino acid residues in Table 7, 8, 9, 10, 11, or any combinations thereof.

In another embodiment, the one or more insertion sites are located in one or more permissive loops of mature native human FVIII. In other embodiments, the one or more insertion sites are located in the a3 region of mature native human FVIII. For example, an XTEN sequence can be inserted immediately downstream of amino acid 1656 corresponding to SEQ ID NO: 4 (full length mature FVIII). In other embodiments, a FVIII protein is linked to at least two XTEN sequences, a first XTEN sequence inserted within the a3 region, and a second XTEN sequence inserted within a permissive loop in the FVIII protein (e.g., A1-1, A1-2, A2-1, A2-2, A3-1, or A3-2). In still other embodiments, a FVIII protein is linked to at least three XTEN sequences, a first XTEN sequence inserted within the a3 region and a second XTEN sequence and a third XTEN sequence inserted within one or two permissive loop in the FVIII protein (e.g., A1-1, A1-2, A2-1, A2-2, A3-1, or A3-2).

In certain embodiments, the one or more insertion sites for one or more XTEN insertions are immediately downstream of one or more amino acids (numbered relative to mature FVIII sequence) selected from the group consisting of:

| | | |
|---|---|---|
| (1) amino acid 3, | (2) amino acid 18, | (3) amino acid 22, |
| (4) amino acid 26, | (5) amino acid 32, | (6) amino acid 40, |
| (7) amino acid 60, | (8) amino acid 65, | (9) amino acid 81, |
| (10) amino acid 116, | (11) amino acid 119, | (12) amino acid 130, |
| (13) amino acid 188, | (14) amino acid 211, | (15) amino acid 216, |
| (16) amino acid 220, | (17) amino acid 224, | (18) amino acid 230, |
| (19) amino acid 333, | (20) amino acid 336, | (21) amino acid 339, |
| (22) amino acid 375, | (23) amino acid 399, | (24) amino acid 403, |
| (25) amino acid 409, | (26) amino acid 416, | (26) amino acid 442, |
| (28) amino acid 487, | (29) amino acid 490, | (30) amino acid 494, |
| (31) amino acid 500, | (32) amino acid 518, | (33) amino acid 599, |
| (34) amino acid 603, | (35) amino acid 713, | (36) amino acid 745, |
| (37) amino acid 1656, | (38) amino acid 1711, | (39) amino acid 1720, |
| (40) amino acid 1725, | (41) amino acid 1749, | (42) amino acid 1796, |
| (43) amino acid 1802, | (44) amino acid 1827, | (45) amino acid 1861, |
| (46) amino acid 1896, | (47) amino acid 1900, | (48) amino acid 1904, |
| (49) amino acid 1905, | (50) amino acid 1910, | (51) amino acid 1937, |
| (52) amino acid 2019, | (53) amino acid 2068, | (54) amino acid 2111, |
| (55) amino acid 2120, | (56) amino acid 2171, | (57) amino acid 2188, |
| (58) amino acid 2227, | (59) amino acid 2277, and | (60) | insertion sites) or any combinations thereof. One or more insertion sites in the FVIII protein can be located within one or more domains of the FVIII protein selected from the group consisting of the A1 domain, the a1 acidic region, the A2 domain, the a2 acidic region, the A3 domain, the B domain, the C1 domain, the C2 domain, and any combinations thereof or between one or more domains of the FVIII protein selected from the group consisting of the A1 domain and a1 acidic region, the a1 acidic region and A2 domain, the A2 domain and a2 acidic region, the a2 acidic region and B domain, the B domain and A3 domain, the A3 domain and C1 domain, the C1 domain and C2 domain, and any combinations thereof or between two domains of the FVIII protein selected from the group consisting of the A1 domain and a1 acidic region, the a1 acidic region and A2 domain, the A2 domain and a2 acidic region, the a2 acidic region and B domain, the B domain and A3 domain, the A3 domain and C1 domain, the C1 domain and C2 domain, and any combinations thereof.

In one embodiment, the one or more insertion sites are located immediately downstream of one or more amino acids in mature native human FVIII (e.g., SEQ ID NO: 4 two or more combinations thereof.

In some embodiments, one XTEN is inserted in the FVIII protein. In some embodiments, two XTENs are inserted in the FVIII protein. In some embodiments, 3 XTENs are inserted in the FVIII protein.

In a particular example, a first XTEN is inserted immediately downstream of amino acid 26 corresponding to SEQ ID NO: 4, and a second XTEN is inserted immediately downstream of amino acid 1720 corresponding to SEQ ID NO: 4 (full-length mature FVIII). In another example, a first XTEN is inserted immediately downstream of amino acid 403 corresponding to SEQ ID NO: 4, and a second XTEN is inserted immediately downstream of amino acid 1720 corresponding to SEQ ID NO: 4. In some examples, a first XTEN is inserted immediately downstream of amino acid 1656 corresponding to SEQ ID NO: 4, and a second XTEN is inserted immediately downstream of amino acid 1720 corresponding to SEQ ID NO: 4. In other examples, a first XTEN is inserted immediately downstream of amino acid 26 corresponding to SEQ ID NO: 4, a second XTEN is inserted immediately downstream of amino acid 1656 corresponding to SEQ ID NO: 4, and a third XTEN is inserted immediately downstream of amino acid 1720 corresponding to SEQ ID NO: 4. In yet other embodiments, a first XTEN is inserted immediately downstream of amino acid 403 corresponding to SEQ ID NO: 4, a second XTEN is inserted immediately downstream of amino acid 1656 corresponding to SEQ ID NO: 4, and a third XTEN is inserted immediately downstream of amino acid 1720 corresponding to SEQ ID NO: 4. In still other embodiments, a first XTEN is inserted between amino acids 403 and 404 corresponding to SEQ ID NO: 4, a second XTEN is inserted immediately downstream of amino acid 1656 corresponding to SEQ ID NO: 4, and a third XTEN is inserted immediately downstream of amino acid 1720 corresponding to SEQ ID NO: 4. In certain embodiments, a first XTEN is inserted immediately downstream of amino acid 26 corresponding to SEQ ID NO: 4 (full-length mature FVIII), a second XTEN is inserted immediately downstream of amino acid 1720 corresponding to SEQ ID NO: 4, and a third XTEN is inserted immediately downstream of amino acid 1900 corresponding to SEQ ID NO: 4. In some embodiments, a first XTEN is inserted immediately downstream of amino acid 26 corresponding to SEQ ID NO: 4, a second XTEN is inserted immediately downstream of amino acid 1656 corresponding to SEQ ID NO: 2, a third XTEN is inserted immediately downstream of amino acid 1720 corresponding to SEQ ID NO: 4, and a fourth XTEN is inserted immediately downstream of amino acid 1900 corresponding to SEQ ID NO: 4. In another example, an XTEN is inserted immediately downstream of amino acid 745 corresponding to SEQ ID NO: 4. In an additional example, a first XTEN is inserted immediately downstream of amino acid 1656 corresponding to SEQ ID NO: 4 and a second XTEN is inserted immediately downstream of amino acid 1900 corresponding to SEQ ID NO: 4. In some embodiments, a first XTEN is inserted immediately downstream of amino acid 26 corresponding to SEQ ID NO: 4, a second XTEN is inserted immediately downstream of amino acid 1656 corresponding to SEQ ID NO: 4, and a third XTEN is inserted immediately downstream of amino acid 1900 corresponding to SEQ ID NO: 4. In another example, a first XTEN is immediately inserted downstream of amino acid 403 corresponding to SEQ ID NO: 4 and a second XTEN is inserted immediately downstream of amino acid 745 corresponding to SEQ ID NO: 4. In some embodiments, a first XTEN is inserted immediately downstream of amino acid 745 of corresponding to SEQ ID NO: 4, and a second XTEN is inserted immediately downstream of amino acid 1900 corresponding to SEQ ID NO: 4. In some embodiments, a first XTEN is inserted immediately downstream of amino acid 18 corresponding to SEQ ID NO: 4, and a second XTEN is inserted immediately downstream of amino acid 745 corresponding to SEQ ID NO: 4.

In some embodiments, the FVIII protein is a dual chain FVIII isoform. In some embodiments, the FVIII protein is a single chain FVIII isoform.

In some embodiments, the XTEN that is inserted is SEQ ID NO: 39 (AE288). In some examples, the XTENs that are inserted are SEQ ID NOs: 38 and 37 (AG144 and AE144). In some examples, the XTENs that are inserted are SEQ ID NOs: 37, 38 and 37 (AE144, AG144, and AE144). In some embodiments. the XTENs that are inserted are SEQ ID NOs: 37 and 40 (AE144 and AE288). In some embodiments, the XTENs that are inserted are AE42 (SEQ ID NO: 36), AE72 (SEQ ID NO: 127), AE144_2A (SEQ ID NO: 128), AE144_3B (SEQ ID NO: 129), AE144_4A (SEQ ID NO: 130), AE144_5A (SEQ ID NO: 131), AE144_6B (SEQ ID NO: 132), AG144_A (SEQ ID NO: 133), AG144_B (SEQ ID NO: 134), AG144_C (SEQ ID NO: 135), AG144_F (SEQ ID NO: 136), AE864 (SEQ ID NO: 43), AE576 (SEQ ID NO: 41), AE288 (SEQ ID NO: 39), AE288_2 (SEQ ID NO: 137), AE144 (SEQ ID NO: 37), AG864 (SEQ ID NO: 44), AG576 (SEQ ID NO: 42), AG288 (SEQ ID NO: 40), AG144 (SEQ ID NO: 38), and any combinations thereof.

The FVIII protein useful in the invention can comprise B domain or a portion thereof, e.g., SQ B domain deleted FVIII. In one embodiment, the FVIII protein comprises single chain FVIII. In another embodiment, the single chain FVIII contains at least one amino acid substitution at a residue corresponding to residue 1648, residue 1645, or both of full-length mature Factor VIII polypeptide (SEQ ID NO: 4) or residue 754, residue 751, or both of SQ BDD Factor VIII (SEQ ID NO: 6). In other embodiments, the amino acid substitution is an amino acid other than arginine. In some embodiments, the FVIII protein comprises a heavy chain of FVIII and a light chain of FVIII, wherein the heavy chain and the light chain are associated with each other by a metal bond.

The FVIII protein can have a low affinity to or does not bind to a low-density lipoprotein receptor-related protein (LRP), e.g., by containing at least one amino acid substitution that lowers the affinity to or eliminates the binding to the LRP. Such at least one amino acid substitution can be at a residue corresponding to residue 471, residue 484, residue 487, residue 490, residue 497, residue 2092, residue 2093 or two or more combinations thereof of full-length mature FVIII. In a particular embodiment, the amino acid substitution at residue 471, 484, or 497 is an amino acid other than arginine, the amino acid substitution at residue 487 is an amino acid other than tyrosine, the amino acid substitution at residue 2092 is an amino acid other than lysine, or the amino acid substitution at residue 2093 is an amino acid other than phenylalanine.

In some embodiments, the FVIII protein contains at least one amino acid substitution, which induces the FVIII protein to be more stable than a FVIII protein without the substitution. Such substitutions can be located in the A2 domain and the A3 domain of the FVIII protein, e.g., at a residue corresponding to residue 664, residue 1826, residue 662, residue 1828, or two or more combinations thereof of full-length mature FVIII.

The VWF fragment useful for the present invention comprises a D' domain and D3 domain, which together are capable of binding to FVIII. The VWF fragment can comprise the amino acid sequence of the D' domain is at least 90%, 95%, 96%, 97%, 98%, 99%, or 100% identical to amino acids 764 to 866 of SEQ ID NO: 2 and/or the amino acid sequence of the D3 domain is at least 90%, 95%, 96%, 97%, 98%, 99%, or 100% identical to amino acids 867 to 1240 of SEQ ID NO: 2. In one embodiment, the VWF fragment is a monomer. In another embodiment, the VWF fragment comprises at least two VWF fragments, at least three VWF fragments, at least four VWF fragments, at least five VWF fragments, or at least six VWF fragments. In one embodiment, the two or more VWF fragments may be identical or they may be different. The VWF fragment can comprise an amino acid at least 90%, 95%, 96%, 97%, 98%, 99%, or 100% identical to amino acids 764 to 1240 of SEQ ID NO: 2. The VWF fragment may consist essentially of or consist of amino acids 764 to 1240 of SEQ ID NO: 2. In certain embodiments, the VWF fragment can contain at least one amino acid substitution at a residue corresponding to residue 1099, residue 1142, or both residues 1099 and 1142 of SEQ ID NO: 2. In other embodiments, the VWF fragment further comprises the D1 domain, the D2 domain, or the D1 and D2 domains of VWF.

The VWF fragment may further comprise a VWF domain selected from the group consisting of the A1 domain, the A2 domain, the A3 domain, the D4 domain, the B1 domain, the B2 domain, the B3 domain, the C1 domain, the C2 domain, the CK domain, one or more fragments thereof, and any combinations thereof. For example, the VWF fragment can consist essentially of or consist of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof. In some embodiments, the VWF fragment further comprises a signal peptide of VWF or FVIII which is operably linked to the VWF fragment.

One or more of the linkers useful in the invention have a length of at least about 10, 20, 30, 40, 50, 60, 70, 80, 90, 100, 110, 120, 130, 140, 150, 160, 170, 180, 190, 200, 210, 220, 230, 240, 250, 300, 350, 400, 450, 500, 550, 600, 650, 700, 750, 800, 850, 900, 950, 1000, 1200, 1400, 1600, 1800, or 2000 amino acids. In some embodiments, one or more of the linkers have a length of about 1 to about 2000 amino acids. In one embodiment, one or more of the linkers have a length of at least about 20, 35, 42, 48, 73, 75, 95, 98, 144, 288, 324, 333, 576, or 864 amino acids. In another embodiment, one or more of the linkers comprise a gly/ser peptide, an XTEN sequence, or both. Examples of the gly/ser peptide include, but are not limited to, a formula of (Gly$_4$Ser)$_n$ (SEQ ID NO: 139) or S(Gly$_4$Ser)$_n$ (SEQ ID NO: 140), wherein n is a positive integer selected from the group consisting of 1, 2, 3, 4, 5, 6, 7, 8, 9 and 10. For example, the (Gly$_4$Ser)$_n$ linker can be (Gly$_4$Ser)$_3$ (SEQ ID NO: 63) or (Gly$_4$Ser)$_4$ (SEQ ID NO: 138). In one embodiment, the linker comprises at least one first cleavage site at the N-terminus of the linker, at least one second cleavage site at the C-terminus of the linker, or both. In another embodiment, the linker comprises 20 amino acids, 35 amino acids, 48 amino acids, 73 amino acids, or 95 amino acids thrombin cleavable linker. The cleavable linkers can comprise one or more of the cleavage sites by a protease selected from the group consisting of factor XIa, factor XIIa, kallikrein, factor VIIa, factor IXa, factor Xa, factor IIa (thrombin), Elastase-2, Granzyme-B, TEV, Enterokinase, Protease 3C, Sortase A, MMP-12, MMP-13, MMP-17, and MMP-20, e.g., TLDPRSFLLRNPNDKYEPFWEDEEK (SEQ ID NO: 8). Non-limiting examples of one or more of the cleavage sites comprise an amino acid sequence selected from the group consisting of RRRR (SEQ ID NO: 9), RKRRKR (SEQ ID NO: 10), RRRRS (SEQ ID NO: 11), TQSFNDFTR (SEQ ID NO: 12), SVSQTSKLTR (SEQ ID NO: 13), DFLAEGGGVR (SEQ ID NO: 14), TTKIKPR (SEQ ID NO: 15), LVPRG (SEQ ID NO: 16), ALRPR (SEQ ID NO: 17), KLTRAET (SEQ ID NO: 18), DFTRVVG (SEQ ID NO: 19), TMTRIVGG (SEQ ID NO: 20), SPFRSTGG (SEQ ID NO: 21), LQVRIVGG (SEQ ID NO: 22), PLGRIVGG (SEQ ID NO:23), IEGRTVGG (SEQ ID NO: 24), LTPRSLLV (SEQ ID NO: 25), LGPVSGVP (SEQ ID NO: 26), VAGDSLEE (SEQ ID NO: 27), GPAGLGGA (SEQ ID NO: 28), GPAGLRGA (SEQ ID NO: 29), APLGLRLR (SEQ ID NO: 30), PALPLVAQ (SEQ ID NO: 31), ENLYFQG (SEQ ID NO: 32), DDDKIVGG (SEQ ID NO: 33), LEVLFQGP (SEQ ID NO: 34), and LPKTGSES (SEQ ID NO: 35). In some embodiments, the first cleavage site and the second cleavage site are identical or different.

The XTEN sequence useful for the invention can be selected from the group consisting of AE42 (SEQ ID NO: 36), AE144 (SEQ ID NO: 37), AG144 (SEQ ID NO: 38), AE288 (SEQ ID NO: 39), AG288 (SEQ ID NO: 40), AE576 (SEQ ID NO: 41), AG576 (SEQ ID NO: 42), AE864 (SEQ ID NO: 43), AE72 (SEQ ID NO: 127), AE144_2A (SEQ ID NO: 128), AE144_3B (SEQ ID NO: 129), AE144_4A (SEQ ID NO: 130), AE144_5A (SEQ ID NO: 131), AE144_6B (SEQ ID NO: 132), AG144_A (SEQ ID NO: 133), AG144_B (SEQ ID NO: 134), AG144_C (SEQ ID NO:135), AG144_F (SEQ ID NO: 136), AE288_2 (SEQ ID NO: 137), or AG864 (SEQ ID NO: 44). In a particular embodiment, the XTEN sequence comprises AE288 or AG288.

The chimeric protein of the invention can be polysialylated, pegylated, or hesylated.

The present invention is also directed to a polynucleotide or a set of polynucleotides encoding the chimeric protein. The polynucleotide can further comprise a polynucleotide chain, which encodes PC5 or PC7. The invention is also directed to a vector comprising the polynucleotide or the set of polynucleotides and one or more promoter operably linked to the polynucleotide or the set of polynucleotides. The vector can further comprise an additional vector, which comprises a polynucleotide chain encoding PC5 or PC7. The invention is also drawn to a host cell comprising the polynucleotide or the vector. The host cell can be a mammalian cell, e.g., HEK293 cell, CHO cell, or BHK cell. In some embodiments, the PC5 or PC7 of the host cell cleaves the D1D2 domains of VWF.

The invention is also directed to a pharmaceutical composition comprising the chimeric protein, the polynucleotide, the vector, or the host cell, and a pharmaceutically acceptable carrier. The composition of the invention thus has an extended half-life compared to wild type FVIII protein. The half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. The half-life of Factor VIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

The composition of the present invention can be administered by a route selected from the group consisting of topical administration, intraocular administration, parenteral administration, intrathecal administration, subdural administration and oral administration. In one embodiment, the composition is administered via parenteral administration, e.g., intravenous or subcutaneous administration. The composition of the invention is useful to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In one embodiment, the subject treated with the chimeric protein is scheduled to undergo a surgery. In another embodiment, the treatment is prophylactic or on-demand.

The invention is also directed to a method of preventing or inhibiting binding of a FVIII protein with endogenous VWF comprising adding an effective amount of the chimeric protein, the polynucleotide vector, the host cell, or the composition to a subject in need thereof, wherein the VWF fragment binds to the FVIII protein and thus prevents or inhibits binding of endogenous VWF. The present invention is further directed to a method of extending or increasing the half-life of the FVIII protein, wherein the method comprises administering an effective amount of the chimeric protein, the polynucleotide, the vector, the host cell, or the composition to a subject in need thereof, wherein the VWF fragment binds to the FVIII protein and thus extends or increases the half-life of the FVIII protein. Also provided is a method of preventing or inhibiting clearance of a FVIII protein from a cell, wherein the method comprises administering an effective amount of the chimeric protein, the polynucleotide, the vector, the host cell, or the composition to a cell comprising a FVIII protein or a polynucleotide encoding the FVIII protein, wherein the protein having VWF activity binds to the FVIII protein. The subject useful for the present methods is an animal, e.g., a human, e.g., a patient suffering from hemophilia A.

The present invention also provides a method of treating a bleeding disease or disorder in a subject in need thereof comprising administering an effective amount of the chimeric protein, the polynucleotide, the vector, the host cell, or the composition, wherein the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. The treatment can be prophylactic or on-demand. In one embodiment, the effective amount is 0.1 µg/kg to 500 mg/kg.

The invention also includes a method of making a chimeric protein, comprising transfecting one or more host cell with the polynucleotide or the vector and expressing the chimeric protein in the host cell.

BRIEF DESCRIPTION OF THE DRAWINGS/FIGURES

FIGS. 1A-1D. Schematic diagrams of VWF fragments. FIG. 1A shows three exemplary VWF fragments useful for the invention, e.g., VWF-002, VWF-010, and VWF-013. VWF-002 contains amino acids 1 to 477 of SEQ ID NO: 124 (amino acids 764 to 1240 of SEQ ID NO: 2) and is synthesized without the pre/propeptide sequences. VWF-010 contains the D1D2 domains in addition to the D'D3 domains. VWF-013 contains the D1D2D'D3 domains in addition to alanine residues substituting cysteines at residues 336 and 379 of SEQ ID NO: 123. FIG. 1B shows VWF-031, which contains the D1D2D'D3 domains fused to an Ig constant region or a portion thereof, e.g., an Fc region, by a cleavable linker, e.g., a 48 amino acids thrombin cleavable linker. FIG. 1C shows VWF-025, which is a nucleotide sequence encoding D1D2D'D3 domains contained in pLIVE vector, and VWF-029, which is a nucleotide sequence encoding D1D2D'D3 domains with two amino acid substitutions, C336A and C379A, in pLIVE vector. FIG. 1D shows full-length VWF fragment comprising propeptide (the D1 and D2 domains) and mature subunits (the D', D3, A1, A2, A3, D4, B1-3, C1-2 domains). The VWF fragment is about 250 kDa protein and forms multimers (>20 MDa) by disulfide bonding. The VWF fragment associates with FVIII (95-98%) in non-covalent complex and then extends half-life of FVIII by protecting FVIII from protease cleavage/activation, stabilizing heavy & light chain, and preventing clearance of FVIII by scavenger receptors. The VWF fragment also can limit half-life of FVIII by clearance of FVIII-VWF complex through VWF receptors and preventing pinocytosis and recycling of rFVIIIFc.

FIGS. 2A-2C. Pharmacokinetic profile of rFVIII-XTEN (rFVIII-AE288 or rFVIII-288AE) in VWF D'D3 expression mice or in FVIII and VWF double knockout (DKO) mice. FIG. 2A shows the timeline of hydrodynamic injection (HDI) of the D'D3 domain encoding plasmid DNA (VWF-025) (day −5), intravenous dosing of rFVIII-XTEN AE288 (day 0), and PK sample collection (day 5). FIG. 2B shows FVIII activity measured by a FVIII chromogenic assay after IV dosing of rFVIII-XTEN288 in D1D2D'D3 mice (inverted triangle) and rFVIII-XTEN288 in DKO mice (diamond). FIG. 2C shows the D'D3 plasma level (ng/mL) after administration of VWF-025. The X axis represents time in hours.

FIG. 3. Schematic diagram of exemplary VWF:FVIII heterodimer constructs. The constructs have the common structure represented as formula FVIII-F1-L1-V-X-L2-F2, but contain examples of different variable linkers. The construct (FVIII-161) shown contains a heterodimeric FVIII (the heavy chain and the light chain are associated by a metal bond) linked to a first Fc region and a VWF fragment, which is the D' and D3 domains of VWF (i.e., amino acids 1 to 477 of SEQ ID NO: 2 with amino acid substitutions C336A and C379A) linked to an XTEN sequence, which is further linked to a cleavable linker and a second Fc region. The XTEN sequence contained in FVIII-161 is an XTEN AE288 sequence, and the linker is a thrombin cleavable linker, which has 35 amino acids. In FVIII-161, the FVIII protein linked to the first Fc region is linked to the VWF fragment by a processable linker. Upon expression, the processable linker can be cleaved by an intracellular processing enzyme, thus making the construct three polypeptide chains associated with each other.

FIGS. 4A-4E are schematic diagrams of FVIII-VWF heterodimer or monomer examples. FVIII-168, FVIII-175, FVIII-172, FVIII-174, and FVIII170. Construct FVIII-168 comprises a single chain FVIII sequence (having an alanine residue substitute the arginine residues at residues 1645 and 1648) linked to a first Fc region, which is then fused to a VWF fragment linked to a second Fc region by a thrombin cleavable linker, which has 48 amino acids. AE288 XTEN is inserted in the B domain of the single chain FVIII sequence. The linkage between the first Fc region and the VWF fragment comprises a linker that is capable of being cleaved by an intracellular processing enzyme, i.e., processable linker. Construct FVIII-175 comprises a single chain FVIII (having an alanine residue substitute the arginine residues at residues 1645 and 1648) linked to AE288 XTEN and a first Fc region, which is linked to a second Fc region by a linker, e.g., a processable linker. AE288 XTEN is inserted in the B domain of the single chain FVIII sequence. Construct FVIII-172 comprises two polypeptide chains, a first chain comprising a heavy chain FVIII sequence fused to AE288 XTEN, a second chain comprising a light chain FVIII sequence, a first Fc region, a linker (e.g., a processable linker), a VWF fragment, a thrombin cleavable linker (e.g., 48 amino acids), and a second Fc region. Construct FVIII- 174 comprises two polypeptide chains, a first chain comprising a heavy chain FVIII sequence fused to AE288 XTEN and a second chain comprises a light chain FVIII, a first Fc region, a linker (e.g., a processable linker), and a second Fc region. Construct FVIII-170 comprises a VWF fragment, AE288 XTEN, a linker (e.g., a thrombin cleavable linker, which is 35 amino acids in length), and a single chain FVIII sequence.

FIG. 5. Pharmacokinetic profile of FVIII/VWF heterodimers containing an XTEN sequence in combination with an Fc region. Constructs FVIII-161, FVIII-168, and FVIII-172 were administered to FVIII:VWF double knockout (DKO) mice by Hydrodynamic injection (HDI) at 100 ug/mouse dose. Construct FVIII-170 was administered to FVIII:VWF DKO mice by HDI at 50 μg/mouse dose. The post-HDI plasma FVIII activity was analyzed by FVIII chromogenic assay for 24 hr post-HDI. The FVIII activity of the FVIII:VWF heterodimers containing an XTEN sequence and Fc domains was compared with the FVIII activity of BDD-FVIII without the VWF fragment, XTEN sequence, and Fc domains.

FIGS. 6A-6B. Schematic diagrams of FVIII-VWF heterodimer examples co-transfection system. FIG. 6A. Construct FVIII-169 contains the full-length FVIII sequence (with an alanine residue substituting the arginine residues at 1645 and 1648 and with an XTEN sequence inserted in the single chain FVIII sequence), which is linked to an Fc region. VWF-031 contains the D1D2D'D3 fragment (with an alanine residue substituting the cysteine residues at 336 and 379) which is linked to another Fc region with a 48 thrombin cleavable linker. After intracellular processing, construct FVIII-169 produces a full length single chain FVIII (SCFVIII) fused to one Fc fragment and an XTEN sequence, and construct VWF-031 produces a 477 amino acid D'D3 fragment linked to another Fc fragment. Two covalent bonds can be formed between the Fc fragments that are linked to the SC FVIII or the D'D3 fragment, this in turn allows a non-covalent association of FVIII and D'D3. FIG. 6B. Construct FVIII-173 contains a heterodimeric FVIII sequence, a heavy chain FVIII sequence linked to an XTEN sequence and a light chain FVIII sequence linked to an Fc region. VWF-031 is described above. After intracellular processing, construct FVIII-173 produces a heterodimeric protein, a heavy chain FVIII fused to an XTEN sequence, a light chain FVIII fused to one Fc fragment, and construct VWF-031 produces a 477 amino acid D'D3 fragment linked to another Fc fragment. Two covalent bonds can be formed between the Fc fragments that are linked to the light chain FVIII or the D'D3 fragment, this in turn allows a non-covalent association of FVIII and D'D3.

FIGS. 7A-7B. Binding Affinity of Exemplary FVIII:VWF containing an XTEN sequence and Fc domains to immobilized hVWF in Octet assay. The binding affinity for FVIII-169/VWF-031 and FVIII-057 (rFVIIIFc) fused to immobilized hVWF was tested using biolayer interferometry based measurements (Octet assay). FIG. 7A shows binding response in nanomoles of FVIII169 and FVIIIFc drug substance (a positive control) to immobilized hVWF. FIG. 7B shows binding response of human IgG1 (a negative control) to immobilized human VWF. FVIII-169/VWF-31 has no detectable binding toward immobilized hVWF.

FIGS. 8A-8B. Pharmacokinetic (PK) profile of FVIII-169 in HemA and FVIII:VWF double knockout (DKO) mice. FIG. 8A shows the PK profile of FVIII-169/VWF-031 and FVIIIFc in HemA mice. HemA mice were treated with a single intravenous dose of FVIII-169/VWF-031 at 200 IU/kg. Plasma samples collected from the mice were tested by FVIII chromogenic assay. Half-life of FVIII-169/VWF-031 was calculated using WinNonlin program. FIG. 8B shows the PK profile of FVIII-169/VWF-031, FVIII-169/Fc, and FVIIIFc in FVIII/VWF DKO mice.

FIGS. 9A-9B. PK profile of FVIII-XTEN variants in D'D3 expressing FVIII/VWF DKO mice. FIG. 9A shows comparison of the PK profile of the FVIII-XTEN variants, FVIII with one XTEN, FVIII with two XTENs, and FVIII with three XTENs. One, two, or three XTENs were inserted in various portions of FVIII including C-terminus and B-domain. CT indicates that an XTEN is linked to the C-terminus of FVIII. Insertion site B/CT indicates that one XTEN is inserted between amino acid residue 745 and amino acid residue 746 of the FVIII protein and another XTEN is linked to the C-terminus of the FVIII protein. The amino acid residue numbering corresponds to the SQ BDD FVIII protein sequence. Insertion site 1900/B/CT indicates that a first XTEN is inserted between amino acid residue 1900 and amino acid residue 1901 of FVIII, a second XTEN is inserted between amino acid residue 745 and amino acid residue 746 of FVIII, and a third XTEN is linked to the C-terminus of FVIII. The mouse strain used to administer the FVIII-XTEN variants is a DKO mouse strain expressing D'D3 domains. FIG. 9B shows the PK profile of FVIII-XTEN with three XTEN insertions. The FVIII-XTEN (1900/B/CT) variant was administered to either the FVIII/VWF DKO mice or HemA mice. The half-life of FVIII-XTEN (1900/B/CT) is compared.

FIG. 10. FVIII activity of FVIIIFc (hollow triangle), FVIII169:Fc (filled circle), and FVIII169:VWF31 (hollow triangle) in mouse DKO plasma measured by chromogenic assay. FVIII:Fc contains a dual-chain FVIII (Heavy chain and Light chain) fused to an Fc dimer (i.e., monomer-dimer hybrid). FVIII169 is described above (containing AE288 in the B domain, immediately downstream of amino acid 745 corresponding to mature FVIII sequence). FVIII169:Fc contains FVIII169 fused to an Fc dimer. FVIII169:VWF31 contains VWF31 in addition to the Fc dimer, FVIII169 fused to the first Fc region and VWF31 fused to the second Fc region, wherein the first Fc region and the second Fc region form a covalent bond, e.g., one or more disulfide bonds.

FIG. 11. Effects of Fc, XTEN, and VWF-D'D3 fragments on FVIII half-life extension. BDD-FVIII (REFACTO®) (square), FVIIFc (circle), FVIII169/Fc (triangle), and FVIII169/VWF031 (inverted triangle) were administered to FVIII and VWF double knockout (DKO) mice. The FVIII activity was measured by chromogenic assay, and the half-life was calculated using the WinNonlin-Phoenix program. X-axis shows time, and the Y-axis shows the FVIII plasma activity in mU/mL.

FIGS. 12A-12C. Effects of different XTENs in rFVIII-XTEN/VWF heterodimer in HemA mice. FIG. 12A shows the FVIII plasma activity normalized to 5 min value (%) of two XTENs inserted immediately downstream of residues 1900 and 1656 corresponding to mature FVIII sequence (i.e., FVIII-195 (dual chain FVIII isoform) and FVIII-199 (single chain FVIII isoform)), compared to FVIII-169 containing an XTEN immediately downstream of residue 745 corresponding to mature FVIII sequence. FVIII-169/VWF-031 (filled circle), FVIII-199/VWF-031 (filled square), and FVIII-195/VWF031 (hollow square) were administered in HemA mice to measure the FVIII plasma activity. FIG. 12B shows the half-life extension effect of the second XTEN insertion immediately downstream of residues 403 (A2 domain) and 745 (B domain) (i.e., FVIII-203) and residues 745 (B domain) and 1900 (A3 domain) (FVIII-204) corresponding to mature FVIII sequence compared to FVIII-169

(an XTEN insertion in B domain only). FVIII-204/VWF031 (filled triangle), FVIII-169/VWF-031 (filled circle), FVIII-203/VWF-031 (filled square), and scBDD-FVIII (hollow diamond) were administered to HemA mice. The X-axis shows FVIII plasma activity normalized to 5 min value (%), and the y-axis shows time in hours. FIG. 12C shows the half-life extension effect of the two XTEN insertions immediately downstream of residues 18 (A1 domain) and 745 (B domain) (i.e., FVIII-205) compared to FVIII-169 (a single XTEN insertion in the B domain) and single chain FVIII without any Fc regions or any XTENs (i.e., FVIII-207). FIG. 12C additionally shows the half-life extension effect of three XTEN insertions incorporated immediately downstream of residues 26 (A1 domain), 1656 (A3 domain), and 1900 (A3 domain) (i.e., FVIII-201) compared to FVIII-169 (a single XTEN insertion immediately downstream of residue 745). FVIII-205/VWF-031 (filled square), FVIII-201/VWF-031 (inverted triangle), FVIII-169/VWF-031 (filled circle), and FVIII-207 (hollow diamond) were administered to HemA mice. The FVIII plasma activity normalized to 5 min value (%) (X-axis) was measured over time in hours (Y-axis).

FIG. 13. FVIII activity of rFVIII-XTEN/VWF-XTEN heterodimer in FVIII/VWF DKO mice. FVIII activity of plasma samples was analyzed by FVIII chromogenic assay, and the regression curve of plasma FVIII activity (X-axis) as a function of time (Y-axis) was plotted. FVIII-155 (scFVIIIFc without any XTENs) was co-expressed with VWF-034 (VWF-Fc with AE 288 XTEN plus a 35 residue thrombin cleavable linker). The half-life of FVIII-155/VWF-034 was compared with that of FVIII-169/VWF-031, which has a AE 288 XTEN inserted into the B domain junction (immediately downstream of residue 745 corresponding to mature FVIII polypeptide) of FVIII.

FIGS. 14A-14H. Schematic diagrams of various rFVIII-XTEN/VWF constructs. These constructs are also described in other sections herein. FIG. 14A shows single chain B domain deleted FVIII protein (sometimes indicated herein as scBDD-FVIII). The scBDD-FVIII constructs contain two substitutions at residues 1645 and 1648 from Arg to Ala. FIG. 14B shows two polypeptide chain construct (FVIII155/VWF031), the first chain comprising single chain FVIII linked to an Fc region without any XTENS and the second chain comprising the VWF D'D3 fragment linked to an Fc region. This construct is used as a control. FIG. 14C shows two polypeptide chain construct (FVIII199/VWF031), the first chain comprising single chain FVIII linked to an Fc region, in which a first XTEN is inserted immediately downstream of residue 1900 corresponding to mature FVIII sequence and a second XTEN is inserted immediately downstream of residue 1656 corresponding to mature FVIII sequence, and the second chain comprising the VWF D'D3 fragment linked to an Fc region. FIG. 14D shows two polypeptide chain construct (FVIII201/VWF031), the first chain comprising single chain FVIII protein linked to an Fc region, in which a first XTEN is inserted immediately downstream of residue 26 corresponding to mature FVIII sequence, a second XTEN is inserted immediately downstream of residue 1656 corresponding to mature FVIII sequence, and a third XTEN is inserted immediately downstream of residue 1900 corresponding to mature FVIII sequence, and the second chain comprising the VWF D'D3 fragment linked to an Fc region. FIG. 14E shows two polypeptide chain constructs (FVIII169/VWF031), the first chain comprising single chain FVIII protein linked to an Fc region, in which an XTEN is inserted immediately downstream of residue 745 (indicated as "B") corresponding to mature FVIII sequence, and the second chain comprising the VWF D'D3 fragment linked to an Fc region. FIG. 14F shows two polypeptide chain construct (FVIII203/VWF031), the first chain comprising single chain FVIII protein, in which a first XTEN is inserted at residue 745 ("B") corresponding to mature FVIII sequence and a second XTEN is inserted at residue 1900 corresponding to mature FVIII sequence, and the second chain comprising the VWF D'D3 fragment linked to an Fc region. FIG. 14G shows two polypeptide chain construct (FVIII204/VWF031), the first chain comprising single chain FVIII protein linked to an Fc region, in which a first XTEN is inserted immediately downstream of residue 403 corresponding to mature FVIII sequence and a second XTEN is inserted immediately downstream of residue 745 ("B") corresponding to mature FVIII sequence, and a second chain comprising the VWF D'D3 fragment linked to an Fc region. FIG. 14H shows two polypeptide chain construct (FVIII205/VWF031), the first chain comprising single chain FVIII, in which a first XTEN is inserted immediately downstream of residue 18 corresponding to mature FVIII sequence and a second XTEN is inserted immediately downstream of residue 745 ("B") corresponding to mature FVIII sequence, and the second chain comprising the VWF D'D3 fragment linked to an Fc region.

FIG. 15. FVIII activity of rFVIII-XTEN/VWF and BDD-FVIII in FVIII/VWF DKO mice. FVIII activity of plasma samples was analyzed by FVIII chromogenic assay, and the regression curve of plasma FVIII activity (X-axis) as a function of time (Y-axis) was plotted. The half-life of rFVIII-XTEN/VWF (FVIII-205/VWF-031) was compared with that of BDD-FVIII and rFVIIIFc.

FIG. 16. Efficacy of FVIII-XTEN-Fc:VWF-Fc heterodimers in HemA mice using tail clip bleeding model. The HemA mice tail clip bleeding model was used to compare the efficacy of FVIII169/VWF034, FVIII205/VWF031, and BDD-FVIII. The median blood loss in ml for 200 IU/kg of FVIII169/VWF034 and FVIII205/VWF031 is compared with 200 IU/kg of BDD-FVIII, 65 IU/kg of BDD-FVIII, 20 IU/kg of BDD-FVIII, and vehicle.

DETAILED DESCRIPTION OF THE INVENTION

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a Factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, micro-injection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

As used herein, an "amino acid corresponding to" or an "equivalent amino acid" in a VWF sequence or a FVIII protein sequence is identified by alignment to maximize the identity or similarity between a first VWF or FVIII sequence and a second VWF or FVIII sequence. The number used to identify an equivalent amino acid in a second VWF or FVIII sequence is based on the number used to identify the corresponding amino acid in the first VWF or FVIII sequence.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number being the number of the amino acid in mature native FVIII (SEQ ID NO:4) to which the insertion site corresponds, which is immediately N-terminal to the position of the insertion. For example, the phrase "a3 comprises an XTEN at an insertion site which corresponds to amino acid 1656 of SEQ ID NO: 4" indicates that the heterologous moiety is located between two amino acids corresponding to amino acid 1656 and amino acid 1657 of SEQ ID NO: 4.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which an XTEN or any other polypeptide is inserted between two adjacent amino acids. Thus, the phrases "inserted immediately downstream of an amino acid" and "inserted between two amino acids of an insertion site" are used synonymously with "inserted at an insertion site."

The terms "inserted," "is inserted," "inserted into" or grammatically related terms, as used herein refers to the position of an XTEN in a chimeric polypeptide relative to the analogous position in native mature human FVIII. As used herein the terms refer to the characteristics of the recombinant FVIII polypeptide relative to native mature human FVIII, and do not indicate, imply or infer any methods or process by which the chimeric polypeptide was made. For example, in reference to a chimeric polypeptide provided herein, the phrase "an XTEN is inserted into immediately downstream of residue 745 of the FVIII polypeptide" means that the chimeric polypeptide comprises an XTEN immediately downstream of an amino acid which corresponds to amino acid 745 in native mature human FVIII, e.g., bounded by amino acids corresponding to amino acids 745 and 746 of native mature human FVIII.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the β-phase. The typical β-phase half-life of a human antibody in humans is 21 days.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, Factor XIa or Factor Xa. Exemplary FXIa cleavage sites include, e.g., TQSFNDFTR (SEQ ID NO: 45) and SVSQTSKLTR (SEQ ID NO: 46). Exemplary thrombin cleavage sites include, e.g., DFLAEGGGVR (SEQ ID NO: 47), TTKIKPR (SEQ ID NO: 48), LVPRG (SEQ ID NO: 49) and ALRPR (amino acids 1 to 5 of SEQ ID NO: 50). Other enzymatic cleavage sites are known in the art.

As used herein, the term "processing site" or "intracellular processing site" refers to a type of enzymatic cleavage site in a polypeptide which is a target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

The term "Furin" refers to the enzymes corresponding to EC No. 3.4.21.75. Furin is subtilisin-like proprotein convertase, which is also known as PACE (Paired basic Amino acid Cleaving Enzyme). Furin deletes sections of inactive precursor proteins to convert them into biologically active proteins. During its intracellular transport, pro-peptide of VWF can be cleaved from mature VWF molecule by a Furin enzyme. In some embodiments, Furin cleaves the D1D2 from the D'D3 of VWF. In other embodiments, a nucleotide sequence encoding Furin can be expressed together with the nucleotide sequence encoding a VWF fragment so that D1D2 domains can be cleaved off intracellularly by Furin.

In constructs that include more than one processing or cleavage site, it will be understood that such sites may be the same or different.

A "processable linker" as used herein refers to a linker comprising at least one intracellular processing site, which is described elsewhere herein.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., Von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency, and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The chimeric protein of the invention is also used for on-demand treatment. The term "on-demand treatment" refers to the administration of a chimeric molecule in response to symptoms of a bleeding episode or before an activity that may cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a chimeric protein or a VWF fragment of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

Chimeric Proteins

The present invention is directed to extending the half-life of a Factor VIII protein using a VWF fragment and an XTEN sequence by preventing or inhibiting a FVIII half-life limiting factor, i.e., endogenous VWF, from associating with the FVIII protein. Endogenous VWF associates with about 95% to about 98% of FVIII in non-covalent complexes. While endogenous VWF is a FVIII half-life limiting factor, endogenous VWF bound to a FVIII protein is also known to protect FVIII in various ways. For example, full length VWF (as a multimer having about 250 kDa) can protect FVIII from protease cleavage and FVIII activation, stabilize the FVIII heavy chain and/or light chain, and prevent clearance of FVIII by scavenger receptors. But, at the same time, endogenous VWF limits the FVIII half-life by preventing pinocytosis and by clearing FVIII-VWF complex from the system through the VWF clearance pathway. It is believed, while not bound by a theory, that endogenous VWF is a half-life limiting factor that prevents the half-life of a FVIII protein fused to a half-life extender from being longer than about two-fold that of wild-type FVIII. Therefore, the present invention is directed to preventing or inhibiting interaction between endogenous VWF and a FVIII protein using a VWF fragment, thereby increasing a half-life of the FVIII protein by using an XTEN sequence alone or an XTEN sequence in combination with an Ig constant region or a portion thereof. The XTEN sequence can be linked to the FVIII protein or the VWF fragment. The FVIII protein associated with the VWF fragment is thus cleared from the circulation more slowly by one or more VWF clearance receptors and then can have the full half-life extension of the XTEN sequence or the XTEN sequence in combination of the Ig constant region, as compared to wild type FVIII or a FVIII protein without the VWF fragment.

In one embodiment, a VWF fragment is associated (or linked) with the FVIII protein by a covalent or a non-covalent bond. In some instances, however, the physical blockage or chemical association (e.g., non-covalent bonding) between the VWF fragment and the FVIII protein may not be strong enough to provide a stable complex comprising the FVIII protein and the VWF fragment in the presence of endogenous VWF. For example, a VWF fragment forming a non-covalent bond with a FVIII protein without any other connections may readily be dissociated in vivo from the FVIII protein in the presence of endogenous VWF, replacing the VWF fragment (e.g., recombinant VWF, i.e., rVWF) with endogenous VWF. Therefore, the FVIII protein non-covalently bound to endogenous VWF would undergo the VWF clearance pathway and be readily cleared from the system. In order to prevent the dissociation of the VWF fragment with the FVIII protein, in some embodiments, the association or linkage between the FVIII protein and the VWF fragment is a covalent bond, e.g., a peptide bond, one or more amino acids, or a disulfide bond. In certain embodiments, the association (i.e., linkage) between the adjunct moiety and the FVIII protein is a peptide bond or a linker between the FVIII protein and the VWF fragment ("FVIII/VWF linker"). Non-limiting examples of the linker are described elsewhere herein. In some embodiments, the VWF fragment is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. Non-limiting examples of the VWF fragment are described elsewhere herein.

In certain embodiments, the VWF fragment chemically (e.g., non-covalently) binds to or physically blocks one or more VWF binding sites on a FVIII protein. The VWF binding site on a FVIII protein is located within the A3 domain or the C2 domain of the FVIII protein. In still other embodiments, the VWF binding site on a FVIII protein is located within the A3 domain and C2 domain. For example, the VWF binding site on a FVIII protein can correspond to amino acids 1669 to 1689 and/or 2303 to 2332 of SEQ ID NO: 4 [full-length mature FVIII].

The invention also provides a chimeric protein (comprising a FVIII protein and a VWF fragment) further comprising one or more XTEN sequences, which provide additional half-life extension properties. The one or more XTEN sequences can be inserted within the FVIII protein or the VWF fragment or linked to the N-terminus or the C-terminus of the FVIII protein or the VWF fragment. The invention also includes a FVIII protein linked to an XTEN sequence (a first half-life extending moiety) and an Ig constant region or a portion thereof (a second half-life extending moiety) so that the two half-life extending moieties extend the half-life of the FVIII protein through two different mechanisms.

In some embodiments, a chimeric protein comprises a FVIII protein linked to a first Ig constant region or a portion thereof (e.g., a first FcRn binding partner), a VWF fragment linked to a second Ig constant region or a portion thereof (e.g., a second FcRn binding partner), and one or more XTEN sequences inserted or linked to the FVIII protein or the VWF fragment, wherein the VWF fragment prevents the FVIII half-life limiting factor (e.g., endogenous VWF) from binding to the FVIII protein, wherein the first and second Ig constant regions or portions thereof forms a covalent bond, e.g., a disulfide bond, and the one or more XTEN sequences extends the half-life of the FVIII protein.

In certain embodiments, a chimeric protein of the invention comprises a FVIII protein linked to a VWF fragment by an optional linker (i.e., FVIII/VWF linker) and one or more XTEN sequences inserted or linked to the FVIII protein or the VWF fragment, wherein the VWF fragment prevents the FVIII half-life limiting factor (e.g., endogenous VWF) from binding to the FVIII protein and the one or more XTEN sequences extends the half-life of the FVIII protein. In one aspect, the optional linker (FVIII/VWF linker) comprises a sortase recognition motif. In another aspect, the optional linker (FVIII/VWF linker) comprises a cleavable site. Examples of the cleavage linker (i.e., linker containing one or more cleavage site) are described elsewhere herein.

The chimeric protein of the present invention includes, but is not limited to:
(1) a VWF fragment comprising a D' domain and a D3 domain, an XTEN sequence, and FVIII, wherein the XTEN sequence is linked to the VWF fragment;
(2) a FVIII protein, an XTEN sequence, and an Ig constant region or a portion thereof, wherein the FVIII protein is linked to an XTEN sequence and the Ig constant region or a portion thereof, or
(3) a FVIII protein, an XTEN sequence, and a VWF fragment, wherein the XTEN sequence is linked to the FVIII protein at the C-terminus or N-terminus or inserted immediately downstream of one or more amino acids (e.g., one or more XTEN insertion sites) of FVIII, and the VWF fragment and the FVIII protein are associated with each other.

(1) Von Willebrand Factor (VWF) Fragment Linked to XTEN, and FVIII

The present invention is directed to a chimeric protein comprising (i) a VWF fragment comprising a D' domain and a D3 domain of VWF, (ii) an XTEN sequence, and (iii) a FVIII protein, wherein (i), (ii), and (iii) are linked to or associated with each other. The VWF fragment linked to the XTEN sequence, as a part of a chimeric protein in the present invention, associates with the FVIII protein, thus preventing or inhibiting interaction between endogenous VWF and the FVIII protein. In certain embodiments, the VWF fragment, which is capable of preventing or inhibiting binding of the FVIII protein with endogenous VWF, can at the same time have at least one VWF-like FVIII protecting property. Examples of the VWF-like FVIII protecting properties include, but are not limited to, protecting FVIII from protease cleavage and FVIII activation, stabilizing the FVIII heavy chain and/or light chain, and preventing clearance of FVIII by scavenger receptors. As a result, the VWF fragment can prevent clearance of the FVIII protein through the VWF clearance pathway, thus reducing clearance of FVIII from the circulatory system. In some embodiments, the VWF fragments of the present invention bind to or are associated with a FVIII protein and/or physically or chemically block the VWF binding site on the FVIII protein. The FVIII protein associated with the VWF fragment is thus cleared from the circulation more slowly, as compared to wild type FVIII or FVIII not associated with the VWF fragment.

In one embodiment, the invention is directed to a chimeric protein comprising (i) a VWF fragment comprising the D' domain and the D3 domain of VWF, (ii) an XTEN sequence, and (iii) a FVIII protein, wherein the XTEN sequence is linked to the VWF fragment (e.g., (a1) V-X or (a2) X-V, wherein V comprises a VWF fragment and X comprises an XTEN sequence), and the VWF fragment is linked to or associated with the FVIII protein. In another embodiment, the VWF fragment and the XTEN sequence can be linked by a linker (e.g., (a3) V-L-X or (a4) X-L-V) or a peptide bond. The linker can be a cleavable linker, e.g., a thrombin cleavable linker, which can be cleaved at the site of coagulation. In other embodiments, the VWF fragment, the XTEN sequence, and the FVIII protein are placed in a single polypeptide chain. In still other embodiments, the chimeric protein comprises two polypeptide chains, a first chain comprising the VWF fragment and the XTEN sequence and a second chain comprising the FVIII protein. In yet other embodiments, the chimeric protein comprises three polypeptide chains, a first chain comprising the VWF fragment and the XTEN sequence, a second chain comprising a light chain of FVIII and a third chain comprising a heavy chain of FVIII, wherein the first chain and the second chain are associated with each other (e.g., covalent bond, e.g., disulfide bond), and the second chain and the third chain are associated with each other (e.g., metal bond). In still other embodiments, the XTEN sequence can be linked to the N-terminus or the C-terminus of the VWF fragment or inserted immediately downstream of one or more amino acids in the VWF fragment.

In certain embodiments, a chimeric protein of the invention comprises a formula comprising:
  (a) V-X-FVIII,
  (b) FVIII-X-V,
  (c) V-X:FVIII,
  (d) X-V:FVIII,
  (e) FVIII:V-X,
  (f) FVIII:X-V, or
  (a5) X-V-FVIII,
wherein V comprises a VWF fragment,
X comprises one or more XTEN sequences,
FVIII comprises a FVIII protein;
(-) represents a peptide bond or one or more amino acids; and
(:) is a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula V-X-FVIII means formula NH2-V-X-FVIII-COOH. In one embodiment, the formulas described herein can comprise any additional sequences between the two moieties. For example, formula V-X-FVIII can further comprise any sequences at the N-terminus of V between V and X, between X and FVIII, or at the C-terminus of FVIII unless otherwise specified. In another embodiment, the hyphen (-) indicates a peptide bond.

In other embodiments, a chimeric protein of the invention comprises a formula comprising:
  (a) V(X1)-X2-FVIII,
  (b) FVIII-X2-V(X1),
  (c) V(X1):FVIII,
  (d) FVIII:V(X1), or
  (a5) X2-V(X1)-FVIII,
wherein V(X1) comprises a VWF fragment and a first XTEN sequence (X1), wherein the XTEN sequence is inserted immediately downstream of one or more amino acids in the VWF fragment,
X2 comprises one or more optional XTEN sequences,
FVIII comprises a FVIII protein;
(-) is a peptide bond or one or more amino acids; and
(:) is a chemical association or a physical association.

In some embodiments, a chimeric protein comprises (i) a VWF fragment comprising a D' domain and a D3 domain of VWF, (ii) an XTEN sequence, (iii) a FVIII protein, (iv) a first optional linker, and (v) a second optional linker, wherein the XTEN sequence is linked to the VWF fragment and/or to the FVIII protein by the linker. In certain embodiments, a chimeric protein comprises a formula comprising:
  (b1) V-L1-X-L2-FVIII,
  (b2) FVIII-L2-X-L1-V,
  (b3) V-L1-X:FVIII,
  (b4) X-L1-V:FVIII,
  (b5) FVIII:V-L1-X,
  (b6) FVIII:X-L1-V,
  (b7) X-L1-V-L2-FVIII, or
  (b8) FVIII-L2-V-L1-X,
wherein V comprises a VWF fragment,
X comprises one or more XTEN sequences,
FVIII comprises a FVIII protein,
L1 comprises a first optional linker, e.g., a first cleavable linker,
L2 comprises a second optional linker, e.g., a second cleavable linker or an optional processable linker;
(-) is a peptide bond or one or amino acids; and
(:) is a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula (b1) V-L1-X-L2-FVIII means formula NH2-V-L1-X-L2-FVIII-COOH. In one embodiment, the formulas described herein can comprise any additional sequences between the two moieties. In another embodiment, the hyphen (-) indicates a peptide bond.

Another aspect of the present invention is to provide a FVIII chimeric protein having reduced or no interactions with a FVIII half-life limiting factor, e.g., endogenous VWF, and at the same time maximizing the half-life of the FVIII protein using an XTEN sequence (a first half-life extender) in combination with a second half-life extender or a moiety providing a covalent bond between the FVIII protein and the VWF fragment, e.g., an Ig constant region or a portion thereof. In one embodiment, a chimeric protein of the invention comprises (i) a VWF fragment comprising a D' domain and a D3 domain of VWF, (ii) an XTEN sequence, (iii) a FVIII protein, and (iv) an Ig constant region or a portion thereof (also referred to herein as F), wherein (1) the VWF fragment is linked to the XTEN sequence by an optional linker, e.g., a cleavable linker, (2) the VWF fragment is associated with or linked to the FVIII protein by an additional optional linker, e.g., a cleavable linker, and (3) the Ig constant region or a portion thereof is linked to the VWF fragment, the XTEN sequence, or the FVIII protein. In another embodiment, a chimeric protein of the invention comprises (i) a VWF fragment comprising a D' domain and a D3 domain of VWF, (ii) an XTEN sequence, (iii) a FVIII protein, (iv) an Ig constant region or a portion thereof (F1 or a first Ig constant region or a portion thereof), and (v) an additional Ig constant region or a portion thereof (F2 or a second Ig constant region or a portion thereof), wherein (1) the VWF fragment is linked to the XTEN sequence by an optional linker, e.g., a cleavable linker, (2) the XTEN sequence or the VWF fragment is linked to the Ig constant region or a portion thereof, (3) the FVIII is linked to the additional Ig constant region or a portion thereof, and (4) the Ig constant region or a portion thereof is associated with or linked to the additional Ig constant region or a portion thereof. In one embodiment, the association or linkage between the two Ig constant regions or a portion thereof is a covalent bond, e.g., a disulfide bond. In another embodiment, the association or linkage between the two Ig constant regions or a portion thereof is a processable linker, wherein the processable linker is intracellularly processed by a protease. For example, the chimeric protein comprises a formula comprising:
  (g) V-L2-X-L1-F1:FVIII-L3-F2;
  (h) V-L2-X-L1-F1:F2-L3-FVIII;
  (i) F-L1-X-L2-V:FVIII-L3-F2;
  (j) F-L1-X-L2-V:F2-L3-FVIII;
  (k) V-L2-X-L1-F1-L4-FVIII-L3-F2;
  (l) F2-L3-FVIII-L4-F1-L1-X-L2-V;
  (m) FVIII-L2-F2-L4-V-L2-X-L1-F1; or
  (n) F1-L1-X-L2-V-L4-F2-L2-FVIII,
wherein V comprises a VWF fragment,
each of L1 and L3 comprises an optional linker,
L2 comprises an optional linker, e.g., a cleavable linker,
L4 is an optional linker, e.g., a processable linker,
FVIII comprises a FVIII protein,
X comprises one or more XTEN sequences, F1 comprises an optional Ig constant region or a portion thereof, F2 comprises an optional additional Ig constant region or a portion thereof;

(-) is a peptide bond or one or more amino acids; and (:) is a chemical association or a physical association.

In some embodiments, the FVIII protein in any constructs or formulas disclosed herein can further comprises at least one, at least two, at least three, at least four, at least five, or at least six XTEN sequences, each of the XTEN sequences inserted immediately downstream of one or more amino acids in the FVIII protein or linked to the N-terminus or the C-terminus of the FVIII protein. Non-limiting examples of the XTEN insertion sites are disclosed elsewhere herein.

In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula (n) F1-L1-X-L2-V-L4-F2-L2-FVIII means formula NH2-F1-L1-X-L2-V-L4-F2-L2-FVIII-COOH. In one embodiment, the formulas described herein can comprise any additional sequences between the two moieties. In another embodiment, the hyphen (-) indicates a peptide bond.

In one embodiment, either or both of the Ig constant region or a portion thereof (sometimes indicated herein by "F" or "F1") and the additional Ig constant region or a portion thereof (sometimes indicated herein by "F2") linked to the VWF fragment or the FVIII protein can extend the half-life of the VWF fragment, the FVIII protein, or both. In another embodiment, a pair of the Ig constant region or a portion thereof (sometimes indicated herein by "F" or "F1") and the additional Ig constant region or a portion thereof (sometimes indicated herein by "F2"), each of which are linked to the VWF fragment and the FVIII protein, provides a bond stronger than the non-covalent bond between the FVIII protein and the VWF fragment, i.e., a covalent bond, e.g., a disulfide bond, thereby preventing endogenous VWF from replacing the VWF fragment in vivo. F1 or F2 can comprise an Fc region or an FcRn binding partner. In other embodiments, either or both of F1 and F2 linked to the VWF fragment and/or the FVIII protein form a covalent bond (e.g., a disulfide bond) between F1 and F2, thereby placing the VWF fragment and the FVIII protein in close proximity to prevent interaction of the FVIII protein with the VWF fragment. In some embodiments, F1 and F2 are identical or different. Non-limiting examples of F1 and F2 can be selected from the group consisting of a CH1 domain, a CH2 domain, a CH3 domain, a CH4 domain, a hinge domain, any functional fragments, derivatives, or analogs thereof, and two or more combinations thereof. In one embodiment, F1, F2, or both comprise at least one CH1 domain, at least one CH2 domain, at least one CH3 domain, at least one CH4 domain, or the functional fragments, derivatives, or analogs thereof. In another embodiment, F1, F2, or both comprise at least one hinge domain or portion thereof and at least one CH2 domain or portion thereof (e.g., in the hinge-CH2 orientation). In other embodiments, F1, F2, or both comprise at least one CH2 domain or portion thereof and at least one CH3 domain or portion thereof (e.g., in the CH2-CH3 orientation.) Examples of the combination include, but are not limited to, a CH2 domain, a CH3 domain, and a hinge domain, which are also known as an Fc region (or Fc domain), e.g., a first Fc region or a first FcRn binding partner for F1 and a second Fc region or a second FcRn binding partner for F2. In other embodiments, F1 is linked to the VWF fragment by a linker, and/or F2 is linked to the FVIII protein by a linker. In some embodiments, F1 and/or F2 comprises, consisting essentially of, or consisting of a hinge region. Additional non-limiting examples of the Fc regions or the FcRn binding partners are described elsewhere herein.

In certain embodiments, a chimeric protein of the invention comprises two polypeptide chains, a first polypeptide chain comprising, consisting essentially of, or consisting of a VWF fragment comprising a D' domain and a D3 domain, an XTEN sequence, a first Ig constant region or a portion thereof (e.g., a first Fc region), and an optional linker between the VWF fragment and the XTEN sequence or the XTEN sequence or the first Ig constant region or a portion thereof and a second polypeptide chain comprising, consisting essentially of, or consisting of a FVIII protein and a second Ig constant region or a portion thereof (e.g., a second Fc region). The linker between the VWF fragment and the first Ig constant region or a portion thereof can be a cleavable linker, e.g., a thrombin cleavable linker, which can be cleaved at the site of coagulation. In some embodiments, the first polypeptide chain and the second polypeptide chain are associated with each other. The association between the first chain and the second chain prevents replacement of the first chain comprising the VWF fragment with endogenous VWF in vivo. In one embodiment, the association between the first chain and the second chain can be a covalent bond. In a particular embodiment, the covalent bond is a disulfide bond. In some embodiments, the FVIII protein in the second chain further comprises one or more XTEN sequences linked to the C-terminus or N-terminus of the FVIII protein or inserted immediately downstream of one or more amino acids (e.g., at least one insertion site disclosed herein) in the FVIII protein. Non-limiting examples of the insertion sites are described elsewhere herein.

In other embodiments, a chimeric protein of the invention comprises three polypeptide chains, wherein a first polypeptide chain comprises, consists essentially of, or consists of a heavy chain of a FVIII protein, a second polypeptide chain comprises, consists essentially of, or consists of a light chain of a FVIII protein fused to a first Ig constant region or a portion thereof (e.g., a first Fc region), and a third polypeptide chain comprises, consists essentially of, or consists of a VWF fragment comprising a D' domain and a D3 domain, an XTEN sequence, a second Ig constant region or a portion thereof (e.g., a second Fc region), and an optional linker between the XTEN sequence and the second Ig constant region or a portion thereof or the VWF fragment and the XTEN sequence. The linker in the third chain can be a cleavable linker, which is cleaved at the site of coagulation, e.g., a thrombin cleavage site. In some embodiments, the heavy chain FVIII or the light chain FVIII is linked to one or more XTEN sequences, which can be linked to the N-terminus, the C-terminus, or inserted within one or more insertion sites within the FVIII sequence. Non-limiting examples of the insertion sites are disclosed elsewhere herein.

In yet other embodiments, a chimeric protein of the invention comprises two polypeptide chains, a first polypeptide chain comprising, consisting essentially of, or consisting of a heavy chain of a FVIII protein and a second polypeptide chain comprising, consisting essentially of, or consisting of a light chain of a FVIII protein, a first Ig constant region or a portion thereof (e.g., a first Fc region), a first linker (e.g., a processable linker, which contains one or more protease cleavage sites comprising one or more intracellular processing sites), a VWF fragment, a second linker (e.g., a thrombin cleavable linker), an XTEN sequence, and a second Ig constant region or a portion thereof (e.g., a second Fc region), wherein the light chain of the FVIII protein is linked to the first Ig constant region or a portion thereof (e.g., the first Fc region), which is further linked to the VWF fragment by the first linker, and wherein the VWF fragment is linked to the XTEN sequence, which is further linked to the second Ig constant region or a portion thereof by the second linker. In certain embodiments, the first linker is a processable linker, and the second linker is a cleavable linker. Upon expression, the chimeric protein can be processed by an intracellular processing enzyme, which cleaves the processable linker, and thus the chimeric protein can comprise, consists essentially of, or consists of three polypeptide chains. In addition, the VWF fragment can be cleaved off at the site of coagulation due to the cleavable linker.

In certain embodiments, a chimeric protein of the invention comprises one polypeptide chain, which comprises a single chain FVIII protein, a first Ig constant region or a portion thereof (e.g., a first Fc region), a first linker (e.g., a processable linker), a VWF fragment, an XTEN sequence, a second linker (e.g., a thrombin cleavable linker), and a second Ig constant region or a portion thereof (e.g., a second Fc region), wherein the single chain FVIII protein is linked to the first Ig constant region or a portion thereof, which is also linked to the VWF fragment by the first linker, and the VWF fragment is linked to the XTEN sequence, which is further linked to the second Ig constant region or a portion thereof. In one embodiment, the VWF fragment and the XTEN sequence are linked by the second linker. In another embodiment, the XTEN sequence and the second Ig constant region or a portion thereof are linked by the second linker. In other embodiments, the second chain further comprises a third linker. The single polypeptide chain can thus comprise the VWF fragment linked to the XTEN sequence by the second linker and the XTEN linked to the second Ig constant region or a portion thereof by the third linker. The second linker and the third linker can be identical or different. In one embodiment, the first linker is a processable linker. In another embodiment, the second linker or the third linker is a cleavable linker comprising one or two cleavable sites. In a specific embodiment, the second linker is a thrombin cleavable linker. The linkers useful in the invention are described elsewhere herein.

(2) FVIII, XTEN, and Fc

A chimeric protein of the invention also comprises (i) a FVIII protein, (ii) an XTEN sequence (a first half-life extender), and (iii) an Ig constant region or a portion thereof (a second half-life extender), in which the XTEN sequence is linked to the FVIII protein by an optional linker and the Ig constant region or a portion thereof by an additional optional linker. The XTEN sequence and the Ig constant region or a portion thereof can be used together to extend half-life of the FVIII protein. In one embodiment, the chimeric protein is a monomer. In another embodiment, the chimeric protein is a dimer (a homodimer or a heterodimer).

The present invention is also directed to a chimeric protein comprising (i) a FVIII protein, (ii) an XTEN sequence, (iii) an Ig constant region or a portion thereof (i.e., a first Ig constant region or a portion thereof, "F," or "F1"), and (iv) an additional Ig constant region or a portion thereof (i.e., a second Ig constant region or a portion thereof or "F2"). In one embodiment, the XTEN sequence is linked to the FVIII protein at the C-terminus or the N-terminus or inserted immediately downstream of one or more amino acids in the FVIII protein (e.g., one or more XTEN insertion sites), the FVIII protein is linked to the first Ig constant region or a portion thereof, and the first Ig constant region or a portion thereof and the second Ig constant region or a portion thereof are associated with or linked to each other by an optional linker. In certain aspects, the chimeric protein is a monomer-dimer hybrid, which comprises a first polypeptide chain and a second polypeptide chain, wherein the first polypeptide chain comprises a FVIII protein, an XTEN sequence, and a first Ig constant region or a portion thereof, and the second polypeptide chain comprises, consists essentially of, or consists of a second Ig constant region or a portion thereof without the FVIII protein and wherein the first chain and the second chain are associated with each other. The association between the Ig constant region or a portion thereof (e.g., the first Fc region) and the additional Ig constant region or a portion thereof (e.g., a second Fc region) is a chemical association or a physical association. In certain embodiments, the chemical association is a covalent bond. In other embodiments, the chemical association is a non-covalent interaction, e.g., an ionic interaction, a hydrophobic interaction, a hydrophilic interaction, a Van der Waals interaction, or a hydrogen bond. In other embodiments, the association is a non-peptide covalent bond. In still other embodiments, the association is a peptide bond.

In other aspects, the chimeric protein is a single polypeptide chain comprising a FVIII protein, an XTEN sequence, a first Ig constant region or a portion thereof, a linker, e.g., a processable linker, and a second Ig constant region or a portion thereof, wherein the single polypeptide chain is processed after expression by an intracellular enzyme and becomes two polypeptide chains.

In one embodiment, the Ig constant region or a portion thereof (sometimes indicated herein by "F" or "F1") linked to the FVIII protein can extend the half-life of the FVIII protein together with the XTEN sequence. In another embodiment, the Ig constant region or a portion thereof ("F" or "F1") is an Fc region or an FcRn binding partner described elsewhere herein.

In other embodiments, the additional Ig constant region or a portion thereof (sometimes indicated herein by "F2" or a second Ig constant region or a portion thereof) associated with or linked to the first Ig constant region or a portion thereof can also extend the half-life of the FVIII protein. In other embodiments, the second Ig constant region or a portion thereof ("F2") together with the first Ig constant region or a portion thereof and the XTEN sequence can extend the half-life of the FVIII protein. The additional Ig constant region or a portion thereof can be an Fc region or an FcRn binding partner described elsewhere herein.

In certain embodiments, the second Ig constant region or a portion thereof associated with the first Ig constant region or a portion thereof is further linked to a VWF fragment described elsewhere herein and an optional XTEN sequence.

In some embodiments, either or both of the Ig constant region or a portion thereof ("F" or "F1" or a first Ig constant region or a portion thereof) and an additional Ig constant region or a portion thereof (i.e., a second Ig constant region or a portion thereof or "F2") (indicated in this paragraph as "the Ig constant regions or portion thereof") can include, but not limited to, a CH1 domain, a CH2 domain, a CH3 domain, a CH4 domain, a hinge domain, any functional fragments, derivatives, or analogs thereof or two or more combinations thereof. In one embodiment, the Ig constant region or a portion thereof comprises at least one CH1 domain, at least one CH2 domain, at least one CH3 domain, at least one CH4 domain, or the functional fragments, derivatives, or analogues thereof. In another embodiment, the Ig constant region or a portion thereof comprises at least one hinge domain or portion thereof and at least one CH2 domain or portion thereof (e.g., in the hinge-CH2 orientation). In other embodiments, the Ig constant domain or portion thereof comprises at least one CH2 domain or portion thereof and at least one CH3 domain or portion thereof (e.g., in the CF2-CH3 orientation). Examples of the combination include, but are not limited to, a CH2 domain, a CH3 domain, and a hinge domain, which are also known as an Fc region (or Fc domain), e.g., first Fc region. Additional examples of the Ig constant regions or portion thereof are described elsewhere herein.

The chimeric protein of the invention can have an extended half-life of the FVIII protein compared to wild-type FVIII. In one embodiment, the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of wild type FVIII. In another embodiment, the half-life of the FVIII protein is at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, or at least about 108 hours.

(3) FVIII, XTEN, and VWF

In one aspect, a chimeric protein of the present invention comprises (i) a FVIII protein, (ii) an XTEN sequence, and (iii) a VWF fragment comprising a D' domain and a D3 domain of VWF, wherein the FVIII protein is linked to the XTEN sequence and wherein the FVIII protein is associated with or linked to the VWF fragment. In one embodiment, the VWF fragment of the chimeric protein described herein is not capable of binding to a VWF clearance receptor. In another embodiment, the VWF fragment is capable of protecting the FVIII protein from one or more protease cleavages, protecting the FVIII protein from activation, stabilizing the heavy chain and/or the light chain of the FVIII protein, or preventing clearance of the FVIII protein by one or more scavenger receptors. In other embodiments, the VWF fragment prevents or inhibits binding of endogenous VWF to the VWF binding site in the FVIII protein. The VWF binding site can be located in the A3 domain or the C2 domain of the FVIII protein or both the A3 domain and the C2 domain. In a specific embodiment, the VWF binding site comprises the amino acid sequence corresponding to amino acids 1669 to 1689 and/or amino acids 2303 to 2332 of SEQ ID NO: 2.

In another aspect, a chimeric protein comprises (i) a FVIII protein, (ii) an XTEN sequence, (iii) a VWF fragment, which comprises a D' domain and a D3 domain of VWF, and (iv) an Ig constant region or a portion thereof, wherein the XTEN sequence is linked to the FVIII protein at the C-terminus or the N-terminus or inserted immediately downstream of one or more amino acids (e.g., one or more XTEN insertion sites disclosed herein) in the FVIII protein, the VWF fragment is linked to or associated with the FVIII protein or the XTEN sequence, and the Ig constant region or a portion thereof is linked to the FVIII protein, the XTEN sequence, the VWF fragment, or any combinations thereof. The Ig constant region or a portion thereof useful for chimeric proteins of the invention is described elsewhere herein. In one embodiment, the Ig constant region or a portion thereof is capable of extending the half-life of a FVIII protein. In another embodiment, the Ig constant region or a portion thereof comprises a first Fc region or a first FcRn binding partner. In yet other embodiments, the Ig constant region or a portion thereof is linked to the FVIII protein by an optional linker. In still other embodiments, the linker comprises a cleavable linker. The chimeric protein can be a single polypeptide chain, i.e., a monomer (i.e., a single chain), containing (i), (ii), (iii), and (iv) or two chains containing a first chain comprising (i) and (ii) and a second chain comprising (iii) and (iv). In other aspects, the chimeric protein is a dimer (e.g., a homodimer or a heterodimer). In one embodiment, the chimeric protein comprises two chains, each comprising (i), (ii), (iii), and (iv).

In certain embodiments, a chimeric protein comprises (i) a FVIII protein, (ii) an XTEN sequence, (iii) a VWF fragment, which comprises a D' domain and a D3 domain of VWF, (iv) an Ig constant region or a portion thereof (sometimes also indicated as "F," "a first Ig constant region or a portion thereof", or "F2"), and (v) an additional Ig constant region or a portion thereof (sometimes also indicated as "F2" or "a second Ig constant region or a portion thereof"), wherein (1) the FVIII protein is linked to the XTEN sequence at the C-terminus or N-terminus of the FVIII protein or inserted immediately downstream of one or more amino acids (e.g., one or more XTEN insertion sites disclosed herein) in the FVIII protein, (2) either the XTEN sequence or the FVIII protein is linked to the Ig constant region or a portion thereof, (3) the VWF fragment is linked to the second Ig constant region or a portion thereof, and (4) the Ig constant region or a portion thereof is associated with the second Ig constant region or a portion thereof. In one embodiment, the Ig constant region or a portion thereof linked to the FVII protein or the XTEN sequence is further linked to the VWF fragment by a linker, e.g., a processable linker. In another embodiment, the additional Ig constant region or a portion thereof useful for chimeric proteins of the invention can further be linked to the FVIII protein or the Ig constant region or a portion thereof by an optional linker, e.g., a processable linker. In some embodiments, a pair of the Ig constant region or a portion thereof and the additional Ig constant region or a portion thereof, each of which are linked to the VWF fragment and the FVIII protein, provides a bond stronger than the non-covalent bond between the FVIII protein and the VWF fragment, i.e., a covalent bond, e.g., a disulfide bond, thereby preventing endogenous VWF from replacing the VWF fragment in vivo. In other embodiments, either or both of the Ig constant region or a portion thereof and the additional Ig constant region or a portion thereof are capable of extending a half-life of the FVIII protein or the VWF fragment. In other embodiments, the additional Ig constant region or a portion thereof comprises a second Fc region or an FcRn binding partner. The Ig constant region or a portion thereof and the additional Ig constant region or a portion thereof in the chimeric proteins are identical or different.

In certain embodiments, the Ig constant region or a portion thereof and the additional Ig constant region or a portion thereof are associated by a chemical association or a physical association. In one embodiment, the chemical association, i.e., (:), is at least one non-peptide bond. In certain embodiments, the chemical association, i.e., (:), is a covalent bond. In other embodiments, the chemical association, i.e., (:), is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety. In some embodiments, the association between the Ig constant region or a portion thereof and the additional Ig constant region or a portion thereof can be a covalent bond, e.g., a disulfide bond, which prevents replacement the VWF fragment or the polypeptide containing the VWF fragment with endogenous VWF. Therefore, preventing interaction between the FVIII protein and endogenous VWF reduces or eliminates this half-life limiting factor for the FVIII protein, and thus the half-life of the FVIII protein is extended compared to a FVIII protein without the VWF protein or wild-type FVIII.

In other aspects, a chimeric protein comprises a formula comprising:

(1) FVIII(X1)-L1-F1:V-L2-X2-L3-F2;
(2) FVIII(X1)-L1-F1:F2-L3-X2-L2-V;
(3) F1-L1-FVIII(X1):V-L2-X2-L3-F2;
(4) F1-L1-FVIII(X1):F2-L3-X2-L2-V;
(5) FVIII(X1)-L1-F1-L4-V-L2-X2-L3-F2;
(6) FVIII(X1)-L1-F1-L4-F2-L3-X2-L2-V;
(7) F1-L1-FVIII(X1)-L4-V-L2-X2-L3-F2, or
(8) F1-L1-FVIII(X1)-L4-F2-L3-X2-L2-V, wherein FVIII(X1) comprises a FVIII protein and one or more XTEN sequences, wherein the one or more XTEN sequence are linked to the N-terminus or C-terminus of the FVIII protein or inserted immediately downstream of one or more amino acids (e.g., one or more XTEN insertion sites disclosed herein) in the FVIII protein;

each of L1, L2, or L3 comprises an optional linker, e.g., a cleavable linker;

L4 is a linker, e.g., a processable linker;

X2 comprises one or more optional XTEN sequences;

F1 comprises an Ig constant region or a portion thereof;

F2 comprises an optional additional Ig constant region or a portion thereof, and V comprises a VWF fragment;

(-) is a peptide bond or one or more amino acids; and (:) comprises a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond.

In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula V-X-FVIII means formula NH2-V-X-FVIII-COOH. In one embodiment, the formulas described herein can comprise any additional sequences between the two moieties. For example, formula V-X-FVIII can further comprise any sequences at the N-terminus of V between V and X, between X and FVIII, or at the C-terminus of FVIII unless otherwise specified. In another embodiment, the hyphen (-) indicates a peptide bond.

In one aspect, the chimeric protein comprises two polypeptide chains, (A) a first chain comprising (i) a single chain FVIII protein (ii) an XTEN sequence, and (iii) a first Ig constant region or a portion thereof, e.g., a first Fc region or FcRn binding partner, wherein the XTEN sequence is linked to the FVIII protein at the N-terminus or C-terminus or inserted immediately downstream of one or more amino acids of the FVIII protein (e.g., one or more XTEN insertion sites disclosed herein) and the first Ig constant region or a portion thereof is linked to the XTEN sequence when the XTEN sequence is linked to the FVIII protein at the N-terminus or the C-terminus or the FVIII protein when the XTEN sequence is inserted within the FVIII protein, and (B) a second chain comprising (iv) a VWF fragment comprising a D' domain and a D3 domain, (v) a linker, and (vi) a second Ig constant region or a portion thereof, e.g., a second Fc region or a second FcRn binding partner, wherein the VWF fragment is linked to the linker, e.g., a cleavable linker, which is further linked to the second Ig constant region or a portion thereof, and wherein the first polypeptide chain and the second polypeptide chain are associated with each other, e.g., a covalent bond, e.g., a disulfide bond. In one embodiment, the linker is a cleavable linker described elsewhere herein, e.g., a thrombin cleavable linker. In some embodiments, the second chain comprises one or more XTEN sequences between (iv) and (v) or (v) and (vi).

In other aspects, the chimeric protein comprises one polypeptide chain comprising (i) a single chain FVIII protein (ii) an XTEN sequence, (iii) a first Ig constant region or a portion thereof, e.g., a first Fc region or a first FcRn binding partner, (iv) a first linker, (v) a VWF fragment comprising a D' domain and a D3 domain, (vi) a second linker, and (vii) a second Ig constant region or a portion thereof, e.g., a second Fc region or a second FcRn binding partner, wherein (i) to (vii) are linked in the order or in any orders. In one embodiment, the first linker is a processable linker, which can be intracellularly processed or cleaved after expression and makes the single polypeptide chain into two polypeptide chains. In another embodiment, the second linker is a cleavable linker described herein, e.g., a thrombin cleavable linker. The XTEN sequence used herein can be linked to the FVIII protein by an optional linker at the N-terminus or the C terminus of the FVIII protein or inserted immediately downstream of one or more amino acids (e.g., one or more XTEN insertion sites) in the FVIII protein.

In certain aspects, a chimeric protein comprises three polypeptide chains, (A) a first polypeptide chain comprising (i) a heavy chain of a FVIII protein and (ii) an XTEN sequence, which are linked to each other and (B) a second polypeptide chain comprising (iii) a light chain of the FVIII protein and (iv) a first Ig constant region or a portion thereof, e.g., a first Fc region or a first FcRn binding partner, which are linked to each other, and (C) a third polypeptide chain comprising (v) a VWF fragment comprising a D' domain and a D3 domain, (vi) a linker, and (vii) a second Ig constant region or a portion thereof, e.g., a second Fc region or a second FcRn binding partner, wherein the second chain is associated with the first chain and the third chain. In one embodiment, the association between the first chain and the second chain is a chemical association or a physical association. For example, the association between the first chain and the second chain can be a metal bond. In another embodiment, the association between the second chain and the third chain is also a chemical association or a physical association, e.g., a covalent bond or a non-covalent bond. In certain embodiments, the association between the second chain and the third chain is through the two Ig constant regions or a portion thereof and is a disulfide bond. The bonding between the second chain and the third chain prevents or inhibits binding of the FVIII protein with endogenous VWF, thus preventing the FVIII protein being cleared by the VWF clearance pathway. In some embodiments, the linker is a processable linker, which is intracellularly cleaved after expression in a host cell. The XTEN sequence used herein is linked to the FVIII protein by an optional linker at the N-terminus or C terminus of the FVIII protein or inserted immediately downstream of one or more amino acids (e.g., one or more XTEN insertion sites) in the FVIII protein.

In certain embodiments, the VWF fragment is directly linked to the FVIII protein, which comprises one or more XTENs, by a peptide bond or a linker. As one way of linking the VWF fragment and the FVIII protein, in which one or more XTENs are inserted or linked, through a direct link (e.g. a peptide bond) or a linker, an enzymatic ligation (e.g., sortase) can be employed. For example, sortase refers to a group of prokaryotic enzymes that modify surface proteins by recognizing and cleaving a carboxyl-terminal sorting signal. For most substrates of sortase enzymes, the recognition signal consists of the motif LPXTG (Leu-Pro-any-Thr-Gly (SEQ ID NO: 51), then a highly hydrophobic transmembrane sequence, then a cluster of basic residues such as arginine. Cleavage occurs between the Thr and Gly, with transient attachment through the Thr residue to the active site Cys residue of a ligation partner, followed by transpeptidation that attaches the protein covalently to the cell wall. In some embodiments, the ligation partner contains Gly(n). In other embodiments, the chimeric protein further comprises a sortase recognition motif. In some embodiments, the VWF fragment is attached to FVIII comprising one or more XTENs inserted within or linked to using sortase mediated in vitro protein ligation.

In one embodiment, a VWF fragment linked to a sortase recognition motif by an optional linker can be fused to a FVIII protein linked to Gly(n) by a sortase, wherein n can be any integer and wherein one or more XTENs are inserted within or linked to the FVIII protein. A ligation construct comprises the VWF fragment (N-terminal portion of the construct) and the FVIII protein, in which one or more XTENs are inserted or linked (C-terminal portion of the construct), wherein the sortase recognition motif is inserted in between. Another ligation construct comprises the VWF fragment (N-terminal portion of the construct, the linker, the sortase recognition motif, and the FVIII protein, in which one or more XTENs are inserted or linked (C-terminal portion of the construct). In another embodiment, a FVIII protein linked to a sortase recognition motif by an optional linker can be fused to a VWF fragment linked to Gly(n) by a sortase, wherein n is any integer. A resulting ligation construct comprises the FVIII protein (N-terminal portion of the construct), in which one or more XTENs are inserted or linked, and the VWF fragment (C-terminal portion of the construct), wherein the sortase recognition motif is inserted in between. Another resulting ligation construct comprises the FVIII protein (N-terminal portion of the construct), in which one or more XTENs are inserted or linked, the linker, the sortase recognition motif, and the VWF fragment (C-terminal portion of the construct). In other embodiments, a VWF fragment linked to a sortase recognition motif by a first optional linker can be fused to a heterologous moiety, e.g., an immunoglobulin constant region or a portion thereof, e.g., an Fc region, linked to a thrombin cleavage site by a second optional linker. A resulting construct can comprise the VWF fragment (N-terminal portion), the first linker, the sortase recognition motif, the protease cleavage site, the second optional linker, and the heterologous moiety.

In some embodiments, the VWF fragment is associated with the FVIII protein. The association between the VWF fragment and the FVIII protein can be a chemical association or a physical association. The chemical association can be a non-covalent interaction, e.g., an ionic interaction, a hydrophobic interaction, a hydrophilic interaction, a Van der Waals interaction, or a hydrogen bond. In yet other embodiments, the association between the FVIII protein and the VWF fragment is a physical association between two sequences, e.g., due to an additional association between the sequence having the FVIII protein and the sequence having the VWF fragment, wherein a portion of a first sequence is in close proximity to a second sequence such that the first sequence shields or blocks a portion of the second sequence from interacting with another moiety.

As a result of preventing or inhibiting endogenous VWF interaction with the FVIII protein by the VWF fragment, the chimeric protein described herein have an extended half-life compared to wild-type FVIII or the corresponding chimeric protein without the VWF fragment. In one embodiment, the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than a FVIII protein without the VWF fragment. In another embodiment, the half-life of the FVIII protein is at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, or at least about 108 hours. In a particular embodiment, the half-life of the FVIII protein is extended at least 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, or at least about 27 hours in HemA mice.

A) Von Willebrand Factor (VWF) Fragments

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D'/D3 domain (which binds to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG).

The term "a VWF fragment" as used herein includes, but is not limited to, functional VWF fragments comprising a D' domain and a D3 domain, which are capable of inhibiting binding of endogenous VWF to FVIII. In one embodiment, the VWF fragment binds to the FVIII protein. In another embodiment, the VWF fragment blocks the VWF binding site on the FVIII protein, thereby inhibiting interaction of the FVIII protein with endogenous VWF. The VWF fragments include derivatives, variants, mutants, or analogues that retain these activities of VWF.

The 2813 monomer amino acid sequence for human VWF is reported as Accession Number_NP_000543.2_in Genbank. The nucleotide sequence encoding the human VWF is reported as Accession Number_NM_000552.3_in Genbank. The nucleotide sequence of human VWF is designated as SEQ ID NO: 1. SEQ ID NO: 2 is the amino acid sequence encoded by SEQ ID NO: 1. Each domain of VWF is listed in Table 1.

TABLE 1

VWF Sequences

| VWF domains | Amino acid Sequence | | | | |
|---|---|---|---|---|---|
| VWF Signal Peptide (Amino acids 1 to 22 of SEQ ID NO: 2) | 1 22 | MIPARFAGVL | LALALILPGT | LC | |
| VWF D1D2 region (Amino acids 23 to 763 of SEQ ID NO: 2) | 23 51 101 151 201 251 301 351 401 451 501 551 601 651 701 751 763 | YSFAGYCSYL TVTQGDQRVS SDRYFNKTCG ERASPPSSSC EKTLCECAGG YRQCVSPCAR VHSGKRYPPG NRYFTFSGIC LHNSLVKLKH DWDGRGRLLV NAWKLHGDCQ PLPYLRNCRY NCPKGQVYLQ CVPKAQCPCY AVLSSPLSHR | AEGTRGRS LAGGCQKRSF MPYASKGLYL LCGNFNIFAE NISSGEMQKG LECACPALLE TCQSLHINEM TSLSRDCNTC QYLLARDCQD GAGVAMDGQD KLSPVYAGKT DLQKQHSDPC DVCSCSDGRE CGTPCNLTCR YDGEIFQPED | STARCSLFGS SIIGDFQNGK ETEAGYYKLS DDFMTQEGTL LWEQCQLLKS YARTCAQEGM CQERCVDGCS ICRNSQWICS HSFSIVIETV IQLPLLKGDL CGLCGNYNGN ALNPRMTRFS CLCGALASYA SLSYPDEECN IFSDHHTMCY SKR | DFVNTFDGSM RVSLSVYLGE GEAYGFVARI TSDPYDFANS TSVFARCHPL VLYGWTDHSA CPEGQLLDEG NEECPGECLV QCADDRDAVC RIQHTVTASV QGDDFLTPSG EEACAVLTSP AACAGRGVRV EACLEGCFCP CEDGFMHCTM | FFDIHLFVNG DGSGNFQVLL WALSSGEQWC VDPEPFVALC CSPVPCAGME LCVESTECPC TGQSHFKSFD TRSVTVRLPG RLSYGEDLQM LAEPRVEDFG TFEACHRAVS AWREPGRCEL PGLYMDERGD SGVPGSLLPD |
| VWF D' Domain | 764 801 851 866 | SMGCVSGCLC CRDRKWNCTD | SLSCRPP PPGMVRHENR | MVKLVCPADN CVALERCPCF HVCDAT | LRAEGLECTK HQGKEYAPGE | TCQNYDLECM TVKIGCNTCV |
| VWF D3 Domain | 867 901 951 1001 1051 1101 1151 1201 1240 | NPGTFRILVG THFEVVESGR GIQNNDLTSS MKQTMVDSSC CDTIAAYAHV PACQVTCQHP VAGRRFASGK | CSTI NHGCSHPSVK YIILLLGKAL NLQVEEDPVD RILTSDVFQD CAQHGKVVTW EPLACPVQCV KVTLNPSDPE | GMAHYLTFDG CKKRVTILVE SVVWDRHLSI FGNSWKVSSQ CNKLVDPEPY RTATLCPQSC EGCHAHCPPG HCQICHCDVV | LKYLFPGECQ GGEIELFDGE SVVLKQTYQE CADTRKVPLD LDVCIYDTCS EERNLRENGY KILDELLQTC NLTCEACQEP | YVLVQDYCGS VNVKRPMKDE KVCGLCGNFD SSPATCHNNI CESIGDCACF ECEWRYNSCA VDPEDCPVCE |
| VWF A1 Domain | 1241 1251 1301 1351 1401 1451 1479 | GGLVVPPTDA PVSPTTLYVE VDMMERLRIS GSQVASTSEV VQGLKKKKVI DEIVSYLCDL | DISEPPLHDF QKWVRVAVVE LKYTLFQIFS VIPVGIGPHA APEPPPTLP | YCSRLLDLVF YHDGSHAYIG KIDRPEASRI NLKQIRLIEK PDMAQVTVG | LLDGSSRLSE LKDRKRPSEL ALLLMASQEP QAPENKAFVL | AEFEVLKAFV RRIASQVKYA QRMSRNFVRY SSVDELEQQR |

TABLE 1-continued

VWF Sequences

```
1480                              P GLLGVSTLGP KRNSMVLDVA
1501 FVLEGSDKIG EADFNRSKEF MEEVIQRMDV GQDSIHVTVL QYSYMVTVEY
1551 PFSEAQSKGD ILQRVREIRY QGGNRTNTGL ALRYLSDHSF LVSQGDREQA
1600
1601 PNLVYMVTGN PASDEIKRLP GDIQVVPIGV GPNANVQELE RIGWPNAPIL
1651 IQDFETLPRE APDLVLQRCC SGEGLQIPTL SPAPDCSQPL DVILLLDGSS
1701 SFPASYFDEM KSFAKAFISK ANIGPRLTQV SVLQYGSITT IDVPWNVVPE
1751 KAHLLSLVDV MQREGGPSQI GDALGFAVRY LTSEMHGARP GASKAVVILV
1801 TDVSVDSVDA AADAARSNRV TVFPIGIGDR YDAAQLRILA GPAGDSNVVK
1851 LQRIEDLPTM VTLGNSFLHK LCSGFVRICM DEDGNEKRPG DVWTLPDQCH
1901 TVTCQPDGQT LLKSHRVNCD RGLRPSCPNS QSPVKVEETC GCRWTCPCVC
1951 TGSSTRHIVT FDGQNFKLTG SCSYVLFQNK EQDLEVILHN GACSPGARQG
2001 CMKSIEVKHS ALSVEXHSDM EVTVNGRLVS VPYVGGNMEV NVYGAIMHEV
2051 RFNHLGHIFT FTPQNNEFQL QLSPKTFASK TYGLCGICDE NGANDFMLRD
2101 GTVTTDWKTL VQEWTVQRPG QTCQPILEEQ CLVPDSSHCQ VLLLPLFAEC
2151 HKVLAPATFY AICQQDSCHQ EQVCEVIASY AHLCRTNGVC VDWRTPDFCA
2201 MSCPPSLVYN HCEHGCPRHC DGNVSSCGDH PSEGCFCPPD KVMLEGSCVP
2251 EEACTQCIGE DGVQHQFLEA WVPDHQPCQI CTCLSGRKVN CTTQPCPTAK
2301 APTCGLCEVA RLRQNADQCC PEYECVCDPV SCDLPPVPHC ERGLQPTLTN
2351 PGECRPNFTC ACRKEECKRV SPPSCPPHRL PTLRKTQCCD EYECACNCVN
2401 STVSCPLGYL ASTATNDCGC TTTTCLPDKV CVHRSTIYPV GQFWEEGCDV
2451 CTCTDMEDAV MGLRVAQCSQ KPCEDSCRSG FTYVLHEGEC CGRCLPSACE
2501 VVTGSPRGDS QSSWKSVGSQ WASPENPCLI NECVRVKEEV FIQQRNVSCP
2551 QLEVPVCPSG FQLSCKTSAC CPSCRCERME ACMLNGTVIG PGKTVMIDVC
2601 TTCRCMVQVG VISGFKLECR KTTCNPCPLG YKEENNTGEC CGRCLPTACT
2651 IQLRGGQIMT LKRDETLQDG CDTHFCKVNE RGEYFWEKRV TGCPPFDEHK
2701 CLAEGGKIMK IPGTCCDTCE EPECNDITAR LQYVKVGSCK SEVEVDIHYC
2751 QGKCASKAMY SIDINDVQDQ CSCCSPTRTE PMQVALHCTN GSVVYHEVLN
2801 AMECKCSPRK CSK
```

Nucleotide Sequence (SEQ ID NO: 1)

Full-length VWF
```
   1 ATGATTCCTG CCAGATTTGC CGGGGTGCTG CTTGCTCTGG CCCTCATTTT
  51 GCCAGGGACC CTTTGTGCAG AAGGAACTCG CGGCAGGTCA TCCACGGCCC
 101 GATGCAGCCT TTTCGGAAGT GACTTCGTCA ACACCTTTGA TGGGAGCATG
 151 TACAGCTTTG CGGGATACTG CAGTTACCTC CTGGCAGGGG GCTGCCAGAA
 201 ACGCTCCTTC TCGATTATTG GGACTTCCA GAATGGCAAG AGAGTGAGCC
 251 TCTCCGTGTA TCTTGGGGAA TTTTTTGACA TCCATTTGTT TGTCAATGGT
 301 ACCGTGACAC AGGGGGACCA AAGAGTCTCC ATGCCCTATG CCTCCAAAGG
 351 GCTGTATCTA GAAACTGAGG CTGGGTACTA CAAGCTGTCC GGTGAGGCCT
 401 ATGGCTTTGT GGCCAGGATC GATGGCAGCG GCAACTTTCA AGTCCTGCTG
 451 TCAGACAGAT ACTTCAACAA GACCTGCGGG CTGTGTGGCA ACTTTAACAT
 501 CTTTGCTGAA GATGACTTTA TGACCCAAGA AGGGACCTTG ACCTCGGACC
 551 CTTATGACTT TGCCAACTCA TGGGCTCTGA GCAGTGGAGA ACAGTGGTGT
 601 GAACGGGCAT CTCCTCCCAG CAGCTCATGC AACATCTCCT CTGGGGAAAT
 651 GCAGAAGGGC CTGTGGGAGC AGTGCCAGCT TCTGAAGAGC ACCTCGGTGT
 701 TTGCCCGCTG CCACCCTCTG GTGGACCCCG AGCCTTTTGT GGCCCTGTGT
 751 GAGAAGACTT TGTGTGAGTG TGCTGGGGGG CTGGAGTGCG CCTGCCCTGC
 801 CCTCCTGGAG TACGCCCGGA CCTGTGCCCA GGAGGGAATG GTGCTGTACG
 851 GCTGGACCGA CCACAGCGCG TGCAGCCCAG TGTGCCCTGC TGGTATGGAG
 901 TATAGGCAGT GTGTGTCCCC TTGCGCCAGG ACCTGCCAGA GCCTGCACAT
 951 CAATGAAATG TGTCAGGAGC GATGCGTGGA TGGCTGCAGC TGCCCTGAGG
1001 GACAGCTCCT GGATGAAGGC CTCTGCGTGG AGAGCACCGA GTGTCCCTGC
1051 GTGCATTCCG GAAAGCGCTA CCCTCCCGGC ACCTCCCTCT CTCGAGACTG
1101 CAACACCTGC ATTTGCCGAA ACAGCCAGTG GATCTGCAGC AATGAAGAAT
1151 GTCCAGGGGA GTGCCTTGTC ACTGGTCAAT CCCACTTCAA GAGCTTTGAC
1201 AACAGATACT TCACCTTCAG TGGGATCTGC CAGTACCTGC TGGCCCGGGA
1251 TTGCCAGGAC CACTCCTTCT CCATTGTCAT TGAGACTGTC CAGTGTGCTG
1301 ATGACCGCGA CGCTGTGTGC ACCCGCTCCG TCACCGTCCG GCTGCCTGGC
1351 CTGCACAACA GCCTTGTGAA ACTGAAGCAT GGGGCAGGAG TTGCCATGGA
1401 TGGCCAGGAC ATCCAGCTCC CCCTTCCTGAA AGGTGACCTC CGCATCCAGC
1451 ATACAGTGAC GGCCTCCGTG CGCCTCAGCT ACGGGGAGGA CCTGCAGATG
1501 GACTGGGATG GCCGCGGGAG GCTGCTGGTG AAGCTGTCCC CCGTCTATGC
1551 CGGGAAGACC TGCGGCCTGT GTGGAATTA CAATGGCAAC CAGGGCGACG
1601 ACTTCCTTAC CCCCTCTGGG CTGGCRGAGC CCCGGGTGGA GGACTTCGGA
1651 AACGCCTGGA AGCTGCACGG GGACTGCCAG GACCTGCAGA AGCAGCACAG
1701 CGATCCCTGC GCCCTCAACC CGCGCATGAC CAGGTTCTCC GAGGAGGCGT
1751 GCGCGGTCCT GACGTCCCCC ACATTCGAGG CCTGCCATCG TGCCGTCAGC
1801 CCGCTGCCCT ACCTGCGGAA CTGCCGCTAC GACGTGTGCT CCTGCTCGGA
1851 CGGCCGCGAG TGCCTGTGCG GCGCCCTGGC CAGCTATGCC GCGGCCTGCG
1901 CGGGGAGAGG CGTGCGCGTC GCGTGGCGCG AGCCAGGCCG CTGTGAGCTG
1951 AACTGCCCGA AAGGCCAGGT GTACCTGCAG TGCGGGACCC CTGCAACCT
2001 GACCTGCCGC TCTCTCTCTT ACCCGGATGA GGAATGCAAT GAGGCCTGCC
2051 TGGAGGGCTG CTTCTGCCCC CCAGGGCTCT ACATGGATGA GAGGGGGGAC
2101 TGCGTGCCCA AGGCCCAGTG CCCCTGTTAC TATGACGGTG AGATCTTCCA
2151 GCCAGAAGAC ATCTTCTCAG ACCATCACAC CATGTGCTAC TGTGAGGATG
2201 GCTTCATGCA CTGTACCATG AGTGGAGTCC CCGGAAGCTT GCTGCCTGAC
2251 GCTGTCCTCA GCAGTCCCCT GTCTCATCGC AGCAAAAGGA GCCTATCCTG
```

TABLE 1-continued

| VWF Sequences |
|---|

```
2301 TCGGCCCCCC ATGGTCAAGC TGGTGTGTCC CGCTGACAAC CTGCGGGCTG
2351 AAGGGCTCGA GTGTACCAAA ACGTGCCAGA ACTATGACCT GGAGTGCATG
2401 AGCATGGGCT GTGTCTCTGG CTGCCTCTGC CCCCCGGGCA TGGTCCGGCA
2451 TGAGAACAGA GTGTGTGGCCC TGGAAAGGTG TCCCTGCTTC CATCAGGGCA
2501 AGGAGTATGC CCCTGGAGAA ACAGTGAAGA TTGGCTGCAA CACTTGTGTC
2551 TGTCGGGACC GGAAGTGGAA CTGCACAGAC CATGTGTGTG ATGCCACGTG
2601 CTCCACGATC GGCATGGCCC ACTACCTCAC CTTCGACGGG CTCAAATACC
2651 TGTTCCCCGG GGAGTGCCAG TACGTTCTGG TGCAGGATTA CTGCGGCAGT
2701 AACCCTGGGA CCTTTCGGAT CCTAGTGGGG AATAAGGGAT GCAGCCACCC
2751 CTCAGTGAAA TGCAAGAAAC GGGTCACCAT CCTGGTGGAG GGAGGAGAGA
2801 TTGAGCTGTT TGACGGGGAG GTGAATGTGA AGAGGCCCAT GAAGGATGAG
2851 ACTCACTTTG AGGTGGTGGA GTCTGGCCGG TACATCATTC TGCTGCTGGG
2901 CAAAGCCCTC TCCGTGGTCT GGGACCGCCA CCTGAGCATC TCCGTGGTCC
2951 TGAAGCAGAC ATACCAGGAG AAAGTGTGTG GCCTGTGTGG GAATTTTGAT
3001 GGCATCCAGA ACAATGACCT CACCAGCAGC AACCTCCAAG TGGAGGAAGA
3051 CCCTGTGGAC TTTGGGAACT CCTGGAAAGT GAGCTCGCAG TGTGCTGACA
3101 CCAGAAAAGT GCCTCTGGAC TCATCCCCTG CCACCTGCCA TAACAACATC
3151 ATGAAGCAGA CGATGGTGGA TTCCTCCTGT AGAATCCTTA CCAGTGACGT
3201 CTTCCAGGAC TGCAACAAGC TGGTGGACCC CGAGCCATAT CTGGATGTCT
3251 GCATTTACGA CACCTGCTCC TGTGAGTCCA TTGGGGACTG CGCCTGCTTC
3301 TGCGACACCA TTGCTGCCTA TGCCCACGTG TGTGCCCAGC ATGGCAAGGT
3351 GGTGACCTGG AGGACGGCCA CATTGTGCCC CCAGAGCTGC GAGGAGAGGA
3401 ATCTCCGGGA GAACGGGTAT GAGTGTGAGT GGCGCTATAA CAGCTGTGCA
3451 CCTGCCTGTC AAGTCACGTG TCAGCACCCT GAGCCACTGG CCTGCCCTGT
3501 GCAGTGTGTG GAGGGCTGCC ATGCCCACTG CCCTCCAGGG AAAATCCTGG
3551 ATGAGCTTTT GCAGACCTGC GTTGACCCTG AAGACTGTCC AGTGTGTGAG
3601 GTGGCTGGCC GGCGTTTTGC CTCAGGAAAG AAAGTCACCT TGAATCCCAG
3651 TGACCCTGAG CACTGCCAGA TTTGCCACTG TGATGTTGTC AACCTCACCT
3701 GTGAAGCCTG CCAGGAGCCG GGAGGCCTGG TGGTGCCTCC CACAGATGCC
3751 CCGGTGAGCC CCACCACTCT GTATGTGGAG GACATCTCGG AACCGCCGTT
3801 GCACGATTTC TACTGCAGCA GGCTACTGGA CCTGGTCTTC CTGCTGGATG
3851 GCTCCTCCAG GCTGTCCGAG GCTGAGTTTG AAGTGCTGAA GGCCTTTGTG
3901 GTGGACATGA TGGAGCGGCT GCGCATCTCC CAGAAGTGGG TCCGCGTGGC
3951 CGTGGTGGAG TACCACGACG GCTCCCACGC CTACATCGGG CTCAAGGACC
4001 GGAAGCGACC GTCAGAGCTG CGGCGCATTG CCAGCCAGGT GAAGTATGCG
4051 GGCAGCCAGG TGGCCTCCAC CAGCGAGGTC TTGAAATACA CACTGTTCCA
4101 AATCTTCAGC AAGATCGACC GCCCTGAAGC CTCCCGCATC GCCCTGCTCC
4151 TGATGGCCAG CCAGGAGCCC CAACGGATGT CCCGGAACTT TGTCCGCTAC
4201 GTCCAGGGCC TGAAGAAGAA GAAGGTCATT GTGATCCCGG TGGGCATTGG
4251 GCCCCATGCC AACCTCAAGC AGATCCGCCT CATCGAGAAG CAGGCCCCTG
4301 AGAACAAGGC CTTCGTGCTG AGCAGTGTGG ATGAGCTGGA GCAGCAAAGG
4351 GACGAGATCG TTAGCTACCT CTGTGACCTT GCCCCTGAAG CCCCTCCTCC
4401 TACTCTGCCC CCCGACATGG CACAAGTCAC TGTGGGCCCG GGGCTCTTGG
4451 GGGTTTCGAC CCTGGGGCCC AAGAGGAACT CCATGGTTCT GGATGTGGCC
4501 TTCGTCCTGG AAGGATCGGA CAAAATTGGT GAAGCCGACT TCAACAGGAG
4551 CAAGGAGTTC ATGGAGGAGG TGATTCAGCG GATGGATGTG GGCCAGGACA
4601 GCATCCACGT CACGGTGCTG CAGTACTCCT ACATGGTGAC CGTGGAGTAC
4651 CCCTTCAGCG AGGCACAGTC CAAAGGGGAC ATCCTGCAGC GGGTGCGAGA
4701 GATCCGCTAC CAGGGCGGCA ACAGGACCAA CACTGGGCTG GCCCTGCGGT
4751 ACCTCTCTGA CCACAGCTTC TTGGTCAGCC AGGGTGACCG GGAGCAGGCG
4801 CCCAACCTGG TCTACATGGT CACCGGAAAT CCTGCCTCTG ATGAGATCAA
4851 GAGGCTGCCT GGAGACATCC AGGTGGTGCC CATTGGAGTG GGCCCTAATG
4901 CCAACGTGCA GGAGCTGGAG AGGATTGGCT GGCCCAATGC CCCTATCCTC
4951 ATCCAGGACT TTGAGACGCT CCCCCGAGAG GCTCCTGACC TGGTGCTGCA
5001 GAGGTGCTGC TCCGGAGAGG GGCTGCAGAT CCCCACCCTC TCCCCTGCAC
5051 CTGACTGCAG CCAGCCCCTG GACGTGATCC TTCTCCTGGA TGGCTCCTCA
5101 AGTTTCCCAG CTTCTTATTT TGATGAAATG AAGAGTTTCG CCAAGGCTTT
5151 CATTTCAAAA GCCAATATAG GCCCTCGTCT CACTCAGGTG TCAGTGCTGC
5201 AGTATGGAAG CATCACCACC ATTGACGTGC CATGGAACGT GGTCCCGGAG
5251 AAAGCCCATT TGCTGAGCCT TGTGGACGTC ATGCAGCGGG AGGGAGGCCC
5301 CAGCCAAATC GGGGATGCCT TGGGCTTTGC TGTGCGATAC TTGACTTCAG
5351 AAATGCATGG TGCCAGGCCG GGAGCCTCAA AGGCGGTGGT CATCCTGGTC
5401 ACGGACGTCT CTGTGGATTC AGTGGATGCA GCAGCTGATG CCGCCAGGTC
5451 CAACAGAGTG ACAGTGTTCC CTATTGGAAT TGGAGATCGC TACGATGCAG
5501 CCCAGCTACG GATCTTGGCA GGCCCAGCAG GCGACTCCAA CGTGGTGAAG
5551 CTCCAGCGAA TCGAAGACCT CCCTACCATG GTCACCTTGG CAATTCCTTT
5601 CCTCCACAAA CTGTGCTCTG GATTTGTTAG GATTTGCATG GATGAGGATG
5651 GGAATGAGAA GAGGCCCGGG GACGTCTGGA CCTTGCCAGA CCAGTGCCAC
5701 ACCGTGACTT GCCAGCCAGA TGGCCAGACC TTGCTGAAGA GTCATCGGGT
5751 CAACTGTGAC CGGGGGCTGA GGCCTTCGTG CCCTAACAGC CAGTCCCCTG
5801 TTAAAGTGGA AGAGACCTGT GGCTGCCGCT GGACCTGCCC CTGYGTGTGC
5851 ACAGGCAGCT CCACTCGGCA CATCGTGACC TTTGATGGGC AGAATTTCAA
5901 GCTGACTGGC AGCTGTTCTT ATGTCCTATT TCAAAACAAG GAGCAGGACC
5951 TGGAGGTGAT TCTCCATAAT GGTGCCTGCA GCCCTGGAGC AAGGCAGGGC
6001 TGCATGAAAT CCATCGAGGT GAAGCACAGT GCCCTCTCCG TCGAGSTGCA
6051 CAGTGACATG GAGGTGACGG TGAATGGGAG ACTGGTCTCT GTTCCTTACG
6101 TGGGTGGGAA CATGGAAGTC AACGTTTATG GTGCCATCAT GCATGAGGTC
6151 AGATTCAATC ACCTTGGTCA CATCTTCACA TTCACTCCAC AAAACAATGA
```

TABLE 1-continued

VWF Sequences

```
6201 GTTCCAACTG CAGCTCAGCC CCAAGACTTT TGCTTCAAAG ACGTATGGTC
6251 TGTGTGGGAT CTGTGATGAG AACGGAGCCA ATGACTTCAT GCTGAGGGAT
6301 GGCACAGTCA CCACAGACTG GAAAACACTT GTTCAGGAAT GGACTGTGCA
6351 GCGGCCAGGG CAGACGTGCC AGCCCATCCT GGAGGAGCAG TGTCTTGTCC
6401 CCGACAGCTC CCACTGCCAG GTCCTCCTCT TACCACTGTT TGCTGAATGC
6451 CACAAGGTCC TGGCTCCAGC CACATTCTAT GCCATCTGCC AGCAGGACAG
6501 TTGCCACCAG GAGCAAGTGT GTGAGGTGAT CGCCTCTTAT GCCCACCTCT
6551 GTCGGACCAA CGGGGTCTGC GTTGACTGGA GGACACCTGA TTTCTGTGCT
6601 ATGTCATGCC CACCATCTCT GGTCTACAAC CACTGTGAGC ATGGCTGTCC
6651 CCGGCACTGT GATGGCAACG TGAGCTCCTG TGGGGACCAT CCCTCCGAAG
6701 GCTGTTTCTG CCCTCCAGAT AAAGTCATGT TGGAAGGCAG CTGTGTCCCT
6751 GAAGAGGCCT GCACTCAGTG CATTGGTGAG GATGGAGTCC AGCACCAGTT
6801 CCTGGAAGCC TGGGTCCCGG ACCACCAGCC CTGTCAGATC TGCACATGCC
6851 TCAGCGGGCG GAAGGTCAAC TGCACAACGC AGCCCTGCCC CACGGCCAAA
6901 GCTCCCACGT GTGGCCTGTG TGAAGTAGCC CGCCTCCGCC AGAATGCAGA
6951 CCAGTGCTGC CCCGAGTATG AGTGTGTGTG TGACCCAGTG AGCTGTGACC
7001 TGCCCCCAGT GCCTCACTGT GAACGTGGCC TCCAGCCCAC ACTGACCAAC
7051 CCTGGCGAGT GCAGACCCAA CTTCACCTGC GCCTGCAGGA AGGAGGAGTG
7101 CAAAAGAGTG TCCCCACCCT CCTGCCCCCC GCACCGTTTG CCCACCCTTC
7151 GGAAGACCCA GTGCTGTGAT GAGTATGAGT GTGCCTGCAA CTGTGTCAAC
7201 TCCACAGTGA GCTGTCCCCT TGGGTACTTG GCCTCAACCG CCACCAATGA
7251 CTGTGGCTGT ACCACAACCA CCTGCCTTCC CGACAAGGTG TGTGTCCACC
7301 GAAGCACCAT CTACCCTGTG GGCCAGTTCT GGGAGGAGGG CTGCGATGTG
7351 TGCACCTGCA CCGACATGGA GGATGCCGTG ATGGGCCTCC GCGTGGCCCA
7401 GTGCTCCCAG AAGCCCTGTG AGGACAGCTG TCGGTCGGGC TTCACTTACG
7451 TTCTGCATGA AGGCGAGTGC TGTGGAAGGT GCCTGCCATC TGCCTGTGAG
7501 GTGGTGACTG GCTCACCGCG GGGGGACTCC CAGTCTTCCT GGAAGAGTGT
7551 CGGCTCCCAG TGGGCCTCCC CGGAGAACCC CTGCCTCATC AATGAGTGTG
7601 TCCGAGTGAA GGAGGAGGTC TTTATACAAC AAAGGAACGT CTCCTGCCCC
7651 CAGCTGGAGG TCCCTGTCTG CCCCTCGGGC TTTCAGCTGA GCTGTAAGAC
7701 CTCAGCGTGC TGCCCAAGCT GTCGCTGTGA GCGCATGGAG GCCTGCATGC
7751 TCAATGGCAC TGTCATTGGG CCCGGGAAGA CTGTGATGAT CGATGTGTGC
7801 ACGACCTGCC GCTGCATGGT GCAGGTGGGG GTCATCTCTG GATTCAAGCT
7851 GGAGTGCAGG AAGACCACCT GCAACCCCTG CCCCCTGGGT TACAAGGAAG
7901 AAAATAACAC AGGTGAATGT TGTGGGAGAT GTTTGCCTAC GGCTTGCACC
7951 ATTCAGCTAA GAGGAGGACA GATCATGACA CTGAAGCGTG ATGAGACGCT
8001 CCAGGATGGC TGTGATACTC ACTTCTGCAA GGTCAATGAG AGAGGAGAGT
8051 ACTTCTGGGA GAAGAGGGTC ACAGGCTGCC CACCCTTTGA TGAACACAAG
8101 TGTCTTGCTG AGGGAGGTAA AATTATGAAA ATTCCAGGCA CCTGCTGTGA
8151 CACATGTGAG GAGCCTGAGT GCAACGACAT CACTGCCAGG CTGCAGTATG
8201 TCAAGGTGGG AAGCTGTAAG TCTGAAGTAG AGGTGGATAT CCACTACTGC
8251 CAGGGCAAAT GTGCCAGCAA AGCCATGTAC TCCATTGACA TCAACGATGT
8301 GCAGGACCAG TGCTCCTGCT GCTCTCCGAC ACGGACGGAG CCCATGCAGG
8351 TGGCCCTGCA CTGCACCAAT GGCTCTGTTG TGTACCATGA GGTTCTCAAT
8401 GCCATGGAGT GCAAATGCTC CCCCAGGAAG TGCAGCAAGT GA
```

The VWF fragment as used herein can be a VWF fragment comprising a D' domain and a D3 domain of VWF, wherein the VWF fragment binds to Factor VIII (FVIII) and inhibits binding of endogenous VWF (full-length VWF) to FVIII. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. In one embodiment, a VWF fragment comprises, consists essentially of, or consists of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof. The VWF fragment described herein does not contain a site binding to a VWF clearance receptor. In another embodiment, the VWF fragment described herein is not amino acids 764 to 1274 of SEQ ID NO: 2. The VWF fragment of the present invention can comprise any other sequences linked to or fused to the VWF fragment. For example, a VWF fragment described herein can further comprise a signal peptide.

In one embodiment, the VWF fragment binds to or is associated with a FVIII protein. By binding to or associating with a FVIII protein, a VWF fragment of the invention protects FVIII from protease cleavage and FVIII activation, stabilizes the heavy chain and light chain of FVIII, and prevents clearance of FVIII by scavenger receptors. In another embodiment, the VWF fragment binds to or associates with a FVIII protein and blocks or prevents binding of the FVIII protein to phospholipid and activated Protein C. By preventing or inhibiting binding of the FVIII protein with endogenous, full-length VWF, the VWF fragment of the invention reduces the clearance of FVIII by VWF clearance receptors and thus extends half-life of the FVIII protein. In one embodiment, the half-life extension of a FVIII protein is thus due to the binding of or associating with the VWF fragment lacking a VWF clearance receptor binding site to the FVIII protein and shielding or protecting of the FVIII protein by the VWF fragment from endogenous VWF which contains the VWF clearance receptor binding site. The FVIII protein bound to or protected by the VWF fragment can also allow recycling of a FVIII protein. By eliminating the VWF clearance pathway receptor binding sites contained in the full length VWF molecule, the FVIII/VWF heterodimers of the invention are shielded from the VWF clearance pathway, further extending FVIII half-life.

In one embodiment, a VWF fragment of the present invention comprises the D' domain and the D3 domain of VWF, wherein the D' domain is at least 60%, 70%, 80%, 85%, 90%, 95%, 96%, 97%, 98%, 99%, or 100% identical to amino acids 764 to 866 of SEQ ID NO: 2, wherein the VWF fragment prevents binding of endogenous VWF to FVIII. In another embodiment, a VWF fragment comprises the D' domain and the D3 domain of VWF, wherein the D3 domain is at least 60%, 70%, 80%, 85%, 90%, 95%, 96%, 97%, 98%, 99%, or 100% identical to amino acids 867 to 1240 of SEQ ID NO: 2, wherein the VWF fragment prevents binding of endogenous VWF to FVIII. In some embodiments, a VWF fragment described herein comprises, consists essentially of, or consists of the D' domain and D3 domain of VWF, which are at least 60%, 70%, 80%, 85%, 90%, 95%, 96%, 97%, 98%, 99%, or 100% identical to amino acids 764 to 1240 of SEQ ID NO: 2, wherein the VWF fragment prevents binding of endogenous VWF to FVIII. In other embodiments, a VWF fragment comprises, consists essentially of, or consists of the D1, D2, D', and D3 domains at least 60%, 70%, 80%, 85%, 90%, 95%, 96%, 97%, 98%, 99%, or 100% identical to amino acids 23 to 1240 of SEQ ID NO: 2, wherein the VWF fragment prevents binding of endogenous VWF to FVIII. In still other embodiments, the VWF fragment further comprises a signal peptide operably linked thereto.

In some embodiments, a VWF fragment of the invention consists essentially of or consists of (1) the D'D3 domain, the D1D'D3 domain, D2D'D3 domain, or D1D2D'D3 domain and (2) an additional VWF sequence up to about 10 amino acids (e.g., any sequences from amino acids 764 to 1240 of SEQ ID NO: 2 to amino acids 764 to 1250 of SEQ ID NO: 2), up to about 15 amino acids (e.g., any sequences from amino acids 764 to 1240 of SEQ ID NO: 2 to amino acids 764 to 1255 of SEQ ID NO: 2), up to about 20 amino acids (e.g., any sequences from amino acids 764 to 1240 of SEQ ID NO: 2 to amino acids 764 to 1260 of SEQ ID NO: 2), up to about 25 amino acids (e.g., any sequences from amino acids 764 to 1240 of SEQ ID NO: 2 to amino acids 764 to 1265 of SEQ ID NO: 2), or up to about 30 amino acids (e.g., any sequences from amino acids 764 to 1240 of SEQ ID NO: 2 to amino acids 764 to 1260 of SEQ ID NO: 2). In a particular embodiment, the VWF fragment comprising or consisting essentially of the D' domain and the D3 domain is neither amino acids 764 to 1274 of SEQ ID NO: 2 nor the full-length mature VWF. In some embodiments, the D1D2 domain is expressed in trans with the D'D3 domain. In some embodiments, the D1D2 domain is expressed in cis with the D'D3 domain.

In other embodiments, the VWF fragment comprising the D'D3 domains linked to the D1D2 domains further comprises an intracellular cleavage site, e.g., (a cleavage site by PACE (furin) or PC5), allowing cleavage of the D1D2 domains from the D'D3 domains upon expression. Non-limiting examples of the intracellular cleavage site are disclosed elsewhere herein.

In yet other embodiments, a VWF fragment comprises the D' domain and the D3 domain, but does not comprise an amino acid sequence selected from the group consisting of (1) amino acids 1241 to 2813 of SEQ ID NO: 2, (2) amino acids 1270 to amino acids 2813 of SEQ ID NO: 2, (3) amino acids 1271 to amino acids 2813 of SEQ ID NO: 2, (4) amino acids 1272 to amino acids 2813 of SEQ ID NO: 2, (5) amino acids 1273 to amino acids 2813 of SEQ ID NO: 2, (6) amino acids 1274 to amino acids 2813 of SEQ ID NO: 2, and any combinations thereof.

In still other embodiments, a VWF fragment of the present invention comprises, consists essentially of, or consists of an amino acid sequence corresponding to the D' domain, D3 domain, and A1 domain, wherein the amino acid sequence is at least 60%, 70%, 75%, 80%, 85%, 90%, 95%, 96%, 97%, 98%, 99%, or 100% identical to amino acid 764 to 1479 of SEQ ID NO: 2, wherein the VWF fragment prevents binding of endogenous VWF to FVIII. In a particular embodiment, the VWF fragment is not amino acids 764 to 1274 of SEQ ID NO: 2.

In some embodiments, a VWF fragment of the invention comprises the D' domain and the D3 domain, but does not comprise at least one VWF domain selected from the group consisting of (1) an A1 domain, (2) an A2 domain, (3) an A3 domain, (4) a D4 domain, (5) a B1 domain, (6) a B2 domain, (7) a B3 domain, (8) a C1 domain, (9) a C2 domain, (10) a CK domain, (11) a CK domain and C2 domain, (12) a CK domain, a C2 domain, and a C1 domain, (13) a CK domain, a C2 domain, a C1 domain, a B3 domain, (14) a CK domain, a C2 domain, a C1 domain, a B3 domain, a B2 domain, (15) a CK domain, a C2 domain, a C1 domain, a B3 domain, a B2 domain, and a B1 domain, (16) a CK domain, a C2 domain, a C1 domain, a B3 domain, a B2 domain, a B1 domain, and a D4 domain, (17) a CK domain, a C2 domain, a C1 domain, a B3 domain, a B2 domain, a B1 domain, a D4 domain, and an A3 domain, (18) a CK domain, a C2 domain, a C1 domain, a B3 domain, a B2 domain, a B1 domain, a D4 domain, an A3 domain, and an A2 domain, (19) a CK domain, a C2 domain, a C1 domain, a B3 domain, a B2 domain, a B1 domain, a D4 domain, an A3 domain, an A2 domain, and an A1 domain, and (20) any combinations thereof.

In yet other embodiments, the VWF fragment comprises the D'D3 domains and one or more domains or modules. Examples of such domains or modules include, but are not limited to, the domains and modules disclosed in Zhour et al., Blood published online Apr. 6, 2012: DOI 10.1182/blood-2012-01-405134. For example, the VWF fragment can comprise the D'D3 domain and one or more domains or modules selected from the group consisting of A1 domain, A2 domain, A3 domain, D4N module, VWD4 module, C8-4 module, TIL-4 module, C1 module, C2 module, C3 module, C4 module, C5 module, C5 module, C6 module, and any combinations thereof.

In still other embodiments, the VWF fragment is linked to a heterologous moiety, wherein the heterologous moiety is linked to the N-terminus or the C-terminus of the VWF fragment or inserted immediately downstream of one or more amino acids (e.g., one or more XTEN insertion sites) in the FVIII protein in the VWF fragment. For example, the insertion sites for the heterologous moiety in the VWF fragment can be in the D' domain, the D3 domain, or both. The heterologous moiety can be a half-life extender.

In certain embodiments, a VWF fragment of the invention forms a multimer, e.g., dimer, trimer, tetramer, pentamer, hexamer, heptamer, or the higher order multimers. In other embodiments, the VWF fragment is a monomer having only one VWF fragment. In some embodiments, the VWF fragment of the present invention can have one or more amino acid substitutions, deletions, additions, or modifications. In one embodiment, the VWF fragment can include amino acid substitutions, deletions, additions, or modifications such that the VWF fragment is not capable of forming a disulfide bond or forming a dimer or a multimer. In another embodiment, the amino acid substitution is within the D' domain and the D3 domain. In a particular embodiment, a VWF fragment of the invention contains at least one amino acid substitution at a residue corresponding to residue 1099, residue 1142, or both residues 1099 and 1142 of SEQ ID NO: 2. The at least one amino acid substitution can be any amino acids that are not occurring naturally in the wild type VWF. For example, the amino acid substitution can be any amino acids other than cysteine, e.g., Isoleucine, Alanine, Leucine, Asparagine, Lysine, Aspartic acid, Methionine, Phenylalanine, Glutamic acid, Threonine, Glutamine, Tryptophan, Glycine, Valine, Proline, Serine, Tyrosine, Arginine, or Histidine. In another example, the amino acid substitution has one or more amino acids that prevent or inhibit the VWF fragments from forming multimers.

In certain embodiments, the VWF fragment useful herein can be further modified to improve its interaction with FVIII, e.g., to improve binding affinity to FVIII. As a non-limiting example, the VWF fragment comprises a serine residue at the residue corresponding to amino acid 764 of SEQ ID NO: 2 and a lysine residue at the residue corresponding to amino acid 773 of SEQ ID NO: 2. Residues 764 and/or 773 can contribute to the binding affinity of the VWF fragments to FVIII. In other embodiments, the VWF fragments useful for the invention can have other modifications, e.g., the protein can be pegylated, glycosylated, hesylated, or polysialylated.

B) XTEN Sequences

As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties when linked to a VWF fragment or a FVIII sequence of the invention to create a chimeric protein. Such desirable properties include but are not limited to enhanced pharmacokinetic parameters and solubility characteristics. As used herein, "XTEN" specifically excludes antibodies or antibody fragments such as single-chain antibodies or Fc fragments of a light chain or a heavy chain.

In some embodiments, the XTEN sequence of the invention is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

The XTEN sequence of the invention can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 2A, resulting in a family sequence. As used herein, "family" means that the XTEN has motifs selected only from a single motif category from Table 2A; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII or VWF. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 2A. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 2A

XTEN Sequence Motifs of 12 Amino Acids and Motif Families

| Motif Family* | MOTIF SEQUENCE | SEQ ID NO: |
|---|---|---|
| AD | GESPGGSSGSES | 141 |
| AD | GSEGSSGPGESS | 142 |
| AD | GSSESGSSEGGP | 143 |
| AD | GSGGEPSESGSS | 144 |
| AE, AM | GSPAGSPTSTEE | 145 |
| AE, AM, AQ | GSEPATSGSETP | 146 |
| AE, AM, AQ | GTSESATPESGP | 147 |
| AE, AM, AQ | GTSTEPSEGSAP | 148 |
| AF, AM | GSTSESPSGTAP | 149 |
| AF, AM | GTSTPESGSASP | 150 |
| AF, AM | GTSPSGESSTAP | 151 |
| AF, AM | GSTSSTAESPGP | 152 |
| AG, AM | GTPGSGTASSSP | 153 |
| AG, AM | GSSTPSGATGSP | 154 |
| AG, AM | GSSPSASTGTGP | 155 |
| AG, AM | GASPGTSSTGSP | 156 |
| AQ | GEPAGSPTSTSE | 157 |
| AQ | GTGEPSSTPASE | 158 |

TABLE 2A-continued

XTEN Sequence Motifs of 12 Amino Acids and Motif Families

| Motif Family* | MOTIF SEQUENCE | SEQ ID NO: |
|---|---|---|
| AQ | GSGPSTESAPTE | 159 |
| AQ | GSETPSGPSETA | 160 |
| AQ | GPSETSTSEPGA | 161 |
| AQ | GSPSEPTEGTSA | 162 |
| BC | GSGASEPTSTEP | 163 |
| BC | GSEPATSGTEPS | 164 |
| BC | GTSEPSTSEPGA | 165 |
| BC | GTSTEPSEPGSA | 166 |
| BD | GSTAGSETSTEA | 167 |
| BD | GSETATSGSETA | 168 |
| BD | GTSESATSESGA | 169 |
| BD | GTSTEASEGSAS | 170 |

*Denotes individual motif sequences that, when used together in various permutations, results in a "family sequence"

XTEN can have varying lengths for insertion into or linkage to FVIII or VWF. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN include short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to FVIII or VWF can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length. The precise length of an XTEN inserted into or linked to FVIII or VWF can vary without adversely affecting the activity of the FVIII or VWF. In one embodiment, one or more of the XTEN used herein has 36 amino acids, 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the XTEN sequence used in the invention is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, and AG2004. See US 2010-0239554 A1.

In one embodiment, the XTEN sequence is at least 60%, 70%, 80%, 90%, 95%, 96%, 97%, 98%, 99% or 100% identical to an amino acid sequence selected from the group consisting of AE42 (SEQ ID NO: 36), AE72 (SEQ ID NO: 127), AE144_2A (SEQ ID NO: 128), AE144_3B (SEQ ID NO: 129), AE144_4A (SEQ ID NO: 130), AE144_5A (SEQ ID NO: 131), AE144_6B (SEQ ID NO: 132), AG144_A (SEQ ID NO: 133), AG144_B (SEQ ID NO: 134), AG144_C (SEQ ID NO: 135), AG144_F (SEQ ID NO: 136), AE864 (SEQ ID NO: 43), AE576 (SEQ ID NO: 41), AE288 (SEQ ID NO: 39), AE288_2 (SEQ ID NO: 137), AE144 (SEQ ID NO: 37), AG864 (SEQ ID NO: 44), AG576 (SEQ ID NO: 42), AG288 (SEQ ID NO: 40), AG144 (SEQ ID NO: 38), and any combinations thereof.

In some embodiments, less than 100% of amino acids of an XTEN are selected from glycine (G), alanine (A), serine (S), threonine (T), glutamate (E) and proline (P), or less than 100% of the sequence consists of the sequence motifs from Table 2A or the XTEN sequences of Table 2B. In such embodiments, the remaining amino acid residues of the XTEN are selected from any of the other 14 natural L-amino acids, but may be preferentially selected from hydrophilic amino acids such that the XTEN sequence contains at least about 90%, 91%, 92%, 93%, 94%, 95%, 96%, 97%, 98%, or at least about 99% hydrophilic amino acids. The content of hydrophobic amino acids in the XTEN utilized in the conjugation constructs may be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, XTEN sequences may contain less than 5% or less than 4% or less than 3% or less than 2% or less than 1% or none of the following amino acids: methionine (for example, to avoid oxidation), or asparagine and glutamine (to avoid desamidation).

In another embodiment, the XTEN sequence is selected from the group consisting of AE42 (SEQ ID NO: 36), AE72 (SEQ ID NO: 127), AE144_2A (SEQ ID NO: 128), AE144_3B (SEQ ID NO: 129), AE144_4A (SEQ ID NO: 130), AE144_5A (SEQ ID NO: 131), AE144_6B (SEQ ID NO: 132), AG144_A (SEQ ID NO: 133), AG144_B (SEQ ID NO: 134), AG144_C (SEQ ID NO: 135), AG144_F (SEQ ID NO: 136), AE864 (SEQ ID NO: 43), AE576 (SEQ ID NO: 41), AE288 (SEQ ID NO: 39), AE288_2 (SEQ ID NO: 137), AE144 (SEQ ID NO: 37), AG864 (SEQ ID NO: 44), AG576 (SEQ ID NO: 42), AG288 (SEQ ID NO: 40), AG144 (SEQ ID NO: 38), and any combinations thereof. In a specific embodiment, the XTEN sequence is AE288. The amino acid sequences for certain XTEN sequences of the invention are shown in Table 2B.

TABLE 2B

XTEN Sequences

| XTEN | Amino Acid Sequence |
|---|---|
| AE42<br>SEQ ID NO: 36 | GAPGSPAGSPTSTEEGTSESATPESGPGSEPATSGSETPASS |
| AE72<br>SEQ ID NO: 127 | GAPTSESATPESGPGSEPATSGSETPGTSESATPESGPGSEPATSGSETPGTSESA<br>TPESGPGTSTEPSEGSAPGASS |
| AE144<br>SEQ ID NO: 37 | GSEPATSGSETPGTSESATPESGPGSEPATSGSETPGSPAGSPTSTEEGTSTEPSE<br>GSAPGSEPATSGSETPGSEPATSGSETPGSEPATSGSETPGTSTEPSEGSAPGTSE<br>SAPESGPGSEPATSGSETPGTSTEPSEGSAP |
| AE144_2A<br>(SEQ ID NO: 128) | TSTEPSEGSAPGSPAGSPTSTEEGTSTEPSEGSAPGTSTEPSEGSAPGTSESATPE<br>SGPGTSTEPSEGSAPGTSESATPESGPGSEPATSGSETPGTSTEPSEGSAPGTSTE<br>PSEGSAPGTSESATPESGPGTSESATPESGPG |
| AE144_3B<br>(SEQ ID NO: 129) | SPAGSPTSTEEGTSESATPESGPGSEPATSGSETPGTSESATPESGPGTSTEPSEG<br>SAPGTSTEPSEGSAPGTSTEPSEGSAPGTSTEPSEGSAPGTSTEPSEGSAPGTSTE<br>PSEGSAPGSPAGSPTSTEEGTSTEPSEGSAPG |
| AE144_4A<br>(SEQ ID NO: 130) | TSESATPESGPGSEPATSGSETPGTSESATPESGPGSEPATSGSETPGTSESATPE<br>SGPGTSTEPSEGSAPGTSESATPESGPGSPAGSPTSTEEGSPAGSPTSTEEGSPAG<br>SPTSTEEGTSESATPESGPGTSTEPSEGSAPG |
| AE144_5A<br>(SEQ ID NO: 131) | TSESATPESGPGSEPATSGSETPGTSESATPESGPGSEPATSGSETPGTSESATPE<br>SGPGTSTEPSEGSAPGSPAGSPTSTEEGTSESATPESGPGSEPATSGSETPGTSES<br>ATPESGPGSPAGSPTSTEEGSPAGSPTSTEEG |
| AE144_6B<br>(SEQ ID NO: 132) | TSTEPSEGSAPGTSESATPESGPGTSESATPESGPGTSESATPESGPGSEPATSGS<br>ETPGSEPATSGSETPGSPAGSPTSTEEGTSTEPSEGSAPGTSTEPSEGSAPGSEPA<br>TSGSETPGTSESATPESGPGTSTEPSEGSAPG |
| AG144<br>SEQ ID NO: 38 | GTPGSGTASSSPGSSTPSGATGSPGSSPSASTGTGPGSSPSASTGTGPGASPGTSS<br>TGSPGASPGTSSTGSPGSSTPSGATGSPGSSPSASTGTGPGASPGTSSTGSPGSSP<br>SASTGTGPGTPGSGTASSSPGSSTPSGATGSP |
| AG144_A<br>(SEQ ID NO: 133) | GASPGTSSTGSPGSSPSASTGTGPGSSPSASTGTGPGTPGSGTASSSPGSSTPSGA<br>TGSPGSSPSASTGTGPGASPGTSSTGSPGTPGSGTASSSPGSSTPSGATGSPGTPG<br>SGTASSSPGASPGTSSTGSPGASPGTSSTGSP |
| AG144_B<br>(SEQ ID NO: 134) | GTPGSGTASSSPGSSTPSGATGSPGASPGTSSTGSPGTPGSGTASSSPGSSTPSGA<br>TGSPGSSPSASTGTGPGSSPSASTGTGPGSSTPSGATGSPGSSTPSGATGSPGASP<br>GTSSTGSPGASPGTSSTGSPGASPGTSSTGSP |
| AG144_C<br>(SEQ ID NO: 135) | GTPGSGTASSSPGASPGTSSTGSPGASPGTSSTGSPGASPGTSSTGSPGSSPSAST<br>GTGPGTPGSGTASSSPGASPGTSSTGSPGASPGTSSTGSPGASPGTSSTGSPGSST<br>PSGATGSPGSSTPSGATGSPGASPGTSSTGSP |
| AG144_F<br>(SEQ ID NO: 136) | GSSPSASTGTGPGSSPSASTGTGPGASPGTSSTGSPGASPGTSSTGSPGSSTPSGA<br>TGSPGSSPSASTGTGPGASPGTSSTGSPGSSPSASTGTGPGTPGSGTASSSPGSST<br>PSGATGSPGSSTPSGATGSPGASPGTSSTGSP |
| AE288<br>SEQ ID NO: 39 | GTSESATPESGPGSEPATSGSETPGTSESATPESGPGSEPATSGSETPGTSESATP<br>ESGPGTSTEPSEGSAPGSPAGSPTSTEEGTSESATPESGPGSEPATSGSETPGTSE<br>SATPESGPGSPAGSPTSTEEGSPAGSPTSTEEGTSTEPSEGSAPGTSESATPESGP<br>GTSESATPESGPGTSESATPESGPGSEPATSGSETPGSEPATSGSETPGSPAGSPT<br>STEEGTSTEPSEGSAPGTSTEPSEGSAPGSEPATSGSETPGTSESATPESGPGTST<br>EPSEGSAP |
| AE288_2<br>(SEQ ID NO: 137) | GSPAGSPTSTEEGTSESATPESGPGSEPATSGSETPGTSESATPESGPGTSTEPSE<br>GSAPGTSTEPSEGSAPGTSTEPSEGSAPGTSTEPSEGSAPGTSTEPSEGSAPGTST<br>EPSEGSAPGSPAGSPTSTEEGTSTEPSEGSAPGTSESATPESGPGSEPATSGSETP<br>GTSESATPESGPGSEPATSGSETPGTSESATPESGPGTSTEPSEGSAPGTSESATP<br>ESGPGSPAGSPTSTEEGSPAGSPTSTEEGSPAGSPTSTEEGTSESATPESGPGTST<br>EPSEGSAP |
| AG288<br>SEQ ID NO: 40 | PGASPGTSSTGSPGASPGTSSTGSPGTPGSGTASSSPGSSTPSGATGSPGTPGSGT<br>ASSSPGSSTPSGATGSPGTPGSGTASSSPGSSTPSGATGSPGSSTPSGATGSPGSS<br>PSASTGTGPGSSPSASTGTGPGASPGTSSTGSPGTPGSGTASSSPGSSTPSGATGS<br>PGSSPSASTGTGPGSSPSASTGTGPGASPGTSSTGSPGSSTPSG<br>ATGSPGSSPSASTGTGPGASPGTSSTGSPGSSPSASTGTGPGTPGSGTASSSPGSS<br>TPSGATGS |
| AE576<br>SEQ ID NO: 41 | GSPAGSPTSTEEGTSESATPESGPGTSTEPSEGSAPGSPAGSPTSTEEGTSTEPSE<br>GSAPGTSTEPSEGSAPGTSESATPESGPGSEPATSGSETPGSEPATSGSETPGSPA<br>GSPTSTEEGTSESATPESGPGTSTEPSEGSAPGTSTEPSEGSAPGSPAGSPTSTEE<br>GTSTEPSEGSAPGTSTEPSEGSAPGTSESATPESGPGTSTEPSEGSAPGTSESATP<br>ESGPGSEPATSGSETPGTSTEPSEGSAPGTSTEPSEGSAPGTSESATPESGPGTSE |

TABLE 2B-continued

XTEN Sequences

| XTEN | Amino Acid Sequence |
|---|---|
| | SATPESGPGSPAGSPTSTEEGTSESATPESGPGSEPATSGSETPGTSESATPESGP<br>GTSTEPSEGSAPGTSTEPSEGSAPGTSTEPSEGSAPGTSTEPSEGSAPGTSTEPSE<br>GSAPGTSTEPSEGSAPGSPAGSPTSTEEGTSTEPSEGSAPGTSESATPESGPGSEP<br>ATSGSETPGTSESATPESGPGSEPATSGSETPGTSESATPESGPGTSTEPSEGSAP<br>GTSESATPESGPGSPAGSPTSTEEGSPAGSPTSTEEGSPAGSPTSTEEGTSESATP<br>ESGPGTSTEPSEGSAP |
| AG576<br>SEQ ID NO: 42 | PGTPGSGTASSSPGSSTPSGATGSPGSSPSASTGTGPGSSPSASTGTGPGSSTPSG<br>ATGSPGSSTPSGATGSPGASPGTSSTGSPGASPGTSSTGSPGASPGTSSTGSPGTP<br>GSGTASSSPGASPGTSSTGSPGASPGTSSTGSPGASPGTSSTGSPGSSPSASTGTG<br>PGTPGSGTASSSPGASPGTSSTGSPGASPGTSSTGSPGASPGTSSTGSPGSSTPSG<br>ATGSPGSSTPSGATGSPGASPGTSSTGSPGTPGSGTASSSPGSSTPSGATGSPGSS<br>TPSGATGSPGSSTPSGATGSPGSSPSASTGTGPGASPGTSSTGSPGASPGTSSTGS<br>PGTPGSGTASSSPGASPGTSSTGSPGASPGTSSTGSPGASPGTSSTGSPGASPGTS<br>STGSPGTPGSGTASSSPGSSTPSGATGSPGTPGSGTASSSPGSSTPSGATGSPGTP<br>GSGTASSSPGSSTPSGATGSPGSSTPSGATGSPGSSPSASTGTGPGSSPSASTGTG<br>PGASPGTSSTGSPGTPGSGTASSSPGSSTPSGATGSPGSSPSASTGTGPGSSPSAS<br>TGTGPGASPGTSSTGS |
| AE864<br>SEQ ID NO: 43 | GSPAGSPTSTEEGTSESATPESGPGTSTEPSEGSAPGSPAGSPTSTEEGTSTEPSE<br>GSAPGTSTEPSEGSAPGTSESATPESGPGSEPATSGSETPGSEPATSGSETPGSPA<br>GSPTSTEEGTSESATPESGPGTSTEPSEGSAPGTSTEPSEGSAPGSPAGSPTSTEE<br>GTSTEPSEGSAPGTSTEPSEGSAPGTSESATPESGPGTSTEPSEGSAPGTSESATP<br>ESGPGSEPATSGSETPGTSTEPSEGSAPGTSTEPSEGSAPGTSESATPESGPGTSE<br>SATPESGPGSPAGSPTSTEEGTSESATPESGPGSEPATSGSETPGTSESATPESGP<br>GTSTEPSEGSAPGTSTEPSEGSAPGTSTEPSEGSAPGTSTEPSEGSAPGTSTEPSE<br>GSAPGTSTEPSEGSAPGSPAGSPTSTEEGTSTEPSEGSAPGTSESATPESGPGSEP<br>ATSGSETPGTSESATPESGPGSEPATSGSETPGTSESATPESGPGTSTEPSEGSAP<br>GTSESATPESGPGSPAGSPTSTEEGSPAGSPTSTEEGSPAGSPTSTEEGTSESATP<br>ESGPGTSTEPSEGSAPGTSESATPESGPGSEPATSGSETPGTSESATPESGPGSEP<br>ATSGSETPGTSESATPESGPGTSTEPSEGSAPGSPAGSPTSTEEGTSESATPESGP<br>GSEPATSGSETPGTSESATPESGPGSPAGSPTSTEEGSPAGSPTSTEEGTSTEPSE<br>GSAPGTSESATPESGPGTSESATPESGPGTSESATPESGPGSEPATSGSETPGSEP<br>ATSGSETPGSPAGSPTSTEEGTSTEPSEGSAPGTSTEPSEGSAPGSEPATSGSETP<br>GTSESATPESGPGTSTEPSEGSAP |
| AG864<br>SEQ ID NO: 44 | GASPGTSSTGSPGSSPSASTGTGPGSSPSASTGTGPGTPGSGTASSSPGSSTPSGA<br>TGSPGSSPSASTGTGPGASPGTSSTGSPGTPGSGTASSSPGSSTPSGATGSPGTPG<br>SGTASSSPGASPGTSSTGSPGASPGTSSTGSPGTPGSGTASSSPGSSTPSGATGSP<br>GASPGTSSTGSPGTPGSGTASSSPGSSTPSGATGSPGSSPSASTGTGPGSSPSAST<br>GTGPGSSTPSGATGSPGSSTPSGATGSPGASPGTSSTGSPGASPGTSSTGSPGASP<br>GTSSTGSPGTPGSGTASSSPGASPGTSSTGSPGASPGTSSTGSPGASPGTSSTGSP<br>GSSPSASTGTGPGTPGSGTASSSPGASPGTSSTGSPGASPGTSSTGSPGASPGTSS<br>TGSPGSSTPSGATGSPGSSTPSGATGSPGASPGTSSTGSPGTPGSGTASSSPGSST<br>PSGATGSPGSSTPSGATGSPGSSTPSGATGSPGSSPSASTGTGPGASPGTSSTGSP<br>GASPGTSSTGSPGTPGSGTASSSPGASPGTSSTGSPGASPGTSSTGSPGASPGTSS<br>TGSPGASPGTSSTGSPGTPGSGTASSSPGSSTPSGATGSPGTPGSGTASSSPGSST<br>PSGATGSPGTPGSGTASSSPGSSTPSGATGSPGSSTPSGATGSPGSSPSASTGTGP<br>GSSPSASTGTGPGASPGTSSTGSPGTPGSGTASSSPGSSTPSGATGSPGSSPSAST<br>GTGPGSSPSASTGTGPGASPGTSSTGSPGASPGTSSTGSPGSSTPSGATGSPGSSP<br>SASTGTGPGASPGTSSTGSPGSSPSASTGTGPGTPGSGTASSSPGSSTPSGATGSP<br>GSSTPSGATGSPGASPGTSSTGSP |

In further embodiments, the XTEN sequence used in the invention affects the physical or chemical property, e.g., pharmacokinetics, of the chimeric protein of the present invention. The XTEN sequence used in the present invention can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN sequence linked to a FVIII protein in this invention increases pharmacokinetic properties such as longer terminal half-life or increased area under the curve (AUC), so that the chimeric protein described herein stays in vivo for an increased period of time compared to wild type FVIII. In further embodiments, the XTEN sequence used in this invention increases pharmacokinetic properties such as longer terminal half-life or increased area under the curve (AUC), so that FVIII protein stays in vivo for an increased period of time compared to wild type FVIII.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2.

C) Factor VIII (FVIII) Protein

"A FVIII protein" as used herein means a functional FVIII polypeptide in its normal role in coagulation, unless otherwise specified. The term a FVIII protein includes a functional fragment, variant, analog, or derivative thereof that retains the function of full-length wild-type Factor VIII in the coagulation pathway. "A FVIII protein" is used interchangeably with FVIII polypeptide (or protein) or FVIII. Examples of the FVIII functions include, but not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632).

A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The FVIII polypeptide and polynucleotide sequences are known, as are many functional fragments, mutants and modified versions. Examples of human FVIII sequences (full-length) are shown below.

TABLE 3

Amino Acid Sequence of Full-length Factor VIII (Full-length FVIII (FVIII signal peptide underlined; FVIII heavy chain is double underlined; B domain is italicized; and FVIII light chain is in plain text)

Signal Peptide: (SEQ ID NO: 3)

MQIELSTCFFLCLLRFCFS

Mature Factor VIII (SEQ ID NO: 4)*

ATRRYYLGAVELSWDYMQSDLGELPVDARFPPRVPKSFPFNTSVVYKKTL

FVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVNRSLPGLIGCHR

KSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDL

TDSEMDVVRFDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPHPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

GMTALLKVSSCDKNTGDYYEDSYEDISAYLLSKNNAIEPR*SFSQNSRHPS*

*TRQKQFNATTIPENDIEKTDPWFAHRTPMPKIQNVSSSDLLMLLRQSPTP*

*HGLSLSDLQEAKYETFSDDPSPGAIDSNNSLSEMTHFRPQLHHSGDMVFT*

*PESGLQLRLNEKLGTTAATELKKLDFKVSSTSNNLISTIPSDNLAAGTDN*

*TSSLGPPSMPVHYDSQLDTTLFGKKSSPLETSGGPLSLSEENNDSKLLES*

*GLMNSQESSWGKNVSSTESGRLFKGKRAHGPALLTKDNALFKVSISLLKT*

*NKTSNNSATNRKTHIDGPSLLIENSPSVWQNILESDTEFKKVTPLIHDRM*

*LMDKNATALRLNHMSNKTTSSKNMEMVQQKKEGPIPPDAQNPDMSFFKML*

*FLPESARWIQRTHGKNSLNSGQGPSPKQLVSLGPEKSVEGQNFLSEKNKV*

*VVGKGEFTKDVGLKEMVFPSSRNLFLTNLDNLHENNTHNQEKKIQEEIEK*

*KETLIQENVVLPQIHTVTGTKNFMKNLFLLSTRQNVEGSYDGAYAPVLQD*

*FRSLNDSTNRTKKHTAHFSKKGEEENLEGLGNQTKQIVEKYACTTRISPN*

*TSQQNFVTQRSKRALKQFRLPLEETELEKRIIVDDTSTQWSKNMKHLTPS*

*TLTQIDYNEKEKGAITQSPLSDCLTRSHSIPQANRSPLPIAKVSSFPSIR*

*PIYLTRVLFQDNSSHLPAASYRKKDSGVQESSHFLQGAKKNNLSLAILTL*

*EMTGDQREVGSLGTSATNSVTYKKVENTVLPKPDLPKTSGKVELLPKVHI*

*YQKDLFPTETSNGSPGHLDLVEGSLLQGTEGAIKWNEANRPGKVPFLRVA*

*TESSAKTPSKLLDPLAWDNHYGTQIPKEEWKSQEKSPEKTAFKKKDTILS*

LNACESNHAIAAINEGQNKPEIEVTWAKQGRTERLCSQNPPVLKRHQREI

TRTTLQSDQEEIDYDDTISVEMKKEDFDIYDEDENQSPRSFQKKTRHYFI

TABLE 3-continued

Amino Acid Sequence of Full-length Factor VIII (Full-length FVIII (FVIII signal peptide underlined; FVIII heavy chain is double underlined; B domain is italicized; and FVIII light chain is in plain text)

AAVERLWDYGMSSSPHVLRNRAQSGSVPQFKKVVFQEFTDGSFTQPLYRG

ELNEHLGLLGPYIRAEVEDNIMVTFRNQASRPYSFYSSLISYEEDQRQGA

EPRKNFVKPNETKTYFWKVQHHMAPTKDEFDCKAWAYFSDVDLEKDVHSG

LIGPLLVCHTNTLNPAHGRQVTVQEFALFFTIFDETKSWYFTENMERNCR

APCNIQMEDPTFKENYRFHAINGYIMDTLPGLVMAQDQRIRWYLLSMGSN

ENIHSIHFSGHVFTVRKKEEYKMALYNLYPGVFETVEMLPSKAGIWRVEC

LIGEHLHAGMSTLFLVYSNKCQTPLGMASGHIRDFQITASGQYGQWAPKL

TABLE 3-continued

Amino Acid Sequence of Full-length Factor VIII (Full-length FVIII (FVIII signal peptide underlined; FVIII heavy chain is double underlined; B domain is italicized; and FVIII light chain is in plain text)

ARLHYSGSINAWSTKEPFSWIKVDLLAPMIIHGIKTQGARQKFSSLYISQ

FIIMYSLDGKKWQTYRGNSTGTLMVFFGNVDSSGIKHNIFNPPIIARYIR

LHPTHYSIRSTLRMELMGCDLNSCSMPLGMESKAISDAQITASSYFTNMF

ATWSPSKARLHLQGRSNAWRPQVNNPKEWLQVDFQKTMKVTGVTTQGVKS

LLTSMYVKEFLISSSQDGHQWTLFFQNGKVKVFQGNQDSFTPVVNSLDPP

LLTRYLRIHPQSWVHQIALRMEVLGCEAQDLY

TABLE 4

Nucleotide Sequence Encoding Full-Length FVIII (SEQ ID NO: 5)*

661                                                                                                ATG

CAAATAGAGC TCTCCACCTG

721 CTTCTTTCTG TGCCTTTTGC GATTCTGCTT TAGTGCCACC AGAAGATACT ACCTGGGTGC

781 AGTGGAACTG TCATGGGACT ATATGCAAAG TGATCTCGGT GAGCTGCCTG TGGACGCAAG

841 ATTTCCTCCT AGAGTGCCAA ATCTTTTCC ATTCAACACC TCAGTCGTGT ACAAAAAGAC

901 TCTGTTTGTA GAATTCACGA TCACCTTTT CAACATCGCT AAGCCAAGGC CACCCTGGAT

961 GGGTCTGCTA GGTCCTACCA TCCAGGCTGA GGTTTATGAT ACAGTGGTCA TTACACTTAA

1021 GAACATGGCT TCCCATCCTG TCAGTCTTCA TGCTGTTGGT GTATCCTACT GGAAAGCTTC

1081 TGAGGGAGCT GAATATGATG ATCAGACCAG TCAAAGGGAG AAAGAAGATG ATAAAGTCTT

1141 CCCTGGTGGA AGCCATACAT ATGTCTGGCA GGTCCTGAAA GAGAATGGTC CAATGGCCTC

1201 TGACCCACTG TGCCTTACCT ACTCATATCT TTCTCATGTG GACCTGGTAA AAGACTTGAA

1261 TTCAGGCCTC ATTGGAGCCC TACTAGTATG TAGAGAAGGG AGTCTGGCCA AGGAAAAGAC

1321 ACAGACCTTG CACAAATTTA TACTACTTTT TGCTGTATTT GATGAAGGGA AAAGTTGGCA

1381 CTCAGAAACA AAGAACTCCT TGATGCAGGA TAGGGATGCT GCATCTGCTC GGGCCTGGCC

1441 TAAAATGCAC ACAGTCAATG GTTATGTAAA CAGGTCTCTG CCAGGTCTGA TTGGATGCCA

1501 CAGGAAATCA GTCTATTGGC ATGTGATTGG AATGGGCACC ACTCCTGAAG TGCACTCAAT

1561 ATTCCTCGAA GGTCACACAT TTCTTGTGAG GAACCATCGC CAGGCGTCCT TGGAAATCTC

1621 GCCAATAACT TCCTTACTG CTCAAACACT CTTGATGGAC CTTGGACAGT TTCTACTGTT

1681 TTGTCATATC TCTTCCCACC AACATGATGG CATGGAAGCT TATGTCAAAG TAGACAGCTG

1741 TCCAGAGGAA CCCCAACTAC GAATGAAAAA TAATGAAGAA GCGGAAGACT ATGATGATGA

1801 TCTTACTGAT TCTGAAATGG ATGTGGTCAG GTTTGATGAT GACAACTCTC CTTCCTTTAT

1861 CCAAATTCGC TCAGTTGCCA GAAGCATCC TAAAACTTGG GTACATTACA TTGCTGCTGA

1921 AGAGGAGGAC TGGGACTATG CTCCCTTAGT CCTCGCCCCC GATGACAGAA GTTATAAAAG

1981 TCAATATTTG AACAATGGCC CTCAGCGGAT TGGTAGGAAG TACAAAAAAG TCCGATTTAT

2041 GGCATACACA GATGAAACCT TTAAGACTCG TGAAGCTATT CAGCATGAAT CAGGAATCTT

2101 GGGACCTTTA CTTTATGGGG AAGTTGGAGA CACACTGTTG ATTATATTA AGAATCAAGC

2161 AAGCAGACCA TATAACATCT ACCCTCACGG AATCACTGAT GTCCGTCCTT TGTATTCAAG

TABLE 4-continued

Nucleotide Sequence Encoding Full-Length FVIII (SEQ ID NO: 5)*

```
2221 GAGATTACCA AAAGGTGTAA ACATTTGAA GGATTTTCCA ATTCTGCCAG GAGAAATATT
2281 CAAATATAAA TGGACAGTGA CTGTAGAAGA TGGGCCAACT AAATCAGATC CTCGGTGCCT
2341 GACCCGCTAT TACTCTAGTT TCGTTAATAT GGAGAGAGAT CTAGCTTCAG GACTCATTGG
2401 CCCTCTCCTC ATCTGCTACA AGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
2881 TAGTTGTGAC AAGAACACTG GTGATTATTA CGAGGACAGT TATGAAGATA TTTCAGCATA
2941 CTTGCTGAGT AAAAACAATG CCATTGAACC AAGAAGCTTC TCCCAGAATT CAAGACACCC
3001 TAGCACTAGG CAAAAGCAAT TTAATGCCAC CACAATTCCA GAAAATGACA TAGAGAAGAC
3061 TGACCCTTGG TTTGCACACA GAACACCTAT GCCTAAAATA CAAAATGTCT CCTCTAGTGA
3121 TTTGTTGATG CTCTTGCGAC AGAGTCCTAC TCCACATGGG CTATCCTTAT CTGATCTCCA
3181 AGAAGCCAAA TATGAGACTT TTTCTGATGA TCCATCACCT GGAGCAATAG ACAGTAATAA
3241 CAGCCTGTCT GAAATGACAC ACTTCAGGCC ACAGCTCCAT CACAGTGGGG ACATGGTATT
3301 TACCCCTGAG TCAGGCCTCC AATTAAGATT AAATGAGAAA CTGGGGACAA CTGCAGCAAC
3361 AGAGTTGAAG AAACTTGATT TCAAAGTTTC TAGTACATCA AATAATCTGA TTTCAACAAT
3421 TCCATCAGAC AATTTGGCAG CAGGTACTGA TAATACAAGT TCCTTAGGAC CCCCAAGTAT
3481 GCCAGTTCAT TATGATAGTC AATTAGATAC CACTCTATTT GGCAAAAAGT CATCTCCCCT
3541 TACTGAGTCT GGTGGACCTC TGAGCTTGAG TGAAGAAAAT AATGATTCAA AGTTGTTAGA
3601 ATCAGGTTTA ATGAATAGCC AAGAAAGTTC ATGGGGAAAA AATGTATCGT CAACAGAGAG
3661 TGGTAGGTTA TTTAAAGGGA AAAGAGCTCA TGGACCTGCT TTGTTGACTA AAGATAATGC
3721 CTTATTCAAA GTTAGCATCT CTTTGTTAAA GACAAACAAA ACTTCCAATA ATTCAGCAAC
3781 TAATAGAAAG ACTCACATTG ATGGCCCATC ATTATTAATT GAGAATAGTC CATCAGTCTG
3841 GCAAAATATA TTAGAAAGTG ACACTGAGTT TAAAAAAGTG ACACCTTTGA TTCATGACAG
3901 AATGCTTATG GACAAAAATG CTACAGCTTT GAGGCTAAAT CATATGTCAA ATAAAACTAC
3961 TTCATCAAAA AACATGGAAA TGGTCCAACA GAAAAAAGAG GGCCCCATTC CACCAGATGC
4021 ACAAAATCCA GATATGTCGT TCTTTAAGAT GCTATTCTTG CCAGAATCAG CAAGGTGGAT
4081 ACAAAGGACT CATGGAAAGA ACTCTCTGAA CTCTGGGCAA GGCCCCAGTC CAAAGCAATT
4141 AGTATCCTTA GGACCAGAAA ATCTGTGGA AGGTCAGAAT TCTTGTCTG AGAAAACAA
4201 AGTGGTAGTA GGAAAGGGTG AATTTACAAA GGACGTAGGA CTCAAAGAGA TGGTTTTTCC
4261 AAGCAGCAGA AACCTATTTC TTACTAACTT GGATAATTTA CATGAAAATA ATACACACAA
4321 TCAAGAAAAA AAATTCAGG AAGAAATAGA AAAGAAGGAA ACATTAATCC AAGAGAATGT
4381 AGTTTTGCCT CAGATACATA CAGTGACTGG CACTAAGAAT TTCATGAAGA ACCTTTTCTT
4441 ACTGAGCACT AGGCAAAATG TAGAAGGTTC ATATGACGGG GCATATGCTC CAGTACTTCA
4501 AGATTTTAGG TCATTAAATG ATTCAACAAA TAGAACAAAG AAACACACAG CTCATTTCTC
```

TABLE 4-continued

Nucleotide Sequence Encoding Full-Length FVIII (SEQ ID NO: 5)*

```
4561 AAAAAAGGG GAGGAAGAAA ACTTGGAAGG CTTGGGAAAT CAAACCAAGC AAATTGTAGA
4621 GAAATATGCA TGCACCACAA GGATATCTCC TAATACAAGC CAGCAGAATT TTGTCACGCA
4681 ACGTAGTAAG AGAGCTTTGA ACAATTCAG ACTCCCACTA GAAGAAACAG AACTTGAAAA
4741 AAGGATAATT GTGGATGACA CCTCAACCCA GTGGTCCAAA ACATGAAAC ATTTGACCCC
4801 GAGCACCCTC ACACAGATAG ACTACAATGA GAAGGAGAAA GGGGCCATTA CTCAGTCTCC
4861 CTTATCAGAT TGCCTTACGA GGAGTCATAG CATCCCTCAA GCAAATAGAT CTCCATTACC
4921 CATTGCAAAG GTATCATCAT TTCCATCTAT TAGACCTATA TATCTGACCA GGGTCCTATT
4981 CCAAGACAAC TCTTCTCATC TTCCAGCAGC ATCTTATAGA AGAAAGATT CTGGGGTCCA
5041 AGAAAGCAGT CATTTCTTAC AAGGAGCCAA AAAAAATAAC CTTTCTTTAG CCATTCTAAC
5101 CTTGGAGATG ACTGGTGATC AAAGAGAGGT TGGCTCCCTG GGACAAGTG CCACAAATTC
5161 AGTCACATAC AAGAAAGTTG AGAACACTGT TCTCCCGAAA CCAGACTTGC CAAAACATC
5221 TGGCAAAGTT GAATTGCTTC AAAAGTTCA CATTTATCAG AAGGACCTAT TCCCTACGGA
5281 AACTAGCAAT GGGTCTCCTG GCCATCTGGA TCTCGTGGAA GGGAGCCTTC TCAGGGAAC
5341 AGAGGGAGCG ATTAAGTGGA ATGAAGCAAA CAGACCTGGA AAAGTTCCCT TTCTGAGAGT
5401 AGCAACAGAA AGCTCTGCAA AGACTCCCTC CAAGCTATTG GATCCTCTTG CTTGGGATAA
5461 CCACTATGGT ACTCAGATAC AAAAGAAGA GTGGAAATCC CAAGAGAAGT CACCAGAAAA
5521 AACAGCTTTT AAGAAAAAGG ATACCATTTT GTCCCTGAAC GCTTGTGAAA GCAATCATGC
5581 AATAGCAGCA ATAAATGAGG GACAAAATAA GCCCGAAATA GAAGTCACCT GGGCAAAGCA
5641 AGGTAGGACT GAAAGGCTGT GCTCTCAAAA CCCACCAGTC TTGAAACGCC ATCAACGGGA
5701 AATAACTCGT ACTACTCTTC AGTCAGATCA AGAGGAAATT GACTATGATG ATACCATATC
5761 AGTTGAAATG AAGAAGGAAG ATTTTGACAT TTATGATGAG GATGAAAATC AGAGCCCCCG
5821 CAGCTTTCAA AAGAAAACAC GACACTATTT TATTGCTGCA GTGGAGAGGC TCTGGGATTA
5881 TGGGATGAGT AGCTCCCCAC ATGTTCTAAG AAACAGGGCT CAGAGTGGCA GTGTCCCTCA
5941 GTTCAAGAAA GTTGTTTTCC AGGAATTTAC TGATGGCTCC TTTACTCAGC CCTTATACCG
6001 TGGAGAACTA AATGAACATT TGGGACTCCT GGGGCCATAT ATAAGAGCAG AAGTTGAAGA
6061 TAATATCATG GTAACTTTCA GAAATCAGGC CTCTCGTCCC TATTCCTTCT ATTCTAGCCT
6121 TATTTCTTAT GAGGAAGATC AGAGGCAAGG AGCAGAACCT AGAAAAAACT TTGTCAAGCC
6181 TAATGAAACC AAAACTTACT TTTGGAAAGT GCAACATCAT ATGGCACCCA CTAAAGATGA
6241 GTTTGACTGC AAAGCCTGGG CTTATTTCTC TGATGTTGAC CTGGAAAAAG ATGTGCACTC
6301 AGGCCTGATT GGACCCCTTC TGGTCTGCCA CACTAACACA CTGAACCCTG CTCATGGGAG
6361 ACAAGTGACA GTACAGGAAT TTGCTCTGTT TTTCACCATC TTTGATGAGA CCAAAAGCTG
6421 GTACTTCACT GAAAATATGG AAAGAAACTG CAGGGCTCCC TGCAATATCC AGATGGAAGA
6481 TCCCACTTTT AAAGAGAATT ATCGCTTCCA TGCAATCAAT GGCTACATAA TGGATACACT
6541 ACCTGGCTTA GTAATGGCTC AGGATCAAAG GATTCGATGG TATCTGCTCA GCATGGGCAG
6601 CAATGAAAAC ATCCATTCTA TTCATTTCAG TGGACATGTG TTCACTGTAC GAAAAAAGA
6661 GGAGTATAAA ATGGCACTGT ACAATCTCTA TCCAGGTGTT TTTGAGACAG TGGAAATGTT
6721 ACCATCCAAA GCTGGAATTT GGCGGGTGGA ATGCCTTATT GGCGAGCATC TACATGCTGG
6781 GATGAGCACA CTTTTTCTGG TGTACAGCAA TAAGTGTCAG ACTCCCCTGG GAATGGCTTC
6841 TGGACACATT AGAGATTTTC AGATTACAGC TTCAGGACAA TATGGACAGT GGGCCCCAAA
```

TABLE 4-continued

Nucleotide Sequence Encoding Full-Length FVIII (SEQ ID NO: 5)*

| | | | | | |
|---|---|---|---|---|---|
| 6901 | GCTGGCCAGA | CTTCATTATT | CCGGATCAAT | CAATGCCTGG | AGCACCAAGG | AGCCCTTTTC |
| 6961 | TTGGATCAAG | GTGGATCTGT | TGGCACCAAT | GATTATTCAC | GGCATCAAGA | CCCAGGGTGC |
| 7021 | CCGTCAGAAG | TTCTCCAGCC | TCTACATCTC | TCAGTTTATC | ATCATGTATA | GTCTTGATGG |
| 7081 | GAAGAAGTGG | CAGACTTATC | GAGGAAATTC | CACTGGAACC | TTAATGGTCT | TCTTTGGCAA |
| 7141 | TGTGGATTCA | TCTGGGATAA | AACACAATAT | TTTTAACCCT | CCAATTATTG | CTCGATACAT |
| 1201 | CCGTTTGCAC | CCAACTCATT | ATAGCATTCG | CAGCACTCTT | CGCATGGAGT | TGATGGGCTG |
| 7261 | TGATTTAAAT | AGTTGCAGCA | TGCCATTGGG | AATGGAGAGT | AAAGCAATAT | CAGATGCACA |
| 7321 | GATTACTGCT | TCATCCTACT | TTACCAATAT | GTTTGCCACC | TGGTCTCCTT | CAAAAGCTCG |
| 7381 | ACTTCACCTC | CAAGGGAGGA | GTAATGCCTG | GAGACCTCAG | GTGAATAATC | CAAAAGAGTG |
| 7441 | GCTGCAAGTG | GACTTCCAGA | AGACAATGAA | AGTCACAGGA | GTAACTACTC | AGGGAGTAAA |
| 7501 | ATCTCTGCTT | ACCAGCATGT | ATGTGAAGGA | GTTCCTCATC | TCCAGCAGTC | AAGATGGCCA |
| 7561 | TCAGTGGACT | CTCTTTTTTC | AGAATGGCAA | AGTAAAGGTT | TTTCAGGGAA | ATCAAGACTC |
| 7621 | CTTCACACCT | GTGGTGAACT | CTCTAGACCC | ACCGTTACTG | ACTCGCTACC | TTCGAATTCA |
| 7641 | CCCCCAGAGT | TGGGTGCACC | AGATTGCCCT | GAGGATGGAG | GTTCTGGGCT | GCGAGGCACA |
| 7711 | GGACCTCTAC | | | | | |

*The underlined nucleic acids encode a signal peptide.

FVIII polypeptides include full-length FVIII, full-length FVIII minus Met at the N-terminus, mature FVIII (minus the signal sequence), mature FVIII with an additional Met at the N-terminus, and/or FVIII with a full or partial deletion of the B domain. In certain embodiments, FVIII variants include B domain deletions, whether partial or full deletions.

The sequence of native mature human FVIII is presented as SEQ ID NO: 4. A native FVIII protein has the following formula: A1-a1-A2-a2-B-a3-A3-C1-C2, where A1, A2, and A3 are the structurally-related "A domains," B is the "B domain," C1 and C2 are the structurally-related "C domains," and a1, a2 and a3 are acidic spacer regions. Referring to the primary amino acid sequence position in SEQ ID NO:4, the A1 domain of human FVIII extends from Ala1 to about Arg336, the a1 spacer region extends from about Met337 to about Val374, the A2 domain extends from about Ala375 to about Tyr719, the a2 spacer region extends from about Glu720 to about Arg740, the B domain extends from about Ser741 to about Arg 1648, the a3 spacer region extends from about Glu1649 to about Arg1689, the A3 domain extends from about Ser1690 to about Leu2025, the C1 domain extends from about Gly2026 to about Asn2072, and the C2 domain extends from about Ser2073 to Tyr2332. Other than specific proteolytic cleavage sites, designation of the locations of the boundaries between the domains and regions of FVIII can vary in different literature references. The boundaries noted herein are therefore designated as approximate by use of the term "about."

The human FVIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; and U.S. Pat. No. 4,757,006). The FVIII amino acid sequence was deduced from cDNA as shown in U.S. Pat. No. 4,965,199. In addition, partially or fully B-domain deleted FVIII is shown in U.S. Pat. Nos. 4,994,371 and 4,868,112. In some embodiments, the human FVIII B-domain is replaced with the human Factor V B-domain as shown in U.S. Pat. No. 5,004,803. The cDNA sequence encoding human Factor VIII and amino acid sequence are shown in SEQ ID NOs: 4 and 5, respectively, of US Application Publ. No. 2005/0100990.

The porcine FVIII sequence is published in Toole, J. J., et al., Proc. Natl. Acad. Sci. USA 83:5939-5942 (1986). Further, the complete porcine cDNA sequence obtained from PCR amplification of FVIII sequences from a pig spleen cDNA library has been reported in Healey, J. F., et al., Blood 88:4209-4214 (1996). Hybrid human/porcine FVIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503. U.S. Pat. No. 5,859,204, Lollar, J. S., also discloses the porcine cDNA and deduced amino acid sequences. U.S. Pat. No. 6,458,563 discloses a B-domain-deleted porcine FVIII.

U.S. Pat. No. 5,859,204 to Lollar, J. S. reports functional mutants of FVIII having reduced antigenicity and reduced immunoreactivity. U.S. Pat. No. 6,376,463 to Lollar, J. S. also reports mutants of FVIII having reduced immunoreactivity. US Appl. Publ. No. 2005/0100990 to Saenko et al. reports functional mutations in the A2 domain of FVIII.

In one embodiment, the FVIII (or FVIII portion of a chimeric protein) may be at least 50%, 60%, 70%, 80%, 90%, 95%, 96%, 97%, 98%, 99%, or 100% identical to a FVIII amino acid sequence of amino acids 1 to 1438 of SEQ ID NO: 6 or amino acids 1 to 2332 of SEQ ID NO: 4 (without a signal sequence) or a FVIII amino acid sequence of amino acids 1 to 19 of SEQ ID NO: 3 and 1 to 1438 of SEQ ID NO: 6 or amino acids 1 to 19 of SEQ ID NO: 3 and amino acids 1 to 2332 of SEQ ID NO: 4 (with a signal sequence), wherein the FVIII has a clotting activity, e.g., activates Factor IX as a cofactor to convert Factor X to activated Factor X. The FVIII (or FVIII portion of a chimeric protein) may be identical to a FVIII amino acid sequence of amino acids 1 to 1438 of SEQ ID NO: 6 or amino acids 1 to 2332 of SEQ ID NO: 4 (without a signal sequence). The FVIII may further comprise a signal sequence.

The "B-domain" of FVIII, as used herein, is the same as the B-domain known in the art that is defined by internal amino acid sequence identity and sites of proteolytic cleavage, e.g., residues Ser741-Arg1648 of full-length human FVIII. The other human FVIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine FVIII are also known in the art. In one embodiment, the B domain of FVIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 5. (BDD FVIII heavy chain is double underlined; B domain is italicized; and BDD FVIII light chain is in plain text). A nucleotide sequence encoding the amino acid sequence set forth in Table 5 (SEQ ID NO: 7) is shown in Table 6.

TABLE 5

Amino Acid Sequence of B-domain Deleted Factor VIII (BDD FVIII)

BDD FVIII (SEQ ID NO: 6)

ATRRYYLGAVELSWDYMQSDLGELPVDARFPPRVPKSFPFNTSVVYKKTL

FVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAKEKTQTLHKFILLFA

TABLE 5-continued

Amino Acid Sequence of B-domain Deleted Factor VIII (BDD FVIII)

VFDEGKSWHSETKNSLMQDRDAASARAWPKMHTVNGYVNRSLPGLIGCHR

KSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDL

TDSEMDVVRFDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

GMTALLKVSSCDKNTGDYYEDSYEDISAYLLSKNNAIEPR*SFSQNPPVLK*

*RHQ*REITRTTLQSDQEEIDYDDTISVEMKKEDFDIYDEDENQSPRSFQKK

TRHYFIAAVERLWDYGMSSSPHVLRNRAQSGSVPQFKKVVFQEFTDGSFT

QPLYRGELNEHLGLLGPYIRAEVEDNIMVTFRNQASRPYSFYSSLISYEE

DQRQGAEPRKNFVKPNETKTYFWKVQHHMAPTKDEFDCKAWAYFSDVDLE

KDVHSGLIGPLLVCHTNTLNPAHGRQVTVQEFALFFTIFDETKSWYFTEN

MERNCRAPCNIQMEDPTFKENYRFHAINGYIMDTLPGLVMAQDQRIRWYL

LSMGSNENIHSIHFSGHVFTVRKKEEYKMALYNLYPGVFETVEMLPSKAG

IWRVECLIGEHLHAGMSTLFLVYSNKCQTPLGMASGHIRDFQITASGQYG

QWAPKLARLHYSGSINAWSTKEPFSWIKVDLLAPMIIHGIKTQGARQKFS

SLYISQFIIMYSLDGKKWQTYRGNSTGTLMVFFGNVDSSGIKHNIFNPPI

IARYIRLHPTHYSIRSTLRMELMGCDLNSCSMPLGMESKAISDAQITASS

YFTNMFATWSPSKARLHLQGRSNAWRPQVNNPKEWLQVDFQKTMKVTGVT

TQGVKSLLTSMYVKEFLISSSQDGHQWTLFFQNGKVKVFQGNQDSFTPVV

NSLDPPLLTRYLRIHPQSWVHQIALRMEVLGCEAQDLY

TABLE 6

Nucleotide Sequence Encoding BDD FVIII (SEQ ID NO: 7)*

661                                              A TGCAAATAGA

GCTCTCCACC TGCTTCTTTC

721 TGTGCCTTTT GCGATTCTGC TTTAGTGCCA CCAGAAGATA CTACCTGGGT GCAGTGGAAC

781 TGTCATGGGA CTATATGCAA AGTGATCTCG GTGAGCTGCC TGTGGACGCA AGATTTCCTC

841 CTAGAGTGCC AAAATCTTTT CCATTCAACA CCTCAGTCGT GTACAAAAAG ACTCTGTTTG

901 TAGAATTCAC GGATCACCTT TTCAACATCG CTAAGCCAAG GCCACCCTGG ATGGGTCTGC

961 TAGGTCCTAC CATCCAGGCT GAGGTTTATG ATACAGTGGT CATTACACTT AAGAACATGG

1021 CTTCCCATCC TGTCAGTCTT CATGCTGTTG GTGTATCCTA CTGGAAAGCT TCTGAGGGAG

1081 CTGAATATGA TGATCAGACC AGTCAAAGGG AGAAAGAAGA TGATAAAGTC TTCCCTGGTG

1141 GAAGCCATAC ATATGTCTGG CAGGTCCTGA AAGAGAATGG TCCAATGGCC TCTGACCCAC

TABLE 6-continued

Nucleotide Sequence Encoding BDD FVIII (SEQ ID NO: 7)*

```
1201 TGTGCCTTAC CTACTCATAT CTTTCTCATG TGGACCTGGT AAAAGACTTG AATTCAGGCC
1261 TCATTGGAGC CCTACTAGTA TGTAGAGAAG GGAGTCTGGC CAAGGAAAAG ACACAGACCT
1321 TGCACAAATT TATACTACTT TTTGCTGTAT TTGATGAAGG GAAAGTTGG CACTCAGAAA
1381 CAAAGAACTC CTTGATGCAG GATAGGGATG CTGCATCTGC TCGGGCCTGG CCTAAAATGC
1441 ACACAGTCAA TGGTTATGTA AACAGGTCTC TGCCAGGTCT GATTGGATGC ACAGGAAAT
1501 CAGTCTATTG GCATGTGATT GGAATGGGCA CCACTCCTGA AGTGCACTCA ATATTCCTCG
1561 AAGGTCACAC ATTTCTTGTG AGGAACCATC GCCAGGCGTC CTTGGAAATC TCGCCAATAA
1621 CTTTCCTTAC TGCTCAAACA CTCTTGATGG ACCTTGGACA GTTTCTACTG TTTTGTCATA
1681 TCTCTTCCCA CCAACATGAT GGCATGGAAG CTTATGTCAA GTAGACAGC TGTCCAGAGG
1741 AACCCCAACT ACGAATGAAA ATAATGAAG AAGCGGAAGA CTATGATGAT GATCTTACTG
1801 ATTCTGAAAT GGATGTGGTC AGGTTTGATG ATGACAACTC TCCTTCCTTT ATCCAAATTC
1861 GCTCAGTTGC CAAGAAGCAT CCTAAAACTT GGGTACATTA CATTGCTGCT GAAGAGGAGG
1921 ACTGGGACTA TGCTCCCTTA GTCCTCGCCC CCGATGACAG AAGTTATAAA AGTCAATATT
1981 TGAACAATGG CCCTCAGCGG ATTGGTAGGA AGTACAAAAA AGTCCGATTT ATGGCATACA
2041 CAGATGAAAC CTTTAAGACT CGTGAAGCTA TTCAGCATGA ATCAGGAATC TTGGGACCTT
2101 TACTTTATGG GGAAGTTGGA GACACACTGT TGATTATATT TAAGAATCAA GCAAGCAGAC
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAAACCC AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTTCAGCA TACTTGCTGA
2941 GTAAAAACAA TGCCATTGAA CCAAGAAGCT TCTCTCAAAA CCCACCAGTC TTGAAACGCC
3001 ATCAACGGGA ATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
```

TABLE 6-continued

Nucleotide Sequence Encoding BDD FVIII (SEQ ID NO: 7)*

```
3541 CTAAAGATGA GTTTGACTGC AAAGCCTGGG CTTATTTCTC TGATGTTGAC CTGGAAAAAG

3601 ATGTGCACTC AGGCCTGATT GGACCCCTTC TGGTCTGCCA CACTAACACA CTGAACCCTG

3661 CTCATGGGAG ACAAGTGACA GTACAGGAAT TTGCTCTGTT TTTCACCATC TTTGATGAGA

3721 CCAAAAGCTG GTACTTCACT GAAAATATGG AAAGAAACTG CAGGGCTCCC TGCAATATCC

3781 AGATGGAAGA TCCCACTTTT AAAGAGAATT ATCGCTTCCA TGCAATCAAT GGCTACATAA

3841 TGGATACACT ACCTGGCTTA GTAATGGCTC AGGATCAAAG GATTCGATGG TATCTGCTCA

3901 GCATGGGCAG CAATGAAAAC ATCCATTCTA TTCATTTCAG TGGACATGTG TTCACTGTAC

3961 GAAAAAAAGA GGAGTATAAA ATGGCACTGT ACAATCTCTA TCCAGGTGTT TTTGAGACAG

4021 TGGAAATGTT ACCATCCAAA GCTGGAATTT GGCGGGTGGA ATGCCTTATT GGCGAGCATC

4081 TACATGCTGG GATGAGCACA CTTTTTCTGG TGTACAGCAA TAAGTGTCAG ACTCCCCTGG

4141 GAATGGCTTC TGGACACATT AGAGATTTTC AGATTACAGC TTCAGGACAA TATGGACAGT

4201 GGGCCCCAAA GCTGGCCAGA CTTCATTATT CCGGATCAAT CAATGCCTGG AGCACCAAGG

4261 AGCCCTTTTC TTGGATCAAG GTGGATCTGT TGGCACCAAT GATTATTCAC GGCATCAAGA

4321 CCCAGGGTGC CCGTCAGAAG TTCTCCAGCC TCTACATCTC TCAGTTTATC ATCATGTATA

4381 GTCTTGATGG GAAGAAGTGG CAGACTTATC GAGGAAATTC CACTGGAACC TTAATGGTCT

4441 TCTTTGGCAA TGTGGATTCA TCTGGGATAA AACACAATAT TTTTAACCCT CCAATTATTG

4501 CTCGATACAT CCGTTTGCAC CCAACTCATT ATAGCATTCG CAGCACTCTT CGCATGGAGT

4561 TGATGGGCTG TGATTTAAAT AGTTGCAGCA TGCCATTGGG AATGGAGAGT AAAGCAATAT

4621 CAGATGCACA GATTACTGCT TCATCCTACT TTACCAATAT GTTTGCCACC TGGTCTCCTT

4681 CAAAAGCTCG ACTTCACCTC CAAGGGAGGA GTAATGCCTG GAGACCTCAG GTGAATAATC

4741 CAAAGAGTG GCTGCAAGTG GACTTCCAGA AGACAATGAA AGTCACAGGA GTAACTACTC

4801 AGGGAGTAAA ATCTCTGCTT ACCAGCATGT ATGTGAAGGA GTTCCTCATC TCCAGCAGTC

4861 AAGATGGCCA TCAGTGGACT CTCTTTTTTC AGAATGGCAA AGTAAAGGTT TTTCAGGGAA

4921 ATCAAGACTC CTTCACACCT GTGGTGAACT CTCTAGACCC ACCGTTACTG ACTCGCTACC

4981 TTCGAATTCA CCCCCAGAGT TGGGTGCACC AGATTGCCCT GAGGATGGAG GTTCTGGGCT

5041 GCGAGGCACA GGACCTCTAC
```

*The underlined nucleic acids encode a signal peptide.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563. In some embodiments, a B-domain-deleted FVIII sequence of the present invention comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of SEQ ID NO: 4, i.e., SEQ ID NO: 6). In some embodiments, a B-domain-deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions may be made in any FVIII sequence.

In some embodiments, the FVIII has a partial B-domain. In some embodiments, the FVIII protein with a partial B-domain is FVIII198 (SEQ ID NO: 89). FVIII198 is a partial B-domain containing single chain FVIIIFc molecule-226N6. 226 represents the N-terminus 226 amino acid of the FVIII B-domain, and N6 represents six N-glycosylation sites in the B-domain.

In one embodiment, FVIII is cleaved right after arginine at amino acid 1648 (in full-length Factor VIII or SEQ ID NO: 4), amino acid 754 (in the S743/Q1638 B-domain deleted Factor VIII or SEQ ID NO: 6), or the corresponding arginine residue (in other variants), thereby resulting in a heavy chain and a light chain. In another embodiment, FVIII comprises a heavy chain and a light chain, which are linked or associated by a metal ion-mediated non-covalent bond.

In other embodiments, FVIII is a single chain FVIII that has not been cleaved right after Arginine at amino acid 1648 (in full-length FVIII or SEQ ID NO: 4), amino acid 754 (in the S743/Q1638 B-domain-deleted FVIII or SEQ ID NO: 6), or the corresponding Arginine residue (in other variants). A single chain FVIII may comprise one or more amino acid substitutions. In one embodiment, the amino acid substitution is at a residue corresponding to residue 1648, residue 1645, or both of full-length mature Factor VIII polypeptide (SEQ ID NO: 4) or residue 754, residue 751, or both of SQ BDD Factor VIII (SEQ ID NO: 6). The amino acid substitution can be any amino acids other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine.

FVIII can further be cleaved by thrombin and then activated as FVIIIa, serving as a cofactor for activated Factor IX (FIXa). And the activated FIX together with activated FVIII forms a Xase complex and converts Factor X to activated Factor X (FXa). For activation, FVIII is cleaved by thrombin after three Arginine residues, at amino acids 372, 740, and 1689 (corresponding to amino acids 372, 740, and 795 in the B-domain deleted FVIII sequence), the cleavage generating FVIIIa having the 50 kDa A1, 43 kDa A2, and 73 kDa A3-C1-C2 chains. In one embodiment, the FVIII protein useful for the present invention is non-active FVIII. In another embodiment, the FVIII protein is an activated FVIII.

The protein having FVIII polypeptide linked to or associated with the VWF fragment can comprise a sequence at least 50%, 60%, 70%, 80%, 90%, 95%, 96%, 97%, 98%, 99%, or 100% identical to SEQ ID NO: 4 or 6, wherein the sequence has the FVIII clotting activity, e.g., activating Factor IX as a cofactor to convert Factor X to activated Factor X (FXa).

"Hybrid" or "chimeric" polypeptides and proteins, as used herein, includes a combination of a first polypeptide chain, e.g., the VWF fragment, optionally fused to a first Ig constant region or a portion thereof, with a second polypeptide chain, e.g., a FVIII protein linked to an XTEN sequence, optionally fused to a second Ig constant region or a portion thereof, thereby forming a heterodimer. In one embodiment, the first polypeptide and the second polypeptide in a hybrid are associated with each other via protein-protein interactions, such as charge-charge or hydrophobic interactions. In another embodiment, the first polypeptide and the second polypeptide in a hybrid are associated with each other via disulfide or other covalent bond(s). Hybrids are described, for example, in US 2004/101740 and US 2006/074199. The second polypeptide may be an identical copy of the first polypeptide or a non-identical polypeptide. In one embodiment, the first polypeptide is a FVIII protein(X)-Fc fusion protein, and the second polypeptide is a polypeptide comprising, consisting essentially of, or consisting of an Fc region, wherein the first polypeptide and the second polypeptide are associated with each other. In another embodiment, the first polypeptide comprises a VWF fragment-XTEN-Fc fusion protein, and the second polypeptide comprises FVIII-Fc fusion protein, making the hybrid a heterodimer. In other embodiments, the first polypeptide comprises a VWF fragment-Fc fusion protein, and the second polypeptide comprises FVIII(X)-Fc fusion protein, making the hybrid a heterodimer. In yet other embodiments, the first polypeptide comprises a VWF fragment-XTEN-Fc fusion protein, and the second polypeptide comprises FVIII (X)-Fc fusion protein. The first polypeptide and the second polypeptide can be associated through a covalent bond, e.g., a disulfide bond, between the first Fc region and the second Fc region. The first polypeptide and the second polypeptide can further be associated with each other by binding between the VWF fragment and the FVIII protein.

A FVIII protein useful in the present invention can include FVIII having one or more additional XTEN sequences, which do not affect the FVIII coagulation activity. Such XTEN sequences can be fused to the C-terminus or N-terminus of the FVIII protein or inserted between one or more of the two amino acid residues in the FVIII protein wherein the insertions do not affect the FVIII coagulation activity or FVIII function. In one embodiment, the insertions improve pharmacokinetic properties of the FVIII protein (e.g., half-life). In another embodiment, the insertions can be multiple insertions, e.g., more than two, three, four, five, six, seven, eight, nine, or ten insertions. Examples of the insertion sites include, but are not limited to, the sites listed in Tables 7, 8, 9, 10, 11, 12, 13, 14, 15 or any combinations thereof.

The FVIII protein linked to one or more XTEN sequences can be represented as FVIII(X), FVIII(X1), FVIII$_{(a \to b)}$-X-FVIII$_{(c \to d)}$, wherein FVIII$_{(a \to b)}$ comprises, consists essentially of, or consists of a first portion of a FVIII protein from amino acid residue "a" to amino acid residue "b"; X or X1 comprises, consists essentially of, or consists of one or more XTEN sequences, FVIII$_{(c \to d)}$ comprises, consists essentially of, or consists of a second portion of a FVIII protein from amino acid residue "c" to amino acid residue "d";

a is the N-terminal amino acid residue of the first portion of the FVIII protein, b is the C-terminal amino acid residue of the first portion of the FVIII protein but is also the N-terminal amino acid residue of the two amino acids of an insertion site in which the XTEN sequence is inserted, c is the N-terminal amino acid residue of the second portion of the FVIII protein but is also the C-terminal amino acid residue of the two amino acids of an insertion site in which the XTEN sequence is inserted, and d is the C-terminal amino acid residue of the FVIII protein, and wherein the first portion of the FVIII protein and the second portion of the FVIII protein are not identical to each other and are of sufficient length together such that the FVIII protein has a FVIII coagulation activity.

In one embodiment, the first portion of the FVIII protein and the second portion of the FVIII protein are fragments of SEQ ID NO: 4 [full length mature FVIII sequence] or SEQ ID NO: 6 [B-domain deleted FVIII], e.g., N-terminal portion and C-terminal portion, respectively. In certain embodiments, the first portion of the FVIII protein comprises the A1 domain and the A2 domain of the FVIII protein. The second portion of the FVIII protein comprises the A3 domain, the C1 domain, and optionally the C2 domain. In yet other embodiments, the first portion of the FVIII protein comprises the A1 domain and A2 domain, and the second portion of the FVIII protein comprises a portion of the B domain, the A3 domain, the C1 domain, and optionally the C2 domain. In still other embodiments, the first portion of the FVIII protein comprises the A1 domain, A2 domain, and a portion of the B domain of the FVIII protein, and the second portion of the FVIII protein comprises the A3 domain, the C1 domain, and optionally the C2 domain. In still other embodiments, the first portion of the FVIII protein comprises the A1 domain, A2 domain, and a first portion of the B domain of the FVIII protein. The second portion of the FVIII protein comprises a second portion of the B domain, the A3 domain, the C1 domain, and optionally the C2 domain. In some embodiments, the two amino acids ("b" and "c") can be any one or more of the amino acid residues insertion sites shown in Tables 7, 8, 9, 10, 11, 12, 13, 14, and 15. For example, "b" can be the amino acid residue immediately upstream of the site in which one or more XTEN sequences are inserted or linked, and "c" can be the amino acid residue immediately downstream of the site in which the one or more XTEN sequences are inserted or linked. In some embodiments, "a" is the first mature amino acid sequence of a FVIII protein, and "d" is the last amino acid sequence of a FVIII protein. For example, FVIII$_{(a \to b)}$ can be an amino acid sequence at least 70%, 80%, 90%, 95%, 96%, 97%, 98%, 99%, or 100% identical to amino acids 1 to 745 of SEQ ID NO: 6 [B domain deleted FVIII amino acid sequence] or SEQ ID NO: 4 [full length FVIII] and FVIII$_{(c \to d)}$ can be amino acids 746 to 1438 of SEQ ID NO: 6 or amino acids 1641 to 2332 of SEQ ID NO: 4, respectively.

In some aspects, the insertion site in the FVIII protein is located in one or more domains of the FVIII protein, which is the N-terminus, the A1 domain, the A2 domain, the A3 domain, the B domain, the C1 domain, the C2 domain, the C-terminus, or two or more combinations thereof or between two domains of the FVIII protein, which are the A1 domain and a1 acidic region, and the a1 acidic region and A2 domain, the A2 domain and a2 acidic region, the a2 acidic region and B domain, the B domain and A3 domain, and the A3 domain and C1 domain, the C1 domain and C2 domain, or any combinations thereof. For example, the insertion sites in which the XTEN sequence can be inserted are selected from the group consisting of the N-terminus and A1 domain, the N-terminus and A2 domain, the N-terminus and A3 domain, the N-terminus and B domain, the N-terminus and C1 domain, the N-terminus and C2 domain, the N-terminus and the C-terminus, the A1 and A2 domains, the A1 and A3 domains, the A1 and B domains, the A1 and C1 domains, the A1 and C2 domains, the A1 domain and the C-terminus, the A2 and A3 domains, the A2 and B domains, the A2 and C1 domains, the A2 and C2 domains, the A2 domain and the C-terminus, the A3 and B domains, the A3 and C1 domains, the A3 and C2 domains, the A3 domain and the C-terminus, the B and C1 domains, the B and C2 domains, the B domain and the C-terminus, the C1 and C2 domains, the C1 and the C-terminus, the C2 domain, and the C-terminus, and two or more combinations thereof. Non-limiting examples of the insertion sites are listed in Tables 7, 8, 9, 10, 11, 12, 13, 14, and 15.

The FVIII protein, in which the XTEN sequence is inserted immediately downstream of one or more amino acids (e.g., one or more XTEN insertion sites) in the FVIII protein or linked at the C-terminus or the N-terminus, retains the FVIII activity after linkage to or insertion by the XTEN sequence. The XTEN sequence can be inserted in the FVIII protein once or more than once, twice, three times, four times, five times, or six times such that the insertions do not affect the FVIII activity (i.e., the FVIII protein still retains the coagulation property).

The FVIII protein useful in the present invention can be linked to one or more XTEN polypeptides at the N-terminus or C-terminus of the FVIII protein by an optional linker or inserted immediately downstream of one or more amino acids (e.g., one or more XTEN insertion sites) in the FVIII protein by one or more optional linkers. In one embodiment, the two amino acid residues in which the XTEN sequence is inserted or the amino acid residue to which the XTEN sequence is linked correspond to the two or one amino acid residues of SEQ ID NO: 4 [full length mature FVIII] selected from the group consisting of the residues in Table 7, Table 8, Table 9, and Table 10 and any combinations thereof.

In other embodiments, at least one XTEN sequence is inserted in any one or more XTEN insertion sites disclosed herein or any combinations thereof. In one aspect, at least one XTEN sequence is inserted in one or more XTEN insertion sites disclosed in one or more amino acids disclosed in Table 7.

TABLE 7

Exemplary XTEN Insertion Sites

| No. | XTEN Insertion Point* | Insertion Residue | FVIII BDD Downstream Sequence | FVIII Domain |
|---|---|---|---|---|
| 1 | 0 | (N-terminus) | ATR | A1 |
| 2 | 3 | R | RYY | A1 |
| 3 | 17 | M | QSD | A1 |
| 4 | 18 | Q | SDL | A1 |
| 5 | 22 | G | ELP | A1 |
| 6 | 24 | L | PVD | A1 |
| 7 | 26 | V | DAR | A1 |
| 8 | 28 | A | RFP | A1 |
| 9 | 32 | P | RVP | A1 |
| 10 | 38 | F | PFN | A1 |
| 11 | 40 | F | NTS | A1 |
| 12 | 41 | N | TSV | A1 |
| 13 | 60 | N | IAK | A1 |
| 14 | 61 | I | AKP | A1 |
| 15 | 65 | R | PPW | A1 |
| 16 | 81 | Y | DTV | A1 |
| 17 | 111 | G | AEY | A1 |
| 18 | 116 | D | QTS | A1 |
| 19 | 119 | S | QRE | A1 |
| 20 | 120 | Q | REK | A1 |
| 21 | 128 | V | FPG | A1 |
| 22 | 129 | F | PGG | A1 |
| 23 | 130 | P | GGS | A1 |
| 24 | 182 | G | SLA | A1 |
| 25 | 185 | A | KEK | A1 |
| 26 | 188 | K | TQT | A1 |
| 27 | 205 | G | KSW | A1 |
| 28 | 210 | S | ETK | A1 |
| 29 | 211 | E | TKN | A1 |
| 30 | 216 | L | MQD | A1 |
| 31 | 220 | R | DAA | A1 |
| 32 | 222 | A | ASA | A1 |
| 33 | 223 | A | SAR | A1 |
| 34 | 224 | S | ARA | A1 |
| 35 | 230 | K | MHT | A1 |
| 36 | 243 | P | GLI | A1 |
| 37 | 244 | G | LIG | A1 |
| 38 | 250 | R | KSV | A1 |
| 39 | 318 | D | GME | A1 |
| 40 | 333 | P | QLR | A1 |
| 41 | 334 | Q | LRM | A1 |
| 42 | 336 | R | MKN | a1 |
| 43 | 339 | N | NEE | a1 |
| 44 | 345 | D | YDD | a1 |
| 45 | 357 | V | VRF | a1 |
| 46 | 367 | S | FIQ | a1 |
| 47 | 370 | S | RPY | a1 |
| 48 | 375 | A | KKH | A2 |
| 49 | 376 | K | KHP | A2 |
| 50 | 378 | H | PKT | A2 |
| 51 | 399 | V | LAP | A2 |
| 52 | 403 | D | DRS | A2 |
| 53 | 405 | R | SYK | A2 |
| 54 | 409 | S | QYL | A2 |
| 55 | 416 | P | QRI | A2 |
| 56 | 434 | E | TFK | A2 |
| 57 | 438 | T | REA | A2 |
| 58 | 441 | A | IQH | A2 |
| 59 | 442 | I | QHE | A2 |
| 60 | 463 | I | IFK | A2 |
| 61 | 487 | Y | SRR | A2 |
| 62 | 490 | R | LPK | A2 |
| 63 | 492 | P | KGV | A2 |
| 64 | 493 | K | GVK | A2 |
| 65 | 494 | G | VKH | A2 |
| 66 | 500 | D | FPI | A2 |
| 67 | 506 | G | EIF | A2 |
| 68 | 518 | E | DGP | A2 |
| 69 | 556 | K | ESV | A2 |
| 70 | 565 | Q | IMS | A2 |
| 71 | 566 | I | MSD | A2 |
| 72 | 598 | P | AGV | A2 |
| 73 | 599 | A | GVQ | A2 |
| 74 | 603 | L | EDP | A2 |
| 75 | 616 | S | ING | A2 |
| 76 | 686 | G | LWI | A2 |
| 77 | 713 | K | NTG | A2 |
| 78 | 719 | Y | EDS | A2 |
| 79 | 730 | L | LSK | A2 |
| 80 | 733 | K | NNA | A2 |
| 81 | 745 | N | PPV** | B |
| 82 | 1640 | P | PVL | B |
| 83 | 1652 | R | TTL | B |
| 84 | 1656 | Q | SDQ | A3 |
| 85 | 1685 | N | QSP | A3 |
| 86 | 1711 | M | SSS | A3 |
| 87 | 1713 | S | SPH | A3 |
| 88 | 1720 | N | RAQ | A3 |
| 89 | 1724 | S | GSV | A3 |
| 90 | 1725 | G | SVP | A3 |
| 91 | 1726 | S | VPQ | A3 |
| 92 | 1741 | G | SFT | A3 |
| 93 | 1744 | T | QPL | A3 |
| 94 | 1749 | R | GEL | A3 |
| 95 | 1773 | V | TFR | A3 |
| 96 | 1792 | Y | EED | A3 |
| 97 | 1793 | E | EDQ | A3 |
| 98 | 1796 | Q | RQG | A3 |
| 99 | 1798 | Q | GAE | A3 |
| 100 | 1799 | G | AEP | A3 |
| 101 | 1802 | P | RKN | A3 |
| 102 | 1803 | R | KNF | A3 |
| 103 | 1807 | V | KPN | A3 |
| 104 | 1808 | K | PNE | A3 |
| 105 | 1827 | K | DEF | A3 |
| 106 | 1844 | E | KDV | A3 |
| 107 | 1861 | N | TLN | A3 |
| 108 | 1863 | L | NPA | A3 |
| 109 | 1896 | E | RNC | A3 |
| 110 | 1900 | R | APC | A3 |
| 111 | 1904 | N | IQM | A3 |
| 112 | 1905 | I | QME | A3 |
| 113 | 1910 | P | TFK | A3 |
| 114 | 1920 | A | ING | A3 |
| 115 | 1937 | D | QRI | A3 |
| 116 | 1981 | G | VFE | A3 |
| 117 | 2019 | N | KCQ | A3 |
| 118 | 2020 | K | CQT | C1 |
| 119 | 2044 | G | QWA | C1 |
| 120 | 2068 | F | SWI | C1 |
| 121 | 2073 | V | DLL | C1 |
| 122 | 2090 | R | QKF | C1 |
| 123 | 2092 | K | FSS | C1 |
| 124 | 2093 | F | SSL | C1 |
| 125 | 2111 | K | WQT | C1 |
| 126 | 2115 | Y | RGN | C1 |
| 127 | 2120 | T | GTL | C1 |
| 128 | 2125 | V | FFG | C1 |
| 129 | 2171 | L | NSC | C1 |
| 130 | 2173 | S | CSM | C2 |
| 131 | 2188 | A | QIT | C2 |
| 132 | 2223 | V | NNP | C2 |
| 133 | 2224 | N | NPK | C2 |
| 134 | 2227 | K | EWL | C2 |
| 135 | 2268 | G | HQW | C2 |
| 136 | 2277 | N | GKV | C2 |
| 137 | 2278 | G | KVK | C2 |
| 138 | 2290 | F | TPV | C2 |
| 139 | 2332 | Y | C terminus of FVIII | CT |

*Indicates an insertion point for XTEN based on the amino acid number of mature full-length human FVIII, wherein the insertion could be either on the N- or C-terminal side of the indicated amino acid.

In some embodiments, one or more XTEN sequences are inserted within about six amino acids up or down from amino acids 32, 220, 224, 336, 339, 399, 416, 603, 1656, 1711, 1725, 1905, or 1910, corresponding to SEQ ID NO: 4 or any combinations thereof.

TABLE 8

Exemplary XTEN Insertion Ranges

| No. | XTEN Insertion Point | Insertion Residue | FVIII BDD Downstream Sequence | FVIII Domain | Distance from insertion residue* |
|---|---|---|---|---|---|
| 9 | 32 | P | RVP | A1 | −3, +6 |
| 31 | 220 | R | DAA | A1 | — |
| 34 | 224 | S | ARA | A1 | +5 |
| 43 | 336 | R | MKN | a1 | −1, +6 |
| 44 | 339 | N | NEE | a1 | −4, +5 |
| 52 | 399 | V | LAP | A2 | −6, +3 |
| 56 | 416 | P | QRI | A2 | +6 |
| 75 | 603 | L | EDP | A2 | −6, +6 |
| 85 | 1656 | Q | SDQ | B | −3, +6 |
| 87 | 1711 | M | SSS | A3 | −6, +1 |
| 91 | 1725 | G | SVP | A3 | +6 |
| 113 | 1905 | I | QME | A3 | +6 |
| 114 | 1910 | P | TFK | A3 | −5, +6 |

*Distance from insertion residue refers to the relative number of amino acids away from the N-terminus (negative numbers) or C-terminus (positive numbers) of the designated insertion residue (residue "0") where an insertion may be made. The designation "−x" refers to an insertion site which is x amino acids away on the N-terminal side of the designated insertion residue. Similarly, the designation "+x" refers to an insertion site which is x amino acids away on the C-terminal side of the designated insertion residue. For example, "−1, +2" indicates that the insertion is made at the N-terminus or C-terminus of amino acid residues denoted −1, 0, +1 or +2.

In other embodiments, one or more XTEN sequences are inserted immediately down stream of one or more amino acids corresponding to the full-length mature human FVIII selected from the group consisting of one or more insertion sites in Table 9.

TABLE 9

Exemplary XTEN Insertion Sites or Ranges

| No. | XTEN Insertion Point Range* | First Insertion Residue | FVIII Domain |
|---|---|---|---|
| 3 | 18-32 | Q | A1 |
| 8 | 40 | F | A1 |
| 18 | 211-224 | E | A1 |
| 27 | 336-403 | R | A1, A2 |
| 43 | 599 | A | A2 |
| 47 | 745-1640 | N | B |
| 50 | 1656-1728 | Q | B, a3, A3 |
| 57 | 1796-1804 | R | A3 |
| 65 | 1900-1912 | R | A3 |
| 81 | 2171-2332 | L | C1, C2 |

*indicates range of insertion sites numbered relative to the amino acid number of mature human FVIII In yet other embodiments, one or more XTENs are inserted in the B domain of FVIII. In one example, an XTEN is inserted between amino acids 740 and 1640 corresponding to SEQ ID NO: 4, wherein the FVIII sequence between amino acids 740 and 1640 is optionally not present. In another example, an XTEN is inserted between amino acids 741 and 1690 corresponding to SEQ ID NO: 4, wherein the FVIII sequence between amino acids 740 and 1690 is optionally not present. In other examples, an XTEN is inserted between amino acids 741 and 1648 corresponding to SEQ ID NO: 4, wherein the FVIII sequence between amino acids 741 and 1648 is optionally not present. In yet other examples, an XTEN is inserted between amino acids 743 and 1638 corresponding to SEQ ID NO: 4, wherein the FVIII sequence between amino acids 743 and 1638 is optionally not present. In still other examples, an XTEN is inserted between amino acids 745 and 1656 corresponding to SEQ ID NO: 4, wherein the FVIII sequence between amino acids 745 and 1656 is optionally not present. In some examples, an XTEN is inserted between amino acids 745 and 1657 corresponding to SEQ ID NO: 4, wherein the FVIII sequence between amino acids 745 and 1657 is optionally not present. In certain examples, an XTEN is inserted between amino acids 745 and 1667 corresponding to SEQ ID NO: 4, wherein the FVIII sequence between amino acids 745 and 1667 is optionally not present. In still other examples, an XTEN is inserted between amino acids 745 and 1686 corresponding to SEQ ID NO: 4, wherein the FVIII sequence between amino acids 745 and 1686 is optionally not present. In some other examples, an XTEN is inserted between amino acids 747 and 1642 corresponding to SEQ ID NO: 4, wherein the FVIII sequence between amino acids 747 and 1642 is optionally not present. In still other examples, an XTEN is inserted between amino acids 751 and 1667 corresponding to SEQ ID NO: 4, wherein the FVIII sequence between amino acids 751 and 1667 is optionally not present.

In some embodiments, one or more XTENs are inserted in one or more amino acids immediately downstream of an amino acid of an insertion site selected from the group consisting of the amino acid residues in Table 10.

TABLE 10

FVIII XTEN insertion sites and construct designations

| Construct Number | Domain | Upstream Residue No.* | Downstream Residue No.* | Upstream Sequence | Downstream Sequence |
|---|---|---|---|---|---|
| F8X-1 | A1 | 3 | 4 | ATR | RYY |
| F8X-2 | A1 | 18 | 19 | YMQ | SDL |
| F8X-3 | A1 | 22 | 23 | DLG | ELP |
| F8X-4 | A1 | 26 | 27 | LPV | DAR |
| F8X-5 | A1 | 40 | 41 | FPF | NTS |
| F8X-6 | A1 | 60 | 61 | LFN | IAK |
| F8X-7 | A1 | 116 | 117 | YDD | QTS |
| F8X-8 | A1 | 130 | 131 | VFP | GGS |
| F8X-9 | A1 | 188 | 189 | KEK | TQT |
| F8X-10 | A1 | 216 | 217 | NSL | MQD |
| F8X-11 | A1 | 230 | 231 | WPK | MHT |
| F8X-12 | A1 | 333 | 334 | EEP | QLR |
| F8X-13 | A2 | 375 | 376 | SVA | KKH |
| F8X-14 | A2 | 403 | 404 | APD | DRS |
| F8X-15 | A2 | 442 | 443 | EAI | QHE |
| F8X-16 | A2 | 490 | 491 | RRL | PKG |
| F8X-17 | A2 | 518 | 519 | TVE | DGP |
| F8X-18 | A2 | 599 | 600 | NPA | GVQ |
| F8X-19 | A2 | 713 | 714 | CDK | NTG |
| F8X-20 | BD | 745 | 746 | SQN | PPV |
| F8X-21 | BD | 745 | 746 | SQN | PPV |
| F8X-22 | BD** | 745 | 746 | SQN | PPV |
| F8X-23 | A3 | 1720 | 1721 | APT | KDE |
| F8X-24 | A3 | 1796 | 1797 | EDQ | RQG |
| F8X-25 | A3 | 1802 | 1803 | AEP | RKN |
| F8X-26 | A3 | 1827 | 1828 | PTK | DEF |
| F8X-27 | A3 | 1861 | 1862 | HTN | TLN |
| F8X-28 | A3 | 1896 | 1897 | NME | RNC |
| F8X-29 | A3 | 1900 | 1901 | NCR | APC |
| F8X-30 | A3 | 1904 | 1905 | PCN | IQM |
| F8X-31 | A3 | 1937 | 1938 | AQD | QRI |
| F8X-32 | C1 | 2019 | 2020 | YSN | KCQ |
| F8X-33 | C1 | 2068 | 2069 | EPF | SWI |
| F8X-34 | C1 | 2111 | 2112 | GKK | WQT |
| F8X-35 | C1 | 2120 | 2121 | NST | GTL |
| F8X-36 | C2 | 2171 | 2172 | CDL | NSC |
| F8X-37 | C2 | 2188 | 2189 | SDA | QIT |
| F8X-38 | C2 | 2227 | 2228 | NPK | EWL |
| F8X-39 | C2 | 2277 | 2278 | FQN | GKV |
| F8X-40 | CT | 2332 | NA | DLY | NA |
| F8X-41 | CT | 2332 | NA | DLY | NA |
| F8X-42 | A1 | 3 | 4 | ATR | ATR |
| pSD0001 | A2 | 403 | 404 | | |
| pSD0002 | A2 | 599 | 600 | | |
| pSD0021 | N-term | 0 | 1 | | |
| pSD0022 | A1 | 32 | 33 | | |

TABLE 10-continued

FVIII XTEN insertion sites and construct designations

| Construct Number | Domain | Upstream Residue No.* | Downstream Residue No.* | Upstream Sequence | Downstream Sequence |
|---|---|---|---|---|---|
| pSD0023 | A1 | 65 | 66 | | |
| pSD0024 | A1 | 81 | 82 | | |
| pSD0025 | A1 | 119 | 120 | | |
| pSD0026 | A1 | 211 | 212 | | |
| pSD0027 | A1 | 220 | 221 | | |
| pSD0028 | A1 | 224 | 225 | | |
| pSD0029 | A1 | 336 | 337 | | |
| pSD0030 | A1 | 339 | 340 | | |
| pSD0031 | A2 | 378 | 379 | | |
| pSD0032 | A2 | 399 | 400 | | |
| pSD0033 | A2 | 409 | 410 | | |
| pSD0034 | A2 | 416 | 417 | | |
| pSD0035 | A2 | 487 | 488 | | |
| pSD0036 | A2 | 494 | 495 | | |
| pSD0037 | A2 | 500 | 501 | | |
| pSD0038 | A2 | 603 | 604 | | |
| pSD0039 | A3 | 1656 | 1657 | | |
| pSD0040 | A3 | 1711 | 1712 | | |
| pSD0041 | A3 | 1725 | 1726 | | |
| pSD0042 | A3 | 1749 | 1750 | | |
| pSD0043 | A3 | 1905 | 1906 | | |
| pSD0044 | A3 | 1910 | 1911 | | |
| pDS0062 | A3 | 1900 | 1901 | | |

*Indicates the amino acid number of the mature FVIII protein

In one embodiment, the one or more XTEN insertion sites are located within one or more surface-exposed, flexible loop structure of the FVIII protein (e.g., a permissive loop). For example, at least one XTEN sequence can be inserted in each FVIII "A" domain comprising at least two "permissive loops" into which at least one XTEN polypeptide can be inserted without eliminating procoagulant activity of the recombinant protein, or the ability of the recombinant proteins to be expressed in vivo or in vitro in a host cell. The permissive loops are regions that allow insertion of at least one XTEN sequence with, among other attributes, high surface or solvent exposure and high conformational flexibility. The A1 domain comprises a permissive loop-1 (A1-1) region and a permissive loop-2 (A1-2) region, the A2 domain comprises a permissive loop-1 (A2-1) region and a permissive loop-2 (A2-2) region, the A3 domain comprises a permissive loop-1 (A3-1) region and a permissive loop-2 (A3-2) region.

In one aspect, a first permissive loop in the FVIII A1 domain (A1-1) is located between beta strand 1 and beta strand 2, and a second permissive loop in the FVIII A2 domain (A1-2) is located between beta strand 11 and beta strand 12. A first permissive loop in the FVIII A2 domain (A2-1) is located between beta strand 22 and beta strand 23, and a second permissive loop in the FVIII A2 domain (A2-2) is located between beta strand 32 and beta strand 33. A first permissive loop in the FVIII A3 domain (A3-1) is located between beta strand 38 and beta strand 39, and a second permissive loop in the FVIII A3 (A3-2) is located between beta strand 45 and beta strand 46. In certain aspects, the surface-exposed, flexible loop structure comprising A1-1 corresponds to a region in native mature human FVIII from about amino acid 15 to about amino acid 45 of SEQ ID NO: 4, e.g., from about amino acid 18 to about amino acid 41 of SEQ ID NO: 4. In other aspects, the surface-exposed, flexible loop structure comprising A1-2 corresponds to a region in native mature human FVIII from about amino acid 201 to about amino acid 232 of SEQ ID NO: 4, e.g., from about amino acid 218 to about amino acid 229 of SEQ ID NO: 4. In yet other aspects, the surface-exposed, flexible loop structure comprising A2-1 corresponds to a region in native mature human FVIII from about amino acid 395 to about amino acid 421 of SEQ ID NO: 4, e.g. from about amino acid 397 to about amino acid 418 of SEQ ID NO: 4. In still other embodiments, the surface-exposed, flexible loop structure comprising A2-2 corresponds to a region in native mature human FVIII from about amino acid 577 to about amino acid 635 of SEQ ID NO: 4, e.g., from about amino acid 595 to about amino acid 607 of SEQ ID NO: 4. In certain aspects the surface-exposed, flexible loop structure comprising A3-1 corresponds to a region in native mature human FVIII from about amino acid 1705 to about amino acid 1732 of SEQ ID NO: 4, e.g., from about amino acid 1711 to about amino acid 1725 of SEQ ID NO: 4. In yet other aspects, the surface-exposed, flexible loop structure comprising A3-2 corresponds to a region in native mature human FVIII from about amino acid 1884 to about amino acid 1917 of SEQ ID NO: 4, e.g., from about amino acid 1899 to about amino acid 1911 of SEQ ID NO: 4.

In another embodiment, the one or more amino acids in which at least one XTEN sequence is inserted is located within a3 domain, e.g., amino acids 1649 to 1689, corresponding to full-length mature FVIII polypeptide. In a particular embodiment, an XTEN sequence is inserted between amino acids 1656 and 1657 of SEQ ID NO: 4 (full-length mature FVIII). In a specific embodiment, a FVIII protein comprising an XTEN sequence inserted immediately downstream of amino acid 1656 corresponding to SEQ ID NO: 4 further comprises a deletion from amino acid 745 to amino acid 1656 corresponding to SEQ ID NO: 4.

In some embodiments, the one or more insertion sites for one or more XTEN insertions are immediately downstream of one or more amino acids selected from the group consisting of:

| | | |
|---|---|---|
| (1) amino acid 3, | (2) amino acid 18, | (3) amino acid 22, |
| (4) amino acid 26, | (5) amino acid 32, | (6) amino acid 40, |
| (7) amino acid 60, | (8) amino acid 65, | (9) amino acid 81, |
| (10) amino acid 116, | (11) amino acid 119, | (12) amino acid 130, |
| (13) amino acid 188, | (14) amino acid 211, | (15) amino acid 216, |
| (16) amino acid 220, | (17) amino acid 224, | (18) amino acid 230, |
| (19) amino acid 333, | (20) amino acid 336, | (21) amino acid 339, |
| (22) amino acid 375, | (23) amino acid 399, | (24) amino acid 403, |
| (25) amino acid 409, | (26) amino acid 416, | (26) amino acid 442, |
| (28) amino acid 487, | (29) amino acid 490, | (30) amino acid 494, |
| (31) amino acid 500, | (32) amino acid 518, | (33) amino acid 599, |
| (34) amino acid 603, | (35) amino acid 713, | (36) amino acid 745, |
| (37) amino acid 1656, | (38) amino acid 1711, | (39) amino acid 1720, |
| (40) amino acid 1725, | (41) amino acid 1749, | (42) amino acid 1796, |
| (43) amino acid 1802, | (44) amino acid 1827, | (45) amino acid 1861, |

-continued

| | | |
|---|---|---|
| (46) amino acid 1896, | (47) amino acid 1900, | (48) amino acid 1904, |
| (49) amino acid 1905, | (50) amino acid 1910, | (51) amino acid 1937, |
| (52) amino acid 2019, | (53) amino acid 2068, | (54) amino acid 2111, |
| (55) amino acid 2120, | (56) amino acid 2171, | (57) amino acid 2188, |
| (58) amino acid 2227, | (59) amino acid 2277, and | (60) | two or more combinations thereof.

In one embodiment, a FVIII protein useful for the invention comprises two XTEN sequences, a first XTEN sequence inserted into a first XTEN insertion site and a second XTEN inserted into a second XTEN insertion site. Non-limiting examples of the first XTEN insertion site and the second XTEN insertion site are listed in Table 11.

TABLE 11

Exemplary Insertion Sites for Two XTENs

| Insertion 1 | | Insertion 2 | |
|---|---|---|---|
| Insertion Site | Domain | Insertion Site | Domain |
| 745 | B | 2332 | CT |
| 26 | A1 | 403 | A2 |
| 40 | A1 | 403 | A2 |
| 18 | A1 | 403 | A2 |
| 26 | A1 | 599 | A2 |
| 40 | A1 | 599 | A2 |
| 18 | A1 | 599 | A2 |
| 1720 | A3 | 1900 | A3 |
| 1725 | A3 | 1900 | A3 |
| 1711 | A3 | 1905 | A3 |
| 1720 | A3 | 1905 | A3 |
| 1725 | A3 | 1905 | A3 |
| 1656 | A3 | 26 | A1 |
| 1656 | A3 | 18 | A1 |
| 1656 | A3 | 40 | A1 |
| 1656 | A3 | 399 | A2 |
| 1656 | A3 | 403 | A2 |
| 1656 | A3 | 1725 | A3 |
| 1656 | A3 | 1720 | A3 |
| 1900 | A3 | 18 | A1 |
| 1900 | A3 | 26 | A1 |
| 1900 | A3 | 40 | A1 |
| 1905 | A3 | 18 | A1 |
| 1905 | A3 | 40 | A1 |
| 1905 | A3 | 26 | A1 |
| 1910 | A3 | 26 | A1 |
| 18 | A1 | 399 | A2 |
| 26 | A1 | 399 | A2 |
| 40 | A1 | 399 | A2 |
| 18 | A1 | 403 | A2 |
| 1656 | A3 | 1900 | A3 |
| 1656 | A3 | 1905 | A3 |
| 1711 | A3 | 40 | A1 |
| 1711 | A3 | 26 | A1 |
| 1720 | A3 | 26 | A1 |
| 1720 | A3 | 40 | A1 |
| 1720 | A3 | 18 | A1 |
| 1725 | A3 | 26 | A1 |
| 1725 | A3 | 40 | A1 |
| 1725 | A3 | 18 | A1 |
| 1720 | A3 | 403 | A2 |
| 1720 | A3 | 399 | A2 |
| 1711 | A3 | 403 | A2 |
| 1720 | A3 | 403 | A2 |
| 1725 | A3 | 403 | A2 |
| 1725 | A3 | 399 | A2 |
| 1711 | A3 | 403 | A2 |
| 1900 | A3 | 399 | A2 |
| 1900 | A3 | 403 | A2 |
| 1905 | A3 | 403 | A2 |
| 1905 | A3 | 399 | A2 |
| 1910 | A3 | 403 | A2 |

The two XTENs inserted or linked to the FVIII protein can be identical or different. In some embodiments, a FVIII protein useful for the invention comprises two XTEN sequences inserted in the FVIII protein, a first XTEN sequence inserted immediately downstream of amino acid 745 corresponding to SEQ ID NO: 4, and a second XTEN sequence inserted immediately downstream of amino acid 2332 corresponding to SEQ ID NO: 4 (the C-terminus). In other embodiments, the first XTEN sequence is inserted immediately downstream of amino acid 18, 26, 40, 1656, or 1720 corresponding to SEQ ID NO: 4, and a second XTEN sequence inserted immediately downstream of amino acid 403 corresponding to SEQ ID NO: 4. In yet other embodiments, the first XTEN sequence is inserted immediately downstream of amino acid 18, 26, or 40 corresponding to SEQ ID NO: 4, and a second XTEN sequence inserted immediately downstream of amino acid 599 corresponding to SEQ ID NO: 4. In still other embodiments, the first XTEN sequence is inserted immediately downstream of amino acid 1656 corresponding to SEQ ID NO: 4, and a second XTEN sequence inserted immediately downstream of amino acid 18, 26, 40, 399, 403, 1725, 1720, 1900, 1905, or 2332 corresponding to SEQ ID NO: 4. In certain embodiments, the first XTEN sequence is inserted immediately downstream of amino acid 1900 corresponding to SEQ ID NO: 4, and a second XTEN sequence inserted immediately downstream of amino acid 18, 26, or 40 corresponding to SEQ ID NO: 4. In some embodiments, the first XTEN sequence is inserted immediately downstream of amino acid 18, 26, or 40 corresponding to SEQ ID NO: 4, and a second XTEN sequence inserted immediately downstream of amino acid 399 corresponding to SEQ ID NO: 4. In other embodiments, the first XTEN sequence is inserted immediately downstream of amino acid 1720 corresponding to SEQ ID NO: 4, and a second XTEN sequence inserted immediately downstream of amino acid 18, 26, or 40 corresponding to SEQ ID NO: 4. In still other embodiments, the first XTEN sequence is inserted immediately downstream of amino acid 1720 corresponding to SEQ ID NO: 4, and a second XTEN sequence inserted immediately downstream of amino acid 18 corresponding to SEQ ID NO: 4. In a particular embodiment, the FVIII protein comprising two XTEN sequences, a first XTEN sequence inserted immediately downstream of amino acid 745 corresponding to SEQ ID NO: 4 and a second XTEN sequence inserted immediately downstream of amino acid 2332 corresponding to SEQ ID NO: 4, wherein the FVIII protein further has a deletion from amino acid 745 corresponding to SEQ ID NO: 4 to amino acid 1685 corresponding to SEQ ID NO: 4, a mutation or substitution at amino acid 1680 corresponding to SEQ ID NO: 4, e.g., Y1680F, a mutation or substitution at amino acid 1648 corresponding to SEQ ID NO: 4, e.g., R1648A, or at least two mutations or substitutions at amino acid 1648 corresponding to SEQ ID NO: 4, e.g., R1648A, and amino acid 1680 corresponding to SEQ ID NO: 4, e.g., Y1680F. In a specific embodiment, the FVIII protein comprises two XTEN sequences, a first XTEN inserted immediately downstream of amino acid 1656 corresponding to SEQ ID NO: 4 and a second XTEN sequence inserted immediately downstream of amino acid 2332 of SEQ ID NO: 4, wherein the FVIII protein further has a deletion from amino acid 745 to amino acid 1656 corresponding to SEQ ID NO: 4.

In certain embodiments, a FVIII protein comprises three XTEN sequences, a first XTEN sequence inserted into a first XTEN insertion site, a second XTEN sequence inserted into a second XTEN sequence, and a third XTEN sequence inserted into a third XTEN insertion site. The first, second, or third XTEN sequences can be identical or different. The first, second, and third insertion sites can be selected from the group of any one of the insertion sites disclosed herein. In some embodiments, the FVIII protein comprising three XTEN sequences can further comprise a mutation or substitution, e.g., amino acid 1648 corresponding to SEQ ID NO: 4, e.g., R1648A. For example, non-limiting examples of the first, second, and third XTEN insertion sites are listed in Table 12.

TABLE 12

Exemplary Insertion Sites for Three XTENs

| Insertion 1 | | Insertion 2 | | Insertion 3 | |
|---|---|---|---|---|---|
| Insertion Site | Domain | Insertion Site | Domain | Insertion Site | Domain |
| 26 | A1 | 403 | A2 | 1656 | A3 |
| 26 | A1 | 403 | A2 | 1720 | A3 |
| 26 | A1 | 403 | A2 | 1900 | A3 |
| 26 | A1 | 1656 | A3 | 1720 | A3 |
| 26 | A1 | 1656 | A3 | 1900 | A3 |
| 26 | A1 | 1720 | A3 | 1900 | A3 |
| 403 | A2 | 1656 | A3 | 1720 | A3 |
| 403 | A2 | 1656 | A3 | 1900 | A3 |
| 403 | A2 | 1720 | A3 | 1900 | A3 |
| 1656 | A3 | 1720 | A3 | 1900 | A3 |
| 745 | B | 1900 | | 2332 | CT |
| 18 | A1 | 745 | B | 2332 | CT |
| 26 | A1 | 745 | B | 2332 | CT |
| 40 | A1 | 745 | B | 2332 | CT |
| 18 | A1 | 745 | B | 2332 | CT |
| 40 | A1 | 745 | B | 2332 | CT |
| 403 | A2 | 745 | B | 2332 | CT |
| 399 | A2 | 745 | B | 2332 | CT |
| 1725 | A3 | 745 | B | 2332 | CT |
| 1720 | A3 | 745 | B | 2332 | CT |
| 1711 | A3 | 745 | B | 2332 | CT |
| 1900 | A3 | 745 | B | 2332 | CT |
| 1905 | A3 | 745 | B | 2332 | CT |
| 1910 | A3 | 745 | B | 2332 | CT |

In some embodiments, a FVIII protein comprises three XTEN sequences, a first XTEN sequence inserted immediately downstream of amino acid 26 corresponding to SEQ ID NO: 4, a second XTEN sequence inserted downstream of amino acid 403 corresponding to SEQ ID NO: 4, and a third XTEN sequence inserted downstream of amino acid 1656, 1720, or 1900 corresponding to SEQ ID NO: 4. In other embodiments, the first XTEN sequence is inserted immediately downstream of amino acid 26 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In yet other embodiments, the first XTEN sequence is inserted immediately downstream of amino acid 26 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In still other embodiments, the first XTEN sequence is inserted immediately downstream of amino acid 403 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In other embodiments, the first XTEN sequence is inserted immediately downstream of amino acid 403 or 1656 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In other embodiments, the first XTEN sequence is inserted immediately downstream of amino acid 18, 26, 40, 399, 403, 1711, 1720, 1725, 1900, 1905, or 1910 corresponding to SEQ ID NO: 4, a second XTEN sequence is inserted downstream of amino acid 745 corresponding to SEQ ID NO: 4, and a third XTEN sequence is inserted downstream of amino acid 2332 corresponding to SEQ ID NO: 4.

In other embodiments, a FVIII protein in the invention comprises four XTEN sequences, a first XTEN sequence inserted into a first insertion site, a second XTEN sequence inserted into a second insertion site, a third XTEN sequence inserted into a third insertion site, and a fourth XTEN sequence inserted into a fourth insertion site. The first, second, third, and fourth XTEN sequences can be identical, different, or combinations thereof. In some embodiments, the FVIII protein comprising four XTEN sequences can further comprise a mutation or substitution, e.g., amino acid 1648 corresponding to SEQ ID NO: 4, e.g., R1648A. Non-limiting examples of the first, second, third, and fourth XTEN insertion sites are listed in Table 13.

TABLE 13

Exemplary Insertion Sites for Four XTENs

| Insertion 1 | | Insertion 2 | | Insertion 3 | | Insertion 4 | |
|---|---|---|---|---|---|---|---|
| Insertion Site | Domain | Insertion Site | Domain | Insertion Site | Domain | Insertion Site | Domain |
| 26 | A1 | 403 | A2 | 1656 | a3 | 1720 | A3 |
| 26 | A1 | 403 | A2 | 1656 | a3 | 1900 | A3 |
| 26 | A1 | 403 | A2 | 1720 | A3 | 1900 | A3 |
| 26 | A1 | 1656 | a3 | 1720 | A3 | 1900 | A3 |
| 403 | A2 | 1656 | a3 | 1720 | A3 | 1900 | A3 |
| 0040 | A1 | 0403 | A2 | 745 | B | 2332 | CT |
| 0040 | A1 | 0403 | A2 | 745 | B | 2332 | CT |
| 0018 | A1 | 0409 | A2 | 745 | B | 2332 | CT |
| 0040 | A1 | 0409 | A2 | 745 | B | 2332 | CT |
| 0040 | A1 | 0409 | A2 | 745 | B | 2332 | CT |
| 0018 | A1 | 0409 | A2 | 745 | B | 2332 | CT |
| 0040 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1900 | A3 | 745 | B | 2332 | CT |
| 0018 | A1 | 1900 | A3 | 745 | B | 2332 | CT |
| 0026 | A1 | 1900 | A3 | 745 | B | 2332 | CT |
| 0040 | A1 | 1900 | A3 | 745 | B | 2332 | CT |
| 0040 | A1 | 1905 | A3 | 745 | B | 2332 | CT |
| 0018 | A1 | 1905 | A3 | 745 | B | 2332 | CT |
| 0040 | A1 | 1905 | A3 | 745 | B | 2332 | CT |
| 0026 | A1 | 1905 | A3 | 745 | B | 2332 | CT |
| 0018 | A1 | 1905 | A3 | 745 | B | 2332 | CT |
| 0018 | A1 | 1910 | A3 | 745 | B | 2332 | CT |
| 0018 | A1 | 1910 | A3 | 745 | B | 2332 | CT |
| 0040 | A1 | 1910 | A3 | 745 | B | 2332 | CT |
| 0026 | A1 | 1910 | A3 | 745 | B | 2332 | CT |
| 0018 | A1 | 1910 | A3 | 745 | B | 2332 | CT |

TABLE 13-continued

Exemplary Insertion Sites for Four XTENs

| Insertion 1 | | Insertion 2 | | Insertion 3 | | Insertion 4 | |
|---|---|---|---|---|---|---|---|
| Insertion Site | Domain | Insertion Site | Domain | Insertion Site | Domain | Insertion Site | Domain |
| 0026 | A1 | 1910 | A3 | 745 | B | 2332 | CT |
| 0040 | A1 | 1910 | A3 | 745 | B | 2332 | CT |
| 0018 | A1 | 1910 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0403 | A2 | 1720 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0409 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 1720 | A3 | 1900 | A3 | 745 | B | 2332 | CT |
| 1720 | A3 | 1905 | A3 | 745 | B | 2332 | CT |
| 1720 | A3 | 1910 | A3 | 745 | B | 2332 | CT |
| 1720 | A3 | 1910 | A3 | 745 | B | 2332 | CT |
| 0403 | A2 | 1656 | a3 | 1720 | A3 | 2332 | CT |
| 0403 | A2 | 1656 | a3 | 1900 | A3 | 2332 | CT |
| 0403 | A2 | 1720 | A3 | 1900 | A3 | 2332 | CT |
| 1656 | a3 | 1720 | A3 | 1900 | A3 | 2332 | CT |
| 0018 | A1 | 0403 | A2 | 1656 | a3 | 2332 | CT |
| 0018 | A1 | 0403 | A2 | 1720 | A3 | 2332 | CT |
| 0018 | A1 | 0403 | A2 | 1900 | A3 | 2332 | CT |
| 0018 | A1 | 1656 | a3 | 1720 | A3 | 2332 | CT |
| 0018 | A1 | 1656 | a3 | 1900 | A3 | 2332 | CT |
| 0018 | A1 | 1720 | A3 | 1900 | A3 | 2332 | CT |
| 0018 | A1 | 0403 | A2 | 0745 | B | 2332 | CT |
| 0018 | A1 | 0745 | B | 1720 | A3 | 2332 | CT |
| 0018 | A1 | 0745 | B | 1900 | A3 | 2332 | CT |
| 0403 | A2 | 0745 | B | 1720 | A3 | 2332 | CT |
| 0403 | A2 | 0745 | B | 1900 | A3 | 2332 | CT |
| 0745 | B | 1720 | A3 | 1900 | A3 | 2332 | CT |
| 0188 | A1 | 1900 | A3 | 0745 | B | 2332 | CT |
| 0599 | | 1900 | A3 | 0745 | B | 2332 | CT |
| 2068 | | 1900 | A3 | 0745 | B | 2332 | CT |
| 2171 | | 1900 | A3 | 0745 | B | 2332 | CT |
| 2227 | | 1900 | A3 | 0745 | B | 2332 | CT |
| 2277 | | 1900 | A3 | 0745 | B | 2332 | CT |

In some embodiments, a FVIII protein comprises five XTEN sequences, a first XTEN sequence inserted into a first insertion site, a second XTEN sequence inserted into a second insertion site, a third XTEN sequence inserted into a third XTEN insertion site, a fourth XTEN sequence inserted into a fourth XTEN insertion site, and a fifth XTEN sequence inserted into a fifth XTEN insertion site. The first, second, third, fourth, of fifth XTEN sequences can be identical, different, or combinations thereof. Non-limiting examples of the first, second, third, fourth, and fifth insertion sites are listed in Table 14.

TABLE 14

Exemplary Insertion Sites for Five XTENs

| XTEN Insertion 1 | XTEN insertion 2 | XTEN Insertion 3 | XTEN Insertion 4 | XTEN Insertion 5 |
|---|---|---|---|---|
| 0403 | 1656 | 1720 | 1900 | 2332 |
| 0018 | 0403 | 1656 | 1720 | 2332 |
| 0018 | 0403 | 1656 | 1900 | 2332 |
| 0018 | 0403 | 1720 | 1900 | 2332 |
| 0018 | 1656 | 1720 | 1900 | 2332 |
| 0018 | 0403 | 0745 | 1720 | 2332 |
| 0018 | 0403 | 0745 | 1900 | 2332 |
| 0018 | 0745 | 1720 | 1900 | 2332 |
| 0403 | 0745 | 1720 | 1900 | 2332 |

In certain embodiments, a FVIII protein comprises six XTEN sequences, a first XTEN sequence inserted into a first XTEN insertion site, a second XTEN sequence inserted into a second XTEN insertion site, a third XTEN sequence inserted into a third XTEN insertion site, a fourth XTEN sequence inserted into a fourth XTEN insertion site, a fifth XTEN sequence inserted into a fifth XTEN insertion site, and a sixth XTEN sequence inserted into a sixth XTEN insertion site. The first, second, third, fourth, fifth, or sixth XTEN sequences can be identical, different, or combinations thereof. Examples of the six XTEN insertion sites include, but are not limited to the insertion sites listed in Table 15.

TABLE 15

Exemplary XTEN Insertion Sites for Six XTENs

| XTEN Insertion 1 | XTEN insertion 2 | XTEN Insertion 3 | XTEN Insertion 4 | XTEN Insertion 5 | XTEN Insertion 6 |
|---|---|---|---|---|---|
| 0018 | 0403 | 1656 | 1720 | 1900 | 2332 |
| 0018 | 0403 | 0745 | 1720 | 1900 | 2332 |

In a particular example, a first XTEN is inserted between amino acids 26 and 27 corresponding to SEQ ID NO: 4, and a second XTEN is inserted between amino acids 1720 and 1721 corresponding to SEQ ID NO: 4 (full-length mature FVIII). In another example, a first XTEN is inserted between amino acids 403 and 404 corresponding to SEQ ID NO: 4, and a second XTEN is inserted between amino acids 1720 and 1721 corresponding to SEQ ID NO: 4. In some examples, a first XTEN is inserted between amino acids 1656 and 1657 corresponding to SEQ ID NO: 4, and a second XTEN is inserted between amino acids 1720 and 1721 corresponding to SEQ ID NO: 4. In other examples, a first XTEN is inserted between amino acids 26 and 27 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In yet other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In still other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In certain embodiments, a first XTEN is inserted between amino acids 26 and 27 corresponding to SEQ ID NO: 4, a second XTEN is inserted between amino acids 1720 and 1721 corresponding to SEQ ID NO: 4, and a third XTEN is inserted between amino acids 1900 and 1901 corresponding to SEQ ID NO: 4. In some embodiments, a first XTEN is inserted between amino acids 26 and 27 corresponding to SEQ ID NO: 4, a second XTEN is inserted between amino acids 1656 and 1657 corresponding to SEQ ID NO: 4, a third XTEN is inserted between amino acids 1720 and 1721 corresponding to SEQ ID NO: 4, and a fourth XTEN is inserted between 1900 and 1901 corresponding to SEQ ID NO: 4.

In a particular embodiment, an XTEN sequence is inserted between amino acids 745 and 746 of a full-length Factor VIII or the corresponding insertion site of the B-domain deleted Factor VIII.

In some embodiments, a chimeric protein of the invention comprises two polypeptide sequences, a first polypeptide sequence comprising an amino acid sequence at least about 80%, 90%, 95%, or 100% identical to a sequence selected from FVIII-161 (SEQ ID NO: 101), FVIII-169 (SEQ ID NO: 103), FVIII-170 (SEQ ID NO: 102), FVIII-173 (SEQ ID NO: 104); FVIII-195 (SEQ ID NO: 105); FVIII-196 (SEQ ID NO: 106), FVIII-199 (SEQ ID NO: 107), FVIII-201 (SEQ ID NO: 108); FVIII-203 (SEQ ID NO: 109), FVIII-204 (SEQ ID NO: 110), FVIII-205 (SEQ ID NO: 111), FVIII-266 (SEQ ID NO:112), FVIII-267 (SEQ ID NO: 113), FVIII-268 (SEQ ID NO: 114), FVIII-269 (SEQ ID NO: 115), FVIII-271 (SEQ ID NO: 116), or FVIII-272 (SEQ ID NO: 117) and a second polypeptide sequence comprising an amino acid sequence at least about 80%, 90%, 95%, or 100% identical to a sequence selected from VWF031 (SEQ ID NO: 118), VWF034 (SEQ ID NO: 119), or VWF-036 (SEQ ID NO: 120).

D) Ig Constant Region or a Portion Thereof

The VWF fragment or the FVIII protein linked to an XTEN sequence in the present invention can further comprise an Ig constant region or a portion thereof. The Ig constant region or a portion thereof can improve pharmacokinetic or pharmacodynamic properties of the VWF fragment or the FVIII protein in combination with the XTEN sequence. In certain embodiments, the Ig constant region or a portion thereof extends a half-life of a molecule fused to the Ig constant region or a portion thereof.

An Ig constant region is comprised of domains denoted CH (constant heavy) domains (CH1, CH2, etc.). Depending on the isotype, (i.e. IgG, IgM, IgA, IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An Ig constant region or a portion thereof for producing the chimeric protein of the present invention may be obtained from a number of different sources. In some embodiments, an Ig constant region or a portion thereof is derived from a human Ig. It is understood, however, that the Ig constant region or a portion thereof may be derived from an Ig of another mammalian species, including for example, a rodent (e.g. a mouse, rat, rabbit, guinea pig) or non-human primate (e.g. chimpanzee, macaque) species. Moreover, the Ig constant region or a portion thereof may be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Ig constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the Ig constant region or a portion thereof can be cloned, e.g., using the polymerase chain reaction and primers which are selected to amplify the domain of interest. To clone a sequence of the Ig constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An Ig constant region used herein can include all domains and the hinge region or portions thereof. In one embodiment, the Ig constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An Ig constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an Ig that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of Igs or Ig fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of Ig constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

Certain of the above mutations may confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the Ig constant region or a portion thereof, e.g, an Fc region, is a polypeptide including the sequence PKNSSMISNTP (SEQ ID NO: 52) and optionally further including a sequence selected from HQSLGTQ (SEQ ID NO: 53), HQNLSDGK (SEQ ID NO: 54), HQNIS-DGK (SEQ ID NO: 55), or VISSHLGQ (SEQ ID NO: 56) (U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The disulfide bond by the immunoglobulin constant region or a portion thereof places the first polypeptide comprising FVIII and the second polypeptide comprising the VWF fragment together so that endogenous VWF does not replace the VWF fragment and does not bind to the FVIII. Therefore, the disulfide bond between the first immunoglobulin constant region or a portion thereof and a second immunoglobulin constant region or a portion thereof prevents interaction between endogenous VWF and the FVIII protein. This inhibition of interaction between the VWF and the FVIII protein allows the half-life of the FVIII protein to go beyond the two fold limit. The hinge region or a portion thereof can further be linked to one or more domains of CH1, CH2, CH3, a fragment thereof, and any combinations thereof. In a particular embodiment, the immunoglobulin constant region or a portion thereof is a hinge region and CH2.

In certain embodiments, the Ig constant region or a portion thereof is hemi-glycosylated. For example, the chimeric protein comprising two Fc regions or FcRn binding partners may contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an Ig constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner used in the invention may also comprise an art recognized amino acid substitution which alters the glycosylation of the chimeric protein. For example, the Fc region or FcRn binding partner of the chimeric protein linked to a VWF fragment or a FVIII protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention may differ in sequence at one or more amino acid positions. For example, at least two of the Fc regions or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

E) Linkers

The chimeric protein of the present invention further comprises one or more linkers. One type of the linkers is a cleavable linker, which can be cleaved by various proteases when administered to a subject in vivo, e.g., at a site of coagulation. In one embodiment, the cleavable linker allows cleavage of moiety, e.g., a VWF fragment, from the chimeric protein at the site of the coagulation cascade, thus allowing activated FVIII (FVIIIa) to have its FVIIIa activity. Another type of the linkers is a processable linker, which contains an intracellular cleavage site and thus can be cleaved by an intracellular processing enzyme in a host cell, allowing convenient expression of a polypeptide and formation of a chimeric protein.

One or more linkers can be present between any two proteins in the chimeric protein. In one embodiment, a chimeric protein comprises (i) a VWF fragment, (ii) an XTEN sequence, and (iii) a FVIII protein, wherein the VWF fragment is linked to the XTEN sequence by a linker, e.g., a cleavable linker, and the XTEN sequence is further linked to the FVIII protein (i.e., V-L-X-FVIII). In another embodiment, a chimeric protein comprises (i) a VWF fragment, (ii) an XTEN sequence, and (iii) a FVIII protein, wherein the VWF fragment is linked to the XTEN sequence, and the XTEN sequence is linked to the FVIII protein by a linker, e.g., a cleavable linker (i.e., V-X-L-FVIII).

In certain embodiments, a chimeric protein comprises (i) a VWF fragment, (ii) an XTEN sequence, (iii) a first Ig constant region or a portion thereof (e.g., a first Fc region), (iv) a FVIII protein, and (v) a second Ig constant region or a portion thereof (e.g., a second Fc region), wherein the VWF fragment is linked to the XTEN sequence by an optional linker, e.g., a cleavable linker. The XTEN sequence can be further linked to the first Ig constant region or a portion thereof by a linker, e.g., a cleavable linker. The FVIII protein (with or without an XTEN sequence) can also be linked to the second Ig constant region or a portion thereof by an optional linker, e.g. a cleavable linker. In certain embodiments, the chimeric protein further comprises one or more linkers, e.g., processable linkers, between the first Ig constant region or a portion thereof (e.g., first Fc region) and the second Ig constant region or a portion thereof (e.g., second Fc region), between the VWF fragment and the second Ig constant region or a portion thereof, or between the FVIII protein and the first Ig constant region or a portion thereof (e.g., first Fc region).

In some embodiments, the present invention includes a chimeric protein comprising (i) a FVIII protein, (ii) an XTEN sequence, (iii) a first Ig constant region or a portion thereof, and (iv) a second Ig constant region or a portion thereof, wherein the first Ig constant region or a portion thereof and the second Ig constant region or a portion thereof are linked by a processable linker.

The linker useful in the present invention can comprise any organic molecule. In one embodiment, the linker comprises a polymer, e.g., polyethylene glycol (PEG) or hydroxyethyl starch (HES). In another embodiment, the linker comprises an amino acids sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids. In one embodiment, the linker comprises an XTEN sequence. Additional examples of XTEN can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2. In another embodiment, the linker is a PAS sequence.

The linker useful in the present invention can comprise any organic molecule. In one embodiment, the linker is a polymer, e.g., polyethylene glycol (PEG) or hydroxyethyl starch (HES). In another embodiment, the linker is an amino acid sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of linkers are well known in the art. In one embodiment, the linker comprises the sequence $G_n$. The linker can comprise the sequence $(GA)_n$. The linker can comprise the sequence $(GGS)_n$. In other embodiments, the linker comprises $(GGGS)_n$ (SEQ ID NO: 57). In still other embodiments, the linker comprises the sequence $(GGS)_n$ (GGGGS)$_n$ (SEQ ID NO: 58). In these instances, n may be an integer from 1-100. In other instances, n may be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 59), GGSGGSGGSGGSGGG (SEQ ID NO: 60), GGSGGSGGGGSGGGGS (SEQ ID NO: 61), GGSGGSGGSGGSGGSGGS (SEQ ID NO: 62), or GGGGSGGGGSGGGGS (SEQ ID NO: 63). The linker does not eliminate or diminish the VWF fragment activity or the clotting activity of Factor VIII. Optionally, the linker enhances the VWF fragment activity or the clotting activity of Factor VIII protein, e.g., by further diminishing the effects of steric hindrance and making the VWF fragment or Factor VIII portion more accessible to its target binding site.

In one embodiment, the linker useful for the chimeric protein is 15-25 amino acids long. In another embodiment, the linker useful for the chimeric protein is 15-20 amino acids long. In some embodiments, the linker for the chimeric protein is 10-25 amino acids long. In other embodiments, the linker for the chimeric protein is 15 amino acids long. In still other embodiments, the linker for the chimeric protein is $(GGGGS)_n$ (SEQ ID NO: 64) where G represents glycine, S represents serine and n is an integer from 1-20.

F) Cleavage Sites

The linker may also incorporate a moiety capable of being cleaved either chemically (e.g., hydrolysis of an ester bond), enzymatically (i.e., incorporation of a protease cleavage sequence), or photolytically (e.g., a chromophore such as 3-amino-3-(2-nitrophenyl) proprionic acid (ANP)) in order to release one molecule from another.

In one embodiment, the linker is a cleavable linker. The cleavable linkers can comprise one or more cleavage sites at the N-terminus or C-terminus or both. In another embodiment, the cleavable linker consists essentially of or consists of one or more cleavable sites. In other embodiments, the cleavable linker comprises heterologous amino acid linker sequences described herein or polymers and one or more cleavable sites.

In certain embodiments, a cleavable linker comprises one or more cleavage sites that can be cleaved in a host cell (i.e., intracellular processing sites). Non limiting examples of the cleavage site include RRRR (SEQ ID NO: 9), RKRRKR (SEQ ID NO: 10), and RRRRS (SEQ ID NO: 11).

In other embodiments, a cleavable linker comprises one or more cleavage sites that are cleaved by a protease after a chimeric protein comprising the cleavable linker is administered to a subject. In one embodiment, the cleavage site is cleaved by a protease selected from the group consisting of factor XIa, factor XIIa, kallikrein, factor VIIa, factor IXa, factor Xa, factor IIa (thrombin), Elastase-2, MMP-12, MMP-13, MMP-17, and MMP-20. In another embodiment, the cleavage site is selected from the group consisting of a FXIa cleavage site (e.g., KLTR↓AET (SEQ ID NO: 65)), a FXIa cleavage site (e.g, DFTR↓VVG (SEQ ID NO: 66)), a FXIIa cleavage site (e.g., TMTR↓IVGG (SEQ ID NO: 67)), a Kallikrein cleavage site (e.g., SPFR↓STGG (SEQ ID NO: 68)), a FVIIa cleavage site (e.g., LQVR↓IVGG (SEQ ID NO: 69)), a FIXa cleavage site (e.g., PLGR↓IVGG (SEQ ID NO: 70)), a FXa cleavage site (e.g., IEGR↓TVGG (SEQ ID NO: 71)), a FIIa (thrombin) cleavage site (e.g, LTPR↓SLLV (SEQ ID NO: 72)), a Elastase-2 cleavage site (e.g, LGPV↓SGVP (SEQ ID NO: 73)), a Granzyme-B cleavage (e.g, VAGD↓SLEE (SEQ ID NO: 74)), a MMP-12 cleavage site (e.g., GPAG↓LGGA (SEQ ID NO: 75)), a MMP-13 cleavage site (e.g., GPAG↓LRGA (SEQ ID NO: 76)), a MMP-17 cleavage site (e.g., APLG↓LRLR (SEQ ID NO: 77)), a MMP-20 cleavage site (e.g., PALP↓LVAQ (SEQ ID NO: 78)), a TEV cleavage site (e.g., ENLYFQ↓G (SEQ ID NO: 79)), a Enterokinase cleavage site (e.g., DDDK↓IVGG (SEQ ID NO: 80)), a Protease 3C (PRESCISSION™) cleavage site (e.g., LEVLFQ↓GP (SEQ ID NO: 81)), and a Sortase A cleavage site (e.g., LPKT↓GSES) (SEQ ID NO: 82). In certain embodiments, the FXIa cleavage sites include, but are not limited to, e.g., TQSFNDFTR (SEQ ID NO: 83) and SVSQTSKLTR (SEQ ID NO: 84). Non-limiting exemplary thrombin cleavage sites include, e.g., DFLAEGGGVR (SEQ ID NO: 85), TTKIKPR (SEQ ID NO: 86), or LVPRG (SEQ ID NO: 87), and a sequence comprising, consisting essentially of, or consisting of ALRPR (SEQ ID NO: 17) (e.g., ALRPRVVGGA (SEQ ID NO: 88)).

In a specific embodiment, the cleavage site is TLDPRSFLLRNPNDKYEPFWEDEEK (SEQ ID NO: 8).

Polynucleotides, Vectors, and Host Cells

Also provided in the invention is a polynucleotide encoding (a) a VWF fragment linked to an XTEN sequence and a FVIII protein, (b) a FVIII protein linked to an XTEN sequence and Fc, or (c) a FVIII protein linked to an XTEN sequence and a VWF fragment described herein. When a chimeric protein is a single polypeptide chain (e.g., F2-L2-X-V-L1-F1-FVIII, wherein FVIII comprises a FVIII protein, F1 comprises a first Ig constant region or a portion thereof, e.g., a first Fc region, L1 comprises a first linker, V comprises a VWF fragment, X comprises an XTEN sequence, L2 comprises a second linker, and F2 comprises a second Ig constant region or a portion thereof, e.g., a second Fc region), the invention is drawn to a single polynucleotide chain encoding the single polypeptide chain. When the chimeric protein comprises a first and a second polypeptide chains (F2-L2-X-V:FVIII-F1), the first polypeptide chain comprising a VWF fragment linked to a XTEN sequence, which is further linked to a first Ig constant region or a portion thereof (e.g., a first Fc region) by a cleavable linker (e.g., F2-L2-X-V) and the second polypeptide chain comprising a FVIII protein and a second Ig constant region or a portion thereof (e.g., a second Fc region) (e.g, FVIII-F1), wherein the first polypeptide chain and the second polypeptide chain are associated with each other, a polynucleotide can comprise the first nucleotide sequence and the second nucleotide sequence. In one embodiment, the first polypeptide chain and the second polypeptide chain can be encoded by a single polynucleotide chain. In another embodiment, the first polypeptide chain and the second polypeptide chain are encoded by two different polynucleotides, i.e., a first nucleotide sequence and a second nucleotide sequence. In another embodiment, the first nucleotide sequence and the second nucleotide sequence are on two different polynucleotides (e.g., different vectors). In certain embodiments, the present invention is directed to a set of polynucleotides comprising a first nucleotide chain and a second nucleotide chain, wherein the first nucleotide chain encodes the VWF fragment of the chimeric protein and the second nucleotide chain encodes the FVIII protein. In some embodiments, a chimeric protein comprising two polypeptide chains or three polypeptide chains can be encoded by a single polynucleotide chain, and then processed into two or three (or more) polypeptide chains. In yet other embodiments, a chimeric protein comprising these polypeptide chains can be encoded by two or three polynucleotide chains.

In other embodiments, the set of the polynucleotides further comprises an additional nucleotide chain (e.g., a second nucleotide chain when the chimeric polypeptide is encoded by a single polynucleotide chain or a third nucleotide chain when the chimeric protein is encoded by two polynucleotide chains) which encodes a protein convertase. The protein convertase can be selected from the group consisting of proprotein convertase subtilisin/kexin type 5 (PCSK5 or PC5), proprotein convertase subtilisin/kexin type 7 (PCSK7 or PC5), a yeast Kex 2, proprotein convertase subtilisin/kexin type 3 (PACE or PCSK3), and two or more combinations thereof. In some embodiments, the protein convertase is PACE, PC5, or PC7. In a specific embodiment, the protein convertase is PC5 or PC7. See International Application no. PCT/US2011/043568.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding the chimeric protein described herein. In one embodiment, one or more of the coding sequences for the VWF fragment and XTEN, the FVIII protein and XTEN, or both are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Clifton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, Autographa californica nuclear polyhidrosis virus (AcNPV) is used as a vector to express the foreign genes. The virus grows in Spodoptera frugiperda cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed. (see, e.g., Smith et al. (1983) J Virol 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase the yield of polypeptides driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit easy purification of the recombinantly produced protein. Examples include, but are not limited to, vector pUR278 (Ruther et al. (1983) *EMBO J* 2:1791), in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid including a FVIII(X)-Fc fusion coding sequence, a VWF fragment-L-Fc fusion coding sequence, or both and a selectable marker, e.g., zeocin resistance, are transfected into HEK 293 cells, for production of a chimeric protein.

In another embodiment, a plasmid including a FVIII-Fc fusion coding sequence, a VWF fragment-XTEN-L-Fc fusion coding sequence, or both and a selectable marker, e.g., zeocin resistance, are transfected into HEK 293 cells, for production of a chimeric protein.

In other embodiments, a plasmid including a FVIII(X)-Fc fusion coding sequence, a Fc coding sequence, or both and a selectable marker, e.g., zeocin resistance, are transfected into HEK 293 cells, for production of a chimeric protein.

In some embodiments, a first plasmid including a FVIII (X)-Fc fusion coding sequence and a first selectable marker, e.g., a zeocin resistance gene, and a second plasmid including an Fc coding sequence or a VWF fragment-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In still other embodiments, a first plasmid including a FVIII-Fc fusion coding sequence and a first selectable marker, e.g., a zeocin resistance gene, and a second plasmid including a VWF fragment-XTEN-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In yet other embodiments, a first plasmid including a FVIII(X)-Fc fusion coding sequence and a first selectable marker, e.g., a zeocin resistance gene, and a second plasmid including a VWF fragment-XTEN-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In certain embodiments, a first plasmid, including a chimeric protein encoding FVIII (with or without XTEN)-F1-L1-V-XTEN-L2-F2 coding sequence and a first selectable marker, e.g., a zeocin resistance gene, and a second plasmid including a protein convertase coding sequence and a second selectable marker, e.g., a hygromycin resistance gene, are cotransfected into HEK 293 cells, for production of the chimeric protein. The promoters for the FVIII(X)-Fc coding sequence and the VWF-XTEN-Fc coding sequence can be different or they can be the same.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CD293 (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

In order to co-express the two polypeptide chains of the chimeric protein, the host cells are cultured under conditions that allow expression of both chains. As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow association of the VWF fragment with the FVIII protein. Conditions that allow expression of the VWF fragment and/or the FVIII protein may include the presence of a source of vitamin K. For example, in one embodiment, stably transfected HEK 293 cells are cultured in CD293 media (Invitrogen, Carlsbad, Calif.) or OptiCHO media (Invitrogen, Carlsbad, Calif.) supplemented with 4 mM glutamine.

In one aspect, the present invention is directed to a method of expressing, making, or producing the chimeric protein of the invention comprising a) transfecting a host cell comprising a polynucleotide encoding the chimeric protein and b) culturing the host cell in a culture medium under a condition suitable for expressing the chimeric protein, wherein the chimeric protein is expressed.

In further embodiments, the protein product containing the VWF fragment linked to an XTEN sequence or the FVIII protein linked to an XTEN sequence is secreted into the media. Media is separated from the cells, concentrated, filtered, and then passed over two or three affinity columns, e.g., a protein A column and one or two anion exchange columns.

In certain aspects, the present invention relates to the chimeric protein produced by the methods described herein.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

Pharmaceutical Composition

Compositions containing the chimeric protein of the present invention may contain a suitable pharmaceutically acceptable carrier. For example, they may contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, including, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include antifibrinolytic drugs, e.g., epsilon-amino-caproic acid, tranexamic acid.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a chimeric protein, the polynucleotide encoding the chimeric protein, the vector comprising the polynucleotide, or the host cell comprising the vector, and a pharmaceutically acceptable carrier. The FVIII protein in a chimeric protein has extended half-life compared to wild type FVIII protein or the corresponding FVIII protein without the VWF fragment. In one embodiment, wherein the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of Factor VIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Gene Therapy

A chimeric protein thereof of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of a suitable chimeric protein-encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal may not be exposed to a nucleic acid encoding a selectable marker gene. In other embodiments, the sequences are incorporated into a non-viral vector known to those skilled in the art.

Methods of Using Chimeric Protein

The present invention is directed to a method of using a chimeric protein described herein to prevent or inhibit endogenous VWF binding to a FVIII protein. The present invention is also directed to a method of using a chimeric protein having a FVIII protein linked to XTEN and an Ig constant region or a portion thereof.

One aspect of the present invention is directed to preventing or inhibiting FVIII interaction with endogenous VWF by blocking or shielding the VWF binding site on the FVIII from endogenous VWF and at the same time extending half-life of the FVIII protein using an XTEN sequence in combination with an Ig constant region or a portion thereof, which can also be a half-life extender. In one embodiment, the invention is directed to a method of constructing a FVIII protein having half-life longer than wild-type FVIII. In one embodiment, an XTEN sequence inhibits or prevents interaction of a FVIII protein in a chimeric protein with endogenous VWF. In another embodiment, an Ig constant region or a portion thereof inhibits or prevents interaction of the FVIII protein with endogenous VWF. The chimeric protein useful in the method includes any one or more chimeric protein described herein.

Another aspect of the invention includes a method of administering to a subject in need thereof a chimeric protein comprising a FVIII protein having half-life longer than wild-type FVIII, wherein the method comprises administering the chimeric protein described herein to the subject.

In one embodiment, the invention is directed to a method of using an XTEN sequence and an Ig constant region or a portion thereof to extend a half-life of a FVIII protein and a VWF fragment to prevent or inhibit endogenous VWF interaction with a FVIII protein. A FVIII protein linked to an XTEN sequence (e.g., FVIII(X)) and then bound to or associated with a VWF fragment is shielded or protected from the clearance pathway of VWF and thus has reduced clearance compared to the FVIII protein not bound to the VWF fragment. The shielded FVIII protein thus has maximum extension of a half-life compared to a FVIII protein not bound to or associated with the XTEN sequence and the VWF fragment. In certain embodiments, the FVIII protein associated with or protected by a VWF fragment and linked to an XTEN sequence is not cleared by a VWF clearance receptor. In other embodiments, the FVIII protein associated with or protected by a VWF fragment and linked to an XTEN sequence is cleared from the system slower than the FVIII protein that is not associated with or protected by the VWF fragment and linked to the XTEN sequence.

In one aspect, the chimeric protein comprising the FVIII protein linked to an XTEN sequence or the FVIII protein bound to or associated with a VWF fragment linked to XTEN has reduced clearance from circulation as the VWF fragment does not contain a VWF clearance receptor binding site. The VWF fragment prevents or inhibits clearance of FVIII bound to or associated with the VWF fragment from the system through the VWF clearance pathway. The VWF fragments useful for the present invention can also provide at least one or more VWF-like FVIII protection properties that are provided by endogenous VWF. In certain embodiments, the VWF fragment or the XTEN sequence can also mask one or more FVIII clearance receptor binding site, thereby preventing clearance of FVIII by its own clearance pathway.

In some embodiments, the prevention or inhibition of a FVIII protein binding to endogenous VWF by the VWF fragment or the XTEN sequence can be in vitro or in vivo.

Also provided is a method of increasing the half-life of a FVIII protein comprising administering the chimeric protein described herein to a subject in need thereof. The half-life of non-activated FVIII bound to or associated with full-length VWF is about 12 to 14 hours in plasma. In VWD type 3, wherein there is almost no VWF in circulation, the half-life of FVIII is only about six hours, leading to symptoms of mild to moderate hemophilia A in such patients due to decreased concentrations of FVIII. The half-life of the FVIII protein linked to or associated with the VWF fragment or the XTEN sequence of the present invention can increase at least about 1.5 times, 1.6 times, 1.7 times, 1.8 times, 1.9 times, 2.0 times, 2.1 times, 2.2 times, 2.3 times, 2.4 times, 2.6 times, 2.7. times, 2.8 times, 2.9 times, 3.0 times, 3.1 times, 3.2 times, 3.3 times, 3.4 times, 3.5 times, 3.6 times, 3.7 times, 3.8 times, 3.9 times, or 4.0 times higher than the half-life of the non-activated FVIII bound to or associated with full-length VWF.

In one embodiment, the half-life of the FVIII protein linked to or associated with the VWF fragment or linked to an Ig constant region or a portion thereof in the chimeric protein comprising an XTEN sequence increases at least about 2 times, 2.5 times, 3.0 times, 3.5 times, 4.0 times, 4.5 times, 5.0 times, 5.5 times, 6.0 times, 7 times, 8 times, 9 times, or 10 times higher than the half-life of the non-activated FVIII bound to or associated with full-length VWF. In another embodiment, the half-life of the FVIII protein linked to or associated with the VWF fragment or an Ig constant region or a portion thereof in the chimeric protein comprising an XTEN sequence increases about 2 to about 5 times, about 3 to about 10 times, about 5 to about 15 times, about 10 to about 20 times, about 15 to about 25 times, about 20 to about 30 times, about 25 to about 35 times, about 30 to about 40 times, about 35 to about 45 times higher than the half-life of the non-activated FVIII bound to or associated with full-length VWF or wild type FVIII. In a specific embodiment, the half-life of the FVIII protein linked to or associated with the VWF fragment or linked to an Ig constant region in the chimeric protein comprising an XTEN sequence increases at least about 30, 31, 32, 33, 34, 35, 36, 37, 38, 39, or 40 times higher than the half-life of the wild type FVIII in a FVIII and VWF double knockout mouse.

In some embodiments, the half-life of the chimeric protein comprising the VWF fragment fused to a first Ig constant region or a portion thereof, e.g., a first Fc region and an XTEN sequence, and a FVIII protein linked to an XTEN sequence and a second Ig constant region or a portion thereof, e.g., a second Fc region, is longer than the half-life of a FVIII associated with endogenous VWF. In other embodiments, the half-life of the chimeric protein is at least about 1.5 times, 2 times, 2.5 times, 3.5 times, 3.6 times, 3.7 times, 3.8 times, 3.9 times, 4.0 times, 4.5 times, or 5.0 times the half-life of wild type FVIII or a FVIII protein associated with endogenous VWF.

In some embodiments, as a result of the invention the half-life of the FVIII protein is extended compared to a FVIII protein without the VWF fragment or wild-type FVIII. The half-life of the chimeric protein of the invention is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a FVIII protein without the VWF fragment or wild-type FVIII. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF fragment. In other embodiments, the half-life of the chimeric protein of the invention is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of the chimeric protein of the invention is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the chimeric protein of the invention per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In addition, the invention provides a method of treating or preventing a bleeding disease or disorder comprising administering an effective amount of a chimeric protein. In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In a specific embodiment, the bleeding disease or disorder is hemophilia A.

The chimeric protein comprising an XTEN sequence and an Ig constant region or a portion thereof in combination with a VWF fragment described herein, that prevents or inhibits interaction of the FVIII protein with endogenous VWF prepared by the invention, has many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of the chimeric protein.

The FVIII protein portion in the chimeric protein treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor VIIIa increases the maximum velocity of Factor X activation by Factor IXa, by approximately 200,000-fold, leading to the large second burst of thrombin generation.

The chimeric protein of the invention can be used to treat any hemostatic disorder. The hemostatic disorders that may be treated by administration of the chimeric protein of the invention include, but are not limited to, hemophilia A, as well as deficiencies or structural abnormalities relating to Factor VIII. In one embodiment, the hemostatic disorder is hemophilia A.

The chimeric protein of the invention can be used prophylactically to treat a subject with a hemostatic disorder. The chimeric protein of the invention can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

The invention also relates to methods of treating a subject that does not have a congenital hemostatic disorder, but has a secondary disease or condition resulting in acquisition of a hemostatic disorder, e.g., due to development of an anti-FVIII antibody or a surgery. The invention thus relates to a method of treating a subject in need of a general hemostatic agent comprising administering a therapeutically effective amount of the chimeric protein prepared by the present methods.

The present invention is also related to methods of reducing immunogenicity of FVIII or inducing less immunogenicity against FVIII comprising administering an effective amount of the chimeric proteins described herein, or the polynucleotides encoding the same.

In one embodiment, the subject in need of a general hemostatic agent is undergoing, or is about to undergo, surgery. The chimeric protein of the invention can be administered prior to, during, or after surgery as a prophylactic regimen. The chimeric protein of the invention can be administered prior to, during, or after surgery to control an acute bleeding episode.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding. Non limiting examples of bleeding episodes include a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, and any combinations thereof.

In prophylactic applications, one or more compositions containing the chimeric protein of the invention or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radio-immuno conjugates and higher doses for cytotoxin-drug modified polypeptides) at relatively short intervals is sometimes required until progression of the disease is reduced or terminated, and until the patient shows partial or complete amelioration of symptoms of disease. Thereafter, the patient can be administered a prophylactic regime.

In some embodiments, a chimeric protein or a composition of the invention is used for on-demand treatment, which includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, the chimeric protein of the present invention is administered intravenously, subcutaneously, intramuscularly, or via any mucosal surface, e.g., orally, sublingually, buccally, nasally, rectally, vaginally or via pulmonary route. The chimeric protein comprising a VWF fragment and a FVIII protein of the present invention can be implanted within or linked to a biopolymer solid support that allows for the slow release of the chimeric protein to the site of bleeding or implanted into bandage/dressing. The dose of the chimeric protein will vary depending on the subject and upon the particular route of administration used. Dosages can range from 0.1 to 100,000 μg/kg body weight. In one embodiment, the dosing range is 0.1-1,000 μg/kg. In another embodiment, the dosing range is 0.1-500 μg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay or ROTEM clotting assay. Additionally, effective doses may be extrapolated from dose-response curves obtained from animal models, e.g., a hemophiliac dog (Mount et al. 2002, *Blood* 99(8):2670).

Having now described the present invention in detail, the same will be more clearly understood by reference to the following examples, which are included herewith for purposes of illustration only and are not intended to be limiting of the invention. All patents, publications, and articles referred to herein are expressly and specifically incorporated herein by reference.

EXAMPLES

Throughout the examples, the following materials and methods were used unless otherwise stated.
Materials and Methods In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1

Cloning Different VWF Domains (FIGS. 1A-1D)

(a) Cloning of pSYN-VWF-002 pSYN-VWF-002 contains nucleotide sequences encoding a VWF fragment, which are amino acids 1-477 of SEQ ID NO: 100. [VWF-D'D3 protein sequence] Amino acid numbering represents the mature VWF sequence without propeptide and corresponds to amino acids 764-1240 of SEQ ID NO: 2. pSYN-VWF-002 construct has the FVIII signal peptide at N-terminus, which allows proper secretion of the synthesized protein and followed by a 6× His tag at C-terminus, which is used for protein purification. It was synthesized by using following primer combinations:

```
ESC48-Fwd-VWF-D'D3 with VIII signal and BsiW1 site
                                       (SEQ ID NO: 90)
TCGCGACGTACGGCCGCCACCATGCAAATAGAGCTCTCCACCTGCTTCTT

TCTGTGCCTTTTGCGATTCTGCTTTAGCCTATCCTGTCGGCCCCCCATG

ESC51-Rev-VWF D'D3 (1-477 amino acid) with 6His
and Not 1 site
                                       (SEQ ID NO: 91)
TGACCTCGAGCGGCCGCTCAGTGGTGATGGTGATGATGCGGCTCCTGGCA

GGCTTCACAGGTGAGGTTGACAAC
```

A 50 μl PCR reaction was carried out with ESC 48/ESC 51 primer combinations and full length VWF plasmid as the template, using the 2 step PCR amplification cycle: 94° C. 2 minutes; 21 cycles of (96° C. 30 seconds, 68° C. 2 minute). The 1460 bp band was gel purified with a Gel Extraction kit (Qiagen, Valencia, Calif.) and cloned into the BsiWI and Not1 restriction sites of pcDNA 4 to generate pSYN-VWF 002.

(b) Cloning of pSYN-VWF-010 and 013 pSYN-VWF-010 was constructed using pSYN-VWF-008 and pSYN-VWF-002. pSYN-VWF-008 contains the full-length VWF sequence in pcDNA 3.1 (amino acids 1-2813 of SEQ ID NO: 2), it includes 763 amino acid propeptide (i.e., D1D2 domains) followed by remaining 2050 amino acids sequence of mature VWF. The FVIII signal peptide in pSYN-VWF-002 was replaced with D1D2 domains from pSYN-VWF-008, the resulting construct is pSYN-VWF-010. pSYN-VWF-008 has a BamH1 site at Arg907 and Not1 site at the end of coding region (after stop codon). pSYN-VWF-008 and 002 were digested with BamH1 and Not1 restriction enzymes. Inserts from pSYN-VWF-002 (1026 bp) were ligated into bamH1/Not1 digested pSYN-VWF-008 (8242 bp) to obtain pSYN-VWF-010 (D1D2D'D3: amino acid 1-1240 of SEQ ID NO: 2), a 6× His tag was also added at the C-terminus. In transformed cells pSYN-VWF-010 is synthesized with propeptide but due to intracellular processing the secreted products do not contain any propeptide (D1D2). Protein from VWF-010 exists as dimer.

pSYN-VWF-010 was used to generate pSYN-VWF-013 which has two point mutations at C336A and C379A corresponding to SEQ ID NO: 100 (amino acid numbering represents mature VWF sequence without D1D2 domain-VWF sequence 2). These mutations are predicted to prevent dimerization of VWF D'D3 domain.

(c) Cloning of pSYN-VWF-025 and pSYN-VWF-029 pSYN-VWF-025 contains wild type D1D2D'D3 sequences of full-length VWF in pLIVE vector, and pSYN-VWF-029 contains D1D2D'D3 sequence with C336A and C379A mutation. For cloning pSYN-VWF-025, the following primer combination was used:

```
ESC 89-fwd with NheI site =
                                       (SEQ ID NO: 92)
CTCACTATAGGGAGACCCAAGCTGGCTAGCCG ESC 91-rev with SalI =
                                       (SEQ ID NO: 93)
CTGGATCCCGGGAGTCGACTCGTCAGTGGTGATGGTGATGATG
```

A 50 μl PCR reaction was carried out with ESC 89/ESC91 primer combinations and either pSYN-VWF 010 (for pSYN-VWF-025) or pSYN-VWF 013 (for pSYN-VWF- 029) plasmid as the template using the 3 step PCR amplification cycle: 94° C. 2 minutes; 21 cycles of (96° C.-30 seconds, 55° C.-30 second, 68° C.-4 minutes). The expected sized band (~3800 bp) was gel purified with a Gel Extraction kit (Qiagen, Valencia, Calif.) and cloned into the Nhe1 and Sal1 restriction sites of pLIVE-Mirus vector (Invitrogen, Carlsbad, Calif.) to generate pSYN-VWF 025 and 029.

(d) Cloning pSYN-VWF-031 pSYN-VWF-031 is a D1D2D'D3(C336A/C379A)-Fc construct which has a 48 amino acid long thrombin cleavable linker (8× GGGGS (SEQ ID NO 94)+thrombin site) in between the VWF D1D2D'D3(C336A/C379A) and the Fc sequences. To make this construct, VWF-Fc region was amplified from construct pSYN-FVIII-064 (refer FVIII-VWF construct below). pSYN-FVIII-VWF was digested with Xba1 and Nhe1. Resulting insert region of 4165 bp, containing the VWF fragment and Fc region was used as a template for amplifying the VWF and Fc region by primer combinations LW 22/LW23.

```
LW 22-FWD-VWF-D'D3 with FVIII signal sequence and
BsiW1 site
                                        (SEQ ID NO: 95)
GCGCCGGCCGTACGATGCAAATAGAGCTCTCCACCTGCTTCTTTCTGTGC

CTTTTGCGATTCTGCTTTAGCCTATCCTGTCGGCCCCCCATG
```

```
LW 23-Rev-Fc with stop codon and Not1 site
                                        (SEQ ID NO: 96)
TCATCAATGTATCTTATCATGTCTGAATTCGCGGCCGCTCATTTACC
```

The PCR product obtained from LW22/LW23 amplification (~2300 bp) was cloned in BsiW1/Not1 digested pSYN-VWF-002 to obtain pSYN-VWF-014 intermediate. pSYN-VWF-014 contains FVIII signal peptide-D'D3-20 amino acid thrombin cleavable linker followed by the Fc region.

To generate the D1D2D'D3-Fc construct, the D1D2D'D3 region was amplified from pSYN-VWF-013 using primer combination LW24/LW27 by standard PCR method.

```
LW24-Fwd-VWF D1D2D'D3 cloning oligo with BsiW1
site
                                        (SEQ ID NO: 97)
GCGCCGGCCGTACGATGATTCCTGCCAGATTTGCCGGGGTG
```

```
LW27-Rev-VWF D'D3 oligo with EcoRV
                                        (SEQ ID NO: 98)
CCACCGCCAGATATCGGCTCCTGGCAGGCTTCACAGGTGAG
```

The PCR product obtained from LW22/LW23 amplification (~3750 bp) was cloned in BsiW1/EcoRV digested pSYN-VWF-014 to obtain pSYN-VWF-015 intermediate. The linker length between the VWF fragment and Fc region was changed to obtain pSYN-VWF-031.

```
VWF-D1D2D'D3 protein sequence 1
                                        (SEQ ID NO: 99)
   1 MIPARFAGVL LALALILPGT LCAEGTRGRS STARCSLFGS DFVNTFDGSM

51 YSFAGYCSYL LAGGCQKRSF SIIGDFQNGK RVSLSVYLGE FFDIHLFVNG

101 TVTQGDQRVS MPYASKGLYL ETEAGYYKLS GEAYGFVARI DGSGNFQVLL

151 SDRYFNKTCG LCGNFNIFAE DDFMTQEGTL TSDPYDFANS WALSSGEQWC

201 ERASPPSSSC NISSGEMQKG LWEQCQLLKS TSVFARCHPL VDPEPFVALC

251 EKTLCECAGG LECACPALLE YARTCAQEGM VLYGWTDHSA CSPVCPAGME

301 YRQCVSPCAR TCQSLHINEM CQERCVDGCS CPEGQLLDEG LCVESTECPC

351 VHSGKRYPPG TSLSRDCNTC ICRNSQWICS NEECPGECLV TGQSHFKSFD

401 NRYFTFSGIC QYLLARDCQD HSFSIVIETV QCADDRDAVC TRSVTVRLPG

451 LHNSLVKLKH GAGVAMDGQD IQLPLLKGDL RIQHTVTASV RLSYGEDLQM

501 DWDGRGRLLV KLSPVYAGKT CGLCGNYNGN QGDDFLTPSG LAEPRVEDFG

551 NAWKLHGDCQ DLQKQHSDPC ALNPRMTRFS EEACAVLTSP TFEACHRAVS

601 PLPYLRNCRY DVCSCSDGRE CLCGALASYA AACAGRGVRV AWREPGRCEL

651 NCPKGQVYLQ CGTPCNLTCR SLSYPDEECN EACLEGCFCP PGLYMDERGD

701 CVPKAQCPCY YDGEIFQPED IFSDHHTMCY CEDGFMHCTM SGVPGSLLPD

751 AVLSSPLSHR SKRSLSCRPP MVKLVCPADN LRAEGLECTK TCQNYDLECM

801 SMGCVSGCLC PPGMVRHENR CVALERCPCF HQGKEYAPGE TVKIGCNTCV

851 CRDRKWNCTD HVCDATCSTI GMAHYLTFDG LKYLFPGECQ YVLVQDYCGS

901 NPGTFRILVG NKGCSHPSVK CKKRVTILVE GGEIELFDGE VNVKRPMKDE

951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

1051 MKQTMVDSSC RILTSDVFQD CNKLVDPEPY LDVCIYDTCS CESIGDCACF
```

-continued
```
1101 CDTIAAYAHV CAQHGKVVTW RTATLCPQSC EERNLRENGY ECEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP*

VWF-D'D3 protein sequence 2
                                                (SEQ ID NO: 100)
  1 SLSCRPPMVK LVCPADNLRA EGLECTKTCQ NYDLECMSMG CVSGCLCPPG

51 MVRHENRCVA LERCPCFHQG KEYAPGETVK IGCNTCVCRD RKWNCTDHVC

101 DATCSTIGMA HYLTFDGLKY LFPGECQYVL VQDYCGSNPG TFRILVGNKG

151 CSHPSVKCKK RVTILVEGGE IELFDGEVNV KRPMKDETHF EVVESGRYII

201 LLLGKALSVV WDRHLSISVV LKQTYQEKVC GLCGNFDGIQ NNDLTSSNLQ

251 VEEDPVDFGN SWKVSSQCAD TRKVPLDSSP ATCHNNIMKQ TMVDSSCRIL

301 TSDVFQDCNK LVDPEPYLDV CIYDTCSCES IGDCACFCDT IAAYAHVCAQ

351 HGKVVTWRTA TLCPQSCEER NLRENGYECE WRYNSCAPAC QVTCQHPEPL

401 ACPVQCVEGC HAHCPPGKIL DELLQTCVDP EDCPVCEVAG RRFASGKKVT

451 LNPSDPEHCQ ICHCDVVNLT CEACQEP
```

Example 2

Effects of D'D3 and XTEN Fusion on FVIII Half-Life Extension

To evaluate D'D3 FVIII half-life extension potential on rFVIII-XTEN fusion protein, a VWF D'D3 dimer was introduced into FVIII-VWF DKO mice by hydrodynamic injection of its corresponding DNA construct VWF-025 (Example 1). After D'D3 has reached the steady state expression (day 5 post injection), a single dose of rFVIII-XTEN was administered by IV injection at 200 IU/kg dose. Blood samples were collected up to 120 hrs post rFVIII-XTEN dosing. Plasma FVIII activity was analyzed by a FVIII chromogenic assay. The D'D3 expression level was measured by VWF ELISA, and rFVIIIFc PK profile was analyzed using WinNonlin program.

The study results were shown in FIGS. 2A-2C, and the PK parameter of rFVIII-XTEN with/without D'D3 in circulation was listed in Table 16. The D'D3 dimer further extended rFIII-XTEN $t_{1/2}$ from 3.4 hr to 17.8 hr, a 5 fold increase. In addition to half-life, 5 fold of increase on MRT, 3.6 fold increases on AUC, 3.8 fold decreases on clearance were also observed.

We have observed a synergistic effect of D'D3 fragment and XTEN technology, a serial of FVIII/VWF/XTEN constructs will be evaluated for their FVIII half-life extension potential in Hemophilic animals.

TABLE 16 rFVIII-XTEN PK parameter with/without D'D3 in blood circulation

| Treatment | 5 min Recovery (%) | $t_{1/2}$ (hr) | MRT (hr) | Cl (mL/hr/kg) | Vss (mL/kg) | AUC_D (hr*kg*mIU/mL/mIU) |
|---|---|---|---|---|---|---|
| rFVIIIXTEN VWF-025 | 80 | 17.8 | 19.3 | 3.5 | 67.4 | 0.29 |
| rFVIIIXTEN | 74 | 3.4 | 3.8 | 13.1 | 63.68 | 0.08 |
| Improvement fold | 1.1 | 5.2 | 5.1 | 3.8 | 0.9 | 3.6 |

Protein Purification of FVIII-XTEN

An AE288 XTEN was inserted at the C-terminus of BDD-FVIII for this study. To purify this protein, a tangential flow filtration (TFF) step was used first to buffer exchange the conditioned media. Products in the filtrate were then captured using a strong anion exchange chromatography, and then further purified using affinity chromatography. Purity of the molecule was acceptable by HPLC-SEC and was further confirmed by western blotting. The specific activity of the molecule was comparable to B-domain deleted FVIII, as measured by aPTT assay and ELISA.

FVIII Chromogenic Assay

The FVIII activity was measured using the COATEST SP FVIII kit from DiaPharma (lot #N089019) and all incubations were performed on a 37° C. plate heater with shaking.

The range of rFVIII standard was from 100 mIU/mL to 0.78 mIU/mL. A pooled normal human plasma assay control and plasma samples (diluted with 1× Coatest buffer) were added into Immulon 2HB 96-well plates in duplicate (25 μL/well). Freshly prepared IXa/FX/Phospholipid mix (50 μL), 25 μL of 25 mM CaCl2, and 50 μL of FXa substrate were added sequentially into each well with 5 minutes incubation between each addition. After incubating with the substrate, 25 μL of 20% Acetic Acid was added to terminate the color reaction, and the absorbance of OD405 was measured with a SpectraMAX plus (Molecular Devices) instrument. Data were analyzed with SoftMax Pro software (version 5.2). The Lowest Level of Quantification (LLOQ) is 7.8 mIU/mL.

VWF ELISA:

Goat anti-human VWF antibody (Affinity purified, affinity biological, GAVWF-AP) was used as the capture antibody at 0.5 ug/well and VWF-EIA-D (Affinity Biologicals, VWF-EIA-D, 1:100 dilution) was used as the detecting antibody for the VWF ELISA. ELISA assay was performed following the standard ELISA procedure, TMB was used as the HRP substrate, PBST/1.5% BSA/0.5M NaCl buffer was used as blocking and binding buffer. The assay standard range is 100 ng to 0.78 ng, and assay's lowest limit of quantification (LLOQ) is 7.8 ng/mL.

Example 3

Plasmid Construction of XTEN Containing FVIII/VWF Constructs (a) Cloning of pSYN-FVIII-161 (FIG. 3)

The FVIII-161 plasmid comprises a single chain Fc (scFc) scaffold with enzyme cleavage sites which are processed during synthesis in a cell. The construct has a FVIII binding domain of full-length VWF (D'D3).

Plasmid (pSYN-FVIII-161) was designed for the expression FVIII-Fc and VWF-Fc heterodimer, where the D'D3 domains to bind FVIII and prevents FVIII interaction with phospholipids and activated protein C. Protein from pSYN-FVIII-161 is expressed in the cell as a single polypeptide where the C-terminus of the FVIII-Fc subunit is linked to the N-terminus of the VWF D'D3-Fc subunit by a 6× (GGGGS) polypeptide linker (SEQ ID NO: 64). In addition, RRRRS (SEQ ID NO: 11) and RKRRKR (SEQ ID NO: 10) sequences were inserted at the 5' and 3' end of the polypeptide linker, respectively, for intracellular cleavage by pro-protein convertases following the last Arg at each sequence. Hence, the cells can express a double chain FVIII-Fc/D'D3-Fc heterodimer where the FVIII-Fc chain has a RRRRS sequence (SEQ ID NO: 11) at the C-terminus, but the remainder of the linker sequence has been removed. An AE288 XTEN fragment immediately followed by IS{5X (GGGGS)}LVPRGSGG (SEQ ID NO: 122) polypeptide (contains thrombin cleavage site) is introduced in between the VWF domains and the Fc region to facilitate release of the VWF fragment from FVIII once the FVIII-VWF heterodimeric protein is activated by thrombin allowing interaction of FVIII with other clotting factors.

pSYN-FVIII-161 (SEQ ID NO: 101).protein sequence (FVIII sequence amino acid position 1-1457; underlined region represents Fc region; curvy underline represents cleavable linker in between first Fc and VWF fragment; double underlined region represents VWF fragment; bold region represents cleavable linker in between VWF fragment and Fc.

```
pSYN-FVIII-161 (SEQ ID NO: 101). protein sequence (FVIII sequence
amino acid position 1-1457; underlined region represents Fc region; curvy
underline represents cleavable linker in between first Fc and VWF fragment;
double underlined region represents VWF fragment; bold region represents
cleavable linker in between VWF fragment and Fc.
   1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNPPVLKR HQREITRTIL QSDQEEIDYD DTISVEMKKE

801 DFDIYDEDEN QSPRSFQKKT RHYFIAAVER LWDYGMSSSP HVLRNRAQSG

851 SVPQFKKVVF QEFTDGSFTQ PLYRGELNEH LGLLGPYIRA EVEDNIMVTF

901 RNQASRPYSF YSSLISYEED QRQGAEPRKN FVKPNETKTY FWKVQHHMAP

951 TKDEFDCKAW AYFSDVDLEK DVHSGLIGPL LVCHTNTLNP AHGRQVTVQE

1001 FALFFTIFDE TKSWYFTENM ERNCRAPCNI QMEDPTFKEN YRFHAINGYI

1051 MDTLPGLVMA QDQRIRWYLL SMGSNENIHS IHFSGHVFTV RKKEEYKMAL

1101 YNLYPGVFET VEMLPSKAGI WRVECLIGEH LHAGMSTLFL VYSNKCQTPL

1151 GMASGHIRDF QITASGQYGQ WAPKLARLHY SGSINAWSTK EPFSWIKVDL

1201 LAPMIIHGIK TQGARQKFSS LYISQFIIMY SLDGKKWQTY RGNSTGTLMV
```

```
                           -continued
1251 FFGNVDSSGI KHNIFNPPII ARYIRLHPTH YSIRSTLRME LMGCDLNSCS

1301 MPLGMESKAI SDAQITASSY FTNMFATWSP SKARLHLQGR SNAWRPQVNN

1351 PKEWLQVDFQ KTMKVTGVTT QGVKSLLTSM YVKEFLISSS QDGHQWTLFF

1401 QNGKVKVFQG NQDSFTPVVN SLDPPLLTRY LRIHPQSWVH QIALRMEVLG

1451 CEAQDLYDKT HTCPPCPAPE LLGGPSVFLF PPKPKDTLMI SRTPEVTCVV

1501 VDVSHEDPEV KFNWYVDGVE VHNAKTKPRE EQYNSTYRVV SVLTVLHQDW

1551 LNGKEYKCKV SNKALPAPIE KTISKAKGQP REPQVYTLPP SRDELTKNQV

1601 SLTCLVKGFY PSDIAVEWES NGQPENNYKT TPPVLDSDGS FFLYSKLTVD

1651 KSRWQQGNVF SCSVMHEALH NHYTQKSLSL SPGKRRRRSG GGGSGGGGSG

1701 GGGSGGGGSG GGGSGGGGSR KRRKRSLSCR PPMVKLVCPA DNLRAEGLEC

1751 TKTCQNYDLE CMSMGCVSGC LCPPGMVRHE NRCVALERCP CFHQGKEYAP

1801 GETVKIGCNT CVCRDRKWNC TDHVCDATCS TIGMAHYLTF DGLKYLFPGE

1851 CQYVLVQDYC GSNPGTFRIL VGNKGCSHPS VKCKKRVTIL VEGGEIELFD

1901 GEVNVKRPMK DETHFEVVES GRYIILLLGK ALSVVWDRHL SISVVLKQTY

1951 QEKVCGLCGN FDGIQNNDLT SSNLQVEEDP VDFGNSWKVS SQCADTRKVP

2001 LDSSPATCHN NIMKQTMVDS SCRILTSDVF QDCNKLVDPE PYLDVCIYDT

2051 CSCESIGDCA AFCDTIAAYA HVCAQHGKVV TWRIATLCPQ SCEERNLREN

2101 GYEAEWRYNS CAPACQVTCQ HPEPLACPVQ CVEGCHAHCP PGKILDELLQ

2151 TCVDPEDCPV CEVAGRRFAS GKKVTLNPSD PEHCQICHCD VVNLICEACQ

2201 EPISGTSESA TPESGPGSEP ATSGSETPGT SESATPESGP GSEPATSGSE

2251 TPGTSESATP ESGPGTSTEP SEGSAPGSPA GSPTSTEEGT SESATPESGP

2301 GSEPATSGSE TPGTSESATP ESGPGSPAGS PTSTEEGSPA GSPTSTEEGT

2351 STEPSEGSAP GTSESATPES GPGTSESATP ESGPGTSESA TPESGPGSEP

2401 ATSGSETPGS EPATSGSETP GSPAGSPTST EEGTSTEPSE GSAPGTSTEP

2451 SEGSAPGSEP ATSGSETPGT SESATPESGP GTSTEPSEGS APDSGGGGSG

2501 GGGSGGGGSG GGGSGGGGSL VPRGSGGDKT HTCPPCPAPE LLGGPSVFLF

2551 PPKPKDTLMI SRTPEVTCVV VDVSHEDPEV KFNWYVDGVE VHNAKTKPRE

2601 EQYNSTYRVV SVLTVLHQDW LNGKEYKCKV SNKALPAPIE KTISKAKGQP

2651 REPQVYTLPP SRDELTKNQV SLTCLVKGFY PSDIAVEWES NGQPENNYKT

2701 TPPVLDSDGS FFLYSKLTVD KSRWQQGNVF SCSVMHEALH NHYTQKSLSL

2751 SPGK
```

(b) Cloning of pSYN-FVIII-168, 175, 172 and 174 (FIGS. 4A-4D)

pSYN-FVIII-168, 172, 174 and 175 are derivatives of pSYN-FVIII-161. R1645A/R1648A mutations were introduced into pSYN-FVIII-161 to form pSYN-FVIII-168, which produces a SC-FVIII isoform, and an AE288 XTEN was directly fused into the C-terminus of FVIII-HC for further half-life extension. To construct pSYN-FVIII-175, the D'D3 codon sequence was remove form pSYN-FVIII-168 for evaluation of the effect of Fc and XTEN technology on FVIII half-life extension.

To construct pSYN-FVIII-172, the AE288 XTEN fragment was directly fused into the C-terminus of FVIII-HC for further half-life extension, and the D'D3 codon sequence was removed from pSYN-FVIII-172 to form pSYN-FVIII-174 for evaluation of the effect of Fc and XTEN technology on FVIII half-life extension.

(c) Cloning of pSYN-FVIII-170 (FIG. 4E)

pSYN-FVIII-170 was constructed to evaluate the effect of XTEN and D'D3 fragment on FVIII half-life extension. The codon sequence VWF-D1D2D'D3 fragment and BDD-FVIII were introduced into the 5' and 3' end of expression casket, an AE288 XTEN codon sequence which followed by a 35 aa thrombin cleavable linker was used to connect the VWF and FVIII molecule. After intra cellular processing, the secreted protein comprises a polypeptide contains the D'D3 fragment of mature VWF molecule which is linked to the N-terminus of mature BDD-FVIII by an AE288 XTEN/35 aa thrombin cleavable linker.

pSYN-FVIII-170 protein sequence (SEQ ID NO: 102)

```
   1 SLSCRPPMVK LVCPADNLRA EGLECTKTCQ NYDLECMSMG CVSGCLCPPG
  51 MVRHENRCVA LERCPCFHQG KEYAPGETVK IGCNTCVCRD RKWNCTDHVC
 101 DATCSTIGMA HYLTFDGLKY LFPGECQYVL VQDYCGSNPG TFRILVGNKG
 151 CSHPSVKCKK RVTILVEGGE IELFDGEVNV KRPMKDETHF EVVESGRYII
 201 LLLGKALSVV WDRHLSISVV LKQTYQEKVC GLCGNFDGIQ NNDLTSSNLQ
 251 VEEDPVDFGN SWKVSSQCAD TRKVPLDSSP ATCHNNIMKQ TMVDSSCRIL
 301 TSDVFQDCNK LVDPEPYLDV CIYDTCSCES IGDCAAFCDT IAAYAHVCAQ
 351 HGKVVTWRTA TLCPQSCEER NLRENGYEAE WRYNSCAPAC QVTCQHPEPL
 401 ACPVQCVEGC HAHCPPGKIL DELLQTCVDP EDCPVCEVAG RRFASGKKVT
 451 LNPSDPEHCQ ICHCDVVNLT CEACQEPISG TSESATPESG PGSEPATSGS
 501 ETPGTSESAT PESGPGSEPA TSGSETPGTS ESATPESGPG TSTEPSEGSA
 551 PGSPAGSPTS TEEGTSESAT PESGPGSEPA TSGSETPGTS ESATPESGPG
 601 SPAGSPTSTE EGSPAGSPTS TEEGTSTEPS EGSAPGTSES ATPESGPGTS
 651 ESATPESGPG TSESATPESG PGSEPATSGS ETPGSEPATS GSETPGSPAG
 701 SPTSTEEGTS TEPSEGSAPG TSTEPSEGSA PGSEPATSGS ETPGTSESAT
 751 PESGPGTSTE PSEGSAPDSG GGGSGGGGSG GGGSGGGGSG GGGSLVPRGS
 801 GGASATRRYY LGAVELSWDY MQSDLGELPV DARFPPRVPK SFPFNTSVVY
 851 KKTLFVEFTD HLFNIAKPRP PWMGLLGPTI QAEVYDTVVI TLKNMASHPV
 901 SLHAVGVSYW KASEGAEYDD QTSQREKEDD KVFPGGSHTY VWQVLKENGP
 951 MASDPLCLTY SYLSHVDLVK DLNSGLIGAL LVCREGSLAK EKTQTLHKFI
1001 LLFAVFDEGK SWHSETKNSL MQDRDAASAR AWPKMHTVNG YVNRSLPGLI
1051 GCHRKSVYWH VIGMGTTPEV HSIFLEGHTF LVRNHRQASL EISPITFLTA
1101 QTLLMDLGQF LLFCHISSHQ HDGMEAYVKV DSCPEEPQLR MKNNEEAEDY
1151 DDDLTDSEMD VVRFDDDNSP SFIQIRSVAK KHPKTWVHYI AAEEEDWDYA
1201 PLVLAPDDRS YKSQYLNNGP QRIGRKYKKV RFMAYTDETF KTREAIQHES
1251 GILGPLLYGE VGDTLLIIFK NQASRPYNIY PHGITDVRPL YSRRLPKGVK
1301 HLKDFPILPG EIFKYKWTVT VEDGPTKSDP RCLTRYYSSF VNMERDLASG
1351 LIGPLLICYK ESVDQRGNQI MSDKRNVILF SVFDENRSWY LTENIQRFLP
1401 NPAGVQLEDP EFQASNIMHS INGYVFDSLQ LSVCLHEVAY WYILSIGAQT
1451 DFLSVFFSGY TFKHKMVYED TLTLFPFSGE TVFMSMENPG LWILGCHNSD
1501 FRNRGMTALL KVSSCDKNTG DYYEDSYEDI SAYLLSKNNA IEPRSFSQNP
1551 PVLKRHQREI TRTTLQSDQE EIDYDDTISV EMKKEDFDIY DEDENQSPRS
1601 FQKKTRHYFI AAVERLWDYG MSSSPHVLRN RAQSGSVPQF KKVVFQEFTD
1651 GSFTQPLYRG ELNEHLGLLG PYIRAEVEDN IMVTFRNQAS RPYSFYSSLI
1701 SYEEDQRQGA EPRKNPVKPN ETKTYFWKVQ HHMAPTKDEF DCKAWAYFSD
1751 VDLEKDVHSG LIGPLLVCHT NTLNPAHGRQ VTVQEFALFF TIFDETKSWY
1801 FTENMERNCR APCNIQMEDP TFKENYRFHA INGYIMDTLP GLVMAQDQRI
1851 RWYLLSMGSN ENIHSIHFSG HVFTVRKKEE YKMALYNLYP GVFETVEMLP
1901 SKAGIWRVEC LIGEHLHAGM STLFLVYSNK CQTPLGMASG HIRDFQITAS
1951 GQYGQWAPKL ARLHYSGSIN AWSTKEPFSW IKVDLLAPMI IHGIKTQGAR
```

-continued

```
2001 QKFSSLYISQ FIIMYSLDGK KWQTYRGNST GTLMVFFGNV DSSGIKHNIF

2051 NPPIIARYIR LHPTHYSIRS TLRMELMGCD LNSCSMPLGM ESKAISDAQI

2101 TASSYFTNMF ATWSPSKARL HLQGRSNAWR PQVNNPKEWL QVDFQKTMKV

2151 TGVTTQGVKS LLTSMYVKEF LISSSQDGHQ WTLFFQNGKV KVFQGNQDSF

2201 TPVVNSLDPP LLTRYLRIHP QSWVHQIALR MEVLGCEAQD LY
```

Example 4

Hydrodynamic Injection of XTEN Containing FVIIIF/VWF Constructs in FVIII and VWF Deficient Mice The XTEN containing DNA constructs in FIGS. 3 and 4A-4E have combined 2-3 half-life extension elements together. To evaluate their FVIII half-life extension potential, a selective group of DNA constructs in FIGS. 3 and 4A-4E were introduced into FVIII/VWF double knockout (DKO) mice by Hydrodynamic injection (HDI) at 100 ug/mouse dose. Blood samples were then collected by retro orbital blood collection at 24 hr post HDI. The post HDI plasma FVIII activity was analyzed by FVIII chromogenic assay, and results were listed in Table 17 and FIG. 5. Compared to wild type BDD-FVIII, all XTEN containing DNA constructs yield significantly higher FVIII plasma activity at 24 hr post HDI, indicating the corresponding molecules had significant longer circulating protein half-life than BDD-FVIII. The application of the combination of those half-life extending elements was further evaluated in Hemophilic animals.

TABLE 17

FVIII plasma activity 24 hr post HDI in FVIII/VWF DKO mice

| DNA Construct | BDD-FVIII | FVIII-161 | FVIII-168 | FVIII-172 | BDD-FVIII | FVIII-170 |
|---|---|---|---|---|---|---|
| DNA Dose (µg/mouse) | 100 | 100 | 100 | 100 | 50 | 50 |
| FVIII Activity (mU/mL) | 219 ± 72 | 2446 ± 1012 | 2209 ± 609 | 1671 ± 223 | 197 ± 21 | 399 ± 30 |

Hydrodynamic Injection:

Hydrodynamic Injection is an efficient and safe non-viral gene delivery method to the liver in small animals, such as mice and rats. It was originally described as a rapid injection of a naked plasmid DNA/saline solution free of endotoxin at a tenth volume of the animal's body weight in about 5-7 seconds. The naked plasmid DNA contains the gene of interest and the liver produced in a tenth volume of the animal's body weight. The targeted protein is produced in the liver from the injected DNA and can be detected within 24 hours post-injection. Plasma samples were then collected to study the therapeutic property of the expressed protein.

For all the hydrodynamic injections that were performed herein, 2 ml of plasmid DNA in 0.9% sterile saline solution was delivered via intravenous tail vein injection within about 4-7 seconds to mice weighing 20-35 grams. The mice were closely monitored for the first couple of hours until the normal activity resumed. After the blood samples were collected via retro orbital blood collection, plasma samples were then obtained and stored at −80° C. for further analysis.

Example 5

Plasmid Construction of Co-Transfection System for FVIIIFc-VWF Heterodimer Contain XTEN Insertions (FIGS. 6A-6B)

To increase the protein production yield, two co-transfection systems were generated for protein production, which contains three DNA constructs. The first DNA construct encoded a FVIII-Fc fusion protein in which a AE288 XTEN fragment was directly fuse to the C-terminus of the FVIII heavy chain and followed by either a wild type FVIII light chain fragment (pSYN-FVIII-173, FIG. 6B) or a FVIII light chain fragment with R1645A/R1648A mutations (pSYN-FVIII-169, FIG. 6A), the FVIII light chain was then directly fused to a single Fc fragment. The second DNA construct is pSYN-VWF-031 which encoding a D'D3-Fc fusion protein (Example 1). HEK293F cells were transfected with the two plasmid along with a third plasmid (PC5) at 80:15:5 ratio. The synthesized proteins were secreted as FVIII (XTEN) Fc/D'D3Fc heterodimer and D'D3Fc dimer and the FVIII (XTEN) Fc/D'D3Fc heterodimer was separated from the D'D3Fc dimer by protein purification.

```
pSYN-FVIII-169 mature Protein sequence (SEQ ID NO: 103):
  1 ATRRYYLGAV ELSWDYMQSD LGELPVDARF PPRVPKSFPF NTSVVYKKTL

51 FVEFTDHLFN IAKPRPPWMG LLGPTIQAEV YDTVVITLKN MASHPVSLHA

101 VGVSYWKASE GAEYDDQTSQ REKEDDKVFP GGSHTYVWQV LKENGPMASD

151 PLCLTYSYLS HVDLVKDLNS GLIGALLVCR EGSLAKEKTQ TLHKFILLFA

201 VFDEGKSWHS ETKNSLMQDR DAASARAWPK MHTVNGYVNR SLPGLIGCHR

251 KSVYWHVIGM GTTPEVHSIF LEGHTFLVRN HRQASLEISP ITFLTAQTLL

301 MDLGQFLLFC HISSHQHDGM EAYVKVDSCP EEPQLRMKNN EEAEDYDDDL

351 TDSEMDVVRF DDDNSPSFIQ IRSVAKKHPK TWVHYIAAEE EDWDYAPLVL
```

-continued

```
 401 APDDRSYKSQ YLNNGPQRIG RKYKKVRFMA YTDETFKTRE AIQHESGILG

451 PLLYGEVGDT LLIIFKNQAS RPYNIYPHGI TDVRPLYSRR LPKGVKHLKD

501 FPILPGEIFK YKWTVTVEDG PTKSDPRCLT RYYSSFVNME RDLASGLIGP

551 LLICYKESVD QRGNQIMSDK RNVILFSVFD ENRSWYLTEN IQRFLPNPAG

601 VQLEDPEFQA SNIMHSINGY VFDSLQLSVC LHEVAYWYIL SIGAQTDFLS

651 VFFSGYTFKH KMVYEDTLTL FPFSGETVFM SMENPGLWIL GCHNSDFRNR

701 GMTALLKVSS CDKNTGDYYE DSYEDISAYL LSKNNAIEPR SFSQNGAPGT

751 SESATPESGP GSEPATSGSE TPGTSESATP ESGPGSEPAT SGSETPGTSE

801 SATPESGPGT STEPSEGSAP GSPAGSPTST EEGTSESATP ESGPGSEPAT

851 SGSETPGTSE SATPESGPGS PAGSPTSTEE GSPAGSPTST EEGTSTEPSE

901 GSAPGTSESA TPESGPGTSE SATPESGPGT SESATPESGP GSEPATSGSE

951 TPGSEPATSG SETPGSPAGS PTSTEEGTST EPSEGSAPGT STEPSEGSAP

1001 GSEPATSGSE TPGTSESATP ESGPGTSTEP SEGSAPASSP PVLKRHQAEI

1051 TRTTLQSDQE EIDYDDTISV EMKKEDFDIY DEDENQSPRS FQKKTRHYFI

1101 AAVERLWDYG MSSSPHVLRN RAQSGSVPQF KKVVFQEFTD GSFTQPLYRG

1151 ELNEHLGLLG PYIRAEVEDN IMVTFRNQAS RPYSFYSSLI SYEEDQRQGA

1201 EPRKNFVKPN ETKTYFWKVQ HHMAPTKDEF DCKAWAYFSD VDLEKDVHSG

1251 LIGPLLVCHT NTLNPAHGRQ VTVQEFALFF TIFDETKSWY FTENMERNCR

1301 APCNIQMEDP TFKENYRFHA INGYIMDTLP GLVMAQDQRI RWYLLSMGSN

1351 ENIHSIHFSG HVFTVRKKEE YKMALYNLYP GVFETVEMLP SKAGIWRVEC

1401 LIGEHLHAGM STLFLVYSNK CQTPLGMASG HIRDFQITAS GQYGQWAPKL

1451 ARLHYSGSIN AWSTKEPFSW IKVDLLAPMI IHGIKTQGAR QKFSSLYISQ

1501 FIIMYSLDGK KWQTYRGNST GTLMVFFGNV DSSGIKHNIF NPPIIARYIR

1551 LHPTHYSIRS TLRMELMGCD LNSCSMPLGM ESKAISDAQI TASSYFTNMF

1601 ATWSPSKARL HLQGRSNAWR PQVNNPKEWL QVDFQKTMKV TGVTTQGVKS

1651 LLTSMYVKEF LISSSQDGHQ WTLFFQNGKV KVFQGNQDSF TPVVNSLDPP

1701 LLTRYLRIHP QSWVHQIALR MEVLGCEAQD LYDKTHTCPP CPAPELLGGP

1751 SVFLFPPKPK DTLMISRTPE VTCVVVDVSH EDPEVKFNWY VDGVEVHNAK

1801 TKPREEQYNS TYRVVSVLTV LHQDWLNGKE YKCKVSNKAL PAPIEKTISK

1851 AKGQPREPQV YTLPPSRDEL TKNQVSLTCL VKGFYPSDIA VEWESNGQPE

1901 NNYKTTPPVL DSDGSFFLYS KLTVDKSRWQ QGNVFSCSVM HEALHNHYTQ

1951 KSLSLSPGK
``` pSYN-FVIII-173 mature Protein sequencing (SEQ ID NO: 104):

```
   1 ATRRYYLGAV ELSWDYMQSD LGELPVDARF PPRVPKSFPF NTSVVYKKTL

51 FVEFTDHLFN IAKPRPPWMG LLGPTIQAEV YDTVVITLKN MASHPVSLHA

101 VGVSYWKASE GAEYDDQTSQ REKEDDKVFP GGSHTYVWQV LKENGPMASD

151 PLCLTYSYLS HVDLVKDLNS GLIGALLVCR EGSLAKEKTQ TLHKFILLFA

201 VFDEGKSWHS ETKNSLMQDR DAASARAWPK MHTVNGYVNR SLPGLIGCHR

251 KSVYWHVIGM GTTPEVHSIF LEGHTFLVRN HRQASLEISP ITFLTAQTLL

301 MDLGQFLLFC HISSHQHDGM EAYVKVDSCP EEPQLRMKNN EEAEDYDDDL

351 TDSEMDVVRF DDDNSPSFIQ IRSVAKKHPK TWVHYIAAEE EDWDYAPLVL
```

-continued

```
 401 APDDRSYKSQ YLNNGPQRIG RKYKKVRFMA YTDETFKTRE AIQHESGILG

451 PLLYGEVGDT LLIIFKNQAS RPYNIYPHGI TDVRPLYSRR LPKGVKHLKD

501 FPILPGEIFK YKWTVTVEDG PTKSDPRCLT RYYSSFVNME RDLASGLIGP

551 LLICYKESVD QRGNQIMSDK RNVILFSVFD ENRSWYLTEN IQRFLPNPAG

601 VQLEDPEFQA SNIMHSINGY VFDSLQLSVC LHEVAYWYIL SIGAQTDFLS

651 VFFSGYTFKH KMVYEDTLTL FPFSGETVFM SMENPGLWIL GCHNSDFRNR

701 GMTALLKVSS CDKNTGDYYE DSYEDISAYL LSKNNAIEPR SFSQNGAPGT

751 SESATPESGP GSEPATSGSE TPGTSESATP ESGPGSEPAT SGSETPGTSE

801 SATPESGPGT STEPSEGSAP GSPAGSPTST EEGTSESATP ESGPGSEPAT

851 SGSETPGTSE SATPESGPGS PAGSPTSTEE GSPAGSPTST EEGTSTEPSE

901 GSAPGTSESA TPESGPGTSE SATPESGPGT SESATPESGP GSEPATSGSE

951 TPGSEPATSG SETPGSPAGS PTSTEEGTST EPSEGSAPGT STEPSEGSAP

1001 GSEPATSGSE TPGTSESATP ESGPGTSTEP SEGSAPASSP PVLKRHQREI

1051 TRTTLQSDQE EIDYDDTISV EMKKEDFDIY DEDENQSPRS FQKKTRHYFI

1101 AAVERLWDYG MSSSPHVLRN RAQSGSVPQF KKVVFQEFTD GSFTQPLYRG

1151 ELNEHLGLLG PYIRAEVEDN IMVTFRNQAS RPYSFYSSLI SYEEDQRQGA

1201 EPRKNFVKPN ETKTYFWKVQ HHMAPTKDEF DCKAWAYFSD VDLEKDVHSG

1251 LIGPLLVCHT NTLNPAHGRQ VTVQEFALFF TIFDETKSWY FTENMERNCR

1301 APCNIQMEDP TFKENYRFHA INGYIMDTLP GLVMAQDQRI RWYLLSMGSN

1351 ENIHSIHFSG HVFTVRKKEE YKMALYNLYP GVFETVEMLP SKAGIWRVEC

1401 LIGEHLHAGM STLFLVYSNK CQTPLGMASG HIRDFQITAS GQYGQWAPKL

1451 ARLHYSGSIN AWSTKEPFSW IKVDLLAPMI IHGIKTQGAR QKFSSLYISQ

1501 FIIMYSLDGK KWQTYRGNST GTLMVFFGNV DSSGIKHNIF NPPIIARYIR

1551 LHPTHYSIRS TLRMELMGCD LNSCSMPLGM ESKAISDAQI TASSYFTNMF

1601 ATWSPSKARL HLQGRSNAWR PQVNNPKEWL QVDFQKTMKV TGVTTQGVKS

1651 LLTSMYVKEF LISSSQDGHQ WTLFFQNGKV KVFQGNQDSF TPVVNSLDPP

1701 LLTRYLRIHP QSWVHQIALR MEVLGCEAQD LYDKTHTCPP CPAPELLGGP

1751 SVFLFPPKPK DTLMISRTPE VTCVVVDVSH EDPEVKFNWY VDGVEVHNAK

1801 TKPREEQYNS TYRVVSVLTV LHQDWLNGKE YKCKVSNKAL PAPIEKTISK

1851 AKGQPREPQV YTLPPSRDEL TKNQVSLTCL VKGFYPSDIA VEWESNGQPE

1901 NNYKTTPPVL DSDGSFFLYS KLTVDKSRWQ QGNVFSCSVM HEALHNHYTQ

1951 KSLSLSPGK
```

Example 6

Protein Purification for FVIII-169/VWF-031 and FVIII-173/VWF-031

A tangential flow filtration (TFF) step was used to buffer exchange the clarified conditioned media. The FVIII-169/VWF-031 or FVIII-173/VWF-031 heterodimer was then purified using a two-step chromatography process. A weak anion exchange resin was used, followed by affinity chromatography. The final purified product had acceptable purity by SEC-HPLC. The specific activity was compatible to B-domain deleted FVIII, as measured by FVIII chromogenic assay and A280 concentration. Purity and the presence of each moiety of this molecule were confirmed by SDS-PAGE and western blotting.

Example 7

Evaluation the VWF Binding Ability of FVIII-169/VWF-031 by Octet Assay

The VWF binding ability of FVIII-169/VWF-031 was obtained by Bio-Layer Interferometry (BLI) based measurements (Octet assay) at 25° C. with a ForteBio Octet 384 instrument, using Tris binding buffer (50 mM Tris, pH 7.2, 150 mM NaCl, 5 mM $CaCl_2$). The Octet assay for determining FVIII binding was based on the hydrophobic immobilization of Human von Willebrand Factor (Haematologic Technologies Catalog No. HCVWF-0191) onto the APS Biosensor, then followed by the binding of 1.0% Bovine Serum Albumin (Jackson ImmunoResearch Catalog No. 001-000-161). Briefly, hvWF (20 µg/mL) was diluted in Tris buffer and loaded across APS Biosensors for 600 sec, yielding approximately 3.0-3.5 nm binding on the reaction probes. Control APS probes were loaded with 1.0% BSA in the absence of hvWF for reference subtraction. After loading, all probes were incubated in Tris buffer for 300 sec to establish a new baseline. Subsequently, biosensor probes were incubated in solutions of FVIII-XTEN 169 or FVIIIFc Drug Substance (0, 0.6, 2, 6, 20, 60, 200, 600 IU/mL) for 5 min at room temperature, followed by a 5 min dissociation step. Using the Octet data analysis software, the binding response (nm) was derived from the subtracted data (Reaction probe minus Reference probe). No binding to immobilized VWF was detected for FVIII-169/VWF-031 (FIGS. 7A-7B), indicating a complete shielding of FVIII from full length VWF molecule by the D'D3 fragment.

Example 8

FVIII-169/VWF-031 PK in HemA and FVIII/VWF DKO Mice

The PK profile of FVIII-169/VWF-031 was tested in HemA and FVIII/VWF DKO mice to evaluate the ability of the D'D3 fragment to shield the FVIII moiety from the endogenous VWF. HemA or FVIII/VWF DKO mice were treated with a single intravenous dose of FVIII-169/VWF-031 at 200 IU/kg, plasma samples were then collected at 5 min, 8 hr, 24 hr, 48 hr and 72 hours post dosing. The FVIII activity of plasma sample was tested by FVIII chromogenic assay, and half-life of FVIII-169/VWF-031 was calculated using WinNonlin program.

Complete inhibition of the constructs' binding to immobilized VWF was demonstrated by biolayer interferometry (FIGS. 7A-7B) for FVIII-169/VWF-031. This indicates the D'D3 fragment in the molecule had successfully blocked the FVIII binding to native VWF molecules, therefor similar half-life of FVIII-169/VWF-031 was predicted in the two different mouse strains. As shown in FIG. 8A and Table 18, as expected, FVIII-169/VWF-031 had similar PK profile in both HemA and FVIII/VWF DKO mice, which has demonstrated that the half-life of FVIIIFc/VWF heterodimer is independent from the half-life of endogenous VWF. The separation of the FVIIIFc/VWF heterodimer half-life from the endogenous VWF half-life, eliminated the FVIII extension ceiling and opened the possibility of further extending FVIII half-life beyond the 2 fold half-life limit imposed by endogenous VWF.

TABLE 18

FVIII-169/VWF-031 PK in HemA and FVIII/VWF DKO mice

| Mouse Strain | Recovery (%) | $t_{1/2}$ (hr) | MRT (hr) | Cl (mL/hr/kg) | Vss (mL/kg) | AUC (hr*kg*mIU/mL/mIU) |
|---|---|---|---|---|---|---|
| FVIII/NWF DKO | 69 | 17.94 | 20.1 | 4.06 | 81.69 | 0.2461 |
| HemA | 83 | 16.65 | 18.44 | 3.57 | 85.72 | 0.28 |

The FVIII protecting ability of the XTEN insertion and D'D3 fragment was evaluated by comparing the half-life of FVIII-169/VWF-031 with FVIII-169/Fc and FVIIIFc in FVIII/VWF DKO mice. After a single IV administration, blood samples were collected at 5 min, 8 hr, 24 hr, 48 hr and 72 hr for FVIII-169/VWF-031, 5 min, 8 hr, 24 hr, 32 hr, 48 hr for FVIII-169/Fc and at 5 min, 1, 2, 4, 6 and 8 hrs for FVIIIFc. The FVIII activity of plasma sample was tested by FVIII chromogenic assay, and half-life of FVIII-155/VWF-031 was calculated using WinNonlin program.

The study results were summarized in FIG. 8B and Table 19, rFVIIIFc has a 1.6 hr half-life in DKO mice due to the loss of VWF protection. When an XTEN insertion was introduced into the FVIIIFc molecule, the resulting FVIII-169/Fc molecule has a 7 hr half-life, a 4 fold half-life extension by the XTEN insertion. Finally, when D'D3 fragment was incorporated into the molecule to form FVIII-169/VWF-031, a 17 hr half-life was observed, another 2.5 fold further increase by the D'D3 fragment. In addition of the half-life improvement, improved Mean residency time (MRT), Clearance (Cl) and AUC were also observed as shown in Table 19.

FVIII-169/VWF-031 has achieved 17-18 hr $t_{1/2}$ in both HemA and FVIII/VWF DKO mice, which is the upper limit of the $t_{1/2}$ extension ceiling that imposed by VWF clearance. More $t_{1/2}$ extension elements can be further incorporated into this molecule, such as a second XTEN insertion within FVIII. The synergistic effect of D'D3 fragment and XTEN insertions provided the possibility of the complete protection for FVIII from its clearance pathway, a final breakthrough of the 2 fold FVIII $t_{1/2}$ extension limit might be achieved by the FVIIIFc/XTEN/VWF variants.

TABLE 19

FVIII-169/VWF-031 PK in FVIII/VWF DKO mice

| Mouse Strain | Treatment | Recovery (%) | $t_{1/2}$ (hr) | MRT (hr) | Cl (mL/hr/kg) | Vss (mL/kg) | AUC/D (hr*kg*mIU/mL/mIU) |
|---|---|---|---|---|---|---|---|
| FVIII/VWF DKO | rFVIIIFc | 35 | 1.6 | 2.1 | 57.7 | 120.2 | 0.0173 |
| | rFVIII-169/Fc | 77 | 7.0 | 6.2 | 6.4 | 39.2 | 0.1573 |
| | rFVIII-169/VWF-031 | 69 | 17.9 | 20.1 | 4.1 | 81.7 | 0.2461 |

Example 9

FVIII-XTEN Variants Cell Media Concentrate PK in D'D3 Expressing FVIII/VWF DKO Mice The ability of D'D3 fragment to extend the $t_{1/2}$ of FVII-XTEN was evaluated in the D'D3 expressing FVIII/VWF DKO mouse model (described in example 2). In this study, instead of using VWF-025 to introduce the D'D3 dimer into the circulation, VWF-029 construct was used to introduce the D'D3 monomer into the circulation. To prepare FVIII-XTEN variants protein, a small scale (50-100 mL) transient transfection culture media was prepared, at day 4 post transfection, cell culture was harvested and concentrated to reach 10-20 IU/mL of FVIII activity range which is suitable for PK study. The concentrated cell media were then used for standard PK study in FVIII/VWF DKO mice with or without D'D3 in the circulation.

Total of 6 FVIII-XTEN variants that contains 1-3 XTEN insertions were tested in the system, their $t_{1/2}$ were summarized in Table 20 and data from representative variants were plotted in FIG. 9A.

Longer half-life was observed for all the FVIII-XTEN variants with the presents of D'D3 fragment in the circulation (Table 20), which demonstrated the D'D3 protection for FVIII-XTEN from its clearance pathways. Furthermore, when compared to its 14 hr half-life in HemA mice, LSD0055.021 has a 20.4 hr $t_{1/2}$ in D'D3 expressing DKO mice (FIG. 9B, Table 20), indicates the final breakthrough of the 2 fold half-life extension ceiling for FVIII molecules. By further modify the FVIII(XTEN)/VWF molecule, we could potentially achieve even longer FVIII $t_{1/2}$, and provide HemA patients a FVIII protein that only requires once weekly or less frequent dosing regimen.

TABLE 20

FVIII-XTEN $t_{1/2}$ in D'D3 expressing FVIII/VWF DKO mice

| FVIII-XTEN ID | # of XTEN insertions | Insertion sites | XTEN size | $t_{1/2}$ (hr) DKO mice | $t_{1/2}$ (hr) pLIVE-D'D3/ DKO mice | $t_{1/2}$ (hr) HemA mice |
|---|---|---|---|---|---|---|
| pSD-0013 | 1 | CT | 144 | 3.3 | 7.9 | |
| LSD0003.009 | 2 | B*/CT | 144/288 | 9.7 | 16.4 | |
| LSD0038.015 | 2 | 1656/26 | 144/144 | 7.8 | 17.2 | |
| LSD0049.002 | 3 | 18/ B*/CT | 144/ 144/288 | 12.6 | 17.5 | |
| LSD0051.002 | 3 | 403/ B*/CT | 144/ 144/288 | 11.1 | 19.9 | |
| LSD0055.021 | 3 | 1900/B*/ CT | 144/ 144/288 | 16 | 20.4 | 14 |

*B indicates an XTEN sequence (e.g., 144) is inserted immediately downstream of amino acid residue 745 corresponding to mature FVIII sequence.

Example 10

Stability of VWF- and XTEN-Containing FVIII Variants in FVIII/VWF Double Knockout (DKO) Plasma Plasma stability of rFVIIIFc protein variants was tested in FVIII/VWF double knockout (DKO) mouse plasma. For the stability assay, HEK293 cells were co-transfected with plasmids directing the expression of rFVIIIFc or FVIII-169 (rFVIIIFc with 288 AE XTEN inserted at the B-domain junction) and plasmids directing the expression of either IgG-Fc or VWF-031 (VWF D'D3 region fused to IgG-Fc). At day four post-transfection, cell culture media was harvested and concentrated to 30 IU/mL based on FVIII chromogenic activity. Concentrated cell culture medium was then added into DKO mouse plasma to yield a FVIII activity of 5 IU/mL and incubated at 37° C. Aliquots were collected at different time points for activity measurement by chromogenic assay. Activity at each time point was measured in duplicate, and the average activity was plotted as a function of time. The activity of FVIIIFc, a dual chain (dc) FVIII molecule in which heavy and light chains are held together by non-covalent interaction, decreases with time in DKO mouse plasma (FIG. 10). The activity of FVIII-169:Fc, which contains a 288 AE XTEN insertion at the B-domain junction, decays at a reduced rate relative to rFVIIIFc, indicating that enhanced stability is conferred by the XTEN insertion. Given that VWF has been proposed to enhance the stability of FVIII in vivo, we evaluated the plasma stability of FVIII-169:VWF-031. This heterodimeric molecule, in which the FVIII element and the VWF D'D3 element are fused to respective hemi-domains of Fc, exhibited additional plasma stability relative to FVIII-169:Fc, indicating that the VWF D'D3 domain and XTEN have a synergistic effect on the plasma stability of rFVIIIFc.

Example 11

The Effect on FVIII Half-Life of Fc Fusion, XTEN Insertion and the D'D3 Fragment of VWF To assess the effect of Fc fusion, XTEN insertion and D'D3 fragment of VWF on the half-life of FVIII, the pharmacokinetic properties of B domain deleted recombinant FVIII (rBDD-FVIII), rFVIIIFc, FVIII-169:Fc and FVIII-169:VWF-031 were evaluated in FVIII/VWF double knockout (DKO) mice.

DKO mice were treated with a single intra venous administration of 200 IU/kg of FVIII proteins, and plasma samples were collected at designated time points as indicated in FIG. 11. FVIII activity of the plasma samples were analyzed by FVIII chromogenic assay and half-life was calculated using the WinNonlin-Phoenix program. The pharmacokinetic parameters of the tested molecules are listed in Table 21. The time regression curve of plasma FVIII activity for each FVIII variants were plotted in FIG. 11.

Unmodified BDD-FVIII had a half-life of 0.23 hr in DKO mice, the FVIIIFc fusion protein has an extended half-life of 1.66 hr in DKO mice due to the recycling of FVIIIFc protein through the Fc:FcRn interaction. When a 288 residue of AEXTEN polypeptide was incorporated into the B domain region of FVIII within the FVIIIFc molecule, the half-life of the resulting FVIII169/Fc protein was further extended to 7.41 hr in DKO mice. Finally, with the addition of the D'D3 domain of VWF, the half-life of FVIII169/VWF031 heterodimer has reached 17.9 hr in DKO mice (FIG. 11, Table 21). In addition of the half-life, all of the other PK parameters also improved proportionally with the addition of each element (Table 21). FVIII can tolerate multiple half-life extension elements, and this synergistic effect of the three elements on FVIII half-life extension, enabled the further improvement of the half-life of FVIII-XTEN VWF heterodimers.

TABLE 21

PK parameters of FVIII variants

| FVIII | FVIII Isoform | XTEN Insertions Site | XTEN Length | $T_{1/2}$ (hr) | MRT (hr) | Cl (mL/hr/kg) | Vss (mL/kg) | AUC_D kg*hr/mL |
|---|---|---|---|---|---|---|---|---|
| BDD-FVIII | dc | | | 0.23 | 0.24 | 407.72 | 97.42 | 0.0025 |
| FVIIIFc | dc | | | 1.66 | 2.06 | 62.66 | 128.82 | 0.0161 |
| FVIII169/Fc | sc | B* | AE288 | 7.41 | 6.67 | 6.24 | 41.61 | 0.1603 |
| FVIII169/VWF031 | sc | B* | AE288 | 17.94 | 20.1 | 4.06 | 81.69 | 0.2463 |

*B indicates an XTEN sequence (e.g., 144) is inserted immediately downstream of amino acid residue 745 corresponding to mature FVIII sequence.

Example 12

Pharmacokinetic Properties of Different FVIII-XTEN_VWF Heterodimers

To evaluate the combined effect of the VWF-D'D3 fragment and XTEN insertions on the FVIII half-life, the pharmacokinetic properties of FVIII-XTEN-Fc:VWF-Fc heterodimers were tested in HemA mice and compared to those of the single chain isoform of BDD-FVIII (scBDD-FVIII) and FVIII-169:VWF-031 (example 10). Seven new FVIII-XTEN-Fc constructs were generated (protein sequences were listed in Table 24). Schematic diagrams of those constructs are shown in FIGS. 14A-14H. FVIII-195 and FVIII-199, respectively, are the FVIII dual chain and single chain isoforms that each contains two XTEN insertions at positions 1900 and 1656. FVIII-196 and FVIII-201, respectively, are the FVIII dual chain and single chain isoforms that each contains three XTEN insertions at positions 26, 1656 and 1900. FVIII-203, -204 and -205 are sc-FVIIIFc molecules with two XTEN insertions at the B domain junction and at positions 1900, 403 or 18, respectively. Each FVIII-XTEN-Fc construct was co-expressed with VWF-031 in HEK293 cells to produce FVIII-XTEN-Fc/VWF heterodimeric proteins. At day four post-transfection, cell culture medium was harvested and either concentrated to 20 IU/mL based on FVIII chromogenic activity (FVIII-195:VWF-031, FVIII-196:VWF-031, FVIII-199:VWF-031, FVIII-203:VWF-031 and FVIII-204:VWF-031) or purified (scBDD-FVIII, FVIII-169:VWF-031, FVIII-201:VWF-031 and FVIII-205:VWF-031). Having demonstrated the complete intra-molecular shielding of FVIII molecule from the endogenous VWF by the D'D3 fragment in the FVIII-XTEN-Fc:VWF-Fc heterodimer (FVIII-169:VWF-031, Example 5), HemA mice was chosen for the PK evaluations. Purified protein or concentrated cell culture medium was administered to 8-12 week-old HemA mice by intravenous administration at a dose of 200 IU/10 mL/kg. Plasma samples were collected at 5 min, 8 hr, 16 hr, 24 hr, 32 hr, 48 hr, 72 hr and 96 hr post-dosing. FVIII activity of the plasma samples were analyzed by FVIII chromogenic assay and half-life was calculated using the WinNonlin-Phoenix program. The pharmacokinetic parameters of the tested molecules are listed in Table 22. The plasma FVIII activities at selected time points for FVIII-XTEN-Fc/VWF-Fc variants were plotted in FIGS. 12A-12C.

When XTEN was inserted into positions 1900 and 1656 (FVIII-195, FVIII-199), moderate improvement in half-life was observed for the scFVIII isoform (FVIII-199:VWF-031) compared to FVIII-169:VWF-031. However, the dcFVIII isoform exhibited a shorter half-life than did FVIII-169:VWF-031, indicating that the single chain isoform might be significantly more stable than the corresponding dual chain isoform (Table 22 and FIG. 12A). When a third XTEN insertion was incorporated into FVIII-199 at position 26, the half-life of the resulting molecule FVIII-201:VWF-031 had reached 24.6 hr, which represents greater than a threefold half-life improvement relative to scBDD-FVIII (Table 22 and FIG. 12C). We have also tested the half-life extension effect of the second XTEN insertion at position 403 (A2 domain), 1900 (A3 domain) and 18 (A1 domain) each in combination with the B domain XTEN insertion. While the addition of the A2 or A3 XTEN insertion did not confer an additional half-life benefit (Table 22, FIG. 12B), the addition of the A1 insertion further extended the half-life of the FVIII-XTEN-Fc:VWF-Fc heterodimer to 29.4 hr (Table 22, FIG. 12C), which is greater than threefold longer than that of scBDD-FVIII.

When XTENs were incorporated into the FVIIIFc/VWF heterodimer construct, degree of half-life improvement of the resulting molecules was variable, and no obvious correlation was observed between half-lives and either the site or number of XTEN insertion, suggesting that the half-life of the FVIII-XTEN-Fc/VWF heterodimer is determined by the integrity of the whole molecule rather than by the number or placement of XTEN insertions.

The 24.6 hr and 29.4 hr half-lives observed for FVIII-XTEN-Fc:VWF-Fc heterodimers clearly exceeded the 1.6- to 2-fold limitation on FVIII half-life extension. If this finding translates for HemA patients, it will allow once-weekly or less frequent dosing for FVIII prophylaxis.

TABLE 22

PK parameters of FVIII-XTEN-Fc/VWF-Fc heterodimers

| FVIII | FVIII Isoform | XTEN Insertions | | $T_{1/2}$ (hr) | MRT (hr) | Cl (mL/hr/kg) | Vss (mL/kg) | AUC_D (kg*hr/mL) |
|---|---|---|---|---|---|---|---|---|
| | | Site | XTEN Length | | | | | |
| scBDD-FVIII | sc | | | 7.16 | 10.16 | 4.38 | 44.44 | 0.23 |
| FVIII169/VWF031 | sc | B* | AE288 | 16.65 | 18.44 | 3.57 | 65.79 | 0.28 |
| FVIII195/VWF031 | dc | 1656/1900 | AG144/AE144 | 12.56 | 13.88 | 9.04 | 125.48 | 0.11 |
| FVIII199/VWF031 | sc | 1656/1900 | AG144/AE144 | 18.57 | 20.09 | 6.24 | 125.28 | 0.16 |
| FVIII201/VWF031 | sc | 26/1656/1900 | AG144/AG144/AE144 | 24.63 | 33.67 | 1.9 | 63.97 | 0.53 |
| FVIII203/VWF031 | sc | 403/B* | AE144/AE288 | 15.52 | 18 | 3.65 | 65.61 | 0.27 |
| FVIII204/VWF031 | sc | 1900/B* | AE144/AE288 | 16.3 | 20.63 | 2.87 | 59.14 | 0.35 |
| FVIII205/VWF031 | sc | 18/B* | AE144/AE288 | 29.4 | 37.06 | 1.82 | 67.39 | 0.55 |

*B indicates an XTEN sequence (e.g., 144) is inserted immediately downstream of amino acid residue 745 corresponding to mature FVIII sequence.

In addition to incorporating XTEN into the FVIII molecule, we also evaluated the potential half-life extension benefit of incorporating XTEN as a linker between the D'D3 and Fc fragment. FVIII-155 (scFVIIIFc) was co-expressed with VWF-034 (VWF-Fc with AE 288 XTEN plus a 35 residue thrombin cleavable linker) in HEK293 cells. At day 4 post-transfection, cell culture medium was harvested and concentrated to 20 IU/mL based on FVIII activity assay. FVIII/VWF DKO mice were dosed with concentrated cell culture media at 200 IU/10 mL/kg with a single intravenous injection. Plasma samples were collected at 5 min, 8 hr, 24 hr, 48 hr, 72 hr and 96 hr post-dosing. The FVIII activity of plasma samples was analyzed by FVIII chromogenic assay, and the regression curve of plasma FVIII activity as a function of time was plotted (FIG. 13). FVIII-155/VWF-034 exhibited the same improvement in half-life as FVIII-169/VWF-031, which has AE 288 XTEN inserted into the B domain junction of FVIII, as illustrated by the over lapping regression curves for the two molecules (FIG. 13). The demonstration that XTEN insertion into the VWF-Fc polypeptide confers half-life improvement of a magnitude similar to that conferred by XTEN insertion at the B domain junction of the FVIII polypeptide suggests that further half-life improvement may be possible in a heterodimeric molecule in which intra-molecular XTEN insertion in the FVIII polypeptide is combined with inter-domain XTEN insertion between the VWF and Fc elements of the VWF-Fc polypeptide.

Example 13A

Pharmacokinetic Properties of Additional FVIII-XTEN_VWF Heterodimers

In addition to the FVIII-XTEN VWF heterodimers that were listed in Table 22, FVIII-XTEN VWF heterodimers containing different composition of XTEN insertions, single chain and dual chain version of FVIII (Table 23A) are either tested or will be tested in HemA for their pharmacokinetic properties. Various FVIII constructs (Table 23B) and VWF constructs (Table 23C) are also disclosed below. HemA mice will be treated with a single dose of intravenous administration of the heterodimer proteins at 200 IU/10 mL/kg. Plasma samples will then be collected at 5 min, 24, 48, 72, 96 and 120 hrs post-dosing. FVIII activity of the plasma samples will be analyzed by FVIII chromogenic assay and half-life will be calculated using the WinNonlin-Phoenix program. The protein sequences of the listed heterodimers were listed in Table 25.

TABLE 23A

Plausible FVIII-XTEN-Fc:VWF-Fc heterodimer combinations for PK and activity improvement.

| | pSYN VWF-015 | pSYN VWF-031 | pSYN VWF-034 ** | pSYN VWF-036 |
|---|---|---|---|---|
| pSYN FVIII 010 | — | $t_{1/2}$ 8.7 hr DKO mice | To be tested | — |
| pSYN FVIII 155 | $t_{1/2}$ 6.3 hr DKO mice | $t_{1/2}$ 10.8 hr HemA mice | $t_{1/2}$ 18.6 hr HemA mice | $t_{1/2}$ 13.3 hr HemA mice |
| pSYN FVIII 169 ** | — | $t_{1/2}$ 16.7 hr HemA mice | $t_{1/2}$ 31.1 hr HemA mice | — |
| pSYN FVIII 173 ** | — | $t_{1/2}$ 15.2 hr DKO mice | $t_{1/2}$ 28.9 hr HemA mice | To be tested |
| pSYN FVIII 205 | — | $t_{1/2}$ 29.4 hr HemA mice | $t_{1/2}$ 32.4 hr HemA mice | $t_{1/2}$ 29.7 hr HemA mice |
| pSYN FVIII 266 | — | $t_{1/2}$ 24.5 hr HemA mice | $t_{1/2}$ 27.4 hr HemA mice | — |
| pSYN FVII 267 | — | $t_{1/2}$ 23.0 hr HemA mice | $t_{1/2}$ 25.7 hr HemA mice | — |
| pSYN FVIII 268 | — | To be tested | To be tested | To be tested |
| Dual chain isoform of pSYN FVIII 268 | — | To be tested | To be tested | To be tested |

** Length of XTEN can be changed to 72, 144, 288, 324, 333, 576, or 864.

TABLE 23B

FVIII Constructs:

| | |
|---|---|
| pSYN FVIII 010 | dual chain FVIIIFc |
| pSYN FVIII 169 | Single chain FVIIIFc with 288 AE XTEN in B-domain |
| pSYN FVIII 173 | dual chain FVIIIFc with 288 AE XTEN in B-domain |
| pSYN FVIII 195 | dual chain FVIIIFc with two 144 XTENs at amino acid 1656 and 1900 |
| pSYN FVIII 196 | dual chain FVIIIFc with three 144 XTENs at amino acid 26, 1656 and 1900 |
| pSYN FVIII 199 | Single chain FVIIIFc with two 144 XTENs at amino acid 1656 and 1900 |
| pSYN FVIII 201 | Single chain FVIIIFc with three 144 XTENs at amino acid 26, 1656 and 1900 |
| pSYN FVIII 203 | Single chain FVIIIFc with 144 AE XTEN at amino acid 1900 and 288 AE XTEN in B-domain |
| pSYN FVIII 204 | Single chain FVIIIFc with 144 AE XTEN at amino acid 403 and 288 AE XTEN in B-domain |
| pSYN FVIII 205 | Single chain FVIIIFc with 144 AE XTEN at amino acid 18 and 288 AE XTEN in B-domain |
| pSYN FVIII 207 | Single chain FVIII (no Fc, no XTEN) |
| pSYN FVIII 266 | Single chain FVIIIFc with 42 AE XTEN at amino acid 18 and 288 AE XTEN in B-domain |
| pSYN FVIII 267 | Single chain FVIIIFc with 72 AE XTEN at amino acid 18 and 288 AE XTEN in B-domain |
| pSYN FVIII 268 | Single chain FVIIIFc with 144 AE XTEN at amino acid 18 |
| pSYN FVIII 269 | Single chain FVIIIFc with 72 AE XTEN at amino acid 18 |
| pSYN FVIII 271 | Single chain FVIIIFc with 42 AE XTEN at amino acid 18 |
| pSYN FVIII 272 | Single chain FVIII with 144 AE XTEN at amino acid 18 and 288 AE XTEN in B-domain (no Fc) |

TABLE 23C

VWF Constructs:

| | |
|---|---|
| pSYN VWF031 | VWF-D1D2D'D3- 48aa long thrombin cleavable GS linker-Fc with C1099A/C1142A |
| pSYN VWF034 | VWF-D1D2D'D3- 288AE XTEN + 35aa long thrombin cleavable GS linker-Fc with C1099A/C1142A |
| pSYN VWF035 | VWF-D1D2D'D3- 72aa long thrombin cleavable GS linker-Fc with C1099A/C1142A |
| pSYN VWF036 | VWF-D1D2D'D3- 98aa long thrombin cleavable GS linker-Fc with C1099A/C1142A |
| pSYN VWF041 | VWF-D1D2D'D3 with 288 AE XTEN in D3 and 48aa long thrombin cleavable GS linker after D3-Fc with C1099A/C1142A |

Example 13B

Pharmacokinetic Properties of Additional FVIII-XTEN_VWF Heterodimers

FVIII-XTEN_VWF heterodimers were tested in HemA mice for their pharmacokinetic properties. The heterodimers tested are FVIII169/VWF034, FVIII205/VWF034, FVIII205/VWF036 and FVIII266/VWF031. HemA mice were administered with a single intravenous dose of various heterodimer proteins at 200 IU/10 mL/kg. Plasma samples were collected at 5 min, 24, 48, 72, 96 and 120 hrs post-dosing. FVIII activity of the plasma samples were analyzed by FVIII chromogenic assay, and half-lives were calculated using the WinNonlin-Phoenix program. The PK results are shown below in Table 24.

TABLE 24

Additional FVIII-XTEN_VWF-PK in HemA Mice

| Treatment | 5 min recovery (%) | HL (hr) | MRT (hr) | Cl (mL/hr/kg) | Vss (mL/kg) | AUC_D (hr*kg* mIU/mL/mIU) | Fold of $t_{1/2}$ increase vs scBDD-FVIII |
|---|---|---|---|---|---|---|---|
| ScBDD-FVIII | | 7.16 | 10.16 | 4.83 | 44.44 | 0.23 | — |
| FVIII169/ VWF034 | 76 | 31.1 | 34.57 | 1.73 | 59.77 | 0.58 | 4.3 |
| FVIII205/ VWF034 | 68 | 32.41 | 39.79 | 1.55 | 61.73 | 0.64 | 4.6 |
| FVIII205/ VWF036 | 74 | 29.71 | 36.35 | 1.61 | 58.43 | 0.62 | 4.1 |
| FVIII266/ VWF031 | 66 | 24.45 | 22.75 | 2.67 | 60.83 | 0.37 | 3.4 | pSYNFVIII 010 nucleotide sequence-(Dual chain FVIIIFc)
(SEQ ID NO: 125)

```
   1 ATGCAAATAG AGCTCTCCAC CTGCTTCTTT CTGTGCCTTT TGCGATTCTG
  51 CTTTAGTGCC ACCAGAAGAT ACTACCTGGG TGCAGTGGAA CTGTCATGGG
 101 ACTATATGCA AAGTGATCTC GGTGAGCTGC CTGTGGACGC AAGATTTCCT
 151 CCTAGAGTGC AAAATCTTT TCCATTCAAC ACCTCAGTCG TGTACAAAAA
 201 GACTCTGTTT GTAGAATTCA CGGATCACCT TTTCAACATC GCTAAGCCAA
 251 GGCCACCCTG GATGGGTCTG CTAGGTCCTA CCATCCAGGC TGAGGTTTAT
 301 GATACAGTGG TCATTACACT TAAGAACATG GCTTCCCATC CTGTCAGTCT
 351 TCATGCTGTT GGTGTATCCT ACTGGAAAGC TTCTGAGGGA GCTGAATATG
 401 ATGATCAGAC CAGTCAAAGG GAGAAAGAAG ATGATAAAGT CTTCCCTGGT
 451 GGAAGCCATA CATATGTCTG GCAGGTCCTG AAAGAGAATG GTCCAATGGC
 501 CTCTGACCCA CTGTGCCTTA CCTACTCATA TCTTTCTCAT GTGGACCTGG
 551 TAAAAGACTT GAATTCAGGC CTCATTGGAG CCCTACTAGT ATGTAGAGAA
 601 GGGAGTCTGG CCAAGGAAAA GACACAGACC TTGCACAAAT TTATACTACT
 651 TTTTGCTGTA TTTGATGAAG GGAAAAGTTG GCACTCAGAA ACAAAGAACT
 701 CCTTGATGCA GGATAGGGAT GCTGCATCTG CTCGGGCCTG GCCTAAAATG
 751 CACACAGTCA ATGGTTATGT AAACAGGTCT CTGCCAGGTC TGATTGGATG
 801 CCACAGGAAA TCAGTCTATT GGCATGTGAT TGGAATGGGC ACCACTCCTG
 851 AAGTGCACTC AATATTCCTC GAAGGTCACA CATTTCTTGT GAGGAACCAT
 901 CGCCAGGCGT CCTTGGAAAT CTCGCCAATA ACTTTCCTTA CTGCTCAAAC
 951 ACTCTTGATG GACCTTGGAC AGTTTCTACT GTTTTGTCAT ATCTCTTCCC
1001 ACCAACATGA TGGCATGGAA GCTTATGTCA AAGTAGACAG CTGTCCAGAG
1051 GAACCCCAAC TACGAATGAA AAATAATGAA GAAGCGGAAG ACTATGATGA
1101 TGATCTTACT GATTCTGAAA TGGATGTGGT CAGGTTTGAT GATGACAACT
1151 CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT
1251 AGTCCTCGCC CCCGATGACA GAAGTTATAA AAGTCAATAT TTGAACAATG
1301 GCCCTCAGCG GATTGGTAGG AAGTACAAAA AGTCCGATT TATGGCATAC
1351 ACAGATGAAA CCTTTAAGAC TCGTGAAGCT ATTCAGCATG AATCAGGAAT
1401 CTTGGGACCT TTACTTTATG GGGAAGTTGG AGACACACTG TTGATTATAT
1451 TTAAGAATCA AGCAAGCAGA CCATATAACA TCTACCCTCA CGGAATCACT
```

```
1501 GATGTCCGTC CTTTGTATTC AAGGAGATTA CCAAAAGGTG TAAAACATTT
1551 GAAGGATTTT CCAATTCTGC CAGGAGAAAT ATTCAAATAT AAATGGACAG
1601 TGACTGTAGA AGATGGGCCA ACTAAATCAG ATCCTCGGTG CCTGACCCGC
1651 TATTACTCTA GTTTCGTTAA TATGGAGAGA GATCTAGCTT CAGGACTCAT
1701 TGGCCCTCTC CTCATCTGCT ACAAAGAATC TGTAGATCAA AGAGGAAACC
1751 AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC
1851 AGCTGGAGTG CAGCTTGAGG ATCCAGAGTT CCAAGCCTCC AACATCATGC
1901 ACAGCATCAA TGGCTATGTT TTTGATAGTT TGCAGTTGTC AGTTTGTTTG
1951 CATGAGGTGG CATACTGGTA CATTCTAAGC ATTGGAGCAC AGACTGACTT
2001 CCTTTCTGTC TTCTTCTCTG GATATACCTT CAAACACAAA ATGGTCTATG
2051 AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG
2151 GAACAGAGGC ATGACCGCCT TACTGAAGGT TTCTAGTTGT GACAAGAACA
2201 CTGGTGATTA TTACGAGGAC AGTTATGAAG ATATTTCAGC ATACTTGCTG
2251 AGTAAAAACA ATGCCATTGA ACCAAGAAGC TTCTCTCAAA ACCCACCAGT
2301 CTTGAAACGC CATCAACGGG AAATAACTCG TACTACTCTT CAGTCAGATC
2351 AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA
2451 AAAGAAAACA CGACACTATT TTATTGCTGC AGTGGAGAGG CTCTGGGATT
2501 ATGGGATGAG TAGCTCCCCA CATGTTCTAA GAAACAGGGC TCAGAGTGGC
2551 AGTGTCCCTC AGTTCAAGAA AGTTGTTTTC CAGGAATTTA CTGATGGCTC
2601 CTTTACTCAG CCCTTATACC GTGGAGAACT AAATGAACAT TTGGGACTCC
2651 TGGGGCCATA TATAAGAGCA GAAGTTGAAG ATAATATCAT GGTAACTTTC
2701 AGAAATCAGG CCTCTCGTCC CTATTCCTTC TATTCTAGCC TTATTTCTTA
2751 TGAGGAAGAT CAGAGGCAAG GAGCAGAACC TAGAAAAAAC TTTGTCAAGC
2801 CTAATGAAAC CAAAACTTAC TTTTGGAAAG TGCAACATCA TATGGCACCC
2851 ACTAAAGATG AGTTTGACTG CAAAGCCTGG GCTTATTTCT CTGATGTTGA
2901 CCTGGAAAAA GATGTGCACT CAGGCCTGAT TGGACCCCTT CTGGTCTGCC
2951 ACACTAACAC ACTGAACCCT GCTCATGGGA GACAAGTGAC AGTACAGGAA
3001 TTTGCTCTGT TTTTCACCAT CTTTGATGAG ACCAAAAGCT GGTACTTCAC
3051 TGAAAATATG GAAAGAAACT GCAGGGCTCC CTGCAATATC CAGATGGAAG
3101 ATCCCACTTT TAAAGAGAAT TATCGCTTCC ATGCAATCAA TGGCTACATA
3151 ATGGATACAC TACCTGGCTT AGTAATGGCT CAGGATCAAA GGATTCGATG
3201 GTATCTGCTC AGCATGGGCA GCAATGAAAA CATCCATTCT ATTCATTTCA
3251 GTGGACATGT GTTCACTGTA CGAAAAAAAG AGGAGTATAA AATGGCACTG
3301 TACAATCTCT ATCCAGGTGT TTTTGAGACA GTGGAAATGT TACCATCCAA
3351 AGCTGGAATT TGGCGGGTGG AATGCCTTAT TGGCGAGCAT CTACATGCTG
3401 GGATGAGCAC ACTTTTTCTG GTGTACAGCA ATAAGTGTCA GACTCCCCTG
3451 GGAATGGCTT CTGGACACAT TAGAGATTTT CAGATTACAG CTTCAGGACA
```

-continued

```
3501 ATATGGACAG TGGGCCCCAA AGCTGGCCAG ACTTCATTAT TCCGGATCAA
3551 TCAATGCCTG GAGCACCAAG GAGCCCTTTT CTTGGATCAA GGTGGATCTG
3601 TTGGCACCAA TGATTATTCA CGGCATCAAG ACCCAGGGTG CCCGTCAGAA
3651 GTTCTCCAGC CTCTACATCT CTCAGTTTAT CATCATGTAT AGTCTTGATG
3701 GGAAGAAGTG GCAGACTTAT CGAGGAAATT CCACTGGAAC CTTAATGGTC
3751 TTCTTTGGCA ATGTGGATTC ATCTGGGATA AACACAATA TTTTTAACCC
3801 TCCAATTATT GCTCGATACA TCCGTTTGCA CCCAACTCAT TATAGCATTC
3851 GCAGCACTCT TCGCATGGAG TTGATGGGCT GTGATTTAAA TAGTTGCAGC
3901 ATGCCATTGG GAATGGAGAG TAAAGCAATA TCAGATGCAC AGATTACTGC
3951 TTCATCCTAC TTTACCAATA TGTTTGCCAC CTGGTCTCCT TCAAAAGCTC
4001 GACTTCACCT CCAAGGGAGG AGTAATGCCT GGAGACCTCA GGTGAATAAT
4051 CCAAAAGAGT GGCTGCAAGT GGACTTCCAG AAGACAATGA AAGTCACAGG
4101 AGTAACTACT CAGGGAGTAA AATCTCTGCT TACCAGCATG TATGTGAAGG
4151 AGTTCCTCAT CTCCAGCAGT CAAGATGGCC ATCAGTGGAC TCTCTTTTTT
4201 CAGAATGGCA AAGTAAAGGT TTTTCAGGGA AATCAAGACT CCTTCACACC
4251 TGTGGTGAAC TCTCTAGACC CACCGTTACT GACTCGCTAC CTTCGAATTC
4301 ACCCCCAGAG TTGGGTGCAC CAGATTGCCC TGAGGATGGA GGTTCTGGGC
4351 TGCGAGGCAC AGGACCTCTA CGACAAAACT CACACATGCC CACCGTGCCC
4401 AGCTCCAGAA CTCCTGGGCG GACCGTCAGT CTTCCTCTTC CCCCCAAAAC
4451 CCAAGGACAC CCTCATGATC TCCCGGACCC CTGAGGTCAC ATGCGTGGTG
4501 GTGGACGTGA GCCACGAAGA CCCTGAGGTC AAGTTCAACT GGTACGTGGA
4551 CGGCGTGGAG GTGCATAATG CCAAGACAAA GCCGCGGGAG GAGCAGTACA
4601 ACAGCACGTA CCGTGTGGTC AGCGTCCTCA CCGTCCTGCA CCAGGACTGG
4651 CTGAATGGCA AGGAGTACAA GTGCAAGGTC TCCAACAAAG CCCTCCCAGC
4701 CCCCATCGAG AAAACCATCT CCAAAGCCAA AGGGCAGCCC CGAGAACCAC
4751 AGGTGTACAC CCTGCCCCCA TCCCGGGATG AGCTGACCAA GAACCAGGTC
4801 AGCCTGACCT GCCTGGTCAA AGGCTTCTAT CCCAGCGACA TCGCCGTGGA
4851 GTGGGAGAGC AATGGGCAGC CGGAGAACAA CTACAAGACC ACGCCTCCCG
4901 TGTTGGACTC CGACGGCTCC TTCTTCCTCT ACAGCAAGCT CACCGTGGAC
4951 AAGAGCAGGT GGCAGCAGGG GAACGTCTTC TCATGCTCCG TGATGCATGA
5001 GGCTCTGCAC AACCACTACA CGCAGAAGAG CCTCTCCCTG TCTCCGGGTA
5051 AATGA
``` pSYNFVIII 010 protein sequence-(Dual chain FVIIIFc)
(SEQ ID NO: 126)

```
  1 MQIELSTCFF LCLLRFCFSA TRRYYLGAVE LSWDYMQSDL GELPVDARFP
 51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
```

```
-continued

401  WVHYIAAEEE  DWDYAPLVLA  PDDRSYKSQY  LNNGPQRIGR  KYKKVRFMAY

451  TDETFKTREA  IQHESGILGP  LLYGEVGDTL  LIIFKNQASR  PYNIYPHGIT

501  DVRPLYSRRL  PKGVKHLKDF  PILPGEIFKY  KWTVTVEDGP  TKSDPRCLTR

551  YYSSFVNMER  DLASGLIGPL  LICYKESVDQ  RGNQIMSDKR  NVILFSVFDE

601  NRSWYLTENI  QRFLPNPAGV  QLEDPEFQAS  NIMHSINGYV  FDSLQLSVCL

651  HEVAYWYILS  IGAQTDFLSV  FFSGYTFKHK  MVYEDTLTLF  PFSGETVFMS

701  MENPGLWILG  CHNSDFRNRG  MTALLKVSSC  DKNTGDYYED  SYEDISAYLL

751  SKNNAIEPRS  FSQNPPVLKR  HQREITRTTL  QSDQEEIDYD  DTISVEMKKE

801  DFDIYDEDEN  QSPRSFQKKT  RHYFIAAVER  LWDYGMSSSP  HVLRNRAQSG

851  SVPQFKKVVF  QEFTDGSFTQ  PLYRGELNEH  LGLLGPYIRA  EVEDNIMVTF

901  RNQASRPYSF  YSSLISYEED  QRQGAEPRKN  FVKPNETKTY  FWKVQHHMAP

951  TKDEFDCKAW  AYFSDVDLEK  DVHSGLIGPL  LVCHTNTLNP  AHGRQVTVQE

1001  FALFFTIFDE  TKSWYFTENM  ERNCRAPCNI  QMEDPTFKEN  YRFHAINGYI

1051  MDTLPGLVMA  QDQRIRWYLL  SMGSNENIHS  IHFSGHVFTV  RKKEEYKMAL

1101  YNLYPGVFET  VEMLPSKAGI  WRVECLIGEH  LHAGMSTLFL  VYSNKCQTPL

1151  GMASGHIRDF  QITASGQYGQ  WAPKLARLHY  SGSINAWSTK  EPFSWIKVDL

1201  LAPMIIHGIK  TQGARQKFSS  LYISQFIIMY  SLDGKKWQTY  RGNSTGTLMV

1251  FFGNVDSSGI  KHNIFNPPII  ARYIRLHPTH  YSIRSTLRME  LMGCDLNSCS

1301  MPLGMESKAI  SDAQITASSY  FTNMFATWSP  SKARLHLQGR  SNAWRPQVNN

1351  PKEWLQVDFQ  KTMKVTGVTT  QGVKSLLTSM  YVKEFLISSS  QDGHQWTLFF

1401  QNGKVKVFQG  NQDSFTPVVN  SLDPPLLTRY  LRIHPQSWVH  QIALRMEVLG

1451  CEAQDLYDKT  HTCPPCPAPE  LLGGPSVFLF  PPKPKDTLMI  SRTPEVTCVV

1501  VDVSHEDPEV  KFNWYVDGVE  VHNAKTKPRE  EQYNSTYRVV  SVLTVLHQDW

1551  LNGKEYKCKV  SNKALPAPIE  KTISKAKGQP  REPQVYTLPP  SRDELTKNQV

1601  SLTCLVKGFY  PSDIAVEWES  NGQPENNYKT  TPPVLDSDGS  FFLYSKLTVD

1651  KSRWQQGNVF  SCSVMHEALH  NHYTQKSLSL  SPGK*
```

Example 14

A New Class of Coagulation Factor VIII Molecules with Greater than Three-Fold Half-Life Extension in Hemophilia A Mice The new class of FVIII molecules was designed to contain two polypeptides; one that consists of a single chain B-domain deleted (BDD) FVIII with XTEN inserted at one or more locations within the FVIII sequence, and one that is composed of the D′D3 region of VWF. Each polypeptide was also recombinantly fused to the Fc region of IgG1 to enable the D′D3 region to be correctly aligned to bind the FVIII moiety. The resulting FVIII variants were expressed in HEK 293 cells by transient transfection, and purified from the conditioned media. FVIII activity was evaluated by FVIII chromogenic assay and the pharmacokinetic properties were assessed in both FVIII knockout (HemA) and FVIII/VWF double knock-out (DKO) mice.

Incorporating XTEN and D′D3 region of VWF into rFVIII led to the uncoupling of the clearance of the fusion proteins from endogenous VWF while extending their circulating half-life. FVIII in this fusion configuration is completely shielded from interacting with VWF, as measured by biolayer interferometry (Octet) analysis. Consistent with this, their pharmacokinetic profiles in HemA and DKO mice were found to be identical, indicating that their clearance rate in mice was effectively disconnected from VWF. Optimization of XTEN length and the locations for inserting XTEN identified a subset of the proteins that have exceeded the VWF limitation (16 hours), reaching a circulating half-life of up to 30 hours in HemA mice representing a 4-fold improvement over BDD-FVIII. Importantly, these proteins maintained their functionality, as judged by FVIII chromogenic assay.

The VWF dependency has set a fundamental limitation for half-life of therapeutic FVIII. Uncoupling FVIII from VWF clearance pathways while extending half-life by the fusion of D′D3 region of VWF and XTEN has generated a novel FVIII molecule with a 4-fold half-life extension. This is the first report of an engineered FVIII that has exceeded the half-life limitation observed through industry-wide efforts in development of long-lasting FVIII, representing a potentially significant advancement in prophylactic treatment of hemophilia A.

TABLE 25

Protein sequences of FVIII-XTEN-Fc and VWF-Fc constructs
FVIII 195 protein sequence (dual chain FVIIIFc with two
144 AE XTENs at amino acid 1656 and 1900) (SEQ ID NO: 105)

```
   1 MQIELSTCFF LCLLRFCFSA TRRYYLGAVE LSWDYMQSDL GELPVDARFP
  51 PRVPKSFPFN TSVVYKKTLF VEFTDHLFNI AKPRPPWMGL LGPTIQAEVY
 101 DTVVITLKNM ASHPVSLHAV GVSYWKASEG AEYDDQTSQR EKEDDKVFPG
 151 GSHTYVWQVL KENGPMASDP LCLTYSYLSH VDLVKDLNSG LIGALLVCRE
 201 GSLAKEKTQT LHKFILLFAV FDEGKSWHSE TKNSLMQDRD AASARAWPKM
 251 HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE
 351 EPQLRMKNNE EAEDYDDDLT DSEMDVVRFD DDNSPSFIQI RSVAKKHPKT
 401 WVHYIAAEEE DWDYAPLVLA PDDRSYKSQY LNNGPQRIGR KYKKVRFMAY
 451 TDETFKTREA IQHESGILGP LLYGEVGDTL LIIFKNQASR PYNIYPHGIT
 501 DVRPLYSRRL PKGVKHLKDF PILPGEIFKY KWTVTVEDGP TKSDPRCLTR
 551 YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL
 651 HEVAYWYILS IGAQTDFLSV FFSGYTFKHK MVYEDTLTLF PFSGETVFMS
 701 MENPGLWILG CHNSDFRNRG MTALLKVSSC DKNTGDYYED SYEDISAYLL
 751 SKNNAIEPRS FSQNPPVLKR HQREITRTTL QGAPGTPGSG TASSSPGASP
 801 GTSSTGSPGA SPGTSSTGSP GASPGTSSTG SPGSSPSAST GTGPGTPGSG
 851 TASSSPGASP GTSSTGSPGA SPGTSSTGSP GASPGTSSTG SPGSSTPSGA
 901 TGSPGSSTPS GATGSPGASP GTSSTGSPAS SSDQEEIDYD DTISVEMKKE
 951 DFDIYDEDEN QSPRSFQKKT RHYFIAAVER LWDYGMSSSP HVLRNRAQSG
1001 SVPQFKKVVF QEFTDGSFTQ PLYRGELNEH LGLLGPYIRA EVEDNIMVTF
1051 RNQASRPYSF YSSLISYEED QRQGAEPRKN FVKPNETKTY FWKVQHHMAP
1101 TKDEFDCKAW AYFSDVDLEK DVHSGLIGPL LVCHTNTLNP AHGRQVTVQE
1151 FALFFTIFDE TKSWYFTENM ERNCRGAPTS ESATPESGPG SEPATSGSET
1201 PGTSESATPE SGPGSEPATS GSETPGTSES ATPESGPGTS TEPSEGSAPG
1251 TSESATPESG PGSPAGSPTS TEEGSPAGSP TSTEEGSPAG SPTSTEEGTS
1301 ESATPESGPG TSTEPSEGSA PGASSAPCNI QMEDPTFKEN YRFHAINGYI
1351 MDTLPGLVMA QDQRIRWYLL SMGSNENIHS IHFSGHVFTV RKKEEYKMAL
1401 YNLYPGVFET VEMLPSKAGI WRVECLIGEH LHAGMSTLFL VYSNKCQTPL
1451 GMASGHIRDF QITASGQYGQ WAPKLARLHY SGSINAWSTK EPFSWIKVDL
1501 LAPMIIHGIK TQGARQKFSS LYISQFIIMY SLDGKKWQTY RGNSTGTLMV
1551 FFGNVDSSGI KHNIFNPPII ARYIRLHPTH YSIRSTLRME LMGCDLNSCS
1601 MPLGMESKAI SDAQITASSY FTNMFATWSP SKARLHLQGR SNAWRPQVNN
1651 PKEWLQVDFQ KTMKVTGVTT QGVKSLLTSM YVKEFLISSS QDGHQWTLFF
1701 QNGKVKVFQG NQDSFTPVVN SLDPPLLTRY LRIHPQSWVH QIALRMEVLG
1751 CEAQDLYDKT HTCPPCPAPE LLGGPSVFLF PPKPKDTLMI SRTPEVTCVV
1801 VDVSHEDPEV KFNWYVDGVE VHNAKTKPRE EQYNSTYRVV SVLTVLHQDW
1851 LNGKEYKCKV SNKALPAPIE KTISKAKGQP REPQVYTLPP SRDELTKNQV
```

TABLE 25-continued

```
1901 SLTCLVKGFY PSDIAVEWES NGQPENNYKT TPPVLDSDGS FFLYSKLTVD
1951 KSRWQQGNVF SCSVMHEALH NHYTQKSLSL SPGK*
```

FVIII 196 protein sequence (dual chain FVIIIFc with three
144 AE XTENs at amino acid 26, 1656 and 1900)
(SEQ ID NO: 106)

```
   1 MQIELSTCFF LCLLRFCFSA TRRYYLGAVE LSWDYMQSDL GELPVGAPGS
  51 SPSASTGTGP GSSPSASTGT GPGASPGTSS TGSPGASPGT SSTGSPGSST
 101 PSGATGSPGS SPSASTGTGP GASPGTSSTG SPGSSPSAST GTGPGTPGSG
 151 TASSSPGSST PSGATGSPGS STPSGATGSP GASPGTSSTG SPASSDARFP
 201 PRVPKSFPFN TSVVYKKTLF VEFTDHLFNI AKPRPPWMGL LGPTIQAEVY
 251 DTVVITLKNM ASHPVSLHAV GVSYWKASEG AEYDDQTSQR EKEDDKVFPG
 301 GSHTYVWQVL KENGPMASDP LCLTYSYLSH VDLVKDLNSG LIGALLVCRE
 351 GSLAKEKTQT LHKFILLFAV FDEGKSWHSE TKNSLMQDRD AASARAWPKM
 401 HTVNGYVNRS LPGLIGCHRK SVYWHVIGMG TTPEVHSIFL EGHTFLVRNH
 451 RQASLEISPI TFLTAQTLLM DLGQFLLFCH ISSHQHDGME AYVKVDSCPE
 501 EPQLRMKNNE EAEDYDDDLT DSEMDVVRFD DDNSPSFIQI RSVAKKHPKT
 551 WVHYIAAEEE DWDYAPLVLA PDDRSYKSQY LNNGPQRIGR KYKKVRFMAY
 601 TDETFKTREA IQHESGILGP LLYGEVGDTL LIIFKNQASR PYNIYPHGIT
 651 DVRPLYSRRL PKGVKHLKDF PILPGEIFKY KWTVTVEDGP TKSDPRCLTR
 701 YYSSFVNMER DLASGLIGPL LICYKESVDQ RGNQIMSDKR NVILFSVFDE
 751 NRSWYLTENI QRFLPNPAGV QLEDPEFQAS NIMHSINGYV FDSLQLSVCL
 801 HEVAYWYILS IGAQTDFLSV FFSGYTFKHK MVYEDTLTLF PFSGETVFMS
 851 MENPGLWILG CHNSDFRNRG MTALLKVSSC DKNTGDYYED SYEDISAYLL
 901 SKNNAIEPRS FSQNPPVLKR HQREITRTTL QGAPGTPGSG TASSSPGASP
 951 GTSSTGSPGA SPGTSSTGSP GASPGTSSTG SPGSSPSAST GTGPGTPGSG
1001 TASSSPGASP GTSSTGSPGA SPGTSSTGSP GASPGTSSTG SPGSSTPSGA
1051 TGSPGSSTPS GATGSPGASP GTSSTGSPAS SSDQEEIDYD DTISVEMKKE
1101 DFDIYDEDEN QSPRSFQKKT RHYFIAAVER LWDYGMSSSP HVLRNRAQSG
1151 SVPQFKKVVF QEFTDGSFTQ PLYRGELNEH LGLLGPYIRA EVEDNIMVTF
1201 RNQASRPYSF YSSLISYEED QRQGAEPRKN FVKPNETKTY FWKVQHHMAP
1251 TKDEFDCKAW AYFSDVDLEK DVHSGLIGPL LVCHTNTLNP AHGRQVTVQE
1301 FALFFTIFDE TKSWYFTENM ERNCRGAPTS ESATPESGPG SEPATSGSET
1351 PGTSESATPE SGPGSEPATS GSETPGTSES ATPESGPGTS TEPSEGSAPG
1401 TSESATPESG PGSPAGSPTS TEEGSPAGSP TSTEEGSPAG SPTSTEEGTS
1451 ESATPESGPG TSTEPSEGSA PGASSAPCNI QMEDPTFKEN YRFHAINGYI
1501 MDTLPGLVMA QDQRIRWYLL SMGSNENIHS IHFSGHVFTV RKKEEYKMAL
1551 YNLYPGVFET VEMLPSKAGI WRVECLIGEH LHAGMSTLFL VYSNKCQTPL
1601 GMASGHIRDF QITASGQYGQ WAPKLARLHY SGSINAWSTK EPFSWIKVDL
1651 LAPMIIHGIK TQGARQKFSS LYISQFIIMY SLDGKKWQTY RGNSTGTLMV
1701 FFGNVDSSGI KHNIFNPPII ARYIRLHPTH YSIRSTLRME LMGCDLNSCS
1751 MPLGMESKAI SDAQITASSY FTNMFATWSP SKARLHLQGR SNAWRPQVNN
```

TABLE 25-continued

```
1801 PKEWLQVDFQ KTMKVTGVTT QGVKSLLTSM YVKEFLISSS QDGHQWTLFF

1851 QNGKVKVFQG NQDSFTPVVN SLDPPLLTRY LRIHPQSWVH QIALRMEVLG

1901 CEAQDLYDKT HTCPPCPAPE LLGGPSVFLF PPKPKDTLMI SRTPEVTCVV

1951 VDVSHEDPEV KFNWYVDGVE VHNAKTKPRE EQYNSTYRVV SVLTVLHQDW

2001 LNGKEYKCKV SNKALPAPIE KTISKAKGQP REPQVYTLPP SRDELTKNQV

2051 SLTCLVKGFY PSDIAVEWES NGQPENNYKT TPPVLDSDGS FFLYSKLTVD

2101 KSRWQQGNVF SCSVMHEALH NHYTQKSLSL SPGK*
```

FVIII 199 protein sequence (single chain FVIIIFc with three
144 AE XTENs at amino acid 1656 and 1900) (SEQ ID NO: 107)

```
   1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNPPVLKR HQAEITRTTL QGAPGTPGSG TASSSPGASP

801 GTSSTGSPGA SPGTSSTGSP GASPGTSSTG SPGSSPSAST GTGPGTPGSG

851 TASSSPGASP GTSSTGSPGA SPGTSSTGSP GASPGTSSTG SPGSSTPSGA

901 TGSPGSSTPS GATGSPGASP GTSSTGSPAS SSDQEEIDYD DTISVEMKKE

951 DFDIYDEDEN QSPRSFQKKT RHYFIAAVER LWDYGMSSSP HVLRNRAQSG

1001 SVPQFKKVVF QEFTDGSFTQ PLYRGELNEH LGLLGPYIRA EVEDNIMVTF

1051 RNQASRPYSF YSSLISYEED QRQGAEPRKN FVKPNETKTY FWKVQHHMAP

1101 TKDEFDCKAW AYFSDVDLEK DVHSGLIGPL LVCHTNTLNP AHGRQVTVQE

1151 FALFFTIFDE TKSWYFTENM ERNCRGAPTS ESATPESGPG SEPATSGSET

1201 PGTSESATPE SGPGSEPATS GSETPGTSES ATPESGPGTS TEPSEGSAPG

1251 TSESATPESG PGSPAGSPTS TEEGSPAGSP TSTEEGSPAG SPTSTEEGTS

1301 ESATPESGPG TSTEPSEGSA PGASSAPCNI QMEDPTFKEN YRFHAINGYI

1351 MDTLPGLVMA QDQRIRWYLL SMGSNENIHS IHFSGHVFTV RKKEEYKMAL

1401 YNLYPGVFET VEMLPSKAGI WRVECLIGEH LHAGMSTLFL VYSNKCQTPL

1451 GMASGHIRDF QITASGQYGQ WAPKLARLHY SGSINAWSTK EPFSWIKVDL

1501 LAPMIIHGIK TQGARQKFSS LYISQFIIMY SLDGKKWQTY RGNSTGTLMV

1551 FFGNVDSSGI KHNIFNPPII ARYIRLHPTH YSIRSTLRME LMGCDLNSCS
```

TABLE 25-continued

```
1601 MPLGMESKAI SDAQITASSY FTNMFATWSP SKARLHLQGR SNAWRPQVNN

1651 PKEWLQVDFQ KTMKVTGVTT QGVKSLLTSM YVKEFLISSS QDGHQWTLFF

1701 QNGKVKVFQG NQDSFTPVVN SLDPPLLTRY LRIHPQSWVH QIALRMEVLG

1751 CEAQDLYDKT HTCPPCPAPE LLGGPSVFLF PPKPKDTLMI SRTPEVTCVV

1801 VDVSHEDPEV KFNWYVDGVE VHNAKTKPRE EQYNSTYRVV SVLTVLHQDW

1851 LNGKEYKCKV SNKALPAPIE KTISKAKGQP REPQVYTLPP SRDELTKNQV

1901 SLTCLVKGFY PSDIAVEWES NGQPENNYKT TPPVLDSDGS FFLYSKLTVD

1951 KSRWQQGNVF SCSVMHEALH NHYTQKSLSL SPGK*
```

FVIII 201 protein sequence (single chain FVIIIFc with three 144 AE XTENs at amino acid 26, 1656 & 1900) (SEQ ID NO: 108)

```
   1 MQIELSTCFF LCLLRFCFSA TRRYYLGAVE LSWDYMQSDL GELPVGAPGS

51 SPSASTGTGP GSSPSASTGT GPGASPGTSS TGSPGASPGT SSTGSPGSST

101 PSGATGSPGS SPSASTGTGP GASPGTSSTG SPGSSPSAST GTGPGTPGSG

151 TASSSPGSST PSGATGSPGS STPSGATGSP GASPGTSSTG SPASSDARFP

201 PRVPKSFPFN TSVVYKKTLF VEFTDHLFNI AKPRPPWMGL LGPTIQAEVY

251 DTVVITLKNM ASHPVSLHAV GVSYWKASEG AEYDDQTSQR EKEDDKVFPG

301 GSHTYVWQVL KENGPMASDP LCLTYSYLSH VDLVKDLNSG LIGALLVCRE

351 GSLAKEKTQT LHKFILLFAV FDEGKSWHSE TKNSLMQDRD AASARAWPKM

401 HTVNGYVNRS LPGLIGCHRK SVYWHVIGMG TTPEVHSIFL EGHTFLVRNH

451 RQASLEISPI TFLTAQTLLM DLGQFLLFCH ISSHQHDGME AYVKVDSCPE

501 EPQLRMKNNE EAEDYDDDLT DSEMDVVRFD DDNSPSFIQI RSVAKKHPKT

551 WVHYIAAEEE DWDYAPLVLA PDDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNPPVLKR HQAEITRTTL QGAPGTPGSG TASSSPGASP

951 GTSSTGSPGA SPGTSSTGSP GASPGTSSTG SPGSSPSAST GTGPGTPGSG

1001 TASSSPGASP GTSSTGSPGA SPGTSSTGSP GASPGTSSTG SPGSSTPSGA

1051 TGSPGSSTPS GATGSPGASP GTSSTGSPAS SSDQEEIDYD DTISVEMKKE

1101 DFDIYDEDEN QSPRSFQKKT RHYFIAAVER LWDYGMSSSP HVLRNRAQSG

1151 SVPQFKKVVF QEFTDGSFTQ PLYRGELNEH LGLLGPYIRA EVEDNIMVTF

1201 RNQASRPYSF YSSLISYEED QRQGAEPRKN FVKPNETKTY FWKVQHHMAP

1251 TKDEFDCKAW AYFSDVDLEK DVHSGLIGPL LVCHTNTLNP AHGRQVTVQE

1301 FALFFTIFDE TKSWYFTENM ERNCRGAPTS ESATPESGPG SEPATSGSET

1351 PGTSESATPE SGPGSEPATS GSETPGTSES ATPESGPGTS TEPSEGSAPG

1401 TSESATPESG PGSPAGSPTS TEEGSPAGSP TSTEEGSPAG SPTSTEEGTS

1451 ESATPESGPG TSTEPSEGSA PGASSAPCNI QMEDPTFKEN YRFHAINGYI
```

TABLE 25-continued

```
1501 MDTLPGLVMA QDQRIRWYLL SMGSNENIHS IHFSGHVFTV RKKEEYKMAL

1551 YNLYPGVFET VEMLPSKAGI WRVECLIGEH LHAGMSTLFL VYSNKCQTPL

1601 GMASGHIRDF QITASGQYGQ WAPKLARLHY SGSINAWSTK EPFSWIKVDL

1651 LAPMIIHGIK TQGARQKFSS LYISQFIIMY SLDGKKWQTY RGNSTGTLMV

1701 FFGNVDSSGI KHNIFNPPII ARYIRLHPTH YSIRSTLRME LMGCDLNSCS

1751 MPLGMESKAI SDAQITASSY FTNMFATWSP SKARLHLQGR SNAWRPQVNN

1801 PKEWLQVDFQ KTMKVTGVTT QGVKSLLTSM YVKEFLISSS QDGHQWTLFF

1851 QNGKVKVFQG NQDSFTPVVN SLDPPLLTRY LRIHPQSWVH QIALRMEVLG

1901 CEAQDLYDKT HTCPPCPAPE LLGGPSVFLF PPKPKDTLMI SRTPEVTCVV

1951 VDVSHEDPEV KFNWYVDGVE VHNAKTKPRE EQYNSTYRVV SVLTVLHQDW

2001 LNGKEYKCKV SNKALPAPIE KTISKAKGQP REPQVYTLPP SRDELTKNQV

2051 SLTCLVKGFY PSDIAVEWES NGQPENNYKT TPPVLDSDGS FFLYSKLTVD

2101 KSRWQQGNVF SCSVMHEALH NHYTQKSLSL SPGK*
```

FVIII 203 protein sequence (single chain FVIIIFc with two AE XTENs; one 288AE XTEN in B-domain and one 144 AE XTEN at amino acid 1900) (SEQ ID NO: 109)

```
   1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNGAPGTS ESATPESGPG SEPATSGSET PGTSESATPE

801 SGPGSEPATS GSETPGTSES ATPESGPGTS TEPSEGSAPG SPAGSPTSTE

851 EGTSESATPE SGPGSEPATS GSETPGTSES ATPESGPGSP AGSPTSTEEG

901 SPAGSPTSTE EGTSTEPSEG SAPGTSESAT PESGPGTSES ATPESGPGTS

951 ESATPESGPG SEPATSGSET PGSEPATSGS ETPGSPAGSP TSTEEGTSTE

1001 PSEGSAPGTS TEPSEGSAPG SEPATSGSET PGTSESATPE SGPGTSTEPS

1051 EGSAPASSPP VLKRHQAEIT RTTLQSDQEE IDYDDTISVE MKKEDFDIYD

1101 EDENQSPRSF QKKTRHYFIA AVERLWDYGM SSSPHVLRNR AQSGSVPQFK

1151 KVVFQEFTDG SFTQPLYRGE LNEHLGLLGP YIRAEVEDNI MVTFRNQASR

1201 PYSFYSSLIS YEEDQRQGAE PRKNFVKPNE TKTYFWKVQH HMAPTKDEFD
```

TABLE 25-continued

```
1251 CKAWAYFSDV DLEKDVHSGL IGPLLVCHTN TLNPAHGRQV TVQEFALFFT

1301 IFDETKSWYF TENMERNCRG APTSESATPE SGPGSEPATS GSETPGTSES

1351 ATPESGPGSE PATSGSETPG TSESATPESG PGTSTEPSEG SAPGTSESAT

1401 PESGPGSPAG SPTSTEEGSP AGSPTSTEEG SPAGSPTSTE EGTSESATPE

1451 SGPGTSTEPS EGSAPGASSA PCNIQMEDPT FKENYRFHAI NGYIMDTLPG

1501 LVMAQDQRIR WYLLSMGSNE NIHSIHFSGH VFTVRKKEEY KMALYNLYPG

1551 VFETVEMLPS KAGIWRVECL IGEHLHAGMS TLFLVYSNKC QTPLGMASGH

1601 IRDFQITASG QYGQWAPKLA RLHYSGSINA WSTKEPFSWI KVDLLAPMII

1651 HGIKTQGARQ KFSSLYISQF IIMYSLDGKK WQTYRGNSTG TLMVFFGNVD

1701 SSGIKHNIFN PPIIARYIRL HPTHYSIRST LRMELMGCDL NSCSMPLGME

1751 SKAISDAQIT ASSYFTNMFA TWSPSKARLH LQGRSNAWRP QVNNPKEWLQ

1801 VDFQKTMKVT GVTTQGVKSL LTSMYVKEFL ISSSQDGHQW TLFFQNGKVK

1851 VFQGNQDSFT PVVNSLDPPL LTRYLRIHPQ SWVHQIALRM EVLGCEAQDL

1901 YDKTHTCPPC PAPELLGGPS VFLFPPKPKD TLMISRTPEV TCVVVDVSHE

1951 DPEVKFNWYV DGVEVHNAKT KPREEQYNST YRVVSVLTVL HQDWLNGKEY

2001 KCKVSNKALP APIEKTISKA KGQPREPQVY TLPPSRDELT KNQVSLTCLV

2051 KGFYPSDIAV EWESNGQPEN NYKTTPPVLD SDGSFFLYSK LTVDKSRWQQ

2101 GNVFSCSVMH EALHNHYTQK SLSLSPGK*
```

FVIII 204 protein sequence (single chain FVIIIFc with two
AE XTENs; one 288AE XTEN in B-domain and one 144 AE XTEN
at amino acid 403) (SEQ ID NO: 110)

```
   1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDGAPTSTEP SEGSAPGSPA GSPTSTEEGT

451 STEPSEGSAP GTSTEPSEGS APGTSESATP ESGPGTSTEP SEGSAPGTSE

501 SATPESGPGS EPATSGSETP GTSTEPSEGS APGTSTEPSE GSAPGTSESA

551 TPESGPGTSE SATPESGPGA SSDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNGAPGTS ESATPESGPG SEPATSGSET PGTSESATPE

951 SGPGSEPATS GSETPGTSES ATPESGPGTS TEPSEGSAPG SPAGSPTSTE
```

TABLE 25-continued

```
1001  EGTSESATPE SGPGSEPATS GSETPGTSES ATPESGPGSP AGSPTSTEEG

1051  SPAGSPTSTE EGTSTEPSEG SAPGTSESAT PESGPGTSES ATPESGPGTS

1101  ESATPESGPG SEPATSGSET PGSEPATSGS ETPGSPAGSP TSTEEGTSTE

1151  PSEGSAPGTS TEPSEGSAPG SEPATSGSET PGTSESATPE SGPGTSTEPS

1201  EGSAPASSPP VLKRHQAEIT RTTLQSDQEE IDYDDTISVE MKKEDFDIYD

1251  EDENQSPRSF QKKTRHYFIA AVERLWDYGM SSSPHVLRNR AQSGSVPQFK

1301  KVVFQEFTDG SFTQPLYRGE LNEHLGLLGP YIRAEVEDNI MVTFRNQASR

1351  PYSFYSSLIS YEEDQRQGAE PRKNFVKPNE TKTYFWKVQH HMAPTKDEFD

1401  CKAWAYFSDV DLEKDVHSGL IGPLLVCHTN TLNPAHGRQV TVQEFALFFT

1451  IFDETKSWYF TENMERNCRA PCNIQMEDPT FKENYRFHAI NGYIMDTLPG

1501  LVMAQDQRIR WYLLSMGSNE NIHSIHFSGH VFTVRKKEEY KMALYNLYPG

1551  VFETVEMLPS KAGIWRVECL IGEHLHAGMS TLFLVYSNKC QTPLGMASGH

1601  IRDFQITASG QYGQWAPKLA RLHYSGSINA WSTKEPFSWI KVDLLAPMII

1651  HGIKTQGARQ KFSSLYISQF IIMYSLDGKK WQTYRGNSTG TLMVFFGNVD

1701  SSGIKHNIFN PPIIARYIRL HPTHYSIRST LRMELMGCDL NSCSMPLGME

1751  SKAISDAQIT ASSYFTNMFA TWSPSKARLH LQGRSNAWRP QVNNPKEWLQ

1801  VDFQKTMKVT GVTTQGVKSL LTSMYVKEFL ISSSQDGHQW TLFFQNGKVK

1851  VFQGNQDSFT PVVNSLDPPL LTRYLRIHPQ SWVHQIALRM EVLGCEAQDL

1901  YDKTHTCPPC PAPELLGGPS VFLFPPKPKD TLMISRTPEV TCVVVDVSHE

1951  DPEVKFNWYV DGVEVHNAKT KPREEQYNST YRVVSVLTVL HQDWLNGKEY

2001  KCKVSNKALP APIEKTISKA KGQPREPQVY TLPPSRDELT KNQVSLTCLV

2051  KGFYPSDIAV EWESNGQPEN NYKTTPPVLD SDGSFFLYSK LTVDKSRWQQ

2101  GNVFSCSVMH EALHNHYTQK SLSLSPGK*
```

FVIII 205 protein sequence (single chain FVIIIFc with two AE XTENs; one 288AE XTEN in B-domain and one 144 AE XTEN at amino acid 18) (SEQ ID NO: 111)

```
  1  MQIELSTCFF LCLLRFCFSA TRRYYLGAVE LSWDYMQGAP TSESATPESG

51  PGSEPATSGS ETPGTSESAT PESGPGSEPA TSGSETPGTS ESATPESGPG

101  TSTEPSEGSA PGSPAGSPTS TEEGTSESAT PESGPGSEPA TSGSETPGTS

151  ESATPESGPG SPAGSPTSTE EGSPAGSPTS TEEGASSSDL GELPVDARFP

201  PRVPKSFPFN TSVVYKKTLF VEFTDHLFNI AKPRPPWMGL LGPTIQAEVY

251  DTVVITLKNM ASHPVSLHAV GVSYWKASEG AEYDDQTSQR EKEDDKVFPG

301  GSHTYVWQVL KENGPMASDP LCLTYSYLSH VDLVKDLNSG LIGALLVCRE

351  GSLAKEKTQT LHKFILLFAV FDEGKSWHSE TKNSLMQDRD AASARAWPKM

401  HTVNGYVNRS LPGLIGCHRK SVYWHVIGMG TTPEVHSIFL EGHTFLVRNH

451  RQASLEISPI TFLTAQTLLM DLGQFLLFCH ISSHQHDGME AYVKVDSCPE

501  EPQLRMKNNE EAEDYDDDLT DSEMDVVRFD DDNSPSFIQI RSVAKKHPKT

551  WVHYIAAEEE DWDYAPLVLA PDDRSYKSQY LNNGPQRIGR KYKKVRFMAY

601  TDETFKTREA IQHESGILGP LLYGEVGDTL LIIFKNQASR PYNIYPHGIT

651  DVRPLYSRRL PKGVKHLKDF PILPGEIFKY KWTVTVEDGP TKSDPRCLTR

701  YYSSFVNMER DLASGLIGPL LICYKESVDQ RGNQIMSDKR NVILFSVFDE
```

TABLE 25-continued

```
 751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNGAPGTS ESATPESGPG SEPATSGSET PGTSESATPE

951 SGPGSEPATS GSETPGTSES ATPESGPGTS TEPSEGSAPG SPAGSPTSTE

1001 EGTSESATPE SGPGSEPATS GSETPGTSES ATPESGPGSP AGSPTSTEEG

1051 SPAGSPTSTE EGTSTEPSEG SAPGTSESAT PESGPGTSES ATPESGPGTS

1101 ESATPESGPG SEPATSGSET PGSEPATSGS ETPGSPAGSP TSTEEGTSTE

1151 PSEGSAPGTS TEPSEGSAPG SEPATSGSET PGTSESATPE SGPGTSTEPS

1201 EGSAPASSPP VLKRHQAEIT RTTLQSDQEE IDYDDTISVE MKKEDFDIYD

1251 EDENQSPRSF QKKTRHYFIA AVERLWDYGM SSSPHVLRNR AQSGSVPQFK

1301 KVVFQEFTDG SFTQPLYRGE LNEHLGLLGP YIRAEVEDNI MVTFRNQASR

1351 PYSFYSSLIS YEEDQRQGAE PRKNFVKPNE TKTYFWKVQH HMAPTKDEFD

1401 CKAWAYFSDV DLEKDVHSGL IGPLLVCHTN TLNPAHGRQV TVQEFALFFT

1451 IFDETKSWYF TENMERNCRA PCNIQMEDPT FKENYRFHAI NGYIMDTLPG

1501 LVMAQDQRIR WYLLSMGSNE NIHSIHFSGH VFTVRKKEEY KMALYNLYPG

1551 VFETVEMLPS KAGIWRVECL IGEHLHAGMS TLFLVYSNKC QTPLGMASGH

1601 IRDFQITASG QYGQWAPKLA RLHYSGSINA WSTKEPFSWI KVDLLAPMII

1651 HGIKTQGARQ KFSSLYISQF IIMYSLDGKK WQTYRGNSTG TLMVFFGNVD

1701 SSGIKHNIFN PPIIARYIRL HPTHYSIRST LRMELMGCDL NSCSMPLGME

1751 SKAISDAQIT ASSYFTNMFA TWSPSKARLH LQGRSNAWRP QVNNPKEWLQ

1801 VDFQKTMKVT GVTTQGVKSL LTSMYVKEFL ISSSQDGHQW TLFFQNGKVK

1851 VFQGNQDSFT PVVNSLDPPL LTRYLRIHPQ SWVHQIALRM EVLGCEAQDL

1901 YDKTHTCPPC PAPELLGGPS VFLFPPKPKD TLMISRTPEV TCVVVDVSHE

1951 DPEVKFNWYV DGVEVHNAKT KPREEQYNST YRVVSVLTVL HQDWLNGKEY

2001 KCKVSNKALP APIEKTISKA KGQPREPQVY TLPPSRDELT KNQVSLTCLV

2051 KGFYPSDIAV EWESNGQPEN NYKTTPPVLD SDGSFFLYSK LTVDKSRWQQ

2101 GNVFSCSVMH EALHNHYTQK SLSLSPGK* pSYN FVIII 266 protein sequence (FVIII Fc with 42 AE-XTEN at
 amino acid 18 and 288 AE XTEN in B-domain) SEQ ID NO: 112

1 MQIELSTCFF LCLLRFCFSA TRRYYLGAVE LSWDYMQGAP GSPAGSPTST

51 EEGTSESATP ESGPGSEPAT SGSETPASSS DLGELPVDAR FPPRVPKSFP

101 FNTSVVYKKT LFVEFTDHLF NIAKPRPPWM GLLGPTIQAE VYDTVVITLK

151 NMASHPVSLH AVGVSYWKAS EGAEYDDQTS QREKEDDKVF PGGSHTYVWQ

201 VLKENGPMAS DPLCLTYSYL SHVDLVKDLN SGLIGALLVC REGSLAKEKT

251 QTLHKFILLF AVFDEGKSWH SETKNSLMQD RDAASARAWP KMHTVNGYVN

301 RSLPGLIGCH RKSVYWHVIG MGTTPEVHSI FLEGHTFLVR NHRQASLEIS

351 PITFLTAQTL LMDLGQFLLF CHISSHQHDG MEAYVKVDSC PEEPQLRMKN

401 NEEAEDYDDD LTDSEMDVVR FDDDNSPSFI QIRSVAKKHP KTWVHYIAAE

451 EEDWDYAPLV LAPDDRSYKS QYLNNGPQRI GRKYKKVRFM AYTDETFKTR

501 EAIQHESGIL GPLLYGEVGD TLLIIFKNQA SRPYNIYPHG ITDVRPLYSR
```

TABLE 25-continued

```
 551 RLPKGVKHLK DFPILPGEIF KYKWTVTVED GPTKSDPRCL TRYYSSFVNM

601 ERDLASGLIG PLLICYKESV DQRGNQIMSD KRNVILFSVF DENRSWYLTE

651 NIQRFLPNPA GVQLEDPEFQ ASNIMHSING YVFDSLQLSV CLHEVAYWYI

701 LSIGAQTDFL SVFFSGYTFK HKMVYEDTLT LFPFSGETVF MSMENPGLWI

751 LGCHNSDFRN RGMTALLKVS SCDKNTGDYY EDSYEDISAY LLSKNNAIEP

801 RSFSQNGAPG TSESATPESG PGSEPATSGS ETPGTSESAT PESGPGSEPA

851 TSGSETPGTS ESATPESGPG TSTEPSEGSA PGSPAGSPTS TEEGTSESAT

901 PESGPGSEPA TSGSETPGTS ESATPESGPG SPAGSPTSTE EGSPAGSPTS

951 TEEGTSTEPS EGSAPGTSES ATPESGPGTS ESATPESGPG TSESATPESG

1001 PGSEPATSGS ETPGSEPATS GSETPGSPAG SPTSTEEGTS TEPSEGSAPG

1051 TSTEPSEGSA PGSEPATSGS ETPGTSESAT PESGPGTSTE PSEGSAPASS

1101 PPVLKRHQAE ITRTTLQSDQ EEIDYDDTIS VEMKKEDFDI YDEDENQSPR

1151 SFQKKTRHYF IAAVERLWDY GMSSSPHVLR NRAQSGSVPQ FKKVVFQEFT

1201 DGSFTQPLYR GELNEHLGLL GPYIRAEVED NIMVTFRNQA SRPYSFYSSL

1251 ISYEEDQRQG AEPRKNFVKP NETKTYFWKV QHHMAPTKDE FDCKAWAYFS

1301 DVDLEKDVHS GLIGPLLVCH TNTLNPAHGR QVTVQEFALF FTIFDETKSW

1351 YFTENMERNC RAPCNIQMED PTFKENYRFH AINGYIMDTL PGLVMAQDQR

1401 IRWYLLSMGS NENIHSIHFS GHVFTVRKKE EYKMALYNLY PGVFETVEML

1451 PSKAGIWRVE CLIGEHLHAG MSTLFLVYSN KCQTPLGMAS GHIRDFQITA

1501 SGQYGQWAPK LARLHYSGSI NAWSTKEPFS WIKVDLLAPM IIHGIKTQGA

1551 RQKFSSLYIS QFIIMYSLDG KKWQTYRGNS TGTLMVFFGN VDSSGIKHNI

1601 FNPPIIARYI RLHPTHYSIR STLRMELMGC DLNSCSMPLG MESKAISDAQ

1651 ITASSYFTNM FATWSPSKAR LHLQGRSNAW RPQVNNPKEW LQVDFQKTMK

1701 VTGVTTQGVK SLLTSMYVKE FLISSSQDGH QWTLFFQNGK VKVFQGNQDS

1751 FTPVVNSLDP PLLTRYLRIH PQSWVHQIAL RMEVLGCEAQ DLYDKTHTCP

1801 PCPAPELLGG PSVFLFPPKP KDTLMISRTP EVTCVVVDVS HEDPEVKFNW

1851 YVDGVEVHNA KTKPREEQYN STYRVVSVLT VLHQDWLNGK EYKCKVSNKA

1901 LPAPIEKTIS KAKGQPREPQ VYTLPPSRDE LTKNQVSLTC LVKGFYPSDI

1951 AVEWESNGQP ENNYKTTPPV LDSDGSFFLY SKLTVDKSRW QQGNVFSCSV

2001 MHEALHNHYT QKSLSLSPGK *
``` pSYN FVIII 267 protein sequence (FVIII Fc with 72 4E-XTEN at amino acid 18 and 288 AE XTEN in B-domain) SEQ ID NO: 113

```
  1 MQIELSTCFF LCLLRFCFSA TRRYYLGAVE LSWDYMQGAP TSESATPESG

51 PGSEPATSGS ETPGTSESAT PESGPGSEPA TSGSETPGTS ESATPESGPG

101 TSTEPSEGSA PGASSSDLGE LPVDARFPPR VPKSFPFNTS VVYKKTLFVE

151 FTDHLFNIAK PRPPWMGLLG PTIQAEVYDT VVITLKNMAS HPVSLHAVGV

201 SYWKASEGAE YDDQTSQREK EDDKVFPGGS HTYVWQVLKE NGPMASDPLC

251 LTYSYLSHVD LVKDLNSGLI GALLVCREGS LAKEKTQTLH KFILLFAVFD

301 EGKSWHSETK NSLMQDRDAA SARAWPKMHT VNGYVNRSLP GLIGCHRKSV

351 YWHVIGMGTT PEVHSIFLEG HTFLVRNHRQ ASLEISPITF LTAQTLLMDL
```

TABLE 25-continued

```
 401 GQFLLFCHIS SHQHDGMEAY VKVDSCPEEP QLRMKNNEEA EDYDDDLTDS
 451 EMDVVRFDDD NSPSFIQIRS VAKKHPKTWV HYIAAEEEDW DYAPLVLAPD
 501 DRSYKSQYLN NGPQRIGRKY KKVRFMAYTD ETFKTREAIQ HESGILGPLL
 551 YGEVGDTLLI IFKNQASRPY NIYPHGITDV RPLYSRRLPK GVKHLKDFPI
 601 LPGEIFKYKW TVTVEDGPTK SDPRCLTRYY SSFVNMERDL ASGLIGPLLI
 651 CYKESVDQRG NQIMSDKRNV ILFSVFDENR SWYLTENIQR FLPNPAGVQL
 701 EDPEFQASNI MHSINGYVFD SLQLSVCLHE VAYWYILSIG AQTDFLSVFF
 751 SGYTFKHKMV YEDTLTLFPF SGETVFMSME NPGLWILGCH NSDFRNRGMT
 801 ALLKVSSCDK NTGDYYEDSY EDISAYLLSK NNAIEPRSFS QNGAPGTSES
 851 ATPESGPGSE PATSGSETPG TSESATPESG PGSEPATSGS ETPGTSESAT
 901 PESGPGTSTE PSEGSAPGSP AGSPTSTEEG TSESATPESG PGSEPATSGS
 951 ETPGTSESAT PESGPGSPAG SPTSTEEGSP AGSPTSTEEG TSTEPSEGSA
1001 PGTSESATPE SGPGTSESAT PESGPGTSES ATPESGPGSE PATSGSETPG
1051 SEPATSGSET PGSPAGSPTS TEEGTSTEPS EGSAPGTSTE PSEGSAPGSE
1101 PATSGSETPG TSESATPESG PGTSTEPSEG SAPASSPPVL KRHQAEITRT
1151 TLQSDQEEID YDDTISVEMK KEDFDIYDED ENQSPRSFQK KTRHYFIAAV
1201 ERLWDYGMSS SPHVLRNRAQ SGSVPQFKKV VFQEFTDGSF TQPLYRGELN
1251 EHLGLLGPYI RAEVEDNIMV TFRNQASRPY SFYSSLISYE EDQRQGAEPR
1301 KNFVKPNETK TYFWKVQHHM APTKDEFDCK AWAYFSDVDL EKDVHSGLIG
1351 PLLVCHTNTL NPAHGRQVTV QEFALFFTIF DETKSWYFTE NMERNCRAPC
1401 NIQMEDPTFK ENYRFHAING YIMDTLPGLV MAQDQRIRWY LLSMGSNENI
1451 HSIHFSGHVF TVRKKEEYKM ALYNLYPGVF ETVEMLPSKA GIWRVECLIG
1501 EHLHAGMSTL FLVYSNKCQT PLGMASGHIR DFQITASGQY GQWAPKLARL
1551 HYSGSINAWS TKEPFSWIKV DLLAPMIIHG IKTQGARQKF SSLYISQFII
1601 MYSLDGKKWQ TYRGNSTGTL MVFFGNVDSS GIKHNIFNPP IIARYIRLHP
1651 THYSIRSTLR MELMGCDLNS CSMPLGMESK AISDAQITAS SYFTNMFATW
1701 SPSKARLHLQ GRSNAWRPQV NNPKEWLQVD FQKTMKVTGV TTQGVKSLLT
1751 SMYVKEFLIS SSQDGHQWTL FFQNGKVKVF QGNQDSFTPV VNSLDPPLLT
1801 RYLRIHPQSW VHQIALRMEV LGCEAQDLYD KTHTCPPCPA PELLGGPSVF
1851 LFPPKPKDTL MISRTPEVTC VVVDVSHEDP EVKFNWYVDG VEVHNAKTKP
1901 REEQYNSTYR VVSVLTVLHQ DWLNGKEYKC KVSNKALPAP IEKTISKAKG
1951 QPREPQVYTL PPSRDELTKN QVSLTCLVKG FYPSDIAVEW ESNGQPENNY
2001 KTTPPVLDSD GSFFLYSKLT VDKSRWQQGN VFSCSVMHEA LHNHYTQKSL
2051 SLSPGK*
``` pSYN FVIII 268 protein sequence (FVIII Fc with 144 AE-XTEN at amino acid 18) SEQ ID NO: 114

```
   1 MQIELSTCFF LCLLRFCFSA TRRYYLGAVE LSWDYMQGAP TSESATPESG
  51 PGSEPATSGS ETPGTSESAT PESGPGSEPA TSGSETPGTS ESATPESGPG
 101 TSTEPSEGSA PGSPAGSPTS TEEGTSESAT PESGPGSEPA TSGSETPGTS
 151 ESATPESGPG SPAGSPTSTE EGSPAGSPTS TEEGASSSDL GELPVDARFP
 201 PRVPKSFPFN TSVVYKKTLF VEFTDHLFNI AKPRPPWMGL LGPTIQAEVY
```

TABLE 25-continued

```
 251 DTVVITLKNM ASHPVSLHAV GVSYWKASEG AEYDDQTSQR EKEDDKVFPG

301 GSHTYVWQVL KENGPMASDP LCLTYSYLSH VDLVKDLNSG LIGALLVCRE

351 GSLAKEKTQT LHKFILLFAV FDEGKSWHSE TKNSLMQDRD AASARAWPKM

401 HTVNGYVNRS LPGLIGCHRK SVYWHVIGMG TTPEVHSIFL EGHTFLVRNH

451 RQASLEISPI TFLTAQTLLM DLGQFLLFCH ISSHQHDGME AYVKVDSCPE

501 EPQLRMKNNE EAEDYDDDLT DSEMDVVRFD DDNSPSFIQI RSVAKKHPKT

551 WVHYIAAEEE DWDYAPLVLA PDDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNPPVLKR HQAEITRTTL QSDQEEIDYD DTISVEMKKE

951 DFDIYDEDEN QSPRSFQKKT RHYFIAAVER LWDYGMSSSP HVLRNRAQSG

1001 SVPQFKKVVF QEFTDGSFTQ PLYRGELNEH LGLLGPYIRA EVEDNIMVTF

1051 RNQASRPYSF YSSLISYEED QRQGAEPRKN FVKPNETKTY FWKVQHHMAP

1101 TKDEFDCKAW AYFSDVDLEK DVHSGLIGPL LVCHTNTLNP AHGRQVTVQE

1151 FALFFTIFDE TKSWYFTENM ERNCRAPCNI QMEDPTFKEN YRFHAINGYI

1201 MDTLPGLVMA QDQRIRWYLL SMGSNENIHS IHFSGHVFTV RKKEEYKMAL

1251 YNLYPGVFET VEMLPSKAGI WRVECLIGEH LHAGMSTLFL VYSNKCQTPL

1301 GMASGHIRDF QITASGQYGQ WAPKLARLHY SGSINAWSTK EPFSWIKVDL

1351 LAPMIIHGIK TQGARQKFSS LYISQFIIMY SLDGKKWQTY RGNSTGTLMV

1401 FFGNVDSSGI KHNIFNPPII ARYIRLHPTH YSIRSTLRME LMGCDLNSCS

1451 MPLGMESKAI SDAQITASSY FTNMFATWSP SKARLHLQGR SNAWRPQVNN

1501 PKEWLQVDFQ KTMKVTGVTT QGVKSLLTSM YVKEFLISSS QDGHQWTLFF

1551 QNGKVKVFQG NQDSFTPVVN SLDPPLLTRY LRIHPQSWVH QIALRMEVLG

1601 CEAQDLYDKT HTCPPCPAPE LLGGPSVFLF PPKPKDTLMI SRTPEVTCVV

1651 VDVSHEDPEV KFNWYVDGVE VHNAKTKPRE EQYNSTYRVV SVLTVLHQDW

1701 LNGKEYKCKV SNKALPAPIE KTISKAKGQP REPQVYTLPP SRDELTKNQV

1751 SLTCLVKGFY PSDIAVEWES NGQPENNYKT TPPVLDSDGS FFLYSKLTVD

1801 KSRWQQGNVF SCSVMHEALH NHYTQKSLSL SPGK*
``` pSYN FVIII 269 protein sequence (FVIII Fc with 72 AE-XTEN at amino acid 18) SEQ ID NO: 115

```
  1 MQIELSTCFF LCLLRFCFSA TRRYYLGAVE LSWDYMQGAP TSESATPESG

51 PGSEPATSGS ETPGTSESAT PESGPGSEPA TSGSETPGTS ESATPESGPG

101 TSTEPSEGSA PGASSSDLGE LPVDARFPPR VPKSFPFNTS VVYKKTLFVE

151 FTDHLFNIAK PRPPWMGLLG PTIQAEVYDT VVITLKNMAS HPVSLHAVGV

201 SYWKASEGAE YDDQTSQREK EDDKVFPGGS HTYVWQVLKE NGPMASDPLC

251 LTYSYLSHVD LVKDLNSGLI GALLVCREGS LAKEKTQTLH KFILLFAVFD
```

TABLE 25-continued

```
 301 EGKSWHSETK NSLMQDRDAA SARAWPKMHT VNGYVNRSLP GLIGCHRKSV
 351 YWHVIGMGTT PEVHSIFLEG HTFLVRNHRQ ASLEISPITF LTAQTLLMDL
 401 GQFLLFCHIS SHQHDGMEAY VKVDSCPEEP QLRMKNNEEA EDYDDDLTDS
 451 EMDVVRFDDD NSPSFIQIRS VAKKHPKTWV HYIAAEEEDW DYAPLVLAPD
 501 DRSYKSQYLN NGPQRIGRKY KKVRFMAYTD ETFKTREAIQ HESGILGPLL
 551 YGEVGDTLLI IFKNQASRPY NIYPHGITDV RPLYSRRLPK GVKHLKDFPI
 601 LPGEIFKYKW TVTVEDGPTK SDPRCLTRYY SSFVNMERDL ASGLIGPLLI
 651 CYKESVDQRG NQIMSDKRNV ILFSVFDENR SWYLTENIQR FLPNPAGVQL
 701 EDPEFQASNI MHSINGYVFD SLQLSVCLHE VAYWYILSIG AQTDFLSVFF
 751 SGYTFKHKMV YEDTLTLFPF SGETVFMSME NPGLWILGCH NSDFRNRGMT
 801 ALLKVSSCDK NTGDYYEDSY EDISAYLLSK NNAIEPRSFS QNPPVLKRHQ
 851 AEITRTTLQS DQEEIDYDDT ISVEMKKEDF DIYDEDENQS PRSFQKKTRH
 901 YFIAAVERLW DYGMSSSPHV LRNRAQSGSV PQFKKVVFQE FTDGSFTQPL
 951 YRGELNEHLG LLGPYIRAEV EDNIMVTFRN QASRPYSFYS SLISYEEDQR
1001 QGAEPRKNFV KPNETKTYFW KVQHHMAPTK DEFDCKAWAY FSDVDLEKDV
1051 HSGLIGPLLV CHTNTLNPAH GRQVTVQEFA LFFTIFDETK SWYFTENMER
1101 NCRAPCNIQM EDPTFKENYR FHAINGYIMD TLPGLVMAQD QRIRWYLLSM
1151 GSNENIHSIH FSGHVFTVRK KEEYKMALYN LYPGVFETVE MLPSKAGIWR
1201 VECLIGEHLH AGMSTLFLVY SNKCQTPLGM ASGHIRDFQI TASGQYGQWA
1251 PKLARLHYSG SINAWSTKEP FSWIKVDLLA PMIIHGIKTQ GARQKFSSLY
1301 ISQFIIMYSL DGKKWQTYRG NSTGTLMVFF GNVDSSGIKH NIFNPPIIAR
1351 YIRLHPTHYS IRSTLRMELM GCDLNSCSMP LGMESKAISD AQITASSYFT
1401 NMFATWSPSK ARLHLQGRSN AWRPQVNNPK EWLQVDFQKT MKVTGVTTQG
1451 VKSLLTSMYV KEFLISSSQD GHQWTLFFQN GKVKVFQGNQ DSFTPVVNSL
1501 DPPLLTRYLR IHPQSWVHQI ALRMEVLGCE AQDLYDKTHT CPPCPAPELL
1551 GGPSVFLFPP KPKDTLMISR TPEVTCVVVD VSHEDPEVKF NWYVDGVEVH
1601 NAKTKPREEQ YNSTYRVVSV LTVLHQDWLN GKEYKCKVSN KALPAPIEKT
1651 ISKAKGQPRE PQVYTLPPSR DELTKNQVSL TCLVKGFYPS DIAVEWESNG
1701 QPENNYKTTP PVLDSDGSFF LYSKLTVDKS RWQQGNVFSC SVMHEALHNH
1751 YTQKSLSLSP GK*
``` pSYNFVIII 271 protein sequence (FVIII Fc with 42 AE-XTEN at amino acid 18) SEQ ID NO: 116

```
  1 MQIELSTCFF LCLLRFCFSA TRRYYLGAVE LSWDYMQGAP GSPAGSPTST
 51 EEGTSESATP ESGPGSEPAT SGSETPASSS DLGELPVDAR FPPRVPKSFP
101 FNTSVVYKKT LFVEFTDHLF NIAKPRPPWM GLLGPTIQAE VYDTVVITLK
151 NMASHPVSLH AVGVSYWKAS EGAEYDDQTS QREKEDDKVF PGGSHTYVWQ
201 VLKENGPMAS DPLCLTYSYL SHVDLVKDLN SGLIGALLVC REGSLAKEKT
251 QTLHKFILLF AVFDEGKSWH SETKNSLMQD RDAASARAWP KMHTVNGYVN
301 RSLPGLIGCH RKSVYWHVIG MGTTPEVHSI FLEGHTFLVR NHRQASLEIS
351 PITFLTAQTL LMDLGQFLLF CHISSHQHDG MEAYVKVDSC PEEPQLRMKN
401 NEEAEDYDDD LTDSEMDVVR FDDDNSPSFI QIRSVAKKHP KTWVHYIAAE
```

TABLE 25-continued

```
 451 EEDWDYAPLV LAPDDRSYKS QYLNNGPQRI GRKYKKVRFM AYTDETFKTR
 501 EAIQHESGIL GPLLYGEVGD TLLIIFKNQA SRPYNIYPHG ITDVRPLYSR
 551 RLPKGVKHLK DFPILPGEIF KYKWTVTVED GPTKSDPRCL TRYYSSFVNM
 601 ERDLASGLIG PLLICYKESV DQRGNQIMSD KRNVILFSVF DENRSWYLTE
 651 NIQRFLPNPA GVQLEDPEFQ ASNIMHSING YVFDSLQLSV CLHEVAYWYI
 701 LSIGAQTDFL SVFFSGYTFK HKMVYEDTLT LFPFSGETVF MSMENPGLWI
 751 LGCHNSDFRN RGMTALLKVS SCDKNTGDYY EDSYEDISAY LLSKNNAIEP
 801 RSFSQNPPVL KRHQAEITRT TLQSDQEEID YDDTISVEMK KEDFDIYDED
 851 ENQSPRSFQK KTRHYFIAAV ERLWDYGMSS SPHVLRNRAQ SGSVPQFKKV
 901 VFQEFTDGSF TQPLYRGELN EHLGLLGPYI RAEVEDNIMV TFRNQASRPY
 951 SFYSSLISYE EDQRQGAEPR KNFVKPNETK TYFWKVQHHM APTKDEFDCK
1001 AWAYFSDVDL EKDVHSGLIG PLLVCHTNTL NPAHGRQVTV QEFALFFTIF
1051 DETKSWYFTE NMERNCRAPC NIQMEDPTFK ENYRFHAING YIMDTLPGLV
1101 MAQDQRIRWY LLSMGSNENI HSIHFSGHVF TVRKKEEYKM ALYNLYPGVF
1151 ETVEMLPSKA GIWRVECLIG EHLHAGMSTL FLVYSNKCQT PLGMASGHIR
1201 DFQITASGQY GQWAPKLARL HYSGSINAWS TKEPFSWIKV DLLAPMIIHG
1251 IKTQGARQKF SSLYISQFII MYSLDGKKWQ TYRGNSTGTL MVFFGNVDSS
1301 GIKHNIFNPP IIARYIRLHP THYSIRSTLR MELMGCDLNS CSMPLGMESK
1351 AISDAQITAS SYFTNMFATW SPSKARLHLQ GRSNAWRPQV NNPKEWLQVD
1401 FQKTMKVTGV TTQGVKSLLT SMYVKEFLIS SSQDGHQWTL FFQNGKVKVF
1451 QGNQDSFTPV VNSLDPPLLT RYLRIHPQSW VHQIALRMEV LGCEAQDLYD
1501 KTHTCPPCPA PELLGGPSVF LFPPKPKDTL MISRTPEVTC VVVDVSHEDP
1551 EVKFNWYVDG VEVHNAKTKP REEQYNSTYR VVSVLTVLHQ DWLNGKEYKC
1601 KVSNKALPAP IEKTISKAKG QPREPQVYTL PPSRDELTKN QVSLTCLVKG
1651 FYPSDIAVEW ESNGQPENNY KTTPPVLDSD GSFFLYSKLT VDKSRWQQGN
1701 VFSCSVMHEA LHNHYTQKSL SLSPGK*
``` pSYN FVIII protein sequence 272 (FVIII with 144 AE XTEN at amino acid 18 and 244 AE XTEN in B-domain- no Fc)
SEQ ID NO: 117

```
   1 MQIELSTCFF LCLLRFCFSA TRRYYLGAVE LSWDYMQGAP TSESATPESG
  51 PGSEPATSGS ETPGTSESAT PESGPGSEPA TSGSETPGTS ESATPESGPG
 101 TSTEPSEGSA PGSPAGSPTS TEEGTSESAT PESGPGSEPA TSGSETPGTS
 151 ESATPESGPG SPAGSPTSTE EGSPAGSPTS TEEGASSSDL GELPVDARFP
 201 PRVPKSFPFN TSVVYKKTLF VEFTDHLFNI AKPRPPWMGL LGPTIQAEVY
 251 DTVVITLKNM ASHPVSLHAV GVSYWKASEG AEYDDQTSQR EKEDDKVFPG
 301 GSHTYVWQVL KENGPMASDP LCLTYSYLSH VDLVKDLNSG LIGALLVCRE
 351 GSLAKEKTQT LHKFILLFAV FDEGKSWHSE TKNSLMQDRD AASARAWPKM
 401 HTVNGYVNRS LPGLIGCHRK SVYWHVIGMG TTPEVHSIFL EGHTFLVRNH
 451 RQASLEISPI TFLTAQTLLM DLGQFLLFCH ISSHQHDGME AYVKVDSCPE
 501 EPQLRMKNNE EAEDYDDDLT DSEMDVVRFD DDNSPSFIQI RSVAKKHPKT
 551 WVHYIAAEEE DWDYAPLVLA PDDRSYKSQY LNNGPQRIGR KYKKVRFMAY
```

TABLE 25-continued

| | | | | | |
|---|---|---|---|---|---|
| 601 | TDETFKTREA | IQHESGILGP | LLYGEVGDTL | LIIFKNQASR | PYNIYPHGIT |
| 651 | DVRPLYSRRL | PKGVKHLKDF | PILPGEIFKY | KWTVTVEDGP | TKSDPRCLTR |
| 701 | YYSSFVNMER | DLASGLIGPL | LICYKESVDQ | RGNQIMSDKR | NVILFSVFDE |
| 751 | NRSWYLTENI | QRFLPNPAGV | QLEDPEFQAS | NIMHSINGYV | FDSLQLSVCL |
| 801 | HEVAYWYILS | IGAQTDFLSV | FFSGYTFKHK | MVYEDTLTLF | PFSGETVFMS |
| 851 | MENPGLWILG | CHNSDFRNRG | MTALLKVSSC | DKNTGDYYED | SYEDISAYLL |
| 901 | SKNNAIEPRS | FSQNGAPGTS | ESATPESGPG | SEPATSGSET | PGTSESATPE |
| 951 | SGPGSEPATS | GSETPGTSES | ATPESGPGTS | TEPSEGSAPG | SPAGSPTSTE |
| 1001 | EGTSESATPE | SGPGSEPATS | GSETPGTSES | ATPESGPGSP | AGSPTSTEEG |
| 1051 | SPAGSPTSTE | EGTSTEPSEG | SAPGTSESAT | PESGPGTSES | ATPESGPGTS |
| 1101 | ESATPESGPG | SEPATSGSET | PGSEPATSGS | ETPGSPAGSP | TSTEEGTSTE |
| 1151 | PSEGSAPGTS | TEPSEGSAPG | SEPATSGSET | PGTSESATPE | SGPGTSTEPS |
| 1201 | EGSAPASSPP | VLKRHQAEIT | RTTLQSDQEE | IDYDDTISVE | MKKEDFDIYD |
| 1251 | EDENQSPRSF | QKKTRHYFIA | AVERLWDYGM | SSSPHVLRNR | AQSGSVPQFK |
| 1301 | KVVFQEFTDG | SFTQPLYRGE | LNEHLGLLGP | YIRAEVEDNI | MVTFRNQASR |
| 1351 | PYSFYSSLIS | YEEDQRQGAE | PRKNFVKPNE | TKTYFWKVQH | HMAPTKDEFD |
| 1401 | CKAWAYFSDV | DLEKDVHSGL | IGPLLVCHTN | TLNPAHGRQV | TVQEFALFFT |
| 1451 | IFDETKSWYF | TENMERNCRA | PCNIQMEDPT | FKENYRFHAI | NGYIMDTLPG |
| 1501 | LVMAQDQRIR | WYLLSMGSNE | NIHSIHFSGH | VFTVRKKEEY | KMALYNLYPG |
| 1551 | VFETVEMLPS | KAGIWRVECL | IGEHLHAGMS | TLFLVYSNKC | QTPLGMASGH |
| 1601 | IRDFQITASG | QYGQWAPKLA | RLHYSGSINA | WSTKEPFSWI | KVDLLAPMII |
| 1651 | HGIKTQGARQ | KFSSLYISQF | IIMYSLDGKK | WQTYRGNSTG | TLMVFFGNVD |
| 1701 | SSGIKHNIFN | PPIIARYIRL | HPTHYSIRST | LRMELMGCDL | NSCSMPLGME |
| 1751 | SKAISDAQIT | ASSYFTNMFA | TWSPSKARLH | LQGRSNAWRP | QVNNPKEWLQ |
| 1801 | VDFQKTMKVT | GVTTQGVKSL | LTSMYVKEFL | ISSSQDGHQW | TLFFQNGKVK |
| 1851 | VFQGNQDSFT | PVVNSLDPPL | LTRYLRIHPQ | SWVHQIALRM | EVLGCEAQDL |
| 1901 | Y* | | | | | pSYN VWF 031 protein sequence (VWF D1D2D'D3- 48aa long thrombin cleavable GS linker-Fc) SEQ ID NO: 118

| | | | | | |
|---|---|---|---|---|---|
| 1 | MIPARFAGVL | LALALILPGT | LCAEGTRGRS | STARCSLFGS | DFVNTFDGSM |
| 51 | YSFAGYCSYL | LAGGCQKRSF | SIIGDFQNGK | RVSLSVYLGE | FFDIHLFVNG |
| 101 | TVTQGDQRVS | MPYASKGLYL | ETEAGYYKLS | GEAYGFVARI | DGSGNFQVLL |
| 151 | SDRYFNKTCG | LCGNFNIFAE | DDFMTQEGTL | TSDPYDFANS | WALSSGEQWC |
| 201 | ERASPPSSSC | NISSGEMQKG | LWEQCQLLKS | TSVFARCHPL | VDPEPFVALC |
| 251 | EKTLCECAGG | LECACPALLE | YARTCAQEGM | VLYGWTDHSA | CSPVCPAGME |
| 301 | YRQCVSPCAR | TCQSLHINEM | CQERCVDGCS | CPEGQLLDEG | LCVESTECPC |
| 351 | VHSGKRYPPG | TSLSRDCNTC | ICRNSQWICS | NEECPGECLV | TGQSHFKSFD |
| 401 | NRYFTFSGIC | QYLLARDCQD | HSFSIVIETV | QCADDRDAVC | TRSVTVRLPG |
| 451 | LHNSLVKLKH | GAGVAMDGQD | IQLPLLKGDL | RIQHTVTASV | RLSYGEDLQM |
| 501 | DWDGRGRLLV | KLSPVYAGKT | CGLCGNYNGN | QGDDFLTPSG | LAEPRVEDFG |

TABLE 25-continued

```
 551 NAWKLHGDCQ DLQKQHSDPC ALNPRMTRFS EEACAVLTSP TFEACHRAVS
 601 PLPYLRNCRY DVCSCSDGRE CLCGALASYA AACAGRGVRV AWREPGRCEL
 651 NCPKGQVYLQ CGTPCNLTCR SLSYPDEECN EACLEGCFCP PGLYMDERGD
 701 CVPKAQCPCY YDGEIFQPED IFSDHHTMCY CEDGFMHCTM SGVPGSLLPD
 751 AVLSSPLSHR SKRSLSCRPP MVKLVCPADN LRAEGLECTK TCQNYDLECM
 801 SMGCVSGCLC PPGMVRHENR CVALERCPCF HQGKEYAPGE TVKIGCNTCV
 851 CRDRKWNCTD HVCDATCSTI GMAHYLTFDG LKYLFPGECQ YVLVQDYCGS
 901 NPGTFRILVG NKGCSHPSVK CKKRVTILVE GGEIELFDGE VNVKRPMKDE
 951 THFEVVESGR YIILLLGKAL SVVWDRHLSI SVVLKQTYQE KVCGLCGNFD
1001 GIQNNDLTSS NLQVEEDPVD FGNSWKVSSQ CADTRKVPLD SSPATCHNNI
1051 MKQTMVDSSC RILTSDVFQD CNKLVDPEPY LDVCIYDTCS CESIGDCAAF
1101 CDTIAAYAHV CAQHGKVVTW RTATLCPQSC EERNLRENGY EAEWRYNSCA
1151 PACQVTCQHP EPLACPVQCV EGCHAHCPPG KILDELLQTC VDPEDCPVCE
1201 VAGRRFASGK KVTLNPSDPE HCQICHCDVV NLTCEACQEP ISGGGGSGGG
1251 GSGGGGSGGG GSGGGGSGGG GSLVPRGSGG GGSGGGGSDK THTCPPCPAP
1301 ELLGGPSVFL FPPKPKDTLM ISRTPEVTCV VVDVSHEDPE VKFNWYVDGV
1351 EVHNAKTKPR EEQYNSTYRV VSVLTVLHQD WLNGKEYKCK VSNKALPAPI
1401 EKTISKAKGQ PREPQVYTLP PSRDELTKNQ VSLTCLVKGF YPSDIAVEWE
1451 SNGQPENNYK TTPPVLDSDG SFFLYSKLTV DKSRWQQGNV FSCSVMHEAL
1501 HNHYTQKSLS LSPGK*
``` pSYN VWF 034 protein sequence (VWF D1D2D'D3- 288AE XTEN-35aa long thrombin cleavable GS linker-Fc) SEQ ID NO: 119

```
   1 MIPARFAGVL LALALILPGT LCAEGTRGRS STARCSLFGS DFVNTFDGSM
  51 YSFAGYCSYL LAGGCQKRSF SIIGDFQNGK RVSLSVYLGE FFDIHLFVNG
 101 TVTQGDQRVS MPYASKGLYL ETEAGYYKLS GEAYGFVARI DGSGNFQVLL
 151 SDRYFNKTCG LCGNFNIFAE DDFMTQEGTL TSDPYDFANS WALSSGEQWC
 201 ERASPPSSSC NISSGEMQKG LWEQCQLLKS TSVFARCHPL VDPEPFVALC
 251 EKTLCECAGG LECACPALLE YARTCAQEGM VLYGWTDHSA CSPVCPAGME
 301 YRQCVSPCAR TCQSLHINEM CQERCVDGCS CPEGQLLDEG LCVESTECPC
 351 VHSGKRYPPG TSLSRDCNTC ICRNSQWICS NEECPGECLV TGQSHFKSFD
 401 NRYFTFSGIC QYLLARDCQD HSFSIVIETV QCADDRDAVC TRSVTVRLPG
 451 LHNSLVKLKH GAGVAMDGQD IQLPLLKGDL RIQHTVTASV RLSYGEDLQM
 501 DWDGRGRLLV KLSPVYAGKT CGLCGNYNGN QGDDFLTPSG LAEPRVEDFG
 551 NAWKLHGDCQ DLQKQHSDPC ALNPRMTRFS EEACAVLTSP TFEACHRAVS
 601 PLPYLRNCRY DVCSCSDGRE CLCGALASYA AACAGRGVRV AWREPGRCEL
 651 NCPKGQVYLQ CGTPCNLTCR SLSYPDEECN EACLEGCFCP PGLYMDERGD
 701 CVPKAQCPCY YDGEIFQPED IFSDHHTMCY CEDGFMHCTM SGVPGSLLPD
 751 AVLSSPLSHR SKRSLSCRPP MVKLVCPADN LRAEGLECTK TCQNYDLECM
 801 SMGCVSGCLC PPGMVRHENR CVALERCPCF HQGKEYAPGE TVKIGCNTCV
 851 CRDRKWNCTD HVCDATCSTI GMAHYLTFDG LKYLFPGECQ YVLVQDYCGS
 901 NPGTFRILVG NKGCSHPSVK CKKRVTILVE GGEIELFDGE VNVKRPMKDE
```

TABLE 25-continued

```
 951 THFEVVESGR YIILLLGKAL SVVWDRHLSI SVVLKQTYQE KVCGLCGNFD
1001 GIQNNDLTSS NLQVEEDPVD FGNSWKVSSQ CADTRKVPLD SSPATCHNNI
1051 MKQTMVDSSC RILTSDVFQD CNKLVDPEPY LDVCIYDTCS CESIGDCAAF
1101 CDTIAAYAHV CAQHGKVVTW RTATLCPQSC EERNLRENGY EAEWRYNSCA
1151 PACQVTCQHP EPLACPVQCV EGCHAHCPPG KILDELLQTC VDPEDCPVCE
1201 VAGRRFASGK KVTLNPSDPE HCQICHCDVV NLTCEACQEP ISGTSESATP
1251 ESGPGSEPAT SGSETPGTSE SATPESGPGS EPATSGSETP GTSESATPES
1301 GPGTSTEPSE GSAPGSPAGS PTSTEEGTSE SATPESGPGS EPATSGSETP
1351 GTSESATPES GPGSPAGSPT STEEGSPAGS PTSTEEGTST EPSEGSAPGT
1401 SESATPESGP GTSESATPES GPGTSESATP ESGPGSEPAT SGSETPGSEP
1451 ATSGSETPGS PAGSPTSTEE GTSTEPSEGS APGTSTEPSE GSAPGSEPAT
1501 SGSETPGTSE SATPESGPGT STEPSEGSAP DIGGGGSGG GGSLVPRGSG
1551 GDKTHTCPPC PAPELLGGPS VFLFPPKPKD TLMISRTPEV TCVVVDVSHE
1601 DPEVKFNWYV DGVEVHNAKT KPREEQYNST YRVVSVLTVL HQDWLNGKEY
1651 KCKVSNKALP APIEKTISKA KGQPREPQVY TLPPSRDELT KNQVSLTCLV
1701 KGFYPSDIAV EWESNGQPEN NYKTTPPVLD SDGSFFLYSK LTVDKSRWQQ
1751 GNVFSCSVMH EALHNHYTQK SLSLSPGK*
``` pSYN VWF 036 protein sequence (VWF D1D2D'D-98aa long thrombin cleavable GS linker-Fc) SEQ ID NO: 120

```
   1 MIPARFAGVL LALALILPGT LCAEGTRGRS STARCSLFGS DFVNTFDGSM
  51 YSFAGYCSYL LAGGCQKRSF SIIGDFQNGK RVSLSVYLGE FFDIHLFVNG
 101 TVTQGDQRVS MPYASKGLYL ETEAGYYKLS GEAYGFVARI DGSGNFQVLL
 151 SDRYFNKTCG LCGNFNIFAE DDFMTQEGTL TSDPYDFANS WALSSGEQWC
 201 ERASPPSSSC NISSGEMQKG LWEQCQLLKS TSVFARCHPL VDPEPFVALC
 251 EKTLCECAGG LECACPALLE YARTCAQEGM VLYGWTDHSA CSPVCPAGME
 301 YRQCVSPCAR TCQSLHINEM CQERCVDGCS CPEGQLLDEG LCVESTECPC
 351 VHSGKRYPPG TSLSRDCNTC ICRNSQWICS NEECPGECLV TGQSHFKSFD
 401 NRYFTFSGIC QYLLARDCQD HSFSIVIETV QCADDRDAVC TRSVTVRLPG
 451 LHNSLVKLKH GAGVAMDGQD IQLPLLKGDL RIQHTVTASV RLSYGEDLQM
 501 DWDGRGRLLV KLSPVYAGKT CGLCGNYNGN QGDDFLTPSG LAEPRVEDFG
 551 NAWKLHGDCQ DLQKQHSDPC ALNPRMTRFS EEACAVLTSP TFEACHRAVS
 601 PLPYLRNCRY DVCSCSDGRE CLCGALASYA AACAGRGVRV AWREPGRCEL
 651 NCPKGQVYLQ CGTPCNLTCR SLSYPDEECN EACLEGCFCP PGLYMDERGD
 701 CVPKAQCPCY YDGEIFQPED IFSDHHTMCY CEDGFMHCTM SGVPGSLLPD
 751 AVLSSPLSHR SKRSLSCRPP MVKLVCPADN LRAEGLECTK TCQNYDLECM
 801 SMGCVSGCLC PPGMVRHENR CVALERCPCF HQGKEYAPGE TVKIGCNTCV
 851 CRDRKWNCTD HVCDATCSTI GMAHYLTFDG LKYLFPGECQ YVLVQDYCGS
 901 NPGTFRILVG NKGCSHPSVK CKKRVTILVE GGEIELFDGE VNVKRPMKDE
 951 THFEVVESGR YIILLLGKAL SVVWDRHLSI SVVLKQTYQE KVCGLCGNFD
1001 GIQNNDLTSS NLQVEEDPVD FGNSWKVSSQ CADTRKVPLD SSPATCHNNI
```

TABLE 25-continued

```
1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP ISGGGGSGGG

1251 GSGGGGSGGG GSGGGGSGGG GSGGGGSGGG GSGGGGSGGG GSGGGGSGGG

1301 GSGGGGSGGG GSGGGGSGGG GSLVPRGSGG GGSGGGGSDK THTCPPCPAP

1351 ELLGGPSVFL FPPKPKDTLM ISRTPEVTCV VVDVSHEDPE VKFNWYVDGV

1401 EVHNAKTKPR EEQYNSTYRV VSVLTVLHQD WLNGKEYKCK VSNKALPAPI

1451 EKTISKAKGQ PREPQVYTLP PSRDELTKNQ VSLTCLVKGF YPSDIAVEWE

1501 SNGQPENNYK TTPPVLDSDG SFFLYSKLTV DKSRWQQGNV FSCSVMHEAL

1551 HNHYTQKSLS LSPGK* pSYN Fc-015 protein sequence (IG-Fc domain) SEQ ID NO: 121

1 METDTLLLWV LLLWVPGSTG DKTHTCPPCP APELLGGPSV FLFPPKPKDT

51 LMISRTPEVT CVVVDVSHED PEVKFNWYVD GVEVHNAKTK PREEQYNSTY

101 RVVSVLTVLH QDWLNGKEYK CKVSNKALPA PIEKTISKAK GQPREPQVYT

151 LPPSRDELTK NQVSLTCLVK GFYPSDIAVE WESNGQPENN YKTTPPVLDS

201 DGSFFLYSKL TVDKSRWQQG NVFSCSVMHE ALHNHYTQKS LSLSPGK*
```

Example 15

FVIII-XTEN-Fc:VWF-Fc Heterodimers have Maintained Normal FVIII Specific Activity as Compared to Wild Type BDD-FVIII The FVIII specific activity of FVIII-XTEN-Fc:VWF-Fc heterodimers were determined. Heterodimers were purified using a two-step chromatography process. A weak anion exchange resin was used, followed by affinity chromatography. The final purified product had acceptable purity by SEC-HPLC. The specific activity was compared to B-domain deleted FVIII (BDD-FVIII), as measured by FVIII chromogenic assay and A280 concentration. The data are presented in Table 26. All tested molecules had demonstrated comparable FVIII specific activities to BDD-FVIII. Purity and the presence of each moiety of the molecules were confirmed by SDS-PAGE and western blotting.

The half-lives of rFVIII-XTEN/D'D3 and BDD-FVIII were compared in HemA Mice (FIG. 15; Table 27). As FIG. 15 shows, rFVIII-XTEN/D'D3 achieved a half-life that was four fold longer than the half-life achieved by BDD-FVIII.

TABLE 27 rFVIII-XTEN/D'D3 and BDD-FVIII in HemA mice

| Treatment | 5 minutes Recovery (%) | HL (hr) | MRT (hr) | Cl (mL/hr/kg) | Vss (mL/kg) | AUC_D (hr*kg*mIU/mL/mIU) |
|---|---|---|---|---|---|---|
| BDD-FVIII | 89 | 7.6 | 11 | 4.5 | 49.2 | 0.22 |
| rFVIIIFc | 78 | 16 | 20 | 2.9 | 57.8 | 0.35 |
| rFVIII-XTEN/D'D3 | 86 | 30 | 36 | 1.8 | 63.4 | 0.57 |

TABLE 26

FVIII specific activity of FVIII-XTEN-Fc:VWF-Fc heterodimers

| Construct | FVIII 207 scBDDFVIII | FVIII-66 dcBDD FVIII) | FVIII 155/ vWF31 | FVIII 155/ vWF39 | FVIII 169/ vWF31 | FVIII 205/ vWF31 | FVIII 169/ vWF34 |
|---|---|---|---|---|---|---|---|
| Measured Specific Activity (IU/nmol) | 1473 | 1592 | 1534 | 1796 | 1511 | 1345 | 1505 |

Example 16

FVIII-XTEN-Fc:VWF-Fc Heterodimer's Potency (FVIII Activity) in Hemostasis as Measured by One Stage aPTT Assay The potency of FVIII-XTEN-Fc:VWF-Fc heterodimers in hemostasis was evaluated by their FVIII specific aPTT activity as summarized in Table 28. As demonstrated by Table 28, while the addition of the VWF D'D3 fragment and the insertion of XTEN into the intra-domains of FVIII reduce the FVIII specific aPTT activity of the heterodimers (as indicated by the FVIII155/VWF031 data and the FVIII205/VWF031 data), XTEN insertions in the FVIII B domain region or C-terminus of the VWF D'D3 fragment have no negative effect on the FVIII specific aPTT activity (as indicated by the FVIII169/VWF031 data and the FVIII169/VWF034 data). Compared to dual-chain BDD-FVIII (dcBDD-FVIII), FVIII155/VWF031, FVIII169/VWF031, FVIII169/VWF034 and VWF205/VWF031 showed reduction of specific aPTT activity by 2.5-fold, 2.8-fold, 2.6-fold and 5.5-fold, respectively.

TABLE 28

FVIII specific aPTT activity of FVIII-XTEN-Fc:VWF-Fc heterodimers

| Construct | FVIII 207 scBDD-FVIII | FVIII-66 dcBDD-FVIII | FVIII 155/ VWF31 | FVIII 169/ VWF31 | FVIII 205/ VWF31 | FVIII 169/ VWF34 |
|---|---|---|---|---|---|---|
| Measured Specific aPTT Activity (IU/nmol) | 818 ± 153 | 1188 ± 213 | 448 ± 111 | 416 ± 70 | 214 ± 38 | 436 ± 189 |

FVIII Specific aPTT Assay

FVIII variants were diluted with aPTT buffer (0.15 M NaCl, 0.05 M Tris-HCl, 1% BSA, pH 7.4) to the linear assay range (200-1.6 mU/mL). 50 μL of diluted samples or standards were sequentially mixed with 50 μL of 37° C. naïve human HemA pooled plasma, 50 μL of 37° C. aPTT reagent (ACTIN® FSL activated cephaloplastin reagent—Dade Behring, reference #B4219-2) and incubated at 37° C. for 4 minutes. 50 μl of 20 mM $CaCl_2$ (Dade Behring [reference #ORFO37]) was then added to the reaction mixture to start the clotting reactions. Using the clotting time of each sample (the length of time from the addition of $CaCl_2$ until the onset of clot formation), the aPTT activity was calculated against the standard that was generated with the $8^{th}$ international standard FVIII concentrate. Specific aPTT activity was calculated against the protein concentration of each molecule that measured by OD280.

Example 17

In Vivo Efficacy of FVIII-XTEN-Fc:VWF-Fc Heterodimer in HemA Mice Tail Clip Bleeding Model To further access the hemostasis potency of the heterodimers, the acute efficacy of FVIII169/VWF034 and FVIII205/VWF031 was evaluated in comparison with BDD-FVIII in the HemA mice Tail clip bleeding model. HemA mice were treated with a single IV injection of BDD-FVIII at 200, 65 and 20 IU/kg to generate the post tail clip injury blood loss control level. Blood loss from mice treated with 200 IU/kg of FVIII169/VWF034 or FVIII205/VWF031 was compared to that of the BDD-FVIII treated control group mice to estimate their potency on hemostasis. Vehicle treated animals were used to generate blood loss baseline for the model. As shown in FIG. 16, significant reduction in blood loss was observed from all FVIII treatment groups compared to that of the vehicle treated animals ($p<0.05$). Both FVIII169/VWF034 and FVIII205/VWF031 are efficacious in the HemA mice Tail Clip model. Compared to BDD-FVIII, about 3 fold lower potency was observed for FVIII169/VWF034, as demonstrated by the similar blood loss reduction achieved by 65 IU/kg BDD-FVIII and 200 IU/kg FVIII169/VWF034. As for FVIII205/VWF034, a 10 fold potency reduction has been observed, as demonstrated by the similar blood loss reduction achieved by 20 IU/kg BDD-FVIII and 200 IU/kg FVIII205/VWF031.

Even though FVIII69/VWF034 and FVIII205/VWF031 had similar specific FVIII chromogenic activity compared to rBDD-FVIII, their FVIII aPTT activity and in vivo potency were both reduced due to the modifications of the molecules. Those data indicate that the aPTT activity of a FVIII molecule is a more accurate measurement on predicating its in vivo potency on hemostasis than the FVIII chromogenic activity.

HemA Mice Tail Clip Bleeding Model 8-10 weeks old male HemA mice were used for the study. Prior to tail clip injury, mice were anesthetized with a 50 mg/kg Ketamine/0.5 mg/kg Dexmedetomidine cocktail and placed on a 37° C. heating pad to help maintain the body temperature. The tails of the mice were then be immersed in 37° C. water for 10 minutes to dilate the lateral vein. After vein dilation, rFVIII or vehicle solution were injected via the tail vein and 5 min later, the distal 1 cm of the tail was cut off using a #11 scalpel with straight edge. The shed blood was collected into 13 ml of 37° C. warm saline for 30 minutes and the mice were then euthanized while still under anesthesia by bilateral thoracotomy. Blood loss was quantified gravimetrically by weight change of the blood collection tubes before and after blood was collected in gram, which translated into milliliter (mL) of blood loss volume (1 g weight change=1 mL blood loss).

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

What is claimed is:

1. A set of polynucleotides encoding a chimeric protein, wherein the set of polynucleotides comprises (i) a first polynucleotide and (ii) a second polynucleotide,
   wherein the (i) first polynucleotide encodes a first polypeptide chain comprising:
   (a) a von Willebrand Factor (VWF) fragment comprising a D1 domain, a D2 domain, a D' domain, and a D3 domain of VWF, wherein the VWF fragment encoded by the first polynucleotide comprises an amino acid sequence having at least 95% sequence identity to amino acids 23 to 1240 of SEQ ID NO: 2;
   (b) a first extended length polypeptide (XTEN) sequence, and
   (c) a first Fc region;
   wherein the (ii) second polynucleotide encodes a second polypeptide chain comprising:
   (a) a Factor VIII (FVIII) protein comprising amino acids 1 to 745 of full-length mature human factor VIII (SEQ ID NO: 4) with a second XTEN sequence inserted within the FVIII protein immediately downstream of an insertion site corresponding to residue 745 of full-length mature human FVIII, and
   (b) a second Fc region,
   wherein the VWF fragment prevents binding of endogenous VWF to FVIII;
   wherein the D' domain of VWF encoded by the first polynucleotide comprises an amino acid sequence having at least 95% sequence identity to amino acids 764 to 866 of SEQ ID NO: 2;
   wherein the VWF fragment does not form a dimer or multimer of VWF;
   wherein the first XTEN sequence is linked to or associated with the first Fc region by a thrombin cleavable linker; and
   wherein the first XTEN sequence and the second XTEN sequence comprise the amino acid sequence of SEQ ID NO: 131.

2. The set of polynucleotides of claim 1, further comprising a polynucleotide encoding a Paired basic Amino acid Cleaving Enzyme (PACE).

3. A host cell comprising the set of polynucleotides of claim 1.

4. The host cell of claim 3, wherein the host cell is a mammalian cell.

5. The host cell of claim 4, wherein the mammalian cell is a HEK293 cell, CHO cell, or BHK cell.

6. The host cell of claim 4, wherein the mammalian cell is a HEK293 cell.

7. The host cell of claim 4, wherein the mammalian cell is a HEK293F cell.

8. The host cell of claim 3, wherein the set of polynucleotides are stably transfected in the host cell.

9. A stable cell line comprising the host cell of claim 8.

10. A host cell comprising the set of polynucleotides according to claim 2.

11. The host cell of claim 10, wherein the host cell is a HEK293F cell.

12. The set of polynucleotides of claim 1, wherein the FVIII protein encoded by the second polynucleotide is a single chain FVIII isoform.

13. The set of polynucleotides of claim 1, wherein the D' domain of VWF encoded by the first polynucleotide comprises the amino acid sequence according to amino acids 764 to 866 of SEQ ID NO: 2.

14. The set of polynucleotides of claim 1, wherein the D3 domain of VWF encoded by the first polynucleotide comprises an amino acid sequence having at least 95% sequence identity to amino acids 867 to 1240 of SEQ ID NO: 2.

15. The set of polynucleotides of claim 1, wherein the VWF fragment encoded by the first polynucleotide comprises an amino acid sequence having at least 99% sequence identity to amino acids 23 to 1240 of SEQ ID NO: 2, wherein the VWF fragment further comprises a signal peptide of VWF corresponding to amino acids 1 to 22 of SEQ ID NO: 2.

16. The set of polynucleotides of claim 1, wherein the first polypeptide chain comprises an amino acid sequence having at least 90% sequence identity to the amino acid sequence of SEQ ID NO: 119.

17. The set of polynucleotides of claim 1, wherein the second polypeptide chain comprises an amino acid sequence having at least 80% sequence identity to the amino acid sequence of SEQ ID NO: 103.

18. The set of polynucleotides of claim 1, wherein the VWF fragment encoded by the first polynucleotide comprises amino acids 764 to 1240 of SEQ ID NO: 119.

19. The set of polynucleotides of claim 1, wherein the VWF fragment encoded by the first polynucleotide consists of amino acids 764 to 1240 of SEQ ID NO: 119.

20. The set of polynucleotides of claim 16, wherein the second polypeptide chain comprises an amino acid sequence having at least 80% sequence identity to the amino acid sequence of SEQ ID NO: 103.

* * * * *